US012577625B2

(12) United States Patent
Ott et al.

(10) Patent No.: US 12,577,625 B2
(45) Date of Patent: Mar. 17, 2026

(54) RAPID FIELD-DEPLOYABLE DETECTION OF SARS-CoV-2 VIRUS

(71) Applicants: The J. David Gladstone Institutes, a testamentary trust established under the Will of J. David Gladstone, San Francisco, CA (US); The Regents of the University of California, Oakland, CA (US)

(72) Inventors: Melanie Ott, Mill Valley, CA (US); Parinaz Fozouni, San Francisco, CA (US); Jennifer A. Doudna, Oakland, CA (US); Daniel A. Fletcher, Berkeley, CA (US); David Savage, Berkeley, CA (US); Emeric Charles, Berkeley, CA (US); Sungmin Son, Oakland, CA (US); Gagandeep Renuka Kumar, San Francisco, CA (US); Neil Switz, Oakland, CA (US)

(73) Assignees: The J. David Gladstone Institutes, a testamentary trust established under the Will of J. David Gladstone, San Francisco, CA (US); The Regents of the University of California, Oakland, CA (US)

( * ) Notice: Subject to any disclaimer, the term of this patent is extended or adjusted under 35 U.S.C. 154(b) by 647 days.

(21) Appl. No.: 17/206,020

(22) Filed: Mar. 18, 2021

(65) Prior Publication Data

US 2021/0348243 A1 Nov. 11, 2021

Related U.S. Application Data

(60) Provisional application No. 63/158,297, filed on Mar. 8, 2021, provisional application No. 63/081,168, filed on Sep. 21, 2020, provisional application No. 62/706,488, filed on Aug. 19, 2020, provisional application No. 63/057,082, filed on Jul. 27, 2020, provisional application No. 62/991,827, filed on Mar. 19, 2020.

(51) Int. Cl.
| | |
|---|---|
| *C12Q 1/70* | (2006.01) |
| *C12N 9/22* | (2006.01) |
| *C12N 15/11* | (2006.01) |
| *G01N 21/64* | (2006.01) |

(52) U.S. Cl.
CPC .............. *C12Q 1/701* (2013.01); *C12N 9/22* (2013.01); *C12N 15/11* (2013.01); *G01N 21/6456* (2013.01); *C12N 2310/20* (2017.05); *G01N 2021/6469* (2013.01)

(58) Field of Classification Search
CPC ....... G01N 21/6456; G01N 2021/6469; C12N 2310/20; C12N 9/22; C12N 15/11; C12N 15/113; G02B 21/0076; G02B 13/22; G02B 6/29361; C12Q 1/701; C12Q 1/6825; C12Q 2563/107
See application file for complete search history.

(56) References Cited

U.S. PATENT DOCUMENTS

| | | | |
|---|---|---|---|
| 10,494,664 B2 | 12/2019 | Doudna et al. | |
| 10,542,885 B2 | 1/2020 | Fletcher et al. | |
| 10,578,851 B2 | 3/2020 | Fletcher et al. | |
| 2003/0151735 A1* | 8/2003 | Blumenfeld ....... | G01N 21/6428 356/73 |
| 2006/0114554 A1* | 6/2006 | Suzuki ................. | G02B 21/248 359/368 |
| 2008/0117425 A1* | 5/2008 | Kain .................... | C12Q 1/6837 356/455 |
| 2009/0162863 A1 | 6/2009 | Jematsu et al. | |
| 2012/0135511 A1* | 5/2012 | Battrell ................. | C12M 23/16 435/287.2 |
| 2017/0362644 A1* | 12/2017 | Doudna .............. | C12Q 1/6823 |

FOREIGN PATENT DOCUMENTS

| | | | | |
|---|---|---|---|---|
| CN | 108823291 A | * | 11/2018 | .......... C12Q 1/6851 |
| CN | 116438303 | | 7/2023 | |
| IN | 202217059379 | | 10/2023 | |
| JP | 2019522472 | | 8/2019 | |
| WO | 2020051452 | | 3/2020 | |
| WO | 2021188830 | | 9/2021 | |

(Continued)

OTHER PUBLICATIONS

Katzmeier et al. A low-cost fluorescence reader for in vitro transcription and nucleic acid detection with Cas13a. PLOS ONE, vol. 14, No. 12, e0220091, Dec. 18, 2019, printed as pp. 1/17, 17/17, pp. 1/19, 19/19 of supplementary information. (Year: 2019).*
Li et al. Aptamer-based fluorescent sensor array for multiplexed detection of cyanotoxins on a smartphone. Analytical Chemistry, vol. 91, pp. 10448-10457 and pp. S-1 to S-10, Jun. 13, 2019. (Year: 2019).*
Edmund Optics #54-771 (https://www.meetoptics.com/filters/colored/green-filter/s/edmund-optics/p/54-771, printed as pp. 1/2-2/2 on Feb. 20, 2024. (Year: 2024).*
Hamilton et al. A large field CCD system for quantitative imaging of microarrays. Nucleic Acids Research, vol. 34, No. 8, e58, May 2, 2006, printed as pp. 1/14-14/14. (Year: 2006).*

(Continued)

*Primary Examiner* — Nancy J Leith
(74) *Attorney, Agent, or Firm* — Schwegman Lundberg & Woessner, P.A.

(57) ABSTRACT

The present disclosure relates to methods using CRISPR-Cas13 enzyme, complexed with SARS-CoV-2 crRNA guide RNAs to detect and quantify the presence of SARS-CoV-2 RNA in a sample with enhanced specificity and sensitivity. These methods can be used to diagnose SARS-CoV-2 infection, quantify the concentration of SARS-CoV-2 RNA present in a sample, identify the presence of different SARS-CoV-2 splice variants, subtypes, or mutations, and to monitor reactivation of SARS-CoV-2 transcription.

57 Claims, 82 Drawing Sheets

Specification includes a Sequence Listing.

(56)                  References Cited

FOREIGN PATENT DOCUMENTS

ZA            202211358         6/2024

OTHER PUBLICATIONS

Fozouni et al (Direct detection of SARS-CoV-2 using CRISPR-Cas13a and a mobile phone. medRxiv preprint doi: https://doi.org/10.1101/2020.09.28.20201947, posted Sep. 30, 2020, pp. 1-33. (Year: 2020).*

Wang et al. Rapid design and development of CRISPR-Cas13a targeting SARS-CoV-2 spike protein. Theranostics, vol. 11, No. 2, pp. 649-663, and pp. 1/12-12/12 of Supplementary materials, Jan. 1, 2021. (Year: 2021).*

Abbott et al. Development of CRISPR as an antiviral strategy to combat SARS-CoV-2 and influenza. Cell, vol. 181, pp. 865-876, p. 1/1 of Figure S1, and p. 1/46 to 46/46 of Table S1, May 14, 2020. (Year: 2020).*

Machine translation of the description and Fig. 2 of CN-108823291-A, printed as pp. 1-13 on Oct. 5, 2024. (Year: 2024).*

"International Application Serial No. PCT US2021 023025, Invitation to Pay Additional Fees mailed Jul. 30, 2021", 3 pgs.

"International Application Serial No. PCT US2021 023025, International Search Report mailed Oct. 1, 2021", 6 pgs.

"International Application Serial No. PCT US2021 023025, Written Opinion mailed Oct. 1, 2021", 8 pgs.

Chen, "Mobile Platform for Multiplexed Detection and Differentiation of Disease-Specific Nucleic Acid Sequences, Using Microfluidic Loop-Mediated Isothermal Amplification and Smartphone Detection", Anal Chem vol. 89 No. 21, (Nov. 7, 2017), 11219-11226.

Han, "SARS-CoV-2 RNA more readily detected in induced sputum than in throat swabs of convalescent COVID-19 patients", Lancet Infect Dis. vol. 20 No. 6, (Mar. 12, 2020), 655-656.

"Chinese Application Serial No. 202180036013.2, Notification to Make Rectification mailed Feb. 22, 2023", With English machine translation, 3 pgs.

"Chinese Application Serial No. 202180036013.2, Response filed Apr. 6, 2023 to Notification to Make Rectification mailed Feb. 22, 2023", With English machine translation, 298 pgs.

"European Application Serial No. 21772507.6, Response to Communication pursuant to Rules 161(2) and 162 EPC filed May 10, 2023", 11 pgs.

"Chinese Application Serial No. 202180036013.2, Notification to Make Rectification mailed Apr. 27, 2023", With English machine translation, 3 pgs.

"Israel Application Serial No. 296569, Notification Prior to Examination mailed Apr. 23, 2023", W English Translation, 4 pgs.

"Chinese Application Serial No. 202180036013.2, Response filed Jun. 2, 2023 to Notification to Make Rectification mailed Apr. 27, 2023", w English claims, 159 pgs.

"Israel Application Serial No. 296569, Office Action mailed Sep. 1, 2023", With English Machine Translation, 3 pgs.

"Japanese Application Serial No. 2022-556273, Notification of Reasons for Refusal mailed Nov. 28, 2023", With English Machine Translation, 17 pgs.

"Enabling coronavirus detection using CRISPR-Cas13:An open-access SHERLOCK research protocol", McGovern Institute, Retrieved from the Internet, URL: https: mcgovern.mit.edu 2020 02 14 enabling-coronavirus-detection-using-crispr-cas13-an-open-access-sherlock-research-protocol retrieved on Nov. 20, 2023, (Feb. 14, 2020).

"Israel Application Serial No. 296569, Response filed Nov. 28, 23 to Office Action mailed Sep. 1, 23", w English claims, 14 pgs.

"Canadian Application Serial No. 3, 178,847, Examiners Rule 86(2) Report mailed Nov. 27, 23", 3 pgs.

"Brazilian Application Serial No. BR112022018769-6, Voluntary Amendment filed Feb. 16, 24", 11 pgs.

"Canadian Application Serial No. 3, 178,847, Response filed Mar. 27, 24 to Examiners Rule 86(2) Report mailed Nov. 27, 23", 22 pgs.

"European Application Serial No. 21772507.6, Communication pursuant to Rule 164(1) EPC mailed Apr. 15, 2024", 15 pgs.

"Australian Application Serial No. 2021236681, First Examination Report mailed May 6, 2024", 4 pgs.

"Japanese Application Serial No. 2022-556273, Response filed May 28, 2024 to Notification of Reasons for Refusal mailed Nov. 28, 2023", W English Claims, 18 pgs.

"European Application Serial No. 21772507.6, Extended European Search Report mailed Jul. 8, 2024", 14 pgs.

"Japanese Application Serial No. 2022-556273, Decision of Rejection mailed Aug. 20, 2024", w English Translation, 6 pgs.

"Australian Application Serial No. 2021236681, Response filed Apr. 11, 2025 to First Examination Report mailed May 6, 2024", 20 pgs.

"Canadian Application Serial No. 3,178,847, Examiners Rule 86(2) Report mailed Dec. 18, 2024", 4 pgs.

"Canadian Application Serial No. 3,178,847, Response filed Apr. 17, 2025 to Examiners Rule 86(2) Report mailed Dec. 18, 2024", 11 pgs.

"European Application Serial No. 21772507.6, Response filed Jan. 28, 2025 to Extended European Search Report mailed Jul. 8, 2024", 10 pgs.

"Mexican Application Serial No. MX/a/2024/000971, Voluntary Amendment filed Apr. 11, 2025", w/English claims, 22 pgs.

"United Arab Emirates Application Serial No. P6001901/2022, Response filed Mar. 10, 2025 to Substantive Examination Report mailed Dec. 22, 2024", w/English claims, 14 pgs.

"United Arab Emirates Application Serial No. P6001901/2022, Substantive Examination Report mailed Dec. 22, 2024", 11 pgs.

* cited by examiner

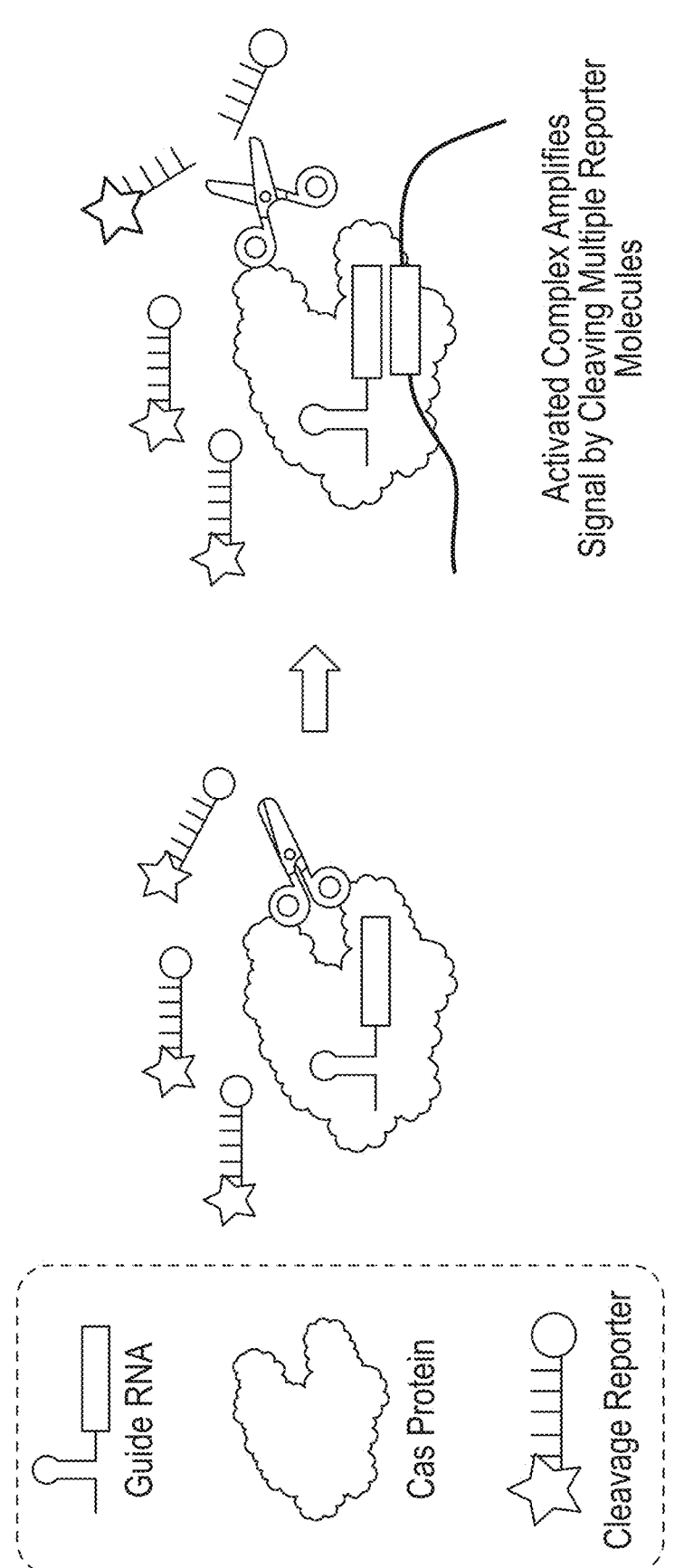

CRISPR-Cas13a Allows for Specific & Direct Detection of RNA

Guide RNA

Cas Protein

Cleavage Reporter

Activated Complex Amplifies Signal by Cleaving Multiple Reporter Molecules

• Cas13a Binds and Cleaves RNA (Unlike Cas9, which Cleaves DNA)

• By Changing Sequence of Guide RNA (crRNA), you Can Direct it to Any Specific Target RNA

• Once Cas13 is Activated by Target RNA, it Cleaves Indiscriminately, Allowing us to Detect Targets by Including a RNA-based Reporter that Fluoresces upon Cleavage by Cas13a

FIG. 1A

A Simple, CRISPR-Cas13a Based POC Diagnostic to Rapidly & Directly Detect SARS-CoV-2 RNA CRISPR-Cas13a RNPs SARS-CoV-2

Viral Lysis

1 Step Reaction with Pre-formed RNPs + Reporter

Computational Subtraction of Background Fluorescence from Control Reactions

Fluorescence Detection

"CellScope" Mobile Phone

Mobile Phone-based Viral Detection

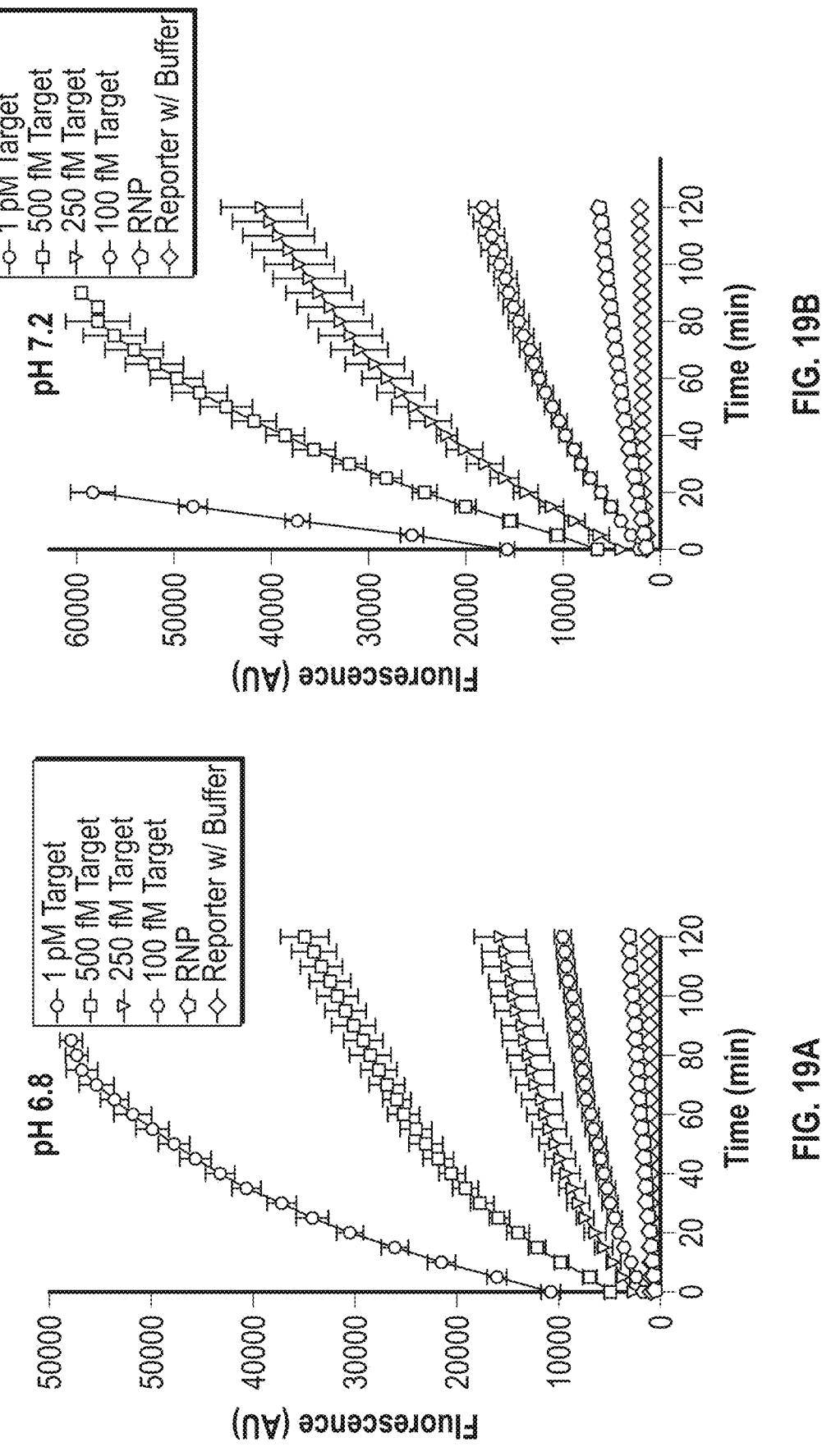

+IVT 1e6/20uL, 2hrs          No IVT Control, 2hrs

Droplet Size CDF

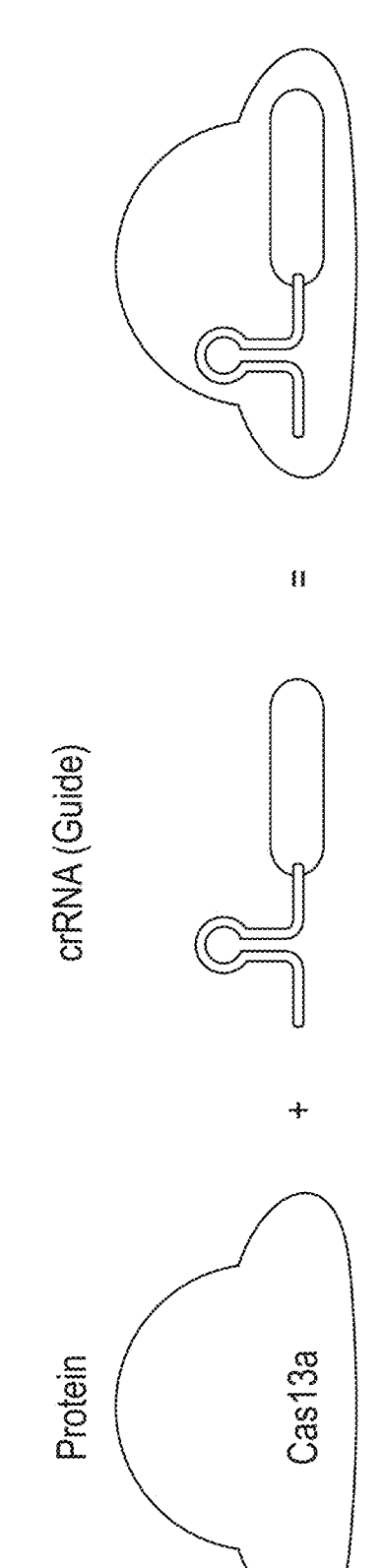
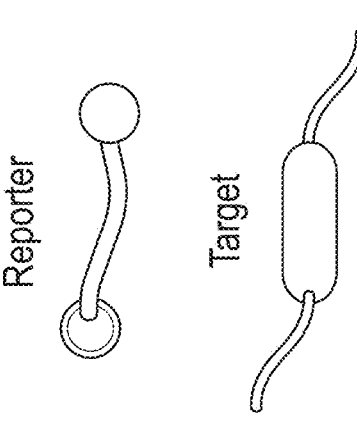
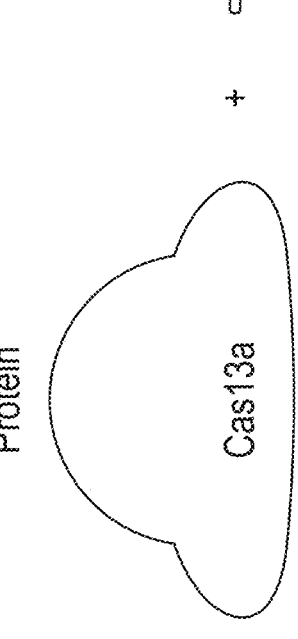
FIG. 26

Direct RNA Detection by CRISPR/Cas13a
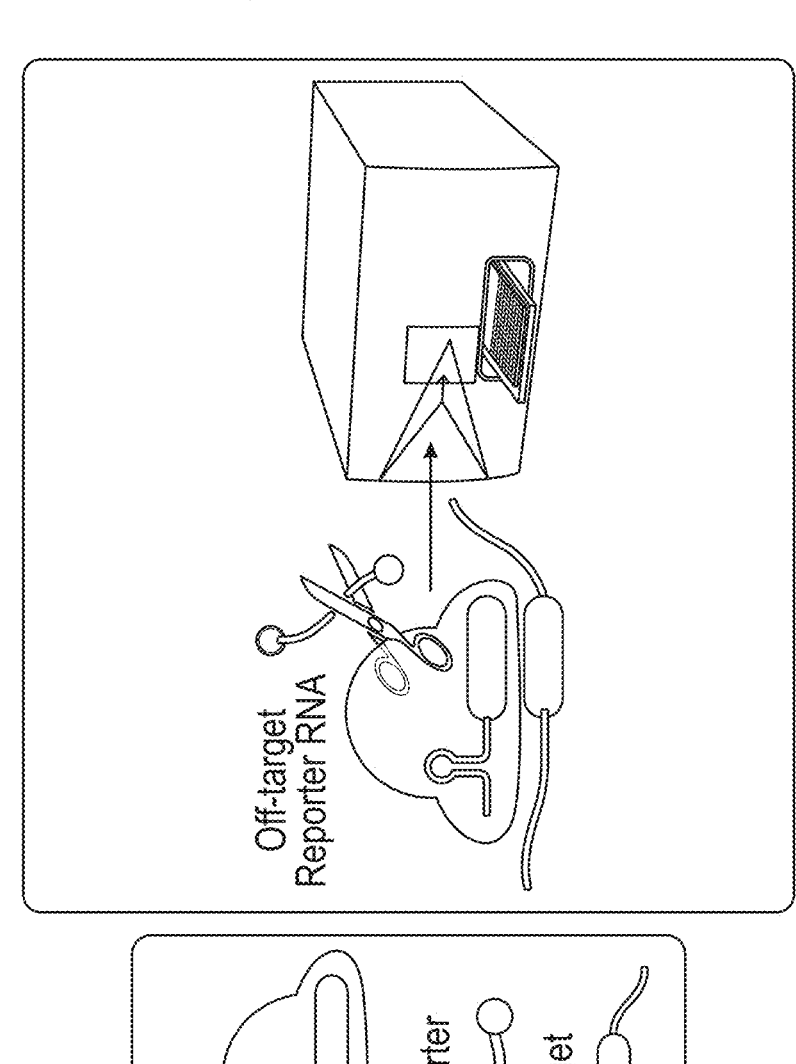
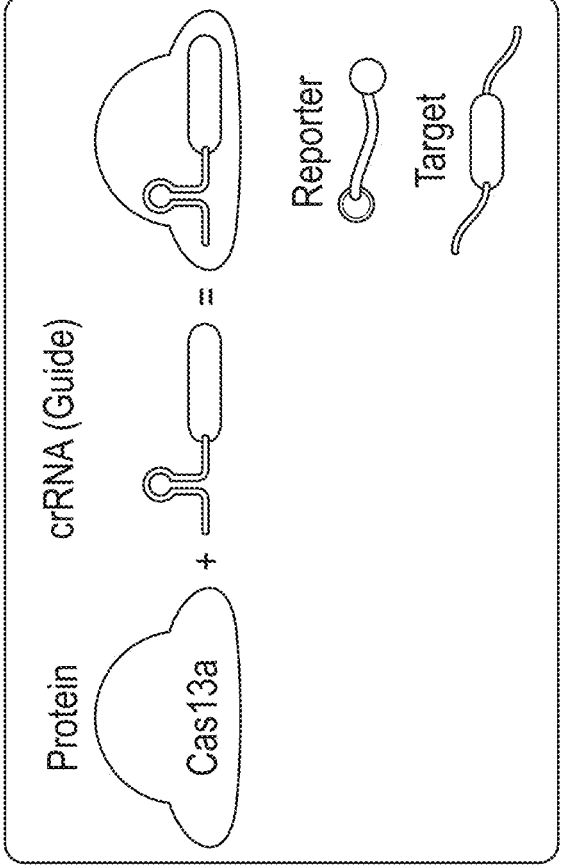
FIG. 27

SHERLOCK Detection by CRISPR/Cas13a

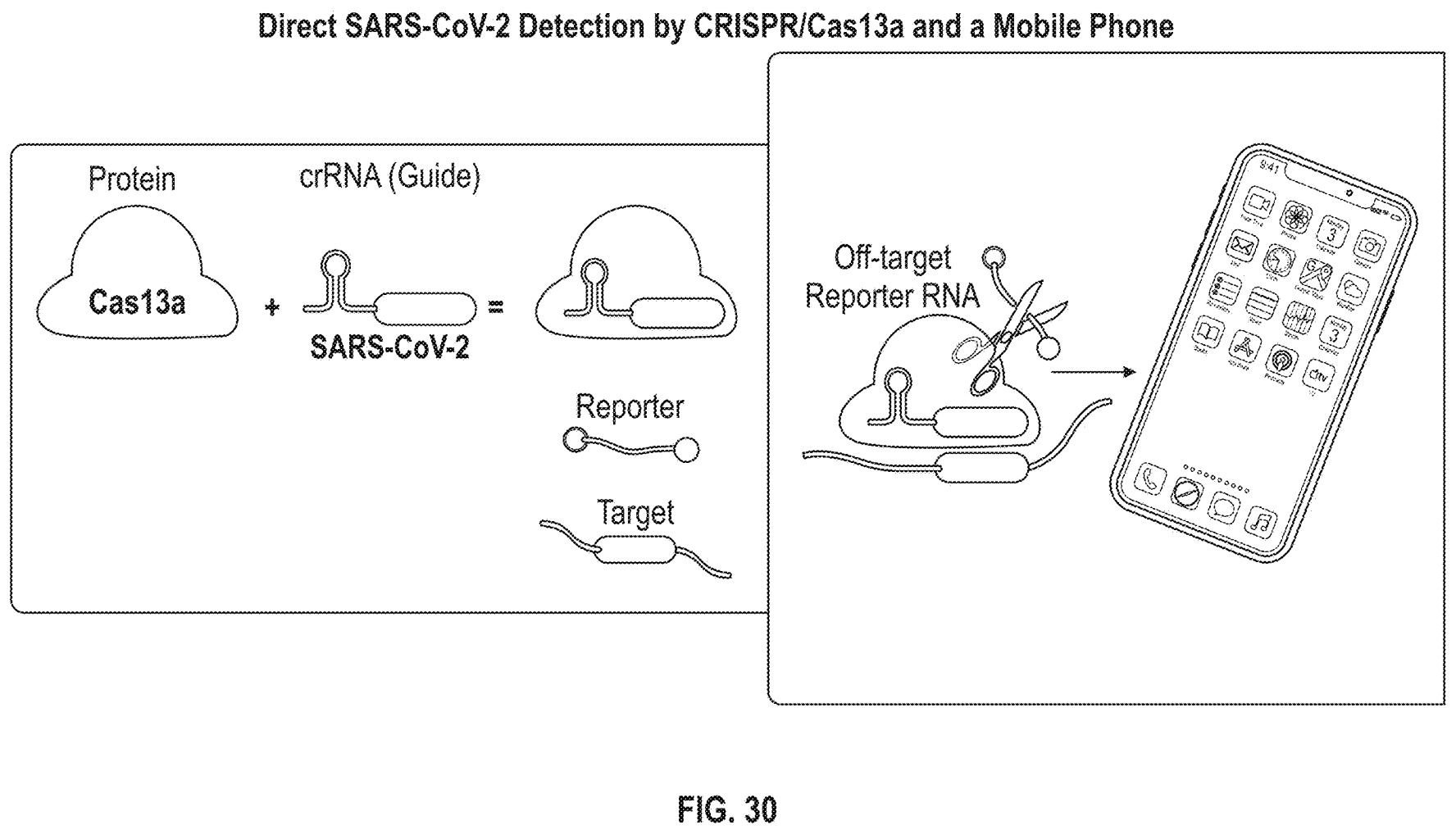

Direct SARS-CoV-2 Detection by CRISPR/Cas13a and a Mobile Phone

Protein

Cas13a crRNA (Guide)

= SARS-CoV-2

SARS-CoV-2

Reporter

Target

Off-target Reporter RNA

FIG. 30

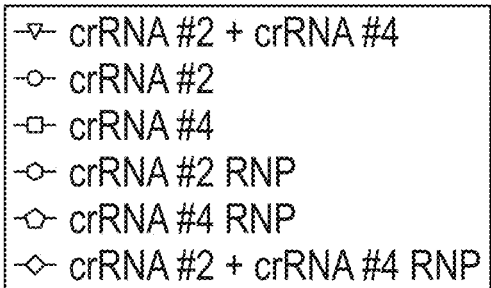
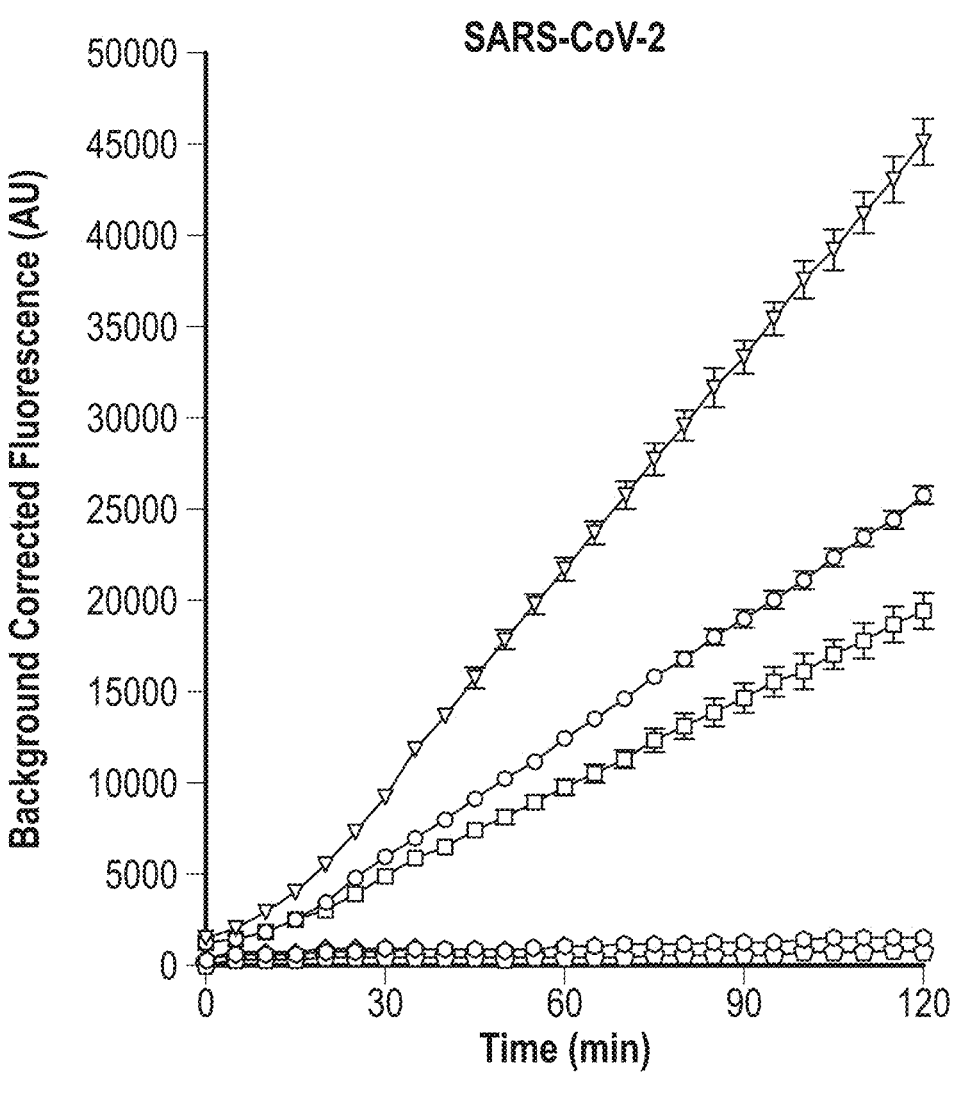
FIG. 33A

Mobile Phone Microscopy

"CellScope"

Cas13 Assay on a Mobile Phone

Cas13 Assay Example (IVT 1e6)

- RNP 100nM (Single Guide)
- RNP 100nM (Double Guide)

Benchtop Prototype

Prototype Device

Prototype Device

| Swab ID | Average Ct (N1/N2) | Copies/mL | Copies in Reaction (Copies/ul) |
|---|---|---|---|
| Positive #1 | 14.37 | $2.08 \times 10^{10}$ | $3.20 \times 10^5$ |
| Positive #2 | 15.02 | $1.36 \times 10^{10}$ | $2.09 \times 10^5$ |
| Positive #3 | 17.65 | $2.41 \times 10^9$ | $3.71 \times 10^4$ |
| Positive #4 | 20.37 | $4.04 \times 10^8$ | $6.21 \times 10^3$ |
| Positive #5 | 22.13 | $1.27 \times 10^8$ | $1.65 \times 10^3$ |

| Positive Swab ID | Avg Count (CDC N1+N2) | Copies/mL (by qPCR) | Copies/µL (CaS13 Reaction) |
|:---:|:---:|:---:|:---:|
| #1 | 14.37 | $2.08 \times 10^{10}$ | $3.20 \times 10^{5}$ |
| #2 | 15.02 | $1.36 \times 10^{10}$ | $2.09 \times 10^{5}$ |
| #3 | 17.65 | $2.41 \times 10^{10}$ | $3.71 \times 10^{4}$ |
| #4 | 20.37 | $4.04 \times 10^{8}$ | $6.21 \times 10^{3}$ |
| #5 | 22.13 | $1.27 \times 10^{8}$ | $1.65 \times 10^{3}$ |

FIG. 45F

Time (min)

SARS-CoV-2 8-Guide Combination Limit of Detection (LoD) Using Two Methods

Limit of Detection (LoD) Method A 100, 50, or 10 Copies Per ul at 30 min, 60 min, or 120 min When Comparing Each of the 20 Replicates Individually (FDA guidelines)

Limit of Detection (LoD) Method B

50 Copies or 100 Copies Per ul at 30 min or 120 min When Comparing Average of 20 Replicates 8 Guide Performance with SARS-CoV-2 Viral RNA from BEI

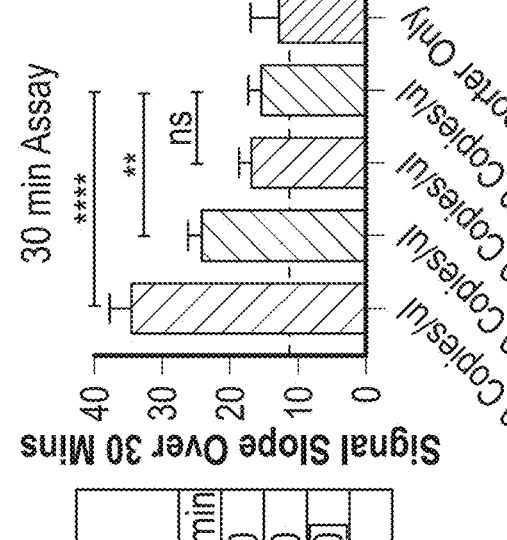

| Copies/ul | 8g combo vs. RNP (replicates positive out of 20) | | | |
|---|---|---|---|---|
| | 10 min | 30 min | 60 min | 120 min |
| 100 | 1 | 20 | 20 | 20 |
| 50 | 0 | 14 | 20 | 20 |
| 10 | 0 | 1 | 5 | 20 |
| 0 | 0 | 0 | 0 | 0 |

FIG. 49A

8 Guide Performance with SARS-CoV-2 Viral RNA from BEI 30 min Assay

FIG. 49B

8 Guide Performance with SARS-CoV-2 Viral RNA from BEI

2 Hours Assay

FIG. 49C

VARIANT MUTATION DETECTION & GRAPH KEY

EXPERIMENT AND ANALYSIS DETAILS:

- Wa1 GUIDES (WT, US STRAIN) AND VARIANT GUIDES (E.G. CA, UK, ETC.) ARE TESTED AGAINST WA1 OR VARIANT TARGET RNA
  - (EX: SARS-COV-2 RNA SUCH AS GENOMIC RNA, IN VITRO TRANSCRIBED RNA, SYNTHETIC RNA, ETC.)
- SIGNAL OF EACH REACTION IS MEASURED OVER 2 HOURS AND SLOPE IS CALCULATED.
- SLOPE RATIO IS CALCULATED BY DIVIDING SLOPE OF GUIDE RNA + TARGET (IE RNP + TARGET RNA) BY THE SLOP OF GUIDE RNA + NO TARGET (I.E. RNP ONLY).
- SLOPE RATIO OF WA1 (WT STRAIN) IS DIVIDED BY SLOPE RATIO OF VARIANT STRAIN TO DETERMINE COMPARATIVE RATIO BETWEEN WT AND VARIANT DETECTION.
  - Y-AXIS IS LOG2 SCALE
  - HIGH (RATIO>1)=GUIDE RNAS THAT DETECT WT WA1 MORE EFFICIENTLY
  - LOW (RATIO<1)=GUIDE RNAS THAT DETECT VARIANT MORE EFFICIENTLY
- NOTE:
  - PREVIOUS GRAPHS SO FAR (THIS DOCUMENT) HAVE SHOWN SLOPE OR SLOPE RATIO
  - WT VS. VARIANT GRAPHS GO A STEP FURTHER AND SHOW COMPARISON OF WT VS. VARIANT SLOPE RATIOS

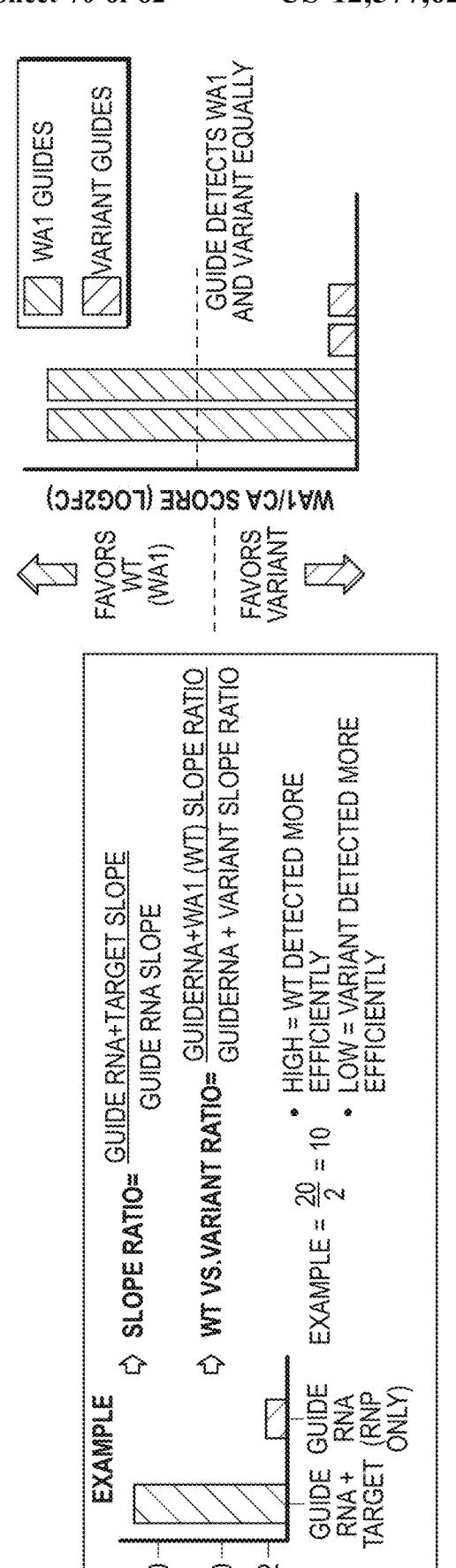

EXAMPLE

⇨ SLOPE RATIO = $\dfrac{\text{GUIDE RNA+TARGET SLOPE}}{\text{GUIDE RNA SLOPE}}$ ⇨ WT VS. VARIANT RATIO = $\dfrac{\text{GUIDERNA+WA1 (WT) SLOPE RATIO}}{\text{GUIDERNA + VARIANT SLOPE RATIO}}$ EXAMPLE = $\dfrac{20}{2}$ = 10

- HIGH = WT DETECTED MORE EFFICIENTLY
- LOW = VARIANT DETECTED MORE EFFICIENTLY

GUIDE GUIDE RNA + TARGET RNA (RNP ONLY)

GRAPH KEY

☐ WA1 GUIDES
☐ VARIANT GUIDES

WA1/CA SCORE (LOG2FC)

FAVORS WT (WA1)

FAVORS VARIANT

GUIDE DETECTS WA1 AND VARIANT EQUALLY

FIG. 51B

Ratio>1 = Guide RNAs That Detect WT WA1 More Efficiently    VARIANT MUTATION DETECTION: CA (B.1.429)
Ratio<1 = Guide RNAs That Detect Variant More Efficiently

FIG. 53A

| Guide | Target | Mutation |
|---|---|---|
| JS_cr033_I4205V_mutA | CA clade 20C | ORF1AB:I4205V_mut |
| JS_cr034_I4205V_wtA | WT | ORF1AB:I4205_wt |
| JS_cr035_D1183Y_mutA | CA clade 20C | ORF1AB:D1183Y_mut |
| JS_cr036_D1183Y_wtA | WT | ORF1AB:D1183_wt |
| JS_cr037_S13I_mutA | CA clade 20C | S13I_mut |
| JS_cr038_S13_wtA | WT | S13_wt |
| JS_cr039_W152C_mutA | CA clade 20C | W152C_mut |
| JS_cr040_W152_wtA | WT | W152_wt |

FIG. 53B

| Guide | Target | Mutation |
|---|---|---|
| JS_cr041_I4205V_mutB | CA clade 20C | ORF1AB:I4205V_mut |
| JS_cr042_I4205V_wtB | WT | ORF1AB:I4205_wt |
| JS_cr043_D1183Y_mutB | CA clade 20C | ORF1AB:D1183Y_mut |
| JS_cr044_D1183Y_wtB | WT | ORF1AB:D1183_wt |
| JS_cr045_S13I_mutB | CA clade 20C | S13I_mut |
| JS_cr046_S13_wtB | WT | S13_wt |
| JS_cr047_W152C_mutB | CA clade 20C | W152C_mut |
| JS_cr048_W152_wtB | WT | W152C_wt |

RAPID FIELD-DEPLOYABLE DETECTION OF SARS-CoV-2 VIRUS

PRIORITY APPLICATIONS

This application claims benefit of priority to the filing date of U.S. Provisional Application Ser. No. 62/991,827 (filed Mar. 19, 2020), 63/057,082 (filed Jul. 27, 2020), 62/706,488 (filed Aug. 19, 2020), 63/081,168 (filed Sep. 21, 2020), and 63/158,297 (filed Mar. 8, 2021) the contents of which applications are specifically incorporated herein by reference in their entireties.

GOVERNMENT FUNDING

This invention was made with government support under AI140465 and AI143401 awarded by the National Institutes of Health. The government has certain rights in the invention.

INCORPORATION BY REFERENCE OF SEQUENCE LISTING

A Sequence Listing is provided herewith as a text file, "2125540.txt" created on Jun. 28, 2021 and having a size of 202,914 bytes. The contents of the text file are incorporated by reference herein in their entirety.

BACKGROUND

Detection of the highly infectious coronavirus, officially called SARS-CoV-2, which causes the disease COVID-19, is critical for targeting locations that need medical assistance. For example, by mid-March 2020 only about 17,000 tests for its detection had been performed at the Center for Disease Control and Prevention (CDC) and US public health laboratories. By September 2020 and even March 2021 the number of COVID-19 infections are still increasing and COVID-19 is not under control in the United States.

Although, asymptomatic individuals make up as many as 42% of confirmed infections (Lavezzo et al., 2020), such asymptomatic individuals can still spread SARS-CoV-2 infection. COVID-19 also spreads before symptoms are obvious. Hence, screening for symptoms by temperature checks have failed to reliably identify infected individuals or contain the pandemic.

In addition, new SARS-CoV-2 variants and mutations are arising, and some are not only more infectious but also may increase the risk of death or serious illness. For example, researchers identified at least fourteen strains of SARS-CoV-2.

Recent modeling of viral dynamics indicates that frequent testing with fast turn-around times for results is required to bring the transmission of COVID-19 under control (Larremore et al., 2020). Detection of viral RNA by PCR is currently the gold standard of SARS-CoV-2 diagnostics, but that method involves laboratory access and days-long turnaround times. It certainly cannot provide timely results at crucial community convergence points, such as airports, nursing homes or schools. There is a critical need to develop new technologies for rapid, easy-to-handle detection of SARS-CoV-2 RNA. Failure to address this need will delay effective containment of the current outbreak and increase chances that person-to-person spread will exponentially increase in the US, claiming lives of thousands of US citizens, especially the elderly and those with pre-existing medical conditions (Young et al. (March 2020); Wang et al. (February 2020): Wu et al. (February 2020)).

Hence, faster and more effective testing procedures are needed for identifying those infected with SARS-CoV-2.

SUMMARY

Described herein are methods, compositions, and devices for detecting and quantifying SARS-CoV-2 that are faster and more readily deployed in the field than currently available methods and devices. In addition, the methods, compositions, and devices can just as readily detect and distinguish mutants and variants of SARS-CoV-2.

The methods described herein can include (a) incubating a sample suspected of containing SARS-CoV-2 RNA with a Cas13 protein, at least one CRISPR guide RNA (crRNA), and a reporter RNA for a period of time sufficient to form one or more reporter RNA cleavage product(s); and (b) detecting level(s) of reporter RNA cleavage product(s) with a detector. In some cases, SARS-CoV-2 RNA and/or reporter RNA cleavage product(s) are not reverse transcribed prior to the detecting step. Such methods are useful for detecting whether the sample contains one or more copies of a SARS-CoV-2 RNA. The methods are also useful for detecting the absence of a SARS-CoV-2 infection. Moreover, the methods and compositions described herein can also readily identify whether a variant or mutant strain of SARS-CoV-2 is present in a sample, and what is the variant or mutation.

In some aspects the disclosure provides methods for quantifying SARS-CoV-2 RNA concentration in a sample suspected of containing SARS-CoV-2 RNA comprising (a) incubating the sample with a Cas13 protein, at least one CRISPR guide RNA (crRNA), and at least one reporter RNA for a period of time sufficient to form one or more reporter RNA cleavage product(s); and (b) analyzing reporter RNA cleavage product(s) quantity or concentration with a detector. In some cases, SARS-CoV-2 RNA and/or reporter RNA cleavage product(s) are not reverse transcribed prior to the detecting step.

A single type of reporter RNA can be used. The reporter RNA can be configured so that upon cleavage, a detectable signal occurs. For example, the reporter RNA can have a fluorophore at one location (e.g., one end) and a quencher at another location (e.g., the other end). In another example, the reporter RNA can have an electrochemical moiety (e.g., ferrocene, or dye), which upon cleavage by a Cas13 protein can provide electron transfer to a redox probe or transducer. In another example, the reporter RNA can have a dye, so that upon cleavage of the reporter RNA the dye is detected by a transducer. In some cases, one end of the reporter RNA can be bonded to a solid surface. For example, a reporter RNA can be configured as a cantilever, which upon cleavage releases a signal. A surface of the assay vessel or the assay material can have a detector for sensing release of the signal. The signal can be or can include a light signal (e.g., fluorescence or a detectable dye), an electronic signal, an electrochemical signal, an electrostatic signal, a steric signal, a van der Waals interaction signal, a hydration signal, a Resonant frequency shift signal, or a combination thereof. In some cases, it may be convenient to attach the reporter RNA to a solid surface. However, in other cases, a signal may be improved by use of an unattached reporter RNA (e.g., not covalently bond to a solid surface).

In some cases, the detector is a fluorescence detector, optionally a short quenched-fluorescent RNA detector, or Total Internal Reflection Fluorescence (TIRF) detector. For example, the fluorescence detector can detect fluorescence from fluorescence dyes such as Alexa Fluor® 430, STAR 520, Brilliant Violet™510, Brilliant Violet™605, Brilliant Violet™610, or a combination thereof.

In some aspects the disclosure provides methods for identifying the presence or absence of SARS-CoV-2 splice variants and/or mutations in SARS-CoV-2 RNA in a sample comprising (a) incubating a mixture comprising a sample suspected of containing SARS-CoV-2 RNA, a Cas13 protein, and at least one CRISPR guide RNA (crRNA) for a period of time sufficient to form one or more RNA cleavage product(s); and (b) detecting any SARS-CoV-2 splice variants and/or mutations in SARS-CoV-2 RNA by analyzing any SARS-CoV-2 RNA cleavage product(s) with a detector. In some cases, the SARS-CoV-2 RNA is not reverse transcribed prior to the detecting step.

In some aspects the disclosure provides methods for monitoring reactivation of SARS-CoV-2 transcription comprising (a) incubating a sample suspected of containing RNA with a Cas13 protein, at least one CRISPR guide RNA (crRNA), and a reporter RNA for a period of time sufficient to form any reporter RNA cleavage product(s); and (b) detecting any amount of reporter RNA cleavage product(s) in the sample with a detector. In some cases, SARS-CoV-2 and/or reporter RNA cleavage product(s) in the sample are not reverse transcribed prior to the incubating or detecting step.

In general, SARS-CoV-2 is detected in a sample when a signal from the reporter RNA cleavage product(s) is distinguishable from a control assay signal. Such a control assay can, for example, contain no SARS-CoV-2 viral RNA.

In some cases, the methods further comprise a step of amplification of SARS-CoV-2 RNA in the sample, or amplification of any SARS-CoV-2 or reporter RNA cleavage products that may form. For example, the RNA can be amplified using an RNA-Dependent RNA polymerase, a SARS-CoV2 polymerase, or an RNA replicase (EC 2.7.7.48) that can replicate single-stranded RNA. Examples of such RNA replicases include the QI replicase, the RNA Polymerase from Rabbit Hemorrhagic Disease Virus (PDB: 1KHV): the RNA Polymerase from Sapporo Virus (PDB: 2CKW); the Hepatitis C RNA Polymerase (PDB: 2D41); the *Neurospora Crassa* RNA Polymerase (PDB: 2J7N); the RNA Polymerase Bimavirus (PDB: 2PGG); the RNA Polymerase from Infectious Bursal Disease Virus (PDB: 2PUS): the RNA Polymerase from Rotavirus (PDB: 2R7T); the RNA Polymerase from Infectious Pancreatic Necrosis Virus (PDB: 2YI8); the RNA Polymerase from Cypoviruses (PDB: 3JA4); the Enterovirus A RNA Polymerase (PDB: 3N6L); the RNA Polymerase from Norwalk Virus (PDB: 3UQS); the RNA Polymerase from Rotavirus A (PDB: 4AU6); the RNA Polymerase from Thosea Assigns Virus (PDB: 4XHA); the Rhinovirus A RNA polymerase (PDB: 1XR7); the Enterovirus C RNA polymerase (PDB: 3OL6): the Foot-and-Mouth Disease Virus RNA polymerase (PDB: 1U09); the Cardiovirus A RNA polymerase (PDB: 4NZ0); the Japanese Encephalitis Virus RNA polymerase (PDB: 4HDH); the Bovine Viral Diarrhea Virus 1 RNA polymerase (PDB: IS48); the Qbeta Virus RNA polymerase (PDB: 3MMP); the Reovirus RNA polymerase (PDB: 1MUK); and the La Crosse Bunyavirus RNA polymerase. In some cases, amplification can be by an RNA-Dependent RNA polymerase, a Qβ replicase, a SARS-CoV2 polymerase, or a combination thereof.

In some cases, the SARS-CoV-2 RNA, SARS-CoV-2 cleavage product(s), and/or the reporter RNA cleavage product(s) are not amplified.

While a single guide RNA (crRNA) can be used in the methods and compositions described herein, the sensitivity and/or the limits of detection of the methods and compositions can be improved by using more than one crRNA. The one or more crRNAs employed can have a sequence that is complementary to a portion of a SARS-CoV-2 RNA. The SARS-CoV-2 RNA can be a wild type, variant, or mutant SARS-CoV-2 RNA. In some cases, at least two CRISPR guide RNA (crRNA) are used, or at least three, or at least eight CRISPR guide RNAs (crRNAs).

The crRNA forms a complex with the Cas13 protein and guides the complex to the SARS-COV-2 RNA. Once the crRNA:Cas13 complex is activated by contact with the SARS-COV-2 RNA, the Cas13 protein can cleave RNA somewhat indiscriminately, thereby releasing the signal that is masked or quenched in the reporter RNA. One or more of the Cas13 proteins used can be a Cas13a or Cas13b protein. In some cases, the Cas13 protein(s) employed have one or more of the protein sequences with at least 95% sequence identity to any of SEQ ID NO:36-48. For example, a Cas13 protein with a sequence that has at least 95% sequence identity to SEQ ID NO:43 can be used, wherein the Cas13 protein has a lysine at position 436. Such a Cas13 protein, for example, can have SEQ ID NO:43.

In some cases, the at least one SARS-COV-2 CRISPR guide RNA (crRNA) has a sequence with at least 95% sequence identity to any of SEQ ID NOs: 1-35 or 58-147. In some cases, at least one SARS-COV-2 CRISPR guide RNA (crRNA) has a sequence such as any of SEQ ID NOs: 1-35 or in some cases the crRNA(s) can include those with SEQ ID NO:1-15 or 35. In some cases, at least one SARS-COV-2 CRISPR guide RNA (crRNA) has a sequence such as any of SEQ ID NOs: 27-35, or a combination thereof. In some cases, at least one SARS-COV-2 CRISPR guide RNA (crRNA) has a sequence such as any of SEQ ID NOs: 58-147, or any combination thereof. In some cases, the sample is incubated with at least two, or at least three, or at least four, or at least five, or at least six, or at least seven, or at least eight, or at least nine, or at least nine, or at least ten, or more crRNAs.

The amount of reporter RNA cleavage product detected is directly correlated with the amount of the SARS-CoV-2 RNA. In some cases, the SARS-CoV-2 RNA cleavage product concentration can be quantified or determined by use of a standard curve of the reporter RNA cleavage product(s).

The sample suspected of containing RNA can, for example, include saliva, sputum, mucus, nasopharyngeal materials, blood, serum, plasma, urine, aspirate, biopsy tissue, or a combination thereof. In some cases, the methods described herein can include depleting a portion of the sample prior to other step(s) or inhibiting a nuclease in the sample prior to the other step(s). For example, the sample can be depleted of protein, enzymes, lipids, nucleic acids, or a combination thereof. In some cases, the depleted portion of the sample is a human nucleic acid portion. However, RNA extraction of the sample is preferably not performed.

In some cases, the methods can include removing ribonuclease(s) (RNase) from the sample. In some cases, the RNase is removed from the sample using an RNase inhibitor and/or heat.

In some cases, the Cas13 protein and/or the crRNA is lyophilized prior to incubation with the sample. In some cases, the Cas13 protein, the crRNA, and/or the reporter RNA is lyophilized prior to incubation with the sample.

In some cases, the methods can include treating SARS-CoV-2 in subjects where SARS-CoV-2 is detected or where monitored SARS-CoV-2 levels have increased. Such a method can include administration of a therapeutic agent to a patient with detectable SARS-CoV-2. Such treatment can involve antiviral therapy, antiretroviral therapy (ART), breathing support (oxygen, endotracheal intubation), steroids to reduce inflammation, steroids to reduce lung swelling, blood plasma transfusions, or a combination thereof. For example, patients infected with SARS-CoV-2 can be administered dexamethasone, Remdesivir (Veklury), bamlanivimab, casirivimab, imdevimab, or a combination thereof. The bamlanivimab, casirivimab, and imdevimab therapeutics are available under FDA EUAs for patients at high risk of disease progression and severe illness. Some patients can also benefit from receiving anti-SARS-CoV-2 monoclonal antibodies.

Compositions are described herein that can include one or more CRISPR guide RNA(s) comprising a sequence comprising at least 95% sequence identity to any one of SEQ ID NO:1-35, 58-146, or 147. The compositions can include at least one Cas13a or Cas13b protein. Such Cas13 proteins can be complexed with any of the CRISPR guide RNAs, thereby forming a ribonucleoprotein complex. For example, any of the Cas13 proteins described herein can used, such as any of those with sequences having at least 95% sequence identity to any of SEQ ID NO:36-48.

In addition, a modified Cas13 protein is described herein that has increased in vivo endonuclease activity compared to a corresponding unmodified Cas13 protein, wherein the modified Cas13 protein has a lysine (K) at a position corresponding to position 436 of a wildtype Cas13 protein.

Also described herein are kits that can include a package containing at least one Cas13 protein, at least one SARS-CoV-2-specific CRISPR guide RNA (crRNA), at least one reporter RNA, and instructions for detecting and/or quantifying SARS-CoV-2 RNA in a sample.

A system is also described herein for detecting and/or quantifying SARS-CoV-2 RNA in a sample, where the system can include:

a signal generating system to excite the sample using a signal of a first frequency;

a camera system to detect fluorescence in the sample; and processing circuitry to detect SARS-CoV-2 RNA in the sample based on the fluorescence.

For example a fluorescence imaging system is described herein that can include:

a system housing;

an excitation source configured to generate excitation illumination within the system housing;

a sample cartridge having one or more cartridge chambers, the one or more cartridge chambers configured to retain one or more samples therein; a cartridge socket configured to receive the sample cartridge;

wherein reception of the sample cartridge by the cartridge socket orients the one or more cartridge chambers to an excitation orientation and an observation orientation:

in the excitation orientation the cartridge chambers are aligned with the excitation illumination of the excitation source: and in the observation orientation the cartridge chambers and fluorescence from the cartridge chambers are directed toward an optical sensor.

In an example, the observation orientation scattered illumination from the sample cartridge is misaligned with the optical sensor.

Devices for detecting SARS-CoV-2 viral RNA are also described in more detail herein.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. Furthermore, components can be shown as transparent in certain views for clarity of illustration only and not to indicate that the illustrated component is necessarily transparent.

FIG. 1A-1B illustrate use of CRISPR-Cas13 and CRISPR guide RNAs (crRNAs) to detect target RNA. FIG. 1A is a schematic diagram illustrating CRISPR-Cas13 detection of RNA using a CRISPR-Cas13 protein that binds CRISPR guide RNAs (crRNA) to form a ribonucleoprotein (RNP) complex. The crRNA targets or guides the CRISPR-Cas13 protein to target RNA sequences (e.g., SARS-CoV-2 RNA), where the Cas13 protein is activated to cleave RNA, including the reporter RNA. FIG. 1B is a similar schematic diagram further illustrating a Cas13a:crRNA ribonucleoprotein (RNP) complex binding of target RNA, resulting in activation of the Cas13a nuclease (denoted by scissors). Upon target recognition and RNP activation, Cas13a indiscriminately cleaves a quenched-fluorophore RNA reporter, allowing for fluorescence detection as a proxy for Cas13a activation and the presence of target RNA.

FIG. 4A graphically illustrates detection of SARS-CoV-2 using guide crRNA #1 (with SEQ ID NO:2). As illustrated, the fluorescent signal increased as the amount of SARS-CoV-2 RNA in the sample was increased. Results are reported as "background corrected fluorescence" where control reactions are run and any background fluorescence is computationally subtracted from the results. FIG. 4B shows a similar graph, with crRNA #2, an independent crRNA. Collectively, these data show that these crRNAs can detect virus in the range of $10^6$-$10^7$ copies, which is within the range of average viral loads during the first week of symptoms viral loads on average have been about $10^6$ copies of virus with viral loads as high as $7 \times 10^8$ copies of virus. The two different crRNAs can independently detect the presence of SARS-CoV-2.

FIG. 6A illustrates that by using several crRNAs (e.g., three different crRNAs), the methods described herein can detect as little as 700 copies of virus, or even fewer copies of virus. Hence, multiplexing of guide RNAs can improve the sensitivity and detection limits of the methods. FIG. 6B graphically illustrates wildtype (WT) LbuCas13a detection of differing concentrations of activators, measured by collateral cleavage of RNase Alert. FIG. 6C graphically illustrates LbuCas13a E436K variant detection of differing concentrations of activators, measured by collateral cleavage of RNase Alert. FIG. 6D graphically illustrates normalized observed rates of wild type vs. the modified E436K Cas13a at different concentrations of activators.

FIG. 7A illustrates the limit of detection using a reporter RNA having the STAR 520 fluorophore, when tested using an iPhone 8, a 530-nm laser for illumination, and a 620/60 interference filter (Chroma Technology: ET620/20m). FIG. 7B illustrates the limit of detection using a reporter RNA having the Alexa Fluor® 430, when tested using an iPhone 8, a 405-nm laser for illumination, and an interference filter {Chroma Technology AT535/40m).

FIG. 9A graphically illustrates simulations of 10 nM Cas13a activity and various RNA Alert concentrations. FIG. 9B graphically illustrates simulations of 10 nM Cas13a activity and various RNA Alert concentrations. FIG. 9C graphically illustrates simulations of 1 nM Cas13a activity and various RNA Alert concentrations. FIG. 9D graphically illustrates simulations of 1 nM Cas13a activity and various RNA Alert concentrations. In each of the FIG. 9A-9D graphs, the 500 nM plot is shown at the top, with the 400 nM just below, with the 300 nM just below the 400 nM plot, with the 200 nM just below the 300 nM, and with the 100 nM at the bottom. FIG. 9E graphically illustrates the time course of CRISPR-Cas13a-crRNA assays as the SARS-CoV-2 RNA was detected in nasopharyngeal swabs from three infected patients (positive swabs 1-3) compared to the same assay performed on a non-infected patient (negative swab #1). The fluorescence signal was detected over time for positive swab #1 sample (top plot), for positive swab #2 sample (second from top plot), for positive swab #3 sample (middle plot), for positive swab #1 sample (top plot), negative swab #1 (second plot from bottom), RNP control containing only RNP with crR-NAs #2 and #4 (bottom plot). FIG. 9F graphically illustrates the fluorescence at an endpoint of 30 minutes for CRISPR-Cas13a RNP assays of samples from three infected patients (positive swabs 1-3) compared to the same assay performed on a non-infected patient (negative swab #1). The signal from a control containing CRISPR-Cas13a, crRNA and RNA Alert reagents without sample (RNP only) is also shown.

FIG. 15A shows signals from assay mixtures where the alphacoronavirus HCoV-NL63 RNA was subjected to the single step lysis procedure (heat at 85° C. for 5 min. with 1% Tween-20). Different dilutions of the HCoV-NL63 RNA were evaluated with a crRNA specific for HCoV-NL63 RNA. The bottom plot shows signal from a control assay mixture without alphacoronavirus HCoV-NL63 RNA. FIG. 15B shows signals from assay mixtures with the same dilutions of HCoV-NL63 RNA after RNA extraction. As illustrated, the single step lysis procedure was sufficient and significantly better than traditional extraction methods (where RNA is lost to the extraction protocol).

FIG. 16A shows the reaction mixture without RNA extraction of the HCoV-NL63 RNA samples. FIG. 16B shows the reaction mixture with RNA extraction of the HCoV-NL63 RNA samples.

Signal differences over control/baseline definitively identify that the target RNA is present. As shown, no signal above baseline are observed with and without RNA extraction, and the presence of a non-target crRNA does not significantly increase background. Hence, signals observed when using crRNA guides designed to target a specific RNA (as for FIG. 15) do detect the specific RNA target if that target is present in the reaction mixture. The crRNA designed to detect the target RNA therefore determines the specificity of the assay mixture.

Figure 17:
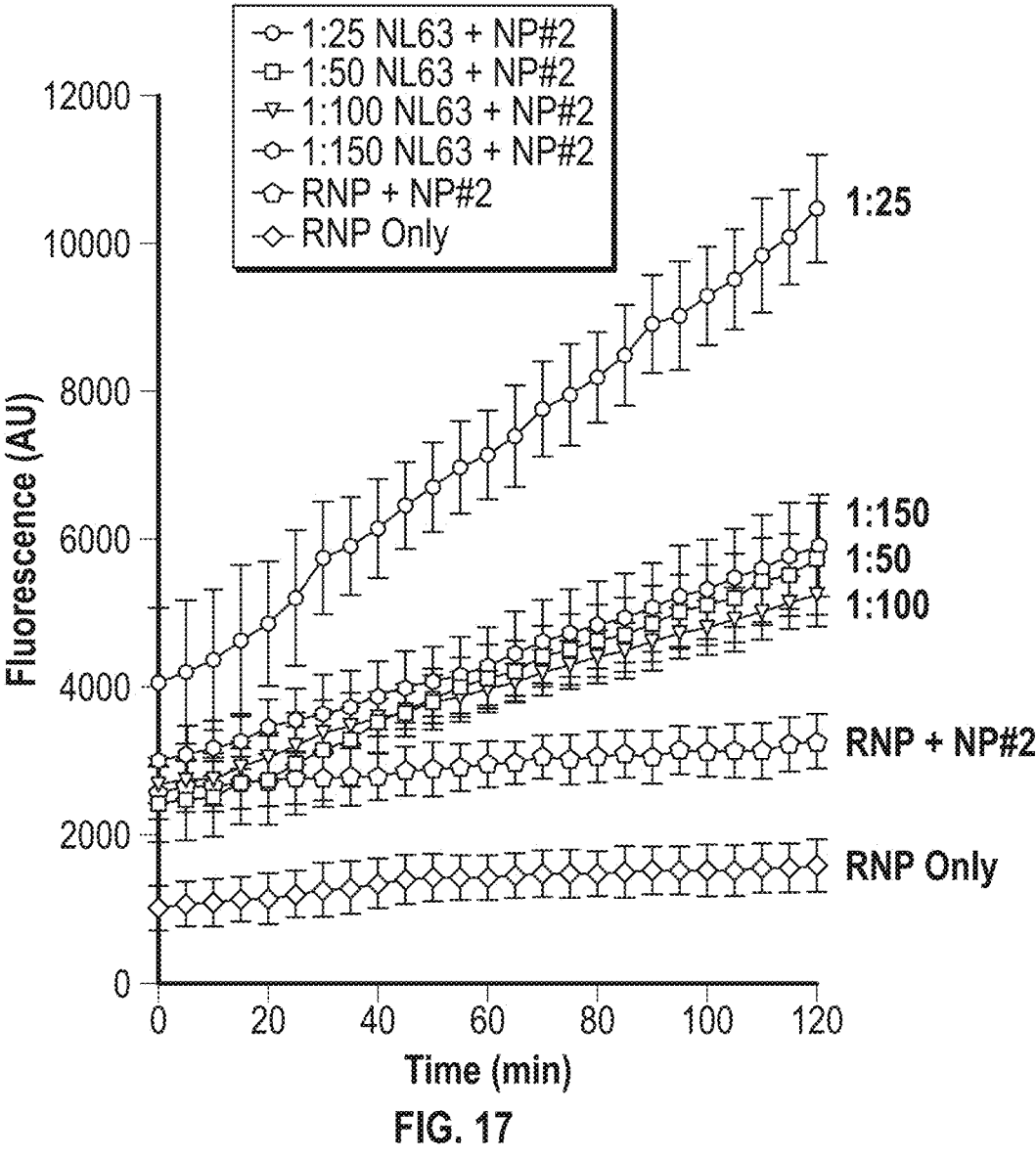

FIG. 17 graphically illustrates that Cas13a can detect HCoV-NL63 viral RNA even with the background of a nasopharyngeal (NP) swab materials when using only 1% Tween-20 and heat for lysis. The plots contained 1:25, 1:50, 1:100, 1:150 dilutions of the HCoV-NL63 viral RNA with the nasopharyngeal (NP) swab materials. The top plot shows the signal from the least diluted (1:25), most concentrated, HCoV-NL63 viral RNA and the other plots were for increasing dilutions of the HCoV-NL63 viral RNA. The lowest plot shows the signal from an RNP only control reaction mixture.

Figures 18A, 18B:
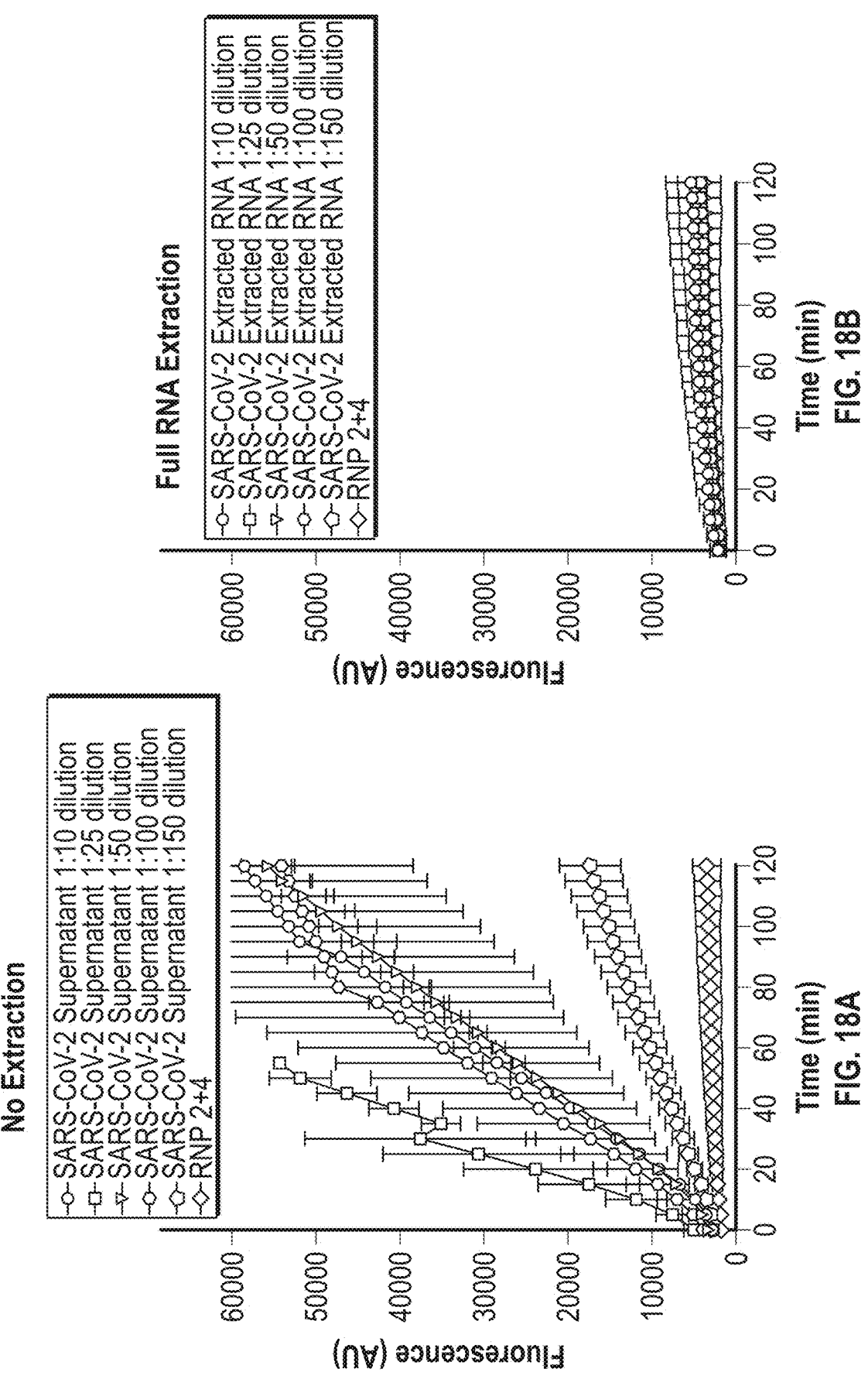

FIG. 18A-18B graphically illustrate that traditional RNA extraction is not needed for detection of SARS-CoV-2 RNA. FIG. 18A graphically illustrates detection of SARS-CoV-2 RNA at different dilutions (1:10, 1:25, 1:50, 1:100 and 1:150) is efficiently detected when the single-step lysis is used (heat at 85° C. for 5 min. with 1% Tween-20). FIG. 18B shows that RNA extraction of SARS-CoV-2 RNA does not aide detection, and actually reduces the available target RNA.

FIG. 19A-19B show that adjusting pH towards 6-carboxyfluorescein (FAM) fluorophore pH preferences improves detection. FIG. 19A shows signals detected from increasing amounts of target sample RNA when the assay is performed at pH 6.8. FIG. 19B shows signals detected from increasing amounts of target sample RNA when the assay is performed at pH 7.2. As illustrated, the slope of the signal increased when pH 7.2 was used. This may be most evident for the more concentrated target (1 pM), though the signal was readily detected with concentrations of target samples as low as 100 fM.

Figures 20A, 20B, 20C:
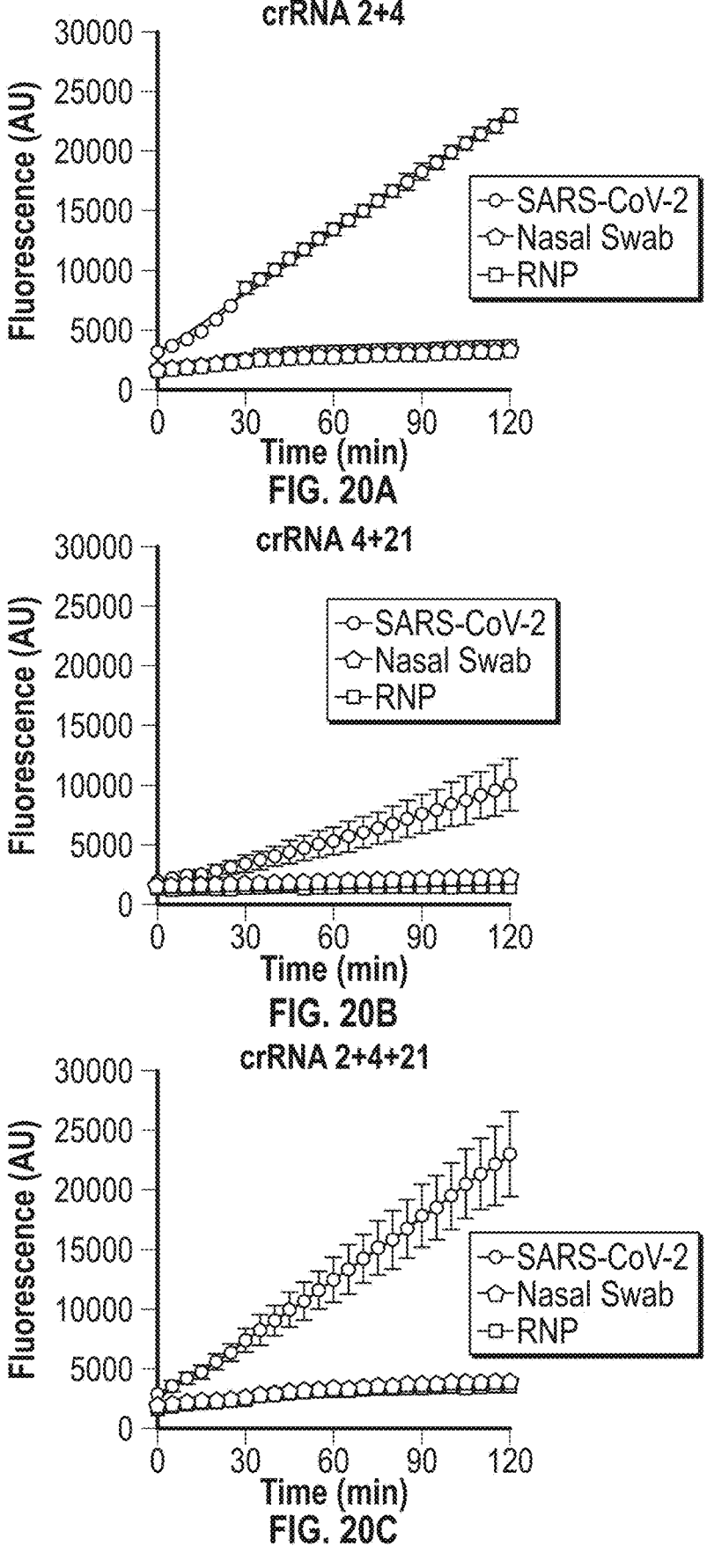

FIG. 20A-20C graphically illustrate that multiplexing crRNA guides increases target detection and that crRNA guides 2+4+21 provide robust detection of SARS-CoV-2 full length virus. FIG. 20A graphically illustrates detection of SARS-CoV-2 full length virus with the combination of crRNA-2 and crRNA-4. FIG. 20B graphically illustrates detection of SARS-CoV-2 full length virus with the combination of crRNA-4 and crRNA-21. FIG. 20C graphically illustrates detection of SARS-CoV-2 full length virus with the combination of crRNA-2, crRNA-4, and crRNA-21.

Figure 21:
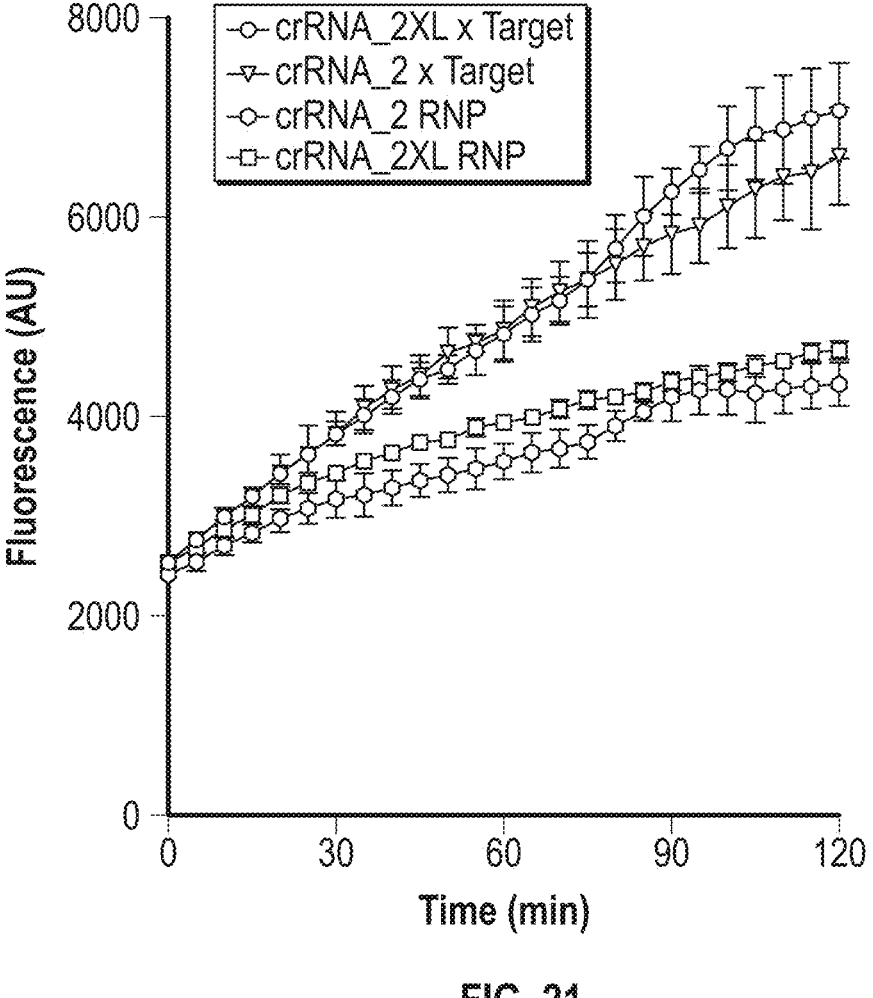

FIG. 21 shows that the sizes of the 30-nucleotide guide (crRNA_2) and 32 nucleotide guide (crRNA_2XL) stem lengths do not influence detection. The top two plots show the signals from reaction mixtures containing target RNAs while the bottom two plots show the signals from reaction mixtures that did not contain target RNAs (RNP only).

Figure 22B:
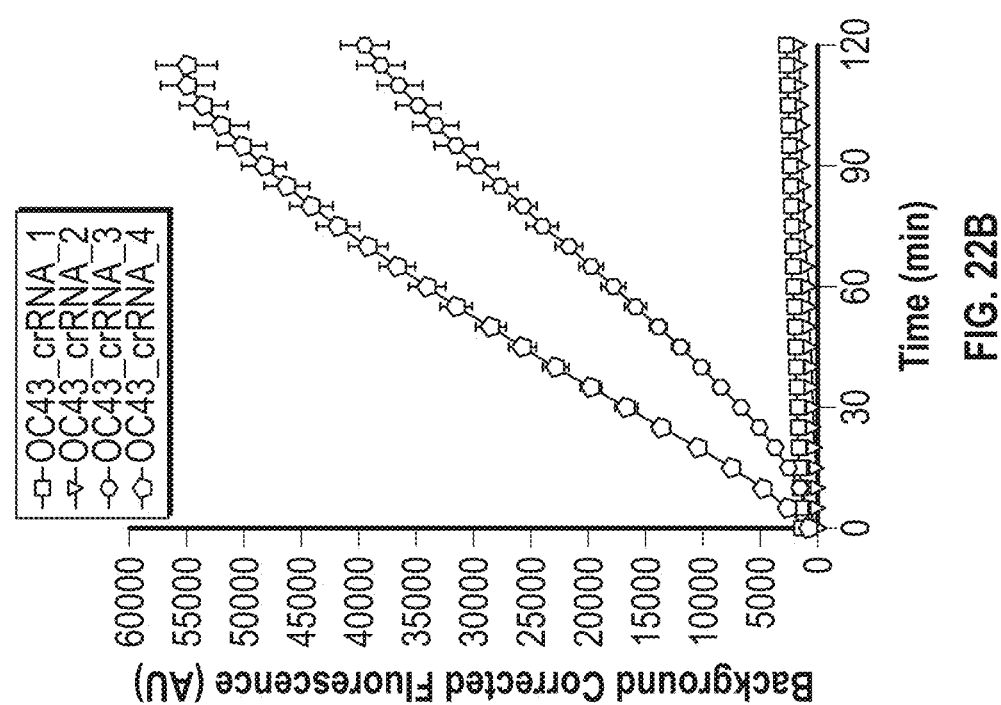
Figure 22A:
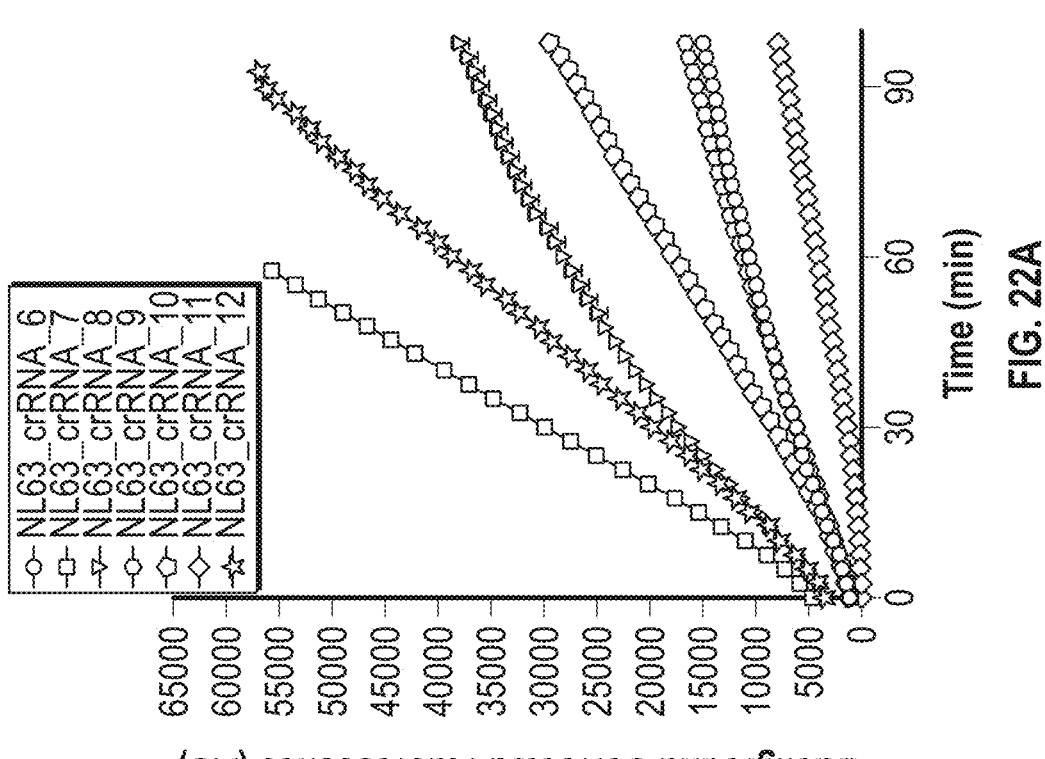

FIG. 22A-22B graphically illustrate that different crRNAs can efficiently detect different target RNAs. FIG. 22A shows detection of NL63 coronavirus target RNA using different NL63 crRNAs. FIG. 22B shows detection of OC43 coronavirus RNA using different OC43 crRNAs. As illustrated, some crRNAs provide better signals than others.

Figure 23:
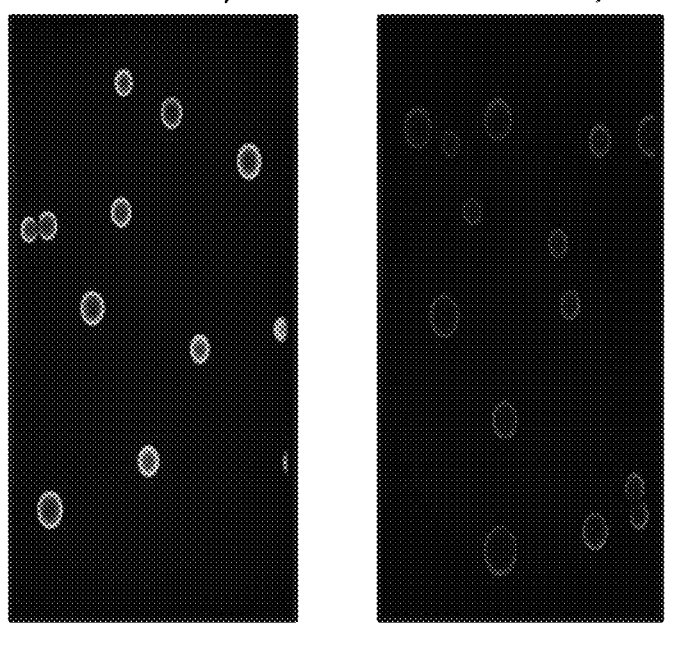

FIG. 23 shows bead-based concentration and membrane-based separation of cleaved probe in the presence of target RNA (left) compared to no target RNA (right).

Figure 24:
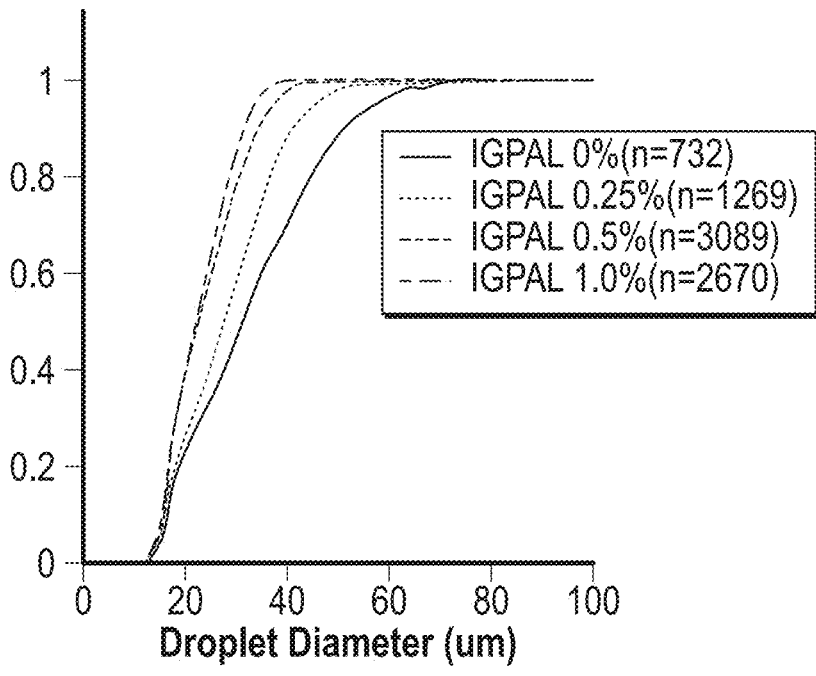

FIG. 24 graphically illustrates the narrow size ranges of polydisperse droplets that can be generated using HFE 7500 oil and water-soluble surfactant IGEPAL. The position of IGPAL concentrations in the key inversely correlates with the droplet size obtained. For example, the lowest plot was obtained when using 0% IGPAL, while the high plot was obtained when using 1.0% IGPAL.

Figure 25:
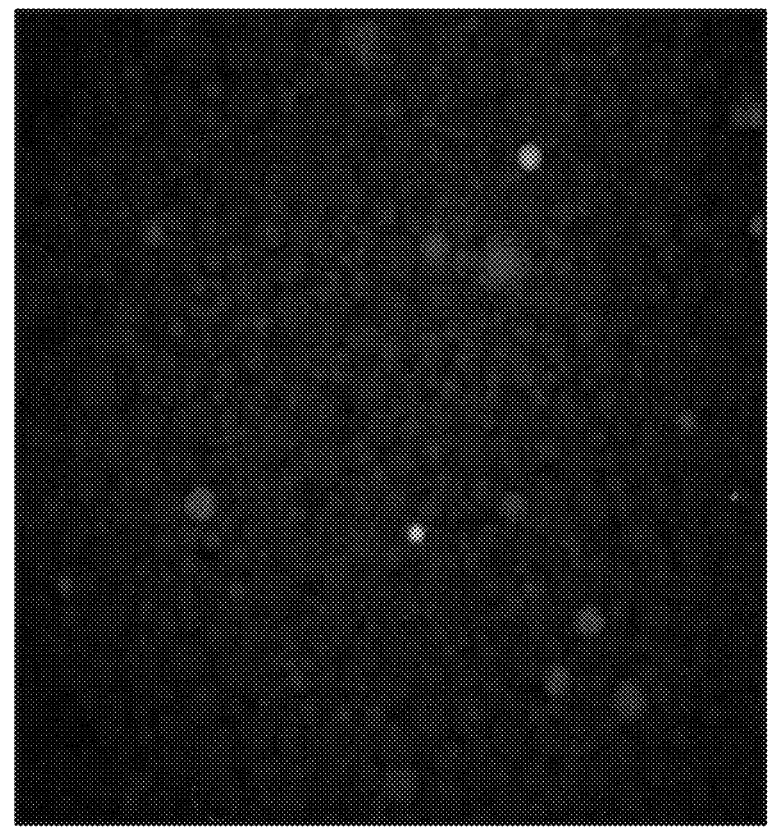

FIG. 25 shows that polydisperse droplet reactions can be used to detect viral genomes.

FIG. 26 is a schematic diagram illustrating the components for direct detection of target RNA, which include one or more crRNA guide RNAs that can bind to a target RNA, a Cas13a nuclease, and a reporter RNA. The Cas13a nuclease and the crRNA form a ribonucleoprotein (RNP) complex that can recognize the target RNA. The reporter RNA has a sequence that is unrelated to the target RNA but does have a fluorophore and a moiety that quenches the fluorescent signal of fluorophore until it is separated from the quencher moiety.

FIG. 27 is a schematic diagram illustrating direct detection of target RNA by cleavage of the reporter RNA via the Cas13a-crRNA complex. Upon recognition of the target RNA by the crRNA, the Cas13a nuclease cleaves the reporter RNA, thereby releasing a fluorescent signal that can be detected using a fluorescent detector.

Figure 28:
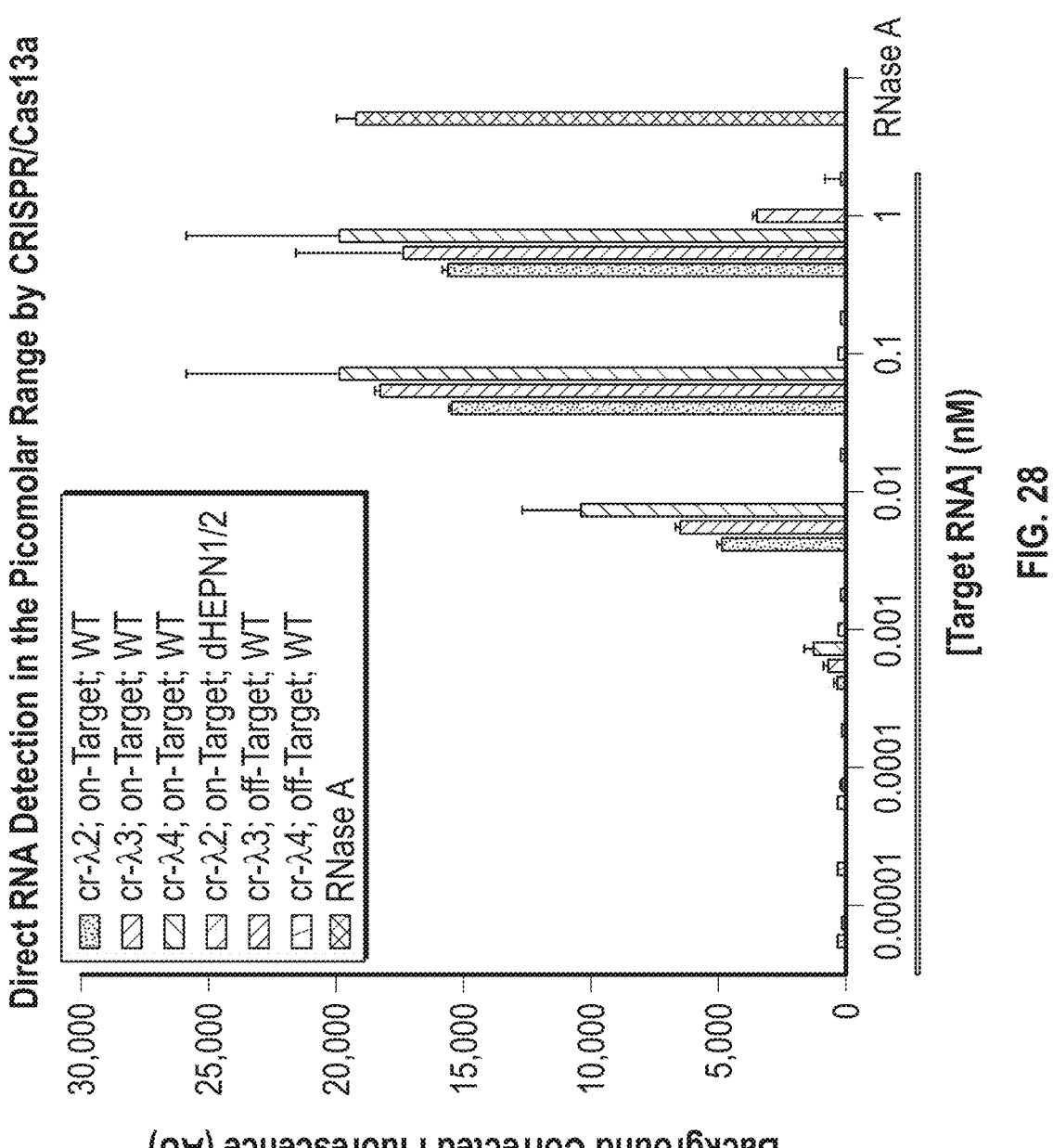

FIG. 28 illustrates that target RNAs can be detected at picomolar concentrations using the CRISPR/Cas3a methods.

Figure 29:
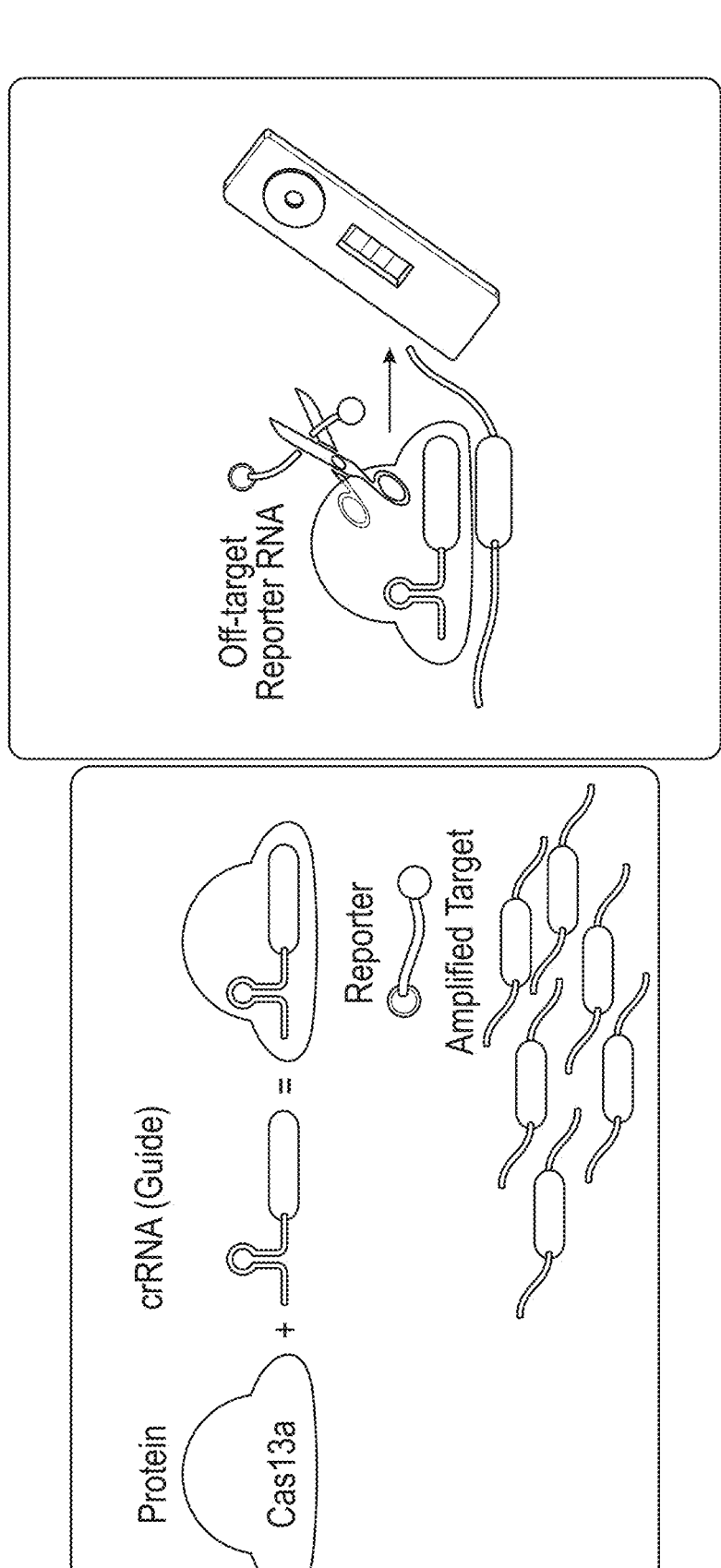

FIG. 29 schematically illustrates an amplification-based SHERLOCK method of nucleic acid detection. This method involves target (sample) RNA amplification prior to being targeted by the Cas13a-crRNA RNP complex. Detection can occur in a lateral flow strip colorometric device. As illustrated in experiments described herein, amplification of sample RNA is not needed—SARS-CoV-2 can be detected and quantified without an amplification step.

FIG. 30 is a schematic diagram illustrating direct detection of target RNA by mobile devices such as mobile phones. When a Cas13a-crRNA guide complex recognizes target RNA the Cas13a nuclease cleaves the reporter RNA, thereby releasing a fluorescent signal that is detected using a mobile device fluorescent detector (e.g., a mobile phone).

Figures 31A, 31B:
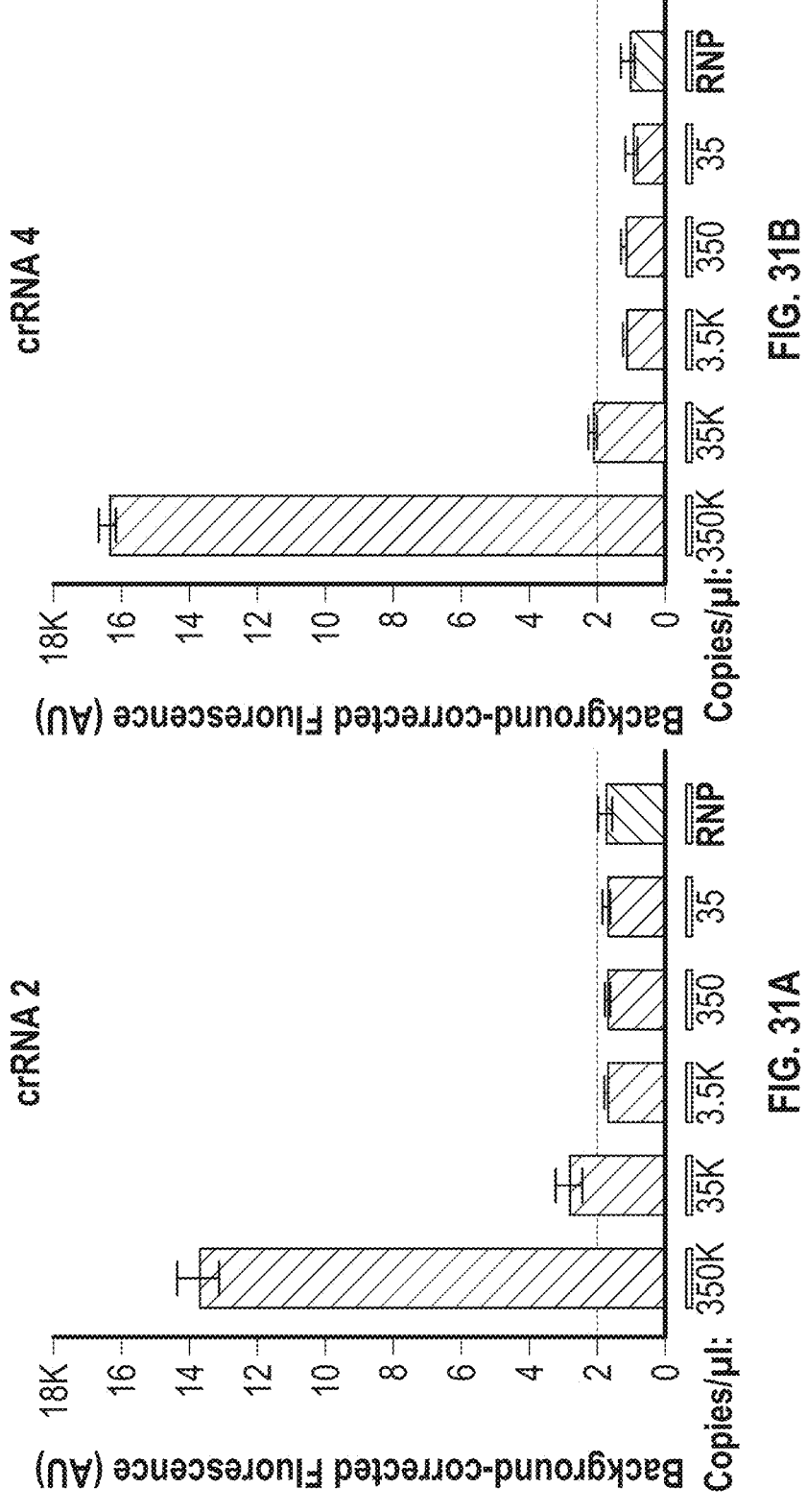

FIG. 31A-31B graphically illustrate that target RNA detection sensitivity is comparatively low when only one crRNA guide is used. FIG. 31A graphically illustrates detection of different amounts of target RNA (copies/µl) using only crRNA 2 (SEQ ID NO:2). FIG. 31B graphically illustrates detection of different amounts of target RNA (copies/µl) using only crRNA 4 (SEQ ID NO:4). When using single guide RNAs crRNA 2 or crRNA 4, the assay mixtures had to have at least 35,000 to 350,000 target RNA copies per microliter to obtain signals above background.

Figure 32:
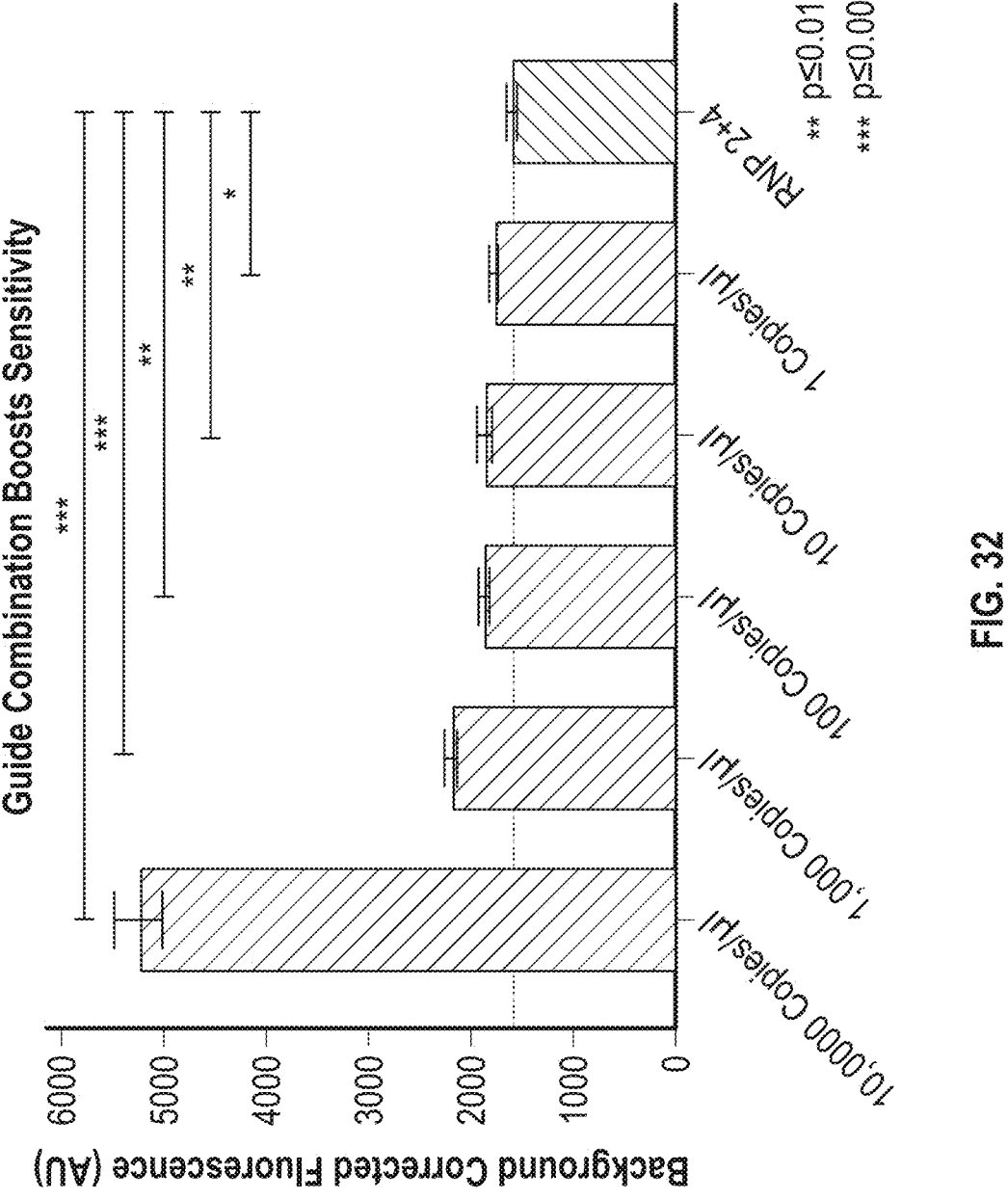

FIG. 32 graphically illustrate that target RNA detection sensitivity is improved when at least two guide RNAs are included in the assay mixtures. As shown, when guide RNAs crRNA 2 and crRNA 4 ar both used, assay mixtures with 1-10,000 target RNA copies per microliter provide detectable signals above background. Note that 1 copy/ul was significantly detected over background (*).

Figures 33B, 33C:
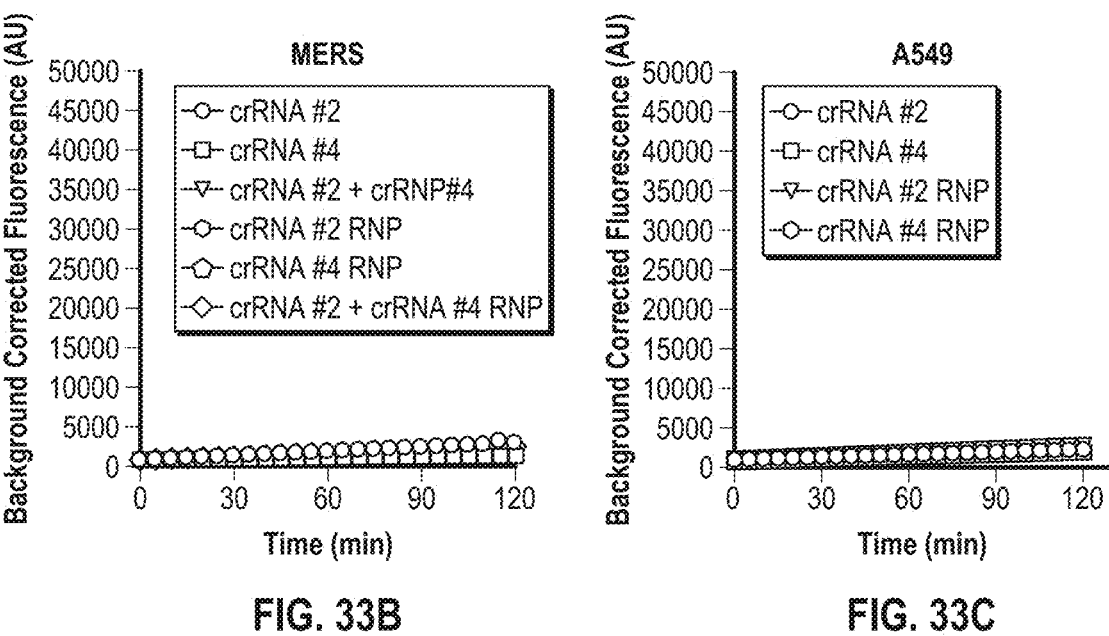

FIG. 33A-33C graphically illustrate that not only target RNA detection sensitivity is improved when at least two guide RNAs are included in the assay mixtures, but the Cas13a-crRNA assays retain excellent specificity for target RNAs even with more than one crRNA in the assay mixture. FIG. 33A graphically illustrates the signal from SARS-CoV-2 RNA assay mixtures containing both guide RNAs crRNA 2 and crRNA 4 compared to the signals when assay mixtures contain just one of guide RNA crRNA 2 or crRNA. FIG. 33B illustrates that little or no signal is observed when assay mixtures containing MERS viral RNA is present when using crRNA 2 and/or crRNA 4 guide RNAs designed to detect SARS-CoV-2 viral RNA. FIG. 33C illustrates that little or no signal is observed when assay mixtures contain A549 RNA from human lung epithelial cells with the crRNA 2 and/or crRNA 4 guide RNAs designed to detect SARS-CoV-2. Hence, the crRNA 2 and crRNA 4 guide RNAs are specific for SARS-CoV-2.

Figures 34A, 34B:
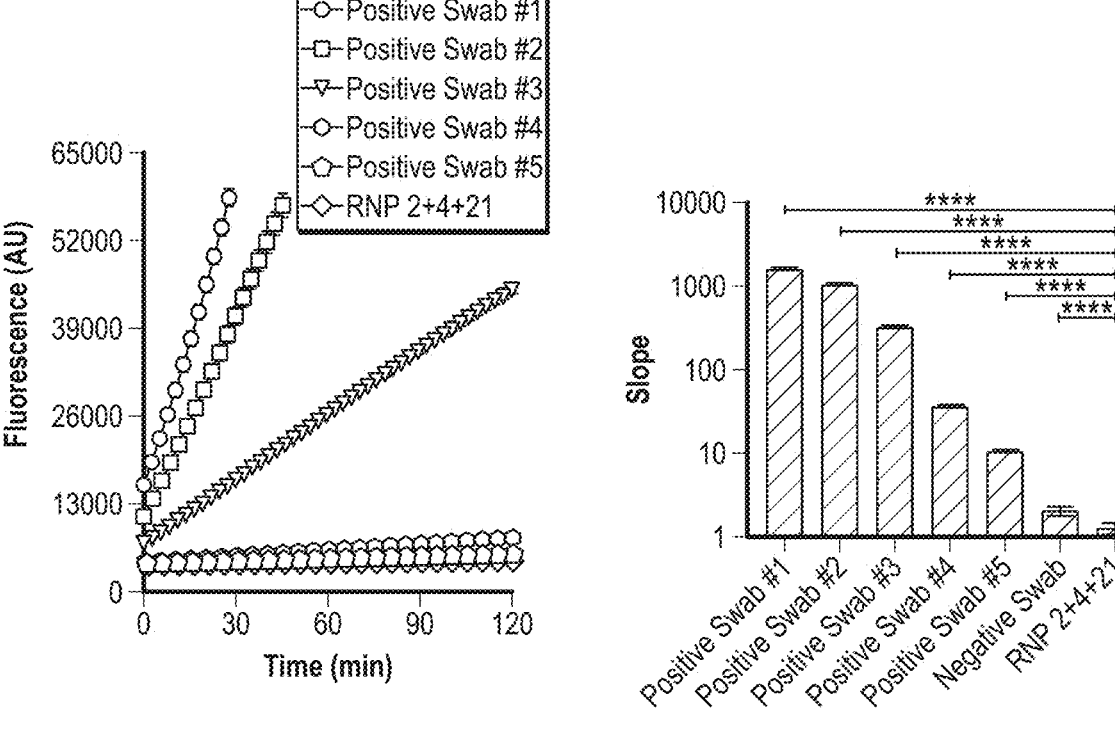

FIG. 34A-34B illustrate assay results for a combination of crRNA 2, crRNA 4, and crRNA 21 using patient swabs known to be positive for SARS-CoV-2. The RNP 2+4+21 is a negative control assay without sample or target RNA. FIG. 34A shows the signals observed over time for positive patient swabs #1 to #5. FIG. 34B shows the slope of the signal over time for assays of positive patient swabs #1 to #5 (data from FIG. 34A). As illustrated, the cas13-crRNA assays can detect even patient samples containing small amounts of SARS-CoV-2 RNA.

Figure 35:
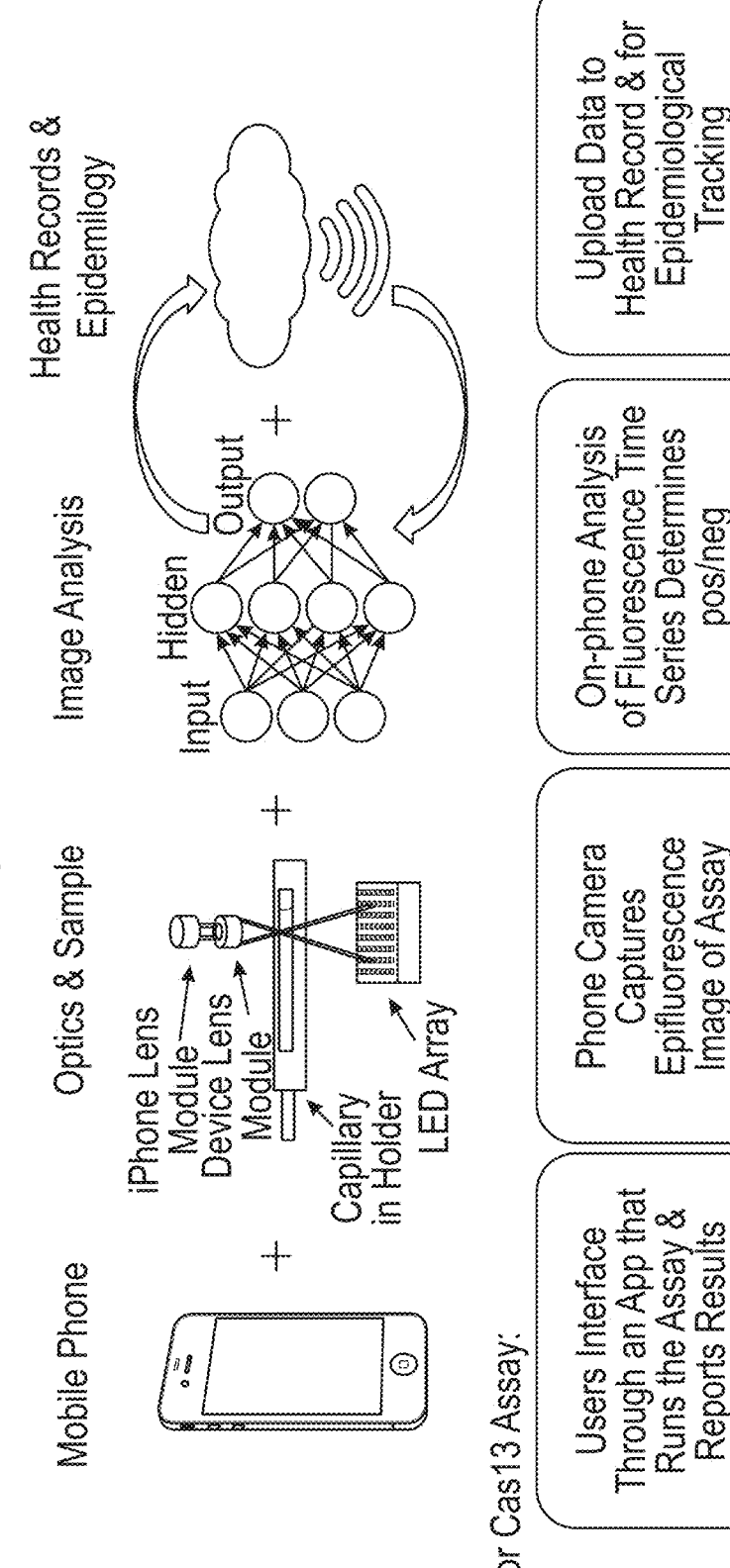

FIG. 35 illustrates use of a mobile device to detect and report results of SARS-CoV-2 testing using the Cas13-crRNA methods.

Figure 36:
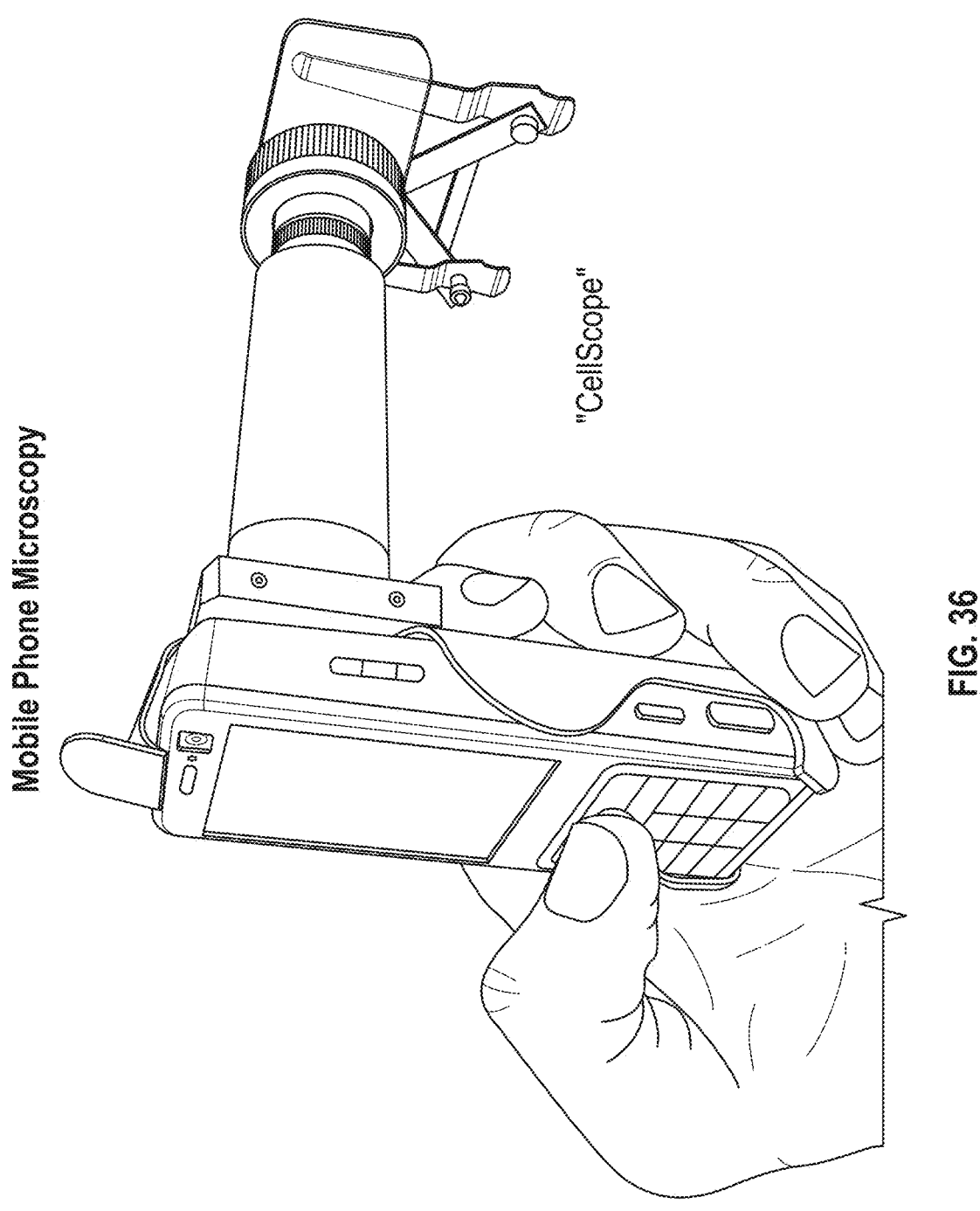

FIG. 36 shows an image of a CellScope device that can be used to detect assay results, including fluorescent signals from the Cas13-crRNA methods.

Figure 37:
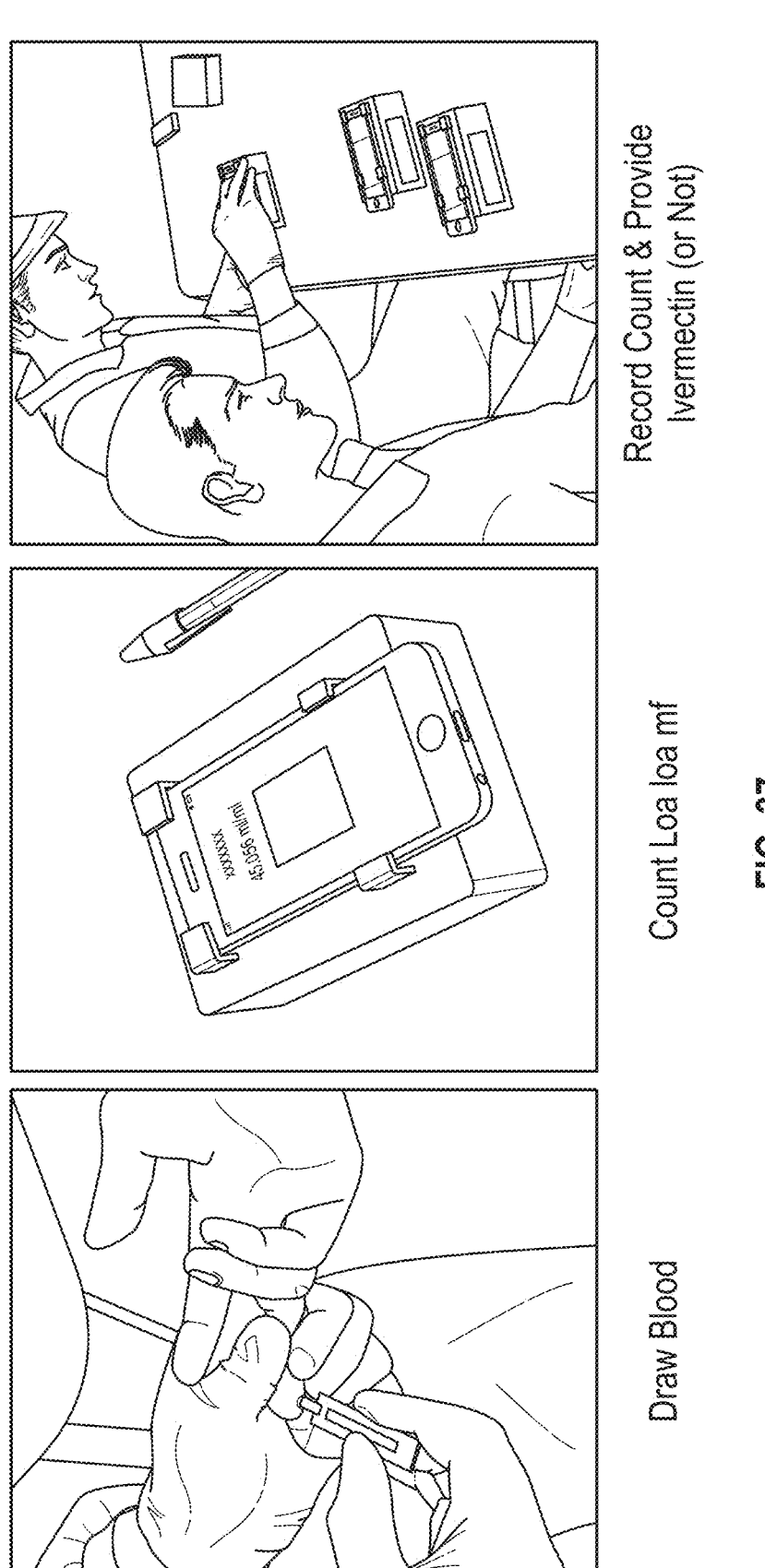

FIG. 37 illustrates detection of River Blindness using a mobile device.

Figure 38B:
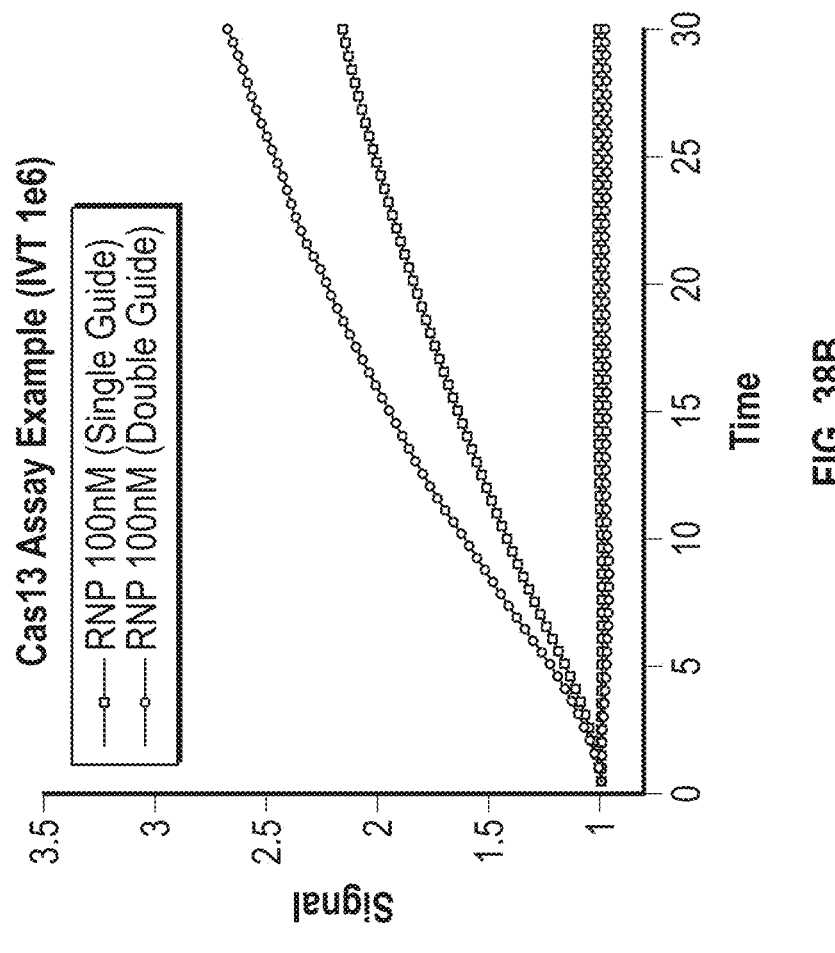
Figure 38A:
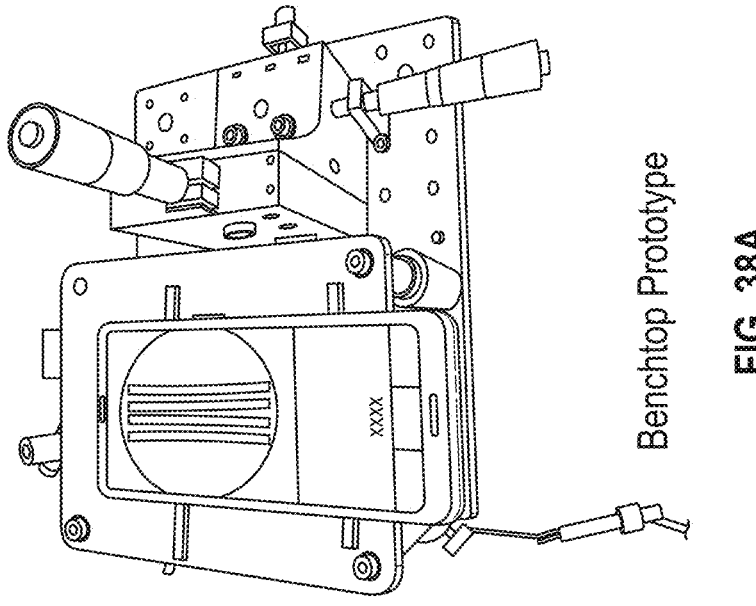

FIG. 38A-38B illustrate detection of $1 \times 10^6$ copies of in vitro transcribed target RNA using the methods described herein with a benchtop prototype with a mobile device. FIG. 38A is an image of a benchtop prototype with the mobile phone. FIG. 38B graphically illustrates signals over time for $1 \times 10^6$ copies of in vitro transcribed target RNA using either one or two guide crRNAs detected with the devices shown in FIG. 38A. As illustrated use of two crRNAs increases the signal.

Figures 39A, 39B:
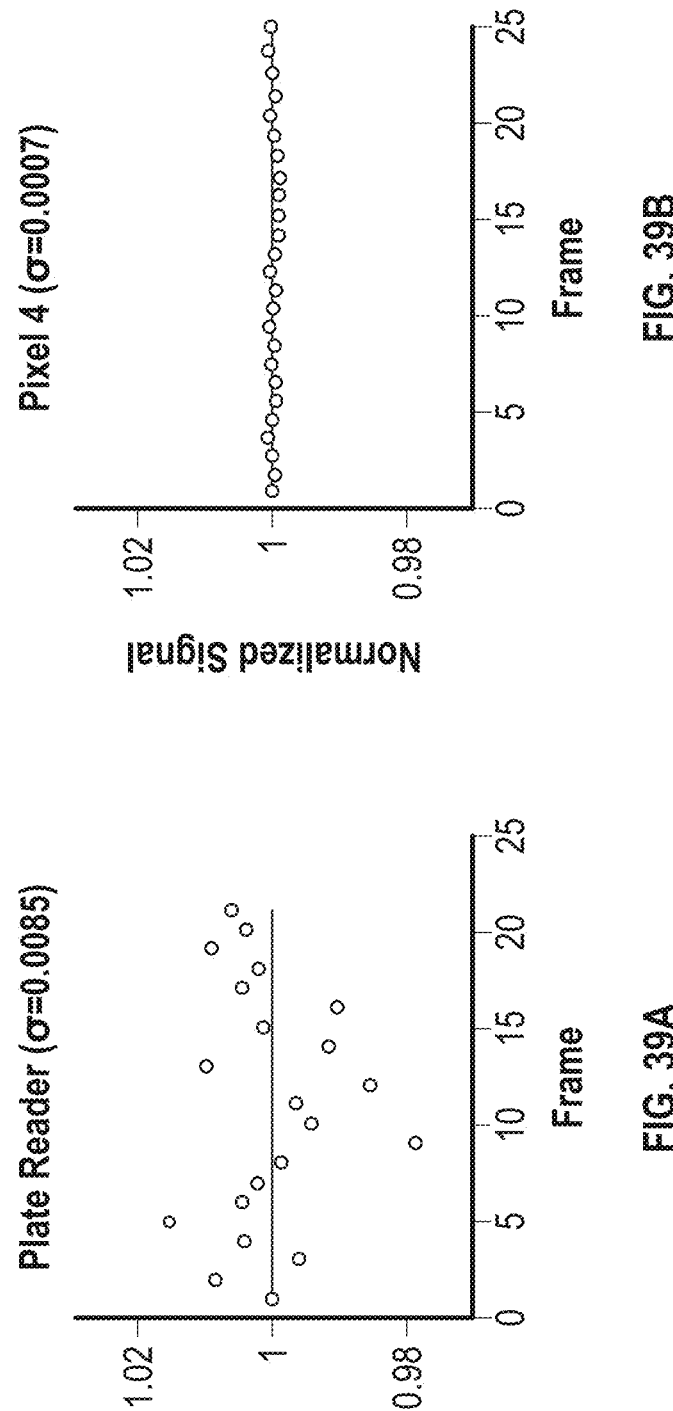

FIG. 39A-39B illustrate measurement sensitivity and noise for an assay where the signal was detected by using a plate reader or a mobile device that can detect pixels. FIG. 39A shows normalized signals for different image frames that were detected using the plate reader. FIG. 39B illustrates the normalized signal detected by a mobile device that detects pixels—as shown the signal does not vary significantly from one frame to another.

Figure 40:
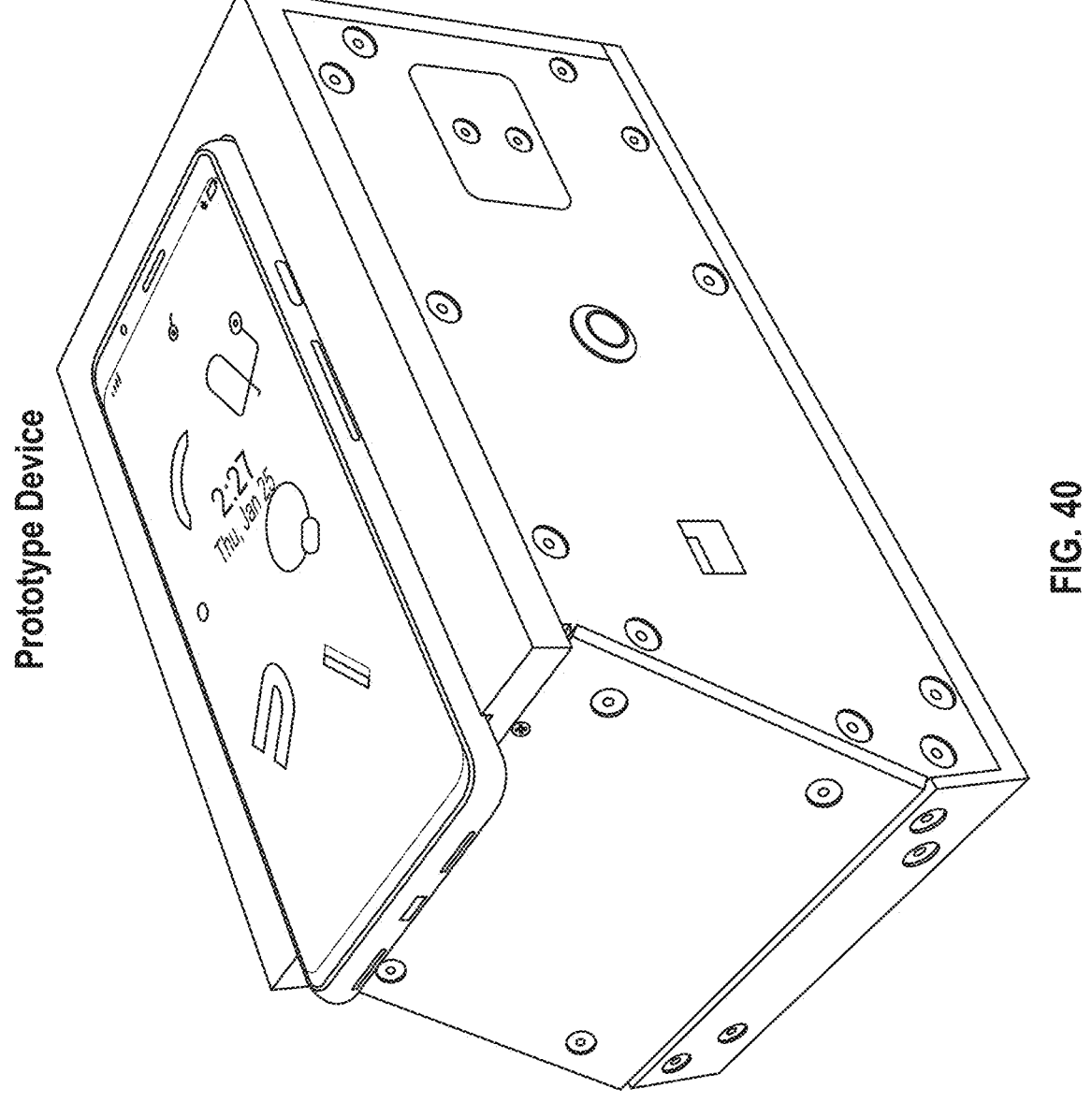

FIG. 40 is an image of an assay device that can be used with a mobile device such as a mobile phone.

Figure 41:
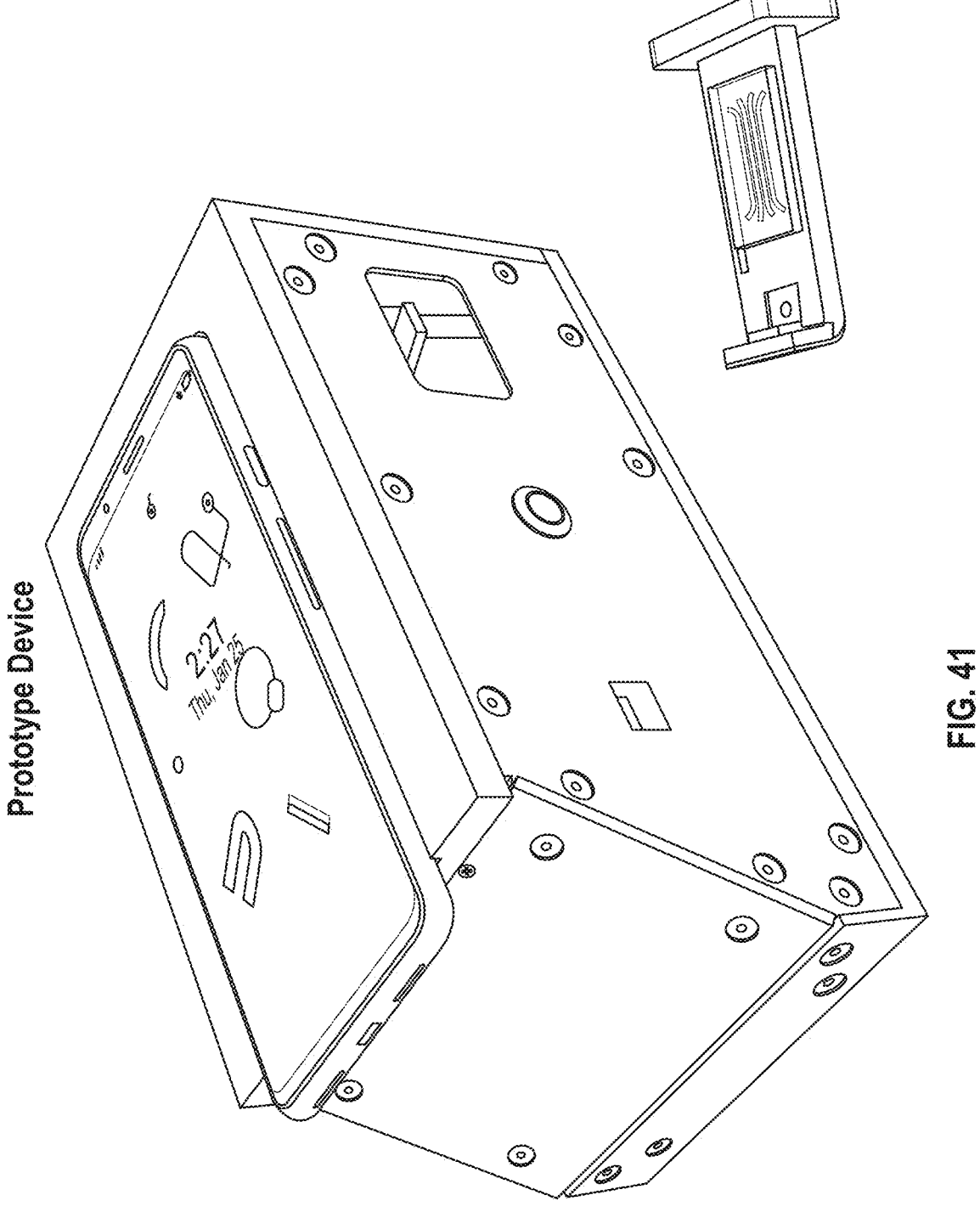

FIG. 41 is an image of an assay device that can be used with a mobile device such as a mobile phone, showing a sample chamber for an assay mixture.

Figures 42A, 42B, 42C:
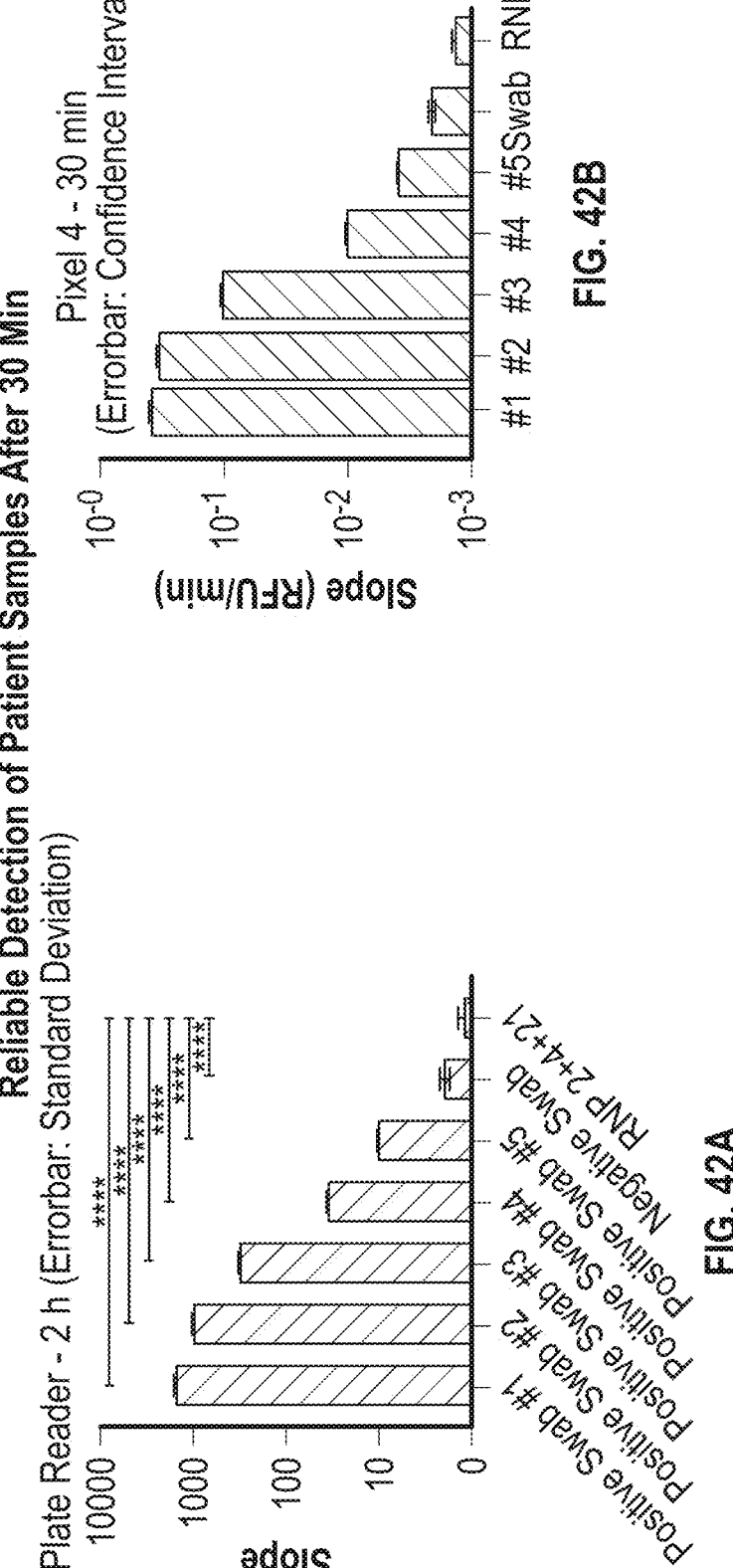

FIG. 42A-42C illustrate reliable detection of target RNA in patient samples using the devices shown in the figures provided herein. FIG. 42A graphically illustrates that patient samples (Positive Swabs #1 to #5) can be detected using the plate reader in 2 hour assays. FIG. 42B graphically illustrates that pixel counts detected from assays of patient samples (Positive Swabs #1 to #5) reliably reflect the quantities of RNA target in the samples when a shorter assay time is used—30 minutes. FIG. 42C illustrates the average Ct values detected by PCR, copies per ml., and copies per microliter in the assay reactions.

Figures 43A, 43B:
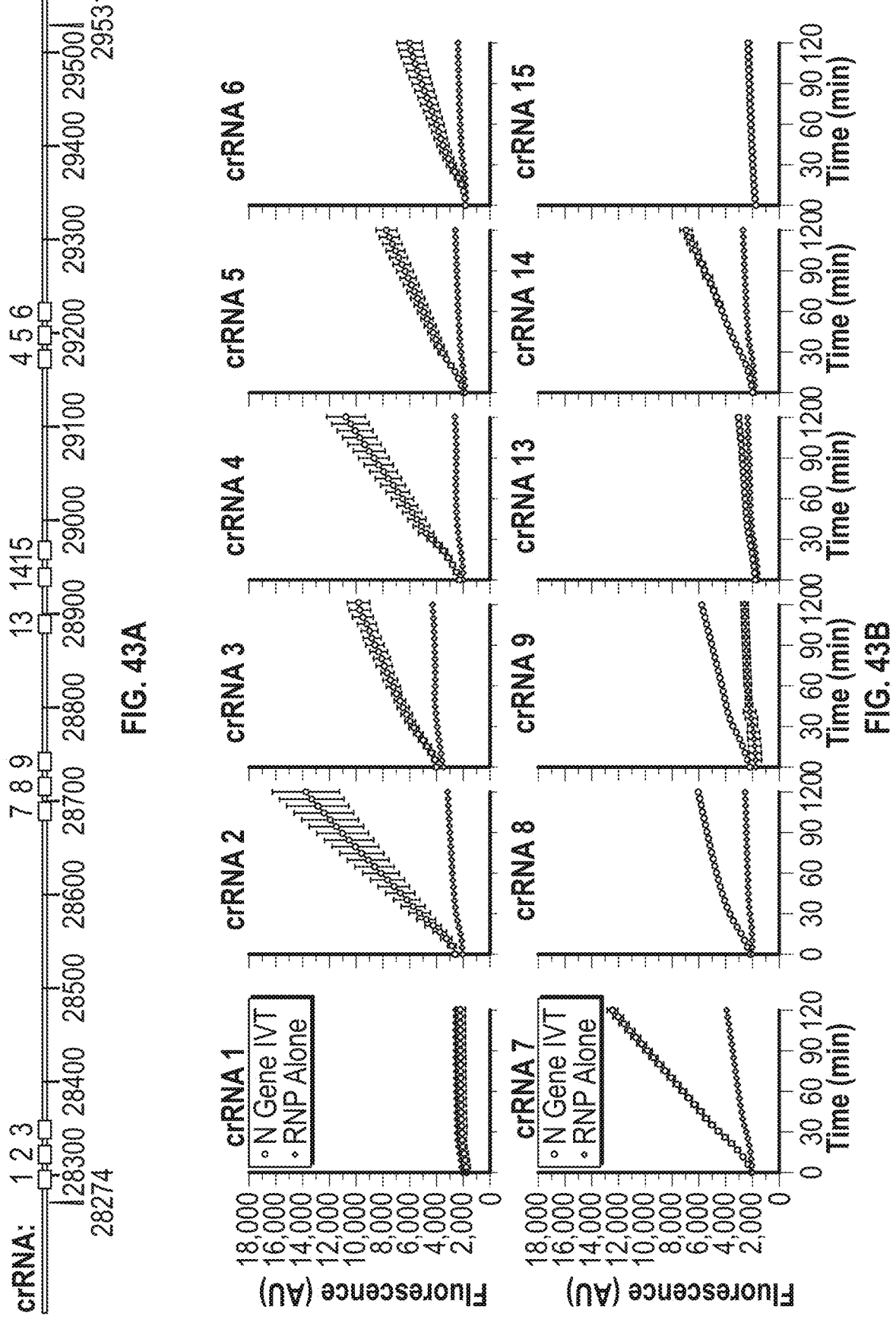
Figure 43C:
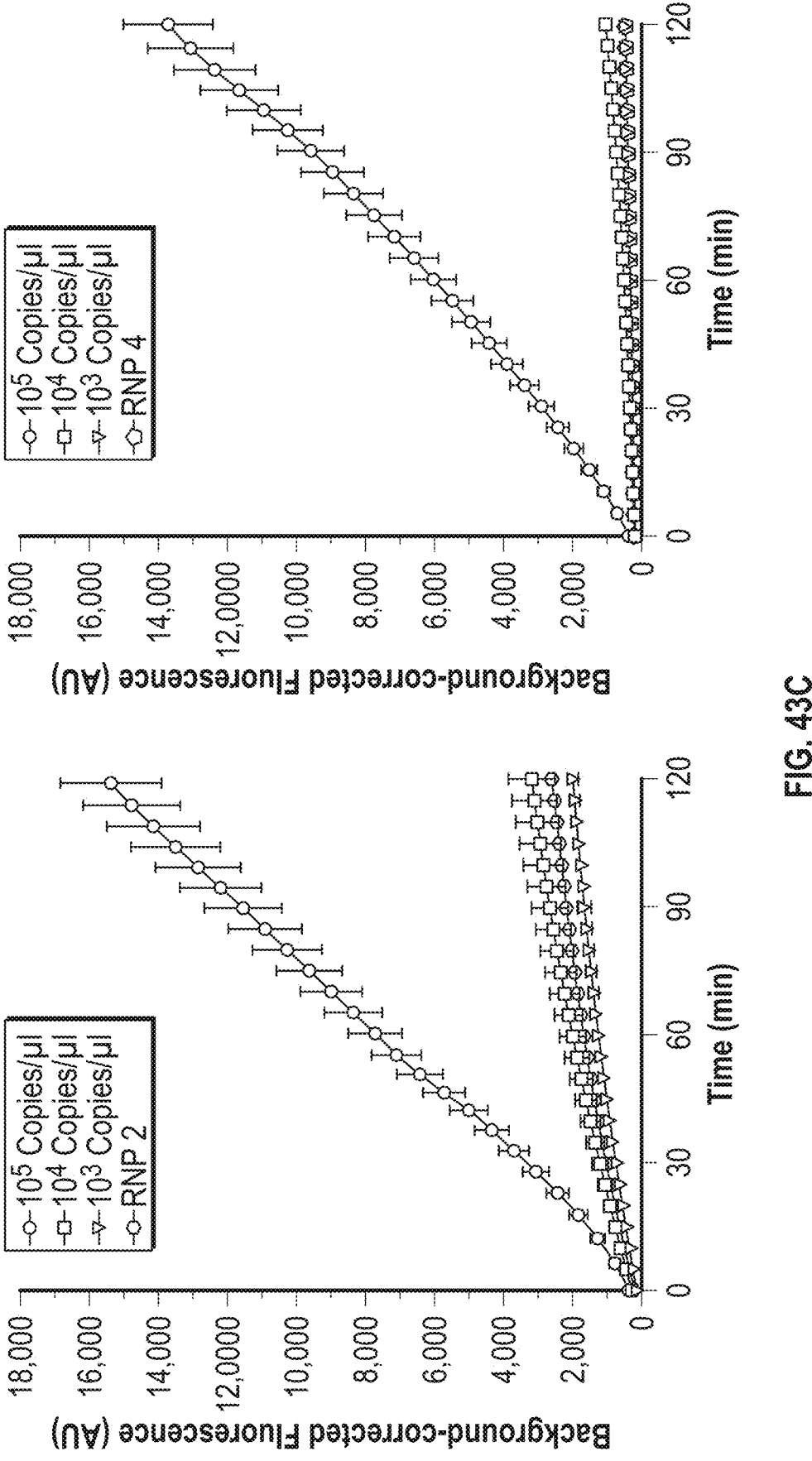
Figure 43D:
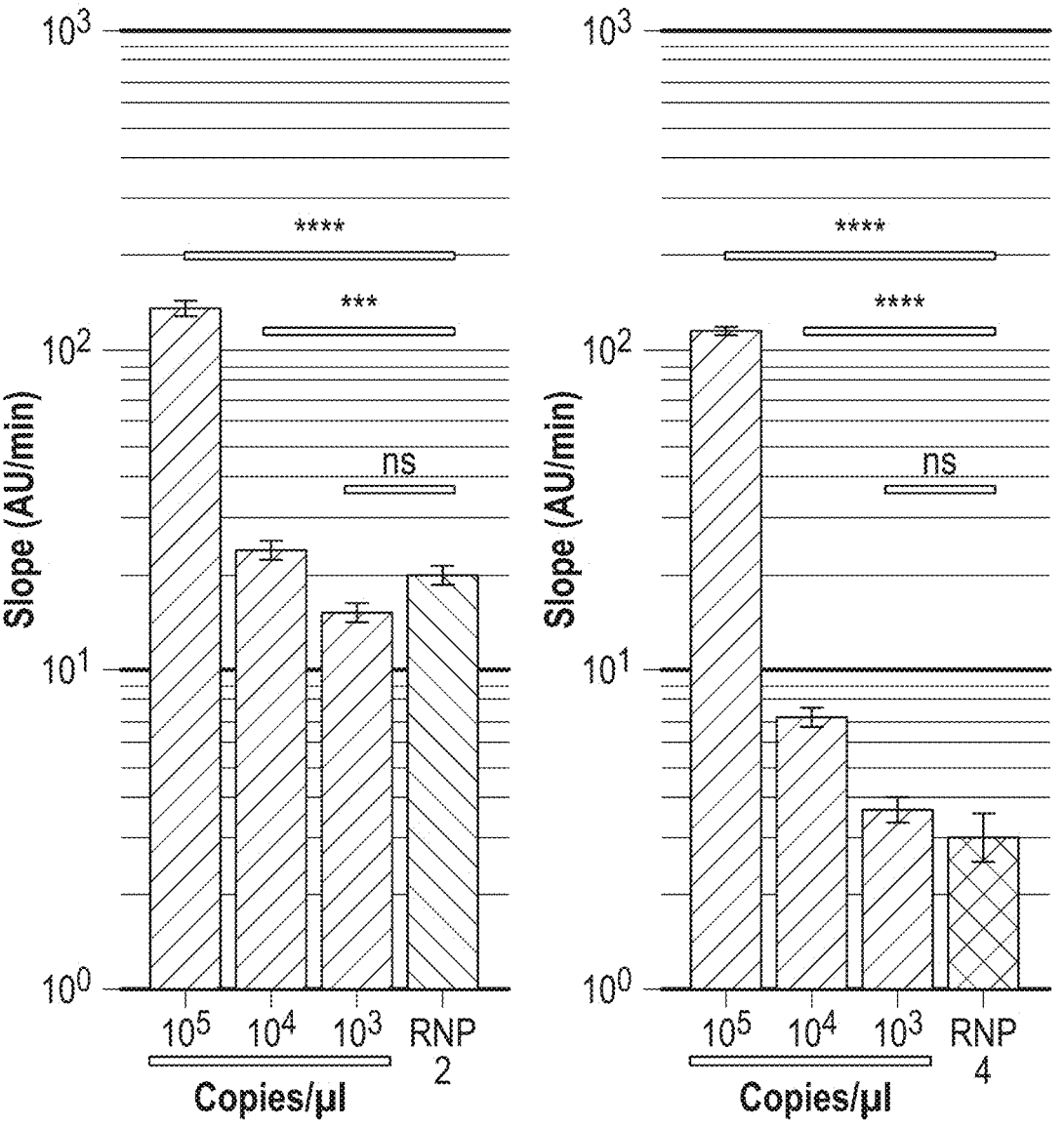
Figure 43E:
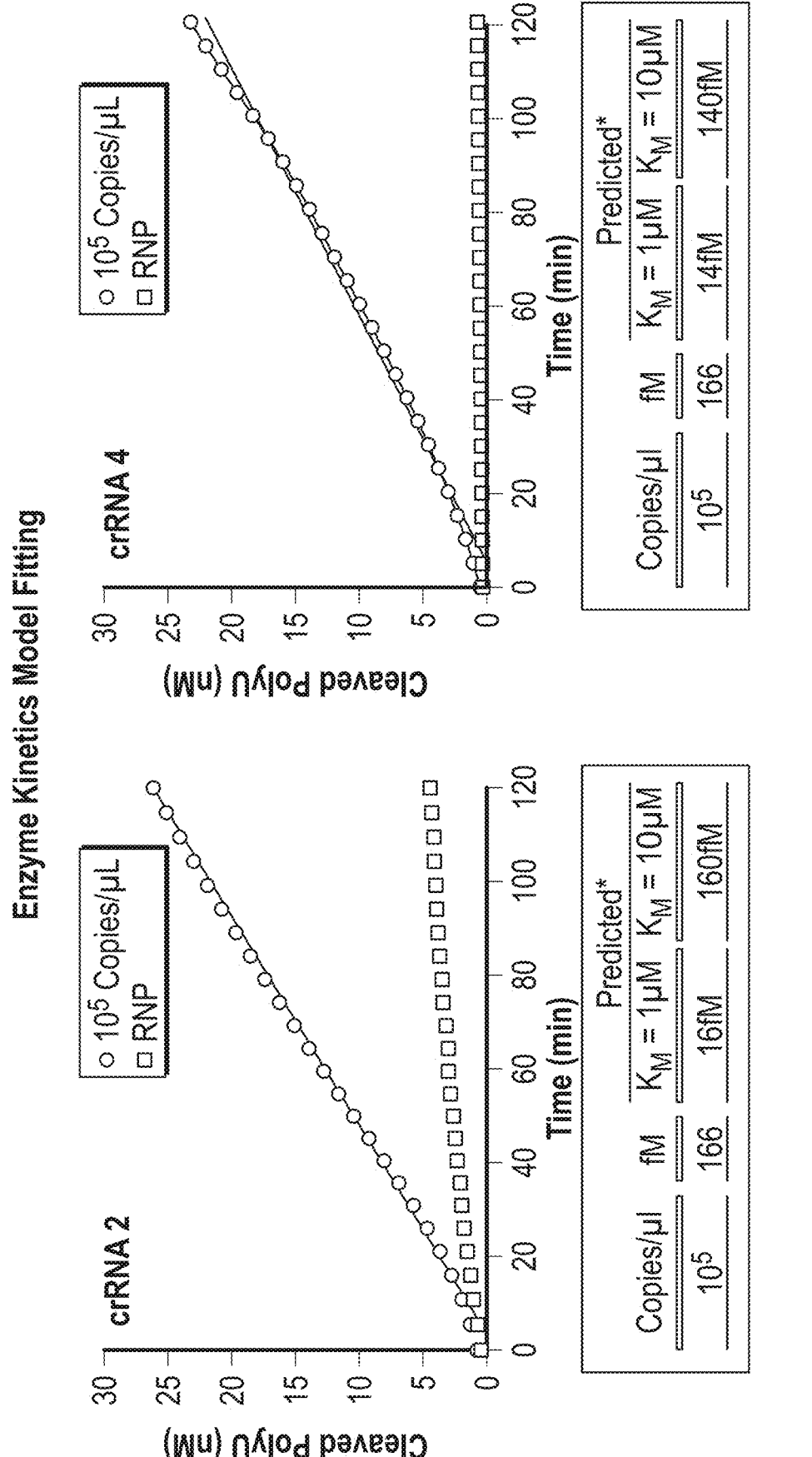

FIG. 43A-43E illustrate detection of SARS-CoV-2 by different crRNAs. FIG. 43A is a schematic diagram showing the SARS-CoV-2 nucleocapsid (N) gene within the genomic SARS-CoV-2 RNA (nucleotide positions 28274-29531), and the corresponding locations of twelve different crRNA spacer regions. FIG. 43B graphically illustrates that ten guides provide signals above the RNP control when tested in assay mixtures. Cas13a RNPs were made individually for crRNA, and the final RNP complex concentration employed in the assays was 50 nM. The target tested was $2.9 \times 10^5$ copies/μL (480 fM) of SARS-CoV-2-in vitro transcribed N gene RNA and the total reaction volume was 20 μL. Background fluorescence by each individual RNP control ("RNP") was detected by performing the control assay with the crRNA:cas13a RNP but without any target RNA. Raw fluorescence values over two hours are shown. Data are represented as mean±standard deviation (SD) of three technical replicates. FIG. 43C graphically illustrates the limits of detection for crRNA 2 and crRNA 4 guide RNAs as determined by testing 100 nM of each crRNA RNP individually against $10^5$, $10^4$, and $10^3$ copies/μL of in vitro transcribed N gene RNA. "RNP 2" and "RNP 4" represent no target RNP controls that contain the crRNA 2 or crRNA 4 guide without the N gene RNA target. Background correction of fluorescence was performed by subtraction of reporter alone-fluorescence values. Data are represented as mean±standard error of the difference between means of three technical replicates. FIG. 43D graphically illustrates the slope±95% confidence interval of the curves shown in FIG. 43C as calculated by simple linear regression over two hours. Slopes were compared to the RNP background control via Analysis of Covariance (ANCOVA): **p<0.0001, *p<0.001, ns=not significantly higher than RNP control. FIG. 43E graphically illustrates kinetic model fitting using plate reader signals of Cas13 reactions that were fit to the Michaelis-Menton kinetics model. 100,000 copies/μL of in vitro transcribed (IVT) N gene RNA was added to the reaction that contained 100 nM of Cas13a RNP—either with crRNA 2 (left) or crRNA 4 (right)—and 400 nM of the 5-U reporter RNA. The line fit (upper red line) indicates a simple exponential curve, which corresponds to the Michaelis-Menton model at a regime where the substrate concentration is significantly low compared to the $K_M$. The concentration of active Cas13a for Kcat=600/s and $K_M$=1 μM or 10 μM was predicted as shown at the bottom.

Figure 44A:
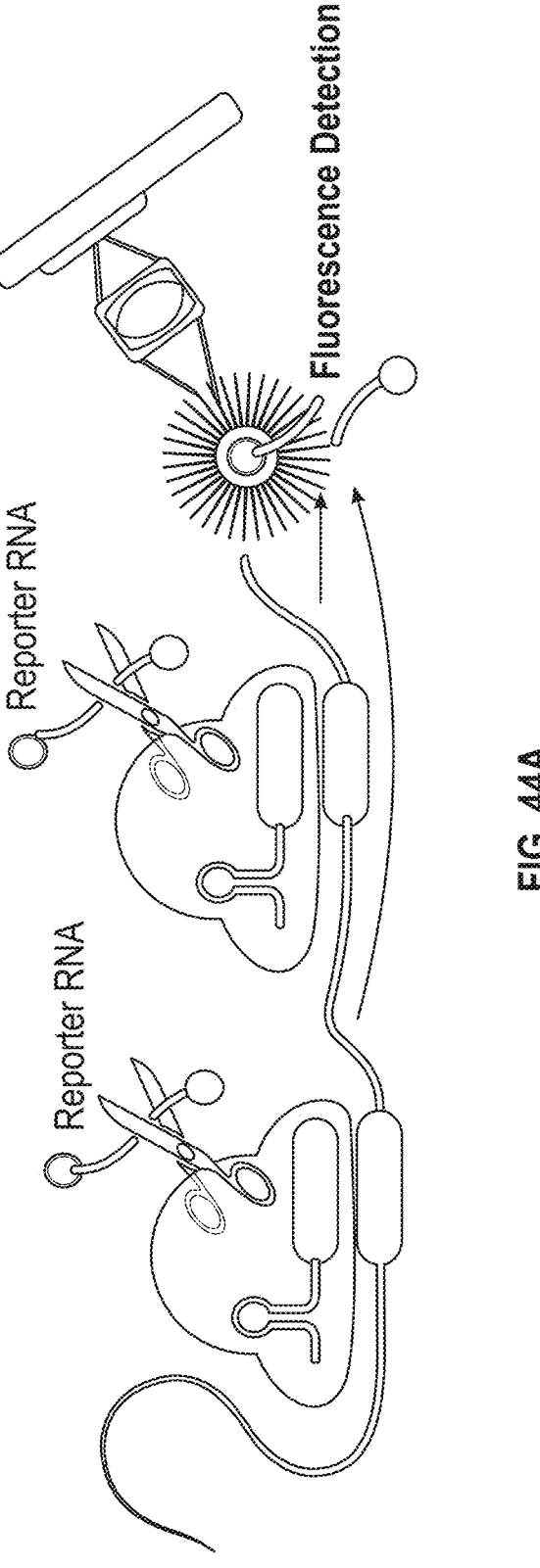
Figure 44B:
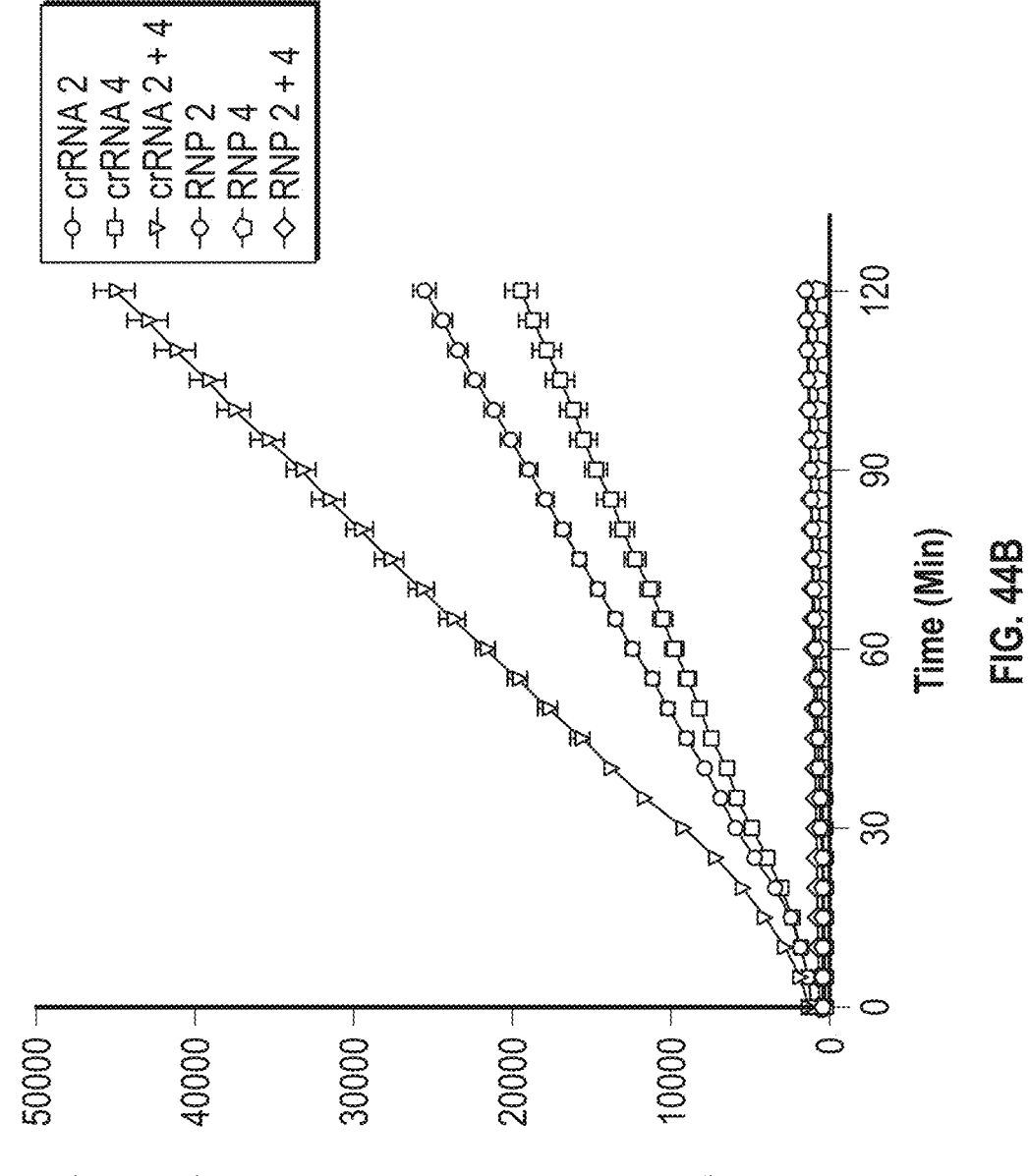
Figure 44D:
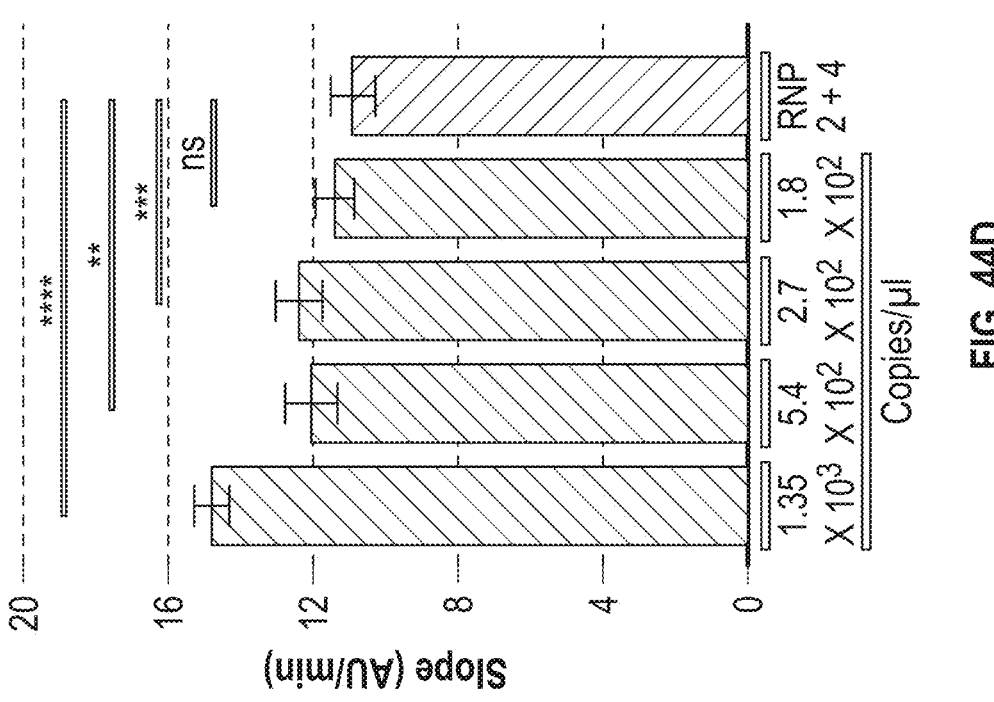
Figure 44C:
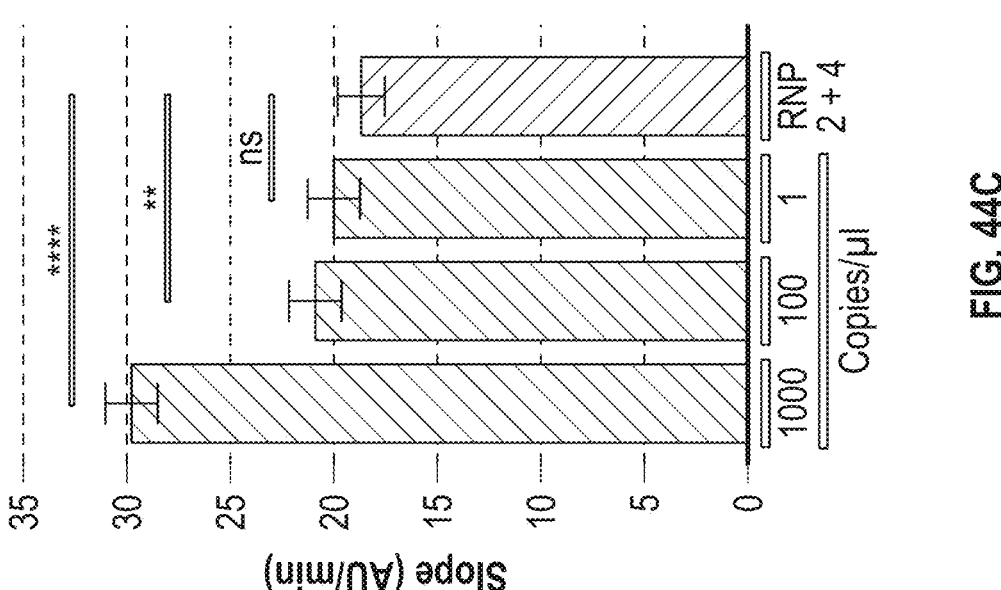

FIG. 44A-44D illustrate the improved detection limits provided by using two crRNAs to detect SARS-CoV-2. FIG. 44A shows a schematic diagram where two crRNA-Cas13a-enzyme RNPs are present at two different locations on the SARS-CoV-2 viral RNA target, leading to cleavage of the RNA reporter and increased fluorescence. FIG. 44B shows that combining crRNA 2 and crRNA 4 markedly increased the slope of a detection assay containing the N gene in vitro transcribed RNA as target. RNPs were individually prepared with Cas13a as well as crRNA 2 or crRNA 4, or a combination thereof. The assay mixtures contained 50 nM total RNP concentration and $2.9 \times 10^5$ copies/mL (480 fM) of SARS-CoV-2 in vitro transcribed N gene RNA for each reaction. The plots shown were labeled as "crRNA 2," "crRNA 4," and "crRNA 2+4" to show which crRNAs were used. The detected fluorescence was compared to fluorescence from no target RNA-RNP only controls (labeled as "RNP 2," "RNP 4," and "RNP 2+4"). Background correction of fluorescence was performed by subtraction of reporter alone fluorescence values. Data are represented as mean±standard error of the difference between means of three technical replicates. FIG. 44C shows that when evaluated with a series of diluted N gene RNAs, use of the combination of crRNA 2 and crRNA 4 shifted the limit of detection by 1000-fold, down to about 10 copies/μL of in vitro transcribed target N gene RNA. Limits of detection of the crRNA 2 and crRNA 4 combination were determined by combining 50 nM of RNP 2 and 50 nM of RNP 4 (100 nM total RNP) with 1,000, 100, or 1 copy/μL of SARS-CoV-2 in vitro transcribed RNA (n=3, technical replicates). Slopes of the curves over two hours were calculated by simple linear regression and are shown as slope±95% confidence interval. Slopes were compared to the no target RNA RNP background control using ANCOVA: **p<0.0001, p=0.0076, ns=not significant. FIG. 44D shows that when using serially diluted full-length SARS-CoV-2 RNA as the target, the detection limit of the crRNA 2 and crRNA 4 guide combination in this experiment was 270 full-length viral copies/μL. Limits of detection of the crRNA 2 and crRNA combination were determined by combining 50 nM of RNP 2 and 50 nM of RNP 4 (100 nM total RNP) with $1.35 \times 10^3$, $5.4 \times 10^2$, $2.7 \times 10^2$, or $1.8 \times 10^2$ copies/μL of SARS-CoV-2 full-length viral RNA (amounts of SARS-CoV-2 full-length viral RNA were quantified by qPCR; n=3, technical replicates). Slope of the curve over two hours was calculated by simple linear regression and is shown as slope f 95% confidence interval. Slopes were compared to the no target RNA RNP background control using ANCOVA: **p<0.0001, *p=0.0002, **p=0.0023, ns=not significant.

Figure 2:
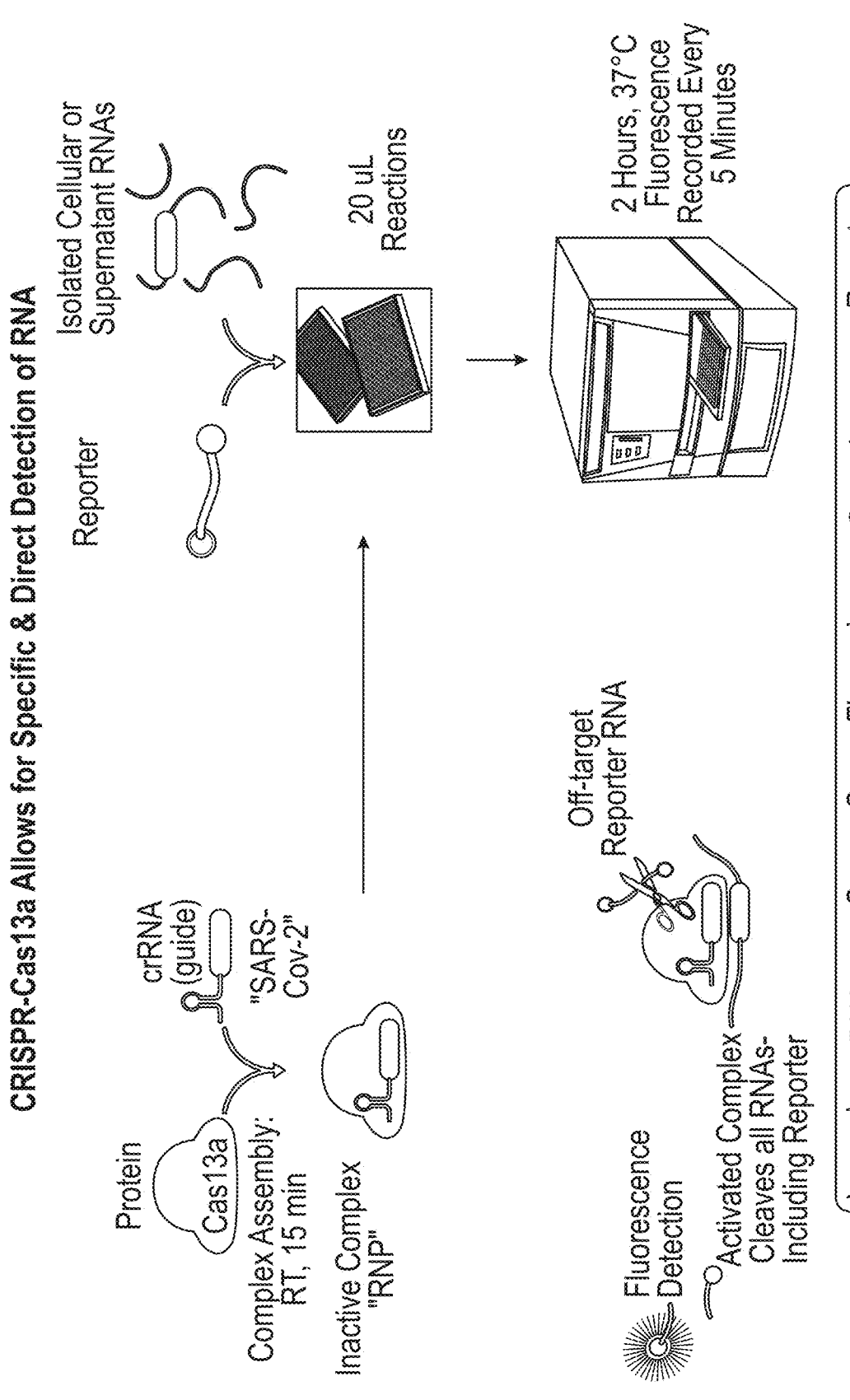
FIG. 2 is a schematic diagram illustrating methods for detection of the SARS-CoV-2 RNA genome and fluorescent detection of reporter RNA. CRISPR guide RNAs (crRNA) that can target or bind to SARS-CoV-2 RNA are used. As illustrated, in a first step the CRISPR-Cas13 protein binds CRISPR guide RNAs (crRNA) to form a ribonucleoprotein (RNP) complex. The RNP complex is inactive but, when mixed with the sample to be tested, binding of the RNP complex to the SARS-CoV-2 RNA in the sample activates the Cas13 protein to cut RNA, including reporter RNA molecules added to the assay mixture. Cleavage of the reporter RNA leads to fluorescence, which can be detected by a fluorescence detector.
Figure 3:
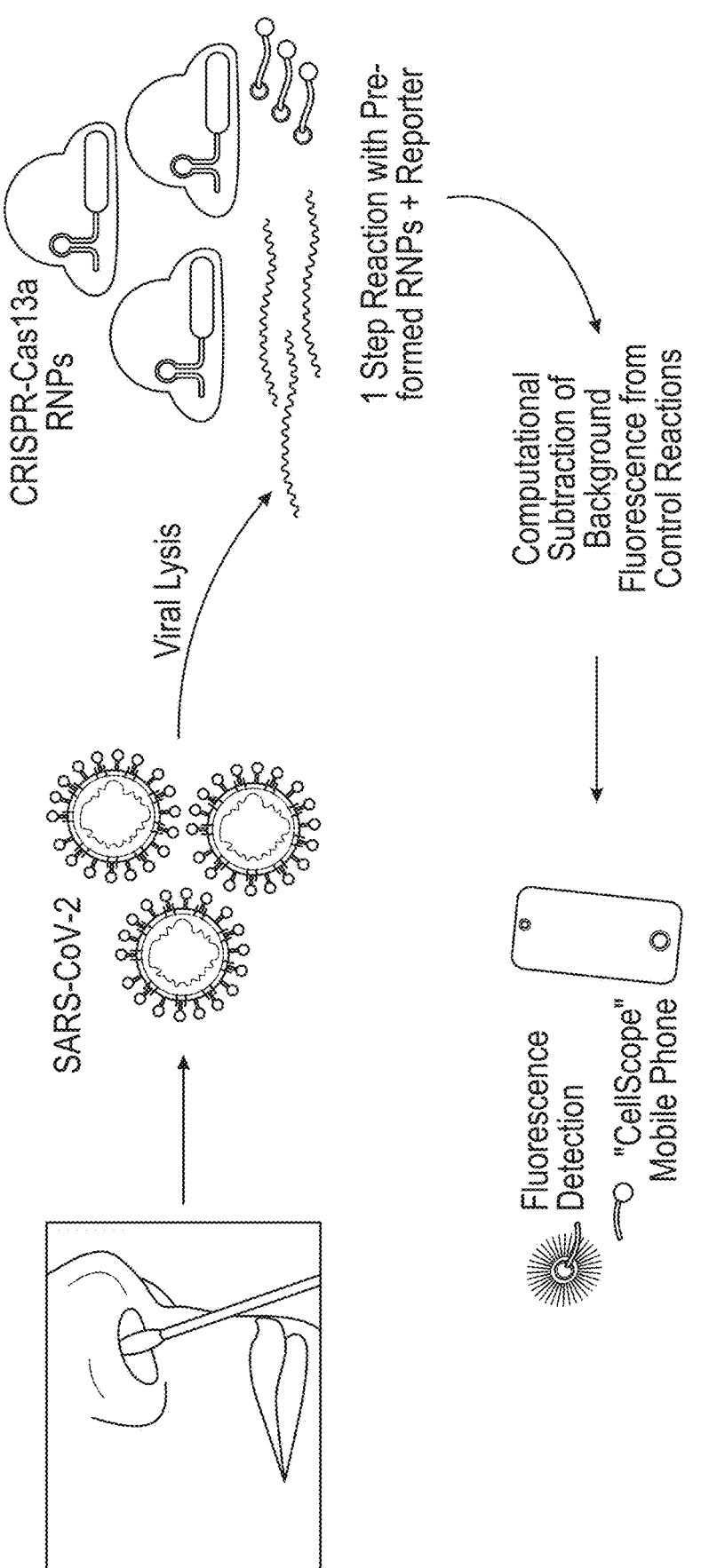
FIG. 3 illustrates a point-of-caring (POC) method for detecting SARS-CoV-2. As illustrated, a sample can be collected (e.g., a patient's saliva, sputum, mucus, or nasopharyngeal sample), the cells and/or viruses in the sample can be lysed to release any viral RNA that may be present, and the RNA from the sample can be mixed with reporter RNAs and a CRISPR-Cas13 protein-crRNA ribonucleoprotein (RNP) complex. Background fluorescence from control reactions can be subtracted and the fluorescence of the sample can be detected. For example, detection can be by a mobile device (e.g., cell phone) that has CellScope detection software. Such point-of-care detection allows mobilization of medical support and medical personnel to areas where CoVID-19 infections occur.
Figure 45A:
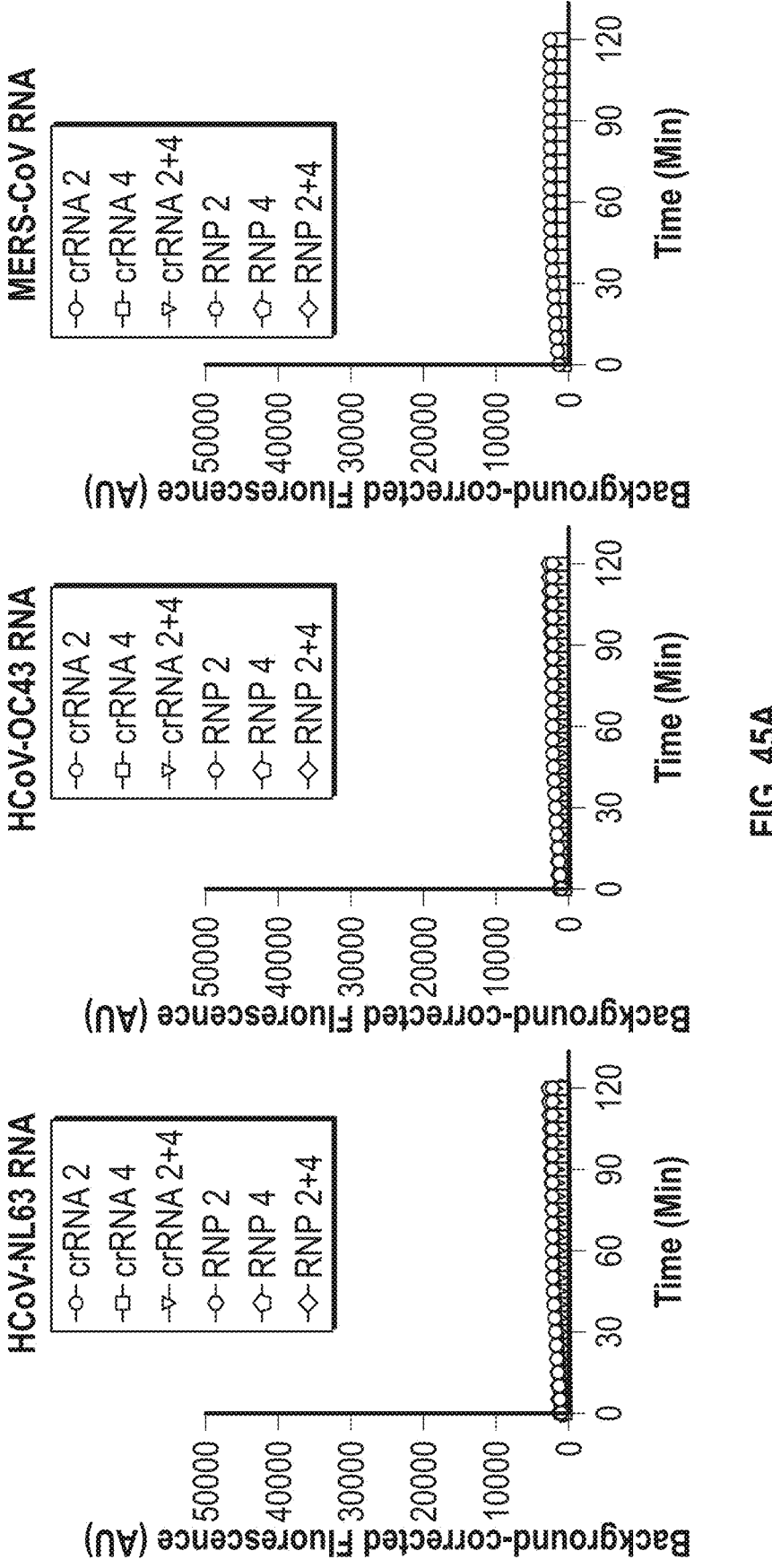
Figure 45B:
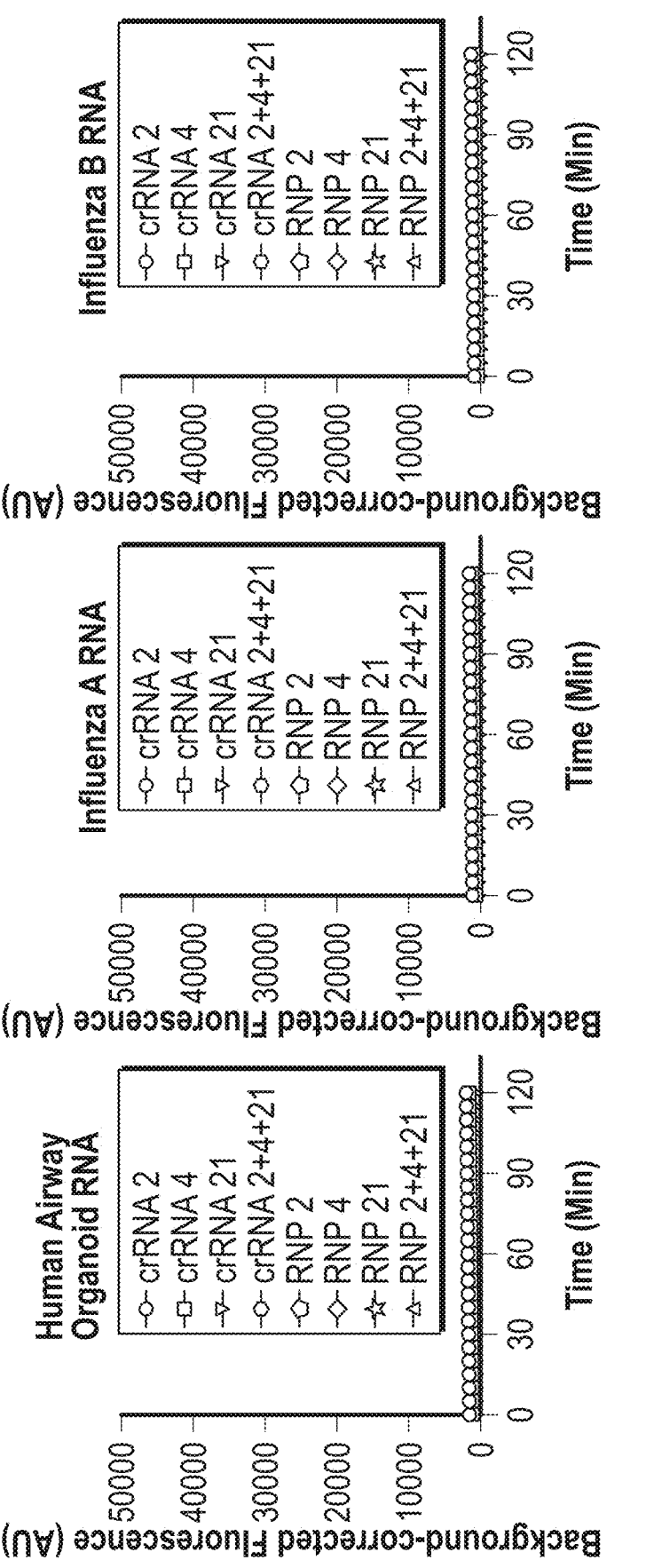
Figures 1, 2, 45C:
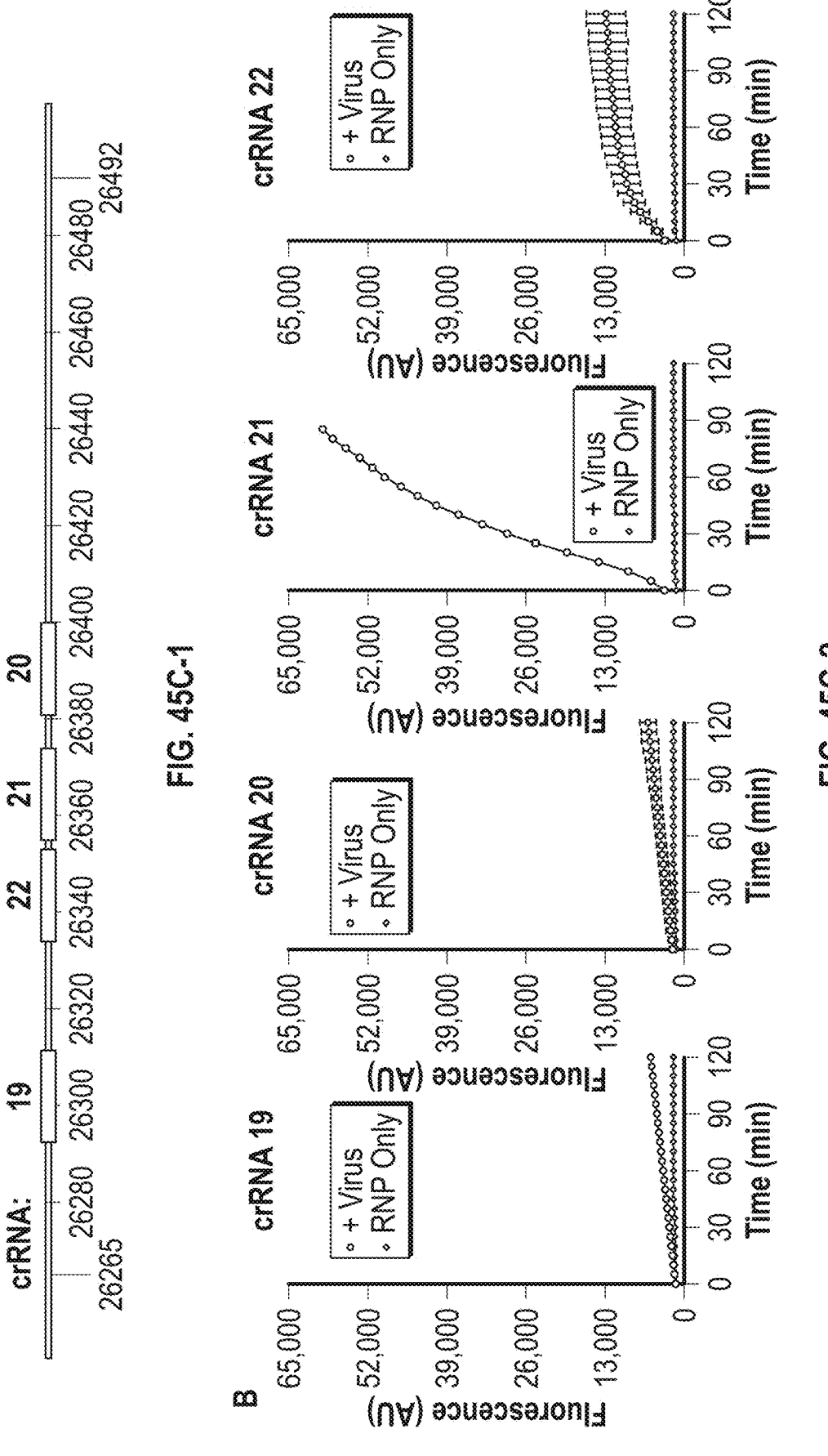
Figures 3, 45C:
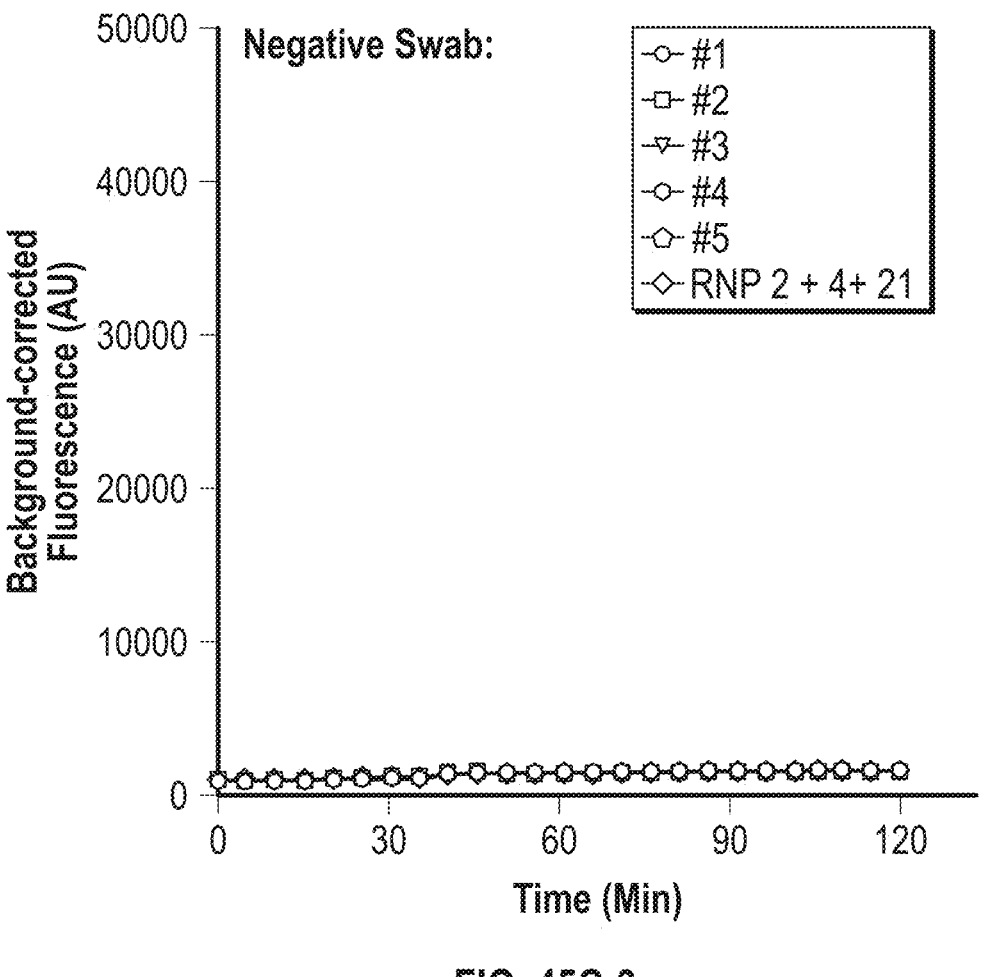
Figure 45D:
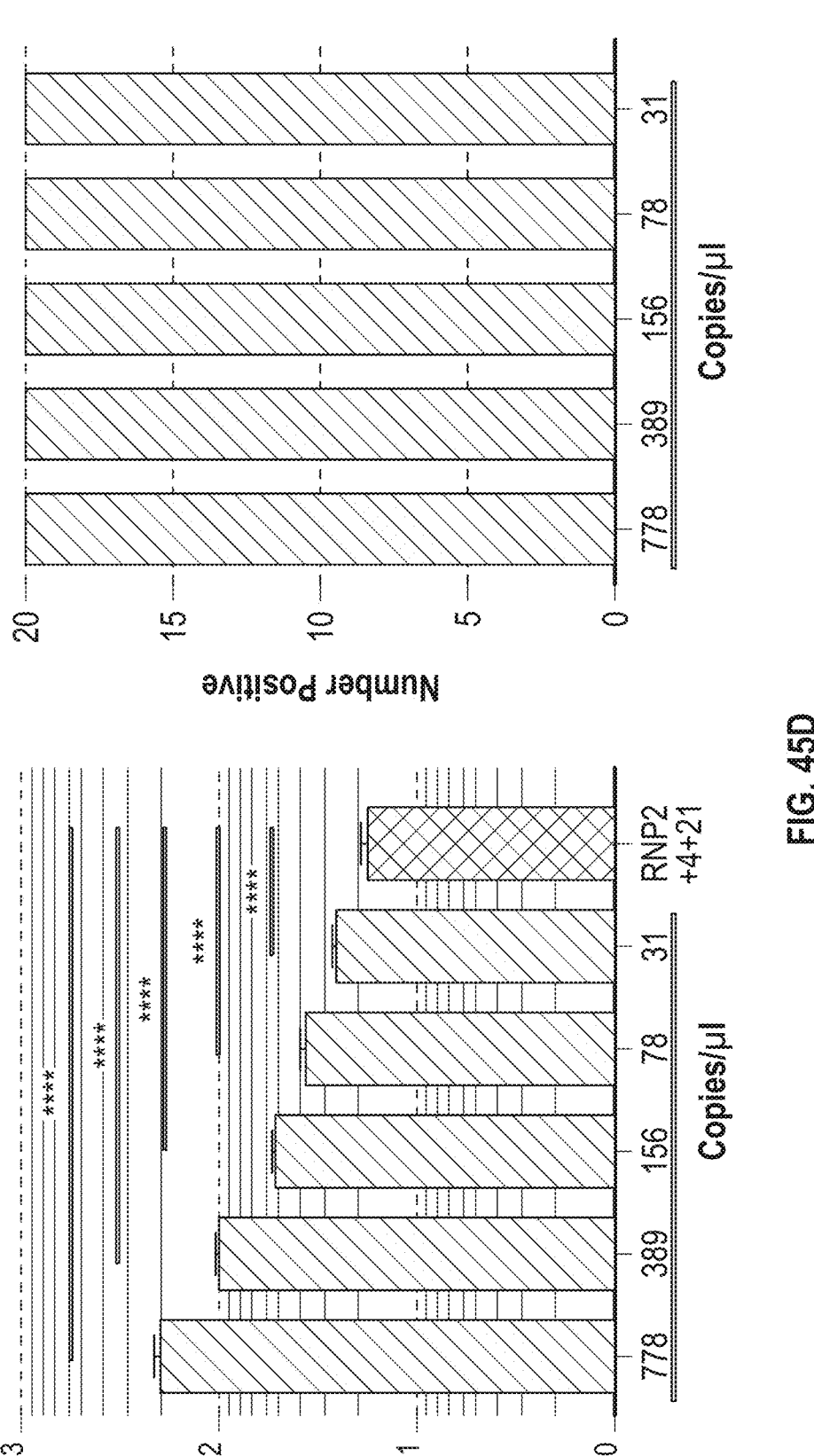
Figure 45E:
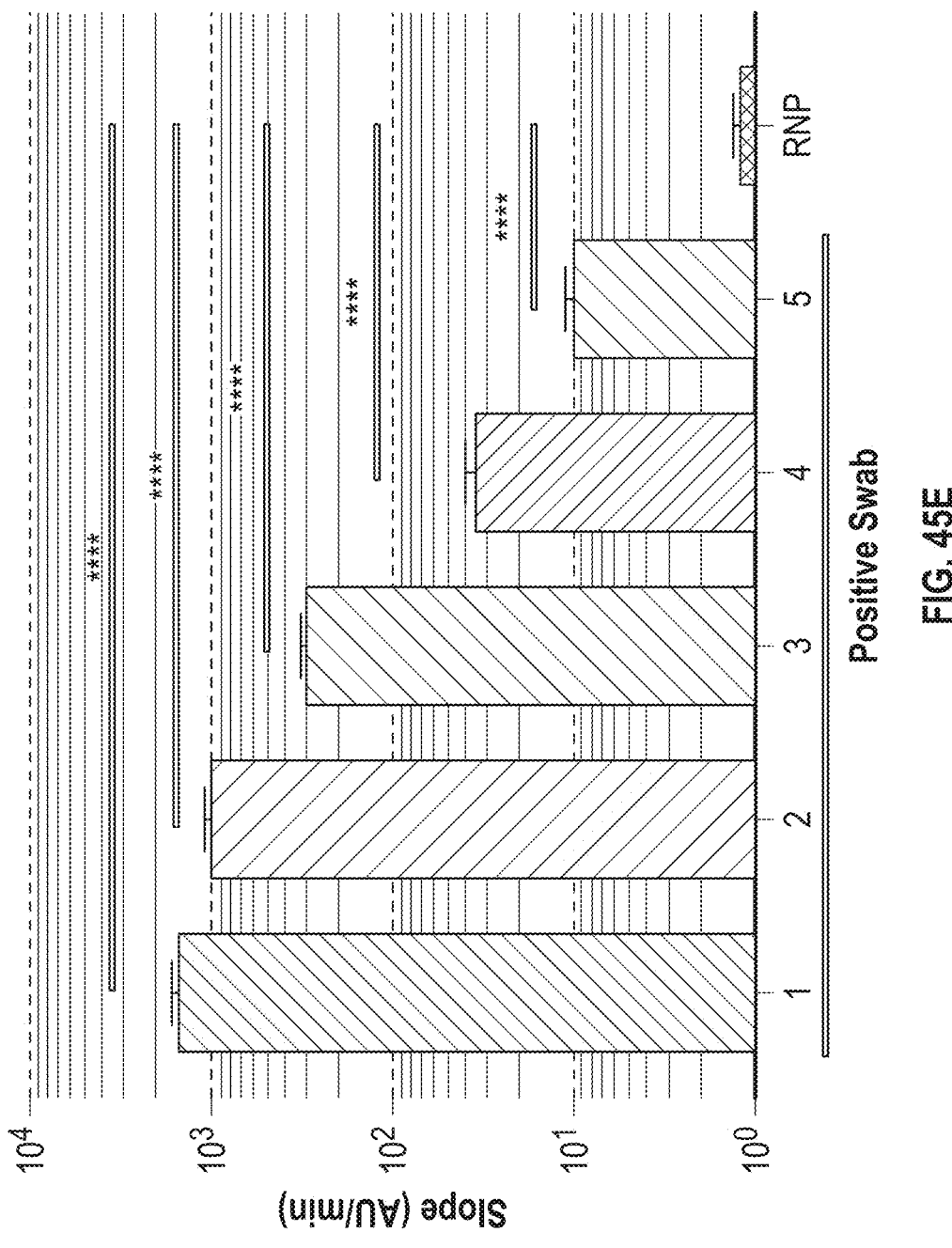

FIG. 45A-45F illustrate that the SARS-CoV-2 detection assay specific for SARS-CoV-2 and the assay directly detects SARS-CoV-2 in patient samples. FIG. 45A shows that no signal was detected above background with guides crRNA 2 and crRNA 4 in assays for the alphacoronavirus HCoV-NL63 (left graph), betacoronavirus HCoV-OC43 (middle graph), and Middle East respiratory syndrome coronavirus (MERS-CoV; right graph) viral RNAs. The crRNA 2 and crRNA 4 guides were tested individually (100 nM total RNP concentration) and in combination (100 nM total RNP concentration: 50 nM each of RNP 2 and RNP 4) using RNA isolated from HCoV-NL63 viral supernatant (left) and HCoV-OC43 viral supernatant (center), or the in vitro transcribed N gene RNA from MERS-CoV (right) as potential target RNA. No-target RNA RNP controls are denoted as "RNP 2," "RNP 4," and "RNP 2+4." Background correction of fluorescence was performed by subtraction of reporter alone fluorescence values. Data are represented as mean f standard error of the difference between means of three technical replicates. FIG. 45B shows that no signal was detected when a different crRNAs (crRNAs 2, 4, 21, or combinations thereof) are used in assay mixtures containing different influenza viruses and human organoid RNA. The assays were performed with potential target RNA extracted from human airway organoids (left), from supernatant of cells infected with the H1N1 strain of influenza A (middle), or from supernatant of cells infected with influenza B (right). FIG. 45C-1, 45-2, and 45C-3 illustrate that four different crRNA exhibit different background-corrected fluorescence signals over control assays. FIG. 45C-1 is a schematic diagram showing nucleotide positions 26265-26492 where the SARS-CoV-2 E gene resides within the genomic SARS-CoV-2 RNA, and the corresponding locations of four crRNA spacer regions (crRNA-19 to crRNA 22). FIG. 45C-2 graphically illustrate detection of SARS-CoV-2 in different assay mixtures using just one of the crRNA 19, crRNA 20, crRNA 21, or crRNA 22 in an RNP. Higher signal plots indicate that the virus is present, while the lower plots are from control assays when the virus is not present in the assay mixture. As shown, the crRNA 21 guide provides the best signal. FIG. 45C-3 illustrates that assay mixtures using the combination of crRNA 2, crRNA 4 and crRNA 21 RNPs have low backgrounds, even when RNA from swabs of individuals without SARS-CoV-2 infection (negative swab) are tested. RNAs from five nasopharyngeal swabs of patients were confirmed negative for SARS-CoV-2 by RT-qPCR when tested against RNP 2+4+21 (100 nM total RNP concentration). The no target RNA RNP control is denoted as "RNP 2+4+21." Background correction of fluorescence was performed by subtraction of reporter alone fluorescence values. Data are represented as mean f standard error of the difference between means of three technical replicates. FIG. 45D graphically illustrates detection of full-length SARS-CoV-2 viral RNA at various copies per ul, demonstrating as low as 31 copies per ul are detected significantly above background (assay with no target) using the combination of crRNA 2, crRNA4, and crRNA 21 guide RNAs from nasal swabs taken from five SARS-CoV-2+ patients. Full length SARS-CoV-2 RNA was independently quantified by the Biodefense and Emerging Infections Research Resources Repository (BEI Resources) using ddPCR, then diluted and tested against RNP 2+4+21 to determine the limit of detection (n=20, technical replicates). In each case, the slope of the signal curve over two hours was calculated by simple linear regression and is shown as slope f SEM (left). Slopes were compared to the no target RNA RNP background control using ANCOVA: **p<0.0001. The graph on the right shows the number of times a viral RNA sample (at a specific copies per μl) is detected above background when tested 20 times (31 copies per ul sample was detected above background 20 out of 20 times). FIG. 45E illustrates that the direct detection assay described herein correctly identified five positive samples, which were all significantly above the signal elicited by the RNP control reaction without target viral RNA. RNA from five nasopharyngeal swabs confirmed positive for SARS-CoV-2 by RT-qPCR was tested against RNP 2+4+21 (100 nM total RNP concentration containing crRNA 2, crRNA 4, and crRNA 21 guide RNAs). The no target RNA RNP control with the crRNA 2, crRNA 4, and crRNA 21 guide RNAs but no sample RNA is denoted as "RNP." Slopes of the curves over two hours were calculated by simple linear regression and shown as slope f 95% confidence interval. Slopes were compared to the no target RNA RNP background control using ANCOVA: p<0.0001. FIG. 45F graphically illustrates the Ct values (Average Ct count using CDC N1 and N2 primers in RT-qPCR), copies/mL (as determined by RT-qPCR), and the copies/μL detected by the Cas13a reactions were tallied for the RNA samples from each positive swab used to generate the data shown in FIG. 45**E.

Figure 46A:
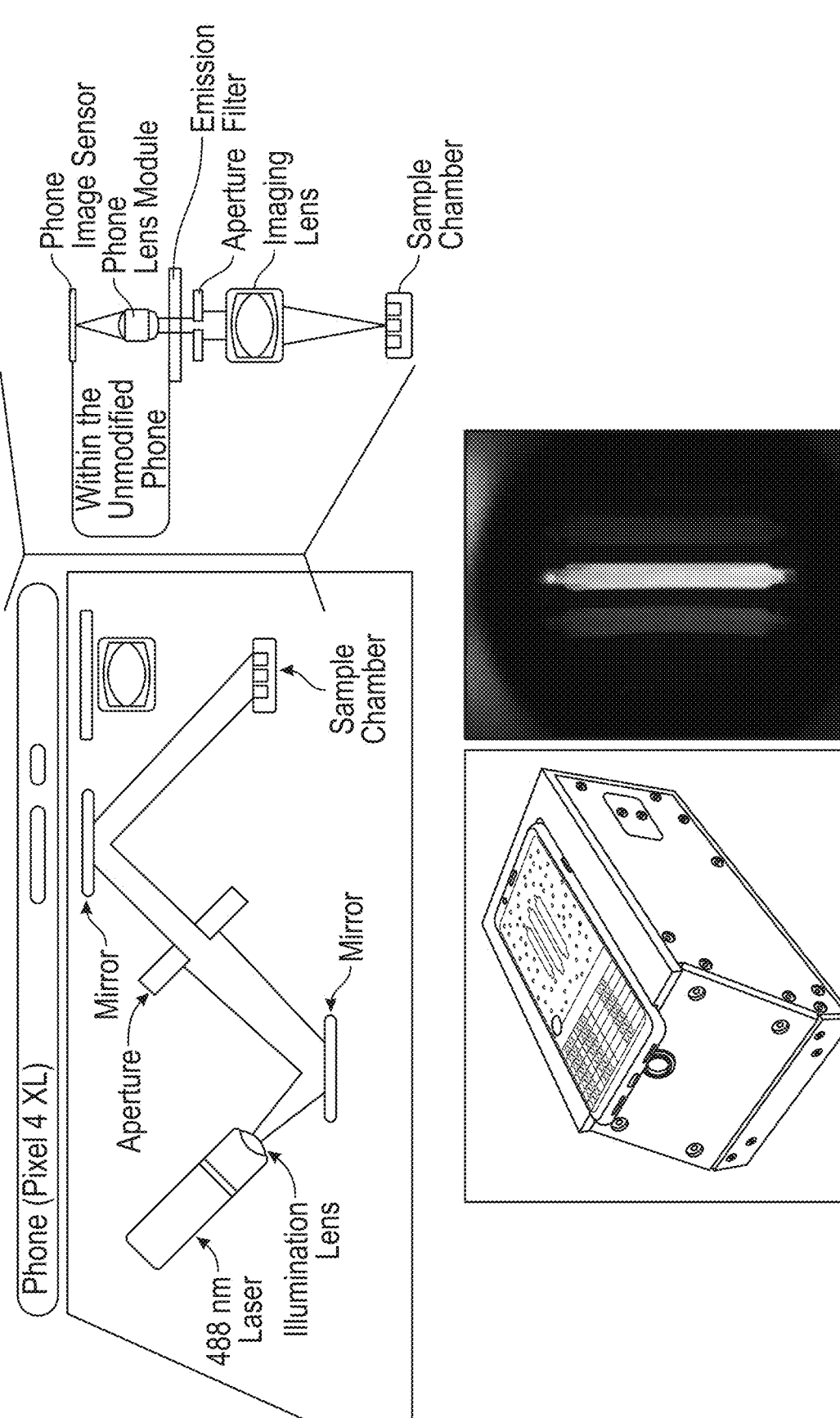
Figure 46B:
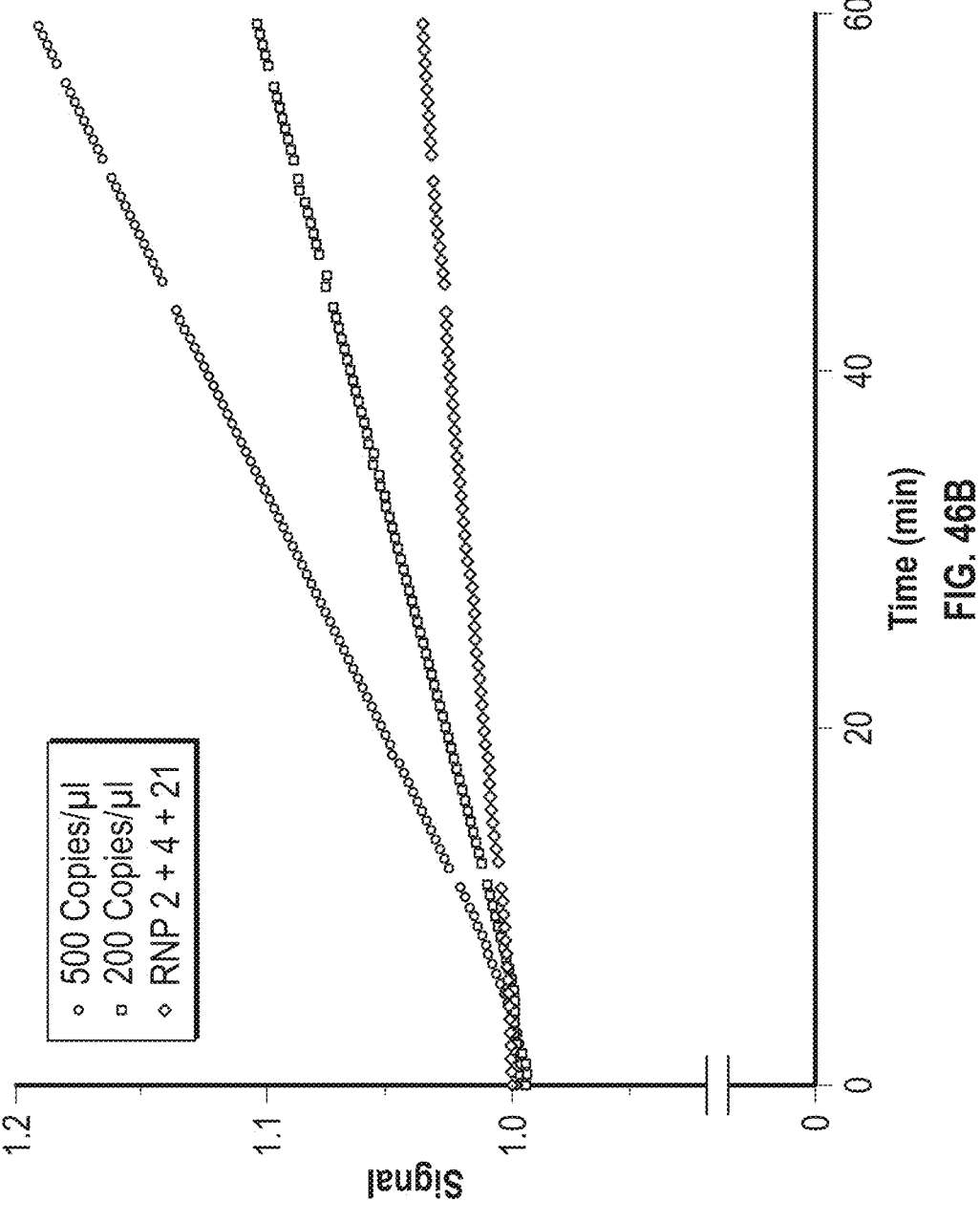
Figures 46C, 46D:
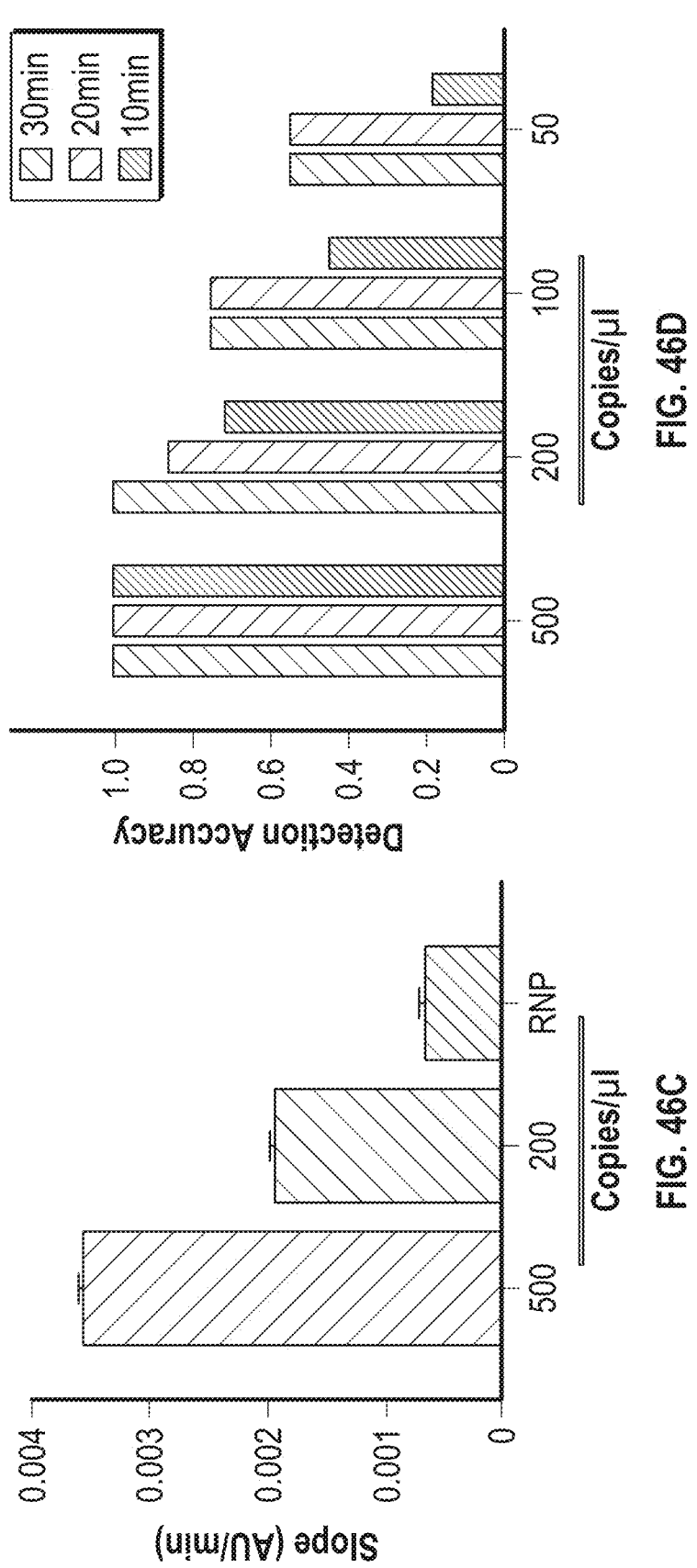
Figure 46E:
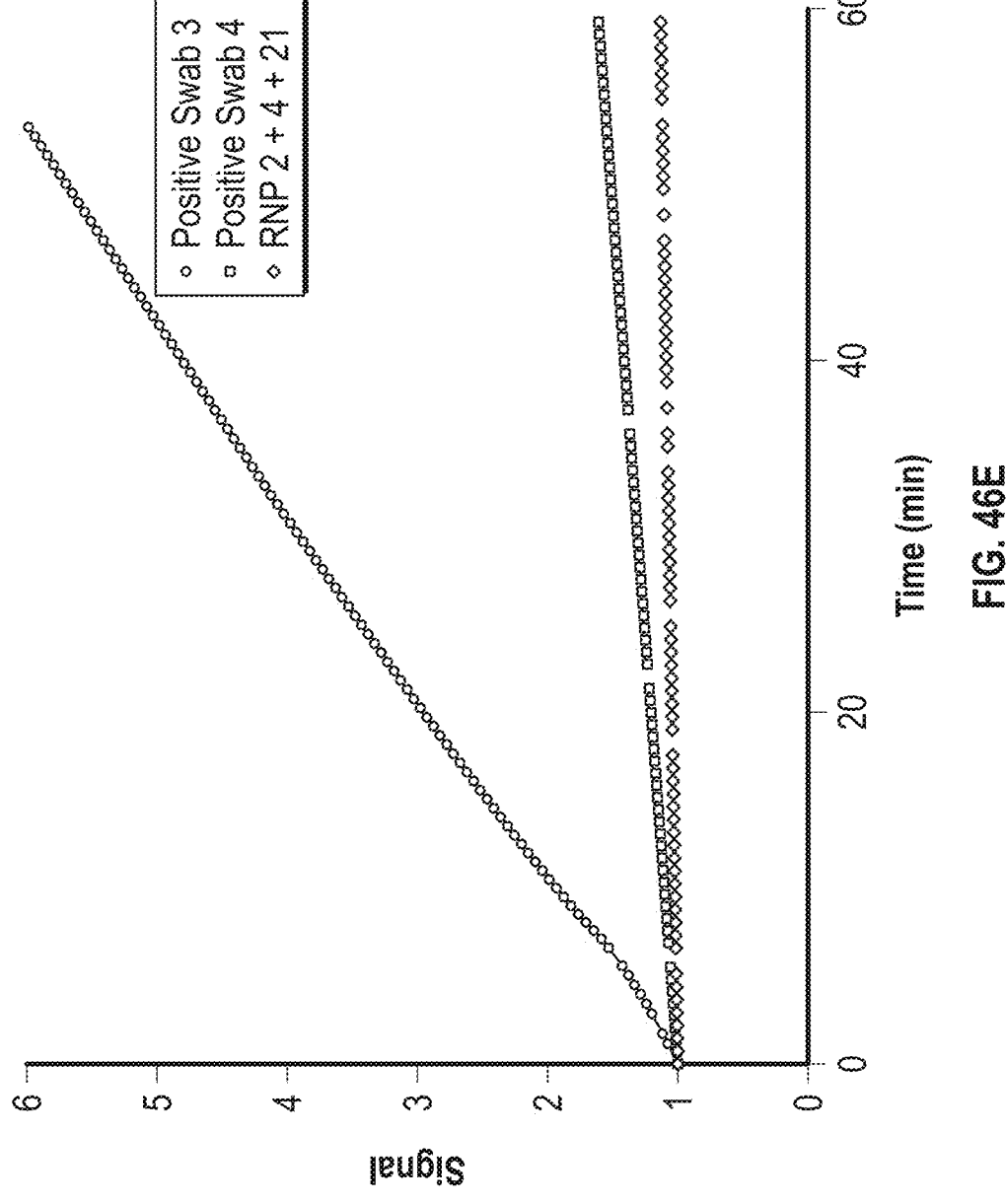
Figures 46F, 46G:
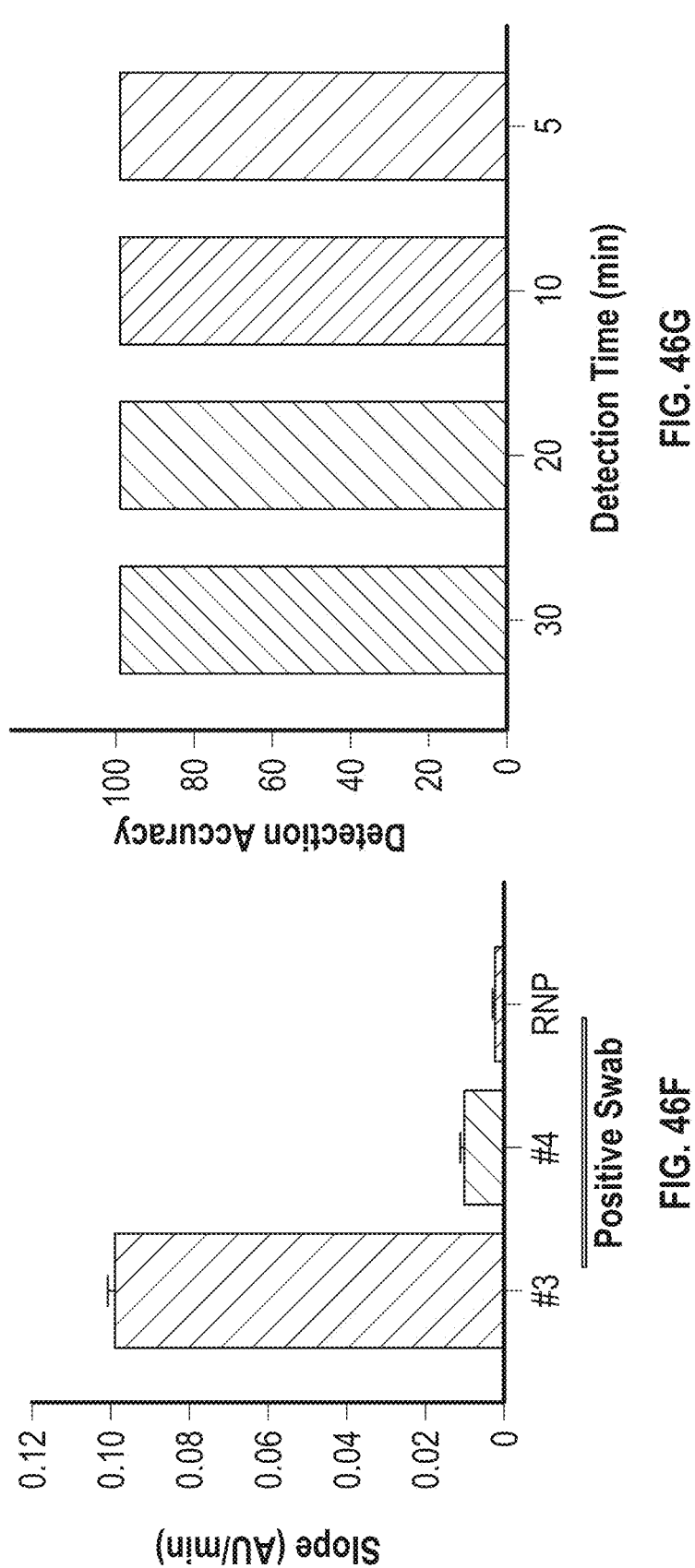

FIG. 46A-46G illustrate harnessing mobile phone cameras as portable plate readers for the COVID-19 detection system. FIG. 46A shows diagrams and images of the mobile phone-based COVID-19 detection system. At the left is shown a schematic of mobile phone-based microscope for fluorescence detection illustrating the illumination and image collection components. At the right are shown pictures of an exemplary assembled device for data collection and sample detection imaging taken by the mobile phone camera after running a Cas13 assay. FIG. 46B graphically illustrates the signals detected from assays of different numbers of SARS-CoV-2 RNA compared to a control assay containing the combined guides (crRNA 2, crRNA 4 and crRNA 21) without SARS-CoV-2 RNA. Results from Cas13 assays were run on the mobile device with two different dilutions of full-length SARS-CoV-2 viral RNA isolated from infected Vero CCL81 cells (500 and 200 copies/μL). Three crRNA guides (crRNA 2, crRNA 4 and crRNA 21) were combined and used to generate RNPs with the Cas13a nuclease. An RNP alone assay containing the crRNAs and the Cas13 protein but no SARS-CoV-2 RNA was used as a control. The Y-axis shows the normalized fluorescent signal obtained by dividing the average signal from the images at each time point by the average signal from the image from the first time point. FIG. 46C graphically illustrates the slope of signal increases for SARS-CoV-2 detection assays for each of the conditions (different copies/µl of SARS-CoV-2) shown in FIG. 46B. Slopes were determined by a linear fit of the signal using a simple linear regression, compared the RNP control (which had no SARS-CoV-2 RNA in the assay). FIG. 46D graphically illustrates the detection accuracy of Cas13 assays run with four different concentrations of SARS-CoV-2 full length viral RNA and evaluated at three different assay times. The slopes for each of the samples and each slope's 95% confidence intervals were determined by a linear fit of the signal using a simple linear regression. The slopes were calculated for the first 10, 20 and 30 minutes of each run, and the samples were considered positive for this time frame if their slope did not overlap with the slope of the RNP control in their 95% intervals. Detection accuracy is the percentage of samples that were correctly identified as positive using this metric. The number of replicates for each concentration is as follows: 500 copies/µL (n=8), 200 copies/µL (n=7), 100 copies/µL (n=8), and 50 copies/µL (n=11). As shown, the assays can provide results in as little as 10 minutes but when low amounts of viral RNA are present, 20-30 minutes can provide more reliable results. FIG. 46E graphically illustrates results from a Cas13 assay run on the mobile device with two different nasopharyngeal samples from human patients, each confirmed as positive for SARS-CoV-2 using RT-qPCR, using the guide combination of crRNA 2, crRNA 4 and crRNA 21. The RNP alone control had no nasopharyngeal sample. FIG. 46F graphically illustrates the final signal slope values determined from the assays described in FIG. 46E after the assay mixtures were incubated for 60 minutes. FIG. 46G graphically illustrates the detection accuracy of Cas13 assays performed on n=5 nasal swab samples from human patients, confirmed as positive by RT-pPCR. Accuracy was assessed in the same way as samples in FIG. 46D, the slopes were evaluated at time=5, 10, 20 and 30 minutes incubation for each sample and compared to the slope of the RNP control at each of these times. As shown, accurate assays can be performed in as little as 5 minutes.

Figure 47A:
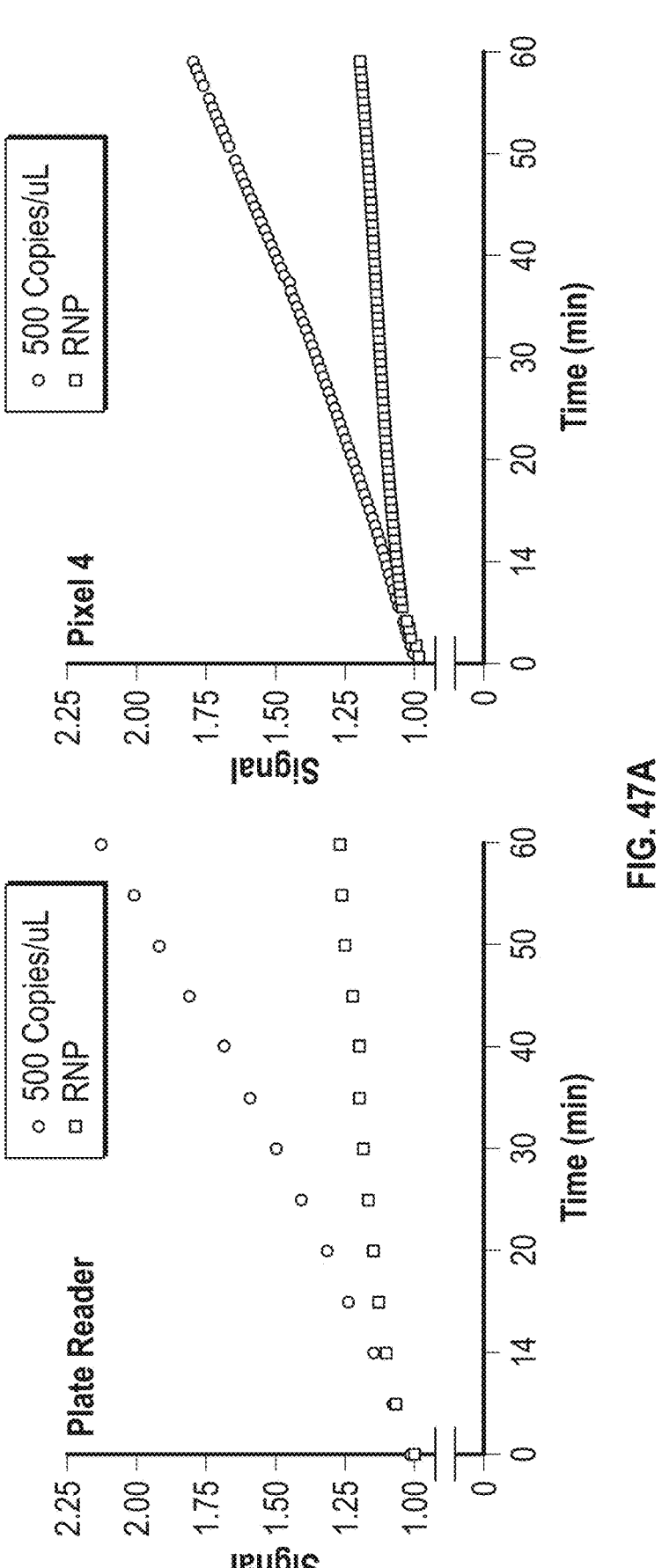
Figure 47B:
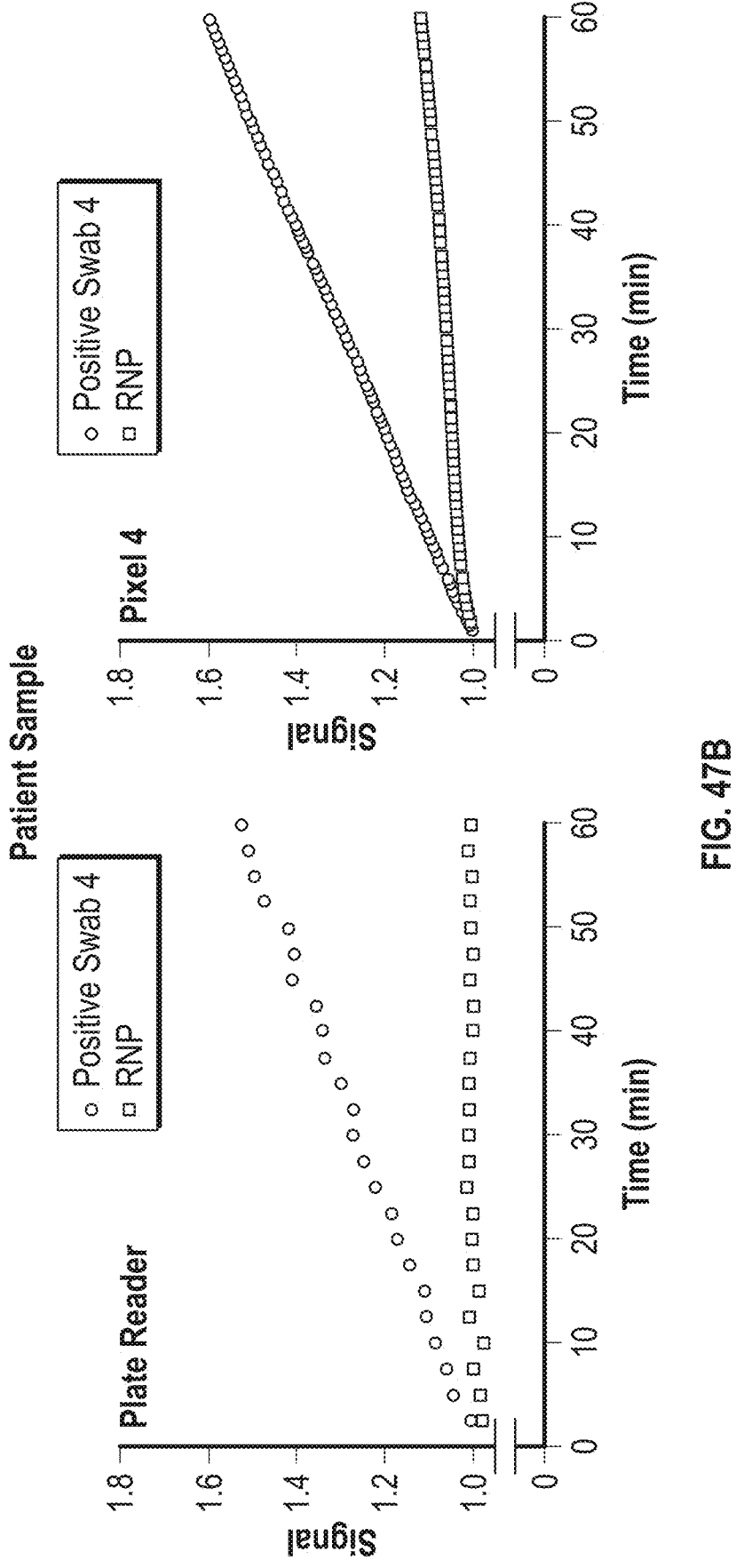

FIG. 47A-47B illustrate SARS-CoV-2 assays measured with a plate reader compared to measurement with the Mobile Phone Device. FIG. 47A graphically illustrates signals detected from SARS-CoV-2 assays of 500 copies/µL of SARS CoV-2 full genome RNA that employed the triple guide combination (crRNA 2, crRNA 4 and crRNA 21). Measurements were with the plate reader (left) or in the mobile phone device (right). FIG. 47B graphically illustrates signals detected from SARS-CoV-2 assays of Positive Swab #4 that employed the triple guide combination (crRNA 2, crRNA 4 and crRNA 21) with measurement in the plate reader (left) or in the mobile phone device (right).

Figure 48:
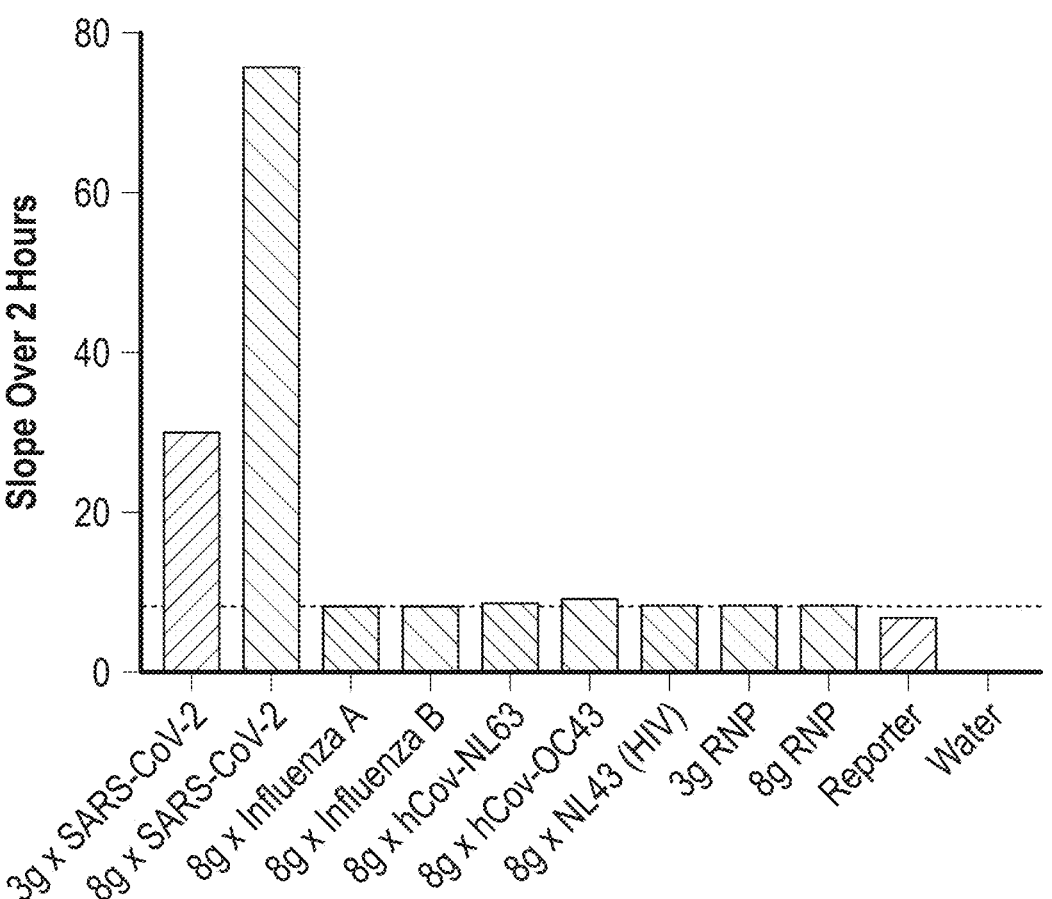

FIG. 48 illustrates that the 8G combination of crRNAs (SEQ ID NOs: 27-34) improved SARS-CoV-2 viral RNA detection compared to the 3G combination of crRNAs (SEQ ID NOs: 27, 28, and 35). The signals from the assay mixtures are shown as the slopes over two hours for each assay mixture. As shown, both of the 3G and 8G crRNA combinations can reliably detect SARS-CoV-2 (slopes greater than RNP controls), and both of the 3G and 8G crRNA combinations are specific for SARS-CoV-2 because signals from Influenza A, Influenza B CoV-NL63, CoV-OC43, and NL43(HIV) assays are indistinguishable from negative control (RNP) signals. However, use of the 8G crRNA combination greatly improving detection.

FIG. 49A-49C illustrate the limits of detection for the 8G combination of crRNAs (SEQ ID NOs: 27-34) using two different methods. FIG. 49A is a chart showing Method A where the number of replicate assays identified as positive are noted, when the different assays were incubated for different times and with different amounts of SARS-CoV-2 RNA. The SARS-CoV-2 RNA was used at 100, 50, or 10 copies per ul in the different assay mixtures and these assay mixtures were incubated for 30 min, 60 min, or 120 min. Twenty (20) replicates were compared individually pursuant to FDA guidelines, with limit of detection (LOD) defined as a concentration (copes per ul) where 19/20 samples are positive. LOD in this assay is 10 copies per ul at 2 hours. FIG. 49B is a graph showing the limits of detection for the 8G combination of crRNAs (SEQ ID NOs: 27-34) determined using Method B when the assays were incubated for 30 minutes. The assay mixtures contained the 8G combination of crRNAs (as RNPs complexed with Cas13a) as well as 0 copies per µl, 10 copies per µl, 50 copies per µl, or 100 copies per µl of SARS-CoV-2 RNA. An average of 20 replicates was compared to determine the limit of detection. FIG. 49C is a graph showing the limits of detection for the 8G combination of crRNAs (SEQ ID NOs: 27-34) determined using Method B when the assays were incubated for 120 minutes. The assay mixtures contained the 8G combination of crRNAs (as RNPs complexed with Cas13a) as well as 0 copies per µl, 10 copies per µl, 50 copies per µl or 100 copies per µl of SARS-CoV-2 RNA. An average of 20 replicates was compared to determine the limit of detection. As illustrated, incubation for 30 minutes is generally sufficient, but longer incubations can be useful for detecting low copy numbers.

Figure 50:
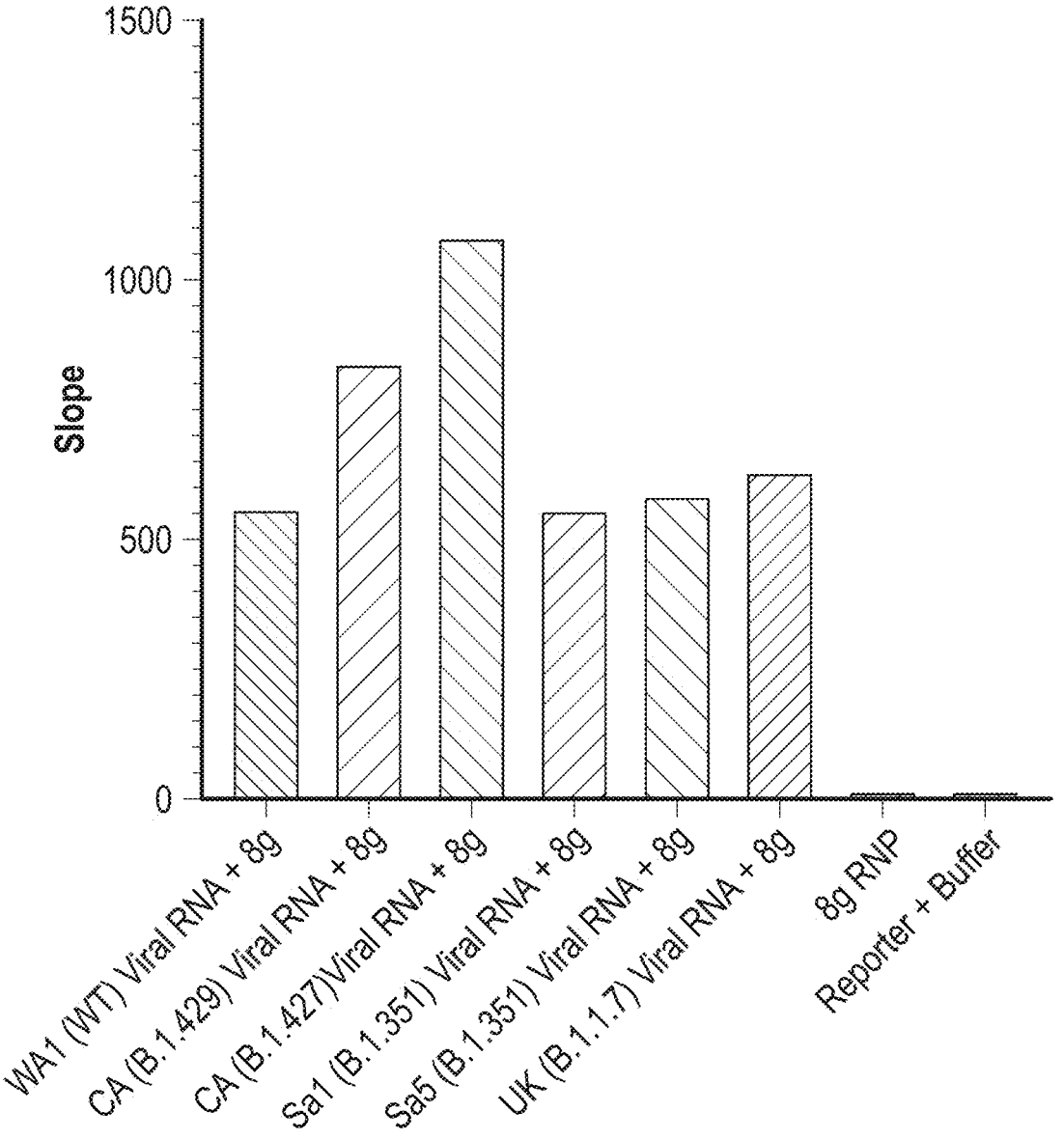

FIG. 50 illustrates detection of several SARS-CoV-2 strains and variants using a combination of eight-crRNA guides (the 8G combination) described in Table 4. As shown, the 8G combination is useful for detecting various SARS-CoV-2 strains, including Wuhan, UK, South Africa, and California variants. The WA1 strain was deemed to be the wild type strain (originally detected and isolated in Washington state).

FIG. 51A-51B illustrate how a key was developed for distinguishing wild type and mutant SARS-CoV-2 strains. FIG. 51A shows an algorithm for determining whether SARS-CoV-2 detected in a sample is wild type SARS-CoV-2 or mutant SARS-CoV-2. The signals from wild type and variant SARS-CoV-2 assays containing crRNAs for wild type SARS-CoV-2 (e.g., the 8G crRNA combination) or for variant SARS-CoV-2 (see Table 5), respectively, were separately measured over 2 hours. The slopes of these signals were calculated. Slope ratios were then calculated by dividing the slope of a guide RNA+target (i.e. RNP+target RNA) reaction by the slope of guide RNA+no target (i.e. RNP only) reaction. The wild type slope ratio is divided by the variant slope ratio to provide a comparative ratio between wild type and variant SARS-CoV-2 strains. FIG. 51B shows a graph key where the comparative ratio between wild type and variant California (CA) SARS-CoV-2 strains is shown on the Y-axis using a log 2 scale. When the comparative ratio is high (greater than 1), the guide RNAs employed in the assay mixture detects wild type (e.g., WA1) strains more efficiently. But when the comparative ratio is low (less than 1), the guide RNAs employed in the assay mixture detect variant strains (e.g., CA variant strains) more efficiently.

Figures 52A, 52B:
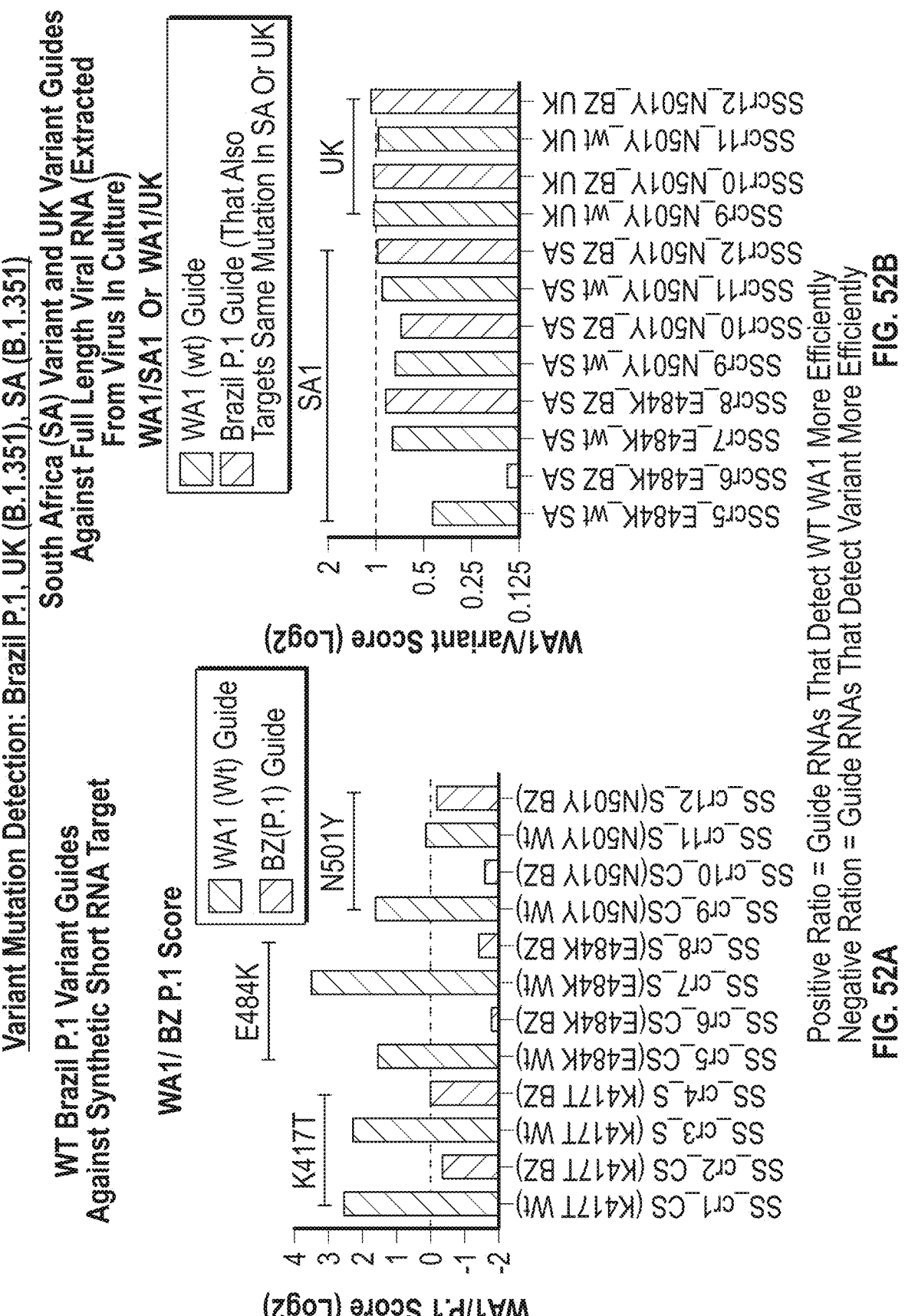

FIG. 52A-52B illustrate wild type:variant comparative scores, illustrating that WA1 (wild type) crRNAs can identify that a SARS-CoV-2 is present and use of the indicated guide RNAs that target specific mutations can identify which variant or mutant SARS-CoV-2 strain is responsible for the infection. FIG. 52A shows a comparative graph illustrating that use of different variant crRNAs designed to detect either wild type or variant SARS-CoV-2 Brazil P.1 strains (see Table 5) can distinguish wild type and variant K417T, E484K, and N501Y mutations in Brazilian SARS-CoV-2 strains when tested against synthetic RNA. The x-axis shows the name of the target RNA employed and whether it is wild or variant SARS-CoV-2. FIG. 52B shows a comparative graph illustrating that the crRNAs also efficiently detected the E484K mutation when tested against full length viral RNA. Such variant crRNAs are designed to be specific for a particular mutation and can detect the same mutation that is in other strains, such as UK and South African SARS-CoV-2 strains. Use of WA1 crRNAs can identify that a SARS-CoV-2 is present and use of the guide RNAs that target specific mutations can identify which variant SARS-CoV-2 strain is responsible for the infection and even which type(s) of SARS-CoV-2 mutations are present.

FIG. 53A-53B illustrate that crRNAs described in Table 5 can distinguish mutant California (CA (B.1.429) strains from their wild type parental strains. FIG. 53A shows detection of wild type and variant strains using crRNAs designed by the Sherlock method. FIG. 53B shows detection of wild type and variant strains using crRNAs designed by the Central Seed (CS) method. As illustrated, the wild type:variant comparative slope ratios identify JS_cr034 crRNA as a WA1 specific guide RNA while the JS_cr037, JS_cr043, JS_cr045, JS_cr047 guides are CA specific guide RNAs. The SARS-CoV-2 wild type and mutation positions detected by the crRNAs are shown below in the graphs. An especially promising guide for detecting a ORF1AB: I4205_wt mutation in a wild strain was identified as being the JS_cr034_14205V_wtA crRNA guide. Promising guides for detecting the Spike S13I_mut mutation found in CA clade 20C were identified as being the JS_cr037_S13I_mutA crRNA and the JS_cr045_S13I_mutB crRNA. A promising guide for detecting ORF1AB:D1183Y_mut mutation found in CA clade 20C was identified as being the JS_cr043_D1183Y_mutB crRNA. A promising guide for detecting Spike:W152C_mut mutation found in CA clade 20C was identified as being the JS_cr047_W152C_mutB crRNA.

Figures 54A, 54B:
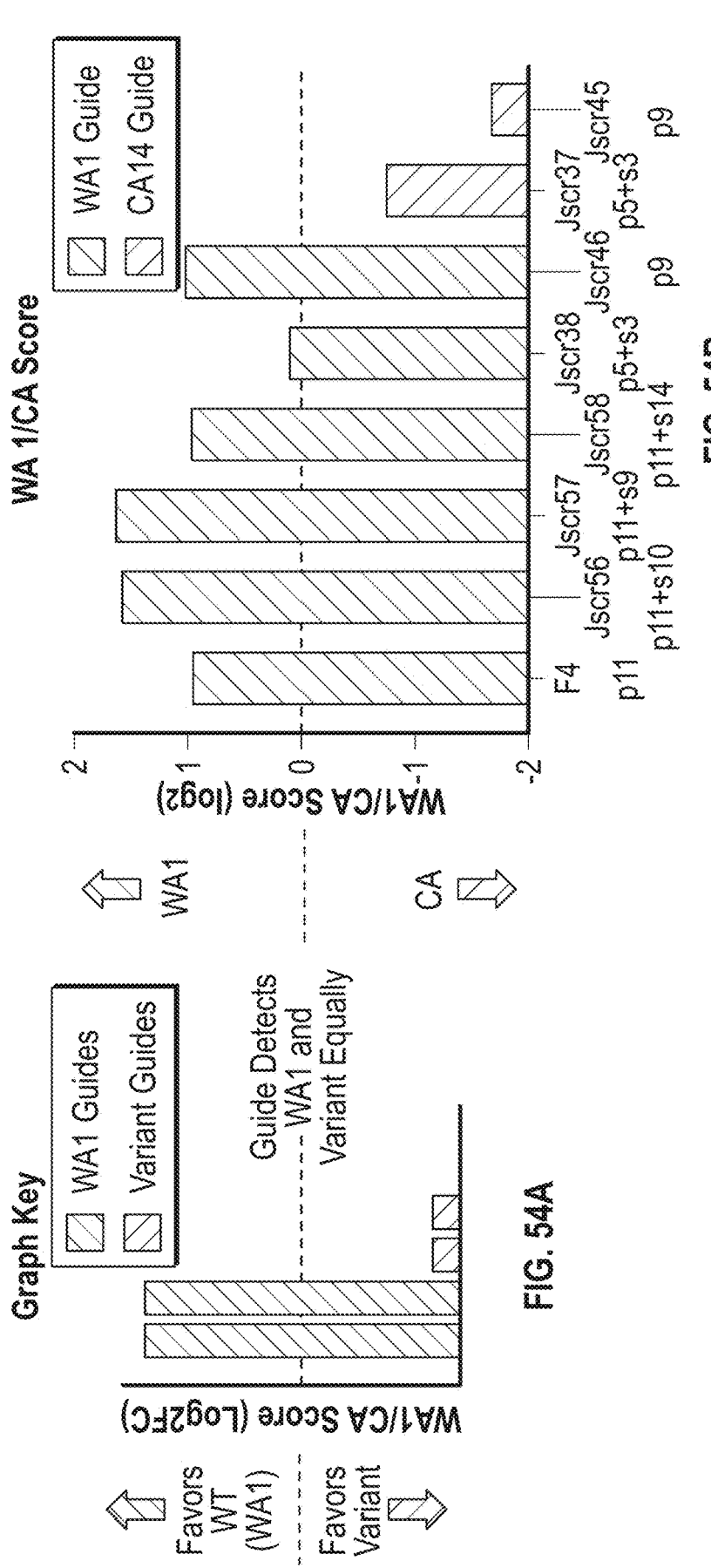

FIG. 54A-54B illustrate that crRNAs described in Table 5 can distinguish variant and mutant California (CA B.1.429) strains. FIG. 54A shows a graph key where the comparative ratio between wild type and variant California (CA) SARS-CoV-2 strains is shown on the Y-axis using a log 2 scale. When the comparative ratio is high (greater than 1), the guide RNAs employed in the assay mixture detects wild type (e.g., WA1) strains more efficiently. But when the comparative ratio is low (less than 1), the guide RNAs employed in the assay mixture detect variant strains (e.g., CA variant strains) more efficiently. FIG. 54B illustrates detection of 20C CA/B.1.429 mutant and wild type SARS-CoV-2 of the California (CA) clade using various crRNAs designed to detect such SARS-CoV-2 strains (see Table 5). Some crRNAs designed by the Sherlock method. This experiment demonstrates that JScr56, JScr57, JScr58, JScr46 guides are specific for WA1 (wt) and JScr37, JScr45 are guides specific for the CA strain.

Figure 55:
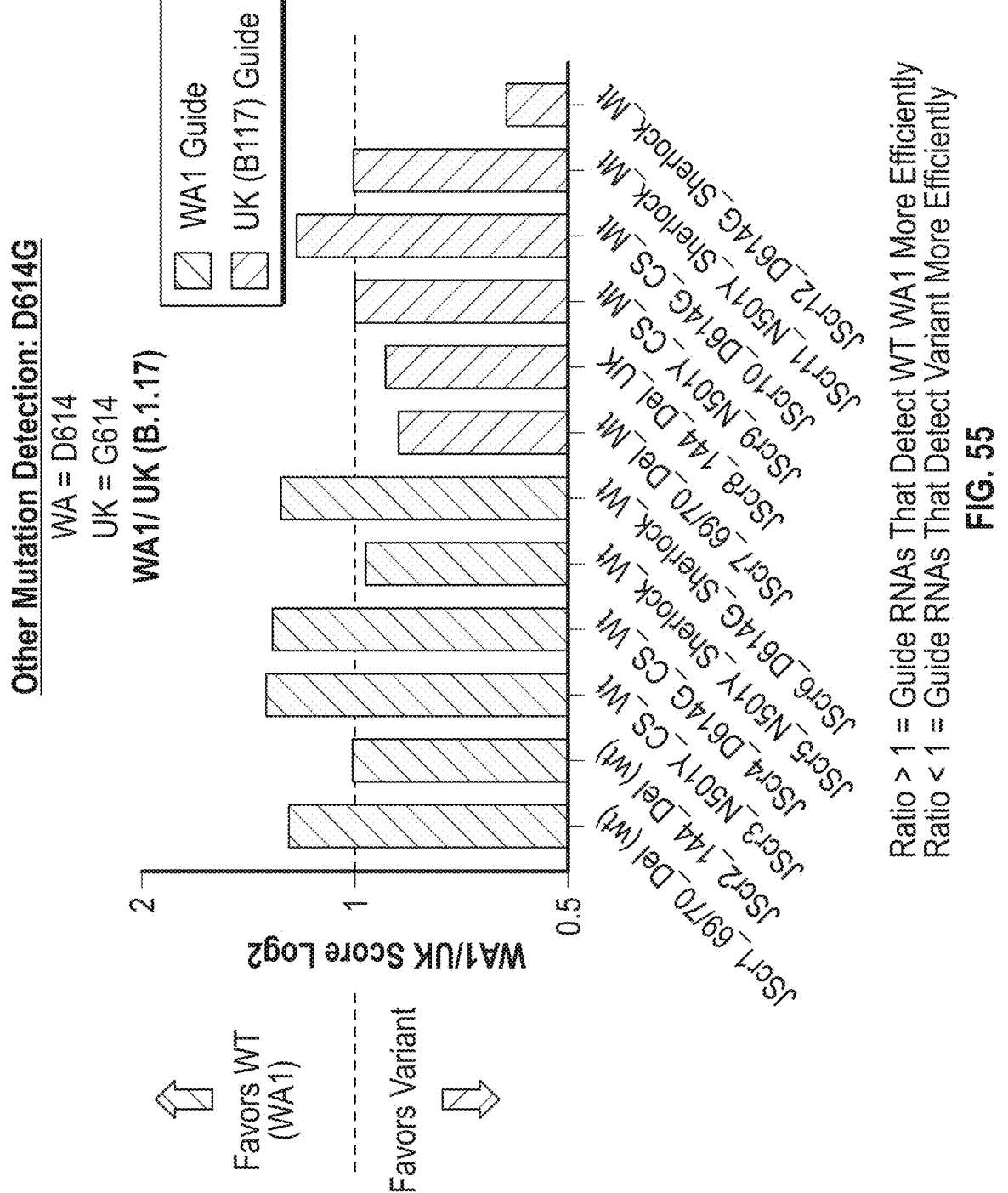

FIG. 55 illustrates detection of a specific mutation (D614G) in wild type SARS-CoV-2 (WA1 with the D614 amino acid in the Spike protein) and variant SARS-CoV-2 (UK and several others with the G614 amino acid in the Spike protein) using some of the crRNAs described in Table 5. To obtain the data in FIG. 55, several crRNA were tested against samples containing various mutations of interest in newly circulating strains. FIG. 55 demonstrates which guide RNAs are good at differentiating between D614 vs. G614 mutations (using JScr4 vs. JScr12, respectively). Hence the crRNAs described herein can detect strains with the spike D614G amino acid mutation caused by an A-to-G nucleotide mutation at position 23,403 in the Wuhan reference strain.

Figure 56:
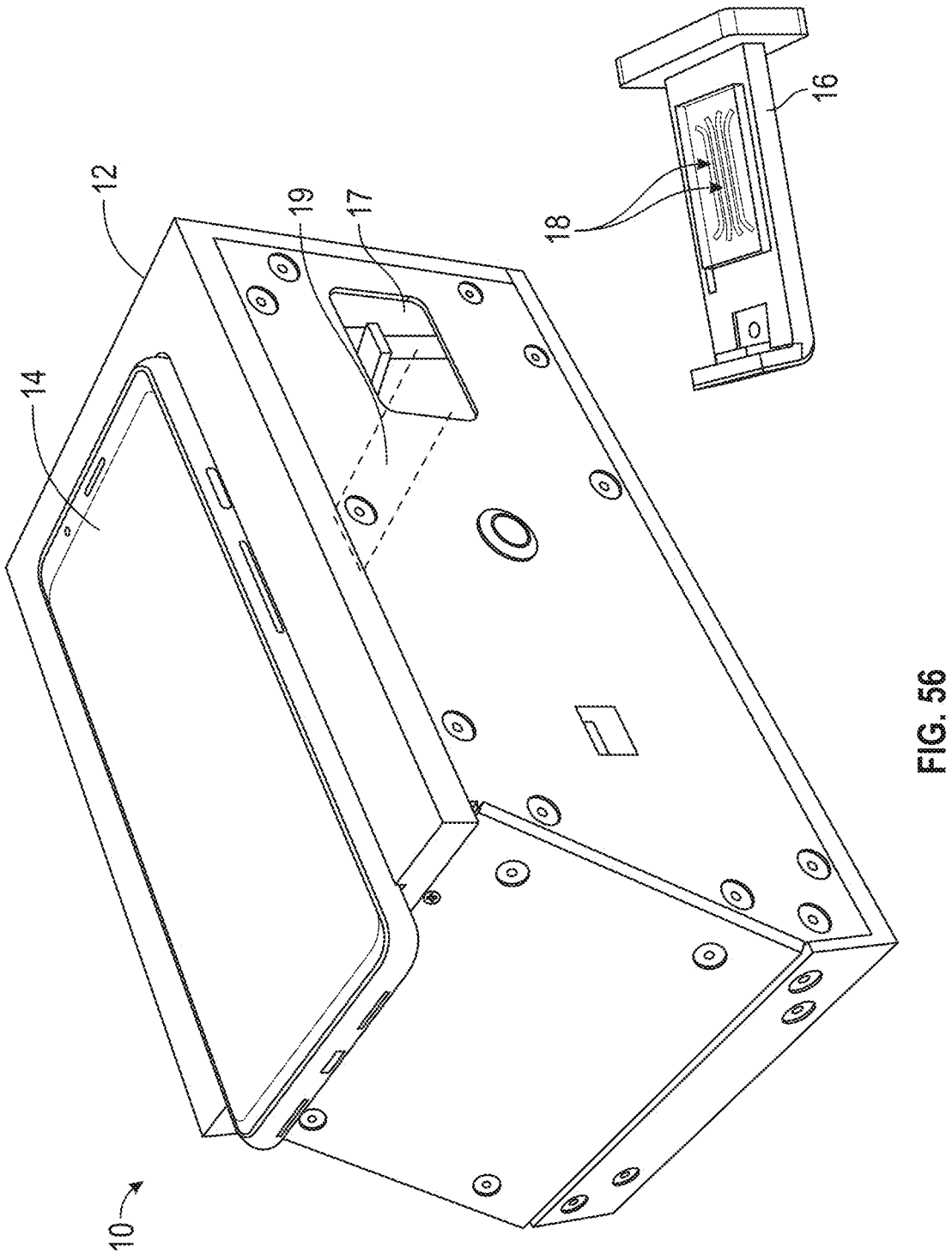

FIG. 56 illustrates one example of a fluorescence imaging system. Example design details are provided herein.

Figure 57:
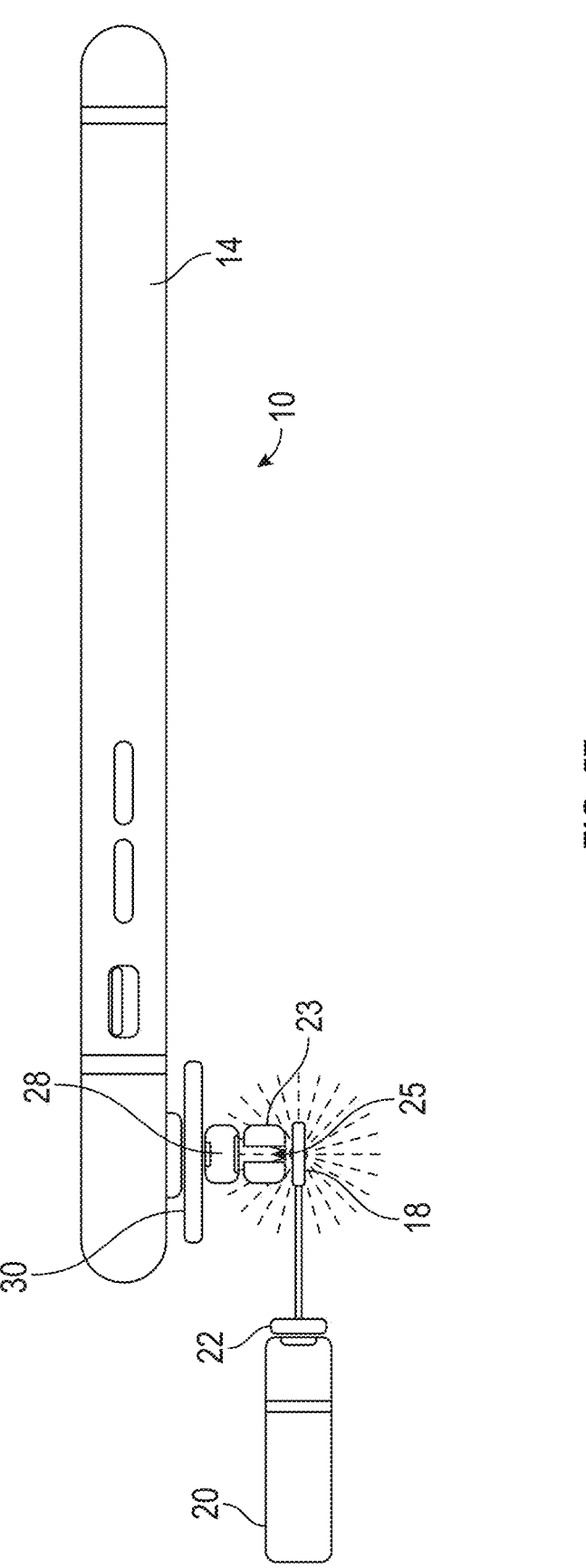
Figure 60:
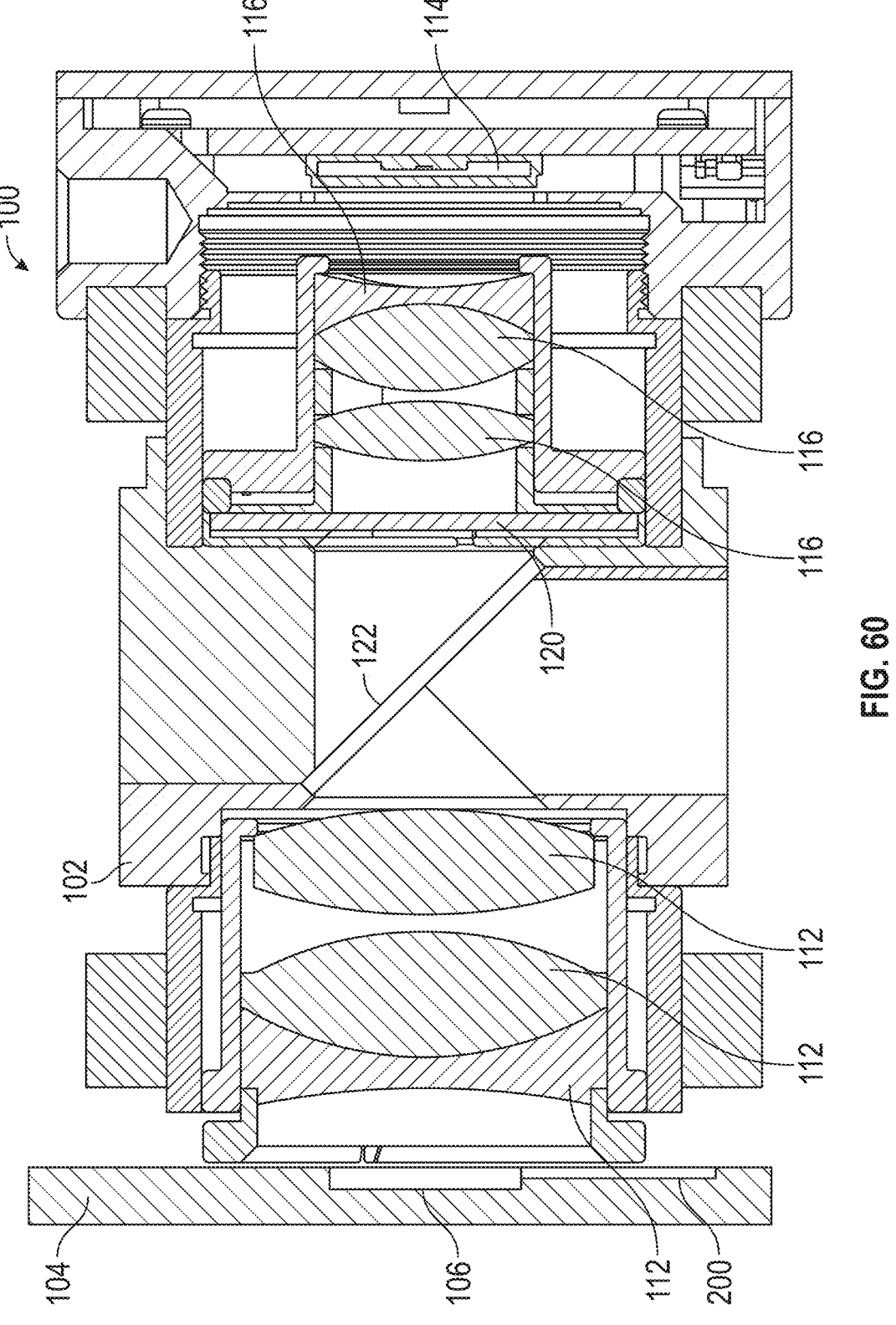

FIG. 57 illustrates a schematic view of the fluorescence imaging system of FIG. 60.

Figure 58A:
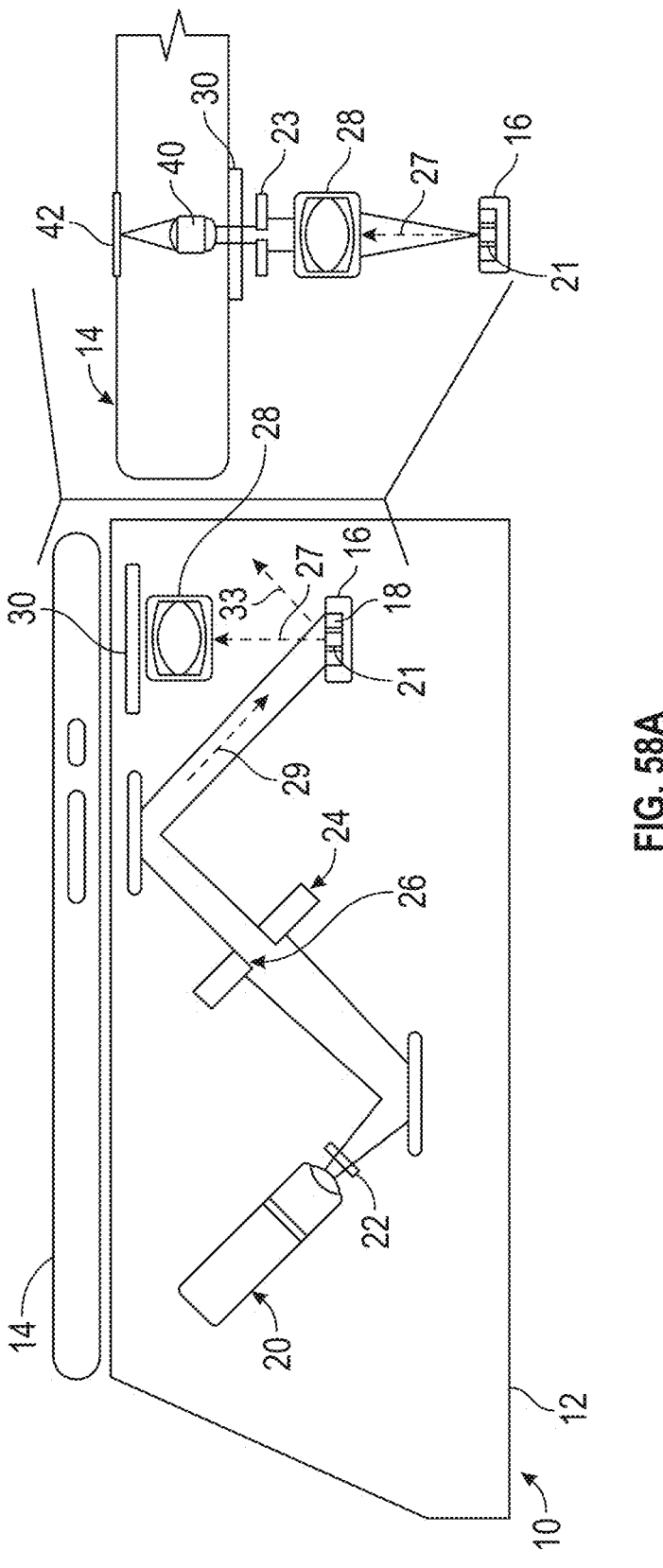

FIG. 58A illustrates companion schematic views of the fluorescence imaging system of FIG. 56 including an observation orientation of samples relative to an excitation source.

Figure 58B:
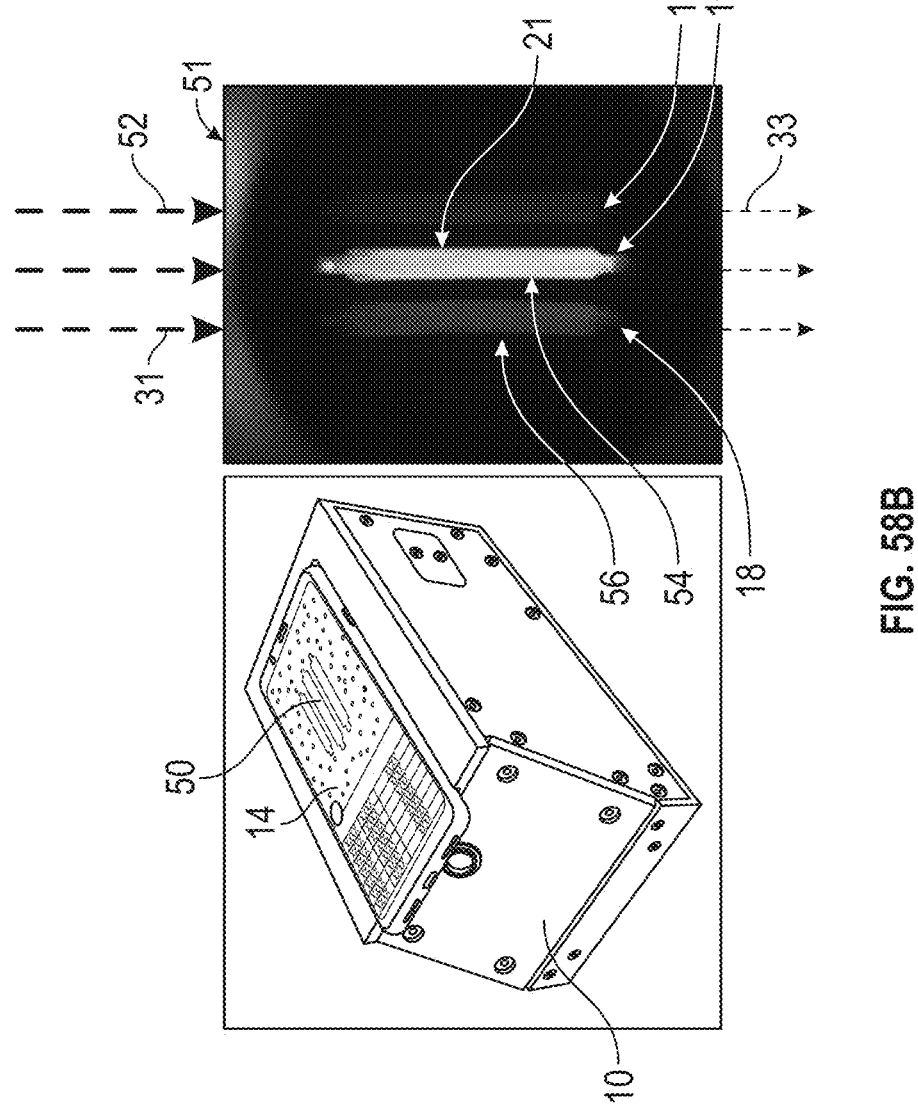

FIG. 58B illustrates companion views of the fluorescence imaging system of FIG. 56 with an example fluorescence profile.

Figure 59A:
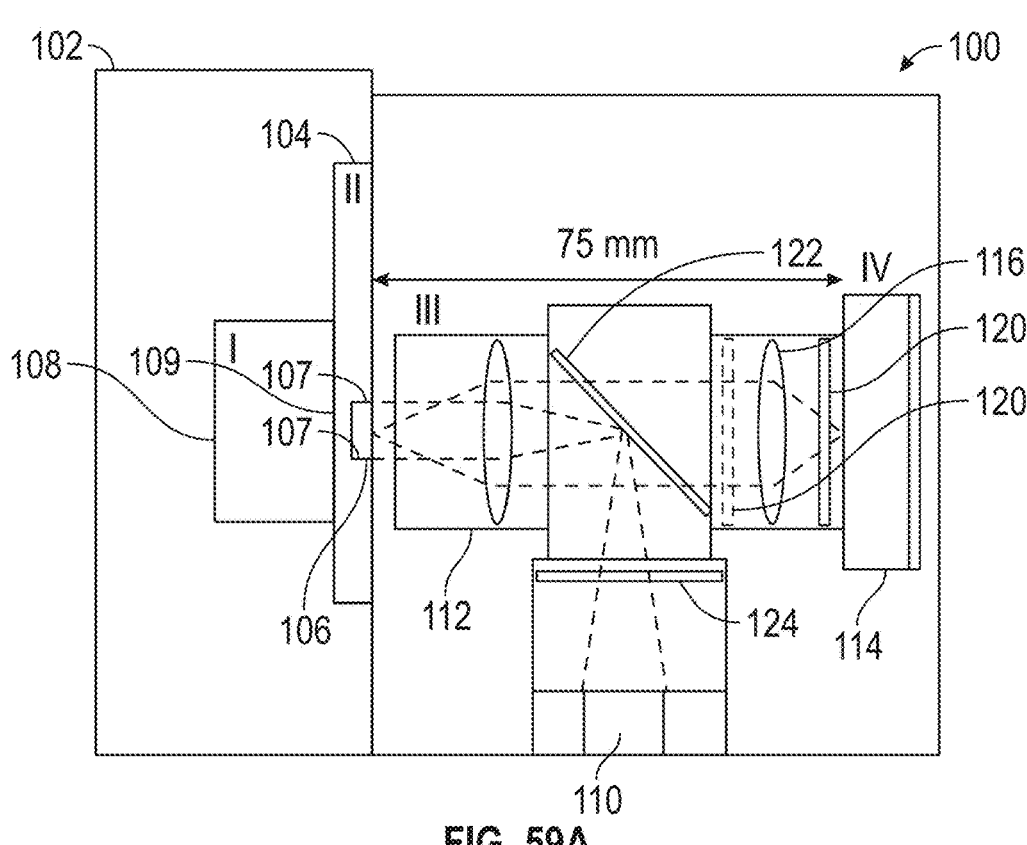

FIG. 59A illustrates another example of a fluorescence imaging system. Example design details are provided herein.

Figure 59B:
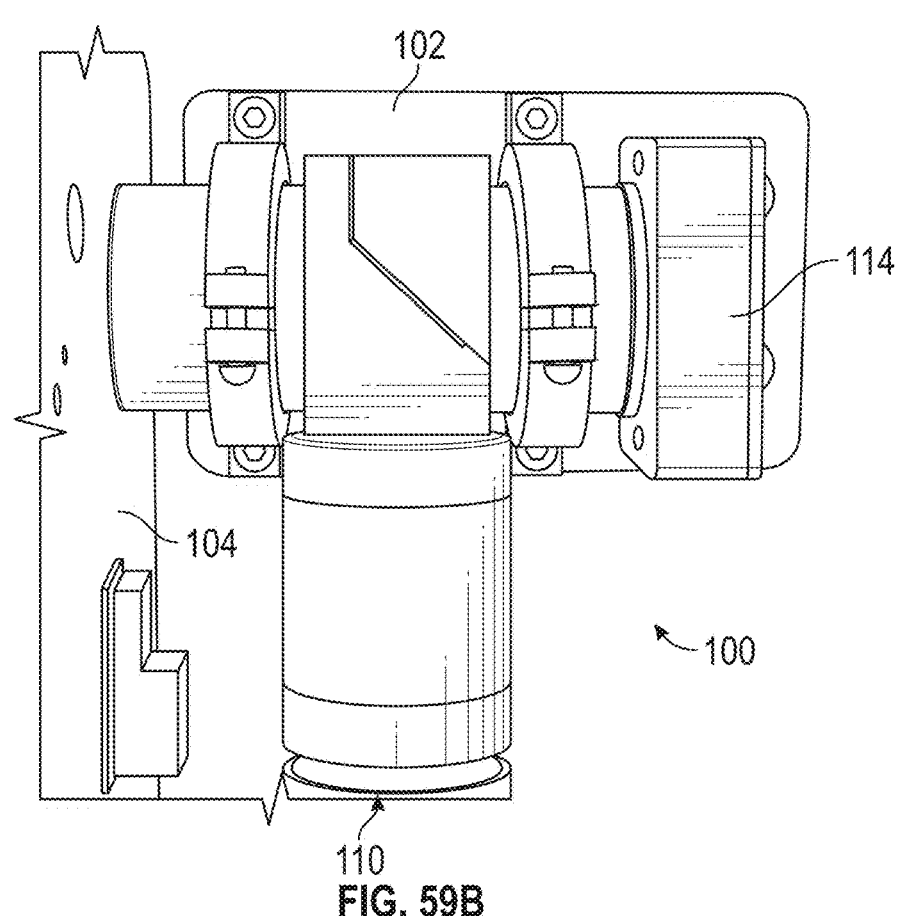

FIG. 59B illustrates a side view of the fluorescence imaging system of FIG. 59A.

FIG. 60 illustrates a cross sectional view of the fluorescence imaging system of FIG. 56B.

Figure 61:
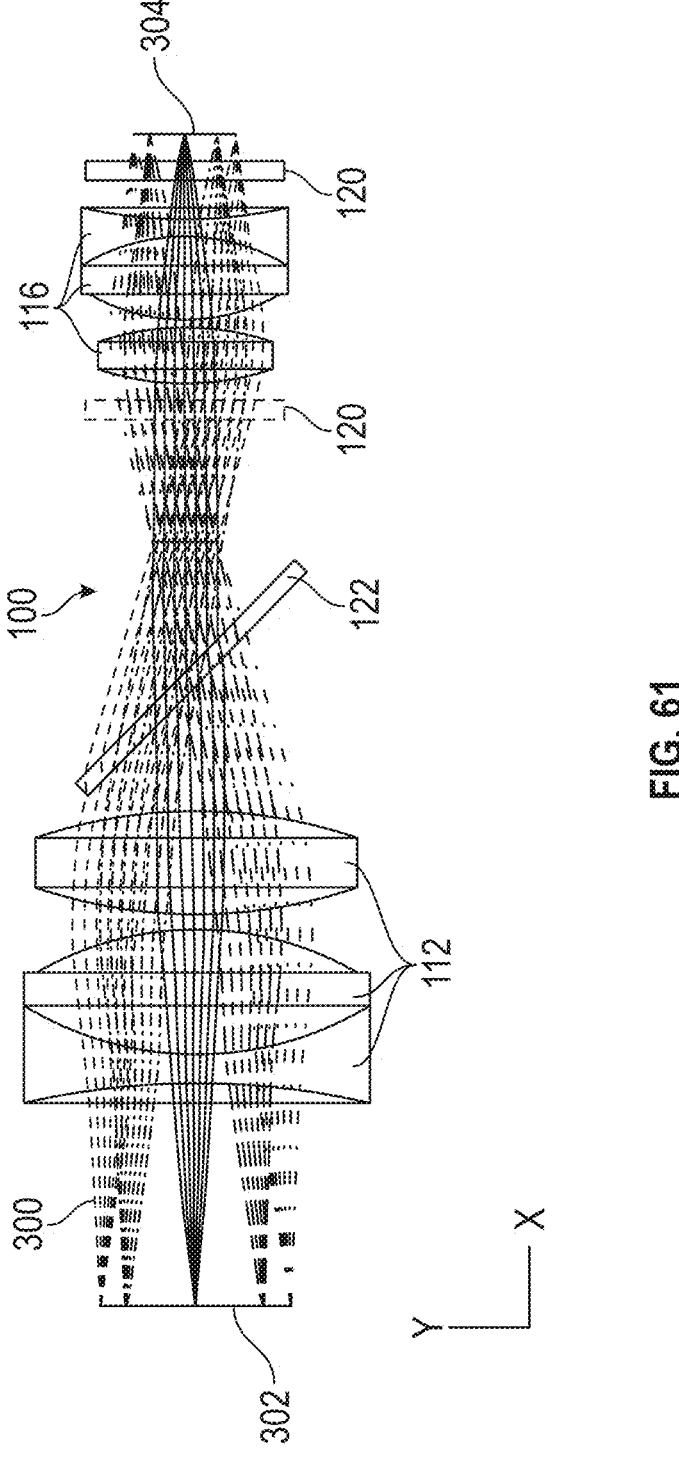

FIG. 61 illustrates one example of an optical layout based on the fluorescence imaging system shown in FIG. 60.

Figures 62A, 62B:
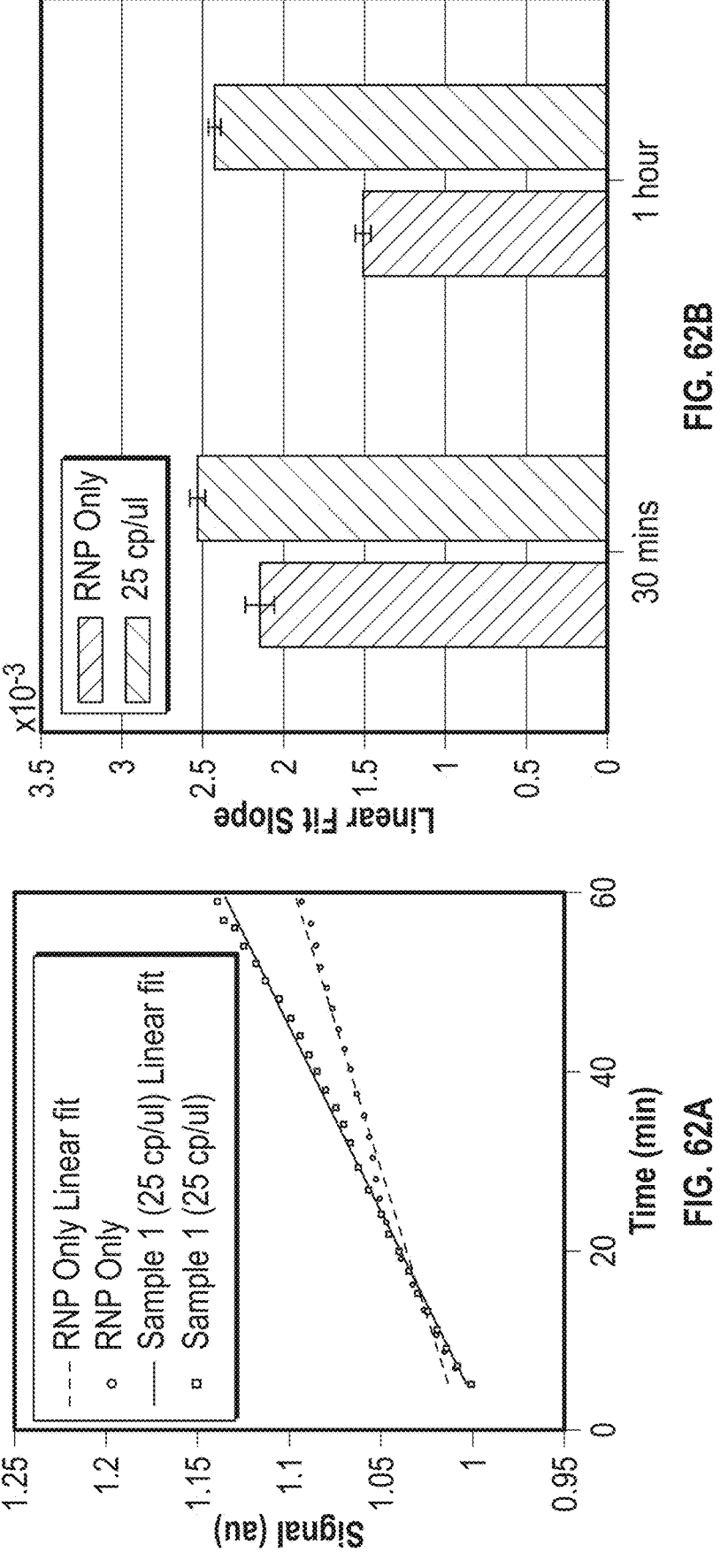

FIGS. 62A-62B illustrate one prophetic example of sensitivity of a fluorescence imaging system described herein.

DETAILED DESCRIPTION

Described herein are methods, kits, compositions, and devices for detecting and/or quantifying SARS-CoV-2 viral infections. Since its emergence in late December 2019 in Wuhan, Hubei Province, China, coronavirus disease 2019 (COVID-19) has infected more than 214,894 people globally (Dong et al. (February 2020)). The novel causative virus, SARS-CoV-2, was determined to belong to the *Betacoronavirus* genera, with 70% similarity at the genome level to SARS-CoV. Similar to SARS-CoV, SARS-CoV-2 uses the angiotensin-converting enzyme 2 (ACE2) as a cellular receptor (Yan et al. (March 2020); Hoffman et al. (March 2020); Walls et al. (March 2020).

As the virus continues to spread globally and in the United States, rapid, accurate testing to diagnose patients has become essential. Current tests for COVID-19 are based on RT-qPCR assays. The World Health Organization reported various primer sets by the governments of China, Germany, Hong Kong, Thailand, and the United States. In the US in particular, technical challenges with the first test developed by the CDC left the nation with minimal diagnostic capacity during the first weeks of the pandemic (Sharfstein et al. (March 2020)). A qualitative test for SARs-CoV-2 RNA that is easy to handle and field-deployable could rapidly increase diagnostic capacity and allow screening at airports, borders, and clinics.

Methods, kits and devices are described herein for rapidly detecting and/or quantifying SARs-CoV-2. The methods can include (a) incubating a sample suspected of containing SARS-CoV-2 RNA with a Cas13 protein, at least one CRISPR guide RNA (crRNA), and a reporter RNA for a period of time sufficient to form one or more reporter RNA cleavage product(s); and (b) detecting level(s) of reporter RNA cleavage product(s) with a detector. Such methods are useful for detecting whether the sample contains one or more copies of a SARS-CoV-2 RNA. The methods are also useful for detecting the absence of a SARS-CoV-2 infection.

In some aspects provided herein are methods for diagnosing the presence or absence of an SARS-CoV-2 infection comprising incubating a mixture comprising a sample suspected of containing SARS-CoV-2 RNA, a Cas13 protein, at least one CRISPR guide RNA (crRNA), and a reporter RNA for a period of time to form any reporter RNA cleavage product(s) that may be present in the mixture; and detecting level(s) of reporter RNA cleavage product(s) that may be present in the mixture with a detector. In some cases, the SARS-CoV-2 RNA in a sample and/or the RNA cleavage products are not reverse transcribed prior to the detecting step. The presence or absence of a SARS-CoV-2 infection in patient is detected by qualitatively or quantitatively detecting level of reporter RNA cleavage product(s) that may be present in the mixture.

The methods described herein have various advantages. For example, the methods described herein can directly detect RNA without additional manipulations. No RNA amplification is generally needed, whereas currently available methods (e.g., SHERLOCK) require RNA amplification to be sufficiently sensitive. The methods, kits, and devices described herein ar rapid, providing results within 30 minutes. Expensive lab equipment and expertise is not needed. The methods described herein are amenable to many different sample types (blood, nasal/oral swab, etc.). The methods, kits, and devices described herein are easily deployable in the field (airport screenings, borders, resource poor areas) so that potentially infected people will not need to go to hospitals and clinics where non-infected patients, vulnerable persons, and highly trained, urgently needed medical people may be. While testing has been largely been performed in medical facilities or clinics, the easy deployment of the methods disclosed herein facilitate rapid testing in the field. Testing can also extend beyond those isolated in facilities needed for vulnerable populations and trained personnel needed for urgent and complex medical procedures.

CRISPR-Cas13 has emerged as a viable alternative to conventional methods of detecting and quantifying RNA by RT-PCR. The advantages of using CRISPR-Cas13 can be leveraged for SARS-CoV-2 diagnostics. The Cas13 protein targets RNA directly, and it can be programmed with crRNAs to provide a platform for specific RNA sensing. By coupling it to an RNA-based reporter, the collateral or non-specific RNase activity of the Cas13 protein can be harnessed for SARS-CoV-2 detection.

Although the limit of detection for SARS-CoV-2 has not been fully explored, recent reports indicate that pharyngeal virus shedding is very high during the first week of symptoms (peak at $7.11 \times 10^1$ copies/throat swab). The average viral RNA load was $6.769 \times 10^5$ copies/swab through day 5 of symptoms (Woelfel (March 2020)). Earlier in 2017 and 2018, the laboratory of Dr. Feng Zhang reported a Cas13-based detection system that reached attomolar and zeptomolar sensitivity in detecting Zika virus, but it included an additional reverse transcription step for isothermal amplification of Zika virus cDNA, which was ultimately back-transcribed into RNA for RNA-based detection, a method referred to as SHERLOCK (Specific High Sensitivity Enzymatic Reporter UnLOCKing) (Gootenberg et al. Science 356(6336):438-42 (2017): Gootenberg et al. Science 360 (6387): 439-44 (2018)). Although this method improved the sensitivity of Cas13, it introduced two unwanted steps involving reverse transcription and in vitro transcription, which minimizes its potential as a field-deployable and point-of-care device.

The present disclosure provides methods and compositions for diagnosing SARS-CoV-2 infections, quantifying SARS-CoV-2 RNA concentrations, identifying the presence of different SARS-CoV-2 splice variants and/or mutations, and/or monitoring reactivation of SARS-CoV-2 transcription.

In some cases, the methods can be performed in a single tube, for example, the same tube used for collection and RNA extraction. This method provides a single step point of care diagnostic method. In other cases, the methods can be performed in a two-chamber system. For example, the collection swab containing a biological sample can be directly inserted into chamber one of such a two chamber system. After agitation, removal of the swab, and lysis of biological materials in the sample, the division between the two chambers can be broken or removed, and the contents of the first chamber can be allowed to flow into the second chamber. The second chamber can contain the Cas13 protein, the selected crRNA(s), and the reporter RNA so that the assay for SARS-CoV-2 can be performed.

Chamber one can contain a buffer that would facilitate lysis of the viral particles and release of genomic material. Examples of lysis buffers that can be used include, but are not limited to PBS, commercial lysis buffers such as Qiagen RLT+buffer or Quick Extract, DNA/RNA Shield, and various concentrations of detergents such as Triton X-100, Tween 20, NP-40, or Oleth-8.

Following agitation and subsequent removal of the swab, the chamber may be briefly (e.g., 2-5 mins) heated (e.g., 55° C. or 95° C.) to further facilitate lysis. Then, the division between the two chambers would be broken or removed, and the nasal extract buffer would be allowed to flow into and reconstitute the second chamber, which would contain the lyophilized reagents for the Cas13 assay (Cas13 RNPs and reporter RNA molecules).

Use of such assay tubes can provide single step point of care diagnostic methods and devices.

The methods, devices and compositions described herein for diagnosing SARS-CoV-2 infection can involve incubating a mixture having a sample suspected of containing SARS-CoV-2 RNA, a Cas13 protein, at least one CRISPR RNA (crRNA), and a reporter RNA for a period of time to form reporter RNA cleavage products that may be present in the mixture and detecting a level of any such reporter RNA cleavage products with a detector. The detector can be a fluorescence detector such as a short quenched-fluorescent RNA detector, or Total Internal Reflection Fluorescence (TIRF) detector.

The reporter RNA can, for example, be at least one quenched-fluorescent RNA reporter. Such quenched-fluorescent RNA reporter can optimize fluorescence detection. The quenched-fluorescent RNA reporters include an RNA oligonucleotide with both a fluorophore and a quencher of the fluorophore. The quencher decreases or eliminates the fluorescence of the fluorophore. When the Cas13 protein cleaves the RNA reporter, the fluorophore is separated from the associated quencher, such that a fluorescence signal becomes detectable.

One example of such a fluorophore quencher-labelled RNA reporter is the RNaseAlert (IDT). RNaseAlert was developed to detect RNase contaminations in a laboratory, and the substrate sequence is optimized for RNase A species. Another approach is to use lateral flow strips to detect a FAM-biotin reporter that, when cleaved by Cas13, is detected by anti-FAM antibody-gold nanoparticle conjugates on the strip. Although this allows for instrument-free detection, it requires 90-120 minutes for readout, compared to under 30 minutes for most fluorescence-based assays (Gootenberg et al. Science. 360(6387):439-44 (April 2018)).

The sequence of the reporter RNA can be optimized for Cas13 cleavage. Different Cas13 homologs can have different sequence preferences at the cleavage site. In some cases, Cas13 preferentially exerts RNase cleavage activity at exposed uridine sites or adenosine sites. There are also secondary preferences for highly active homologs.

The fluorophores used for the fluorophore quencher-labelled RNA reporters can include Alexa Fluor® 430, STAR 520, Brilliant Violet™510, Brilliant Violet™605, Brilliant Violet™610, or a combination thereof.

The fluorophores used for the fluorophore quencher-labelled RNA reporters can include Dabcyl, QSY 7, QSY 9, QSY 21, QSY 35, Iowa Black Quencher (IDT), or a combination thereof. Many quencher moieties are available, for example, from ThermoFisher Scientific.

The inventors have tested 5-mer homopolymers for all ribonucleotides. Based on these preferences, various RNA oligonucleotides, labeled at the 5' and 3' ends of the oligo-nucleotides using an Iowa Black Quencher (IDT) and FAM fluorophore, and systematically test these sequences in the trans-ssRNA cleavage assay as described in the Examples. The best sequence can be used in the methods and devices described herein. Such reporter RNAs can also be used in kits and for mobile device testing.

Various mechanisms and devices can be employed to detect fluorescence. Some mechanism or devices can be used to help eliminate background fluorescence. For example, reducing fluorescence from outside the detection focal plane can improve the signal-to-noise ratio, and consequently, the resolution of signal from the RNA cleavage products of interest. Total internal reflection fluorescence (TIRF) enables very low background fluorescence and single molecule sensitivity with a sufficiently sensitive camera. As described herein mobile phones now have sufficient sensitivity for detection of SARS-CoV-2 RNA.

In some cases, both Cas13 and reporter RNA were tethered to a solid surface, upon addition of crRNA and SARS-CoV-2 RNA samples, an activated Cas13 can generate small fluorescent spots on the solid surface when imaged using Total Internal Reflection Fluorescence (TIRF). To optimize this case, the fluorophore side of reporter RNA is tethered to the solid surface as well so that cleavage permits the quencher portion of the reporter RNA to diffuse away. The Cas13 protein can be tethered to the solid surface with a tether that is long enough to allow it to cleave multiple RNA reporter molecules. Counting the bright spots emerging on the solid surface the viral load can be quantified. Use of TIRF in the portable system facilitates detection and reduces background so that the RNA cleavage product signals can readily be detected.

In some cases, a ribonucleoprotein (RNP) complex of the Cas13 protein and the crRNA can be tethered to the solid surface. The crRNA would then not need to be added later. Instead, only the sample suspected of containing SARS-CoV-2 RNA would need to be contacted with the solid surface.

In some cases, a biological sample is isolated from a patient. Non-limiting examples of suitable biological samples include saliva, sputum, mucus, nasopharyngeal samples, blood, serum, plasma, urine, aspirate, and biopsy samples. Thus, the term "sample" with respect to a patient can include RNA. Biological samples encompass saliva, sputum, mucus, and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, washed, or enrichment for certain cell populations. The definition also includes sample that have been enriched for particular types of molecules, e.g., RNAs. The term "sample" encompasses biological samples such as a clinical sample such as saliva, sputum, mucus, nasopharyngeal samples, blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived from cells and/or viruses (e.g., from infected cells). A sample containing RNAs can be obtained from such cells (e.g., a cell lysate or other cell extract comprising RNAs). A sample can comprise, or can be obtained from, any of a variety of bodily fluids (e.g., saliva, mucus, or sputum), cells, tissues, organs, or acellular fluids.

In some cases, the biological sample is isolated from a patient known to have or suspected to have SARS-CoV-2. In other cases, the biological sample is isolated from a patient not known have SARS-CoV-2. In other cases, the biological sample is isolated from a patient known to have, or suspected to not have, SARS-CoV-2. In other words, the methods and devices described herein can be used to identity subjects that have SARS-CoV-2 infection and to confirm that subjects do not have SARS-CoV-2 RNA infection.

In some cases, it may not be known whether the biological sample contains RNA. How-ever, such biological samples can still be tested using the methods described herein. For example, biological samples can be subjected to lysis. RNA extraction, incubation with Cas13 and crRNAs, etc. whether or not the sample actually contains RNA, and whether or not a sample contains SARS-CoV-2 RNA.

In some cases, sample that may contain RNA that is incubated with a Cas13 protein (some previously known as C2c2). When a crRNA is present, the Cas13 proteins bind and cleave RNA substrates, rather than DNA substrates, to which Cas9 can bind. Cas13 contains two Higher Eukaryotes and Prokaryotes Nucleotide-binding (HEPN) domains for RNA cleavage, consistent with known roles for HEPN domains in other proteins. In some cases, the Cas13 proteins can have sequence variation and/or be from other organisms. For example, the Cas13 proteins can have at least 75%, at least 80%, at least 85%, at least 90%, at least 95%, at least 98%, at least 99%, or 100% sequence identity to any of the foregoing Cas 13 sequences or to a Cas13 in the following bacteria: *Leptotrichia wadei, Leptotrichia buccalis, Rhodobacter capsulatus, Herbinix hemicellulosilytica, Leptotrichia buccalis* (Lbu). *Listeria seeligeri, Paludibacter propionicigenes, Lachnospiraceae bacterium, [Eubacterium] rectale, Listeria newyjorkensis, Clostridium aminophilum,* and/or *Leptotrichia shahii.*

For example, a *Leptotrichia wadei* Cas13a endonuclease can be used that has the following sequence (SEQ ID NO:36; NCBI accession no. WP_036059678.1).

```
  1    MKITKIDGVS HYKKQDKGIL KKKWKDLDER KQREKIEARY

41    NKQIESKIYK EFFRLKNKKR IEKEEDQNIK SLYFFIKELY

81    LNEKNEEWEL KNINLEILDD KERVIKGYKF KEDVYFFKEG
```

-continued

```
 121    YKEYYLRILF NNLIEKVQNE NREKVRKNKE FLDLKEIFKK

161    YKNRKIDLLL KSINNNKINL EYKKENVNEE IYGINPTNDR

201    EMTFYELLKE IIEKKDEQKS ILEEKLDNFD ITNFLENIEK

241    IFNEETEINI IKGKVLNELR EYIKEKEENN SDNKLKQIYN

281    LELKKYIENN FSYKKQKSKS KNGKNDYLYL NFLKKIMFIE

321    EVDEKKEINK EKFKNKINSN FKNLFVQHIL DYGKLLYYKE

361    NDEYIKNTGQ LETKDLEYIK TKETLIRKMA VLVSFAANSY

401    YNLFGRVSGD ILGTEVVKSS KTNVIKVGSH IFKEKMLNYF

441    FDFEIFDANK IVEILESISY SIYNVRNGVG HFNKLILGKY

481    KKKDINTNKR IEEDLNNNEE IKGYFIKKRG EIERKVKEKF

521    LSNNLQYYYS KEKIENYFEV YEFEILKRKI PFAPNEKRII

561    KKGEDLFNNK NNKKYEYFKN FDKNSAEEKK EFLKTRNFLL

601    KELYYNNFYK EFLSKKEEFE KIVLEVKEEK KSRGNINNKK

641    SGVSFQSIDD YDTKINISDY IASIHKKEME RVEKYNEEKQ

681    KDTAKYIRDF VEEIFLTGFI NYLEKDKRLH FLKEEFSILC

721    NNNNNVVDFN ININEEKIKE FLKENDSKTL NLYLFFNMID

761    SKRISEFRNE LVKYKQFTKK RLDEEKEFLG IKIELYETLI

801    EFVILTREKL DTKKSEEIDA WLVDKLYVKD SNEYKEYEEI

841    LKLFVDEKIL SSKEAPYYAT DNKTPILLSN FEKTRKYGTQ

881    SFLSEIQSNY KYSKVEKENI EDYNKKEEIE QKKKSNIEKL

921    QDLKVELHKK WEQNKITEKE IEKYNNTTRK INEYNYLKNK

961    EELQNVYLLH EMLSDLLARN VAFFNKWERD FKFIVIAIKQ

1001    FLRENDKEKV NEFLNPPDNS KGKKVYFSVS KYKNTVENID

1041    GIHKNFMNLI FLNNKFMNRK IDKMNCAIWV YFRNYIAHFL

1081    HLHTKNEKIS LISQMNLLIK LFSYDKKVQN HILKSTKTLL

1121    EKYNIQINFE ISNDKNEVFK YKIKNRLYSK KGKMLGKNNK

1161    LENEFLE NVKAMLEYSE
```

Other sequences for *Leptotrichia wadei* Cas13a endonucleases are also available, such as those NCBI accession nos. BBM46759.1, BBM48616.1, BBM48974.1, BBM48975.1, and WP_021746003.1, 101261 In another example, a *Herbinix hemicellulosilytica* Cas13a endonuclease can be used that has the following sequence (SEQ ID NO:37; NCBI accession no. WP_103203632.1).

```
   1    MKLTRRRISG NSVDQKITAA FYRDMSQGLL YYDSEDNDCT

41    DKVIESMDFE RSWRGRILKN GEDDKNPFYM FVKGLVGSND

81    KIVCEPIDVD SDPDNLDILI NKNLTGFGRN LKAPDSNDTL

121    ENLIRKIQAG IPEEEVLPEL KKIKEMIQKD IVNRKEQLLK

161    SIKNNRIPFS LEGSKLVPST KKMKWLFKLI DVPNKTFNEK

201    MLEKYWEIYD YDKLKANITN RLDKTDKKAR SISRAVSEEL

241    REYHKNLRTN YNRFVSGDRP AAGLDNGGSA KYNPDKEEFL

281    LFLKEVEQYF KKYFPVKSKH SNKSKDKSLV DKYKNYCSYK
```

-continued

```
 321    VVKKEVNRSI INQLVAGLIQ QGKLLYYFYY NDTWQEDFLN

361    SYGLSYIQVE EAFKKSVMTS LSWGINRLTS FFIDDSNTVK

401    FDDITTKKAK EAIESNYFNK LRTCSRMQDH FKEKLAFFYP

441    VYVKDKKDRP DDDIENLIVL VKNAIESVSY LRNRTFHFKE

481    SSLLELLKEL DDKNSGQNKI DYSVAAEFIK RDIENLYDVF

521    REQIRSLGIA EYYKADMISD CFKTCGLEFA LYSPKNSLMP

561    AFKNVYKRGA NLNKAYIRDK GPKETGDQGQ NSYKALEEYR

601    ELTWYIEVKN NDQSYNAYKN LLQLIYYHAF LPEVRENEAL

641    ITDFINRTKE WNRKETEERL NTKNNKKHKN FDENDDITVN

681    TYRYESIPDY QGESLDDYLK VLQRKQMARA KEVNEKEEGN

721    NNYIQFIRDV VVWAFGAYLE NKLKNYKNEL QPPLSKENIG

761    LNDTLKELFP EEKVKSPFNI KCRFSISTFI DNKGKSTDNT

801    SAEAVKTDGK EDEKDKKNIK RKDLLCFYLF LRLLDENEIC

841    KLQHQFIKYR CSLKERRFPG NRTKLEKETE LLAELEELME

881    LVRFTMPSIP EISAKAESGY DTMIKKYFKD FIEKKVFKNP

921    KTSNLYYHSD SKTPVTRKYM ALLMRSAPLH LYKDIFKGYY

961    LITKKECLEY IKLSNIIKDY QNSLNELHEQ LERIKLKSEK

1001    QNGKDSLYLD KKDFYKVKEY VENLEQVARY KHLQHKINFE

1041    SLYRIFRIHV DIAARMVGYT QDWERDMHFL FKALVYNGVL

1081    EERRFEAIFN NNDDNNDGRI VKKIQNNLNN KNRELVSMLC

1121    WNKKLNKNEF GAIIWKRNPI AHLNHFTQTE QNSKSSLESL

1161    INSLRILLAY DRKRQNAVTK TINDLLLNDY HIRIKWEGRV

1201    DEGQIYFNIK EKEDIENEPI IHLKHLHKKD CYIYKNSYMF

1241    DEQKEWICNG IKEEVYDKSI LKCIGNLFKF DYEDKNKSSA

1281    NPKHT
```

However, in some cases the Cas13 proteins with the SEQ ID NO:37 sequence are not used.

In another example, a *Leptotrichia buccalis* Cas13a endonuclease can be used that has the following sequence (SEQ ID NO:38; NCBI accession no. WP_015770004.1).

```
   1    MKVTKVGGIS HKKYTSEGRL VKSESEENRT DERLSALLNM

41    RLDMYIKNPS STETKENQKR IGKLKKFFSN KMVYLKDNTL

81    SLKNGKKENI DREYSETDIL ESDVRDKKNF AVLKKIYLNE

121    NVNSEELEVF RNDIKKKLNK INSLKYSFEK NKANYQKINE

161    NNIEKVEGKS KRNIIYDYYR ESAKRDAYVS NVKEAFDKLY

201    KEEDIAKLVL EIENLTKLEK YKIREFYHEI IGRKNDKENF

241    AKIIYEEIQN VNNMKELIEK VPDMSELKKS QVFYKYYLDK

281    EELNDKNIKY AFCHFVEIEM SQLLKNYVYK RLSNISNDKI

321    KRIFEYQNLK KLIENKLLNK LDTYVRNCGK YNYYLQDGEI

361    ATSDFIARNR QNEAFLRNII GVSSVAYFSL RNILETENEN

401    DITGRMRGKT VKNNKGEEKY VSGEVDKIYN ENKKNEVKEN
```

-continued

```
441    LKMFYSYDFN MDNKNEIEDF FANIDEAISS IRHGIVHFNL

481    ELEGKDIFAF KNIAPSEISK KMFQNEINEK KLKLKIFRQL

521    NSANVFRYLE KYKILNYLKR TRFEFVNKNI PFVPSFTKLY

561    SRIDDLKNSL GIYWKTPKTN DDNKTKEIID AQIYLLKNIY

601    YGEFLNYFMS NNGNFFEISK EIIELNKNDK RNLKTGFYKL

641    QKFEDIQEKI PKEYLANIQS LYMINAGNQD EEEKDTYIDF

681    IQKIFLKGFM TYLANNGRLS LIYIGSDEET NTSLAEKKQE

721    FDKFLKKYEQ NNNIKIPYEI NEFLREIKLG NILKYTERLN

761    MFYLILKLLN HKELTNLKGS LEKYQSANKE EAFSDQLELI

801    NLLNLDNNRV TEDFELEADE IGKFLDFNGN KVKDNKELKK

841    FDTNKIYFDG ENIIKHRAFY NIKKYGMLNL LEKIADKAGY

881    KISIEELKKY SNKKNEIEKN HKMQENLHRK YARPRKDEKF

921    TDEDYESYKQ AIENIEEYTH LKNKVEFNEL NLLQGLLLRI

961    LHRLVGYTSI WERDLRFRLK GEFPENQYIE EIFNFENKKN

1001   VKYKGGQIVE KYIKFYKELH QNDEVKINKY SSANIKVLKQ

1041   EKKDLYIRNY IAHFNYIPHA EISLLEVLEN LRKLLSYDRK

1081   LKNAVMKSVV DILKEYGFVA TFKIGADKKI GIQTLESEKI

1121   VHLKNLKKKK LMTDRNSEEL CKLVKIMFEY KMEEKKSEN
```

However, in some cases the Cas13 proteins with the SEQ ID NO:38 sequence are not used.

In another example, a *Leptotrichia seeligeri* Cas13a endonuclease can be used that has the following sequence (SEQ ID NO:39; NCBI accession no. WP_012985477.1).

```
   1    MWISIKTLIH HLGVLFFCDY MYNRREKKII EVKTMRITKV

41    EVDRKKVLIS RDKNGGKLVY ENEMQDNTEQ IMHHKKSSFY

81    KSVVNKTICR PEQKQMKKLV HGLLQENSQE KIKVSDVTKL

121    NISNFLNHRF KKSLYYFPEN SPDKSEEYRI EINLSQLLED

161    SLKKQQGTFI CWESFSKDME LYINWAENYI SSKTKLIKKS

201    IRNNRIQSTE SRSGQLMDRY MKDILNKNKP FDIQSVSEKY

241    QLEKLTSALK ATFKEAKKND KEINYKLKST LQNHERQIIE

281    ELKENSELNQ FNIEIRKHLE TYFPIKKTNR KVGDIRNLEI

321    GEIQKIVNHR LKNKIVQRIL QEGKLASYEI ESTVNSNSLQ

361    KIKIEEAFAL KFINACLFAS NNLRNMVYPV CKKDILMIGE

401    FKNSFKEIKH KKFIRQWSQF FSQEITVDDI ELASWGLRGA

441    IAPIRNEIIH LKKHSWKKFF NNPTFKVKKS KIINGKTKDV

481    TSEFLYKETL FKDYFYSELD SVPELIINKM ESSKILDYYS

521    SDQLNQVFTI PNFELSLLTS AVPFAPSFKR VYLKGFDYQN

561    QDEAQPDYNL KLNIYNEKAF NSEAFQAQYS LFKMVYYQVF

601    LPQFTTNNDL FKSSVDFILT LNKERKGYAK AFQDIRKMNK

641    DEKPSEYMSY IQSQLMLYQK KQEEKEKINH FEKFINQVFI

681    KGFNSFIEKN RLTYTCHPTK NTVPENDNIE IPFHTDMDDS
```

-continued

```
 721    NIAFWLMCKL LDAKQLSELR NEMIKFSCSL QSTEEISTFT

761    KAREVIGLAL LNGEKGCNDW KELFDDKEAW KKNMSLYVSE

801    ELLQSLPYTQ EDGQTPVINR SIDLVKKYGT ETILEKLFSS

841    SDDYKVSAKD IAKLHEYDVT EKIAQQESLH KQWIEKPGLA

881    RDSAWTKKYQ NVINDISNYQ WAKTKVELTQ VRHLHQLTID

921    LLSRLAGYMS IADRDFQFSS NYILERENSE YRVTSWILLS

961    ENKNKNKYND YELYNLKNAS IKVSSKNDPQ LKVDLKQLRL

1001    TLEYLELFDN RLKEKRNNIS HFNYLNGQLG NSILELFDDA

1041    RDVLSYDRKL KNAVSKSLKE ILSSHGMEVT FKPLYQTNHH

1081    LKIDKLQPKK IHHLGEKSTV SSNQVSNEYC QLVRTLLTMK
```

For example, a *Paludibacter propionicigenes* Cas13a endonuclease can be used that has the following sequence (SEQ ID NO:48; NCBI accession no. WP_013443710.1).

```
   1    MRVSKVKVKD GGKDKMVLVH RKTTGAQLVY SGQPVSNETS

41    NILPEKKRQS FDLSTLNKTI IKFDTAKKQK LNVDQYKIVE

81    KIFKYPKQEL PKQIKAEEIL PFLNHKFQEP VKYWKNGKEE

121    SFNLTLLIVE AVQAQDKRKL QPYYDWKTWY IQTKSDLLKK

161    SIENNRIDLT ENLSKRKKAL LAWETEFTAS GSIDLTHYHK

201    VYMTDVLCKM LQDVKPLTDD KGKINTNAYH RGLKKALQNH

241    QPAIFGTREV PNEANRADNQ LSIYHLEVVK YLEHYFPIKT

281    SKRRNTADDI AHYLKAQTLK TTIEKQLVNA IRANIIQQGK

321    TNHHELKADT TSNDLIRIKT NEAFVLNLTG TCAFAANNIR

361    NMVDNEQTND ILGKGDFIKS LLKDNTNSQL YSFFFGEGLS

401    TNKAEKETQL WGIRGAVQQI RNNVNHYKKD ALKTVFNISN

441    FENPTITDPK QQTNYADTIY KARFINELEK IPEAFAQQLK

481    TGGAVSYYTI ENLKSLLTTF QFSLCRSTIP FAPGFKKVFN

521    GGINYQNAKQ DESFYELMLE QYLRKENFAE ESYNARYFML

561    KLIYNNLFLP GFTTDRKAFA DSVGTVQMQN KKQAEKVNPR

601    KKEAYAFEAV RPMTAADSIA DYMAYVQSEL MQEQNKKEEK

641    VAEETRINFE KFVLQVFIKG FDSFLRAKEF DFVQMPQPQL

681    TATASNQQKA DKLNQLEASI TADCKLTPQY AKADDATHIA

721    FYVFCKLLDA AHLSNLRNEL IKFRESVNEF KFHHLLEIIE

761    ICLLSADVVP TDYRDLYSSE ADCLARLRPF IEQGADITNW

801    SDLFVQSDKH SPVIHANIEL SVKYGTTKLL EQIINKDTQF

841    KTTEANFTAW NTAQKSIEQL IKQREDHHEQ WVKAKNADDK

881    EKQERKREKS NFAQKFIEKH GDDYLDICDY INTYNWLDNK

921    MHFVHLNRLH GLTIELLGRM AGFVALFDRD FQFFDEQQIA

961    DEFKLHGFVN LHSIDKKLNE VPTKKIKEIY DIRNKIIQIN

1001    GNKINESVRA NLIQFISSKR NYYNNAFLHV SNDEIKEKQM

1041    YDIRNHIAHF NYLTKDAADF SLIDLINELR ELLHYDRKLK
```

```
-continued
1081    NAVSKAFIDL FDKHGMILKL KLNADHKLKV ESLEPKKIYH

1121    LGSSAKDKPE YQYCTNQVMM AYCNMCRSLL EMKK
```

For example, a *Lachnospiraceae bacterium* Cas13a endonuclease can be used that has the following sequence (SEQ ID NO:40; NCBT accession no. WP_022785443.1).

```
   1    MKISKVREEN RGAKLTVNAK TAVVSENRSQ EGILYNDPSR

41    YGKSRKNDED RDRYIESRLK SSGKLYRIFN EDKNKRETDE

81    LQWFLSEIVK KINRRNGLVL SDMLSVDDRA FEKAFEKYAE

121    LSYTNRRNKV SGSPAFETCG VDAATAERLK GIISETNFIN

161    RIKNNIDNKV SEDIIDRIIA KYLKKSLCRE RVKRGLKKLL

201    MNAFDLPYSD PDIDVQRDFI DYVLEDFYHV RAKSQVSRSI

241    KNMNMPVQPE GDGKFAITVS KGGTESGNKR SAEKEAFKKF

281    LSDYASLDER VRDDMLRRMR RLVVLYFYGS DDSKLSDVNE

321    KFDVWEDHAA RRVDNREFIK LPLENKLANG KTDKDAERIR

361    KNTVKELYRN QNIGCYRQAV KAVEEDNNGR YFDDKMLNMF

401    FIHRIEYGVE KIYANLKQVT EFKARTGYLS EKIWKDLINY

441    ISIKYIAMGK AVYNYAMDEL NASDKKEIEL GKISEEYLSG

481    ISSFDYELIK AEEMLQRETA VYVAFAARHL SSQTVELDSE

521    NSDFLLLKPK GTMDKNDKNK LASNNILNFL KDKETLRDTI

561    LQYFGGHSLW TDFPFDKYLA GGKDDVDFLT DLKDVIYSMR

601    NDSFHYATEN HNNGKWNKEL ISAMFEHETE RMTVVMKDKF

641    YSNNLPMFYK NDDLKKLLID LYKDNVERAS QVPSFNKVFV

681    RKNFPALVRD KDNLGIELDL KADADKGENE LKFYNALYYM

721    FKEIYYNAFL NDKNVRERFI TKATKVADNY DRNKERNLKD

761    RIKSAGSDEK KKLREQLQNY IAENDFGQRI KNIVQVNPDY

801    TLAQICQLIM TEYNQQNNGC MQKKSAARKD INKDSYQHYK

841    MLLLVNLRKA FLEFIKENYA FVLKPYKHDL CDKADFVPDF

881    AKYVHPYAGL ISRVAGSSEL QKWYIVSRFL SPAQANHMLG

921    FLHSYKQYVW DIYRRASETG TEINHSIAED KIAGVDITDV

961    DAVIDLSVKL CGTISSEISD YFKDDEVYAE YISSYLDFEY

1001    DGGNYKDSLN RFCNSDAVND QKVALYYDGE HPKLNRNIIL

1041    SKLYGERRFL EKITDRVSRS DIVEYYKLKK ETSQYQTKGI

1081    FDSEDEQKNI KKFQEMKNIV EFRDLMDYSE IADELQGQLI

1121    NWIYLRERDL MNFQLGYHYA CLNNDSNKQA TYVTLDYQGK

1161    KNRKINGAIL YQICAMYING LPLYYVDKDS SEWTVSDGKE

1201    STGAKIGEFY RYAKSFENTS DCYASGLEIF ENISEHDNIT

1241    ELRNYIEHFR YYSSFDRSFL GIYSEVFDRF FTYDLKYRKN

1281    VPTILYNILL QHFVNVRFEF VSGKKMIGID KKDRKIAKEK

1321    ECARITIREK NGVYSEQFTY KLKNGTVYVD ARDKRYLQSI

1361    IRLLFYPEKV NMDEMIEVKE KKKPSDNNTG KGYSKRDRQQ

1401    DRKEYDKYKE KKKKEGNFLS GMGGNINWDE INAQLKN
```

For example, a *Leptotrichia shahii* Cas13a endonuclease can be used that has the following sequence (SEQ ID NO:41; NCBI accession no. BBM39911.1).

```
   1    MGNLFGHKRW YEVRDKKDFK IKRKVKVKRN YDGNKYILNI

41    NENNNKEKID NNKFIRKYIN YKKNDNILKE FTRKFHAGNI

81    LFKLKGKEGI IRIENNDDFL ETEEVVLYIE AYGKSEKLKA

121    LGITKKKIID EAIRQGITKD DKKIEIKRQE NEEEIEIDIR

161    DEYTNKTLND CSIILRIIEN DELETKKSIY EIFKNINMSL

201    YKIIEKIIEN ETEKVFENRY YEEHLREKLL KDDKIDVILT

241    NFMEIREKIK SNLEILGFVK FYLNVGGDKK KSKNKKMLVE

281    KILNINVDLT VEDIADFVIK ELEFWNITKR IEKVKKVNNE

321    FLEKRRNRTY IKSYVLLDKH EKFKIERENK KDKIVKFFVE

361    NIKNNSIKEK IEKILAEFKI DELIKKLEKE LKKGNCDTEI

401    FGIFKKHYKV NFDSKKFSKK SDEEKELYKI IYRYLKGRIE

441    KILVNEQKVR LKKMEKIEIE KILNESILSE KILKRVKQYT

481    LEHIMYLGKL RHNDIDMTTV NTDDFSRLHA KEELDLELIT

521    FFASTNMELN KIFSRENINN DENIDFFGGD REKNYVLDKK

561    ILNSKIKIIR DLDFIDNKNN ITNNFIRKFT KIGTNERNRI

601    LHAISKERDL QGTQDDYNKV INIIQNLKIS DEEVSNALNL

641    DVVFKDKKNI ITKINDIKIS EENNNDIKYL PSFSKVLPEI

681    LNLYRNNPKN EPFDTIETEK IVLNALIYVN KELYKKLILE

721    DDLEENESKN IFLQELKKTL GNIDEIDENI IENYYKNAQI

761    SASKGNNKAI KKYQKKVIEC YIGYLRKNYE ELFDFSDFKM

801    NIQEIKKQIK DINDNKTYER ITVKTSDKTI VINDDFEYII

841    SIFALLNSNA VINKIRNRFF ATSVWLNTSE YQNIIDILDE

881    IMQLNTLRNE CITENWNLNL EEFIQKMKEI EKDFDDFKIQ

921    TKKEIFNNYY EDIKNNILTE FKDDINGCDV LEKKLEKIVI

961    FDDETKFEID KKSNILQDEQ RKLSNINKKD LKKKVDQYIK

1001    DKDQEIKSKI LCRIIFNSDF LKKYKKEIDN LIEDMESENE

1041    NKFQEIYYPK ERKNELYIYK KNLFLNIGNP NFDKIYGLIS

1081    NDIKMADAKF LFNIDGKNIR KNKISEIDAI LKNLNDKLNG

1121    YSKEYKEKYI KKLKENDDFF AKNIQNKNYK SFEKDYNRVS

1161    EYKKIRDLVE FNYLNKIESY LIDENWKLAI QMARFERDMH

1201    YIVNGLRELG IIKLSGYNTG ISRAYPKRNG SDGFYTTTAY

1241    YKFFDEESYK NFEKICYGFG IDLSENSEIN KPENESIRNY

1281    ISHFYIVRNP FADYSIAEQI DRVSNLLSYS TRYNNSTYAS

1321    VFEVFKKDVN LDYDELKNKF KLIGNNDILE RLMKPKKVSV

1361    LELESYNSDY IKNLIIELLT KIENTNDTL
```

In another example, a *Leptotrichia buccalis* C-1013-b Cas13a endonuclease can have the following sequence (SEQ ID NO:42, NCBI accession no. C7NBY4; AltName LbuC2c2).

```
  1    MKVTKVGGIS HKKYTSEGRL VKSESEENRT DERLSALLNM

41    RLDMYIKNPS STETKENQKR IGKLKKFFSN KMVYLKDNTL

81    SLKNGKKENI DREYSETDIL ESDVRDKKNF AVLKKIYLNE

121    NVNSEELEVF RNDIKKKLNK INSLLYSFEK NKANYQKINE

161    NNIEKVEGKS KRNIIYDYYR ESAKRDAYVS NVKEAFDKLY

201    KEEDIAKLVL EIENLTKLEK YKIREFYHEI IGRKNDKENF

241    AKIIYEEIQN VNNMKELIEK VPDMSELKKS QVFYKYYLDK

281    EELNDKNIKY AFCHFVEIEM SQLLKNYVYK RLSNISNDKI

321    KRIFEYQNLK KLIENKLLNK LDTYVRNCGK YNYYLQDGEI

361    ATSDFIARNR QNEAFLRNII GVSSVAYFSL RNILETENEN

401    DITGRMRGKT VKNNKGEEKY VSGEVDKIYN ENKKNEVKEN

441    LKMFYSYDFN MDNKNEIEDF FANIDEAISS IRHGIVHFNL

481    ELEGKDIFAF KNIAPSEISK KMFQNEINEK KLKLKIFRQL

521    NSANVFRYLE KYKILNYLKR TRFEFVNKNI PFVPSFTKLY

561    SRIDDLKNSL GIYWKTPKTN DDNKTKEIID AQIYLLKNIY

601    YGEFLNYFMS NNGNFFEISK EIIELNKNDK RNLKTGFYKL

641    QKFEDIQEKI PKEYLANIQS LYMINAGNQD EEEKDTYIDF

681    IQKIFLKGFM TYLANNGRLS LIYIGSDEET NTSLAEKKQE

721    FDKFLKKYEQ NNNIKIPYEI NEFLREIKLG NILKYTERLN

761    MFYLILKLLN HKELTNLKGS LEKYQSANKE EAFSDQLELI

801    NLLNLDNNRV TEDFELEADE IGKFLDFNGN KVKDNKELKK

841    FDTNKIYFDG ENIIKHRAFY NIKKYGMLNL LEKIADKAGY

881    KISIEELKKY SNKKNEIEKN HKMQENLHRK YARPRKDEKF

921    TDEDYESYKQ AIENIEEYTH LKNKVEFNEL NLLQGLLLRI

961    LHRLVGYTSI WERDLRFRLK GEFPENQYIE EIFNFENKKN

1001   VKYKGGQIVE KYIKFYKELH QNDEVKINKY SSANIKVLKQ

1041   EKKDLYIRNY IAHFNYIPHA EISLLEVLEN LRKLLSYDRK

1081   LKNAVMKSVV DILKEYGFVA TFKIGADKKI GIQTLESEKI

1121   VHLKNLKKKK LMTDRNSEEL CKLVKIMFEY KMEEKKSEN
```

In some cases, a modified Cas13 protein can be used. Such a modified Cas 13 protein can have increased in vivo endonuclease activity compared to a corresponding unmodified Cas13 protein. For example, such a modified Cas13 protein can have a lysine (K) at a position corresponding to position 436 of a wildtype Cas13 protein. The lysine (K) at position 436 can replace a glutamic acid (E) in the corresponding wild type Cas13 protein.

One example, of such modified Cas13 protein is a *Leptotrichia buccalis* Cas13a endonuclease with an E436K mutation, and the following sequence (SEQ ID NO:43).

```
  1    MKVTKVGGIS HKKYTSEGRL VKSESEENRT DERLSALLNM

41    RLDMYIKNPS STETKENQKR IGKLKKFFSN KMVYLKDNTL

81    SLKNGKKENI DREYSETDIL ESDVRDKKNF AVLKKIYLNE

121    NVNSEELEVF RNDIKKKLNK INSLKYSFEK NKANYQKINE
```

```
161    NNIEKVEGKS KRNIIYDYYR ESAKRDAYVS NVKEAFDKLY

201    KEEDIAKLVL EIENLTKLEK YKIREFYHEI IGRKNDKENF

241    AKIIYEEIQN VNNMKELIEK VPDMSELKKS QVFYKYYLDK

281    EELNDKNIKY AFCHFVEIEM SQLLKNYVYK RLSNISNDKI

321    KRIFEYQNLK KLIENKLLNK LDTYVRNCGK YNYYLQDGEI

361    ATSDFIARNR QNEAFLRNII GVSSVAYFSL RNILETENEN

401    DITGRMRGKT VKNNKGEEKY VSGEVDKIYN ENKKNKVKEN

441    LKMFYSYDFN MDNKNEIEDF FANIDEAISS IRHGIVHFNL

481    ELEGKDIFAF KNIAPSEISK KMFQNEINEK KLKLKIFRQL

521    NSANVFRYLE KYKILNYLKR TRFEFVNKNI PFVPSFTKLY

561    SRIDDLKNSL GIYWKTPKTN DDNKTKEIID AQIYLLKNIY

601    YGEFLNYFMS NNGNFFEISK EIIELNKNDK RNLKTGFYKL

641    QKFEDIQEKI PKEYLANIQS LYMINAGNQD EEEKDTYIDF

681    IQKIFLKGFM TYLANNGRLS LIYIGSDEET NTSLAEKKQE

721    FDKFLKKYEQ NNNIKIPYEI NEFLREIKLG NILKYTERLN

761    MFYLILKLLN HKELTNLKGS LEKYQSANKE EAFSDQLELI

801    NLLNLDNNRV TEDFELEADE IGKFLDFNGN KVKDNKELKK

841    FDTNKIYFDG ENIIKHRAFY NIKKYGMLNL LEKIADKAGY

881    KISIEELKKY SNKKNEIEKN HKMQENLHRK YARPRKDEKF

921    TDEDYESYKQ AIENIEEYTH LKNKVEFNEL NLLQGLLLRI

961    LHRLVGYTSI WERDLRFRLK GEFPENQYIE EIFNFENKKN

1001   VKYKGGQIVE KYIKFYKELH QNDEVKINKY SSANIKVLKQ

1041   EKKDLYIRNY IAHFNYIPHA EISLLEVLEN LRKLLSYDRK

1081   LKNAVMKSVV DILKEYGFVA TFKIGADKKI GIQTLESEKI

1121   VHLKNLKKKK LMTDRNSEEL CKLVKIMFEY KMEEKKSEN
```

The modified *Leptotrichia buccalis* Cas13a endonuclease with the E436K mutation has increased in vivo endonuclease activity compared to the unmodified *Leptotrichia buccalis* Cas13a endonuclease. Use of the *Leptotrichia buccalis* Cas13a endonuclease with the E436K (e.g., with SEQ ID NO:43) therefore increases sensitivity above background by ~10-100 fold. Hence, the reporter RNA is cleaved faster by the modified Cas13a endonuclease, which increase the sensitivity of the assay.

Such modifications can be present in a variety of Cas13 proteins. For example, modified Cas13 proteins can have a sequence with at least 95% sequence identity to SEQ ID NO:42 or 43, and with a lysine at position 436.

The modified Cas13 proteins, which can increase sensitivity of detecting at least one reporter RNA by about 10-fold to 100-fold are useful, for example, in the methods, kits, systems and devices described herein.

The inventors have evaluated the kinetics of other Cas13a and Cas13b proteins. Such work indicates that in some cases Cas13b works faster in the SARS-CoV-2 RNA detection assay than Cas13a.

For example, a Cas13b from *Prevotella buccae* can be used in the SARS-CoV-2 RNA detection methods, compositions and devices. A sequence for a *Prevotella buccae* Cas13b protein (NCBI accession no. WP_004343973.1) is shown below as SEQ ID NO:44.

```
  1   MQKQDKLFVD RKKNAIFAFP KYITIMENKE KPEPIYYELT

41   DKHFWAAFLN LARHNVYTTI NHINRRLEIA ELKDDGYMMG

81   IKGSWNEQAK KLDKKVRLRD LIMKHFPPFLE AAAYEMTNSK

121   SPNNKEQREK EQSEALSLNN LKNVLFIFLE KLQVLRNYYS

161   HYKYSEESPK PIFETSLLKN MYKVFDANVR LVKRDYMHHE

201   NIDMQRDFTH LNRKKQVGRT KNIIDSPNFH YHFADKEGNM

241   TIAGLLFFVS LFLDKKDAIW MQKKLKGFKD GRNLREQMTN

281   EVFCRSRISL PKLKLENVQT KDWMQLDMLN ELVRCPKSLY

321   ERLREKDRES FKVPFDIFSD DYNAEEEPFK NTLVRHQDRF

361   PYFVLRYFDL NEIFEQLRFQ IDLGTYHFSI YNKRIGDEDE

401   VRHLTHHLYG FARIQDFAPQ NQPEEWRKLV KDLDHFETSQ

441   EPYISKTAPH YHLENEKIGI KFCSAHNNLF PSLQTDKTCN

481   GRSKFNLGTQ FTAEAFLSVH ELLPMMFYYL LLTKDYSRKE

521   SADKVEGIIR KEISNIYAIY DAFANNEINS IADLTRRLQN

561   TNILQGHLPK QMISILKGRQ KDMGKEAERK IGEMIDDTQR

601   RLDLLCKQTN QKIRIGKRNA GLLKSGKIAD WLVNDMMRFQ

641   PVQKDQNNIP INNSKANSTE YRMLQRALAL FGSENFRLKA

681   YFNQMNLVGN DNPHPFLAET QWEHQTNILS FYRNYLEARK

721   KYLKGLKPQN WKQYQHFLIL KVQKTNRNTL VTGWKNSFNL

761   PRGIFTQPIR EWFEKHNNSK RIYDQILSFD RVGFVAKAIP

801   LYFAEEYKDN VQPFYDYPFN IGNRLKPKKR QFLDKKERVE

841   LWQKNKELFK NYPSEKKKTD LAYLDFLSWK KFERELRLIK

881   NQDIVTWLMF KELFNMATVE GLKIGEIHLR DIDTNTANEE

921   SNNILNRIMP MKLPVKTYET DNKGNILKER PLATFYIEET

961   ETKVLKQGNF KALVKDRRLN GLFSFAETTD LNLEEHPISK

1001  LSVDLELIKY QTTRISIFEM TLGLEKKLID KYSTLPTDSF

1041  RNMLERWLQC KANRPELKNY VNSLIAVRNA FSHNQYPMYD

1081  ATLFAEVKKF TLFPSVDTKK IELNIAPQLL EIVGKALKEI

1121  EKSENKN
```

Such a *Prevotella buccae* Cas13b protein can have a Km (Michaelis constant) substrate concentration of about 20 micromoles and a Kcat of about 987/second (see, e.g., Slaymaker et al. Cell Rep 26 (13): 3741-3751 (2019)).

Another *Prevotella buccae* Cas13b protein (NCBI accession no. WP_004343581.1) that can be used in the SARS-CoV-2 RNA detection methods, compositions and devices has the sequence shown below as SEQ ID NO:45.

```
  1   MQKQDKLFVD RKKNAIFAFP KYITIMENQE KPEPIYYELT

41   DKHFWAAFLN LARHNVYTTI NHINRRLEIA ELKDDGYMMD

81   IKGSWNEQAK KLDKKVRLRD LIMKHFPPFLE AAAYEITNSK

121   SPNNKEQREK EQSEALSLNN LKNVLFIFLE KLQVLRNYYS

161   HYKYSEESPK PIFETSLLKN MYKVFDANVR LVKRDYMHHE

201   NIDMQRDFTH LNRKKQVGRT KNIIDSPNFH YHFADKEGNM
```

```
241   TIAGLLFFVS LFLDKKDAIW MQKKLKGFKD GRNLREQMTN

281   EVFCRSRISL PKLKLENVQT KDWMQLDMLN ELVRCPKSLY

321   ERLREKDRES FKVPFDIFSD DYDAEEEPFK NTLVRHQDRF

361   PYFVLRYFDL NEIFEQLRFQ IDLGTYHFSI YNKRIGDEDE

401   VRHLTHHLYG FARIQDFAQQ NQPEVWRKLV KDLDYFEASQ

441   EPYIPKTAPH YHLENEKIGI KFCSTHNNLF PSLKTEKTCN

481   GRSKFNLGTQ FTAEAFLSVH ELLPMMFYYL LLTKDYSRKE

521   SADKVEGIIR KEISNIYAIY DAFANGEINS IADLTCRLQK

561   TNILQGHLPK QMISILEGRQ KDMEKEAERK IGEMIDDTQR

601   RLDLLCKQTN QKIRIGKRNA GLLKSGKIAD WLVNDMMRFQ

641   PVQKDQNNIP INNSKANSTE YRMLQRALAL FGSENFRLKA

681   YFNQMNLVGN DNPHPFLAET QWEHQTNILS FYRNYLEARK

721   KYLKGLKPQN WKQYQHFLIL KVQKTNRNTL VTGWKNSFNL

761   PRGIFTQPIR EWFEKHNNSK RIYDQILSFD RVGFVAKAIP

801   LYFAEEYKDN VQPFYDYPFN IGNKLKPQKG QFLDKKERVE

841   LWQKNKELFK NYPSEKKKTD LAYLDFLSWK KFERELRLIK

881   NQDIVTWLMF KELFNMATVE GLKIGEIHLR DIDTNTANEE

921   SNNILNRIMP MKLPVKTYET DNKGNILKER PLATFYIEET

961   ETKVLKQGNF KVLAKDRRLN GLLSFAETTD IDLEKNPITK

1001  LSVDHELIKY QTTRISIFEM TLGLEKKLIN KYPTLPTDSF

1041  RNMLERWLQC KANRPELKNY VNSLIAVRNA FSHNQYPMYD

1081  ATLFAEVKKF TLFPSVDTKK IELNIAPQLL EIVGKAIKEI

1121  EKSENKN
```

An example of a *Bergeyella zoohelcum* Cas13b (RI177A) mutant sequence (NCBI accession no. 6AAY_A) is shown below as SEQ ID NO:46.

```
  1   XENKTSLGNN IYYNPFKPQD KSYFAGYFNA AXENTDSVFR

41   ELGKRLKGKE YTSENFFDAI FKENISLVEY ERYVKLLSDY

81   FPXARLLDKK EVPIKERKEN FKKNFKGIIK AVRDLRNFYT

121   HKEHGEVEIT DEIFGVLDEX LKSTVLTVKK KKVKTDKTKE

161   ILKKSIEKQL DILCQKKLEY LRDTARKIEE KRRNQRERGE

201   KELVAPFKYS DKRDDLIAAI YNDAFDVYID KKKDSLKESS

241   KAKYNTKSDP QQEEGDLKIP ISKNGVVFLL SLFLTKQEIH

281   AFKSKIAGFK ATVIDEATVS EATVSHGKNS ICFXATHEIF

321   SHLAYKKLKR KVRTAEINYG EAENAEQLSV YAKETLXXQX

361   LDELSKVPDV VYQNLSEDVQ KTFIEDWNEY LKENNGDVGT

401   XEEEQVIHPV IRKRYEDKFN YFAIRFLDEF AQFPTLRFQV

441   HLGNYLHDSR PKENLISDRR IKEKITVFGR LSELEHKKAL

481   FIKNTETNED REHYWEIFPN PNYDFPKENI SVNDKDFPIA

521   GSILDREKQP VAGKIGIKVK LLNQQYVSEV DKAVKAHQLK
```

```
                    -continued
561    QRKASKPSIQ NIIEEIVPIN ESNPKEAIVF GGQPTAYLSX

601    NDIHSILYEF FDKWEKKKEK LEKKGEKELR KEIGKELEKK

641    IVGKIQAQIQ QIIDKDTNAK ILKPYQDGNS TAIDKEKLIK

681    DLKQEQNILQ KLKDEQTVRE KEYNDFIAYQ DKNREINKVR

721    DRNHKQYLKD NLKRKYPEAP ARKEVLYYRE KGKVAVWLAN

761    DIKRFXPTDF KNEWKGEQHS LLQKSLAYYE QCKEELKNLL

801    PEKVFQHLPF KLGGYFQQKY LYQFYTCYLD KRLEYISGLV

841    QQAENFKSEN KVFKKVENEC FKFLKKQNYT HKELDARVQS

881    ILGYPIFLER GFXDEKPTII KGKTFKGNEA LFADWFRYYK

921    EYQNFQTFYD TENYPLVELE KKQADRKRKT KIYQQKKNDV

961    FTLLXAKHIF KSVFKQDSID QFSLEDLYQS REERLGNQER

1001   ARQTGERNTN YIWNKTVDLK LCDGKITVEN VKLKNVGDFI

1041   KYEYDQRVQA FLKYEENIEW QAFLIKESKE EENYPYVVER

1081   EIEQYEKVRR EELLKEVHLI EEYILEKVKD KEILKKGDNQ

1121   NFKYYILNGL LKQLKNEDVE SYNVFNLNTE PEDVNINQLK

1161   QEATDLEQKA FVLTYIANKF AHNQLPKKEF WDYCQEKYGK

1201   IEKEKTYAEY FAEVEKKEKE ALIKLEHHHH HH
```

Another example of a Cas13b protein sequence from *Prevotella* sp. MS-173 (NCBI accession no. WP_007412163.1) that can be used in the SARS-CoV-2 RNA detection methods, compositions and devices has is shown below as SEQ ID NO:47.

```
  1    MQKQDKLFVD RKKNAIFAFP KYITIMENQE KPEPIYYELT

41    DKHFQAAFLN LARHNVYTTI NHINRRLEIA ELKDDGYMMG

81    IKGSWNEQAK KLDKKVRLRD LIMKHFPFLE AAAYEITNSK

121    SPNNKEQREK EQSEALSLNN LKNVLFIFLE KLQVLRNYYS

161    HYKYSEESPK PIFETSLLKN MYKVFDANVR LVKRDYMHHE

201    NIDMQRDFTH LNRKKQVGRT KNIIDSPNFH YHFADKEGNM

241    TIAGLLFFVS LFLDKKDAIW MQKKLKGFKD GRNLREQMTN

281    EVFCRSRISL PKLKLENVQT KDWMQLDMLN ELVRCPKSLY

321    ERLREKDRES FKVPFDIFSD DYDAEEEPFK NTLVRHQDRF

361    PYFVLRYFDL NEIFEQLRFQ IDLGTYHFSI YNKRIGDEDE

401    VRHLTHHLYG FARIQDFAPQ NQPEEWRKLV KDLDHFETSQ

441    EPYISKTAPH YHLENEKIGI KFCSTHNNLF PSLKREKTCN

481    GRSKFNLGTQ FTAEAFLSVH ELLPMMFYYL LLTKDYSRKE

521    SADKVEGIIR HEISNIYAIY DAFANNEINS IADLTCRLQK

561    TNILQGHLPK QMISILEGRQ KDMEKEAERK IGEMIDDTQR

601    RLDLLCKQTN QKIRIGKRNA GLLKSGKIAD WLVSDMMRFQ

641    PVQKDTNNAP INNSKANSTE YRMLQHALAL FGSESSRLKA

681    YFRQMNLVGN ANPHPFLAET QWEHQTNILS FYRNYLEARK

721    KYLKGLKPQN WKQYQHFLIL KVQKTNRNTL VTGWKNSFNL
```

```
                    -continued
761    PRGIFTQPIR EWFEKHNNSK RIYDQILSFD RVGFVAKAIP

801    LYFAEEYKDN VQPFYDYPFN IGNKLKPQKG QFLDKKERVE

841    LWQKNKELFK NYPSEKNKTD LAYLDFLSWK KFERELRLIK

881    NQDIVTWLMF KELFKTTTVE GLKIGEIHLR DIDTNTANEE

921    SNNILNRIMP MKLPVKTYET DNKGNILKER PLATFYIEET

961    ETKVLKQGNF KVLAKDRRLN GLLSFAETTD IDLEKNPITK

1001   LSVDYELIKY QTTRISIFEM TLGLEKKLID KYSTLPTDSF

1041   RNMLERWLQC KANRPELKNY VNSLIAVRNA FSHNQYPMYD

1081   ATLFAEVKKF TLFPSVDTKK IELNIAPQLL EIVGKAIKEI

1121   EKSENKN
```

Hence, the sample can be incubated with at least one CRISPR RNA (crRNA) and at least one Cas13 protein. The Cas13 protein can, for example, be a Cas13a protein, Cas13b protein, or a combination thereof.

Pre-incubation of the crRNA and Cas13 protein without the sample is preferred, so that the crRNA and the Cas13 protein can form a complex.

In some cases, the reporter RNA can be present while the crRNA and the Cas13 protein form a complex. However, in other cases, the reporter RNA can be added after the crRNA and the Cas13 protein already form a complex. Also, after formation of the crRNA/Cas13 complex, the sample RNA (e.g., SARS-CoV-2 RNA) can then be added. The sample RNA (e.g., SARS-CoV-2 RNA) acts as an activating RNA. Once activated by the activating RNA, the crRNA/Cas13 complex becomes a non-specific RNase to produce RNA cleavage products that can be detected using a reporter RNA, for example, a short quenched-fluorescent RNA.

For example, the Cas13 and crRNA are incubated for a period of time to form the inactive complex. In some cases, the Cas13 and crRNA complexes are formed by incubating together at 37° C. for 30 minutes, 1 hour, or 2 hours (for example, 0.5 to 2 hours) to form an inactive complex. The inactive complex can then be incubated with the reporter RNA. One example of a reporter RNA is provided by the RNase Alert system. The sample SARS-CoV-2 RNA can be a ssRNA activator. The Cas13/crRNA with the SARS-CoV-2 RNA sample becomes an activated complex that cleaves in cis and trans. When cleaving in cis, for example, the activated complex can cleave SARS-CoV-2 RNA. When cleaving in trans, the activated complex can cleave the reporter RNA, thereby releasing a signal such as the fluorophore from the reporter RNA.

At least one crRNA can bind to a region in the SARS-CoV-2 RNA genome. In some cases, the region is a single stranded region of the SARS-CoV-2 RNA genome. In other cases, the region is a hairpin region of the SARS-CoV-2 genome.

In some cases, the SARS-CoV-2 crRNA is any one of SEQ ID NOs: 1-35, 58-1-147. In some cases, the at least one crRNA has at least about 70%, at least about 75%, at least about 80%, at least about 85%, at least about 90%, at least about 95%, at least about 98%, or more sequence identity to any SEQ ID NO: 1-35, 58-147.

In some cases, the crRNAs can include additional sequences such as spacer sequences. Tables 1 and 5 provide examples of SARS-CoV-2 crRNA sequences. Table 5 also includes examples of spacer sequences.

TABLE 1

Examples of SARS-CoV-2 crRNA Sequences

| SEQ ID NO | Name | Sequence |
|---|---|---|
| SEQ ID NO: 1 | PF039_crLbu_nCoV_1 (crRNA 1) | GACCACCCCAAAAAUGAAGGGGACUAA AACUUUCGCUGAUUUUGGGGUCC |
| SEQ ID NO: 2 | PF040_crLbu_nCoV_2 (crRNA 2) | GACCACCCCAAAAAUGAAGGGGACUAA AACGGUCCACCAAACGUAAUGCG |
| SEQ ID NO: 3 | PF041_crLbu_nCoV_3 (crRNA 3) | GACCACCCCAAAAAUGAAGGGGACUAA AACUCUGGUUACUGCCAGUUGAA |
| SEQ ID NO: 4 | PF042_crLbu_nCoV_4 (crRNA 4) | GACCACCCCAAAAAUGAAGGGGACUAA AACUUUGCGGCCAAUGUUUGUAA |
| SEQ ID NO: 5 | PF043_crLbu_nCoV_5 (crRNA 5) | GACCACCCCAAAAAUGAAGGGGACUAA AACGAAGCGCUGGGGGCAAAUUG |
| SEQ ID NO: 6 | PF044_crLbu_nCoV_6 (crRNA 6) | GACCACCCCAAAAAUGAAGGGGACUAA AACAUGCGCGACAUUCCGAAGAA |
| SEQ ID NO: 7 | PF045_crLbu_nCoV_7 (crRNA 7) | GACCACCCCAAAAAUGAAGGGGACUAA AACUUGGUGUAUUCAAGGCUCCC |
| SEQ ID NO: 8 | PF046_crLbu_nCoV_8 (crRNA 8) | GACCACCCCAAAAAUGAAGGGGACUAA AACGGAUUGCGGGUGCCAAUGUG |
| SEQ ID NO: 9 | PF047_crLbu_nCoV_9 (crRNA 9) | GACCACCCCAAAAAUGAAGGGGACUAA AACUGUAGCACGAUUGCAGCAUU |
| SEQ ID NO: 10 | PF048_crLbu_nCoV_10 (crRNA 10) | GACCACCCCAAAAAUGAAGGGGACUAA AACUAAGUGUAAAACCCACAGGG |
| SEQ ID NO: 11 | PF049_crLbu_nCoV_11 (crRNA 11) | GACCACCCCAAAAAUGAAGGGGACUAA AACUAACCUUUCCACAUACCGCA |
| SEQ ID NO: 12 | PF050_crLbu_nCoV_12 (crRNA 12) | GACCACCCCAAAAAUGAAGGGGACUAA AACUCAGCUGAUGCACAAUCGUU |
| SEQ ID NO: 13 | PF051_crLbu_nCoV_13 (crRNA 13) | GACCACCCCAAAAAUGAAGGGGACUAA AACUCUAGCAGGAGAAGUUCCCC |
| SEQ ID NO: 14 | PF052_crLbu_nCoV_14 (crRNA 14) | GACCACCCCAAAAAUGAAGGGGACUAA AACUCUGUCAAGCAGCAGCAAAG |
| SEQ ID NO: 15 | PF053_crLbu_nCoV_15 (crRNA 15) | GACCACCCCAAAAAUGAAGGGGACUAA AACCUUUGCUGCUGCUUGACAGA |
| SEQ ID NO: 16 | PF083_crLbu_nCov12v2 | GACCACCCCAAAAAUGAAGGGGACUAA AACAACGAUUGUGCAUCAGCUGA |
| SEQ ID NO: 17 | PF084_crLbu_nCov15v2 | GACCACCCCAAAAAUGAAGGGGACUAA AACGACAUUUUGCUCUCAAGCUG |
| SEQ ID NO: 18 | PF085_crLbu_nCoV_16 (crRNA 16) | GACCACCCCAAAAAUGAAGGGGACUAA AACGUUCCUGGUCCCCAAAAUUU |
| SEQ ID NO: 19 | PF086_crLbu_nCoV_17 (crRNA 17) | GACCACCCCAAAAAUGAAGGGGACUAA AACUGGCACCUGUGUAGGUCAAC |
| SEQ ID NO: 20 | PF087_crLbu_nCoV_18 (crRNA 18) | GACCACCCCAAAAAUGAAGGGGACUAA AACUCCAUGCCAAUGCGCGACAU |
| SEQ ID NO: 21 | PF088_crLbu_nCoV_19 (crRNA 19) | GACCACCCCAAAAAUGAAGGGGACUAA AACCUAUUAACUAUUAACGUACC |
| SEQ ID NO: 22 | PF089_crLbu_nCoV_20 (crRNA 20) | GACCACCCCAAAAAUGAAGGGGACUAA AACUAUUGCAGCAGUACGCACAC |
| SEQ ID NO: 23 | PF090_crLbu_nCoV_21 (crRNA 21) | GACCACCCCAAAAAUGAAGGGGACUAA AACAGCGCAGUAAGGAUGGCUAG |
| SEQ ID NO: 24 | PF091_crLbu_nCoV_22 (crRNA 22) | GACCACCCCAAAAAUGAAGGGGACUAA AACGUAACUAGCAAGAAUACCAC |
| SEQ ID NO: 25 | PF092_crLbu_nCov_2XL (crRNA 2XL) | UAGACCACCCCAAAAAUGAAGGGGACU AAAACGGUCCACCAAACGUAAUGCG |

TABLE 1-continued

Examples of SARS-CoV-2 crRNA Sequences

| SEQ ID NO | Name | Sequence |
|---|---|---|
| SEQ ID NO: 26 | PF093_crLbu_nCov_4XL (crRNA 4XL) | UAGACCACCCCAAAAAUGAAGGGGACU AAAACGGUCCACCAAACGUAAUGCG |
| SEQ ID NO: 27 | cr2 (one of the 8G crRNAs) Lower case: stem sequence Upper case: Target sequence | uagaccaccccaaaaaugaaggggacuaaaacCGCAUU ACGUUUGGUGGACC |
| SEQ ID NO: 28 | cr4 (one of the 8G crRNAs) Lower case: stem sequence Upper case: Target sequence | uagaccacccaaaaaugaaggggacuaaaacUUACAA ACAUUGGCCGCAAA |
| SEQ ID NO: 29 | NCR_542 (one of the 8G crRNAs) Lower case: stem sequence Upper case: Target sequence | uagaccaccccaaaaaugaaggggacuaaaacAAACUA CGUCAUCAAGCCAA |
| SEQ ID NO: 30 | NCR_546 (one of the 8G crRNAs) Lower case: stem sequence Upper case: Target sequence | uagaccaccccaaaaaugaaggggacuaaaacCACAGU CAUAAUCUAUGUUA |
| SEQ ID NO: 31 | NCR_564 (one of the 8G crRNAs) Lower case: stem sequence Upper case: Target sequence | uagaccacccaaaaaugaaggggacuaaaacUCACAC UUUUCUAAUAGCAU |
| SEQ ID NO: 32 | NCR_569 (one of the 8G crRNAs) Lower case: stem sequence Upper case: Target sequence | uagaccacccaaaaaugaaggggacuaaaacUGUAAG AUUAACACACUGAC |
| SEQ ID NO: 33 | NCR_588 (one of the 8G crRNAs) Lower case: stem sequence Upper case: Target sequence | uagaccaccccaaaaaugaaggggacuaaaacUUAAUU GUGUACAAAAACUG |
| SEQ ID NO: 34 | NCR_596 one of the 8G crRNAs) Lower case: stem sequence Upper case: Target sequence | uagaccacccaaaaaugaaggggacuaaaacCAGUUG UGAUGAUUCCUAAG |
| SEQ ID NO: 35 | Guide 21 detecting protein E | uagaccacccaaaaaugaaggggacuaaaacAGCGCA GUAAGGAUGGCUAG |

As illustrated herein, crRNAs 2, 3, 4, 7, 8, 9, and 14 (SEQ ID NOs: 2, 3, 4, 7, 8, 9, and 14) exhibit better signals than crRNAs 1, 13 or 15. Moreover, the combination of the 8G crRNAs (SEQ ID NOs:27-34) significantly improves detection of SARS-CoV-2.

In some cases, the sample is incubated with a single crRNA. In other cases, the sample is incubated with 2, 3, 4, 5, 6, 7, 8, 9, 10 or more crRNAs having a different sequence.

In some cases, the at least one crRNA recognizes the SARS-CoV-2 splice variants and/or mutations.

In some cases, the Cas13 protein and/or crRNA is lyophilized prior to incubation with the sample.

In some cases, the sample suspected of containing SARS-CoV-2 RNA is incubated with the Cas13 protein, crRNA, and reporter RNA for a period of time sufficient to form reporter RNA cleavage products. In some cases, the period of time for incubation is about 5 hours or less, about 4 hours or less, about 3 hours or less, about 2 hours or less, about 1.5 hours or less, about 1 hour or less, about 40 minutes or less, about 35 minutes or less, about 30 minutes or less, about 25 minutes or less, about 20 minutes or less, about 15 minutes or less, about 10 minutes or less, about 5 minutes or less, or about 1 minute or less.

In some cases, the RNA cleavage products (that can include SARS-CoV-2 RNA cleavage products) are detected using reporter RNA that has a fluorescence-emitting dye pair, i.e., a fluorescence resonance energy transfer (FRET) pair and/or a quencher/fluorophore pair.

In some cases, SARS-CoV-2 RNA, and/or the RNA cleavage products are present in the sample or the mixture along with non-target RNA (e.g., non-SARS-CoV-2 RNA).

In some cases, the SARS-CoV-2 RNA is present at from about one copy per $10^{10}$ non-target RNAs (e.g., non-SARS-CoV-2 RNAs) to about one copy per 10 non-target RNAs (e.g., non-SARS-CoV-2 RNAs), at from about one copy per $10^9$ non-target RNAs (e.g., non-SARS-CoV-2 RNAs) to about one copy per $10^2$ non-target RNAs (e.g., non-SARS-CoV-2 RNAs), at from about one copy per $10^8$ non-target RNAs (e.g., non-SARS-CoV-2 RNAs) to about one copy per $10^3$ non-target RNAs (e.g., non-SARS-CoV-2 RNAs), at from about one copy per $10^7$ non-target RNAs (e.g., non-SARS-CoV-2 RNAs) to about one copy per $10^4$ non-target RNAs (e.g., non-SARS-CoV-2 RNAs), at from about one copy per $10^6$ non-target RNAs (e.g., non-SARS-CoV-2 RNAs) to about one copy per $10^5$ non-target RNAs (e.g., non-SARS-CoV-2 RNAs), at from about one copy per $10^{10}$ non-target RNAs (e.g., non-SARS-CoV-2 RNAs) to about one copy per 100 non-target RNAs (e.g. non-SARS-CoV-2 RNAs), at from about one copy per $10^9$ non-target RNAs (e.g., non-SARS-CoV-2 RNAs) to about one copy per 100 non-target RNAs (e.g., non-SARS-CoV-2 RNAs), at from about one copy per $10^8$ non-target RNAs (e.g., non-SARS-CoV-2 RNAs) to about one copy per 100 non-target RNAs (e.g., non-SARS-CoV-2 RNAs), at from about one copy per $10^7$ non-target RNAs (e.g., non-SARS-CoV-2 RNAs) to about one copy per 100 non-target RNAs (e.g., non-SARS-CoV-2 RNAs), at from about one copy per $10^6$ non-target RNAs (e.g., non-SARS-CoV-2 RNAs) to about one copy per 100 non-target RNAs (e.g., non-SARS-CoV-2 RNAs), at from about one copy per 104 non-target RNAs (e.g., non-SARS-CoV-2 RNAs) to about one copy per 100 non-target RNAs (e.g., non-SARS-CoV-2 RNAs), or at from about one copy per $10^3$ non-target RNAs (e.g., non-SARS-CoV-2 RNAs) to about one copy per 100 non-target RNAs (e.g., non-SARS-CoV-2 RNAs).

In some cases, the methods described and disclosed herein can detect an amount of SARS-CoV-2 RNA in an amount of about 10 nM or less, about 5 nM or less, about 1 nM or less, about 0.5 nM or less, about 0.1 nM or less, about 0.05 nM or less, about 0.01 nM or less, about 0.005 nM or less, about 0.001 nM or less, about 0.0005 nM or less, about 0.0001 nM or less, about 0.00005 nM or less, or about 0.00001 nM or less. In some cases, the methods described and disclosed herein can detect an amount of SARS-CoV-2 RNA in an amount of about 10 pM or less, about 5 pM or less, about 1 pM or less, about 0.5 pM or less, about 0.1 pM or less, about 0.05 pM or less, about 0.01 pM or less, about 0.005 pM or less, about 0.001 pM or less, about 0.0005 pM or less, about 0.0001 pM or less, about 0.00005 pM or less, or about 0.00001 pM or less. In some cases, the methods described and disclosed herein can detect an amount of SARS-CoV-2 in an amount of about 100 fM or less, about 50 fM or less, about 25 fM or less, about 20 fM or less, about 15 fM or less, about 10 fM or less, about 5 fM or less, or about 1 fM or less.

In some cases, the methods described and disclosed herein can detect an amount of SARS-CoV-2 RNA in an amount of about 1 fM or more, about 5 fM or more, about 10 fM or more, about 15 fM or more, about 20 fM or more, about 25 fM or more, about 50 fM or more, about 100 fM or more. In some cases, the methods described and disclosed herein can detect an amount of RNA cleavage products (e.g., SARS-CoV-2 RNA cleavage products) in an amount of about 0.00001 pM or more, about 0.00005 pM or more, about 0.0001 pM or more, about 0.0005 pM or more, about 0.001 pM or more, about 0.005 pM or more, about 0.01 pM or more, about 0.05 pM or more, about 0.1 pM or more, about 0.5 pM or more, about 1 pM or more, about 5 pM or more, or about 10 pM or more. In some cases, the methods described and disclosed herein can detect an amount of SARS-CoV-2 RNA in an amount of about 0.00001 nM or more, about 0.00005 nM or more, about 0.0001 nM or more, about 0.0005 nM or more, about 0.001 nM or more, about 0.005 nM or more, about 0.01 nM or more, about 0.05 nM or more, about 0.1 nM or more, about 0.5 nM or more, about 1 nM or more, about 5 nM or more, or about 10 nM or more.

In some cases, the methods described and disclosed herein can detect an amount of SARS-CoV-2 RNA in an amount of from about $10^6$ nM to about 1 nM, from about $10^6$ nM to about $5 \times 10^6$ nM, from about $5 \times 10^6$ nM to about $10^5$ nM, from about $10^5$ nM to about $5 \times 10^5$ nM, from about $5 \times 10^5$ nM to about $10^4$ nM, from about $10^4$ nM to about $5 \times 10^4$ nM, from about $5 \times 10^4$ nM to about $10^3$ nM, from about $10^3$ nM to about $5 \times 10^3$ nM, from about $5 \times 10^3$ nM to about $10^2$ nM, from about $10^2$ nM to about $5 \times 10^2$ nM, from about $5 \times 10^2$ nM to about 0.1 nM, from about 0.1 nM to about 0.5 nM, from about 0.5 nM to about 1 nM, from about 1 nM to about 5 nM, or from about 5 nM to about 10 nM.

In some cases, the methods include detecting a level of the reporter RNA cleavage product (which reports SARS-CoV-2 RNA) with a detector. Detection of the RNA cleavage product can occur by any method known to one of skill in the art. Non-limiting examples of suitable detectors include gold nanoparticle-based detectors, fluorescence polarization, colloid phase transition/dispersion, electrochemical detection, semiconductor-based sensing, and detection of a labeled detector RNA. In some cases, the labeled detector is a fluorescence detector, optionally a short quenched-fluorescent RNA. The readout of such detectors can be any convenient readout, including mobile phone-based detectors, to read a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

In some cases, the RNA cleavage product concentration is determined using a standard curve of the level of the RNA cleavage product correlated with the level of SARS-CoV-2 RNA. Such a standard curve can be prepared by observing the amount of signal from a series of assays containing known but varying amounts of SARS-CoV-2 RNA (target), each with an excess, but non-varying amount of reporter RNA. Fluorescence from such a series of assays can then be tracked over a period of time, for example, over about 10 minutes, over about 20 minutes, over about 30 minutes, over about 45 minutes, over about 1 hour, over about 2 hours, over about 3 hours, over about 4 hours, over about 5 hours, over about 6 hours, or more. In some cases, the fluorescence is tracked for over about 2 hours. The initial rate of each reaction is then determined and plotted to create a linear standard curve. In parallel, a sample of unknown SARS-CoV-2 RNA concentration is also run. The initial rate of the fluorescence curve (e.g., 2-hour fluorescence curve) for the unknown SARS-CoV-2 RNA sample is, for example, plotted on the standard curve to interpolate the concentration of SARS-CoV-2 RNA.

In some cases, the RNA is not reverse transcribed prior to the detecting step. In some cases, the methods further include a step of amplifying RNA from the sample suspected of containing SARS-CoV-2 RNA and/or a step of amplifying the RNA cleavage product. In other cases, the methods do not comprise a step of amplification of the RNA from the sample suspected of containing SARS-CoV-2 RNA and/or the RNA cleavage product. In some cases, the methods do not include reverse transcribing the RNA from the sample suspected of containing SARS-CoV-2 RNA prior to the detecting step and do not amplify the RNA from the sample suspected of containing SARS-CoV-2 RNA and/or RNA cleavage product.

In some cases, a portion of the sample or the reaction mixture is depleted prior to the detecting step. A non-limiting example of a suitable method for depletion is Depletion of Abundant Sequences by Hybridization (DASH) as described in US Publication No. 2018/0051320 which is incorporated by reference in its entirety. In some cases, the portion of the sample that is depleted is a human nucleic acid portion, for example human RNA.

In some cases, RNase is removed from the sample. In some cases, RNase function is removed from the sample using an RNase inhibitor and/or heat.

The CRISPR guide RNAs (crRNAs) can be provided in an array where each crRNA is present within a well of a microarray or where each type of crRNA is attached to a discrete location on a solid surface. The crRNA(s) can be supplied with at least one Cas13a or Cas13b protein. Alternatively, the crRNA(s) can be supplied in a form that allows or facilitates complex formation with at least one Cas13a or Cas13b protein. Any crRNAs that are attached to a solid surface are provided in a manner that does not interfere with complex formation with at least one Cas13a or Cas13b protein.

In some cases, the assays can be performed in small amounts of liquids. For example, a droplet assay system can be used. The term "droplet assay" refers to a reaction performed in a droplet of water, for example, in a well. Preferably, the droplet assay system can be an emulsion droplet assay system, in which the reaction area is a water droplet that is formed in a water-oil emulsion. Techniques for performing droplet assays are described, for example, in Hindson et al., *Anal Chem.* 83:8604-8610 (2011); Pinheiro et al., *Anal Chem,* 84:1003-1011 (2012); and Jones et al., *J. Virological Methods,* 202: 46-53 (2014). Droplet assay systems and emulsion droplet assay systems that are used for polymerase chain reaction (PCR), for example, are commercially available from sources such as, for example, the QX200™ DROPLET DIGITAL™ PCR system (Bio-Rad Laboratories, Inc., Hercules, Calif.).

Rather than allowing cleaved fluorophores to diffuse away in a bulk sample, oil-water emulsions can be formed with droplets that contain on average one Cas13 molecule (or some small number). If the crRNA:Cas13 in a droplet has bound to a viral RNA (e.g., after a defined incubation time prior to droplet formation), then it will cleave all of the RNase Alert in the droplet, creating a bright droplet against a sea of dark droplets. Hence, an emulsion can be formed after or during addition of the target (SARS-CoV-2) RNA, so that complexes of crRNA:Cas13 and the target (SARS-CoV-2) RNA are separated from other complexes of crRNA:Cas13 and the target (SARS-CoV-2) RNA within different droplets. Sufficient reporter RNA is provided so that substantially every droplet has reporter RNA.

When using a droplet assays, fluorescent imaging can be used after a defined reaction time (rather than a time series) and the number of bright droplets can simply be counted to determine the number of viral RNAs present in the sample. This is analogous to droplet PCR but has utility for increasing the diagnostic sensitivity of a Cas13-related assay.

There are several intrinsic advantages to droplet assays compared to traditional assays such as traditional quantitative PCR systems (Hindson, Nat Methods, October; 0(10): 1003-5 (2013): Doi, 2015; Huggett, PLoS One 8(9):e75296 (2013); Racki, Plant Methods 10(1):42,014-0042-6 (2014)).

First, droplet assays allow absolute quantification without the need for normalization, calibrator or external references (Zhao et al., PLoS One 11(7):e0159004 (2016)). This is because Poisson statistics allow direct estimation of template RNA or DNA copies. Second, droplet assays provide a direct measurement expressed as number of copies of target per microliter of reaction (with confidence intervals) (Hindson, 2013). Third, because droplet assays is an end-point binary assay, it is relatively insensitive to technical issues such as PCR inhibitors (Doi, 2015; Huggett, 2013; Racki, 2014). Fourth, droplet assays have predicable technical measurement errors because the underlying binomial distribution can be used to directly compute confidence intervals (Dube et al. PLoS One, 3(8):e2876 (2008). Fifth, droplet assays have been shown to have increased precision and sensitivity in detecting low template copies (Brunetto, J Neurovirol. 20(4):341-51 (2014): Sanders, PLoS One 8(9): e75296 (2013): Zhao et al., J Vet Diagn Invest. 27(6):784-8 (2015)). Sixth, droplet assays can be predictably and reliably run as multiplexed assays. Various publications provide guidelines to facilitate development of good data quality, precision and reproducibility for this highly sensitive technique (Huggett, PLoS One 8(9):e75296 (2013)).

Kits

Also described herein are kits that are useful for performing the methods detailed herein. Such kits can include a package that has at least one Cas13 protein (e.g., a Cas13a or Cas13b protein), at least one CRISPR guide RNA (crRNA), at least one RNA reporter, and instructions for performing a method described herein. In some cases, the Cas13 protein(s) and crRNA(s) are provided as crRNA: Cas13 complexes. The reporter RNA can be packaged separately, or it can be packaged with the at least one Cas13 protein, the at least one CRISPR guide RNA (crRNA), or a complex thereof. In some case, each of the CRISPR guide RNA(s) can have a sequence with at least about 70%, at least about 75%, at least about 80%, at least about 85%, at least about 90%, at least about 95%, at least about 98%, or more sequence identity to any SEQ ID NO: 1-35, 58-147.

The CRISPR guide RNAs (crRNAs) or Cas 13 protein can be provided in an array. For example, each crRNA can be present within a well of a microarray or each crRNA can be attached to a discrete location on a solid surface. The Cas13 protein can be provided as a complex with each of the arrayed crRNAs. Alternatively, the Cas13 protein can be present within a well of a microarray and different crRNA can be within the different wells of the microarray or different crRNAs can be complexed with Cas13 proteins attached to discrete locations on a solid surface. As described herein, any crRNAs or Cas13 proteins that are attached to a solid surface are provided in a manner that does not interfere with crRNA:Cas13 complex formation, activation by SARS-CoV-2 RNA, and reporter RNA cleavage.

The kits can also include components such as one or more fluorescent dyes, fluorescent quenchers, nuclease-free water, buffer components to regulate the pH of a solution, nuclease inhibitor(s) (e.g., an RNase inhibitor), reaction vessel(s), cellular/viral lysis reagent(s), component(s) for stabilizing samples, component(s) for stabilizing RNA, gloves, masks, implements for collection of a sample from a patient, or a combination thereof. For example, the kits can include fluorescent dyes such as Alexa Fluor®430, STAR 520, Brilliant Violet™510, 605 and 610 or a combination thereof. The fluorescent dyes can be used as fluorophores and the Iowa Black FQ and RQ (IDT) can be used as quenchers. The selection of fluorophores and quenchers can be made based on which will give the optimum signal while minimizing any background signal from the excitation light.

Implements for collection of a sample can include at least one swab, receptacle for a sample, alcohol swab, a nuclease inhibitor (e.g., an RNase inhibitor), or a combination thereof.

The kits can also include devices or components for detection of fluorescence. Fluorescence-based read-out technologies increase the sensitivity of the assay and, when combined with mobile detection technologies, enable field-deployable features of the diagnostic. Mobile phones detect light differently than laboratory plate readers but can be adapted for fluorescence detection with proper design of illumination and collection optics. For example, the kit can include the hardware and/or software for the slide scanning system described in U.S. Pat. No. 10,578,851, which can be paired with a mobile device (e.g., a cell phone) to allow detection and/or quantification of fluorescent signals.

To enable testing outside the laboratory, innovative mobile phone-based detection can be used. Cell phone cameras are the most ubiquitous optical sensors in the developed and developing worlds and have been used as microscopes and spectrometers (Smith et al. PLoS ONE. 6(3):c17150 (March 2011); Berg et al. ACS Nano. 9(8): 7857-66 (2015); Skandarajah (2015). In addition, the cell phone having core-processors, data connectivity, and bandwidth provide the computational power that can be utilized for advanced diagnostics applications. Combining the methods described herein and mobile phone-based technologies allows detection of SARS-CoV-2 without sending test samples to testing labs and instead permits detection of CoVID-19 infection in remote locations rather than in laboratories, clinics and hospitals. Hence, methods and kits that combine the assays described herein with sensitive fluorescence-based outreads provide tangible translational progress towards fundamentally new SARS-CoV-2 diagnostics.

The methods, kits, and devices can also include instructions and/or components for reporting the results of the detection procedures to a subject who provided the sample tested, to one or more medical personnel, to one or more government authorities, to a database, or to a combination thereof. The method of methods, kits, and devices can also include reporting the location of the subject who provided a sample that is tested. The results reported can include reports of positive or negative SARS-CoV-2 infection.

Optionally, the methods include a further step of treating SARS-CoV-2 in subjects where SARS-CoV-2 is detected or where monitored SARS-CoV-2 levels have increased. Such a method can include administration of a therapeutic agent to a patient with detectable SARS-CoV-2.

Such treatment when SARS-CoV-2 is detected can involve antiviral therapy, antiretroviral therapy (ART), breathing support (oxygen, endotracheal intubation), steroids to reduce inflammation, steroids to reduce lung swelling, blood plasma transfusions, or a combination thereof. For example, patients infected with SARS-CoV-2 can be administered dexamethasone, Remdesivir (Veklury), bamlanivimab, casirivimab, imdevimab, or a combination thereof. The bamlanivimab, casirivimab, and imdevimab therapeutics are available under FDA EUAs for patients at high risk of disease progression and severe illness. Some patients can also benefit from receiving anti-SARS-CoV-2 monoclonal antibodies.

In some cases, the kits described herein can also include a therapeutic agent for treatment of SARS-CoV-2.

SARA-CoV-2 Sequences

A DNA sequence for the SARS-CoV-2 genome, with coding regions, is available as accession number NC_045512.2 from the NCBI website (provided as SEQ ID NO:55 herein).

```
   1 ATTAAAGGTT TATACCTTCC CAGGTAACAA ACCAACCAAC

41 TTTCGATCTC TTGTAGATCT GTTCTCTAAA CGAACTTTAA

81 AATCTGTGTG GCTGTCACTC GGCTGCATGC TTAGTGCACT

121 CACGCAGTAT AATTAATAAC TAATTACTGT CGTTGACAGG

161 ACACGAGTAA CTCGTCTATC TTCTGCAGGC TGCTTACGGT

201 TTCGTCCGTG TTGCAGCCGA TCATCAGCAC ATCTAGGTTT

241 CGTCCGGGTG TGACCGAAAG GTAAGATGGA GAGCCTTGTC

281 CCTGGTTTCA ACGAGAAAAC ACACGTCCAA CTCAGTTTGC

321 CTGTTTTACA GGTTCGCGAC GTGCTCGTAC GTGGCTTTGG

361 AGACTCCGTG GAGGAGGTCT TATCAGAGGC ACGTCAACAT

401 CTTAAAGATG GCACTTGTGG CTTAGTAGAA GTTGAAAAAG

441 GCGTTTTGCC TCAACTTGAA CAGCCCTATG TGTTCATCAA

481 ACGTTCGGAT GCTCGAACTG CACCTCATGG TCATGTTATG

521 GTTGAGCTGG TAGCAGAACT CGAAGGCATT CAGTACGGTC

561 GTAGTGGTGA GACACTTGGT GTCCTTGTCC CTCATGTGGG

601 CGAAATACCA GTGGCTTACC GCAAGGTTCT TCTTCGTAAG

641 AACGGTAATA AAGGAGCTGG TGGCCATAGT TACGGCGCCG

681 ATCTAAAGTC ATTTGACTTA GGCGACGAGC TTGGCACTGA

721 TCCTTATGAA GATTTTCAAG AAAACTGGAA CACTAAACAT

761 AGCAGTGGTG TTACCCGTGA ACTCATGCGT GAGCTTAACG

801 GAGGGGCATA CACTCGCTAT GTCGATAACA ACTTCTGTGG

841 CCCTGATGGC TACCCTCTTG AGTGCATTAA AGACCTTCTA

881 GCACGTGCTG GTAAAGCTTC ATGCACTTTG TCCGAACAAC

921 TGGACTTTAT TGACACTAAG AGGGGTGTAT ACTGCTGCCG

961 TGAACATGAG CATGAAATTG CTTGGTACAC GGAACGTTCT

1001 GAAAAGAGCT ATGAATTGCA GACACCTTTT GAAATTAAAT

1041 TGGCAAAGAA ATTTGACACC TTCAATGGGG AATGTCCAAA

1081 TTTTGTATTT CCCTTAAATT GCATAATCAA GACTATTCAA
```

-continued

```
1121 CCAAGGGTTG AAAAGAAAAA GGTTGATGGC TTTATGGGTA

1161 GAATTCGATC TGTCTATCCA GTTGCGTCAC CAAATGAATG

1201 CAACCAAATG TGCCTTTCAA CTCTCATGAA GTGTGATCAT

1241 TGTGGTGAAA CTTCATGGCA GACGGGCGAT TTTGTTAAAG

1281 CCACTTGCGA ATTTTGTGGC ACTGAGAATT TGACTAAAGA

1321 AGGTGCCACT ACTTGTGGTT ACTTACCCCA AAATGCTGTT

1361 GTTAAAATTT ATTGTCCAGC ATGTCACAAT TCAGAAGTAG

1401 GACCTGAGCA TAGTCTTGCC GAATACCATA ATGAATCTGG

1441 CTTGAAAACC ATTCTTCGTA AGGGTGGTCG CACTATTGCC

1481 TTTGGAGGCT GTGTGTTCTC TTATGTTGGT TGCCATAACA

1521 AGTGTGCCTA TTGGGTTCCA GGTGCTAGCG CTAACATAGG

1561 TTGTAACCAT ACAGGTGTTG TTGGAGAAGG TTCCGAAGGT

1601 CTTAATGACA ACCTTCTTGA AATACTCCAA AAAGAGAAAG

1641 TCAACATCAA TATTGTTGGT GACTTTAAAC TTAATGAAGA

1681 GATCGCCATT ATTTTGGCAT CTTTTTCTGC TTCCACAAGT

1721 GCTTTTGTGG AAACTGTGAA AGGTTTGGAT TATAAAGCAT

1761 TCAAACAAAT TGTTGAATCC TGTGGTAATT TTAAAGTTAC

1801 AAAAGGAAAA GCTAAAAAAG GTGCCTGGAA TATTGGTGAA

1841 CAGAAATCAA TACTGAGTCC TCTTTATGCA TTTGCATCAG

1881 AGGCTGCTCG TGTTGTACGA TCAATTTTCT CCCGCACTCT

1921 TGAAACTGCT CAAAATTCTG TGCGTGTTTT ACAGAAGGCC

1961 GCTATAACAA TACTAGATGG AATTTCACAG TATTCACTGA

2001 GACTCATTGA TGCTATGATG TTCACATCTG ATTTGGCTAC

2041 TAACAATCTA GTTGTAATGG CCTACATTAC AGGTGGTGTT

2081 GTTCAGTTGA CTTCGCAGTG GCTAACTAAC ATCTTTGGCA

2121 CTGTTTATGA AAAACTCAAA CCCGTCCTTG ATTGGCTTGA

2161 AGAGAAGTTT AAGGAAGGTG TAGAGTTTCT TAGAGACGGT

2201 TGGGAAATTG TTAAATTTAT CTCAACCTGT GCTTGTGAAA

2241 TTGTCGGTGG ACAAATTGTC ACCTGTGCAA AGGAAATTAA

2281 GGAGAGTGTT CAGACATTCT TTAAGCTTGT AAATAAATTT

2321 TTGGCTTTGT GTGCTGAGTC TATCATTATT GGTGGAGCTA

2361 AACTTAAAGC CTTGAATTTA GGTGAAACAT TTGTCACGCA

2401 CTCAAAGGGA TTGTACAGAA AGTGTGTTAA ATCCAGAGAA

2441 GAAACTGGCC TACTCATGCC TCTAAAAGCC CCAAAAGAAA

2481 TTATCTTCTT AGAGGGAGAA ACACTTCCCA CAGAAGTGTT

2521 AACAGAGGAA GTTGTCTTGA AAACTGGTGA TTTACAACCA

2561 TTAGAACAAC CTACTAGTGA AGCTGTTGAA GCTCGATTGG

2601 TTGGTACACC AGTTTGTATT AACGGGCTTA TGTTGCTCGA

2641 AATCAAAGAC ACAGAAAGT ACTGTGCCCT TGCACCTAAT

2681 ATGATGGTAA CAAACAATAC CTTCACACTC AAAGGCGGTG
```

-continued

```
2721 CACCAACAAA GGTTACTTTT GGTGATGACA CTGTGATAGA

2761 AGTGCAAGGT TACAAGAGTG TGAATATCAC TTTTGAACTT

2801 GATGAAAGGA TTGATAAAGT ACTTAATGAG AAGTGCTCTG

2841 CCTATACAGT TGAACTCGGT ACAGAAGTAA ATGAGTTCGC

2881 CTGTGTTGTG GCAGATGCTG TCATAAAAAC TTTGCAACCA

2921 GTATCTGAAT TACTTACACC ACTGGGCATT GATTTAGATG

2961 AGTGGAGTAT GGCTACATAC TACTTATTTG ATGAGTCTGG

3001 TGAGTTTAAA TTGGCTTCAC ATATGTATTG TTCTTTCTAC

3041 CCTCCAGATG AGGATGAAGA AGAAGGTGAT TGTGAAGAAG

3081 AAGAGTTTGA GCCATCAACT CAATATGAGT ATGGTACTGA

3121 AGATGATTAC CAAGGTAAAC CTTTGGAATT TGGTGCCACT

3161 TCTGCTGCTC TTCAACCTGA AGAAGAGCAA GAAGAAGATT

3201 GGTTAGATGA TGATAGTCAA CAAACTGTTG GTCAACAAGA

3241 CGGCAGTGAG GACAATCAGA CAACTACTAT TCAAACAATT

3281 GTTGAGGTTC AACCTCAATT AGAGATGGAA CTTACACCAG

3321 TTGTTCAGAC TATTGAAGTG AATAGTTTTA GTGGTTATTT

3361 AAAACTTACT GACAATGTAT ACATTAAAAA TGCAGACATT

3401 GTGGAAGAAG CTAAAAAGGT AAAACCAACA GTGGTTGTTA

3441 ATGCAGCCAA TGTTTACCTT AAACATGGAG GAGGTGTTGC

3481 AGGAGCCTTA AATAAGGCTA CTAACAATGC CATGCAAGTT

3521 GAATCTGATG ATTACATAGC TACTAATGGA CCACTTAAAG

3561 TGGGTGGTAG TTGTGTTTTA AGCGGACACA ATCTTGCTAA

3601 AGACTGTCTT CATGTTGTCG GCCCAAATGT TAACAAAGGT

3641 GAAGACATTC AACTTCTTAA GAGTGCTTAT GAAAATTTTA

3681 ATCAGCACGA AGTTCTACTT GCACCATTAT TATCAGCTGG

3721 TATTTTTGGT GCTGACCCTA TACATTCTTT AAGAGTTTGT

3761 GTAGATACTG TTCGCACAAA TGTCTACTTA GCTGTCTTTG

3801 ATAAAAATCT CTATGACAAA CTTGTTTCAA GCTTTTTGGA

3841 AATGAAGAGT GAAAAGCAAG TTGAACAAAA GATCGCTGAG

3881 ATTCCTAAAG AGGAAGTTAA GCCATTTATA ACTGAAAGTA

3921 AACCTTCAGT TGAACAGAGA AAACAAGATG ATAAGAAAAT

3961 CAAAGCTTGT GTTGAAGAAG TTACAACAAC TCTGGAAGAA

4001 ACTAAGTTCC TCACAGAAAA CTTGTTACTT TATATTGACA

4041 TTAATGGCAA TCTTCATCCA GATTCTGCCA CTCTTGTTAG

4081 TGACATTGAC ATCACTTTCT TAAAGAAAGA TGCTCCATAT

4121 ATAGTGGGTG ATGTTGTTCA AGAGGGTGTT TTAACTGCTG

4161 TGGTTATACC TACTAAAAAG GCTGGTGGCA CTACTGAAAT

4201 GCTAGCGAAA GCTTTGAGAA AAGTGCCAAC AGACAATTAT

4241 ATAACCACTT ACCCGGGTCA GGGTTTAAAT GGTTACACTG

4281 TAGAGGAGGC AAAGACAGTG CTTAAAAAGT GTAAAAGTGC

4321 CTTTTACATT CTACCATCTA TTATCTCTAA TGAGAAGCAA
```

-continued

4361 GAAATTCTTG GAACTGTTTC TTGGAATTTG CGAGAAATGC

4401 TTGCACATGC AGAAGAAACA CGCAAATTAA TGCCTGTCTG

4441 TGTGGAAACT AAAGCCATAG TTTCAACTAT ACAGCGTAAA

4481 TATAAGGGTA TTAAAATACA AGAGGGTGTG GTTGATTATG

4521 GTGCTAGATT TTACTTTTAC ACCAGTAAAA CAACTGTAGC

4561 GTCACTTATC AACACACTTA ACGATCTAAA TGAAACTCTT

4601 GTTACAATGC CACTTGGCTA TGTAACACAT GGCTTAAATT

4641 TGGAAGAAGC TGCTCGGTAT ATGAGATCTC TCAAAGTGCC

4681 AGCTACAGTT TCTGTTTCTT CACCTGATGC TGTTACAGCG

4721 TATAATGGTT ATCTTACTTC TTCTTCTAAA ACACCTGAAG

4761 AACATTTTAT TGAAACCATC TCACTTGCTG GTTCCTATAA

4801 AGATTGGTCC TATTCTGGAC AATCTACACA ACTAGGTATA

4841 GAATTTCTTA AGAGAGGTGA TAAAAGTGTA TATTACACTA

4881 GTAATCCTAC CACATTCCAC CTAGATGGTG AAGTTATCAC

4921 CTTTGACAAT CTTAAGACAC TTCTTTCTTT GAGAGAAGTG

4961 AGGACTATTA AGGTGTTTAC AACAGTAGAC AACATTAACC

5001 TCCACACGCA AGTTGTGGAC ATGTCAATGA CATATGGACA

5041 ACAGTTTGGT CCAACTTATT TGGATGGAGC TGATGTTACT

5081 AAAATAAAAC CTCATAATTC ACATGAAGGT AAAACATTTT

5121 ATGTTTTACC TAATGATGAC ACTCTACGTG TTGAGGCTTT

5161 TGAGTACTAC CACACAACTG ATCCTAGTTT TCTGGGTAGG

5201 TACATGTCAG CATTAAATCA CACTAAAAAG TGGAAATACC

5241 CACAAGTTAA TGGTTTAACT TCTATTAAAT GGGCAGATAA

5281 CAACTGTTAT CTTGCCACTG CATTGTTAAC ACTCCAACAA

5321 ATAGAGTTGA AGTTTAATCC ACCTGCTCTA CAAGATGCTT

5361 ATTACAGAGC AAGGGCTGGT GAAGCTGCTA ACTTTTGTGC

5401 ACTTATCTTA GCCTACTGTA ATAAGACAGT AGGTGAGTTA

5441 GGTGATGTTA GAGAAAGAAT GAGTTACTTG TTTCAACATG

5481 CCAATTTAGA TTCTTGCAAA AGAGTCTTGA ACGTGGTGTG

5521 TAAAACTTGT GGACAACAGC AGACAACCCT TAAGGGTGTA

5561 GAAGCTGTTA TGTACATGGG CACACTTTCT TATGAACAAT

5601 TTAAGAAAGG TGTTCAGATA CCTTGTACGT GTGGTAAACA

5641 AGCTACAAAA TATCTAGTAC AACAGGAGTC ACCTTTTGTT

5681 ATGATGTCAG CACCACCTGC TCAGTATGAA CTTAAGCATG

5721 GTACATTTAC TTGTGCTAGT GAGTACACTG GTAATTACCA

5761 GTGTGGTCAC TATAAACATA TAACTTCTAA AGAAACTTTG

5801 TATTGCATAG ACGGTGCTTT ACTTACAAAG TCCTCAGAAT

5841 ACAAAGGTCC TATTACGGAT GTTTTCTACA AAGAAAACAG

5881 TTACACAACA ACCATAAAAC CAGTTACTTA TAAATTGGAT

5921 GGTGTTGTTT GTACAGAAAT TGACCCTAAG TTGGACAATT

-continued

5961 ATTATAAGAA AGACAATTCT TATTTCACAG AGCAACCAAT

6001 TGATCTTGTA CCAAACCAAC CATATCCAAA CGCAAGCTTC

6041 GATAATTTTA AGTTTGTATG TGATAATATC AAATTTGCTG

6081 ATGATTTAAA CCAGTTAACT GGTTATAAGA AACCTGCTTC

6121 AAGAGAGCTT AAAGTTACAT TTTTCCCTGA CTTAAATGGT

6161 GATGTGGTGG CTATTGATTA TAAACACTAC ACACCCTCTT

6201 TTAAGAAAGG AGCTAAATTG TTACATAAAC CTATTGTTTG

6241 GCATGTTAAC AATGCAACTA ATAAAGCCAC GTATAAACCA

6281 AATACCTGGT GTATACGTTG TCTTTGGAGC ACAAAACCAG

6321 TTGAAACATC AAATTCGTTT GATGTACTGA AGTCAGAGGA

6361 CGCGCAGGGA ATGGATAATC TTGCCTGCGA AGATCTAAAA

6401 CCAGTCTGTG AAGAAGTACT GGAAAATCCT ACCATACAGA

6441 AAGACGTTCT TGAGTGTAAT GTGAAAACTA CCGAAGTTGT

6481 AGGAGACATT ATACTTAAAC CAGCAAATAA TAGTTTAAAA

6521 ATTACAGAAG AGGTTGGCCA CACAGATCTA ATGGCTGCTT

6561 ATGTAGACAA TTCTAGTCTT ACTATTAAGA AACCTAATGA

6601 ATTATCTAGA GTATTAGGTT TGAAAACCCT TGCTACTCAT

6641 GGTTTAGCTG CTGTTAATAG TGTCCCTTGG GATACTATAG

6681 CTAATTATGC TAAGCCTTTT CTTAACAAAG TTGTTAGTAC

6721 AACTACTAAC ATAGTTACAC GGTGTTTAAA CCGTGTTTGT

6761 ACTAATTATA TGCCTTATTT CTTTACTTTA TTGCTACAAT

6801 TGTGTACTTT TACTAGAAGT ACAAATTCTA GAATTAAAGC

6841 ATCTATGCCG ACTACTATAG CAAAGAATAC TGTTAAGAGT

6881 GTCGGTAAAT TTTGTCTAGA GGCTTCATTT AATTATTTGA

6921 AGTCACCTAA TTTTTCTAAA CTGATAAATA TTATAATTTG

6961 GTTTTTACTA TTAAGTGTTT GCCTAGGTTC TTTAATCTAC

7001 TCAACCGCTG CTTTAGGTGT TTTAATGTCT AATTTAGGCA

7041 TGCCTTCTTA CTGTACTGGT TACAGAGAAG GCTATTTGAA

7081 CTCTACTAAT GTCACTATTG CAACCTACTG TACTGGTTCT

7121 ATACCTTGTA GTGTTTGTCT TAGTGGTTTA GATTCTTTAG

7161 ACACCTATCC TTCTTTAGAA ACTATACAAA TTACGATTTC

7201 ATCTTTTAAA TGGGATTTAA CTGCTTTTGG CTTAGTTGCA

7241 GAGTGGTTTT TGGCATATAT TCTTTTCACT AGGTTTTTCT

7281 ATGTACTTGG ATTGGCTGCA ATCATGCAAT TGTTTTTCAG

7321 CTATTTTGCA GTACATTTTA TTAGTAATTC TTGGCTTATG

7361 TGGTTAATAA TTAATCTTGT ACAAATGGCC CCGATTTCAG

7401 CTATGGTTAG AATGTACATC TTCTTTGCAT CATTTTATTA

7441 TGTATGGAAA AGTTATGTGC ATGTTGTAGA CGGTTGTAAT

7481 TCATCAACTT GTATGATGTG TTACAAACGT AATAGAGCAA

7521 CAAGAGTCGA ATGTAGAACT ATTGTTAATG GTGTTAGAAG

7561 GTCCTTTTAT GTCTATGCTA ATGGAGGTAA AGGCTTTTGC

-continued

```
7601 AAACTAGACA ATTGGAATTG TGTTAATTGT GATACATTCT

7641 GTGCTGGTAC TACATTTATT AGTGATGAAG TTGCGAGAGA

7681 CTTGTCACTA CAGTTTAAAA GACCAATAAA TCCTACTGAC

7721 CAGTCTTCTT ACATCGTTGA TAGTGTTACA GTGAAGAATG

7761 GTTCCATCCA TCTTTACTTT GATAAAGCTG GTCAAAAGAC

7801 TTATGAAAGA CATTCTCTCT CTCATTTTGT TAACTTAGAC

7841 AACCTGAGAG CTAATAACAC TAAAGGTTGA TTGCCTATTA

7881 ATGTTATAGT TTTTGATGGT AAATCAAAAT GTGAAGAATC

7921 ATCTGCAAAA TCAGCGTCTG TTTACTACAG TCAGCTTATG

7961 TGTCAACCTA TACTGTTACT AGATCAGGCA TTAGTGTCTG

8001 ATGTTGGTGA TAGTGCGGAA GTTGCAGTTA AAATGTTTGA

8041 TGCTTACGTT AATACGTTTT CATCAACTTT TAACGTACCA

8081 ATGGAAAAAC TCAAAACACT AGTTGCAACT GCAGAAGCTG

8121 AACTTGCAAA GAATGTGTCC TTAGACAATG TCTTATCTAC

8161 TTTTATTTCA GCAGCTCGGC AAGGGTTTGT TGATTCAGAT

8201 GTAGAAACTA AAGATGTTGT TGAATGTCTT AAATTGTCAC

8241 ATCAATCTGA CATAGAAGTT ACTGGCGATA GTTGTAATAA

8281 CTATATGCTC ACCTATAACA AAGTTGAAAA CATGACACCC

8321 CGTGACCTTG GTGCTTGTAT TGACTGTAGT GCGCGTCATA

8361 TTAATGCGCA GGTAGCAAAA AGTCACAACA TTGCTTTGAT

8401 ATGGAACGTT AAAGATTTCA TGTCATTGTC TGAACAACTA

8441 CGAAACAAA TACGTAGTGC TGCTAAAAAG AATAACTTAC

8481 CTTTTAAGTT GACATGTGCA ACTACTAGAC AAGTTGTTAA

8521 TGTTGTAACA ACAAAGATAG CACTTAAGGG TGGTAAAATT

8561 GTTAATAATT GGTTGAAGCA GTTAATTAAA GTTACACTTG

8601 TGTTCCTTTT TGTTGCTGCT ATTTTCTATT TAATAACACC

8641 TGTTCATGTC ATGTCTAAAC ATACTGACTT TTCAAGTGAA

8681 ATCATAGGAT ACAAGGCTAT TGATGGTGGT GTCACTCGTG

8721 ACATAGCATC TACAGATACT TGTTTTGCTA ACAAACATGC

8761 TGATTTTGAC ACATGGTTTA GCCAGCGTGG TGGTAGTTAT

8801 ACTAATGACA AAGCTTGCCC ATTGATTGCT GCAGTCATAA

8841 CAAGAGAAGT GGGTTTTGTC GTGCCTGGTT TGCCTGGCAC

8881 GATATTACGC ACAACTAATG GTGACTTTTT GCATTTCTTA

8921 CCTAGAGTTT TTAGTGCAGT TGGTAACATC TGTTACACAC

8961 CATCAAAACT TATAGAGTAC ACTGACTTTG CAACATCAGC

9001 TTGTGTTTTG GCTGCTGAAT GTACAATTTT TAAAGATGCT

9041 TCTGGTAAGC CAGTACCATA TTGTTATGAT ACCAATGTAC

9081 TAGAAGGTTC TGTTGCTTAT GAAAGTTTAC GCCCTGACAC

3121 ACGTTATGTG CTCATGGATG GCTCTATTAT TCAATTTCCT

9161 AACACCTACC TTGAAGGTTC TGTTAGAGTG GTAACAACTT
```

-continued

```
9201 TTGATTCTGA GTACTGTAGG CACGGCACTT GTGAAAGATC

9241 AGAAGCTGGT GTTTGTGTAT CTACTAGTGG TAGATGGGTA

9281 CTTAACAATG ATTATTAGAG ATCTTTACCA GGAGTTTTCT

9321 GTGGTGTAGA TGCTGTAAAT TTACTTACTA ATATGTTTAC

9361 ACCACTAATT CAACCTATTG GTGCTTTGGA CATATCAGCA

9401 TCTATAGTAG CTGGTGGTAT TGTAGCTATC GTAGTAACAT

9441 GCCTTGCCTA CTATTTTATG AGGTTTAGAA GAGCTTTTGG

9481 TGAATACAGT CATGTAGTTG CCTTTAATAC TTTACTATTC

9521 CTTATGTCAT TCACTGTACT CTGTTTAACA CCAGTTTACT

9561 CATTCTTACC TGGTGTTTAT TCTGTTATTT ACTTGTACTT

9601 GACATTTTAT CTTACTAATG ATGTTTCTTT TTTAGCACAT

9641 ATTCAGTGGA TGGTTATGTT CACACCTTTA GTACCTTTCT

9681 GGATAACAAT TGCTTATATC ATTTGTATTT CCACAAAGCA

9721 TTTCTATTGG TTCTTTAGTA ATTACCTAAA GAGACGTGTA

9761 GTCTTTAATG GTGTTTCCTT TAGTACTTTT GAAGAAGCTG

9801 CGGTGTGCAC CTTTTTGTTA AATAAAGAAA TGTATCTAAA

9841 GTTGCGTAGT GATGTGCTAT TACCTCTTAC GCAATATAAT

9881 AGATACTTAG CTCTTTATAA TAAGTACAAG TATTTTAGTG

9921 GAGCAATGGA TACAACTAGC TACAGAGAAG CTGCTTGTTG

9961 TCATCTCGCA AAGGCTCTCA ATGACTTCAG TAACTCAGGT

10001 TCTGATGTTC TTTACCAACC ACCACAAACC TCTATCACCT

10041 CAGCTGTTTT GCAGAGTGGT TTTAGAAAAA TGGCATTCCC

10081 ATCTGGTAAA GTTGAGGGTT GTATGGTACA AGTAACTTGT

10121 GGTACAACTA CACTTAACGG TCTTTGGCTT GATGACGTAG

10161 TTTACTGTCC AAGACATGTG ATCTGCACCT CTGAAGACAT

10201 GCTTAACCCT AATTATGAAG ATTTACTCAT TCGTAAGTCT

10241 AATCATAATT TCTTGGTACA GGCTGGTAAT GTTCAACTCA

10281 GGGTTATTGG ACATTCTATG CAAAATTGTG TACTTAAGCT

10321 TAAGGTTGAT ACAGCCAATC CTAAGCACC TAAGTATAAG

10361 TTTGTTCGCA TTCAACCAGG ACAGACTTTT TCAGTGTTAG

10401 CTTGTTACAA TGGTTCACCA TCTGGTGTTT ACCAATGTGC

10441 TATGAGGCCC AATTTCACTA TTAAGGGTTC ATTCCTTAAT

10481 GGTTCATGTG GTAGTGTTGG TTTTAACATA GATTATGACT

10521 GTGTCTCTTT TTGTTACATG CACCATATGG AATTACCAAC

10561 TGGAGTTCAT GCTGGCACAG ACTTAGAAGG TAACTTTTAT

10601 GGACCTTTTG TTGACAGGCA AACAGCACAA GCAGCTGGTA

10641 CGGACACAAC TATTACAGTT AATGTTTTAG CTTGGTTGTA

10681 CGCTGCTGTT ATAAATGGAG ACAGGTGGTT TCTCAATCGA

10721 TTTACCACAA CTCTTAATGA CTTTAACCTT GTGGCTATGA

10761 AGTACAATTA TGAACCTCTA ACACAAGACC ATGTTGACAT

10801 ACTAGGACCT CTTTCTGCTC AAACTGGAAT TGCCGTTTTA
```

51
-continued

```
10841 GATATGTGTG CTTCATTAAA AGAATTACTG CAAAATGGTA

10881 TGAATGGACG TACCATATTG GGTAGTGCTT TATTAGAAGA

10921 TGAATTTACA CCTTTTGATG TTGTTAGACA ATGCTCAGGT

10961 GTTACTTTCC AAAGTGCAGT GAAAAGAACA ATCAAGGGTA

11001 CACACCACTG GTTGTTACTC ACAATTTTGA CTTCACTTTT

11041 AGTTTTAGTC CAGAGTACTC AATGGTCTTT GTTCTTTTTT

11081 TTGTATGAAA ATGCCTTTTT ACCTTTTGCT ATGGGTATTA

11121 TTGCTATGTC TGCTTTTGCA ATGATGTTTG TCAAACATAA

11161 GCATGCATTT CTCTGTTTGT TTTTGTTACC TTCTCTTGCC

11201 ACTGTAGCTT ATTTTAATAT GGTCTATATG CCTGCTAGTT

11241 GGGTGATGCG TATTATGACA TGGTTGGATA TGGTTGATAC

11281 TAGTTTGTCT GGTTTTAAGC TAAAAGACTG TGTTATGTAT

11321 GCATCAGCTG TAGTGTTACT AATCCTTATG ACAGCAAGAA

11361 CTGTGTATGA TGATGGTGCT AGGAGAGTGT GGACACTTAT

11401 GAATGTCTTG ACACTCGTTT ATAAAGTTTA TTATGGTAAT

11441 GCTTTAGATC AAGCCATTTC CATGTGGGCT CTTATAATCT

11481 CTGTTACTTC TAACTACTCA GGTGTAGTTA CAACTGTCAT

11521 GTTTTTGGCC AGAGGTATTG TTTTTATGTG TGTTGAGTAT

11561 TGCCCTATTT TCTTCATAAC TGGTAATACA CTTCAGTGTA

11601 TAATGCTAGT TTATTGTTTC TTAGGCTATT TTTGTACTTG

11641 TTACTTTGGC CTCTTTTGTT TACTCAACCG CTACTTTAGA

11681 CTGACTCTTG GTGTTTATGA TTACTTAGTT TCTACACAGG

11721 AGTTTAGATA TATGAATTCA CAGGGACTAC TCCCACCCAA

11761 GAATAGCATA GATGCCTTCA AACTCAACAT TAAATTGTTG

11801 GGTGTTGGTG GCAAACCTTG TATCAAAGTA GCCACTGTAC

11841 AGTCTAAAAT GTCAGATGTA AAGTGCACAT CAGTAGTCTT

11881 ACTCTCAGTT TTGCAACAAC TCAGAGTAGA ATCATCATCT

11921 AAATTGTGGG CTCAATGTGT CCAGTTACAC AATGACATTC

11961 TCTTAGCTAA AGATACTACT GAAGCCTTTG AAAAAATGGT

12001 TTCACTACTT TCTGTTTTGC TTTCCATGCA GGGTGCTGTA

12041 GACATAAACA AGCTTTGTGA AGAAATGCTG GACAACAGGG

12081 CAACCTTACA AGCTATAGCC TCAGAGTTTA GTTCCCTTCC

12121 ATCATATGCA GCTTTTGCTA CTGCTCAAGA AGCTTATGAG

12161 CAGGCTGTTG CTAATGGTGA TTCTGAAGTT GTTCTTAAAA

12201 AGTTGAAGAA GTCTTTGAAT GTGGCTAAAT CTGAATTTGA

12241 CCGTGATGCA GCCATGCAAC GTAAGTTGGA AAAGATGGCT

12281 GATCAAGCTA TGACCCAAAT GTATAAACAG GCTAGATCTG

12321 AGGACAAGAG GGCAAAAGTT ACTAGTGCTA TGCAGACAAT

12361 GCTTTTCACT ATGCTTAGAA AGTTGGATAA TGATGCACTC

12401 AACAACATTA TCAACAATGC AAGAGATGGT TGTGTTCCCT
```

52
-continued

```
12441 TGAACATAAT ACCTCTTACA ACAGCAGCCA AACTAATGGT

12481 TGTCATACCA GACTATAACA CATATAAAAA TACGTGTGAT

12521 GGTACAACAT TTACTTATGC ATCAGCATTG TGGGAAATCC

12561 AACAGGTTGT AGATGCAGAT AGTAAAATTG TTCAACTTAG

12601 TGAAATTAGT ATGGACAATT CACCTAATTT AGCATGGCCT

12641 CTTATTGTAA CAGCTTTAAG GGCCAATTCT GCTGTCAAAT

12681 TACAGAATAA TGAGCTTAGT CCTGTTGCAC TACGACAGAT

12721 GTCTTGTGCT GCCGGTACTA CACAAACTGC TTGCACTGAT

12761 GACAATGCGT TAGCTTACTA CAACACAACA AAGGGAGGTA

12801 GGTTTGTACT TGCACTGTTA TCCGATTTAC AGGATTTGAA

12841 ATGGGCTAGA TTCCCTAAGA GTGATGGAAC TGGTACTATC

12881 TATACAGAAC TGGAACCACC TTGTAGGTTT GTTACAGACA

12921 CACCTAAAGG TCCTAAAGTG AAGTATTTAT ACTTTATTAA

12961 AGGATTAAAC AACCTAAATA GAGGTATGGT ACTTGGTAGT

13001 TTAGCTGCCA CAGTACGTCT ACAAGCTGGT AATGCAACAG

13041 AAGTGCCTGC CAATTCAACT GTATTATCTT TCTGTGCTTT

13081 TGCTGTAGAT GCTGCTAAAG CTTACAAAGA TTATCTAGCT

13121 AGTGGGGGAC AACCAATCAC TAATTGTGTT AAGATGTTGT

13161 GTACACACAC TGGTACTGGT CAGGCAATAA CAGTTACACC

13201 GGAAGCCAAT ATGGATCAAG AATCCTTTGG TGGTGCATCG

13241 TGTTGTCTGT ACTGCCGTTG CCACATAGAT CATCCAAATC

13281 CTAAAGGATT TTGTGACTTA AAAGGTAAGT ATGTACAAAT

13321 ACCTACAACT TGTGCTAATG ACCCTGTGGG TTTTACACTT

13361 AAAAACACAG TCTGTACCGT CTGCGGTATG TGGAAAGGTT

13401 ATGGCTGTAG TTGTGATCAA CTCCGCGAAC CCATGCTTCA

13441 GTCAGCTGAT GCACAATCGT TTTTAAACGG GTTTGCGGTG

13481 TAAGTGCAGC CCGTCTTACA CCGTGCGGCA CAGGCACTAG

13521 TACTGATGTC GTATACAGGG CTTTTGACAT CTACAATGAT

13561 AAAGTAGCTG GTTTTGCTAA ATTCCTAAAA ACTAATTGTT

13601 GTCGCTTCCA AGAAAAGGAC GAAGATGACA ATTTAATTGA

13641 TTCTTACTTT GTAGTTAAGA GACACACTTT CTCTAACTAC

13681 CAACATGAAG AAACAATTTA TAATTTACTT AAGGATTGTC

13721 CAGCTGTTGC TAAACATGAC TTCTTTAAGT TTAGAATAGA

13761 CGGTGACATG GTACCACATA TATCACGTCA ACGTCTTACT

13801 AAATACACAA TGGCAGACCT CGTCTATGCT TTAAGGCATT

13841 TTGATGAAGG TAATTGTGAC ACATTAAAAG AAATACTTGT

13881 CACATACAAT TGTTGTGATG ATGATTATTT CAATAAAAAG

13921 GACTGGTATG ATTTTGTAGA AAACCCAGAT ATATTACGCG

13961 TATACGCCAA CTTAGGTGAA CGTGTACGCC AAGCTTTGTT

14001 AAAAACAGTA CAATTCTGTG ATGCCATGCG AAATGCTGGT

14041 ATTGTTGGTG TACTGACATT AGATAATCAA GATCTCAATG
```

-continued

```
14081 GTAACTGGTA TGATTTCGGT GATTTCATAC AAACCACGCC

14121 AGGTAGTGGA GTTCCTGTTG TAGATTCTTA TTATTCATTG

14161 TTAATGCCTA TATTAACCTT GACCAGGGCT TTAACTGCAG

14201 AGTCACATGT TGACACTGAC TTAACAAAGC CTTACATTAA

14241 GTGGGATTTG TTAAAATATG ACTTCACGGA AGAGAGGTTA

14281 AAACTCTTTG ACCGTTATTT TAAATATTGG GATCAGACAT

14321 ACCACCCAAA TTGTGTTAAC TGTTTGGATG ACAGATGCAT

14361 TCTGCATTGT GCAAACTTTA ATGTTTTATT CTCTACAGTG

14401 TTCCCACCTA CAAGTTTTGG ACCACTAGTG AGAAAAATAT

14441 TTGTTGATGG TGTTCCATTT GTAGTTTCAA CTGGATACCA

14481 CTTCAGAGAG CTAGGTGTTG TACATAATCA GGATGTAAAC

14521 TTACATAGCT CTAGACTTAG TTTTAAGGAA TTACTTGTGT

14561 ATGCTGCTGA CCCTGCTATG CACGCTGCTT CTGGTAATCT

14601 ATTACTAGAT AAACGCACTA CGTGCTTTTC AGTAGCTGCA

14641 CTTACTAACA ATGTTGCTTT TCAAACTGTC AAACCCGGTA

14681 ATTTTAACAA AGACTTCTAT GACTTTGCTG TGTCTAAGGG

14721 TTTCTTTAAG GAAGGAAGTT CTGTTGAATT AAAACACTTC

14761 TTCTTTGCTC AGGATGGTAA TGCTGCTATC AGCGATTATG

14801 ACTACTATCG TTATAATCTA CCAACAATGT GTGATATCAG

14841 ACAACTACTA TTTGTAGTTG AAGTTGTTGA TAAGTACTTT

14881 GATTGTTACG ATGGTGGCTG TATTAATGCT AACCAAGTCA

14921 TCGTCAACAA CCTAGACAAA TCAGCTGGTT TTCCATTTAA

14961 TAAATGGGGT AAGGCTAGAC TTTATTATGA TTCAATGAGT

15001 TATGAGGATC AAGATGCACT TTTCGCATAT ACAAAACGTA

15041 ATGTCATCCC TACTATAACT CAAATGAATC TTAAGTATGC

15081 CATTAGTGCA AAGAATAGAG CTCGCACCGT AGCTGGTGTC

15121 TCTATCTGTA GTACTATGAC CAATAGACAG TTTCATCAAA

15161 AATTATTGAA ATCAATAGCC GCCACTAGAG GAGCTACTGT

15201 AGTAATTGGA ACAAGCAAAT CTATGGTGG TTGGCACAAC

15241 ATGTTAAAAA CTGTTTATAG TGATGTAGAA AACCCTCACC

15281 TTATGGGTTG GGATTATCCT AAATGTGATA GAGCCATGCC

15321 TAACATGCTT AGAATTATGG CCTCACTTGT TCTTGCTCGC

15361 AAACATACAA CGTGTTGTAG CTTGTCACAC CGTTTCTATA

15401 GATTAGCTAA TGAGTGTGCT CAAGTATTGA GTGAAATGGT

15441 CATGTGTGGC GGTTCACTAT ATGTTAAACC AGGTGGAACC

15481 TCATCAGGAG ATGCCACAAC TGCTTATGCT AATAGTGTTT

15521 TTAACATTTC TCAAGCTGTC ACGGCCAATG TTAATGCACT

15561 TTTATCTACT GATGGTAACA AAATTGCCGA TAAGTATGTC

15601 CGCAATTTAC AACACAGACT TTATGAGTGT CTCTATAGAA

15641 ATAGAGATGT TGACACAGAC TTTGTGAATG AGTTTTACGC
```

-continued

```
15681 ATATTTGCGT AAACATTTCT CAATGATGAT ACTCTCTGAC

15721 GATGCTGTTG TGTGTTTCAA TAGCACTTAT GCATCTCAAG

15761 GTCTAGTGGC TAGCATAAAG AACTTTAAGT CAGTTCTTTA

15801 TTATCAAAAC AATGTTTTTA TGTCTGAAGC AAAATGTTGG

15841 ACTGAGACTG ACCTTACTAA AGGACCTCAT GAATTTTGCT

15881 CTCAACATAC AATGCTAGTT AAAGAGGGTG ATGATTATGT

15921 GTACCTTCCT TACCCAGATC CATCAAGAAT CCTAGGGGCC

15961 GGCTGTTTTG TAGATGATAT CGTAAAAACA GATGGTACAC

16001 TTATGATTGA ACGGTTCGTG TCTTTAGCTA TAGATGCTTA

16041 CCCACTTACT AAACATCCTA ATCAGGAGTA TGCTGATGTC

16081 TTTCATTTGT ACTTAGAATA CATAAGAAAG CTACATGATG

16121 AGTTAACAGG ACACATGTTA GACATGTATT CTGTTATGCT

16161 TACTAATGAT AACACTTCAA GGTATTGGGA ACCTGAGTTT

16201 TATGAGGCTA TGTACACACC GCATACAGTC TTACAGGCTG

16241 TTGGGGCTTG TGTTCTTTGC AATTCACAGA CTTCATTAAG

16281 ATGTGGTGCT TGCATACGTA GACCATTCTT ATGTTGTAAA

16321 TGCTGTTACG ACCATGTCAT ATCAACATCA CATAAATTAG

16361 TCTTGTCTGT TAATCCGTAT GTTTGCAATG CTCCAGGTTG

16401 TGATGTCACA GATGTGACTC AACTTTACTT AGGAGGTATG

16441 AGCTATTATT GTAAATCACA TAAACCACCC ATTAGTTTTC

16481 CATTGTGTGC TAATGGACAA GTTTTTGGTT TATATAAAAA

16521 TACATGTGTT GGTAGCGATA ATGTTACTGA CTTTAATGCA

16561 ATTGCAACAT GTGACTGGAC AAATGCTGGT GATTACATTT

16601 TAGCTAACAC CTGTACTGAA AGACTCAAGC TTTTTGCAGC

16641 AGAAACGCTC AAAGCTACTG AGGAGACATT TAAACTGTCT

16681 TATGGTATTG CTACTGTACG TGAAGTGCTG TCTGACAGAG

16721 AATTACATCT TTCATGGGAA GTTGGTAAAC CTAGACCACC

16761 ACTTAACCGA AATTATGTCT TTAGTGGTTA TCGTGTAACT

16801 AAAAACAGTA AAGTACAAAT AGGAGAGTAC ACCTTTGAAA

16841 AAGGTGACTA TGGTGATGCT GTTGTTTACC GAGGTACAAC

16881 AACTTAGAAA TTAAATGTTG GTGATTATTT TGTGCTGAGA

16921 TCACATACAG TAATGCCATT AAGTGCACCT ACACTAGTGC

16961 CACAAGAGCA CTATGTTAGA ATTACTGGCT TATACCCAAC

17001 ACTCAATATC TCAGATGAGT TTTCTAGCAA TGTTGCAAAT

17041 TATCAAAAGG TTGGTATGCA AAAGTATTCT ACACTCCAGG

17081 GACCACCTGG TACTGGTAAG AGTCATTTTG CTATTGGCCT

17121 AGCTCTCTAC TACCCTTCTG CTCGCATAGT GTATACAGCT

17161 TGCTCTCATG CCGCTGTTGA TGCACTATGT GAGAAGGCAT

17201 TAAAATATTT GCCTATAGAT AAATGTAGTA GAATTATACC

17241 TGCACGTGCT CGTGTAGAGT GTTTTGATAA ATTCAAAGTG

17281 AATTCAACAT TAGAACAGTA TGTCTTTTGT ACTGTAAATG
```

-continued

```
17321 CATTGCCTGA GACGACAGCA GATATAGTTG TCTTTGATGA

17361 AATTTCAATG GCCACAAATT ATGATTTGAG TGTTGTCAAT

17401 GCCAGATTAC GTGCTAAGCA CTATGTGTAC ATTGGCGACC

17441 CTGCTCAATT ACCTGCACCA CGCACATTGC TAACTAAGGG

17481 CACACTAGAA CCAGAATATT TCAATTCAGT GTGTAGACTT

17521 ATGAAAACTA TAGGTCCAGA CATGTTCCTC GGAACTTGTC

17561 GGCGTTGTCC TGCTGAAATT GTTGACACTG TGAGTGCTTT

17601 GGTTTATGAT AATAAGCTTA AAGCACATAA AGACAAATCA

17641 GCTCAATGCT TTAAAATGTT TTATAAGGGT GTTATCACGC

17681 ATGATGTTTC ATCTGCAATT AACAGGCCAC AAATAGGCGT

17721 GGTAAGAGAA TTCCTTACAC GTAACCCTGC TTGGAGAAAA

17761 GCTGTCTTTA TTTCACCTTA TAATTCACAG AATGCTGTAG

17801 CCTCAAAGAT TTTGGGAGTA CCAACTCAAA CTGTTGATTC

17841 ATCACAGGGC TCAGAATATG ACTATGTCAT ATTCACTCAA

17881 ACCACTGAAA CAGCTCACTC TTGTAATGTA AACAGATTTA

17921 ATGTTGCTAT TACCAGAGCA AAAGTAGGCA TACTTTGCAT

17961 AATGTCTGAT AGAGACCTTT ATGACAAGTT GCAATTTACA

18001 AGTCTTGAAA TTCCACGTAG GAATGTGGCA ACTTTACAAG

18041 CTGAAAATGT AACAGGACTC TTTAAAGATT GTAGTAAGGT

18081 AATCACTGGG TTACATCCTA CACAGGCACC TACACACCTC

18121 AGTGTTGACA CTAAATTCAA AACTGAAGGT TTATGTGTTG

18161 ACATACCTGG CATACCTAAG GACATGACCT ATAGAAGACT

18201 CATCTCTATG ATGGGTTTTA AAATGAATTA TCAAGTTAAT

18241 GGTTACCCTA ACATGTTTAT CACCCGCGAA GAAGCTATAA

18281 GACATGTACG TGCATGGATT GGCTTCGATG TCGAGGGGTG

18321 TCATGCTACT AGAGAAGCTG TTGGTACCAA TTTACCTTTA

18361 CAGCTAGGTT TTTCTACAGG TGTTAACCTA GTTGCTGTAC

18401 CTACAGGTTA TGTTGATACA CCTAATAATA CAGATTTTTC

18441 CAGAGTTAGT GCTAAACCAC CGCCTGGAGA TCAATTTAAA

18481 CACCTCATAC CACTTATGTA CAAAGGACTT CCTTGGAATG

18521 TAGTGCGATA AAAGATTGTA CAAATGTTAA GTGACACACT

18561 TAAAAATCTC TCTGACAGAG TCGTATTTGT CTTATGGGCA

18601 CATGGCTTTG AGTTGACATC TATGAAGTAT TTTGTGAAAA

18641 TAGGACCTGA GCGCACCTGT TGTCTATGTG ATAGAGGTGC

18681 CACATGCTTT TCCACTGCTT CAGACACTTA TGCCTGTTGG

18721 CATCATTCTA TTGGATTTGA TTACGTCTAT AATCCGTTTA

18761 TGATTGATGT TCAACAATGG GGTTTTACAG GTAACCTACA

18801 AAGCAACCAT GATCTGTATT GTCAAGTCCA TGGTAATGCA

18841 CATGTAGCTA GTTGTGATGC AATCATGACT AGGTGTCTAG

18881 CTGTCCACGA GTGCTTTGTT AAGCGTGTTG ACTGGACTAT
```

-continued

```
18921 TGAATATCCT ATAATTGGTG ATGAACTGAA GATTAATGCG

18961 GCTTGTAGAA AGGTTCAACA CATGGTTGTT AAAGCTGCAT

19001 TATTAGCAGA CAAATTCCCA GTTCTTCACG ACATTGGTAA

19041 CCCTAAAGCT ATTAAGTGTG TACCTCAAGC TGATGTAGAA

19081 TGGAAGTTCT ATGATGCACA GCCTTGTAGT GACAAAGCTT

19121 ATAAAATAGA AGAATTATTC TATTCTTATG CCACACATTC

19161 TGACAAATTC ACAGATGGTG TATGCCTATT TTGGAATTGC

19201 AATGTCGATA GATATCCTGC TAATTCCATT GTTTGTAGAT

19241 TTGACACTAG AGTGCTATCT AACCTTAACT TGCCTGGTTG

19281 TGATGGTGGC AGTTGTATG TAAATAAACA TGCATTCCAC

19321 ACACCAGCTT TTGATAAAAG TGCTTTTGTT AATTTAAAAC

19361 AATTACCATT TTTCTATTAC TCTGACAGTC CATGTGAGTC

19401 TCATGGAAAA CAAGTAGTGT CAGATATAGA TTATGTACCA

19441 CTAAAGTCTG CTACGTGTAT AACACGTTGC AATTTAGGTG

19481 GTGCTGTCTG TAGACATCAT GCTAATGAGT ACAGATTGTA

19521 TCTCGATGCT TATAACATGA TGATCTCAGC TGGCTTTAGC

19561 TTGTGGGTTT ACAAACAATT TGATACTTAT AACCTCTGGA

19601 ACACTTTTAC AAGACTTCAG AGTTTAGAAA ATGTGGCTTT

19641 TAATGTTGTA AATAAGGGAC ACTTTGATGG ACAACAGGGT

19681 GAAGTACCAG TTTCTATCAT TAATAACACT GTTTACACAA

19721 AAGTTGATGG TGTTGATGTA GAATTGTTTG AAAATAAAAC

19761 AACATTACCT GTTAATGTAG CATTTGAGCT TTGGGCTAAG

19801 CGCAACATTA AACCAGTACC AGAGGTGAAA ATACTCAATA

19841 ATTTGGGTGT GGACATTGCT GCTAATACTG TGATCTGGGA

19881 CTACAAAAGA GATGCTCCAG CACATATATC TACTATTGGT

19921 GTTTGTTCTA TGACTGACAT AGCCAAGAAA CCAACTGAAA

19961 CGATTTGTGC ACCACTCACT GTCTTTTTTG ATGGTAGAGT

20001 TGATGGTCAA GTAGACTTAT TTAGAAATGC CCGTAATGGT

20041 GTTCTTATTA CAGAAGGTAG TGTTAAAGGT TTACAACCAT

20081 CTGTAGGTCC CAAACAAGCT AGTCTTAATG GAGTCACATT

20121 AATTGGAGAA GCCGTAAAAA CACAGTTCAA TTATTATAAG

20161 AAAGTTGATG GTGTTGTCCA ACAATTACCT GAAACTTACT

20201 TTACTCAGAG TAGAAATTTA CAAGAATTTA AACCCAGGAG

20241 TCAAATGGAA ATTGATTTCT TAGAATTAGC TATGGATGAA

20281 TTCATTGAAC GGTATAAATT AGAAGGCTAT GCCTTCGAAC

20321 ATATCGTTTA TGGAGATTTT AGTCATAGTC AGTTAGGTGG

20361 TTTACATCTA CTGATTGGAC TAGCTAAACG TTTTAAGGAA

20401 TCACCTTTTG AATTAGAAGA TTTTATTCCT ATGGACAGTA

20441 CAGTTAAAAA CTATTTCATA ACAGATGCGC AAACAGGTTC

20481 ATCTAAGTGT GTGTGTTCTG TTATTGATTT ATTACTTGAT

20521 GATTTTGTTG AAATAATAAA ATCCCAAGAT TTATCTGTAG
```

-continued

```
20561 TTTCTAAGGT TGTCAAAGTG ACTATTGACT ATACAGAAAT

20601 TTCATTTATG CTTTGGTGTA AAGATGGGCA TGTAGAAACA

20641 TTTTACCCAA AATTACAATC TAGTCAAGCG TGGCAACCGG

20681 GTGTTGCTAT GCCTAATCTT TACAAAATGC AAAGAATGCT

20721 ATTAGAAAAG TGTGACCTTC AAAATTATGG TGATAGTGCA

20761 ACATTACCTA AAGGCATAAT GATGAATGTC GCAAAATATA

20801 CTCAACTGTG TCAATATTTA AACACATTAA CATTAGCTGT

20841 ACCCTATAAT ATGAGAGTTA TACATTTTGG TGCTGGTTCT

20881 GATAAAGGAG TTGCACCAGG TACAGCTGTT TTAAGACAGT

20921 GGTTGCCTAC GGGTACGCTG CTTGTCGATT CAGATCTTAA

20961 TGACTTTGTC TCTGATGCAG ATTCAACTTT GATTGGTGAT

21001 TGTGCAACTG TACATACAGC TAATAAATGG GATCTCATTA

21041 TTAGTGATAT GTACGACCCT AAGACTAAAA ATGTTACAAA

21081 AGAAATGAC TCTAAAGAGG GTTTTTTCAC TTACATTTGT

21121 GGGTTTATAC AAGAAAAGCT AGCTCTTGGA GGTTCCGTGG

21161 CTATAAAGAT AACAGAACAT TCTTGGAATG CTGATCTTTA

21201 TAAGCTCATG GGACACTTCG CATGGTGGAC AGCCTTTGTT

21241 ACTAATGTGA ATGCGTGATC ATCTGAAGCA TTTTTAATTG

21281 GATGTAATTA TCTTGGCAAA CCACGCGAAC AAATAGATGG

21321 TTATGTCATG CATGCAAATT ACATATTTTG GAGGAATACA

21361 AATCCAATTC AGTTGTCTTC CTATTCTTTA TTTGACATGA

21401 GTAAATTTCC CCTTAAATTA AGGGGTACTG CTGTTATGTC

21441 TTTAAAGAA GGTCAAATCA ATGATATGAT TTTATCTCTT

21481 CTTAGTAAAG GTAGACTTAT AATTAGAGAA AACAACAGAG

21521 TTGTTATTTC TAGTGATGTT CTTGTTAACA ACTAAACGAA

21561 CAATGTTTGT TTTTCTTGTT TTATTGCCAC TAGTCTCTAG

21601 TCAGTGTGTT AATCTTACAA CCAGAACTCA ATTACCCCCT

21641 GCATACACTA ATTCTTTCAC ACGTGGTGTT TATTACCCTG

21681 ACAAAGTTTT CAGATCCTCA GTTTTACATT CAACTCAGGA

21721 CTTGTTCTTA CCTTTCTTTT CCAATGTTAC TTGGTTCCAT

21761 GCTATACATG TCTCTGGGAC CAATGGTACT AAGAGGTTTG

21801 ATAACCCTGT CCTACCATTT AATGATGGTG TTTATTTTGC

21841 TTCCACTGAG AAGTCTAACA TAATAAGAGG CTGGATTTTT

21881 GGTACTACTT TAGATTCGAA GACCCAGTCC CTACTTATTG

21921 TTAATAACGC TACTAATGTT GTTATTAAAG TCTGTGAATT

21961 TCAATTTTGT AATGATCCAT TTTTGGGTGT TTATTACCAC

22001 AAAAACAACA AAAGTTGGAT GGAAAGTGAG TTCAGAGTTT

22041 ATTCTAGTGC GAATAATTGC ACTTTTGAAT ATGTCTCTCA

22081 GCCTTTTCTT ATGGACCTTG AAGGAAAACA GGGTAATTTC

22121 AAAAATCTTA GGGAATTTGT GTTTAAGAAT ATTGATGGTT
```

-continued

```
22161 ATTTTAAAAT ATATTCTAAG CACACGCCTA TTAATTTAGT

22201 GCGTGATCTC CCTCAGGGTT TTTGGGCTTT AGAACCATTG

22241 GTAGATTTGC CAATAGGTAT TAACATCACT AGGTTTCAAA

22281 CTTTACTTGC TTTACATAGA AGTTATTTGA CTCCTGGTGA

22321 TTCTTCTTCA GGTTGGACAG CTGGTGCTGC AGCTTATTAT

22361 GTGGGTTATC TTCAACCTAG GACTTTTCTA TTAAAATATA

22401 ATGAAAATGG AACCATTACA GATGCTGTAG ACTGTGCACT

22441 TGACCCTCTC TCAGAAACAA AGTGTACGTT GAAATCCTTC

22481 ACTGTAGAAA AAGGAATCTA TCAAACTTCT AACTTTAGAG

22521 TCCAACCAAC AGAATCTATT GTTAGATTTC CTAATATTAC

22561 AAACTTGTGC CCTTTTGGTG AAGTTTTTAA CGCCACCAGA

22601 TTTGCATCTG TTTATGCTTG GAACAGGAAG AGAATCAGCA

22641 ACTGTGTTGC TGATTATTCT GTCCTATATA ATTCCGCATC

22681 ATTTTCCACT TTTAAGTGTT ATGGAGTGTC TCCTACTAAA

22721 TTAAATGATC TCTGCTTTAC TAATGTCTAT GCAGATTCAT

22761 TTGTAATTAG AGGTGATGAA GTCAGACAAA TCGCTCCAGG

22801 GCAAACTGGA AAGATTGCTG ATTATAATTA TAAATTACCA

22841 GATGATTTTA CAGGCTGCGT TATAGCTTGG AATTCTAACA

22881 ATCTTGATTC TAAGGTTGGT GGTAATTATA ATTACCTGTA

22921 TAGATTGTTT AGGAAGTCTA ATCTCAAACC TTTTGAGAGA

22961 GATATTTCAA CTGAAATCTA TCAGGCCGGT AGCACACCTT

23001 GTAATGGTGT TGAAGGTTTT AATTGTTACT TTCCTTTACA

23041 ATCATATGGT TTCCAACCCA GTAATGGTGT TGGTTACCAA

23081 CCATACAGAG TAGTAGTACT TTCTTTTGAA CTTCTACATG

23121 CACCAGCAAC TGTTTGTGGA CCTAAAAAGT CTACTAATTT

23161 GGTTAAAAAC AAATGTGTCA ATTTCAACTT CAATGGTTTA

23201 ACAGGCACAG GTGTTCTTAC TGAGTCTAAC AAAAAGTTTC

23241 TGCCTTTCCA ACAATTTGGC AGAGACATTG CTGACACTAC

23281 TGATGCTGTC CGTGATCCAC AGACACTTGA GATTCTTGAC

23321 ATTACACCAT GTTCTTTTGG TGGTGTCAGT GTTATAACAC

23361 CAGGAACAAA TACTTCTAAC CAGGTTGCTG TTCTTTATCA

23401 GGATGTTAAC TGCACAGAAG TCCCTGTTGC TATTCATGCA

23441 GATCAACTTA CTCCTACTTG GCGTGTTTAT TCTACAGGTT

23481 CTAATGTTTT TCAAACACGT GCAGGCTGTT TAATAGGGGC

23521 TGAACATGTC AACAACTCAT ATGAGTGTGA CATACCCATT

23561 GGTGCAGGTA TATGCGCTAG TTATCAGACT CAGACTAATT

23601 CTCCTCGGCG GGCACGTAGT GTAGCTAGTC AATCCATCAT

23641 TGCCTACACT ATGTCACTTG GTGCAGAAAA TTCAGTTGCT

23681 TACTCTAATA ACTCTATTGC CATACCCACA AATTTTACTA

23721 TTAGTGTTAC CACAGAAATT CTACCAGTGT CTATGACCAA

23761 GACATCAGTA GATTGTACAA TGTACATTTG TGGTGATTCA
```

-continued

```
23801 ACTGAATGCA GCAATCTTTT GTTGCAATAT GGCAGTTTTT

23841 GTACACAATT AAACCGTGCT TTAACTGGAA TAGCTGTTGA

23881 ACAAGACAAA AACACCCAAG AAGTTTTTGC ACAAGTCAAA

23921 CAAATTTACA AAACACCAGC AATTAAAGAT TTTGGTGGTT

23961 TTAATTTTTC ACAAATATTA CCAGATCCAT CAAAACCAAG

24001 CAAGAGGTCA TTTATTGAAG ATCTACTTTT CAACAAAGTG

24041 ACACTTGCAG ATGCTGGCTT CATCAAACAA TATGGTGATT

24081 GCCTTGGTGA TATTGCTGCT AGAGACCTCA TTTGTGCACA

24121 AAAGTTTAAC GGCCTTACTG TTTTGCCACC TTTGCTCACA

24161 GATGAAATGA TTGCTCAATA CACTTCTGCA CTGTTAGCGG

24201 GTACAATCAC TTCTGGTTGG ACCTTTGGTG CAGGTGCTGC

24241 ATTACAAATA CCATTTGCTA TGCAAATGGC TTATAGGTTT

24281 AATGGTATTG GAGTTACACA GAATGTTCTC TATGAGAACC

24321 AAAAATTGAT TGCCAACCAA TTTAATAGTG CTATTGGCAA

24361 AATTCAAGAC TCACTTTCTT CCACAGCAAG TGCACTTGGA

24401 AAACTTCAAG ATGTGGTCAA CCAAAATGCA CAAGCTTTAA

24441 ACACGCTTGT TAAACAACTT AGCTCCAATT TTGGTGCAAT

24481 TTCAAGTGTT TTAAATGATA TCCTTTTCACG TCTTGACAAA

24521 GTTGAGGCTG AAGTGCAAAT TGATAGGTTG ATCACAGGCA

24561 GACTTCAAAG TTTGCAGACA TATGTGACTC AACAATTAAT

24601 TAGAGCTGCA GAAATCAGAG CTTCTGCTAA TCTTGCTGCT

24641 ACTAAAATGT CAGAGTGTGT ACTTGGACAA TCAAAAAGAG

24681 TTGATTTTTG TGGAAAGGGC TATCATCTTA TGTCCTTCCC

24721 TCAGTCAGCA CCTCATGGTG TAGTCTTCTT GCATGTGACT

24761 TATGTCCCTG CACAAGAAAA GAACTTCACA ACTGCTCCTG

24801 CCATTTGTCA TGATGGAAAA GCACACTTTC CTCGTGAAGG

24841 TGTCTTTGTT TCAAATGGCA CACACTGGTT TGTAACACAA

24881 AGGAATTTTT ATGAACCACA AATCATTACT ACAGACAACA

24921 CATTTGTGTC TGGTAACTGT GATGTTGTAA TAGGAATTGT

24961 CAACAACACA GTTTATGATC CTTTGCAACC TGAATTAGAC

25001 TCATTCAAGG AGGAGTTAGA TAAATATTTT AAGAATCATA

25041 CATCACCAGA TGTTGATTTA GGTGACATCT CTGGCATTAA

25081 TGCTTCAGTT GTAAACATTC AAAAAGAAAT TGACCGCCTC

25121 AATGAGGTTG CCAAGAATTT AAATGAATCT CTCATCGATC

25161 TCCAAGAACT TGGAAAGTAT GAGCAGTATA TAAAATGGCC

25201 ATGGTACATT TGGCTAGGTT TTATAGCTGG CTTGATTGCC

25241 ATAGTAATGG TGACAATTAT GCTTTGCTGT ATGACCAGTT

25281 GCTGTAGTTG TCTCAAGGGC TGTTGTTCTT GTGGATCCTG

25321 CTGCAAATTT GATGAAGACG ACTCTGAGCC AGTGCTCAAA

25361 GGAGTCAAAT TACATTACAC ATAAACGAAC TTATGGATTT
```

-continued

```
25401 GTTTATGAGA ATCTTCACAA TTGGAACTGT AACTTTGAAG

25441 CAAGGTGAAA TCAAGGATGC TACTCCTTCA GATTTTGTTC

25481 GCGCTACTGC AACGATACCG ATACAAGCCT CACTCCCTTT

25521 CGGATGGCTT ATTGTTGGCG TTGCACTTCT TGCTGTTTTT

25561 CAGAGCGCTT CCAAAATCAT AACCCTCAAA AAGAGATGGC

25601 AACTAGCACT CTCCAAGGGT GTTCACTTTG TTTGCAACTT

25641 GGTGTTGTTG TTTGTAACAG TTTACTCACA CCTTTTGCTC

25681 GTTGCTGCTG GCCTTGAAGC CCCTTTTCTC TATCTTTATG

25721 CTTTAGTCTA CTTCTTGCAG AGTATAAACT TTGTAAGAAT

25761 AATAATGAGG CTTTGGCTTT GCTGGAAATG CCGTTCCAAA

25801 AACCCATTAC TTTATGATGC CAACTATTTT CTTTGCTGGC

25841 ATAGTAATTG TTACGACTAT TGTATACCTT ACAATAGTGT

25881 AACTTCTTCA ATTGTCATTA CTTCAGGTGA TGGCACAACA

25921 AGTCCTATTT CTGAACATGA CTACCAGATT GGTGGTTATA

25961 CTGAAAAATG GGAATCTGGA GTAAAGACT GTGTTGTATT

26001 ACACAGTTAC TTCACTTCAG ACTATTACCA GCTGTACTCA

26041 ACTCAATTGA GTACAGACAC TGGTGTTGAA CATGTTACCT

26081 TCTTCATCTA CAATAAAATT GTTGATGAGC CTGAAGAACA

26121 TGTCCAAATT CACACAATCG ACGGTTCATC CGGAGTTGTT

26161 AATCCAGTAA TGGAACCAAT TTATGATGAA CCGACGACGA

26201 CTACTAGCGT GCCTTTGTAA GCACAAGCTG ATGAGTACGA

26241 ACTTATGTAC TCATTCGTTT CGGAAGAGAC AGGTACGTTA

26281 ATAGTTAATA GCGTACTTCT TTTTCTTGCT TTCGTGGTAT

26321 TCTTGCTAGT TACACTAGCC ATCCTTACTG CGCTTCGATT

26361 GTGTGCGTAC TGCTGCAATA TTGTTAACGT GAGTCTTGTA

26401 AAACCTTCTT TTTACGTTTA CTCTCGTGTT AAAAATCTGA

26441 ATTCTTCTAG AGTTCCTGAT CTTCTGGTCT AAACGAACTA

26481 AATATTATAT TAGTTTTTCT GTTTGGAACT TTAATTTTAG

26521 CCATGGCAGA TTCCAACGGT ACTATTACCG TTGAAGAGCT

26561 TAAAAAGCTC CTTGAACAAT GGAACCTAGT AATAGGTTTC

26601 CTATTCCTTA CATGGATTTG TCTTCTACAA TTTGCCTATG

26641 CCAACAGGAA TAGGTTTTTG TATATAATTA AGTTAATTTT

26681 CCTCTGGCTG TTATGGCCAG TAACTTTAGC TTGTTTTGTG

26721 CTTGCTGCTG TTTACAGAAT AAATTGGATC ACCGGTGGAA

26761 TTGCTATCGC AATGGCTTGT CTTGTAGGCT TGATGTGGCT

26801 CAGCTACTTC ATTGCTTCTT TCAGACTGTT TGCGCGTACG

26841 CGTTCCATGT GGTCATTCAA TCCAGAAACT AACATTCTTC

26881 TCAACGTGCC ACTCCATGGC ACTATTCTGA CCAGACCGCT

26921 TCTAGAAAGT GAACTCGTAA TCGGAGCTGT GATCCTTCGT

26961 GGACATCTTC GTATTGCTGG ACACCATCTA GGACGCTGTG

27001 ACATCAAGGA CCTGCCTAAA GAAATCACTG TTGCTACATC
```

-continued

```
27041 ACGAACGCTT TCTTATTACA AATTGGGAGC TTCGCAGCGT

27081 GTAGCAGGTG ACTCAGGTTT TGCTGCATAC AGTCGCTACA

27121 GGATTGGCAA CTATAAATTA AACACAGACC ATTCCAGTAG

27161 CAGTGACAAT ATTGCTTTGC TTGTACAGTA AGTGACAACA

27201 GATGTTTCAT CTCGTTGACT TTCAGGTTAC TATAGCAGAG

27241 ATATTACTAA TTATTATGAG GACTTTTAAA GTTTCCATTT

27281 GGAATCTTGA TTACATCATA AACCTCATAA TTAAAAATTT

27321 ATCTAAGTCA CTAACTGAGA ATAAATATTC TCAATTAGAT

27361 GAAGAGCAAC CAATGGAGAT TGATTAAACG AACATGAAAA

27401 TTATTCTTTT CTTGGCACTG ATAACACTCG CTACTTGTGA

27441 GCTTTATCAC TACCAAGAGT GTGTTAGAGG TACAACAGTA

27481 CTTTTAAAAG AACCTTGCTC TTCTGGAACA TACGAGGGCA

27521 ATTCACCATT TCATCCTCTA GCTGATAACA AATTTGCACT

27561 GACTTGCTTT AGCACTCAAT TTGCTTTTGC TTGTCCTGAC

27601 GGCGTAAAAC ACGTCTATCA GTTACGTGCC AGATCAGTTT

27641 CACCTAAACT GTTCATCAGA CAAGAGGAAG TTCAAGAACT

27681 TTACTCTCCA ATTTTTCTTA TTGTTGCGGC AATAGTGTTT

27721 ATAACACTTT GCTTCACACT CAAAAGAAAG ACAGAATGAT

27761 TGAACTTTCA TTAATTGACT TCTATTTGTG CTTTTTAGCC

27801 TTTCTGCTAT TCCTTGTTTT AATTATGCTT ATTATCTTTT

27841 GGTTCTCACT TGAACTGCAA GATCATAATG AAACTTGTCA

27881 CGCCTAAACG AACATGAAAT TTCTTGTTTT CTTAGGAATC

27921 ATCACAACTG TAGCTGCATT TCACCAAGAA TGTAGTTTAC

27961 AGTCATGTAC TCAACATCAA CCATATGTAG TTGATGACCC

28001 GTGTCCTATT CACTTCTATT CTAAATGGTA TATTAGAGTA

28041 GGAGCTAGAA AATCAGCACC TTTAATTGAA TTGTGCGTGG

28081 ATGAGGCTGG TTCTAAATCA CCCATTCAGT ACATCGATAT

28121 CGGTAATTAT ACAGTTTCCT GTTTACCTTT TACAATTAAT

28161 TGCCAGGAAC CTAAATTGGG TAGTCTTGTA GTGCGTTGTT

28201 CGTTCTATGA AGACTTTTTA GAGTATCATG ACGTTCGTGT

28241 TGTTTTAGAT TTCATCTAAA CGAACAAACT AAAATGTCTG

28281 ATAATGGACC CCAAAATCAG CGAAATGCAC CCCGCATTAC

28321 GTTTGGTGGA CCCTCAGATT CAACTGGCAG TAACCAGAAT

28361 GGAGAACGCA GTGGGGCGCG ATCAAAACAA CGTCGGCCCC

28401 AAGGTTTACC CAATAATACT GCGTCTTGGT TCACCGCTCT

28441 CACTCAACAT GGCAAGGAAG ACCTTAAATT CCCTCGAGGA

28481 CAAGGCGTTC CAATTAACAC CAATAGCAGT CCAGATGACC

28521 AAATTGGCTA CTACCGAAGA GCTACCAGAC GAATTCGTGG

28561 TGGTGACGGT AAAATGAAAG ATCTCAGTCC AAGATGGTAT

28601 TTCTACTACC TAGGAACTGG GCCAGAAGCT GGACTTCCCT
```

-continued

```
28641 ATGGTGCTAA CAAAGACGGC ATCATATGGG TTGCAACTGA

28681 GGGAGCCTTG AATACACCAA AAGATCACAT TGGCACCCGC

28721 AATCCTGCTA ACAATGCTGC AATCGTGCTA CAACTTCCTC

28761 AAGGAACAAC ATTGCCAAAA GGCTTCTACG CAGAAGGGAG

28801 CAGAGGCGGC AGTCAAGCCT CTTCTCGTTC CTCATCACGT

28841 AGTCGCAACA GTTCAAGAAA TTCAACTCCA GGCAGCAGTA

28881 GGGGAACTTC TCCTGCTAGA ATGGCTGGCA ATGGCGGTGA

28921 TGCTGCTCTT GCTTTGCTGC TGCTTGACAG ATTGAACCAG

28961 CTTGAGAGCA AAATGTCTGG TAAAGGCCAA CAACAACAAG

29001 GCCAAACTGT CACTAAGAAA TCTGCTGCTG AGGCTTCTAA

29041 GAAGCCTCGG CAAAAACGTA CTGCCACTAA AGCATACAAT

29081 GTAACACAAG CTTTCGGCAG ACGTGGTCCA GAACAAACCC

29121 AAGGAAATTT TGGGGACCAG GAACTAATCA GACAAGGAAC

29161 TGATTACAAA CATTGGCCGC AAATTGCACA ATTTGCCCCC

29201 AGCGCTTCAG CGTTCTTCGG AATGTCGCGC ATTGGCATGG

29241 AAGTCACACC TTCGGGAACG TGGTTGACCT ACACAGGTGC

29281 CATCAAATTG GATGACAAAG ATCGAAATTT CAAAGATCAA

29321 GTCATTTTGC TGAATAAGCA TATTGACGCA TACAAAACAT

29361 TCCCACCAAC AGAGCCTAAA AAGGACAAAA AGAAGAAGGC

29401 TGATGAAACT CAAGCCTTAC CGCAGAGACA GAAGAAACAG

29441 CAAACTGTGA CTCTTCTTCC TGCTGCAGAT TTGGATGATT

29481 TCTCCAAACA ATTGCAACAA TCCATGAGCA GTGCTGACTC

29521 AACTCAGGCC TAAACTCATG CAGACCACAC AAGGCAGATG

29561 GGCTATATAA ACGTTTTCGC TTTTCCGTTT ACGATATATA

29601 GTCTACTCTT GTGCAGAATG AATTCTCGTA ACTACATAGC

29641 ACAAGTAGAT GTAGTTAACT TTAATCTCAC ATAGCAATCT

29681 TTAATCAGTG TGTAACATTA GGGAGGACTT GAAAGAGCCA

29721 CCACATTTTC ACCGAGGCCA CGCGGAGTAC GATCGAGTGT

29761 ACAGTGAACA ATGCTAGGGA GAGCTGCCTA TATGGAAGAG

29801 CCCTAATGTG TAAAATTAAT TTTAGTAGTG CTATCCCCAT

29841 GTGATTTTAA TAGCTTCTTA GGAGAATGAC AAAAAAAAAA

29881 AAAAAAAAAA AAAAAAAAAA AAA
```

The SARS-CoV-2 viral genome is RNA. Hence, in some cases the SARS-CoV-2 viral genome can be a copy of the foregoing DNA sequence, where the thymine (T) residues are uracil (U) residues. In some cases, the SARS-CoV-2 viral genome can be a complement of the foregoing DNA sequence.

However, the SARS-CoV-2 viral genome can also have sequence variation. For example, the SARS-CoV-2 viral genomes detected by the methods, compositions, and devices described herein can have at least 75%, at least 80%, at least 85%, at least 90%, at least 95%, at least 96%, at least 97%, at least 98%, at least 99%, or 100% sequence identity to an RNA copy or an RNA complement of the SARS-CoV-2 SEQ ID NO:55 nucleic acid.

The SARS-CoV-2 can have a 5' untranslated region (5' UTR; also known as a leader sequence or leader RNA) at positions 1-265 of the SEQ ID NO:55 sequence. Such a 5' UTR can include the region of an mRNA that is directly upstream from the initiation codon. Similarly, the SARS-CoV-2 can have a 3' untranslated region (3' UTR) at positions 29675-29903. In positive strand RNA viruses, the 3'-UTR can play a role in viral RNA replication because the origin of the minus-strand RNA replication intermediate is at the 3'-end of the genome.

The SARS-CoV-2 genome encodes several major structural proteins: the spike (S) protein, nucleocapsid (N) protein, membrane (M) protein, and the envelope (E) protein. Some of these proteins are part of a large polyprotein, which is at positions 266-21555 of the SEQ ID NO:55 sequence.

An RNA-dependent RNA polymerase is encoded at positions 13442-13468 and 13468-16236 of the SARS-CoV-2 SEQ ID NO:55 nucleic acid. This RNA-dependent RNA polymerase has been assigned NCBI accession number YP_009725307 and has the following sequence (SEQ ID NO:56).

```
  1 SADAQSFLNR  VCGVSAARLT  PCGTGTSTDV  VYRAFDIYND

41 KVAGFAKFLK  TNCCRFQEKD  EDDNLIDSYF  VVKRHTFSNY

81 QHEETIYNLL  KDCPAVAKHD  FFKFRIDGDM  VPHISRQRLT

121 KYTMADLVYA  LRHFDEGNCD  TLKEILVTYN  CCDDDYFNKK

161 DWYDFVENPD  ILRVYANLGE  RVRQALLKTV  QFCDAMRNAG

201 IVGVLTLDNQ  DLNGNWYDFG  DFIQTTPGSG  VPVVDSYYSL

241 LMPILTLTRA  LTAESHVDTD  LTKPYIKWDL  LKYDFTEERL

281 KLFDRYFKYW  DQTYHPNCVN  CLDDRCILHC  ANFNVLFSTV

321 FPPTSFGPLV  RKIFVDGVPF  VVSTGYHFRE  LGVVHNQDVN

361 LHSSRLSFKE  LLVYAADPAM  HAASGNLLLD  KRTTCFSVAA

401 LTNNVAFQTV  KPGNFNKDFY  DFAVSKGFFK  EGSSVELKHF

441 FFAQDGNAAI  SDYDYYRYNL  PTMCDIRQLL  FVVEVVDKYF

481 DCYDGGCINA  NQVIVNNLDK  SAGFPFNKWG  KARLYYDSMS

521 YEDQDALFAY  TKRNVIPTIT  QMNLKYAISA  KNRARTVAGV

561 SICSTMTNRQ  FHQKLLKSIA  ATRGATVVIG  TSKFYGGWHN

601 MLKTVYSDVE  NPHLMGWDYP  KCDRAMPNML  RIMASLVLAR

641 KHTTCCSLSH  RFYRLANECA  QVLSEMVMCG  GSLYVKPGGT

681 SSGDATTAYA  NSVFNICQAV  TANVNALLST  DGNKIADKYV

721 RNLQHRLYEC  LYRNRDVDTD  FVNEFYAYLR  KHFSMMILSD

761 DAVVCFNSTY  ASQGLVASIK  NFKSVLYYQN  NVFMSEAKCW

801 TETDLTKGPH  EFCSQHTMLV  KQGDDYVYLP  YPDPSRILGA

841 GCFVDDIVKT  DGTLMIERFV  SLAIDAYPLT  KHPNQEYADV

881 FHLYLQYIRK  LHDELTGHML  DMYSVMLTND  NTSRYWEPEF

921 YEAMYTPHTV  LQ
```

Such a SARS-CoV-2 RNA-dependent RNA polymerase can be used for amplifying RNA, e.g., SARS-CoV-2 RNA.

Devices

Figure 10:
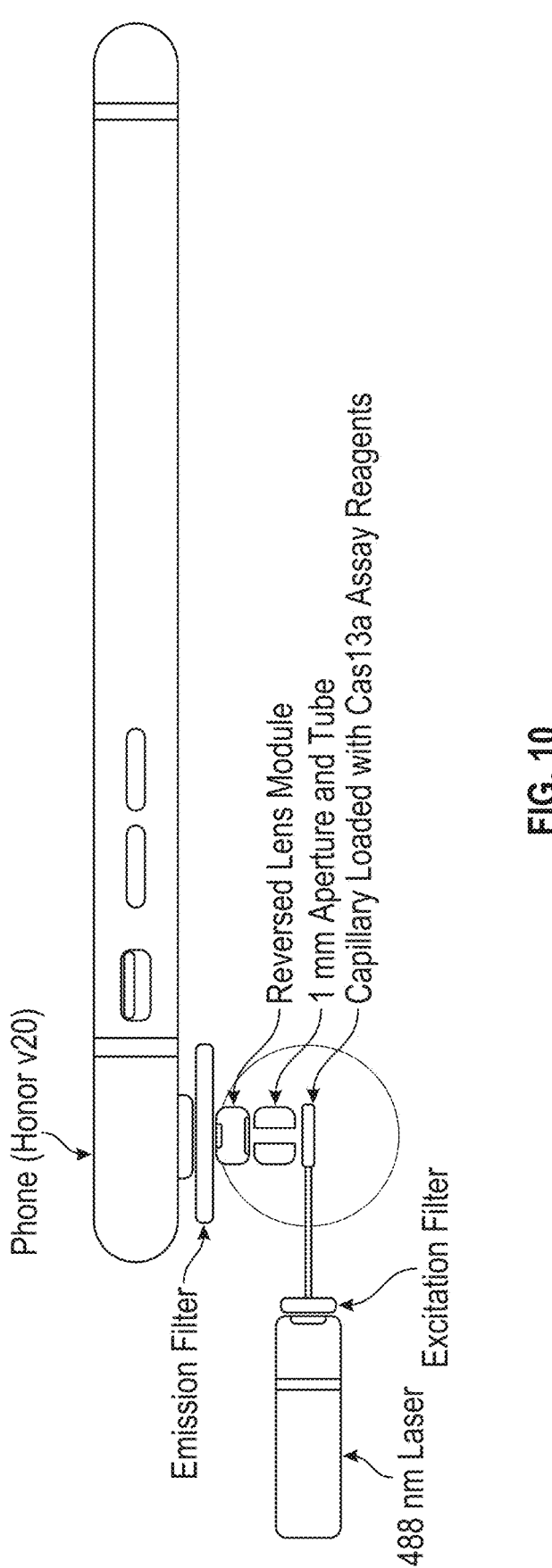
FIG. 10 illustrates a point of care (POC) system including a mobile device for detecting of fluorophore signals from assay mixtures.

FIG. 10 illustrates a point of care (POC) system including a mobile device for detecting of fluorophores according to optical methods. The POC system includes an integrated mobile phone and a specific cartridge that will contain the insert for the swab, the assay, a laser and a capillary to excite and measure fluorescence. Mobile phones detect light differently from laboratory fluorimeters and plate readers but can be adapted for fluorescence detection by adaptation of illumination and collection optics. Mobile phone cameras can use complementary metal-oxide-semiconductor (CMOS) sensors with color filters positioned over alternating pixels (in a Bayer filter mosaic or related pattern) to select wavelengths and capture color images, whereas fluorimeters and plate readers often use diffraction gratings to select wavelengths and photomultiplier tubes for detection.

To adapt the mobile phone camera to fluorescence detection, as described above, new reporter RNAs can be used that include a ribooligonucleotide with both a fluorophore and quencher as described earlier herein. According to a selection process also described earlier herein, ten candidate RNA oligonucleotides are selected and tested, and the best RNA oligonucleotide with associated fluorophore and quencher can be used with mobile devices (e.g., the mobile phone of FIG. 10) for SARS-CoV-2 RNA detection.

Fluorescent dyes, including Alexa Fluor®430, STAR 520, Brilliant VioletTM 510, 605 and 610 or a combination thereof, can be used as fluorophores and the Iowa Black FQ and RQ (IDT) can be used as quenchers to determine which dyes, quenchers or combination thereof will give the optimum signal while minimizing any background signal from the excitation light (e.g., the laser shown in FIG. 10, which can be a 485 nanometer (nm) laser although cases are not limited thereto). A test phone, e.g., a mobile phone or other mobile device as illustrated in FIG. 10, can detect emissions generated by the excitation light at a capillary, wherein the capillary is loaded assay reagents for the Cas13 assay. A color filter transmission spectrum and relative sensitivity can be determined using a fluorimeter adapted for sensor characterization. The fluorescence and background signals of a panel of possible fluorophore/quencher combinations can be characterized in the same fluorimeter, and the total signal and background when combined with the test phone and best available excitation LED or laser and interference filter pair can calculated. The top three candidate fluorophore/quencher combinations will be tested experimentally with a mobile phone-based reversed lens microscopy system set up to measure fluorescence from 20 μl sample volumes loaded in the capillary. Criteria for selection of fluorophore/quencher combinations include reduced background fluorescence in the absence of the test sample (target activator) and maximal cleavage by the selected Cas13 enzyme when a target activator is present. Changes in fluorescence will be measured over time, and sensor integration times can be varied to optimize exposure settings. Concentrations of fluorophore/quencher combinations will be varied, as will be activator RNA concentrations (synthetic or isolated from infected samples) in complex with Cas13a RNPs to determine sample preparation constraints and identify the limit of detection of the assay. While some crRNA and Cas13 protein choices are described, cases are not limited thereto, and other protein choices can be made.

Other cases can use mechanical, rather than optical, processes for detection. In one such case, a microfabricated cantilever-based sensor includes a reference cantilever and a sensor cantilever. Presence of the target species being detected over a transducer surface of the sensor cantilever increases cantilever mass and creates bending due to molecular interactions such as electrostatic repulsions, steric obstructions, van der Waals interactions, or hydration forces. Resonant frequency shifts are also produced.

Figure 11:
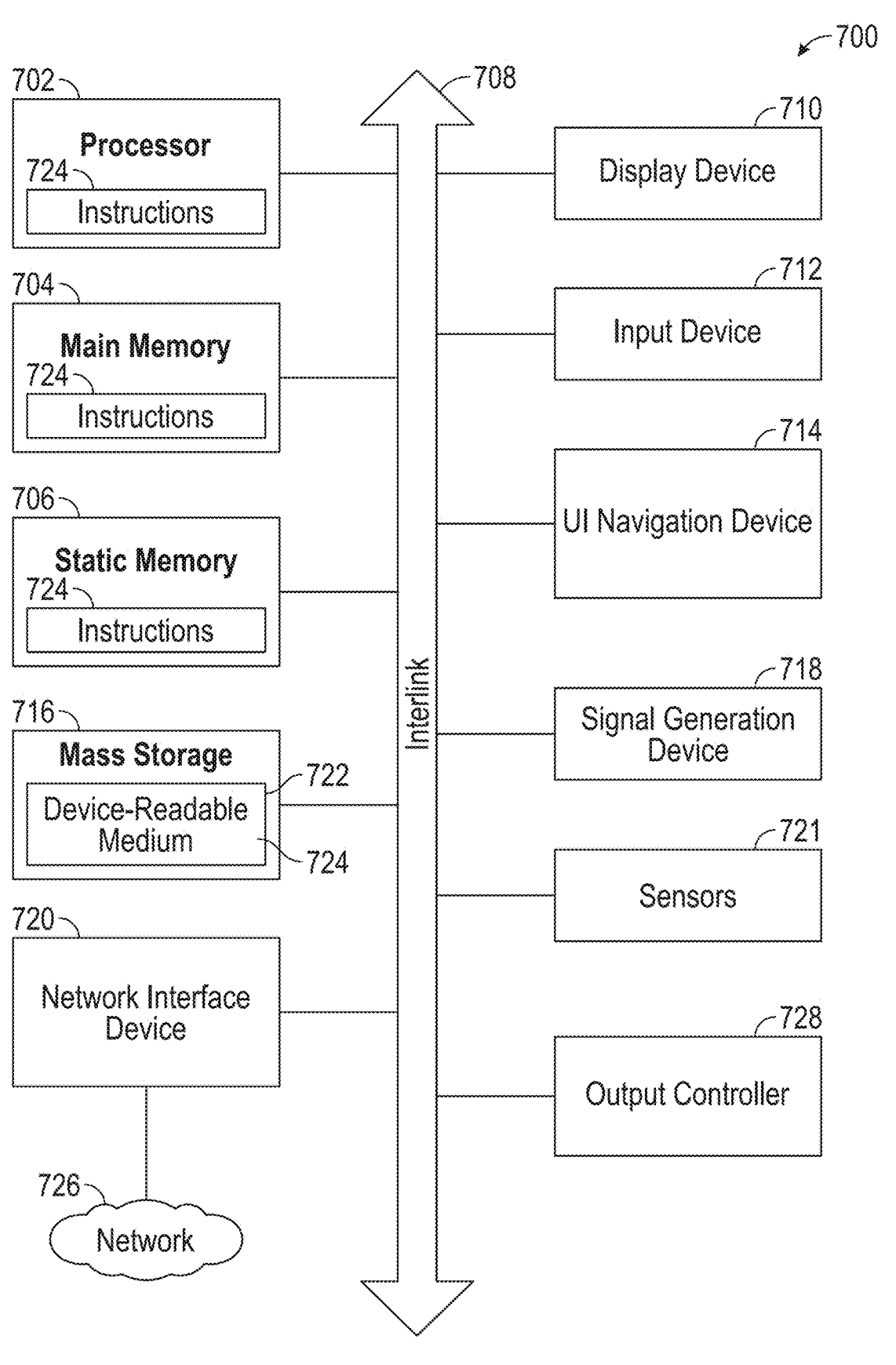
FIG. 11 illustrates a block diagram of an example machine upon which any one or more of the techniques (e.g., methodologies) discussed herein may perform. In alternative implementations, the machine may operate as a standalone device or may be connected (e.g., networked) to other components or machines.

In cases, differential bending of the sensor cantilever relative to the reference cantilever is detected by, for example, processing circuitry or other components of FIG. 10 or machine 700 (FIG. 11). Once activated the Cas13 can cleave RNA that is binding molecules to the sensor cantilever, changing the sensor cantilever bending stiffness resulting in a shift of resonant frequency. Alternatively, active Cas13 can release a molecule that binds to the cantilever, also changing its bending and/or resonant frequency. Such binding or unbinding to the cantilever can be asymmetrically patterned so that bending is promoted, in addition to a change in mass of the cantilever. Detection can be made based on, for example, the degree of bending.

Cantilevers can be sensitive to mass loading and variations in surface elasticity caused by presence of the target molecules. This can create variations in cantilever stiffness capability. Accordingly, materials with a high Young's Modulus should be considered for use in cantilevers. Such materials include diamond. Furthermore, the carbon-terminated surface of diamond may be easily modified by covalent bonding of organic compounds used as sensitive layers.

Cantilever resonant frequency measurements can be made with instruments such as Doppler laser interferometry equipment, which can be included in equipment of machine 700 (FIG. 11). In at least these cases, a coherent laser source emitting in the 620_690 nm range passes through a beam splitter. Half of the beam can be sent to the resonant cantilever surface, where the beam is reflected back to an interferometer and a demodulator for detecting cantilever resonant frequency. The other half of the beam is directly sent to the interferometer for reference. In other cases, alternative electrical processes for detection. In one such case, an electrochemical RNA aptamer-based biosensor is used. An RNA aptamer sequence can be immobilized on an electrode (comprised of, for example, gold), and one end of the electrode can be conjugated with a ferrocene (Fc) redox probe. An RNA aptamer with a charged group bound to a conducting surface is cleaved by active Cas13 (or bound by something released by Cas13 cleavage), inhibiting electron transfer and changing redox current to the conducting surface. Measurement of this current is performed by, for example, processing circuitry or other components of FIG. 10 or machine 700 (FIG. 11)

Adaptors include cartridges having capillaries described above can provided in or included with POC systems illustrated in FIG. 11. The POC system (e.g., processing circuitry, described in FIG. 11 below, of the mobile phone) can include software to measure and transmit detection results. The detection results can be used for contact tracing, based on GPS systems or other location-based systems of the mobile phone. Detection results can be stored or retrieved in anonymous or secure fashion through use of key-based handshaking, passcodes, etc., and results can be gathered for use in bio-surveillance.

FIG. 56 is a perspective view of an example fluorescence imaging system 10. In this example, the system 10 is configured to couple and cooperatively operate with a mobile device 14 including, but not limited to, a mobile phone, tablet pc, laptop or the like. The mobile device 14 shown in the example provided in FIG. 56 includes an optical sensor, such as a camera (e.g., one or more of a video or still camera) and in some examples includes associated mobile device optics.

The fluorescence imaging system 10 includes a system housing 12 having an excitation source (e.g., a light source), optics, filters, and sample retaining features. The fluorescence imaging system 10 is configured, as discussed herein, to detect and optionally quantify antigens in a test sample, such as an assay mixture, by way of fluorescence. As discussed herein, in the example system 100 including the mobile device 14 the device 14 receives fluoresced light from the assay mixture (and optionally a control mixture), for instance at the optical sensor of the mobile device, such as a phone camera. The mobile device 14 optionally includes an onboard controller (e.g., processor, programmed logic controller, circuits, machine readable media, software modules or the like) that interprets the received fluoresced light and provides an indication of one or more antigens in the assay mixture, quantity or concentration of the one or more antigens or the like. For example, the mobile device 14 includes a comparator with one or more static or dynamic thresholds, and the comparator analyses the fluoresced light from the assay mixture relative to the thresholds to indicate the presence of the antigen. In another example, the strength of the fluoresced light (e.g., absorbance, attenuation, brightness, slope of measurements of the same, rates of change of the same or the like) is interpreted to indicate one or more of presence, quantity or concentration of the antigen. In another example, the thresholds are based on one or more control mixtures that are also subjected to excitation illumination, like the assay mixture, and their fluorescence is used as a base threshold for comparison with the fluorescence of the assay mixture. For instance, fluorescence of the assay mixture greater than the control mixture fluorescence (e.g., through analysis with a comparator) is in one example indicative of the presence of an antigen. In another example, the assay mixture fluorescence indicates the presence of the antigen if it is greater than the control mixture fluorescence modified by a specified constant or function-based value. The plotted fluorescence of the assay mixture (alone or relative to the control mixture) relative to time is, in another example, corresponded to quantity or concentration of antigen (e.g., by way of comparison with a look up table, mathematical function or the like).

As further shown in FIG. 56 the system 100 includes a sample cartridge 16 having one or more cartridge chambers 18 (e.g., capillaries, channels, grooves, passages or the like). The cartridge chambers 18 are configured to retain samples including, but not limited to, assay mixtures, controls mixtures or the like for testing with the system 100. The cartridge chambers 18 are, in one example, configured for complementary alignment with excitation illumination from an excitation source, such as an LED generator, laser generator or the like. For example, the cartridge chambers 18 are oriented in line with excitation illumination (e.g., along, parallel to or the like) to expose the cartridge chambers 18 volume (and sample therein) to the excitation illumination while minimizing shadowing or obstruction of portions of the cartridge chambers 18 that may otherwise artificially throttle fluorescence. One example of the orientation of the excitation illumination and cartridge chambers 18 (and samples therein) is shown in the right component view of FIG. 58B.

The sample cartridge 16 having the cartridge chambers 18 is loaded into a cartridge port 17 of the fluorescence imaging system 10. Loading of the cartridge 16 positions the cartridge chambers 18 into a complementary excitation orientation (aligned, parallel, oriented with or the like) relative to the excitation illumination for fluorescence. For example, the system housing 12 includes a cartridge socket 19 configured for reception of the sample cartridge 16. The complementary cartridge socket 19 and sample cartridge 16

(e.g., complementary profiles of both) automatically position the cartridge chambers 18 and their associated samples in the complementary orientations with the excitation source and the optical sensor. For instance, illumination from the excitation source is delivered along at least one common vector that is common to the orientation of the cartridge chambers (as shown in FIG. 58B, the component vector 31 of excitation illumination is oriented with the cartridge chambers 18). Similarly, the loaded sample cartridge 16 having the cartridge chambers 18 is in an observation orientation and fluorescence therefrom is accordingly directed toward the optical sensor. The sample cartridge and complementary cartridge socket 19 facilitate loading, testing and unloading of samples. Repetition of these procedures with additional sample cartridges 16 are thereby readily conducted through automatic orienting of the cartridge chambers 18 to the excitation orientation and observation orientation.

FIG. 57 is a schematic view of one example of the fluorescence imaging system 10 including (in this example) the mobile device 14. The system 10 includes an excitation source 20, for instance a laser generator, and in one example a 488 nanometer (nm) laser generator. An optional, excitation filter 22 is proximate to the excitation source 20 to filter the output excitation illumination prior to delivery to the cartridge chambers 18. For example, the excitation filter 22 filters the excitation illumination to wavelengths between around 450 to 470 nm (e.g., 500 to 570 nm), or to a wavelength that promotes fluorescence with the samples (e.g., assay mixtures, control mixtures or the like).

As further shown in FIG. 57, the cartridge chambers 18 are schematically shown oriented at an oblique angle relative to the excitation illumination (the remainder of the sample cartridge is removed in FIG. 57 to facilitate description). In one example, while the cartridge chambers 18 and the samples therein are obliquely oriented relative to the excitation illumination, one or more component vectors of the illumination are oriented with the cartridge chambers in an excitation orientation. For instance, as shown in FIG. 58B, a component vector 31 of the excitation illumination is oriented with (e.g., parallel, aligned or the like) an elongated profile of the cartridge chambers 18. In one example, this orientation is referred to as an excitation orientation 51 and facilitates illumination of a substantial portion of the cartridge chambers while minimizing obstructed illumination, shadows, scattering of light or the like that may frustrate fluorescence or observation of fluorescence.

Illumination of the cartridge chambers 18 and the samples therein with the excitation illumination generates fluorescence, for instance, when Cas13 assay reagents or the like, are present. Fluorescence is shown in FIG. 57 as radiating generally from the cartridge chambers 18. At least some quantity of the fluorescence is directed toward the mobile device 14 having a camera and associated optical sensor. As shown, one or more additional components are optionally interposed between the cartridge chambers and the mobile device 14 to facilitate observation of fluorescence and the associated detection, identification or determination of quantity or concentration of an antigen.

One example, component includes the aperture 23 having an aperture opening configured to minimize light scatter at the optical sensor and shape illumination in correspondence with the profile (e.g., shape, size or the like) of the cartridge chambers 18. In another example, imaging optics 28 are interposed between the cartridge chambers 18 and the optical sensor of the mobile device 14. The imaging optics 28, in one example, focus fluorescence illumination toward the optical sensor. In another example, the imaging optics 28 cooperate with optics, such as mobile device optics 40 (see FIG. 58A), to collectively focus fluorescence illumination toward the optical sensor of the mobile device 14. For instance, the imaging optics 28 include a reversed lens or reversed lens module that adapts the mobile device optical sensor 42 and mobile device optics 40 for close-up or macro-observations of the cartridge chambers 18 and associated samples.

As described herein, the imaging optics 28 (or 116 in FIGS. 59A, 60) are optionally telecentric and enhance performance of an emission filter by minimizing varied filter performance of one or more locations within the field of view (FOV). Instead, the telecentric imaging optics 28 (or 116) enhance the consistency (including identity) of performance for the entire FOV, minimizes shifts to unspecified colors (such as a blue shift) at one or more locations in the FOV, and provide a consistent fluorescence output for observation and analysis at the optical sensor.

FIG. 58A includes companion schematic views of the fluorescence imaging system 10. The left view of FIG. 58A is from the side of the system 10 with the system housing 12 opened to view the components, while the right review is an end view of the system 10 proximate to the mobile device optical sensor 42 and the sample cartridge 16, and showing delivery of fluorescence from the sample cartridge 16 to the mobile device optical sensor 42.

In the first companion (left) view of the system 10 excitation illumination is generated from the excitation source 20 and optionally filtered with the excitation filter 22. The excitation illumination is directed through the system housing 12 toward the sample cartridge 16 having the cartridge chambers 18 with samples therein. As shown in FIG. 58A the excitation illumination is directed through the support housing 12 with one or more mirrors to redirect the illumination toward the sample cartridge 16. Optionally, an aperture 24 having an aperture opening 26 is interposed between the excitation source 20 and the sample cartridge 16. The aperture 24 minimizes light scatter and directs illumination in a profile (e.g., shape, size or the like) corresponding to the cartridge chambers 18 to ensure illumination of the cartridge chambers 18 while minimizing extraneous illumination that causes light scatter that may saturate the optical sensor or obscure detection of fluorescence generated at the samples in the cartridge chambers 18.

Referring now to FIG. 58A and FIG. 58B delivery of the excitation illumination from the excitation source 20 to the cartridge chambers 18 of the sample cartridge 16 is shown. As shown in FIG. 58A the excitation illumination includes a component illumination vector 29 (also referred to as a component vector of excitation illumination) of the excitation illumination that is oblique to the cartridge chambers 18. For instance, the component illumination vector 29 shown is directed toward the cartridge chambers 18, but is not otherwise aligned, oriented with, parallel to or the like relative to the cartridge chambers 18. The excitation illumination interacts with the samples in the cartridge chambers 18 to generate fluorescence (e.g., cause the samples to fluoresce), and the fluorescence is observed and optionally quantified with an optical sensor, such as the mobile device optical sensor 42. The oblique orientation of the component vector 29 scatters excitation illumination away from the optical sensor 42 to minimize obscuring of fluorescence at the sensor 42, as shown with the scattered light 33 in FIGS. 58A and 58B.

The right component view of FIG. 58B provides a detailed view of an excitation orientation 51 of the cartridge chambers 18 relative to the excitation illumination 52. As shown, the cartridge chambers 18 in this example have an elongated profile with the samples therein (e.g., assay mixtures, control mixtures or the like). As further shown in FIG. 58B the excitation illumination 52 includes another component illumination vector 31 (also referred to as a component vector of excitation illumination). The component vector 31 shown is oriented with the cartridge chambers 18 (e.g., the chamber walls 21 and the sample therein), or conversely the cartridge chambers 18 are oriented with the component vector 31. For instance, the vector 31 is aligned, parallel or oriented with the elongate profile of the cartridge chambers 18 corresponding to the chamber walls 21. The excitation illumination with the excitation orientation 51 is thereby directed into a large portion of the cartridge chambers 18 (e.g., along the elongated profile or dimension) to illuminate a corresponding large portion of the samples therein. Because the cartridge chambers 18 and the samples therein are oriented with the component vector 31 of the excitation illumination obstructions to illumination, shadows cast into cartridge chambers or the like are minimized. Instead, a large portion (e.g., the entire chamber volume, a majority of the volume or a significant majority of the volume, from the sample surface to the chamber bottoms) of the cartridge chambers 18 are illuminated, and the illuminated portions fluoresce based on the presence of an antigen and the appropriate reagents. Conversely, obstructed or shadowed portions of the cartridge chambers 18 that otherwise poorly fluoresce or fail to fluoresce are thereby minimized. As shown in FIG. 58B the fluoresced assay mixture 54 and the fluoresced control mixture 56 each generate fluorescence in a large portion of their respective profiles including at the surface of the samples and throughout the sample volumes, for instance toward the bottom of the chambers 18 (e.g., into the page).

FIG. 58A (both component views) shows one example of an observation orientation 27 of the cartridge chambers 18 and samples therein relative to an optical sensor, such as the mobile device optical sensor 42 of the mobile device 14. As shown, the cartridge chambers 18 and fluorescence from the samples therein (caused by the excitation illumination) are directed toward the optical sensor 42. For example, chamber walls 21 of the cartridge chambers 18 are oriented with (e.g., aligned, parallel or the like) the fluoresced light from the cartridge chambers 18 to the optical sensor 42 (shown with the vertical dashed arrow in both component views of FIG. 58A). Accordingly, fluorescence generated within the cartridge chambers 18 by the samples is delivered with minimized obstructions from the sample cartridge 16 to the optical sensor 42 to facilitate detection of fluorescence. Conversely, the scattered light 33 from the excitation illumination is directed away from the optical sensor 42 and its effect on detection of fluorescence is thereby minimized.

Fluorescence generated with the excitation illumination at the cartridge chambers 18 is directed toward the optical sensor 42 according to the observation orientation 27 (e.g., the positioning of the cartridge 16 and its chambers 18) relative to the optical sensor 42. As shown in FIG. 58A the fluorescence is passed through the emission filter 30 to filter light and preferentially pass fluorescent light to the optical sensor 42. Optionally, the imaging optics 28 (described above) are interposed between the sample cartridge 16 and mobile device optics 40 to cooperate with the mobile device optics 40 to enhance delivery of the fluoresced light to the mobile device optical sensor 42. In another option, an aperture 23 is provided to minimize the passage of scattered light to the optical sensor 42 and shape fluorescence delivered to the optical sensor 42 in correspondence with the profile of the cartridge chambers 18 (e.g., also to minimize the delivery of scattered light to the sensor).

The left component view of FIG. 58B provides one example of a sample fluorescence profile 50 corresponding to the fluoresced assay mixture 54 and the fluoresced control mixture 56 shown in the right component view. In this example, the fluorescence profile 50 is shown on the display of the mobile device 14. The center portion of the fluorescence profile 50 corresponds to the fluoresced assay mixture 54 and has a qualitative higher absorbance (au) in comparison to the left (and/or right) portion of the profile 50 corresponding to the fluoresced control mixture 56. Optionally, the fluorescence imaging system 10, through the mobile device 14 or an associated controller, is configured to quantify the difference between the absorbance of the assay mixture and the control mixture (e.g., with a comparator) and thereby detect the presence of an antigen from the fluoresced assay mixture, or lack thereof, and optionally determine the quantity or concentration of the antigen.

For example, the mobile device 14 (or controller) includes a comparator with one or more static or dynamic thresholds, and the comparator analyses the fluoresced light from the assay mixture (and in one example, the control mixture) relative to the thresholds to indicate the presence of the antigen. In another example, the strength (e.g., absorbance, attenuation, slope of measurements of the same, rates of change of the same or the like) is interpreted to indicate one or more of presence, quantity or concentration of the antigen. In yet another example, the thresholds are based on control mixtures in the other cartridge chambers 18 that are subjected to the excitation illumination, like the assay mixture, and their fluorescence is used as a base threshold for comparison with the fluorescence of the assay mixture. For instance, fluorescence of the fluoresced assay mixture 54 greater than the fluoresced control mixture 56 (e.g., through analysis with a comparator) is in one example indicative of the presence of an antigen. In another example, the assay mixture fluorescence indicates the presence of the antigen if it is greater than the control mixture fluorescence modified by a specified constant or function-based value. The plotted fluorescence of the assay mixture (alone or relative to the control mixture) relative to time as a rate of change or slope is optionally interpreted to determine quantity or concentration of antigen (e.g., by way of comparison with a look up table, mathematical function or the like).

The mobile device 14 optionally provides a controller (e.g., processor, programmed logic controller, circuits, machine readable media, software modules or the like) configured to control or operate the fluorescence imaging system 10, for instance control excitation illumination, check for installation of the sample cartridge 16 (e.g., installed, fully installed, aligned in the excitation and observation orientations or the like), analyze fluorescence to identify, quantify or determination concentration of an antigen or the like. In another example, control of the fluorescence imaging system 10 is conducted with an onboard or remote controller (e.g., wireless or wire connected), such as a processor, programmed logic controller, circuits, machine readable media, software modules or the like, and the controller is interconnected with features of the system 10, such as the excitation source 20, optical sensor 42 or the like. The controller optionally conducts analysis of the samples, such as the fluorescence generated at the samples and detected with the optical sensor 42 to determine one or more of the presence of an antigen, its quantity, concentration or the like.

FIGS. 56-58B show one example of a fluorescence imaging system 10. Example design details for the system 10 are provided herein. The system has collection numerical aperture (NA) of between around 0.04 to 0.08, and in one example an NA of around 0.06; a field of view (FOV) of between around 10×10 mm to 20×20 mm, and in one example around 15×15 mm; and employs laser-based oblique-illumination fluorescence excitation with a power of between around 15-25 mW, and in one example 20 mW across the full FOV.

Sample characteristics, for instance of the sample cartridge 16, associated cartridge chambers 18 or the samples themselves include around 40 µl sample well volumes (i.e., around 40 mm³ volumes, or cubes of around 3.3 mm on a side; in practice volume may have a different aspect ratio), for instance of the cartridge chambers 18. The sample mixture retained in the cartridge chambers 18 includes, but is not limited to, around 400 nM concentrations of quencher-coupled fluorophore (e.g., including, but not limited to, fluorescein-type) in aqueous buffer, where the quencher is liberated (linkage to the fluor is cleaved) from the fluor as part of a biochemical assay. Prior to cleavage of the linkage, quenching is imperfect, with effective fluorophore quantum yield (QY) of around 2 percent of normal.

The fluorescence imaging system 10 includes one or more system characteristics including, but not limited to, field of view (FOV), numeric aperture (NA), collection efficiency (CE), excitation illumination intensity, excitation illumination uniformity or the like. In one example, the system 10 includes a relatively large FOV of around 15 mm diameter, 15×15 mm on a side or the like. The FOV facilitates imaging of multiple sample and control wells, such as the cartridge chambers 18 of the sample cartridge 16.

A system characteristic of the fluorescence imaging system 10 optionally includes one or more characteristics of an associated mobile device, such as a cellphone camera. In one example, an associated cellphone camera is non-telecentric, includes a fairly wide field lens and having Chief Ray Angles (CRA) of up to around 30 degrees (half-angle).

In another example, the system 10 including a mobile device or configured for use with a mobile device (e.g., mobile device 14) includes a numerical aperture (NA) and resultant collection efficiency (CE) for fluorescence imaging. A higher NA generally corresponds to a higher collection efficiency, or capability of detecting observed light, such as fluorescence generated at the samples with excitation illumination. In some examples, higher NA results in more spill-over of collected light beyond the boundaries of the in-focus sample well image, due to out-of-focus light away from the focal plane in deep (e.g. 2-3 mm, as noted above) sample wells (cartridge chambers 18). Spill-over may cause obscuring or confusion between the fluorescence of proximate cartridge chambers. Spill-over is optionally minimized by focusing at the midpoint of the well with corresponding decreased depth of field (DOF). In some examples, there may be a trade-off between increased CE due to higher NA, and the decreased depth-of-field (DOF) resulting from the higher NA and resulting in spill-over of out-of-focus well light into images of adjacent wells. In some examples, spill-over is minimized with increased separation between cartridge chambers.

Excitation intensity is another example of a system characteristic of the fluorescence imaging system 10. In one example, the signal-to-noise ratio (SNR) improves roughly as the square root of the number of collected photons (since signal is proportional to the CE, while the shot noise will be proportional to $\sqrt{CE}$). It is advantageous to maximize the extraction of photons from a fluor. Relatively high excitation intensities accordingly facilitate higher collection efficiency (CE) and in some examples are helpful given the small excitation cross-section (around 1 Å²) of typical molecules (e.g. FITC) used for biochemical fluorescence assays, typical maximum fluorescent photon emissions prior to photobleaching (around $10^5$-$10^7$ emissions for typical fluorophores in biological/biochemical assays) and total assay time around 30 s of total illumination time, spread over approximately 30 minutes in the current case. The excitation source 20 illuminates at intensities of up to around 0.1-10 W/mm² in one example, with the lower portion of the range corresponding to use with more easily bleached fluorophores. In one example, the excitation source 20 includes a laser-illumination system based on a DTR Lasers 55 mW blue (using Sharp Corp. laser diode GH04850B2G, approximately 490 nm output at 55 mW maximum) direct-diode laser that produces approximately 20 mW at the sample, with approximately 0.2 mW/mm².

As previously discussed herein, settings of the mobile device 14 are one example of system characteristics. In one example set up the fluorescence imaging system 10 includes the optical sensor 42 of the mobile device 14 having a camera gain (ISO) setting of 400 ISO and a 2000 msec exposure time.

Use of oblique laser illumination with the excitation source 20, with angle of incidence parallel to the long axis of sample wells, is shown in FIGS. 58A, 58B. Oblique illumination minimizes shadows within the cartridge chambers 18 as excitation illumination is oriented with the profile of the cartridge chamber (e.g., the chamber walls, chamber length or the like). Additionally, oblique illumination minimizes the incidence of background scattered light at the optical sensor 42. Instead, with specular reflection the scattered light misses the optical sensor 42 as shown with schematic scattered light 33 in FIGS. 58A, 58B.

In other examples, with a laser generator as the excitation source 20 expensive excitation filters are optionally avoided because laser emission wavelengths are narrow and have minimal overlap with the fluorescent emission wavelengths. Additionally, because a laser beam is highly directional it is readily directed within the system 10, for instance within the system housing 12 with one or more mirrors to direct the light toward oblique illumination of the sample cartridge 16. Further, a laser generator as the excitation source provides illumination uniformity in other examples. For instance, laser beams have an approximately Gaussian intensity profile. In the fluorescence imaging system 10 the laser beam of the excitation source 20 is optionally expanded (e.g., with approximately a 10 degree divergence half angle) beyond the margins of the sample wells (cartridge chambers 18) such that the central portion of the approximately Gaussian profile is incident on the wells to facilitate enhanced illumination of the wells and the samples therein.

Optionally, the expanded laser beam is further conditioned with an aperture, such as the aperture 24 having the aperture opening 26. In one example, expanding the laser beam to increase illumination uniformity at the sample (e.g., the cartridge chambers 18) may illuminate an overly larger field of view. The illumination of the larger field of view may cause increased illumination scatter into the optical sensor 42. To minimize scatter from the enlarged laser beam the aperture 24 is provided in the beam path and truncates the Gaussian beam profile to the central portion. The resulting illumination at the sample cartridge 16 thereby spans the desired field of view corresponding to the cartridge chambers 18 with uniform illumination provided by the central portion of the Gaussian without the extraneous illumination scatter.

In another example, there may be a tradeoff in illumination power relative to uniformity of illumination with use of the aperture 24. Optionally, in another example of the system 10 an engineered (potentially diffractive) diffuser is included to provide an enhanced flat-top laser beam profile at the sample.

Filter and filter locations are other examples of system characteristics of the fluorescence imaging system 10. As previously discussed, in one example the system 10 optionally does not include an excitation filter associated with the excitation source 20. In other examples an excitation filter 22 is provided, as shown in FIG. 58A. In another option, a dichroic or dichromatic filter is not included with the system 10 because of the oblique laser illumination as the excitation illumination and scattering of extraneous illumination away from the optical sensor 42. The system 100 includes a dichromatic mirror 122 (another example of a filter) as shown in FIGS. 59A, 60. In still another example, an emission filter, such as the emission filter 30, is interposed between the mobile device 14 (e.g., the mobile device optical sensor 42) and the imaging optics 28 of the system 10. As shown in FIG. 58A the emission filter is interposed between the mobile device optics 40 and one or more of the aperture 23 or imaging optics 28 (e.g., f=20 mm compact triplet lens, such as a TRH127-020-A. Thorlabs). At this location the bundle or cluster of (light) rays from any given sample point is approximately parallel, but the incident angle of the bundle of rays varies significantly (from 0 degrees to up to around 30 degrees) across the field of view, for instance increasing at higher field positions. This may cause some degradation of performance (including blue-shift of the filter transmission) toward the edge of the field of view. In another example of the system 10, the filter position is tuned to avoid or minimize this issue.

One test set up of the fluorescence imaging system 10 is described herein based on specified system characteristics. For imaging the approximate 15 µl cartridge chambers 18 a fairly large field of view (FOV) is specified with a modest numerical aperture (NA) that provides significant depth of focus without the images of adjacent cartridge chambers 18 overlapping. The fluorescence imaging system 10 includes these specified characteristics and is a cost-efficient, compact device, that in one variation includes an associated controller such as the mobile device 14 (that provides mobile connectivity, processing power, and a sensitive color camera). The imaging optics 28 (see FIG. 58A) of the system 10 in one example includes an f=20 mm compact triplet lens (TRH127-020-A, Thorlabs) that provides depth of focus. The example system 10 includes an emission filter 30, such as a Chroma 535/40 filter interposed between the imaging optics 28 and the mobile device optics 40. This arrangement provides a compact imaging system 10. As discussed herein, oblique laser illumination was one example excitation source 20 and facilitates light direction to the sample, reasonable intensity at the sample, and (due to beam directionality and oblique incidence) specular reflection from the sample that is not collected ("misses") the optical sensor, such as the mobile device optical sensor 42 thereby minimizing background scatter.

The fluorescence imaging system 100 shown in FIGS. 59A, 59B is another example system having a collection numerical aperture (NA) of around 0.09, field of view (FOV) of around 12 mm diameter, and epi-illumination fluorescence excitation with a power of around 225 mW across the full FOV. The samples, for instance, one or more of assay mixtures, control mixtures, liquids or the like are provided in a sample cartridge 104. The sample cartridge includes in an example one or more cartridge chambers 106 (capillaries, passages, grooves, channels or the like) that retain samples therein (e.g., assay mixtures, control mixtures or the like) and are filled through ports, such as fluid passages 200 (shown in FIG. 60). As described herein the cartridge chambers 106 and the samples therein are illuminated with the system 100. Comparison of generated light (fluorescence) from the samples within the chambers 106 permits detection of one or more characteristics including, but not limited to, the presence of an antigen.

In one example sample characteristics (e.g., characteristics of the cartridge chambers, samples therein or the like) include around 15 µl sample well volumes (i.e., ≥15 mm$^3$ volumes, or cubes having sides of around 2.5 mm, though in practice volume may have a different aspect ratio). One example sample includes around 100 nM concentrations of quencher-coupled fluorophore (including, but not limited to, fluorescein-type) in aqueous buffer, where the quencher is liberated (linkage to the fluor is cleaved) from the fluor as part of a biochemical assay. Prior to cleavage of the linkage, quenching is imperfect, with effective fluorophore quantum yield (QY) of around 1 percent of normal.

The fluorescence imaging system 100 shown in FIG. 59A is configured (e.g., through components, interrelation of components or the like) to provide various system characteristics that facilitate the detection of one or more features in a sample, such as the presence of an antigen. The system characteristics include in one example a field of view, for instance a FOV of around 12 mm diameter, between around 10 mm to 20 mm diameter or the like to facilitate illumination and imaging of multiple sample and control wells, such as the cartridge chambers 106.

In another example, the fluorescence imaging system 100 includes a numerical aperture (NA), another system characteristic, that enhances collection efficiency (CE) of emitted signal photons from the sample (e.g., samples in the cartridge chambers 106). An example NA for the system includes, but is not limited to 0.075 to 0.10, 0.09 or the like.

In one example, a higher NA (e.g., greater than 0.075, greater than 0.09 or the like) results in more spill-over of collected light beyond the boundaries of the in-focus image of a sample well, such as the cartridge chamber (or chambers) 106, due to out-of-focus light reflecting away from the focal plane in sample wells, for instance having a depth of 2-3 mm (2.5 mm) as described herein. Spill-over of light is minimized with one or more features of the system including focusing at the midpoint (cartridge chamber 106) of the well, midpoints of wells (multiple cartridge chambers or the like).

Accordingly, in some examples there may be a trade-off between increased CE due to higher NA, and the decreased depth-of-field (DOF) resulting from the higher NA, and potential related spill-over of out-of-focus well light into images of adjacent wells, cartridge chambers 106 or the like. In another example, the separation between cartridge chambers 106 is increased to address (minimize) spill-over.

The fluorescence imaging system 100 of FIG. 59A is configured to analyze one or more samples for one or more of the presence, quantity or concentration of an antigen. The system 100 shown in FIG. 59A is a relatively compact device having an optical track length (with an epi-illumination Kohler geometry) of approximately 75 mm (e.g., between 70 and 80 mm) as shown in the Figure. In one example, the optical track length is at least an order of magnitude smaller than other Kohler geometry systems. As shown an excitation source 110 is directed toward a dichromatic mirror 122. The excitation source 110 includes, but is not limited to, an LED generator, laser generator, scrambled laser generator or the like. Optionally, the excitation source 110 includes an excitation filter configured to filter excitation illumination to wavelengths that promote fluorescence from the samples.

The FIG. 59A schematic diagram illustrates an example optical path with dashed lines. FIG. 59A includes examples of the components of the system 100 shown in FIG. 60 at approximately similar locations. FIG. 59A is an example of the fluorescence imaging system 100, which is a compact and sensitive fluorescence detector for the LbuCas13-TtCsm6 assay. The heating module (I) (sample heating module 108 for heating the assay and control mixtures), sample cartridge (II) 104, objective optics (III) 112, and camera (IV) (optical sensor 114) are shown by roman numerals.

As further shown in FIG. 59A, excitation illumination is redirected from the dichromatic mirror 122 toward a sample cartridge 104 having one or more cartridge chambers 106 with samples therein (e.g., assay mixtures, control mixtures or the like). Scattering of the excitation illumination is directed away from the optical sensor 114 with the dichromatic mirror 122 to minimize obscuring of fluorescence detected with the optical sensor 114.

The excitation illumination is directed through the objective optics 112 and delivered to the cartridge chambers 106 and samples therein. In one example, the objective optics 112 (e.g., one or more lenses, composite lenses or the like) deliver the excitation illumination telecentrically to the cartridge chambers 106 (instead of focusing the illumination). The cartridge chambers are oriented with the excitation illumination (e.g., in an excitation orientation).

As shown with the optical tracing in FIG. 59A and FIG. 61 the excitation illumination illuminates a substantial portion of the cartridge chambers 106 and the associated samples (e.g., all, a substantial majority or the like). As shown in FIG. 61, the central rays of each of the clusters are incident at distributed locations across the illumination profile 302 corresponding to the cartridge chambers 106. Additionally, the central rays are transverse (e.g., perpendicular) to the illumination profile 302 (and the cartridge chambers 106). Conversely, the illumination (such as the central rays in FIG. 61) is oriented with the chamber walls 107 (e.g., parallel, aligned or the like) and thereby uniformly illuminates the sample within the chambers 106, for instance from the surface of the samples proximate to the objective optics 112 to the lower portion of the chambers 106, such as the chamber well 109 (see FIG. 59A). The telecentric uniform illumination (e.g., like a flashlight aimed down a hole) minimizes interruption of the excitation illumination caused by obstructions, shadows or the like. The illumination correspondingly interacts with a large portion of the sample (including the entire sample, a substantial portion of the sample or the like) to trigger fluorescence if a specified antigen is present along with the reagents described herein.

In another example, the sample cartridge 104 is received in a corresponding cartridge socket of the system housing 102 to position the cartridge chambers complementary to the excitation illumination, for instance in an excitation orientation that aligns the cartridge chambers with the excitation illumination. For example, the system housing 102 includes a cartridge socket having a socket profile that is complementary to a cartridge profile of the sample cartridge 104, and coupling between the socket and the cartridge orients the sample cartridge to the excitation orientation (e.g., in a manner similar to the cartridge socket 10 and sample cartridge 16 shown in FIG. 56). As shown in FIG. 59A, the illumination optical tracing (the horizontal dashed lines) at the cartridge chambers 106 are oriented with (e.g., aligned, parallel or the like) with the chamber walls 107, and the illumination is delivered to a substantial portion of the chambers 106 to accordingly illuminate the samples therein. In another example, orienting of the sample cartridge 104 to the excitation orientation orients the cartridge chambers 106 as shown, for instance to position the chambers within the excitation illumination and also aligns the cartridge chambers with the telecentric uniform illumination (e.g., orients the chambers 106, chamber walls 107 to alignment with the illumination, parallel to the illumination or the like).

As described herein, illumination of the samples in the cartridge chambers 106 interacts with one or more reagents, antigens or the like to generate fluorescent illumination (fluorescence). The fluorescent illumination is shown in FIG. 59A with return optical traces extending from the sample cartridge 104 and toward the optical sensor 114. The objective optics 112 transmit the fluorescence illumination toward the optical sensor 114 through the dichromatic mirror 122.

In one example, the sample cartridge 104 coupled with the system 100, for instance to a cartridge socket provided through the system housing 102, orients the cartridge 104, the associated cartridge chambers 106 (e.g., the chamber walls 107 or the like), the samples therein, or fluorescence therefrom with one or more of the optical sensor 114, the objective optics 112, the imaging optics 116 or the like. For instance, orientation of the cartridge 104, cartridge chambers 106 or the samples therein is referred to as an observation orientation, and in one example reception of the sample cartridge 104 having a complementary cartridge profile to a socket profile of the cartridge socket orients the sample cartridge and its samples to the observation orientation (similar to the cartridge socket 10 and sample cartridge 16 in FIG. 56). The observation orientation of the sample cartridge 104 and the associated cartridge chambers 106 with the optical sensor 114 and associated optics of the system 100 facilitates direction of fluorescence generated at the samples toward the optical sensor 114. In one example, the observation orientation facilitates the telecentric direction of fluorescence from the cartridge chambers 106 and the associated samples to an emission filter 120 (e.g., as shown in FIG. 59A with the emission filter 120 interposed between the imaging optics 116 and the optical sensor 114).

In one example, the emission filter 120 is interposed between the objective optics 112 and the optical sensor 114. The emission filter filters incidental scattered light from the fluorescent light and preferentially passes fluorescent light to the optical sensor 114 for detection of the antigen and optionally determination of quantity or concentration of the antigen in the sample. As shown in FIG. 56A the emission filter 120 is optionally positioned between the imaging optics 116 and the dichromatic mirror 122 or between the imaging optics 116 and the optical sensor 114. In one example, the imaging optics 116 telecentrically delivers fluorescence to the optical sensor 114. As shown with the observation profile 304 of the optical layout 300 in FIG. 61 the central rays of the ray clusters are transverse to the observation profile 304 (e.g., perpendicular or having a field angle close to 0 degrees), and accordingly transverse to the emission filter 120 when interposed between the optics 116 and the optical sensor 114. The emission filter 120, in some examples, uniformly filters telecentric fluorescence in comparison to fluorescent illumination that converges, is angled or the like. For instance, emission filter 120 performance of one or more locations within the field of view (FOV) is consistent and uniform with telecentric fluorescence from the imaging optics 116. The telecentric imaging optics 116 enhance the consistency (including identity) of performance for the entire FOV with the emission filter 120, and minimizes shifts to unspecified colors (such as a blue shift) at one or more locations in the FOV. Instead, the telecentric imaging optics 116 and the emission filter 120 cooperate to provide a consistent fluorescence output for observation and analysis at the optical sensor 114.

In the example system 100 shown in FIGS. 59A, 59B and 60 telecentricity is provided on both the object and image sides of the optical system (double-telecentric), such as imaging with object and image field angles close to 0 degrees. The double-telecentric system minimizes crosstalk between sample wells (samples, cartridge chambers 106 including the samples or the like) and the spill-over of collected light beyond the boundaries of an in-focus sample well image. As shown in the optical layout 300 provided in FIG. 61, the fluorescence imaging system 100 is doubly telecentric at each of the illumination profile 302 (object) and the observation profile 304 (image).

In another example, a system 100 detector, such as the optical sensor 114 includes a relatively high quantum efficiency (QE) (another example of a system characteristic) to maximize signal collection with low readout noise and dark current to minimize noise. However, in one example of tested samples noise is generated due to the significant background signal from incompletely quenched fluorescence. For example, the primary theoretical noise limit is due to the photon shot noise of the background fluorescence, which may dominate the readout noise and shot noise of the dark current during the image exposure. For example, in an example optical sensor 114 (e.g., a camera, such as a Thorlabs CS165MU1) the pixel full-well-capacity (FWC) is around 11,000 photoelectrons (e–), while the read noise is less than 4 e– root mean square (rms). Presuming the bulk of the collected signal is background light from incompletely quenched fluorophores, the shot noise will be around $\sqrt{11,000}$ or approximately 100 e–>>4 e– read noise, or significantly greater than the read noise. Accordingly, lower read noise and dark signal, in at least one example of the system 100, has a lower priority than in other low-background fluorescence measurements. Optionally, this relatively low priority of read noise and dark signal facilitates the use of less costly cameras suitable for deployment in point-of-care diagnostics, such as the example fluorescence imaging system 100 described herein.

Excitation intensity is another example system characteristic of the fluorescence imaging system 100. In one example the signal-to-noise ratio (SNR) improves roughly as the square root of the number of collected photons (because signal is proportional to the CE, while the shot noise will be proportional to 4CE). In such an example, it may be advantageous to extract all photons from a fluor. Relatively high excitation intensities are used with the system 100, given the small (around 1 Å2) excitation cross-section of typical molecules (e.g. FITC) used for biochemical fluorescence assays, typical maximum fluorescent photon emissions prior to photobleaching (around $10^5$-$10^7$ emissions for typical fluorophores in biological/biochemical assays) and total assay time (around 30 s of total illumination time, spread over approximately 30 minutes in the current case). Accordingly, illuminating the sample (e.g., assay mixtures, control mixtures, cartridge chambers 106 including the same, or the like) at intensities of up to order of around 0.1-10 W/mm$^2$ are desirable, for instance with the lower powers corresponding to use with more easily bleached fluorophores. In the example system 100 the excitation source 110 for triggering fluorescence is a light source including, but not limited to, an LED system, for instance based on a Thorlabs M470L4 high-power LED, and produces around 0.225 W at the sample, for an intensity of around 2 mW/mm$^2$.

As described above, the excitation source 110 is optionally an LED system having relatively low illumination spatio-temporal noise (another example system characteristic). In another example, the excitation source 110 includes a laser generator. A laser generator, such as a semiconductor laser, may have laser power noise of around 1 percent. Additionally, semiconductor lasers (and especially inexpensive multimode direct diode lasers) may have substantial spatial fluctuations of the output beam (somewhat akin to pointing instability in gas lasers). Any fluctuations that cause differential changes in illumination between the two (or more) sample and control wells (e.g., cartridge chambers 106) of an assay will limit the detection threshold of the assay to samples which produce signal sufficiently larger than the differential changes due to illumination instability. Accordingly, stable illumination is desirable, and in the example fluorescence imaging system 100 LEDs were used as the excitation source 110 though laser generators could be used. In one example, a scrambled laser generator with corresponding scrambled illumination would work.

In the example fluorescence imaging system 100 signal to noise ratio (SNR) was optionally traded off from potential full photon extraction from sample fluorophores (e.g., using a laser) for the more stable (and less expensive) illumination from an LED system. In another example, an LED system provides a potential further benefit in simpler data analysis due to reduced photobleaching effects.

Referring again to FIGS. 59A, B and 60 imaging of sample chambers (e.g., cartridge chambers 106) having volumes of around 15 µl involves a fairly large field of view (FOV) and a modest numerical aperture (NA) to provide significant depth of focus without images of adjacent sample wells overlapping. The fluorescence imaging system 100 accomplishes these objectives in a relatively low-cost, compact device. The present fluorescence imaging system 100 includes a pair of eyepieces (e.g., Edmund Optics, PN #66-208 and 66-210), yielding a system with numerical aperture (NA) 0.09, field-of-view (FOV) diameter 12.0 mm, and magnification (M) of 0.54, all example system characteristics. The magnification of 0.54 is selected to match the sensor size of the optical sensor 114, such as a Thorlabs CS165MU1 camera, to the FOV. With the fluorescence imaging system 100 it is unnecessary to sample at greater than or equal the Nyquist limit (e.g., of the optical sensor 114) in this "light-bucket" application. The overall system 100 is compact, with nominal track length (sample to camera, or sample to optical sensor 114) of around 70 mm to 80 mm, including around 75 mm.

In one example of the fluorescence imaging system 100 fluorescence filters, such as the chromatic filters 120, 124 and dichromatic mirror 122 include, but are not limited to, Chroma Technologies, ET470/40x (as the excitation filter 124). T4951pxr (as the dichromatic mirror 122), and ET535/70m (as the emission filter 120). In the example system excitation is provided by light generator, such as a 965 mW, 470 nm LED system (e.g., a Thorlabs M470L4) that provides around 225 mW into the 12 mm diameter sample FOV in an epi-illumination Kohler geometry (as shown in FIGS. 59A, 60).

Control of the system 100, for instance imaging hardware, is implemented in MATLAB (2020a), using Thorlabs drivers and SDK (ThorCam) to control the camera acquisition of the optical sensor 114, and serial communication to an Arduino Bluefruit Feather board to electronically trigger the LED illumination through the excitation source 110. Optionally, control of the system 100 is provided with a controller (e.g., as a processor, programmed logic controller, circuits, machine readable media, software modules or the like including instructions, such as machine readable media, for implementation by the system 100) that is associated with a system housing 102 of the system 100 or is remotely connected with the system 100 (e.g., by wired or wireless connection, for instance with a mobile device 14 as shown in FIG. 56).

The fluorescence imaging system 100 optionally includes a controller (e.g., processor, programmed logic controller, machine readable media, software modules or the like) configured to control or operate the fluorescence imaging system 100, for instance control excitation illumination, check for installation of the sample cartridge 106 (e.g., installed, fully installed, aligned in the excitation and observation orientations or the like), analyze fluorescence detected with the optical sensor 114 to identify, quantify or determination concentration of an antigen or the like. In another example, control of the fluorescence imaging system 100 is conducted with an onboard or remote controller (e.g., wireless or wire connected), such as a processor, programmed logic controller, circuits, machine readable media, software modules or the like, and the controller is interconnected with features of the system 100, such as the excitation source 110, optical sensor 114 or the like. The controller optionally conducts analysis of the samples, such as the fluorescence generated at the samples and detected with the optical sensor 114 to determine one or more of the presence of an antigen, its quantity, concentration or the like.

FIG. 60 shows an example arrangement of components of the example fluorescence imaging system 100. In some examples the arrangement is referred to as a Kohler epi-illumination geometry. In this example, the objective optics 112 include one or more component lenses, such as a left lens pair, for instance a 21 mm focal length Edmund RKE eyepiece. As further shown, the imaging optics 116 (e.g., tube lens, imaging lens or the like) include one or more component lenses. For example, the imaging optics 116 shown in FIG. 60 include a multi-component lens set, such as a 12 mm focal length RKE eyepiece. The optical sensor 114 in the example system 100 is a Thorlabs CS165MU1 camera. An emission filter 120, such as a Chroma Technologies ET535/70m emission filter, is positioned anterior to the optical sensor 114. For instance, emission filter 120 is between the imaging optics 116 and the dichromatic mirror 122. In another example, the emission filter 120 is between the imaging optics 116 and the optical sensor 114 (e.g., to benefit from the telecentric set up discussed herein). The dichromatic mirror 122 (e.g., the diagonal element in FIG. 60) is another example of a filter and includes a 10.2×19.2 mm Chroma Technologies T495lpxr dichroic filter. The components described herein are one example of components for the system 100. In other examples, components of the system 100 include different light generators 100, emission filters 120, excitation filters 124, mirrors or filters 122, optical sensors 114, optics 112, 116 or the like that are configured to assess and detect the presence of one or more antigens as discussed herein and their equivalents. An example provides an emission filter interposed between the sample cartridge and the optical sensor, wherein the emission filter is configured to transmit light having a wavelength around 500 to 700 nanometers.

FIG. 61 is an example optical layout 300 (e.g., generated with a ZEMAX modeling program) for the fluorescence imaging system 100 showing the layout between the sample, such as the sample cartridge 104 (FIG. 60) having an assay mixture and control mixture, and the optical sensor 114 (FIG. 60). As shown in FIG. 61, the optical layout 300 includes an illumination profile 302 proximate to the sample cartridge and an observation profile 304 proximate to the optical sensor. In the example layout 300 the total optical track length is around 75 mm (as shown in FIG. 59A), the collection side numerical aperture (NA) is around 0.09, and total magnification is around −0.53. In one example, the system 100 provides a system stop (pupil at center) that is circular with a 2 mm radius. The components shown in FIG. 61 are similarly shown in FIGS. 59A and 60. As further shown with the ray clusters and central rays of each of the ray clusters in FIG. 61 the fluorescence imaging system 100 is doubly-telecentric, for instance the central rays extend to infinity (are not focused), are transverse to the respective illumination and observation profiles 302, 304, have field angles of approximately 0 degrees or the like. As described herein, telecentricity enhances illumination of the sample, such as the cartridge chambers 106 and filtering of fluorescence with the emission filter 120 and imaging of the fluorescence signal at the optical sensor 114 (see FIG. 60).

FIGS. 62A, B illustrate a prophetic example of the sensitivity of the fluorescence imaging system 100 as described herein. An externally validated BEI SARS-CoV-2 RNA (BEI Resources Repository) sample was used to assess sensitivity. LbuCas13 reactions containing 25 cp/μl of SARS-CoV-2 RNA (for an assay mixture) or no RNA (for an example control mixture) were loaded to respective cartridge chambers 106 of the sample cartridge 104. The cartridge chambers 106 were monitored for fluorescence signal for one hour.

As shown in FIGS. 62A, 62B, the slope of the fluorescence signal relative to time was calculated to a 95 percent confidence interval by performing a linear regression to the signal for the duration of 30 minutes (FIG. 62A) or 1 hour (FIG. 62B, note the slope is in units of $10^4$). For both durations, the slope of the positive reaction (Sample 1 in FIG. 62A and 25 cp/μl in FIG. 62B, with RNA sample) was significantly and detectably larger than that of the control (RNP only, without RNA sample). Accordingly, as shown in FIGS. 62A, 62B, the example LbuCas13 reactions containing 25 copies/μl of SARS-CoV-2 RNA or no RNA ran for 30 minutes or one hour, and corresponding slopes presented indicating the feasibility and operability of the system 100. Note slopes of both repetitions of 25 cp/μl are significantly higher (separation>uncertainties) than the corresponding ribonucleoprotein-only (RNP) slopes at the corresponding timepoints. The plots shown in FIGS. 62A-62B are additional examples of fluorescence profiles.

The fluorescence imaging system 100 (or 10, as described herein), through a mobile device or an associated controller, is configured to quantify the difference between the absorbance of the assay mixture and the control mixture (e.g., with a comparator) and thereby detect the presence of an antigen from the fluoresced assay mixture, or lack thereof, and optionally determine the quantity or concentration of the antigen.

For example, the controller includes a comparator with one or more static or dynamic thresholds, and the comparator analyses the fluoresced light from the assay mixture (and in one example, the control mixture) relative to the thresholds to indicate the presence of the antigen. In another example, the fluoresced light (e.g., absorbance, attenuation, slope of measurements of the same like those shown in FIGS. 62A-62B, rates of change of the same or the like) is interpreted to indicate one or more of presence, quantity or concentration of the antigen. In yet another example, the thresholds for comparison are based on control mixtures in the other cartridge chambers 106 that are subjected to excitation illumination, like the assay mixture, and their fluorescence is used as a base threshold for comparison with the fluorescence of the assay mixture. For instance, fluorescence of the fluoresced assay mixture (illustrate with absorbance and slope of absorbance in FIGS. 62A, B) is greater than the fluoresced control mixture and is indicative of the presence of an antigen. In another example, the assay mixture fluorescence indicates the presence of the antigen if it is greater than the control mixture fluorescence modified by a specified constant or function-based value. The plotted fluorescence of the assay mixture (alone or relative to the control mixture) relative to time as a rate of change or slope in another example is interpreted to quantity or determine concentration of antigen (e.g., by way of comparison with a look up table, mathematical function or the like).

Figure 1B:
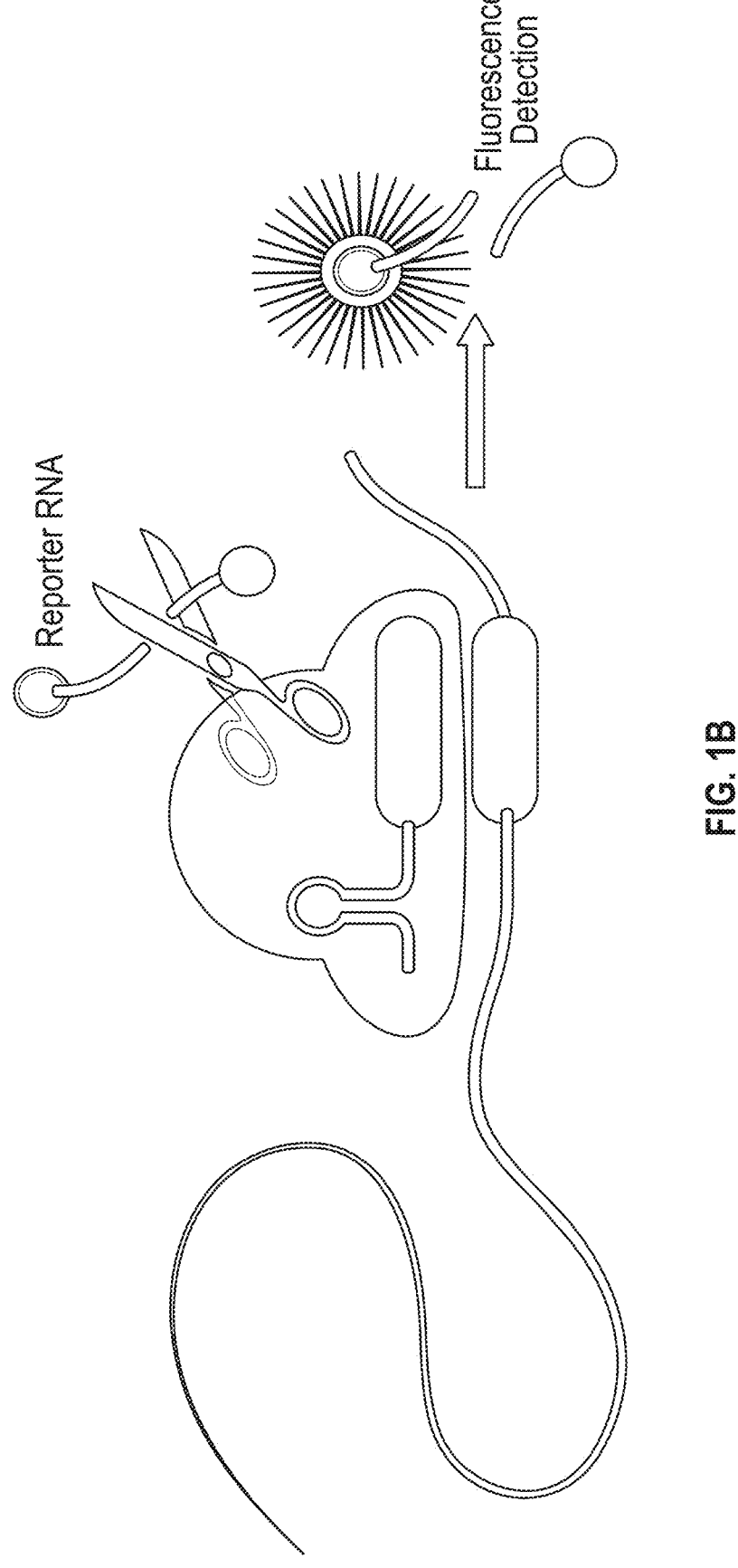

FIG. 1I illustrates a block diagram of an example machine 700 upon which any one or more of the techniques (e.g., methodologies) discussed herein may be performed. In alternative implementations, the machine 700 may operate as a standalone device or may be connected (e.g., networked) to other machines. For example, the machine 700 is one example of a controller as described herein used with one or more of the fluorescence imaging systems 10, 100 or the like.

In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be, or be a part of, a communications network device, a cloud service, a personal computer (PC), a tablet PC, a personal digital assistant (PDA), a mobile telephone, a smart phone, or any machine capable of executing instructions (sequential or otherwise) that specify actions to be taken by that machine. Some components of the machine 700 (e.g., processing circuitry 702) may include elements from mobile device 1100 (FIG. 11).

In some aspects, the machine 700 may be configured to implement a portion of the methods discussed herein. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" or "engine" is understood to encompass a tangible entity, be that an entity that is physically constructed, specifically configured (e.g., hardwired), or temporarily (e.g., transitorily) configured (e.g., programmed) to operate in a specified manner or to perform part, or all, of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a module at one instance of time and to constitute a different module at a different instance of time. A module or engine can be implemented using processing circuitry configured to perform the operations thereof.

Machine (e.g., computer system) 700 may include a hardware processing circuitry 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. Circuitry can further include Doppler laser interferometry equipment or other equipment as described above for capturing resonant frequency measurements.

The machine 700 may further include a display unit 710, an alphanumeric input device 712 (e.g., a keyboard), and a user interface (UI) navigation device 714 (e.g., a mouse). In an example, the display unit 710, input device 712 and UI navigation device 714 may be a touch screen display. The display unit 710 may be configured to indicate results of an assay as described above with respect to FIG. 1-11. The display unit 710 may provide an indication as to whether an infection has been detected, using visual indicators including lights, warning symbols, etc. The display unit 710 can comprise indicator circuitry such as a light-emitting diode (LED). The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or another sensor (e.g., diagnostic sensors and devices) as described earlier herein. The GPS can be used to assist with bio-surveillance, for example, once a SARS-CoV-2 viral infection has been detected. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. For example, the functions can include functions to assess whether an infection, in particular COVID-19 infection, is present and send (e.g., transmit) results to another location such as cloud or edge computing device. The instructions 724 may also reside, completely or at least partially, within the main memory 704, within static memory 706, or within the hardware processing circuitry

702 during execution thereof by the machine 700. In an example, one or any combination of the hardware processing circuitry 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM): Solid State Drives (SSD); and CD-ROM and DVD-ROM disks. In some examples, machine readable media may include non-transitory computer readable media. In some examples, machine readable media may include machine readable media that is not a transitory propagating signal.

The instructions 724 may further be transmitted or received over a communications network 726 using a transmission medium via the network interface device 720. The machine 700 may communicate with one or more other machines utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®, IEEE 802.15.4 family of standards, a Long Term Evolution (LTE) family of standards, a Universal Mobile Telecommunications System (UMTS) family of standards, peer-to-peer (P2P) networks, among others). In an example, the network interface device 720 may include one or more physical jacks (e.g., Ethernet, coaxial, or phone jacks) or one or more antennas to connect to the communications network 726. In an example, the network interface device 720 may include a plurality of antennas for wirelessly communication.

The above detailed description includes references to the accompanying drawings, which form a part of the detailed description. The drawings show, by way of illustration but not by way of limitation, specific implementations in which the disclosure can be practiced. These implementations are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more implementations thereof), either with respect to a particular example (or one or more implementations thereof), or with respect to other examples (or one or more implementations thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a." "an," "the." and "said" are used when introducing elements of implementations of the disclosure, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A." and "A and B," unless otherwise indicated.

In the appended claims, the terms "including" and "in which" are used as the plain-English equivalents of the respective terms "comprising" and "wherein." Also, in the following claims, the terms "comprising," "including." and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Implementations of the disclosure may be implemented with computer-executable instructions. The computer-executable instructions (e.g., software code) may be organized into one or more computer-executable components or modules. Aspects of the disclosure may be implemented with any number and organization of such components or modules. For example, implementations of the disclosure are not limited to the specific computer-executable instructions or the specific components or modules illustrated in the figures and described herein. Other implementations of the disclosure may include different computer-executable instructions or components having more or less functionality than illustrated and described herein.

Method examples (e.g., operations and functions) described herein can be machine or computer-implemented at least in part (e.g., implemented as softhare code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the implementations described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

While the present disclosure is capable of being embodied in various forms, the description below of several embodiments is made with the understanding that the present disclosure is to be considered as an exemplification of the invention and is not intended to limit the invention to the specific embodiments illustrated. Headings are provided for convenience only and are not to be construed to limit the invention in any manner. Embodiments illustrated under any heading may be combined with embodiments illustrated under any other heading.

All numerical designations. e.g., pH, temperature, time, concentration, and molecular weight, including ranges, are approximations which are varied, for example (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that in some cases equivalents may be available in the art.

It must be noted that as used herein and in the appended claims, the singular forms "a", "an", and "the" include plural referents unless the context clearly dictates otherwise. Thus, for example, reference to "a cell" includes a plurality of cells.

The term "about" when used before a numerical designation. e.g., temperature, time, amount, concentration, and such other, including a range, indicates approximations which may vary by (+) or (−) 20%, 10%, 5% or 1%.

Also, as used herein, "and/or" refers to and encompasses any and all possible combinations of one or more of the associated listed items, as well as the lack of combinations when interpreted in the alternative ("or").

The term "treatment" or "treating" in relation to a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing, or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development or further disease/disorder progression if already present.

The following Examples describe some of the materials and experiments used in the develop of the invention. Appendix A included herewith may provide additional information.

EXAMPLES

Example 1: Cas13a Detection of SARS-CoV-2 Transcripts

CRISPR RNA guides (crRNAs) were designed and validated for SARS-CoV-2. Fifteen crRNAs were first designed with 20-nt spacers corresponding to SARS-CoV-2 genome. Additional crRNAs were later designed, bringing the number of crRNAs to 26. Each crRNA includes a crRNA stem that is derived from a bacterial sequence, while the spacer sequence is derived from the SARS-CoV-2 genome (reverse complement). See Table 1 (reproduced below) for crRNA sequences.

TABLE 1

| Examples of SARS-CoV-2 crRNA Sequences | | |
|---|---|---|
| SEQ ID NO | Name | Sequence |
| SEQ ID NO: 1 | PF039_crLbu_ nCoV_1 (crRNA 1) | GACCACCCCAAAAAUGA AGGGGACUAAAACUUUC GCUGAUUUUGGGGUCC |
| SEQ ID NO: 2 | PF040_crLbu_ nCoV_2 (crRNA 2) | GACCACCCCAAAAAUGA AGGGGACUAAAACGGUC CACCAAACGUAAUGCG |
| SEQ ID NO: 3 | PF041_crLbu_ nCoV_3 (crRNA 3) | GACCACCCCAAAAAUGA AGGGGACUAAAACUCUG GUUACUGCCAGUUGAA |
| SEQ ID NO 4 | PF042_crLbu_ nCoV_4 (crRNA 4) | GACCACCCCAAAAAUGA AGGGGACUAAAACUUUG CGGCCAAUGUUUGUAA |
| SEQ ID NO: 5 | PF043_crLbu_ nCoV_5 (crRNA 5) | GACCACCCCAAAAAUGA AGGGGACUAAAACGAAG CGCUGGGGGCAAAUUG |
| SEQ ID NO: 6 | PF044_crLbu_ nCoV_6 (crRNA 6) | GACCACCCCAAAAAUGA AGGGGACUAAAACAUGC GCGACAUUCCGAAGAA |
| SEQ ID NO: 7 | PF045_crLbu_ nCoV_7 (crRNA 7) | GACCACCCCAAAAAUGA AGGGGACUAAAACUUGG UGUAUUCAAGGCUCCC |
| SEQ ID NO: 8 | PF046_crLbu_ nCoV_8 (crRNA 8) | GACCACCCCAAAAAUGA AGGGGACUAAAACGGAU UGCGGGUGCCAAUGUG |
| SEQ ID NO: 9 | PF047_crLbu_ nCoV_9 (crRNA 9) | GACCACCCCAAAAAUGA AGGGGACUAAAACUGUA GCACGAUUGCAGCAUU |
| SEQ ID NO: 10 | PF048_crLbu_ nCoV_10 (crRNA 10) | GACCACCCCAAAAAUGA AGGGGACUAAAACUAAG UGUAAACCCACAGGG |
| SEQ ID NO: 11 | PF049_crLbu_ nCoV_11 (crRNA 11) | GACCACCCCAAAAAUGA AGGGGACUAAAACUAAC CUUUCCACAUACCGCA |
| SEQ ID NO: 12 | PF050_crLbu_ nCoV_12 (crRNA 12) | GACCACCCCAAAAAUGA AGGGGACUAAAACUCAG CUGAUGCACAAUCGUU |

TABLE 1-continued

Examples of SARS-CoV-2 crRNA Sequences

| SEQ ID NO | Name | Sequence |
|---|---|---|
| SEQ ID NO: 13 | PF051_crLbu_ nCoV_13 (crRNA 13) | GACCACCCCAAAAAUGA AGGGGACUAAAACUCUA GCAGGAGAAGUUCCCC |
| SEQ ID NO: 14 | PF052_crLbu_ nCoV_14 (crRNA 14) | GACCACCCCAAAAAUGA AGGGGACUAAAACUCUG UCAAGCAGCAGCAAAG |
| SEQ ID NO: 15 | PF053_crLbu_ nCoV_15 (crRNA 15) | GACCACCCCAAAAAUGA AGGGGACUAAAACCUUU GCUGCUGCUUGACAGA |
| SEQ ID NO: 16 | PF083_crLbu_ nCov_12v2 | GACCACCCCAAAAAUGA AGGGGACUAAAACAACG AUUGUGCAUCAGCUGA |
| SEQ ID NO: 17 | PF084_crLbu_ nCov_15v2 | GACCACCCCAAAAAUGA AGGGGACUAAAACGACA UUUUGCUCUCAAGCUG |
| SEQ ID NO: 18 | PF085_crLbu_ nCoV_16 (crRNA 16) | GACCACCCCAAAAAUGA AGGGGACUAAAACGUUC CUGGUCCCCAAAAUUU |
| SEQ ID NO: 39 | PF086_crLbu_ nCoV_17 (crRNA 17) | GACCACCCCAAAAAUGA AGGGGACUAAAACUGGC ACCUGUGUAGGUCAAC |
| SEQ ID NO: 20 | PF087_crLbu_ nCoV_18 (crRNA 18) | GACCACCCCAAAAAUGA AGGGGACUAAAACUCCA UGCCAAUGCGCGACAU |
| SEQ ID NO: 21 | PF088_crLbu_ nCoV_19 (crRNA 19) | GACCACCCCAAAAAUGA AGGGGACUAAAACCUAU UAACUAUUAACGUACC |
| SEQ ID NO: 22 | PF089_crLbu_ nCoV_20 (crRNA 20) | GACCACCCCAAAAAUGA AGGGGACUAAAACUAUU GCAGCAGUACGCACAC |
| SEQ ID NO: 23 | PF090_crLbu_ nCoV_21 (crRNA 21) | GACCACCCCAAAAAUGA AGGGGACUAAAACAGCG CAGUAAGGAUGGCUAG |
| SEQ ID NO: 24 | PF091_crLbu_ nCoV_22 (crRNA 22) | GACCACCCCAAAAAUGA AGGGGACUAAAACGUAA CUAGCAAGAAUACCAC |
| SEQ ID NO: 25 | PF092_crLbu_ nCov_2XL (crRNA 2XL) | UAGACCACCCCAAAAAU GAAGGGGACUAAAACGG UCCACCAAACGUAAUGC G |
| SEQ ID NO: 26 | PF093_crLbu_ nCov_4XL (crRNA 4XL) | UAGACCACCCCAAAAAU GAAGGGGACUAAAACGG UCCACCAAACGUAAUGC G |
| SEQ ID NO: 27 | cr2 (one of the 8G crRNAs) detecting protein N Lower case: stem sequence Upper case: Target, sequence | uagaccaccccaaaaau gaaggggacuaaaacCG CAUUACGUUUGGUGGAC C |
| SEQ ID NO: 28 | Cr4 (one of the 8G crRNAs) detecting | uagaccaccccaaaaau gaaggggacuaaaacUU ACAAACAUUGGCCGCAA A |

TABLE 1-continued

Examples of SARS-CoV-2 crRNA Sequences

| SEQ ID NO | Name | Sequence |
|---|---|---|
| | protein N Lower case: stem sequence Uppercase: Target sequence | |
| SEQ ID NO: 29 | NCR_542 (one of the 8G crRNAs) detecting ORF1ab (NSP5) Lower case: stem sequence Upper case: Target sequence | uagaccaccccaaaaau gaaggggacuaaaacAA ACUACGUCAUCAAGCCA A |
| SEQ ID NO: 30 | NCR_546 (one of the 8G crRNAs) detecting ORF1ab (NSP5) Lower case: stem sequence Upper case: Target sequence | uagaccaccccaaaaau gaaggggacuaaaacCA CAGUCAUAAUCUAUGUU A |
| SEQ ID NO: 31 | NCR_564 (one of the 8G crRNAs) detecting ORF1ab (NSP16) Lower case: stem sequence Upper case: Target sequence | uagaccaccccaaaaau gaaggggacuaaaacUC ACACUUUCUAAUAGCA U |
| SEQ ID NO: 32 | NCR_569 (one of the 8G crRNAs) detecting the S protein Lower case: stem sequence Upper case: Target sequence | uagaccaccccaaaaau gaaggggacuaaaacUG UAAGAUUAACACACUGA C |
| SEQ ID NO: 33 | NCR_588 (one of the 8G crRNAs) detecting protein N Lower case: stem sequence | uagaccaccccaaaaau gaaggggacuaaaacUU AAUUGUGUACAAAAACU G |

TABLE 1-continued

Examples of SARS-CoV-2 crRNA Sequences

| SEQ ID NO | Name | Sequence |
|---|---|---|
| | Upper case: Target sequence | |
| SEQ ID NO: 34 | NCR_596 (one of the 8G crRNAs) detecting protein ORF8 Lower case: stem sequence Upper case: Target sequence | uagaccaccccaaaaaug aaggggacuaaaacCAGU UGUGAUGAUUCCUAAG |
| SEQ ID NO: 35 | Guide 21 detecting protein E | uagaccaccccaaaaauga aggggacuaaaacAGCGCA GUAAGGAUGGCUAG |

The crRNAs were tested using several SARS-CoV-2 RNA. Initially, the crRNAs were evaluated in a direct detection assay with purified *Leptotrichia buccalis* (Lbu) Cas13a (East-Seletsky et al., 2016) and an RNA reporter quenched fluorescence.

Briefly, crRNAs with SEQ ID NOs: 2 or 4 sequences were diluted to 28 μM in TE buffer, pH 8 and combined with Cas13a protein to form ribonucleoprotein (RNP) complexes. The Cas13a protein-crRNA complex mixtures were then incubated at room temperature for 15 minutes. Test samples with $7 \times 10^6$ or $7 \times 10^7$ SARS-CoV-2 ssRNA targets were prepared at 100 μM in DEPC water and mixed with 5× buffer, DEPC water. DEPC water was added to lyophilized RNaseAlert (ThermoFisher Scientific) to resuspend. The SARS-CoV-2 ssRNA samples were then mixed with the RNase Alert, and the ribonucleoprotein (RNP) complexes. Controls without Cas13a protein were also made. The formation of RNA cleavage products was monitored with a fluorometer. See FIGS. 1-3.

Figures 4A, 4B:
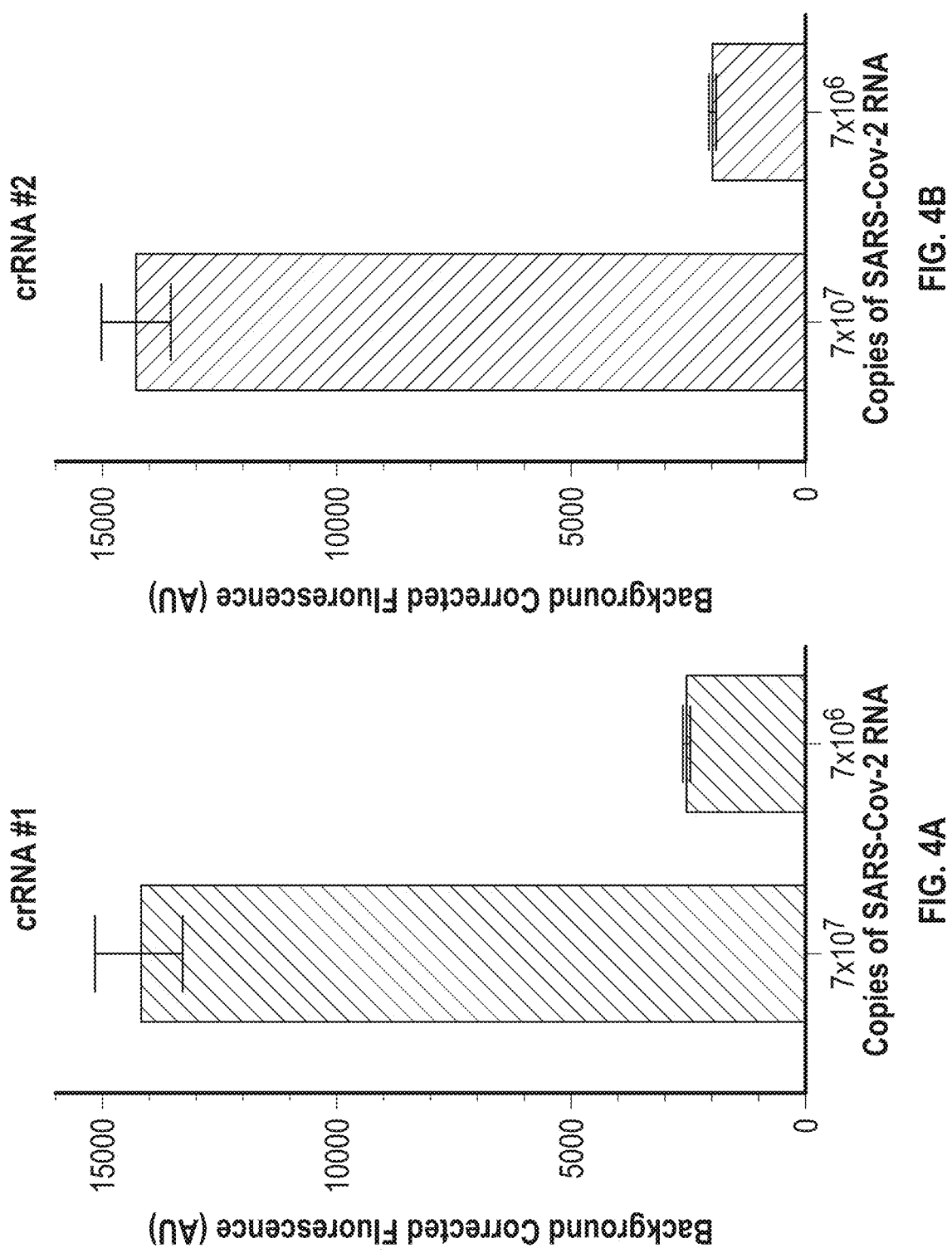
FIG. 4A-4B illustrates that the compositions and methods can robustly detect $10^6$ to $10^7$ or fewer copies of SARS-CoV-2 virus under the conditions used in the experiment.

FIG. 4A-4B illustrate that fluorescent levels detected directly correlate with the amount of SARS-CoV-2 RNA in the different reaction mixtures.

Example 2: Validation of Cas13a Detection of SARS-CoV-2 Transcripts

This Example illustrates that the detection methods and crRNA guide RNAs do not cross-react with human cellular RNAs and can specifically detect SARS-CoV-2.

The Cas13a:crRNA complexes and RNaseAlert detection reagent were prepared as described in Example 1 and mixed with $7 \times 10^5$ copies SARS-CoV-2 RNA or with RNA from human lung epithelial cells (A549 cell line).

Figure 5:
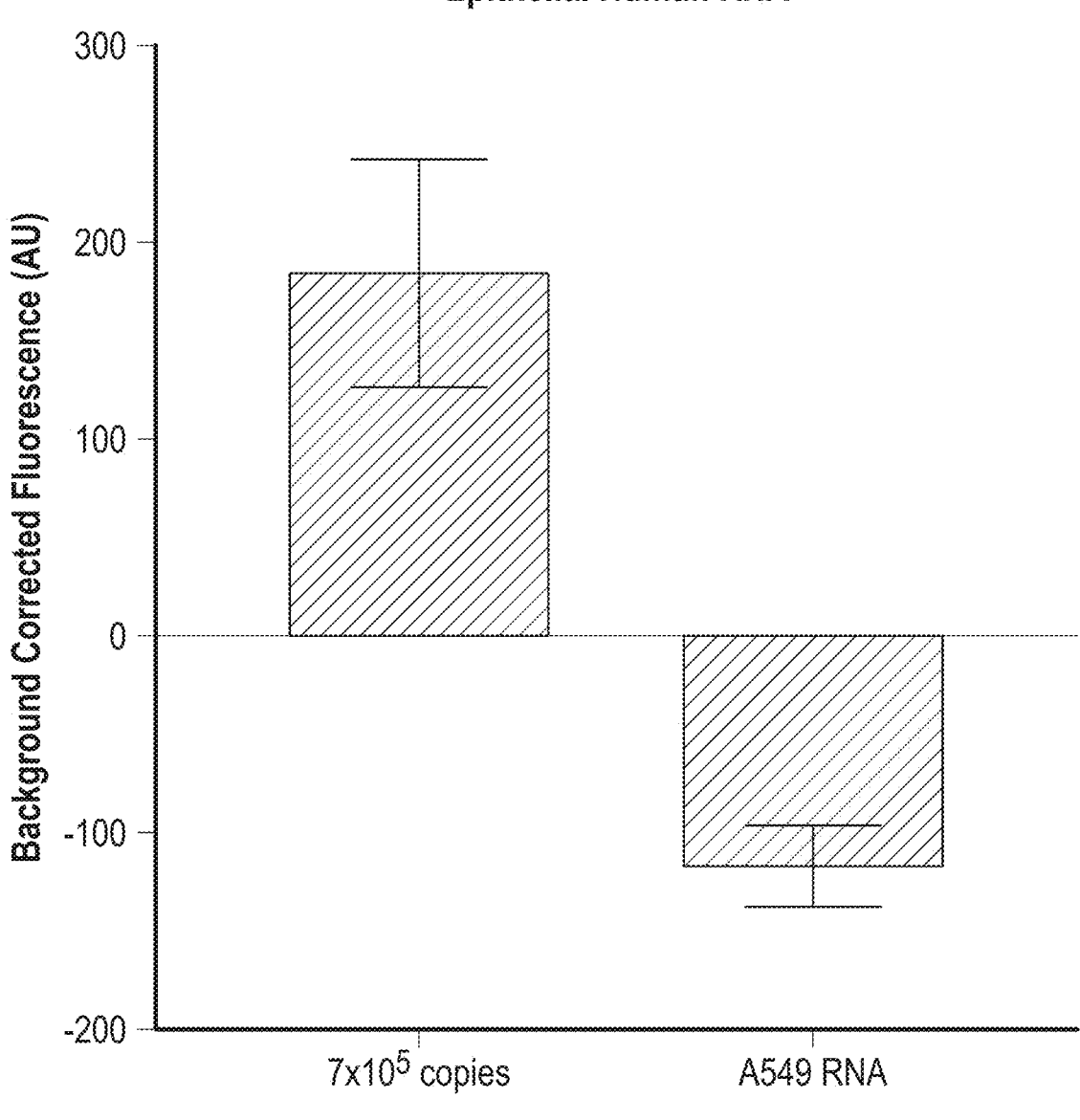
FIG. 5 graphically illustrates that the methods described herein for detecting SARS-CoV-2 using the SARS-CoV-2-specific crRNAs do not cross react with epithelial cell RNA, including the RNA from human lung epithelial cells (A549 cell line). Even when just one crRNA is used, $10^6$ or fewer copies of SARS-CoV-2 virus can readily be detected.

As shown in FIG. 5, the methods described herein can detect less than $7 \times 10^6$ copies SARS-CoV-2 RNA (i.e., $7 \times 10^5$ or fewer copies SARS-CoV-2 RNA). Moreover, FIG. 5 shows that the SARS-CoV-2 assay does not cross react with epithelial human cell RNA from the A548 human lung epithelial cell line.

Figures 6A, 6B:
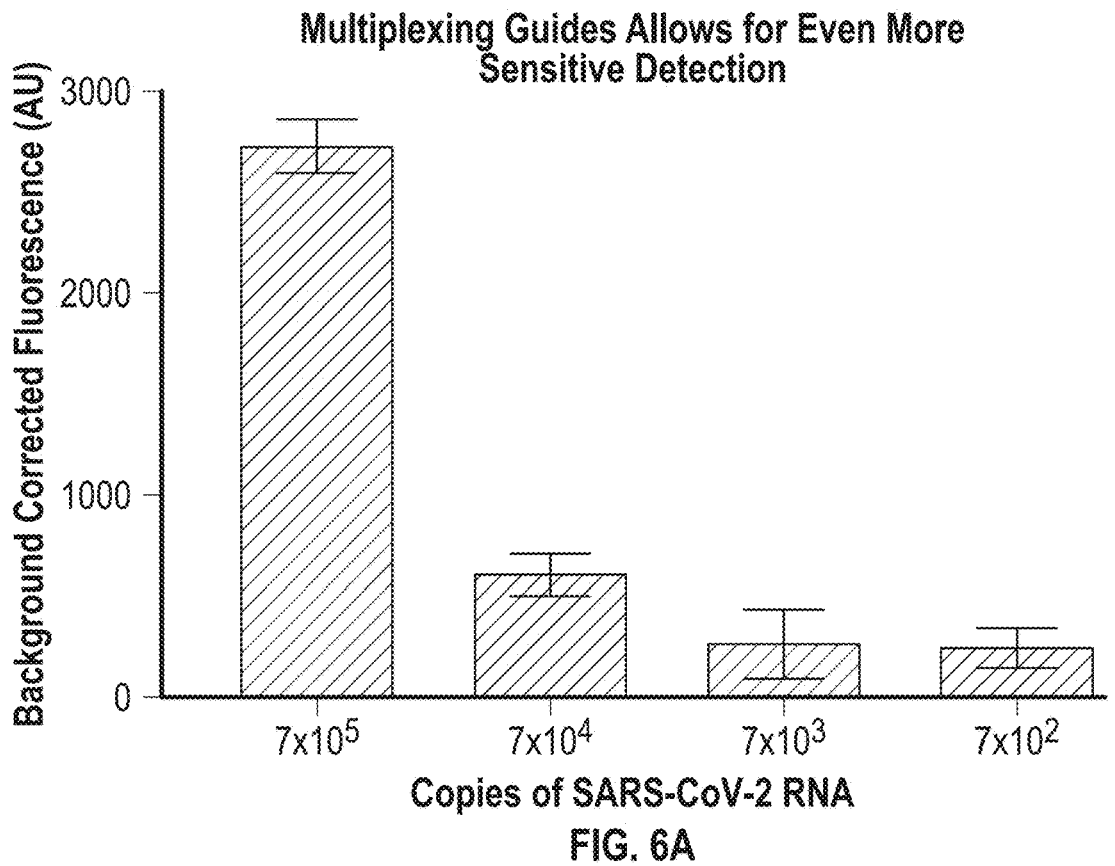
FIG. 6A-6D graphically illustrate the sensitivity of the SARS-CoV-2 detection methods described herein and that Cas13a variants identified through mutagenesis exhibit reduced background fluorescence, enabling improved detection at lower concentrations of activator.
Figures 6C, 6D:
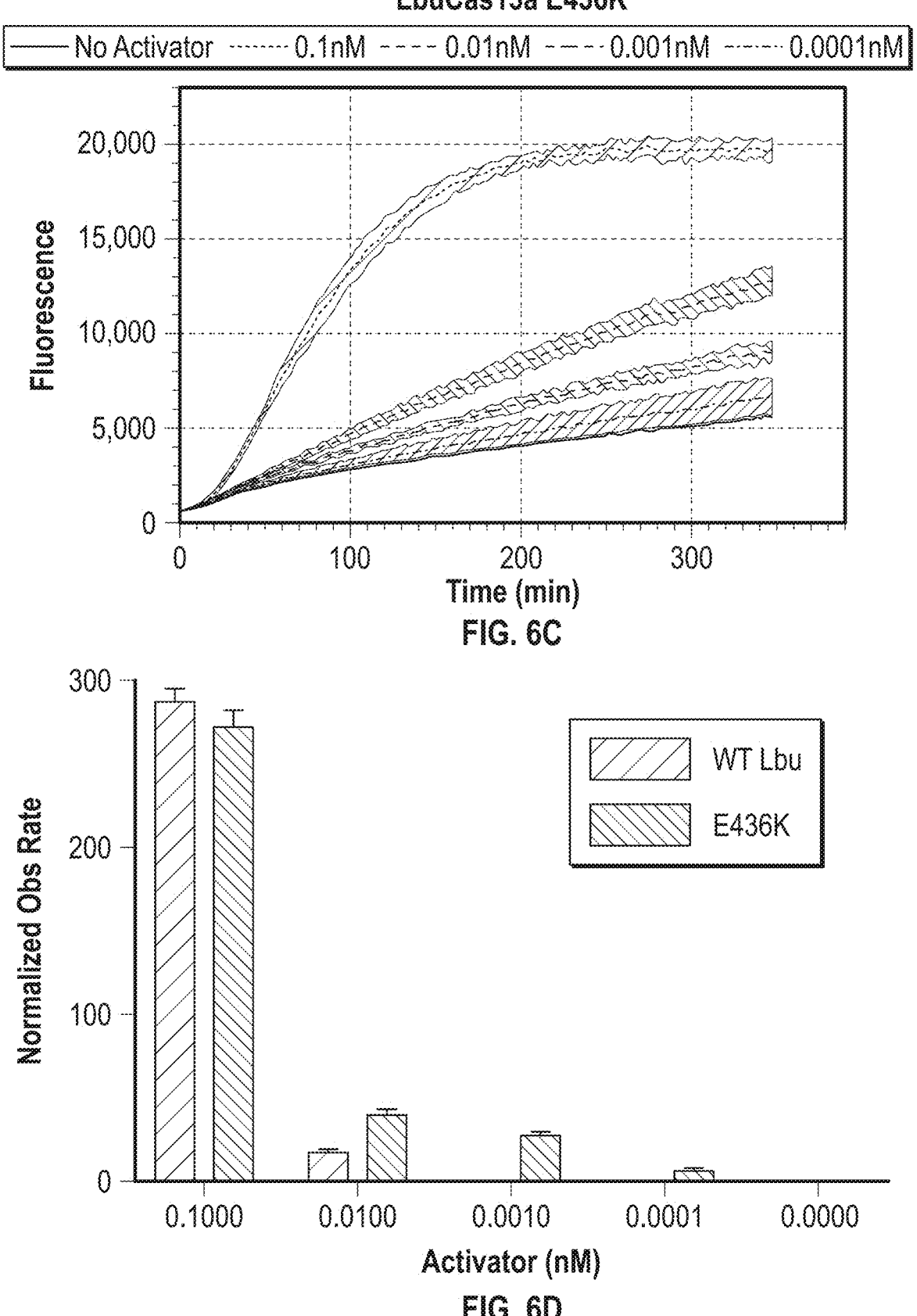

FIG. 6A illustrates that use of more than one crRNA can improve the sensitivity of the SARS-CoV-2 assay. As shown, about $7 \times 10^5$ copies SARS-CoV-2 can be readily detected but as few as $7 \times 10^2$ copies SARS-CoV-2 are also detectable.

For example, the Cas13 protein can have a sequence such as any of SEQ ID NOs:36-48.

An example of a *Leptotrichia buccalis* Cas13a endonuclease can have the following sequence (SEQ ID NO:38; NCBI accession no. WP_015770004.1).

```
  1 MKVTKVGGIS HKKYTSEGRL VKSESEENRT DERLSALLNM

41 RLDMYIKNPS STETKENQKR IGKLKKFFSN KMVYLKDNTL

81 SLKNGKKENI DREYSETDIL SSDVRDKKNF AVLKKIYLNE

121 NVNSEELEVF RNDIKKKLNK INSLKYSFEK NKANYQKINE

161 NNIEKVEGKS KRNIIYDYYR ESAKRDAYVS NVKEAFDKLY

201 KEEDIAKLVL EIENLTKLEK YKIREFYHEI IGRKNDKENF

241 AKIIYEEIQN VNNMKELIEK VPDMSELKKS QVFYKYYLDK

281 EELNDKNIKY AFCHFVEIEM SQLLKNYVYK RLSNISNDKI

321 KRIFEYQNLK KLIENKLLNK LDTYVRNCGK YNYYLQDGEI

361 ATSDFIARNR QNEAFLRNII GVSSVAYFSL RNILETENEN

401 DITGRMRGKT VKNKKGEEKY VSGEVDKIYN ENKKNEVKEN

441 LKMFYSYDFN MDNKNEIEDF FANIDEAISS IRHGIVHFNL

481 ELEGKDIFAF KNIAPSEISK KMFQNEINEK KLKLKIFRQL

521 NSANVFRYLE KYKILNYLKR TRFEFVNKNI PFVPSFTKLY

561 SRIDDLKNSL GIYWKTPKTN DDNKTKEIID AQIYLLKNIY

601 YGEFLNYFMS NNGNFFEISK EIIELNKNDK RNLKTGFYKL

641 QKFEDIQEKI PKEYLANIQS LYMINAGNQD EEEKDTYIDF

681 IQKIFLKGFM TYLANNGRLS LIYIGSDEET NTSLAEKKQE

721 FDKFLKKYEQ NNNIKIPYEI NEFLREIKLG NILKYTERLN

761 MFYLILKLLN HKELTNLKGS LEKYQSANKE EAFSDQLELI

801 NLLNLDNNRV TEDFELEADE IGKFLDFNGN KVKDNKELKK

841 FDTNKIYFDG ENIIKHRAFY NIKKYGMLNL LEKIADKAGY

881 KISIEELKKY SNKKNEIEKN HKMQEMLHRK YARPRKDEKF

921 TDEDYESYKQ AIENIEEYTH LKNKVEFNEL NLLQGLLLRI

961 LHRLVGYTSI WERDLRFRLK GEFPENQYIE EIFNFENKKN

1001 VKYKGGQIVE KYIKFYKELH QNDEVKINKY SSANIKVLKQ

1041 EKKDLYIRNY IAHFNYIPHA EISLLEVLEN LRKLLSYDRK

1081 LKNAVMKSVV DILKEYGFVA TFKIGADKKI GIQTLESEKI

1121 VHLKNLKKKK LMTDRNSEEL CKLVKIMFEY KMEEKKSEN
```

For example, a *Leptotrichia seeligeri* Cas13a endonuclease can have the following sequence (SEQ ID NO: 39, NCBI accession no. WP_012985477.1).

```
  1 MWISIKTLIH HLGVLFFCDY MYNRREKKII EVKTMRITKV

41 EVDRKKVLIS RDKNGGKLVY ENEMQDNTEQ IMHHKKSSFY

81 KSVVNKTICR PEQKQMKKLV HGLLQEMSQE KIKVSDVTKL
```

-continued

```
121 NISNFLNHRF KKSLYYFPEN SPDKSEEYRI EINLSQLLED

161 SLKKQQGTFI CWESFSKDME LYIMWAENYI SSKTKLIKKS

201 IRNNRIQSTE SRSGQLMDRY MKDILNKNKP FDIQSVSEKY

241 QLEKLTSALK ATFKEAKKND KEIMYKLKST LQNHERQIIE

281 ELKENSELNQ FNIEIRKHLE TYFPIKKTNR KVGDIRNLEI

321 GEIQKIVKHR LKNKIVQRIL QEGKLASYEI ESTVNSNSLQ

361 KIKIEEAFAL KFINACLFAS NNLRNMVYPV CKKDILMIGE

401 FKNSFKEIKH KKFIRQWSQF FSQEITVDDI ELASWGLRGA

441 IAPIRNEIIH LKKHSWKKFF NNPTFKVKKS KIINGKTKDV

481 TSEFLYKETL FKDYFYSELD SVPELIINKM ESSKILDYYS

521 SDQLNQVFTI PNFELSLLTS AVPFAPSFKR VYLKGFDYQN

561 QDEAQPDYNL KLNIYNEKAF NSEAFQAQYS LFKMVYYQVF

601 LPQFTTNNDL FKSSVDFILT LNKERKGYAK AFQDIRKMNK

641 DEKPSEYMSY IQSQLMLYQK KQEEKEKINH FEKFINQVFI

681 KGFNSFIEKN RLTYICHPTK NTVPENDNIE IPFHTDMDDS

721 NIAFWLMCKL LDAKQLSELR NEMIKFSCSL QSTEEISTFT

761 KAREVIGLAL LNGEKGCNDW KELFDDKEAW KKNMSLYVSE

801 ELLQSLPYTQ EDGQTPVINR SIDLVKKYGT ETILEKLFSS

841 SDDYKVSAKD IAKLHEYDVT EKIAQQESLH KQWIEKPGLA

881 RDSAWTKKYQ NVINDISNYQ WAKTKVELTQ VRHLHQLTID

921 LLSRLAGYMS IADRDFQFSS NYILERENSE YRVTSWILLS

961 ENKNKNKYND YELYNLKNAS IKVSSKNDPQ LKVDLKQLRL

1001 TLEYLELFDN RLKEKRNNIS HFNYLNGQLG NSILELFDDA

1041 RDVLSYDRKL KNAVSKSLKE ILSSHGMEVT FKPLYQTNHH

1081 LKIDKLQPKK IHHLGEKSTV SSNQVSNEYC QLVRTLLTMK
```

For example, a *Paludibacter propionicigenes* Cas13a endonuclease can have the following sequence (SEQ ID NO:48; NCBI accession no. WP_013443710.1).

```
  1 MRVSKVKVKD GGKDKMVLVH RKTTGAQLVY SGQPVSNETS

41 NILPEKKRQS FDLSTLNKTI IKFDTAKKQK LNVDQYKIVE

81 KIFKYPKQEL PKQIKAEEIL PFLNHKFQEP VKYWKNGKEE

121 SFNLTLLIVE AVQAQDKRKL QPYYDWKTWY IQTKSDLLKK

161 SIENNRIDLT ENLSKRKKAL LAWETEFTAS GSIDLTHYHK

201 VYMTDVLCKM LQDVKPLTDD KGKINTNAYH RGLKKALQNH

241 QPAIFGTREV PNEANRADNQ LSIYHLEVVK YLEHYFPIKT

281 SKRRNTADDI AHYLKAQTLK TTIEKQLVNA IRANIIQQGK

321 TNHHELKADT TSNDLIRIKT NEAFVLNLTG TCAFAANNIR

361 NMVDNEQTND ILGKGDFIKS LLKDNTNSQL YSFFFGEGLS

401 TNKAEKETQL WGIRGAVQQI RNNVNHYKKD ALKTVFNISN

441 FENPTITDPK QQTNYADTIY KARFINELEK IPEAFAQQLK

481 TGGAVSYYTI ENLKSLLTTF QFSLCRSTIP FAPGFKKVFN
```

-continued

```
 521 GGINYQNAKQ DESFYELMLE QYLRKENFAE ESYNARYFML

561 KLIYNNLFLP GFTTDRKAFA DSVGFVQMQN KKQAEKVNPR

601 KKEAYAFEAV RPMTAADSIA DYMAYVQSEL MQEQNKKEEK

641 VAEETRINFE KFVLQVFIKG FDSFLRAKEF DFVQMPQPQL

681 TATASNQQKA DKLNQLEASI TADCKLTPQY AKADDATHIA

721 FYVFCKLLDA AHLSNLRNEL IKFRESVNEF KFHHLLEIIE

761 ICLLSADVVP TDYRDLYSSE ADCLARLRPF IEQGADITNW

801 SDLFVQSDKH SPVIHANIEL SVKYGTTKLL EQIINKDTQF

841 KTTEANFTAW NTAQKSIEQL IKQREDHHEQ WVKAKNADDK

881 EKQERKREKS NFAQKFIEKH GDDYLDICDY INTYNWLDNK

921 MHFVHLNRLH GLTIELLGRM AGFVALFDRD FQFFDEQQIA

961 DEFKLHGFVN LHSIDKKLNE VPTKKIKEIY DIRNKIIQIN

1001 GNKINESVRA NLIQFISSKR NYYNNAFLHV SNDEIKEKQM

1041 YDIRNHIAHF NYLTKDAADF SLIDLINELR ELLHYDRKLK

1081 NAVSKAFIDL FDKHGMILKL KLNADHKLKV ESLEPKKIYH

1121 LGSSAKDKPE YQYCTNQVMM AYCNMCRSLL EMKK
```

For example, a *Lachnospiracae bacterium* Cas13a endonuclease can have the following sequence (SEQ ID NO:40; NCBI accession no. WP_022785443.1).

```
  1 MKISKVREEN RGAKLTVNAK TAVVSENRSQ EGILYNDPSR

41 YGKSRKNDED RDRYIESRLK SSGKLYRIFN EDKNKRETDE

81 LQWFLSEIVK KINRRNGLVL SDMLSVDDRA FEKAFEKYAE

121 LSYTNRRNKV SGSPAFETCG VDAATAERLK GIISETNFIN

161 RIKNNIDNKV SEDIIDRIIA KYLKKSLCRE RVKRGLKKLL

201 MNAFDLPYSD PDIDVQRDFI DYVLEDFYHV RAKSQVSRSI

241 KNMNMPVQPE GDGKFAITVS KGGTESGNKR SAEKEAFKKF

281 LSDYASLDER VRDDMLRRMR RLVVLYFYGS DDSKLSDVNE

321 KFDVWEDHAA RRVDNREFIK LPLENKLANG KTDKDAERIR

361 KNTVKELYRN QNIGCYRQAV KAVEEDNNGR YFDDKMLNMF

401 FIHRIEYGVE KIYANLKQVT EFKARTGYLS EKIWKDLINY

441 ISIKYIAMGK AVYNYAMDEL NASDKKEIEL GKISEEYLSG

481 ISSFDYELIK AEEMLQRETA VYVAFAARHL SSQTVELDSE

521 NSDFLLLKPK GTMDKNDKNK LASNNILNFL KDKETLRDTI

561 LQYFGGHSLW TDFPFDKYLA GGKDDVDFLT DLKDVIYSMR

601 NDSFHYATEN HMNGKWNKEL ISAMFEHETE RMTVVMKDKF

641 YSNNLPMFYK NDDLKKLLID LYKDNVERAS QVPSFNKVFV

681 RKNFPALVRD KDNLGIELDL KADADKGENE LKFYNALYYM

721 FKEIYYNAFL NDKNVRERFI TKATKVADNY DRNKERNLKD

761 RIKSAGSDEK KKLREQLQNY IAENDFGQRI KNIVQVNPDY

801 TLAQICQLIM TEYNQQNNGC MQKKSAARKD INKDSYQHYK
```

```
-continued
 841 MLLLVNLRKA FLEFIKENYA FVLKPYKHDL CDKADFVPDF

881 AKYVKPYAGL ISRVAGSSEL QKWYIVSRFL SPAQANHMLG

921 FLHSYKQYVW DIYRRASETG TEINHSIAED KIAGVDITDV

961 DAVIDLSVKL CGTISSEISD YFKDDEVYAE YISSYLDFEY

1001 DGGNYKDSLN RFCNSDAVND QKVALYYDGE HPKLNRNIIL

1041 SKLYGERRFL EKITDRVSRS DIVEYYKLKK ETSQYQTKGI

1081 FDSEDEQKNI KKFQEMKNIV EFRDLMDYSE IADELQGQLI

1121 NWIYLRERDL MNFQLGYHYA CLNNDSNKQA TYVTLDYQGK

1161 KNRKINGAIL YQICAMYING LPLYYVDKDS SEWTVSDGKE

1201 STGAKIGEFY RYAKSFENTS DCYASGLEIF ENISEHDNIT

1241 ELRNYIEHFR YYSSFDRSFL GIYSEVFDRF FTYDLKYRKN

1281 VPTILYNILL QHFVNVRFEF VSGKKMIGID KKDRKIAKEK

1321 ECARITIREK NGVYSEQFTY KLKNGTVYVD ARDKRYLQSI

1361 IRLLFYPEKV NMDEMIEVKE KKKPSDNNTG KGYSKRDRQQ

1401 DRKEYDKYKE KKKKEGNFLS GMGGNINWDE INAQLKN
```

For example, a *Leptotrichia shahii* Cas13a endonuclease can have the following sequence (SEQ ID NO:41; NCBI accession no. BBM39911.1).

```
   1 MGNLFGHKRW YEVRDKKDFK IKRKVKVKRN YDGNKYILNI

41 NENNNKEKID NNKFIRKYIN YKKNDNILKE FTRKFHAGNI

81 LFKLKGKEGI IRIENNDDFL ETEEVVLYIE AYGKSEKLKA

121 LGITKKKIID EAIRQGITKD DKKIEIKRQE NEEEIEIDIR

161 DEYTNKTLND CSIILRIIEN DELETKKSIY EIFKNINMSL

201 YKIIEKIIEN ETEKVFENRY YEEHLREKLL KDDKIDVILT

241 NFMEIREKIK SNLEILGFVK FYLNVGGDKK KSKNKKMLVE

281 KILNINVDLT VEDIADFVIK ELEFWNITKR IEKVKKVNNE

321 FLEKRRNRTY IKSYVLLDKH EKFKIERENK KDKIVKFFVE

361 NIKNNSIKEK IEKILAEFKI DELIKKLEKE LKKGNCDTEI

401 FGIFPKKHYKV NFDSKKFSKK SDEEKELYKI IYRYLKGRIE

441 KILVNEQKVR LKKMEKIEIE KILNESILSE KILKRVKQYT

481 LEHIMYLGKL RHNDIDMTTV NTDDFSRLHA KEELDLELIT

521 FFASTNMELN KIFSRENINN DENIDFFGGD REKNYVLDKK

561 ILNSKIKIIR DLDFIDNKNN ITNNFIRKFT KIGTNERNRI

601 LHAISKERDL QGTQDDYNKV INIIQNLKIS DEEVSKALNL

641 DVVFKDKKNI ITKINDIKIS EENNNDIKYL PSFSKVLPEI

681 LNLYRNNPKN EPFDTIETEK IVLNALIYVN KELYKKLILE

721 DDLEENESKN IFLQELKKTL GNIDEIDENI IENYYKNAQI

761 SASKGNNKAI KKYQKKVIEC YIGYLRKNYE ELFDFSDFKM

801 NIQEIKKQIK DINDNKTYER ITVKTSDKTI VINDDFEYII

841 SIFALLNSNA VINKIRNRFF ATSVWLNTSE YQNIIDILDE

881 IMQLNTLRNE CITENWNLNL EEFIQKMKEI EKDFDDFKIQ
```

```
-continued
 921 TKKEIFNNYY EDIKNNILTE FKDDINGCDV LEKKLEKIVI

961 FDDETKFEID KKSNILQDEQ RKLSNINKKD LKKKVDQYIK

1001 DKDQEIKSKI LCRIIFNSDF LKKYKKEIDN LIEDMESENE

1041 NKFQEIYYPK ERKNELYIYK KNLFLNIGNP NFDKIYGLIS

1081 NDIKMADAKF LFNIDGKNIR KNKISEIDAI LKNLNDKLNG

1121 YSKEYKEKYI KKLKENDDFF AKNIQNKNYK SFEKDYNRVS

1161 EYKKIRDLVE FNYLNKIESY LIDINWKLAI QMARFERDMH

1201 YIVNGLRELG IIKLSGYNTG ISRAYPKRNG SDGFYTTTAY

1241 YKFFDEESYK KFEKICYGFG IDLSENSEIN KPENESIRNY

1281 ISHFYIVRNP FADYSIAEQI DRVSNLLSYS TRYNNSTYAS

1321 VFEVFKKDVN LDYDELKKKF KLIGNNDILE RLMKPKKVSV

1361 LELESYNSDY IKNLIIELLT KIENTNDTL
```

To increase Cas13a in vivo activity, a random mutagenesis library for *Leptotrichia buccalis* (Lbu) Cas13a was generated and this library was screened for translational repression in *E. coli*. Top variants capable of increased repression contained sets of mutations that were localized in regions that undergo large conformational changes upon ternary complex formation. Analysis of single-point mutations led to identification of E436K (e.g., with SEQ ID NO:43), which dramatically lowers the non-activator-dependent HEPN activation of LbuCas13a, and consequently increases sensitivity above background by ~10-100 fold (FIG. 6B-6D)). The modified *Leptotrichia buccalis* Cas13a endonuclease with the E436K mutation has the following sequence (SEQ ID NO:43).

```
   1 MKVTKVGGIS HKKYTSEGRL VKSESEENRT DERLSALLNM

41 RLDMYIKNPS STETKENQKR IGKLKKFFSN KMVYLKDNTL

81 SLKNGKKENI DREYSETDIL ESDVRDKKNF AVLKKIYLNE

121 NVNSEELEVF RNDIKKKLNK INSLKYSFEK NKANYQKINE

161 NNIEKVEGKS KRNIIYDYYR SSAKRDAYVS NVKEAFDKLY

201 KEEDIAKLVL EIENLTKLEK YKIREFYHEI IGRKNDKENF

241 AKIIYEEIQN VNNMKELIEK VPDMSELKKS QVFYKYYLDK

281 EELNDKNIKY AFCHFVEIEM SQLLKNYVYK RLSNISNDKI

321 KRIFEYQNLK KLIENKLLNK LDTYVRNCGK YNYYLQDGEI

361 ATSDFIARNR QNEAFLRNII GVSSVAYFSL RNILETENEN

401 DITGRMRGKT VKNNKGEEKY VSGEVDKIYN ENKKNKVKEN

441 LKMFYSYDFN MDNKNEIEDF FANIDEAISS IRHGIVHFNL

481 ELEGKDIFAF KNIAPSEISK KMFQNEINEK KLKLKIFRQL

521 NSANVFRYLE KYKILNYLKR TRFEFVNKNI PFVPSFTKLY

561 SRIDDLKNSL GIYWKTPKTN DDNKTKEIID AQIYLLKNIY

601 YGEFLNYFMS NNGMFFEISK EIIELNKNDK RKLKTGFYKL

641 QKFEDIQEKI PKEYLANIQS LYMINAGNQD EEEKDTYIDF

681 IQKIFLKGFM TYLANNGRLS LIYIGSDEET NTSLAEKKQE
```

```
                        -continued
  721 FDKFLKKYEQ NNNIKIPYEI NEFLREIKLG NILKYTERLN

761 MFYLILKLLN HKELTNLKGS LEKYQSANKE EAFSDQLELI

801 NLLNLDNNRV TEDFELEADE IGKFLDFNGN KVKDNKELKK

841 FDTNKIYFDG ENIIKHRAFY NIKKYGMLNL LEKIADKAGY

881 KISIEELKKY SNKKNEIEKN HKMQENLHRK YARPRKDEKF

921 TDEDYESYKQ AIENIEEYTH LKNKVEFNEL NLLQGLLLRI

961 LHRLVGYTSI WERDLRFRLK GEFPENQYIE EIFNFENKKN

1001 VKYKGGQIVE KYIKFYKELH QNDEVKINKY SSANIKVLKQ

1041 EKKDLYIRNY IAHFNYIPHA EISLLEVLEN LRKLLSYDRK

1081 LKNAVMKSVV DILKEYGFVA TFKIGADKKI GIQTLESEKI

1121 VHLKNLKKKK LMTDRNSEEL CKLVKIMFEY KMEEKKSEN
```

The E436 residue is localized in a hinge region of the helix that hydrogen bonds with the catalytic residues in a binary conformation, potentially locking them in an inactive state. The E436K mutation is thought to restrict the movements of the helix in the absence of an activator, therefore lowering the background signal. This enables detection of lower concentrations of activator above background.

Other modified Cas protein can be generated and evaluated in the methods described herein. For example, purified proteins will first be assayed for trans-ssRNA cleavage rates with SARS-CoV-2-specific crRNAs using a reporter RNA. Such a reporter RNA can be a fluorophore quencher-labeled ssRNA. Cleavage of the reporter RNA serves as an outread for complex activation and as a surrogate for the presence of SARS-CoV-2 RNA. Notably, the rate at which trans cleavage reaches saturation varies greatly among Cas13 homologs. If the trans rate is too low, fluorescence outread will be undetectable, especially in the context of an excess of unlabeled human RNA. To systematically study the rate of trans cleavage in this context, the ability of a preassembled ternary complex comprising the Cas13:crRNA ribonucleoprotein (RNP) complex plus a bound synthetic ssRNA activator is tested by observing in trans degradation of the fluorophore quencher-labeled RNaseAlert substrate with and without increasing amounts of tRNAs or purified human non-targeting RNAs. How the rate of trans cleavage reaches saturation over time will be monitored to identify ideal homologs with the fastest rate. Variables tested in this assay include concentrations of the Cas13:crRNA RNP and concentrations of the reporter RNA to achieve optimized rates.

Next, the sensitivity of the homologs for cis cleavage of activating SARS-CoV-2 ssRNA in the context of competitor RNA will be analyzed. A broad range of sensitivities ($\sim 10^7$ fold) exist for these homologs in the context of just isolated activator RNA, but the influence of additional non-targeting RNAs on the cis cleavage rate is unknown. Background RNA, especially at high concentrations, can inhibit access to SARS-CoV-2 RNA, precluding activation of the Cas13:crRNA complex and downstream trans-cleavage. To test the influence of background RNA on cis-cleavage, a high-throughput screen will be used. For each Cas13 homolog, dilutions of the complementary fluorescent ssRNA activator will be systematically added with and without increasing amounts of tRNAs or purified human mRNAs and analyze cis cleavage rates of the reporter over time. Each resulting time course will allow the apparent rate of complementary target sensitivity to be calculated in the context of the defined competitor RNA background.

The specificity of the homologs will also be tested in the context of background competitor RNA to ensure that related RNA sequences cannot aberrantly or non-specifically activate the Cas13:crRNA complex.

Different Cas13 homologs tolerate different numbers of mismatches in the crRNA-target duplex. For example, Cas13a from *Leptotrichia shahii* (LshCas13a) is sensitive to double, but not single, mismatches in the crRNA-target duplex. Moreover, the location of these mismatches within the spacer sequence is important. For example, LshCas13a is sensitive to double mismatches in the center, or in the "seed region," of the crRNA-target duplex, but not at the 5' or 3'ends. It was recently discovered that LbuCas13a has a mismatch sensitive seed region that correlates well with observations for LshCas13a and the structure of LbuCas13a and that LbuCas13a has a mismatch sensitive switch region that effectively communicates activator RNA binding to the Higher Eukaryotes and Prokaryotes Nucleotide-binding (HEPN) nuclease for activation. The inventors have generated a comprehensive mismatch sensitivity profile for LbuCas13a.

Data suggests that the mismatch sensitivity profile of homologs is quite variable. To test this comprehensively across all homologs, each homolog will be tested with crRNAs carrying systematic variations of mismatches against a known complimentary SARS-CoV-2-derived target sequence. Here, positions in the center of the spacer (positions 6 to 16) will be focused on. Double, triple, and quadruple consecutive and non-consecutive mismatches in this region of the crRNA will be generated by mutating the bases to the respective complementary base (e.g., A to U). A 50-nucleotide complimentary target RNAs will also be synthesized based on the no-mismatch crRNA sequence. A high-throughput screen will be used, and the screen mixtures will be fluorescence monitored to determine permissiveness to mismatches. Once the levels of permissiveness for each homolog with complimentary target RNA alone have been determined, the assay will be repeated in the presence of dilutions of tRNAs or human cellular RNAs to test for nonspecific activation of the complex by other RNA sequences. Homologs with some flexibility in low-number base-pair mismatches towards the target RNA will be accepted to allow for sequence variation in the SARS-CoV-2 RNA sequence, but we aim to identify crRNA sequences and Cas13 homologs that together show the lowest aberrant activation by competitor RNAs.

Example 3: Optimized Cas13a or Cas13b Assay for Point-of-Care Testing

Currently testing for SARS-CoV-2 has several limitations: 1) lengthy times for obtaining results: 2) use of RNA amplification, which increases complexity of the test and the time required to obtain results; and 3) need for complicated laboratory equipment. A remaining concern is that RNases present in bodily fluids will non-specifically activate the read-out technology.

Here, a sensitive and single-step test for SARS-CoV-2 RNA detection method is described that can be adapted use in remote locations away from hospitals, laboratories, and clinics.

Cas13 and crRNA samples can be lyophilized to allow electricity independence of the assay.

Briefly, one or more RNase reporter oligonucleotides with fluorescent dyes will be added directly to samples with and without dilutions of SARS-CoV-2-specific Cas13:crRNA RNPs. In some cases, dilutions of purified SARS-CoV-2 of known concentrations can be tested in the same assay methods as controls to facilitate quantification of the SARS-CoV-2 in samples. Additional controls can use include uninfected samples (e.g., uninfected saliva, sputum, mucus, or nasopharyngeal samples).

It is contemplated that some RNase A inhibitors will inhibit RNase A, but not Cas13a or Cas13b. As RNase A is not a HEPN-nuclease, its specific inhibitors are unlikely to inhibit the HEPN-nuclease of Cas13a or Cas13b. Alternatively, samples will be heated to remove RNAse activity.

Previous studies have shown that virions from other RNA viruses (Zika and Dengue) can be spiked into human serum and heated to 95° C. for 1-2 minutes to increase release of viral RNA for detection. It can be determined whether a heating step facilitates detection of SARS-CoV-2 RNA and if it reduces background RNase, but not specific Cas13a or Cas13b activity. Additional testing of other methods (e.g., mechanical or chemical lysis) may also be performed. Read-out fluorescence can be monitored using CellScope (see U.S. Pat. Nos. 10,578,852 and 10,542,885, which are specifically incorporated herein in their entireties), a plate reader, sample chamber reader, or chip reader, or a combination thereof.

Figure 12:
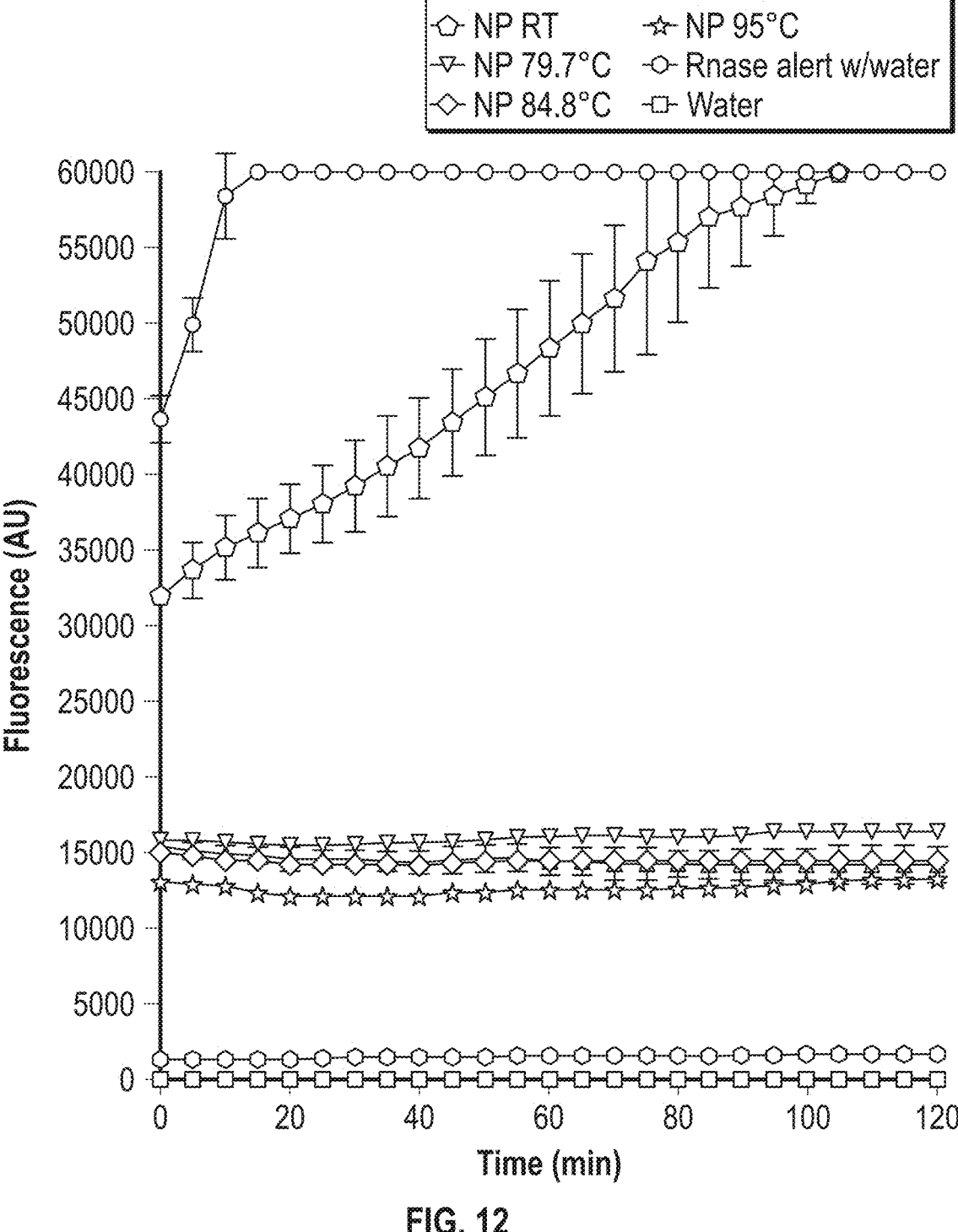
FIG. 12 graphically illustrates that heating of nasopharyngeal (NP) swabs (with RNase Inhibitor) can significantly reduce endogenous RNases. The endogenous RNase activities were detected by mixing nasopharyngeal (NP) swab samples with the reporter RNA. The plot at the top shows the signal that is observed when RNases (e.g., RNase A) are added to the nasopharyngeal (NP) swab sample and the reporter RNA. The plot just below the top plot shows results when nasopharyngeal (NP) swabs are not heated (kept at room temperature) when mixed with the reporter RNA. The bottom graphs show the signals from nasopharyngeal (NP) swabs that were heated (at 79° C. or 84° C.) and then mixed with the reporter RNA. As shown, heating swab samples reduces background signal from endogenous RNases.

FIG. 12 provides a graph depicting the signal from assays after heating of nasopharyngeal swabs (with RNase Inhibitor) to significantly reduce endogenous RNases. The plot at the top of the FIG. 12 graph shows the signal that is observed when RNases (e.g., RNase A) are present. But when RNase activities are inhibited (e.g., by heat at 79° C. or 84° C.), background signals in the assay mixture due to RNases in the sample are substantially reduced or eliminated.

Figure 13:
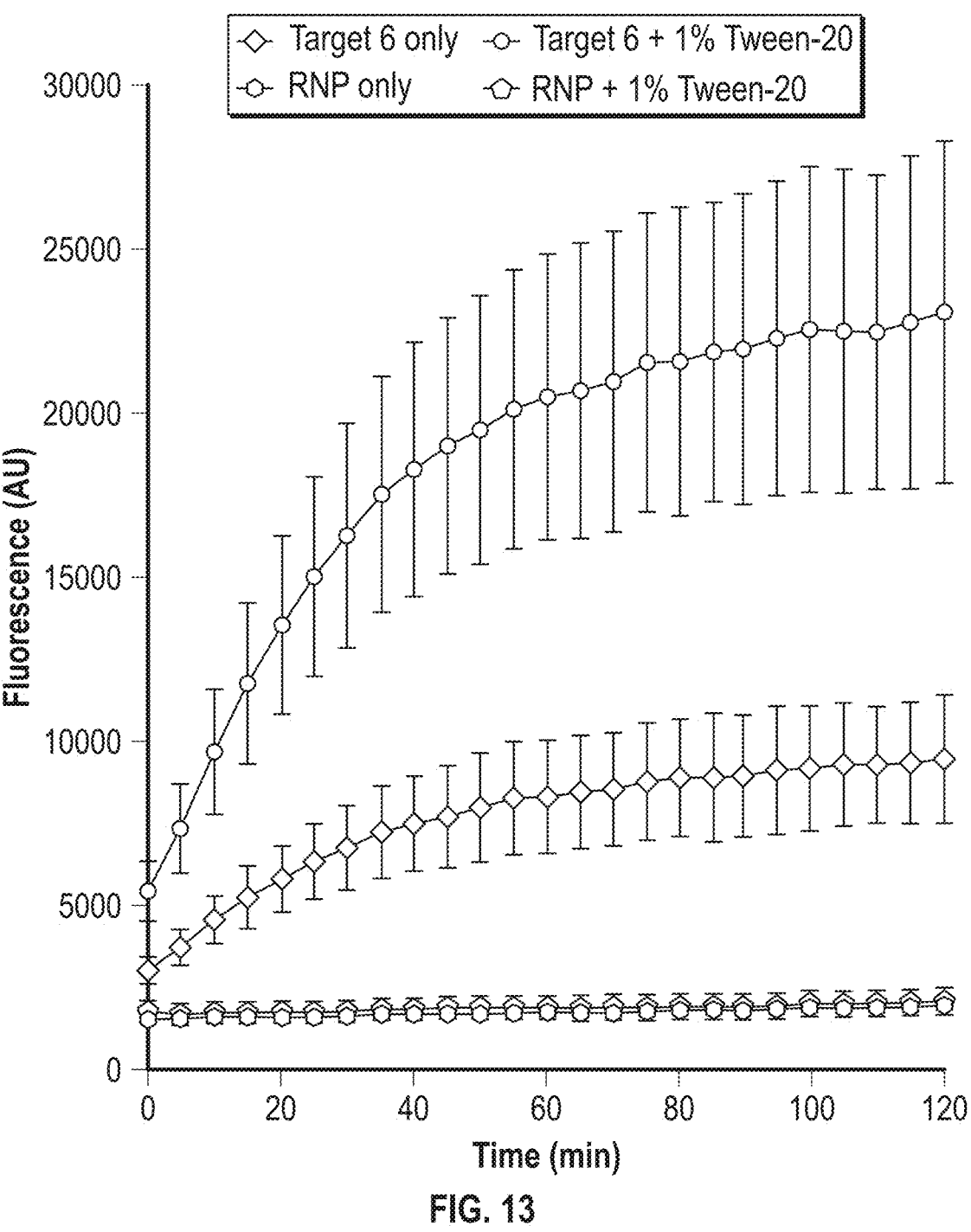
FIG. 13 graphically illustrates that the addition of Tween-20 improves detection, is compatible with Cas13a protein, and does not increase background fluorescence.

FIG. 13 graphically illustrates that the addition of Tween-20 improves detection and is compatible with the Cas13a assay without increasing background fluorescence. The plot at the top of FIG. 13 shows signals from an assay mixture that includes the target 6 RNA, crRNA-Cas13a RNP, and 1% Tween-20. The plot just below the top plot in FIG. 13 shows signals from an assay mixture that includes the target 6 RNA and the crRNA-Cas13a RNP, without Tween-20. Two plots are show at the bottom of FIG. 13 showing signals from RNP alone (no target RNA) with and without the Tween-20.

Figure 14:
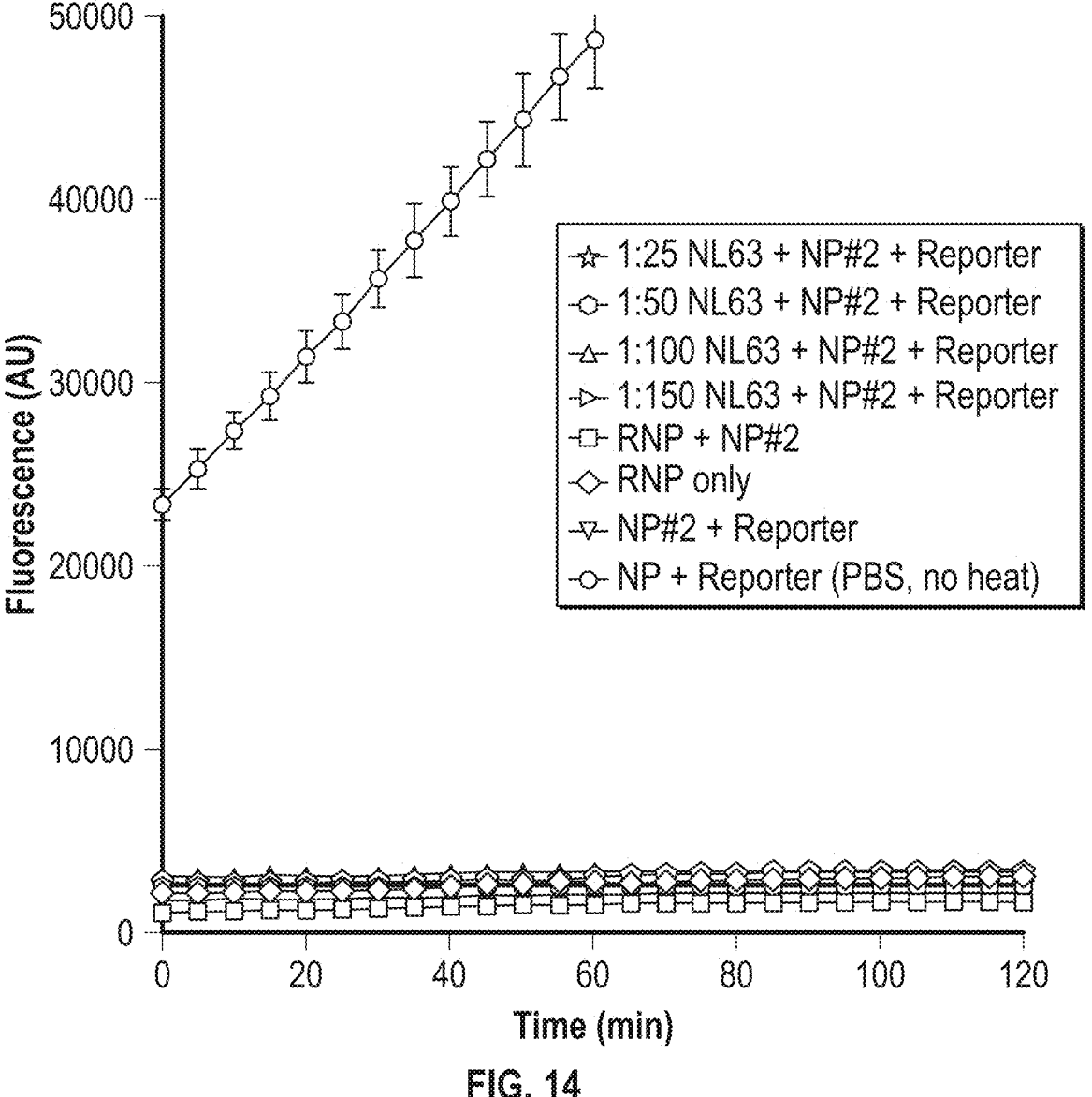
FIG. 14 graphically illustrates that addition of heat (85° C., 5 mins) and 1% Tween-20 minimizes RNase contamination. The top plot shows the signal from a nasopharyngeal (NP) swab that was not heated before incubation with the reporter RNA, showing that the nasopharyngeal (NP) swab sample has RNase enzymes. The other plots (at the bottom of the graph shows the signals from nasopharyngeal (NP) swab samples that were heated before incubation with the reporter RNA, showing that the RNases in the samples were inactivated by heat.

FIG. 14 graphically illustrates that addition of heat (85° C., 5 mins) and 1% Tween-20 minimizes RNase contamination. FIG. 17 graphically illustrates that Cas13a can detect NL63 viral RNA with the background of an NP swab using only 1% Tween-20 and heat for lysis.

Example 4: Readout Quenched-Fluorescent RNA Markers/Reporters

To adapt optimize fluorescence detection, new reporter RNAs can be used that include a ribooligonucleotide with both a fluorophore and a quencher. The sequence of the reporter RNA is optimized for Cas13 cleavage. Cas13 preferentially exerts RNase cleavage activity at exposed uridine or adenosine sites, depending on the Cas13a or Cas13b homolog. There are also secondary preferences for highly active homologs. The inventors have tested 5-mer homopolymers for all ribonucleotides. Based on these preferences, ten candidate RNA oligonucleotides, labeled at the 5' and 3' ends of the oligonucleotides using an Iowa Black Quencher (IDT) and FAM fluorophore, and systematically test these RNA oligonucleotide sequences in ssRNA cleavage assays as illustrated for FIGS. 4-6.

The best RNA oligonucleotide with associated fluorophore and quencher can be used with mobile devices for SARS-CoV-2 RNA detection.

In general, any fluorophore that emits in the red-green-blue (RGB) spectral window of a phone can be detected, which includes most fluorophores (except for those emitting in the far red). Due to the non-telecentric nature and high numerical aperture of the reversed lens module utilized in the CellScope device, fluorophores with long Stokes shifts are preferred to account for bandpass shifts at high angles in the interference filter used for fluorescence collection.

Figures 7A, 7B:
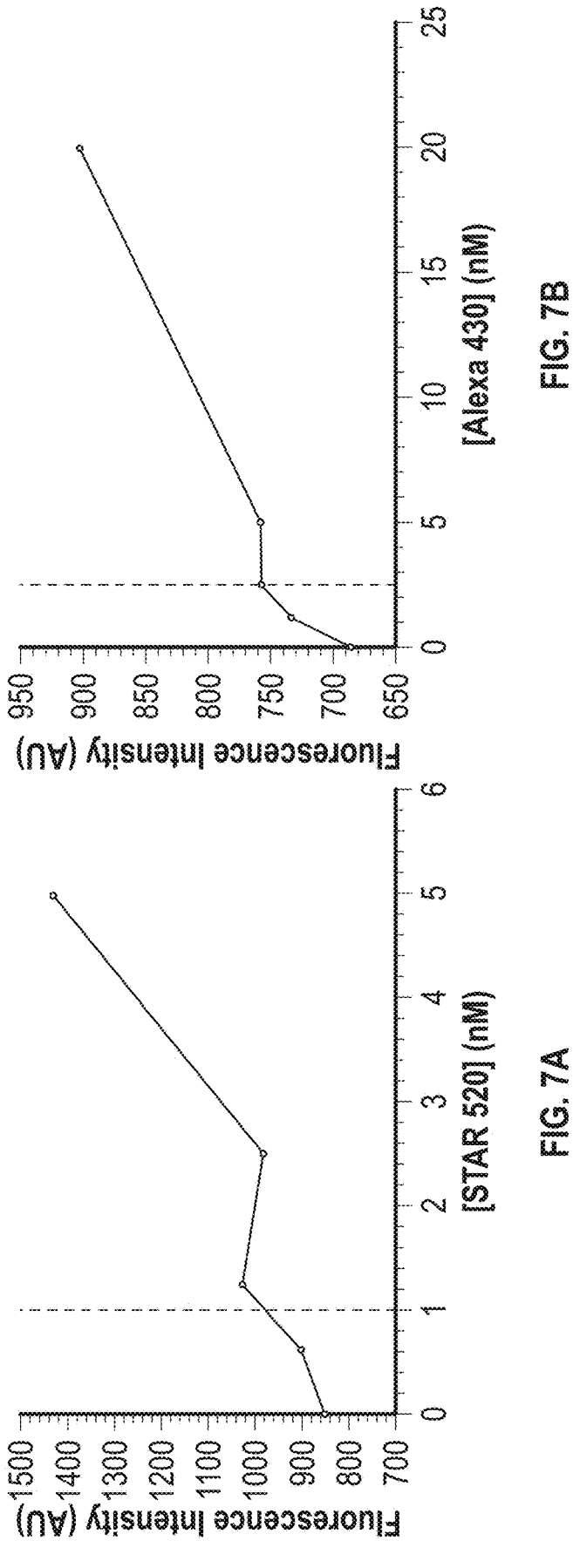
FIG. 7A-7B illustrate the limit of detection of various fluorophores.

Several fluorophores with long Stokes shifts were identified that can be combined with commercially available quenchers. Different concentrations of Alexa430 (Thermofisher) and STAR 520 (Abberior) were tested in 20-μL sample volumes loaded in capillaries using CellScope. A preliminary lower limit of detection was determined to be about 2.5 nM for Alexa430 and about 1 nM for STAR-20 (FIG. 7). Other potential fluorophores with long Stokes shifts are the Brilliant Violet Family series (BioLegend).

In some cases, Brilliant Violet™510, Brilliant Violet™605, and/or Brilliant Violet™610 can be used. Their quantum yield was higher than others in the series. Overall, five possible fluorophores and two possible quenchers were identified that can be used in RNA oligonucleotide-based reporters.

FIG. 19 shows that adjusting pH towards FAM-fluorophore pH preferences improves detection.

Example 5: Amplification of RNA Before Testing

The Example describes amplification of SARS-CoV-2 RNA before testing, for example, using the bacteriophage-derived RNA-dependent RNA polymerase, Qβ replicase (see for example Shah et al (1994) *J Clin Microbiol* 32(11): 2718) or the SARS-CoV2 RNA-dependent RNA polymerase.

The inventors are isolating the minimal SARS-CoV-2 RNA polymerase complex (Nsp12, Nsp7 and Nsp8) from prokaryotic and eukaryotic cells. This minimal SARS-CoV-2 RNA polymerase complex can amplify the viral RNA and enhance sensitivity for an ultra-sensitive Cas13a assay. Hence, such a minimal SARS-CoV-2 RNA polymerase complex can be included in the methods, compositions and devices described herein.

SARS-CoV-2 RNA can be amplified within samples by incubation with nucleotides (NTPs) and with or without Qβ replicase or a SARS-CoV2 polymerase in reaction buffer (100 mM HEPES-NaOH, pH 7.5; 10 mM MgCl$_2$, and 1 mM EDTA). Amplified RNA can be purified using phenol and can then be added to the SARS-CoV-Cas13 assay. In some instances, specified as "no cleanup," the amplified mixture can be directly added to the SARS-CoV-Cas13 assay. No clean-up of the amplified product may be needed before measuring the concentration of SARS-CoV-RNA in the SARS-CoV-2-Cas13 assay.

In some cases, amplified SARS-CoV-2 RNA can provide improved sensitivity in the SARS-CoV-Cas13 assay.

Example 6: Sample RNA Extraction

To facilitate use of the assay, minimal steps between swab collection and entry into swab material can be employed. A system where swabs are directly inserted into chamber one of a two chamber system can be used.

Chamber one can contain a buffer that would facilitate lysis of the viral particles and release of genomic material.

Options for the lysis buffer include, but are not limited to PBS, commercial lysis buffers such as Qiagen RLT+buffer or Quick Extract, DNA/RNA Shield, and various concentrations of detergents such as Triton X-100, Tween 20, NP-40, or Oleth-8.

Following agitation and subsequent removal of the swab, the chamber may be briefly (5 mins) heated (55° C. or 95° C.) to further facilitate lysis. Then, the division between the two chambers would be broken or removed, and the nasal extract buffer would be allowed to flow into and reconstitute the second chamber, which would contain the lyophilized reagents for the Cas13 assay (Cas13 RNPs and reporter molecules).

Figures 15A, 15B:
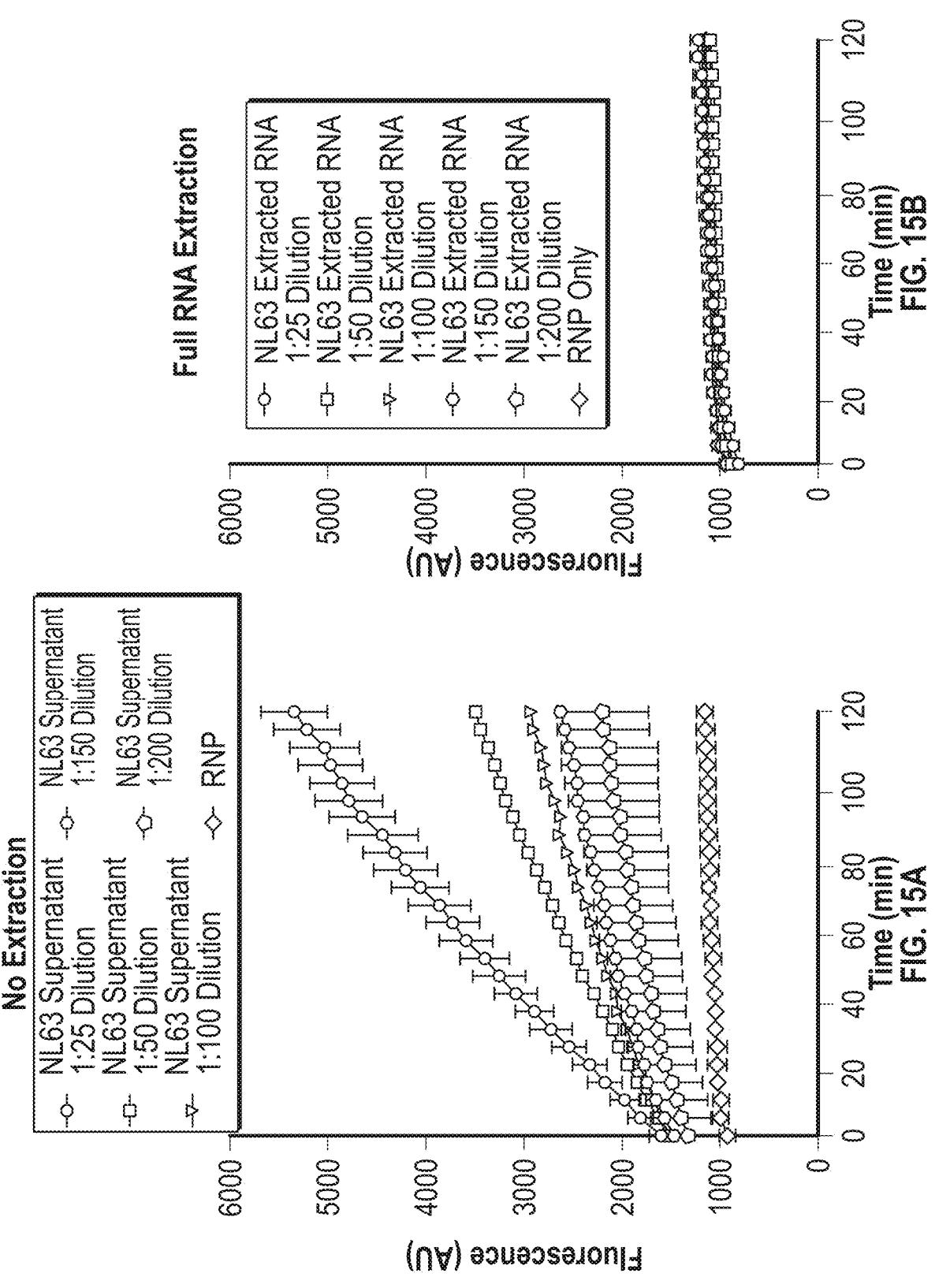
FIG. 15A-15B show that low levels of alphacoronavirus HCoV-NL63 RNA are efficiently detected in assays even when a single-step lysis procedure is used.
Figures 16A, 16B:
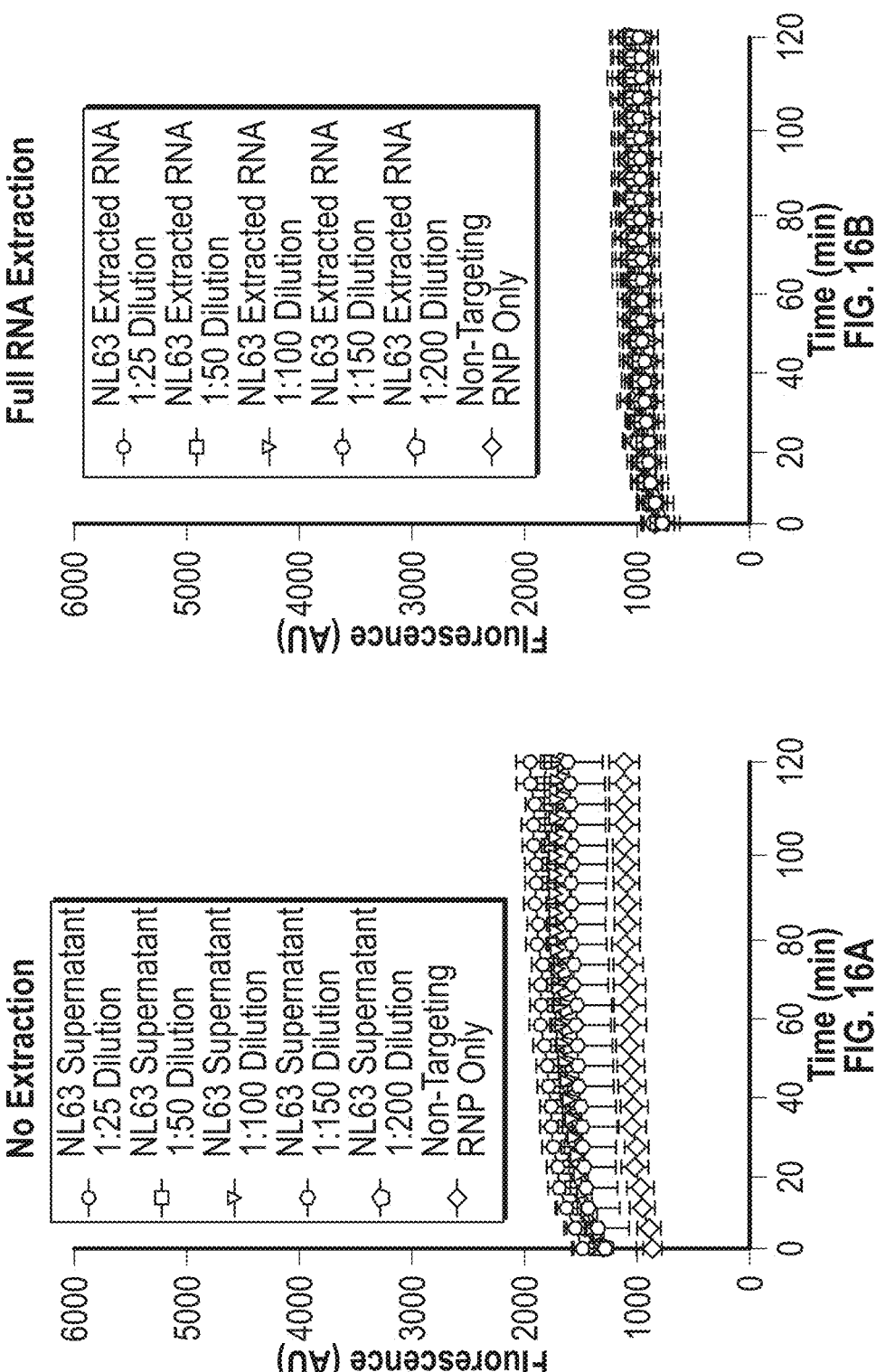
FIG. 16A-16B graphically illustrate signals from reaction mixtures containing HCoV-NL63 RNA samples with and without RNA extraction, and a crRNA guide that does not target or bind to the HCoV-NL63 RNA.

FIG. 15 shows that low levels of NL63 RNA are efficiently detected in the single-step lysis when compared to traditional RNA extraction and FIG. 18 graphically illustrates that SARS-CoV-2 RNA are efficiently detected in the single-step lysis when compared to traditional RNA extraction.

Example 7: Different crRNAs Exhibit Better Sensitivity for SARS-CoV-2

This example illustrates that some crRNAs for detecting SARS-CoV-2 RNA provide better signals than other crRNAs.

Assay mixtures containing the Cas13a protein and crRNAs 1-9, 13, 14, and 15. A549 RNA, containing SARS-CoV-2 RNA, and RNase Alert was added. The reaction mixture was incubated for 120 minutes and the fluorescence was monitored overtime. The reaction was largely complete for most crRNAs within 30-45 minutes.

Figure 8:
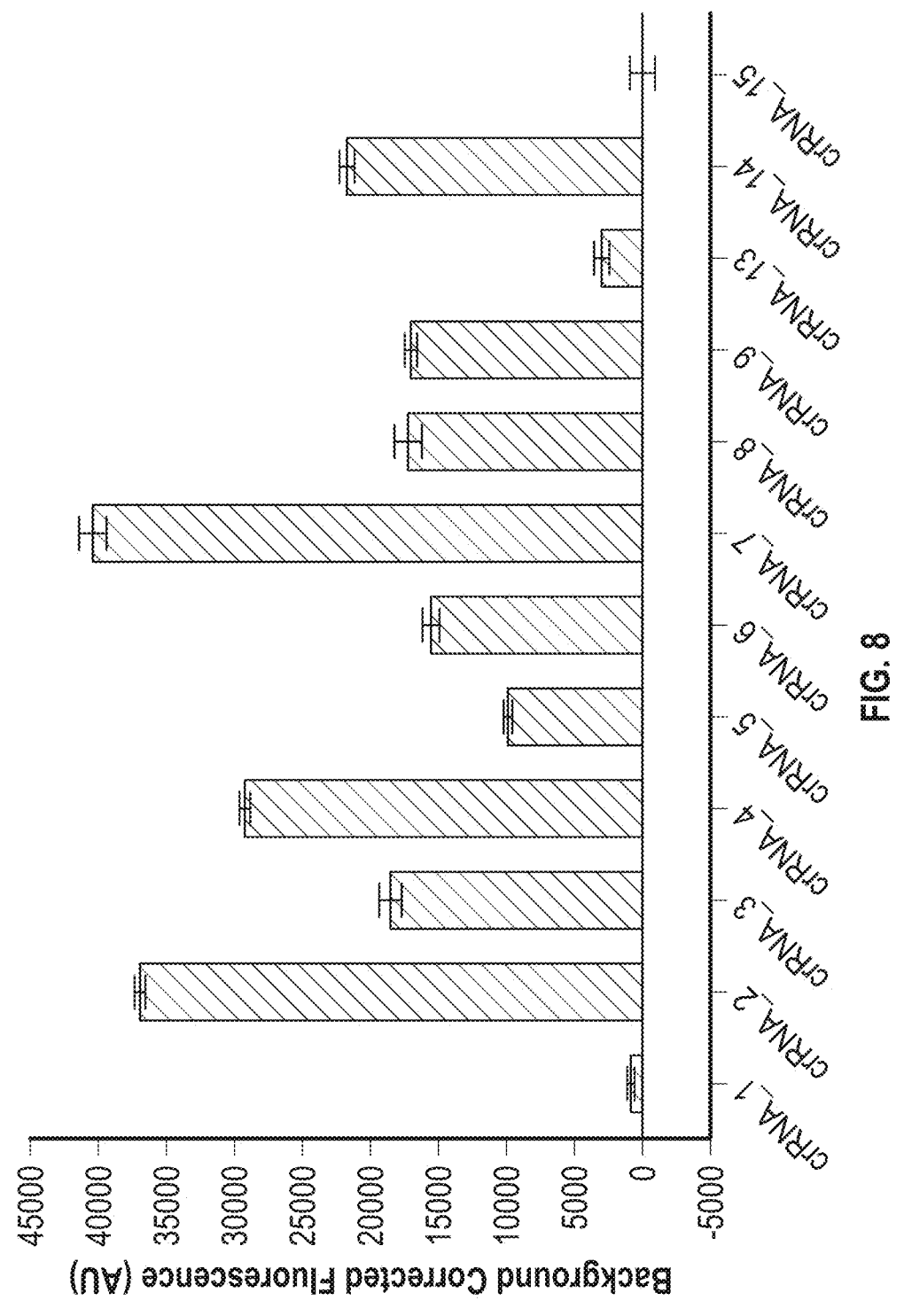
FIG. 8 illustrates the background corrected fluorescence for assay mixtures having different crRNAs and target SARS-CoV-2 RNA. As shown crRNAs 2, 3, 4, 7, 8, 9, and 14 (SEQ ID NOs: 2, 3, 4, 7, 8, 9, and 14) exhibit better signals than crRNAs 1, 13 or 15. Hence, the limits of detection can be improved by selecting the best crRNAs.

FIG. 8 illustrates the background corrected fluorescence for the crRNAs that were tested. As shown, crRNAs 2, 3, 4, 7, 8, 9, and 14 exhibited useful background corrected fluorescence levels. However, the useful background corrected fluorescence levels of crRNAs 1, 13, and 15 was not optimal.

FIG. 20 graphically illustrates that Guides 2+4+21 allow for robust detection of SARS-CoV-2 full length virus. FIG. 21 shows that lengthening the 30 nucleotide (crRNA_2) to the 32 nucleotide (crRNA_2XL) stem length does not influence detection. FIG. 22 graphically illustrates the identification of multiple crRNAs that efficiently detect NL63 or OC43. Further, guide combinations increase/boost sensitivity of assay (while maintaining specificity and reliable detected of positive patient samples).

Example 8: Sensitivity of SARS-CoV-2 Detection

This Example illustrates the sensitivity that may be obtained with the SARS-CoV-2 detection methods and that the methods are effective for detecting Covid-19 infections in patients.

Assay mixtures are prepared containing a Cas13a protein and a selected crRNA. After incubating the crRNA:Cas13a mixture, test RNA (e.g., SARS-CoV-2 RNA) is added with the RNase Alert detector. The mixture is incubated.

FIG. 9A-9D show simulations of the rates of activity at different Cas13a and RNA Alert concentrations based upon the Kcat of Cas13a (Kcat 500/second at about 20 µM substrate, East-Seletsky et al. Mol. Cell. 66: 373-383 (2017)). The inventors have calculated that the Cas13b (Kcat 987/second at about 20 µM substrate, Slaymaker et al. Cell Rep 26 (13): 3741-3751 (2019)) rates would be double these rates.

Three confirmed-positive nasopharyngeal samples were obtained from Covid-19 infected patients for evaluation using the methods described herein. To confirm that these nasopharyngeal samples were positive for SARS-CoV-2 RNA, quantitative PCR was performed with the CDC N1 and N2 primers (see webpage cdc.gov/coronavirus/2019-ncov/downloads/List-of-Acceptable-Commercial-Primers-Probes.pdf). Average Ct (cycle threshold) values were used to obtain the copies/mL of the SARS-CoV-2.

To evaluate the these confirmed-positive nasopharyngeal samples using the methods described herein, each assay mixture contained an extract from a nasopharyngeal swab, crRNA, cas13a, and RNase Alert. A confirmed-negative sample was also evaluated as a control and to illustrate background levels of the reaction mixture. Background subtraction was performed by subtracting reads of RNase Alert substrate with buffer.

Figures 9A, 9B, 9C, 9D:
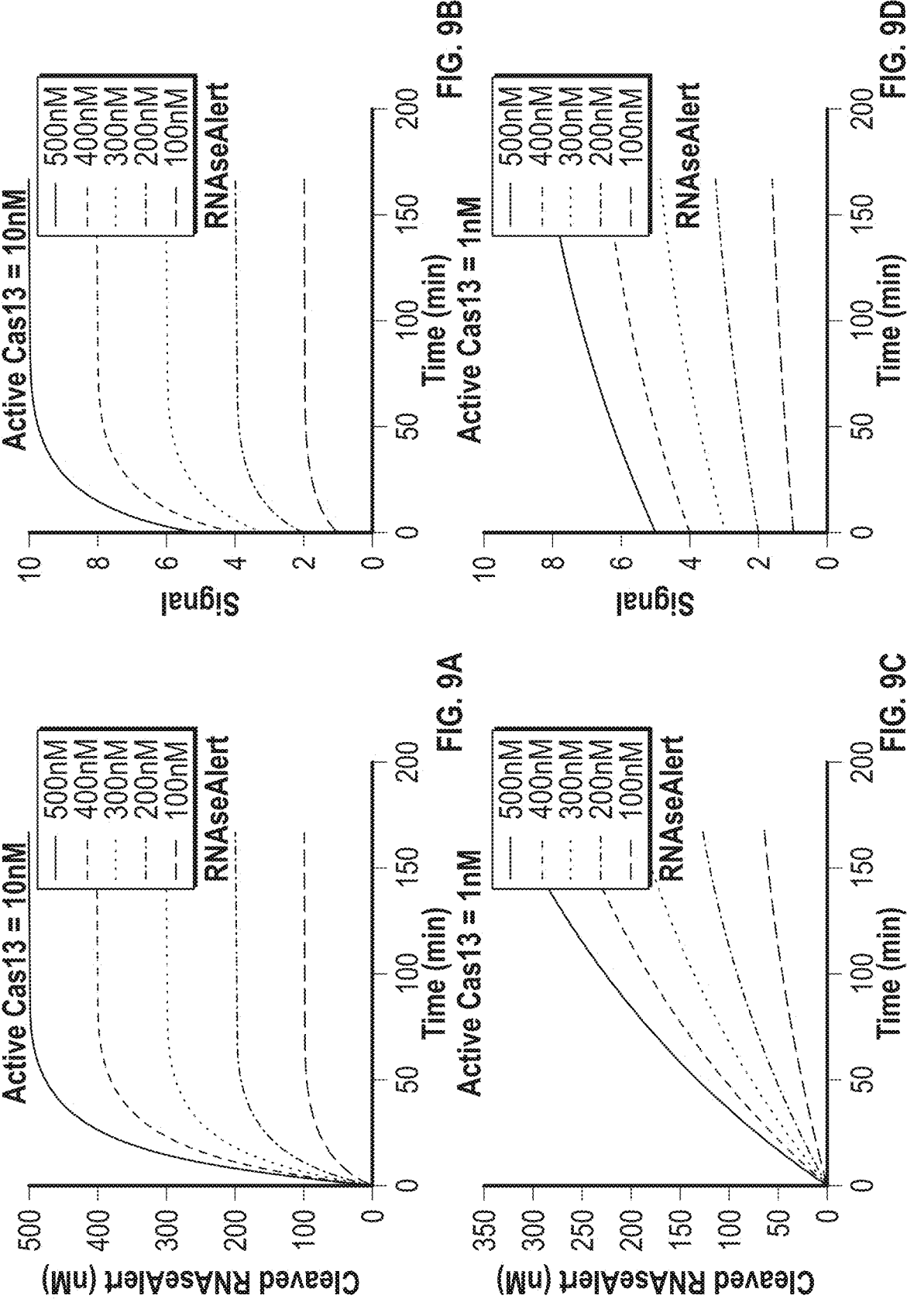
FIG. 9A-9F graphically illustrate simulations of the rates of activity at different Cas13a and RNA Alert (RNA reporter) concentrations for detection of SARS-CoV-2 in samples from patients known to be infected.
Figure 9E:
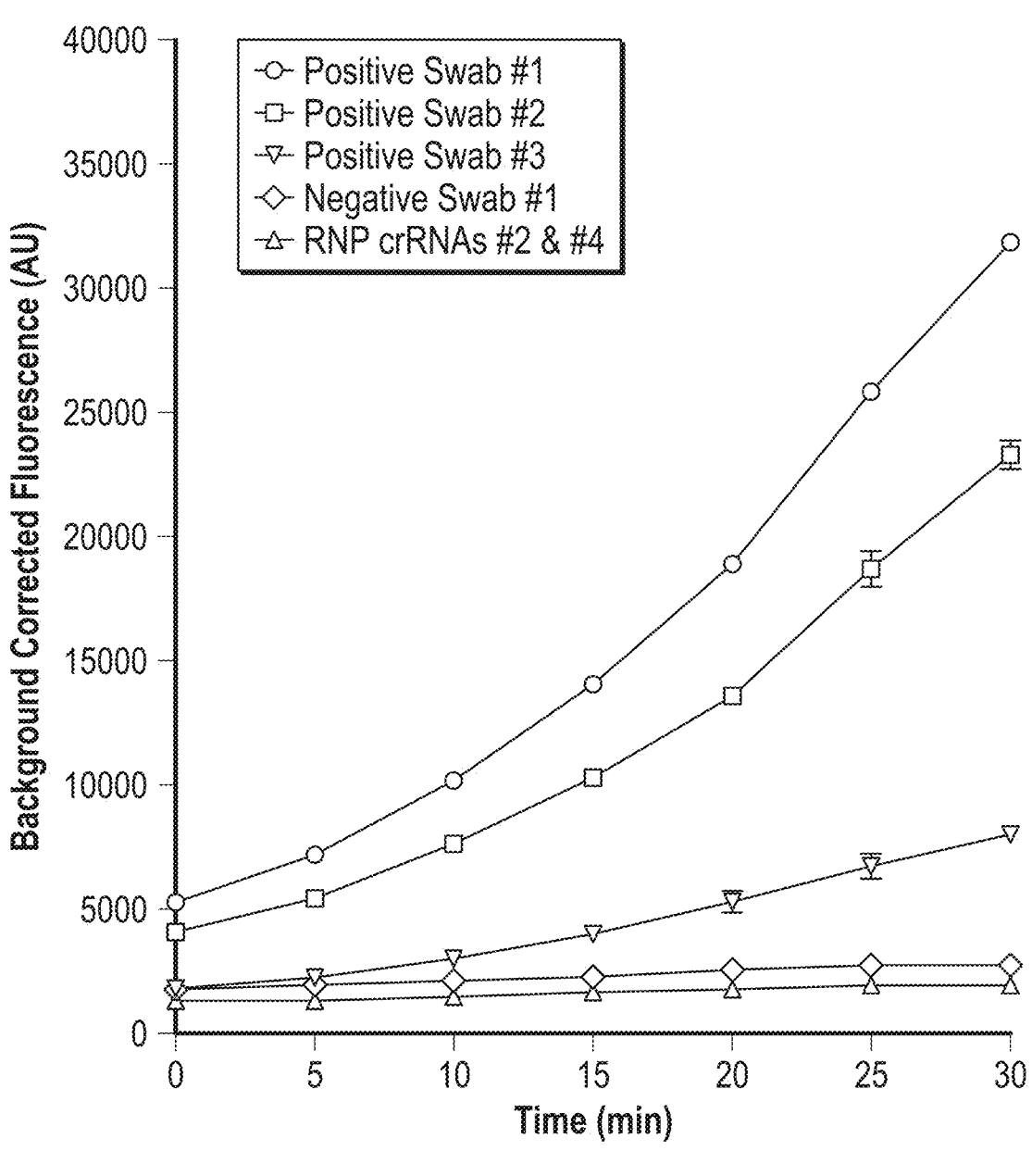
Figure 9F:
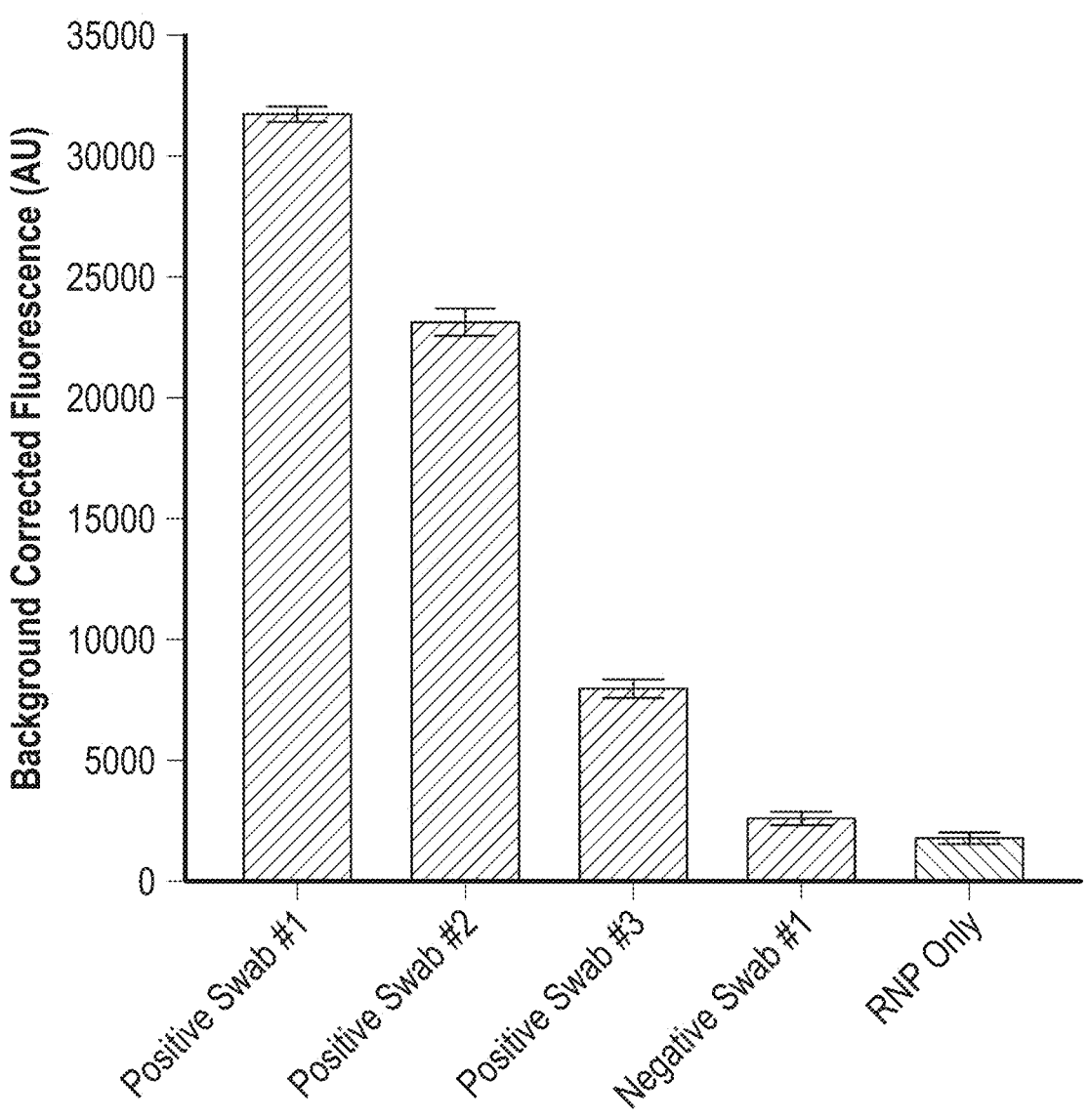

FIG. 9E-9F show the results of testing actual Covid-19 patient samples. FIG. 9E shows the time course of CRISPR-Cas13a RNP assays as the SARS-CoV-2 RNA is detected in nasopharyngeal swabs from three infected patients (positive swabs 1-3) compared to the same assay performed on a non-infected patient (negative swab #1). FIG. 9F graphically illustrates the fluorescence as an endpoint after 30 minutes of CRISPR-Cas13a RNP assays of samples from three infected patients (positive swabs 1-3) compared to the same assay performed on a non-infected patient (negative swab #1) and to an assay mixture containing CRISPR-Cas13a, crRNA and RNA Alert reagents without sample (RNP only).

The following table shows the copies of SARS-CoV-2 RNA detected for three infected patients (positive swabs 1-3) by the Cas13-crRNA methods described herein and by quantitative PCR. The copies detected by quantitative PCR are shown in the second and third columns (Average Ct and Copies/mL), while the copies detected by the Cas13-crRNA methods described herein are shown in the fourth and fifth columns (Copies in 20 µl and Copies per µl in Reaction).

TABLE 2

| Copies of SARS-CoV-2 RNA Detected by qPCR vs. Cas13-crRNA Assays | | | | |
|---|---|---|---|---|
| Swab # | Average Ct (N1/N2) | Copies/mL | Copies in 20 µl Reaction | Copies/µl in Reaction |
| Positive #1 | 14.37 | $1.99 \times 10^{10}$ | $1.54 \times 10^7$ | $7.7 \times 10^5$ |
| Positive #2 | 15.02 | $1.26 \times 10^{10}$ | $9.69 \times 10^6$ | $4.8 \times 10^5$ |
| Positive #3 | 17.66 | $1.99 \times 10^9$ | $1.54 \times 10^6$ | $7.7 \times 10^4$ |

Example 9: Droplet-Based Assays for SARS-CoV-2 Detection

This Example illustrates a droplet-based Cas13 assay that can improve the sensitivity of SARS-CoV-2 detection.

Rather than allowing cleaved fluorophores to diffuse away in a bulk sample, oil-water emulsions can be formed with droplets that contain on average one Cas13 molecule (or some small number). If the Cas13 in a droplet has bound to a viral RNA (after a defined incubation time prior to droplet formation), then it will cleave all of the RNase Alert in the droplet, creating a bright droplet against a sea of dark droplets.

Fluorescent imaging can be used after a defined reaction time (rather than a time series) and the number of bright droplets can simply be counted to determine the number of viral RNAs present in the sample. This is analogous to droplet PCR but has utility for increasing the diagnostic sensitivity of a Cas13-related assay.

Example 10: Mobile Device for SARS-CoV-2 Detection

In an example, a system for detecting for detecting and/or quantifying SARS-CoV-2 RNA (e.g., direct SARs-CoV-2 detection by CRISPR/Cas13a and a mobile phone) in a sample includes a signal generating system to excite the sample using a signal of a first frequency; a camera system to detect fluorescence in the sample; and processing circuitry to detecting SARS-CoV-2 RNA in the sample based on the fluorescence. The camera system can be included within a mobile device (such as a mobile phone; which for example, can include a microscope (e.g., "Cellscope")). The system can include a communication interface, wherein the processing circuitry is configured to provide an indication, over the communication interface, of whether SARS-CoV-2 RNA was detected in the sample. The camera system can include a complementary metal-oxide semiconductor (CMOS) sensor, and the CMOS sensor can include at least one-color filter. The color filter is positioned over alternating pixels in a pattern.

In various implementations of the disclosure, the method of creating a component or module can be implemented in software, hardware, or a combination thereof. The methods provided by various implementations of the present disclosure, for example, can be implemented in software by using standard programming languages such as, for example, C, C++, Java, Python, and the like; and combinations thereof. As used herein, the terms "software" and "firmware" are interchangeable and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in implementations of the disclosure illustrated and described herein is not essential, unless otherwise specified. That is, the operations may be performed in any order, unless otherwise specified, and implementations of the disclosure may include additional or fewer operations than those disclosed herein. For example, it is contemplated that executing or performing a particular operation before, contemporaneously with, or after another operation is within the scope of implementations of the disclosure.

Example 11: SARS-CoV-2 Assay Improvements

Background Reduction with Size-Based Separation of Cleaved and Uncleaved Probe

RNase enzyme activity is commonly detected by fluorescent RNase probes, which emits fluorescent signal upon RNA cleavage that separates the fluorophore in one end from the quencher in the other end. The sensitivity of those fluorescent probes can be limited by incomplete fluorescence quenching in its uncleaved state, which account for the background fluorescence. Provided herein is a method to physically separate the fluorescent, cleaved portion of probe (signal) from the uncleaved construct (background), which allows monitoring of signal with significantly reduced background and improves sensitivity. The system consists of two reservoirs that are separated by a semi-permeable membrane or a gel and a new fluorescent RNase probe, whose fluorescent domain is sufficiently small compared to its quencher domain that it can pass through the separating membrane or gel. By choosing the permeability threshold of the membrane between the size of small fluorescent domain and the large quencher domain of probe, the uncleaved fluorescent probe (which generates the background) can be prevented from entering the reservoir, into which the cleaved fluorescent domain can diffuse and where the signal is monitored.

As a proof-of-principle, LbuCas13a RNase enzyme was used to cleave 8 KDa (18 nucleotides) RNase probe flanked by a FAM fluorophore and an Iowa Black FQ (IBFQ) on either end. The short 5-U sequence next to FAM and the long 13-C sequence next to IBFQ were added. Owing to the sequence preference of LbuCas13a, it was reasoned that the enzyme will predominantly cleave the 5-U sequence near FAM, liberating it from the rest of probe. By using a dialysis membrane with 10 KDa molecular weight cutoff, selective transfer of the small FAM-portion with significantly reduced transfer of uncleaved probe was demonstrated. The same principle can be implemented with various other mechanisms. For example, one can use a large quencher such as gold nanoparticles or quantum dots to increase the size of uncleaved probe without increasing the size of RNA, which can increase RNase substrate and reduce signal. In another implementation, active separation of cleaved versus uncleaved probe can be achieved by electrophoresis and improve the separation speed and efficiency.

Increase in Reaction Signal with Bead-Based Concentration of the Cleaved Probe

In cases of very low RNase enzyme activity, the signal of fluorescent RNase probe can be so small that specialized sensors (e.g., PMTs or APDs) are required to detect it. A simple and cheap method of increasing the probe signal was developed by enriching the probe to a bead based on molecular binding. By including biotin into the RNase probe and using a streptavidin coated bead, enrichment of fluorescent signal on the bead surface was demonstrated. This enrichment method can be readily combined with the separation method described above to selectively increase the signal by concentration while keeping the background low.

As a proof of principle, biotin was added next to FAM and added streptavidin beads in a reservoir separate from the one where RNase enzyme reaction takes place. It was observed that the cleaved portion of probe quickly enriched on the bead surface after freely passing through the semi-permeable membrane, while the uncleaved construct did not (FIG. 23). The same principle can be implemented with various mechanisms. For example, binding between a small-molecule and an antibody can be used instead of biotin-streptavidin. Selective enrichment of signal can be achieved by a mechanism of molecular caging. In this case, a caged binding ligand can be exposed upon RNA cleavage, allowing its binding to a substrate.

Droplet-Based Concentration of Reaction Signal in Small Volumes Using Polydisperse Droplets In cases where the active RNase enzyme concentration is low or the Cas13 target such as virus is present at low concentrations, the RNases reporter signal in a bulk reaction can be very slow due to the low enzyme reaction. A simple method was created to enhance the reaction by confining a single active enzyme within the small volume of droplet, which increases the effective enzyme concentration. By dividing one bulk reaction into many small reactions, this method enables fast and extremely sensitive detection of virus. Rather than conventional droplet-based reactions that rely on uniform droplet geometries produced by complex equipment, we have shown that polydisperse droplets formed by simple agitation can be used to detect viral genomes with high sensitivity.

As a proof of principle, fluorinated oil (HFE 7500) and 2% PEG-based fluorosurfactant (008 surfactant) was used to encapsulate the Cas13-reaction in a water-in-oil droplet. It was found that including PEG-based surfactant at the water-oil interface aids in a successful Cas13 reaction within a droplet in either fluorinated or hydrocarbon oil, while other commonly used non-ionic surfactants inhibits the reaction. It was also found that the low viscosity of fluorinated oil compared to hydrocarbon oils allowed polydisperse droplets to be formed within a narrow size distribution by simple agitation (FIG. 24). Small, heterogeneous size droplets were generated by including 0.5% IGEPAL in aqueous phase before droplet generation. An extremely small amount of SARS-COV2 genome was loaded into the aqueous mix such that each droplet contains either 0 or 1 copy of virus. After 1 hr incubation at 37° C., the droplets containing virus exhibited fluorescent signals that are significantly brighter than the other blank droplets (FIG. 25). In addition, the fluorescent intensity within a droplet was inversely proportional to droplet size. The observations suggest that fast and sensitive detection of extremely low level of virus can be achieved by loading them into sufficiently small volume of droplets (<1 pL). A statistical model was also developed that enables calculation of sample copy numbers based on droplets with heterogeneous size distribution.

Example 12: Quantitative Direct Detection of Viral SARS-CoV-2 RNA with Cas13a

This Example describes experiments relating to quantifying direct detection of SARS-CoV-2 RNA and the development of the Cas13a assay. Initially, individual crRNAs, or guides were tested in assay mixtures with purified *Leptotrichia buccalis* (Lbu) Cas13a. The Cas13:crRNA ribonucleoprotein (RNP) complexes were designed to detect a distinct 20 nucleotide region in the nucleocapsid (N) gene of SARS-CoV-2. Examples are shown in FIG. 43A of the positions along the N gene that are detected by some of the. Initially, 12 guides were designed along the N gene, corresponding to positions of some of the Centers for Disease Control and Prevention (CDC) N primer sets and the N primer set developed early in the pandemic in Wuhan, China (Zhu et al., 2020). Because LbuCas13 lacks a protospacer flanking site (PFS) preference (East-Seletsky et al., 2016), crRNAs were designed corresponding to each primer set.

Each guide was tested individually using an in vitro transcribed (IVT) RNA corresponding to the viral N gene (nucleotide positions 28274-29531) as the target/activator. At a target/activator concentration of 480 fM ($2.89 \times 10^5$ copies/µL), ten guides were identified with reactivity above the RNP control, where the RNP control had the same reaction mixture (same RNP) but without the target/activator RNA (FIG. 43B). The use of RNase-free buffers minimized background fluorescence, and the plate reader gain and filter bandwidth settings were optimized to capture low-level reporter cleavage. Similar results were obtained when full-length viral RNA was used as activator. In these initial studies, two guides (crRNA 2 (SEQ ID NO:2) and crRNA 4 (SEQ ID NO:4)) were selected that generated the greatest Cas13a activation as determined by the fluorescent reporter while maintaining low levels of target-independent fluorescence.

LbuCas13a exhibits detectable reporter cleavage in the presence of as little as 10 fM (~6000 copies/µL) of complementary activator RNA (East-Seletsky et al., 2017). When using individual assay tests on serially diluted, in vitro transcribed viral RNA, crRNA 2 (SEQ ID NO:2) and crRNA 4 (SEQ ID NO:4) could detect the viral RNA with limits of detection that were in a similar range (FIG. 43C). To quantify the results shown in FIG. 43C, the slope for each curve was determined over time. Because the signal from the direct detection assay depends solely on the RNase activity of Cas13a, it should follow Michaelis-Menten enzyme kinetics with rates that have been reported for Cas13a. For low concentrations of target RNA, the change in fluorescence over time was linear, and comparison of the slopes by linear regression was determined for different target RNA concentrations (FIG. 43D) so that the detection limit for viral RNA could be determined. These data confirmed that crRNA 2 and crRNA 4 each facilitated detection of at least 10,000 copies/µL of in vitro transcribed N gene RNA. Because the measured slopes were proportional to the concentration of activated Cas13a, the activated Cas13a scaled could be scaled with the concentration of target RNA (FIG. 43E). Hence, the target RNA concentration can be estimated from the measured slope of the fluorescence production during the detection assay, thereby permitting direct quantification of viral load in unknown samples.

Example 13: Combining Guide RNAs Improves Sensitivity of Cas13a

This Example illustrates that use of two or more crRNAs can enhance Cas13a activation and improve the sensitivity of detecting SARS-CoV-2 RNA. The inventors hypothesized that using two crRNA-Cas13a enzyme RNPs at two different locations on the viral RNA would at least double enzymatic activity and would improve sensitivity (FIG. 44A). In addition, guide RNA combinations may alleviate concerns about sequence variations arising in the viral genome as it evolves.

A combination of the crRNA 2 and crRNA 4 guide RNAs was tested to ascertain whether together they could enhance detection of a single SARS-CoV-2 RNA sample. The total concentration of Cas13a RNPs in the reaction mixes was kept uniform at 100 nM, while the concentration of the crRNA 2 and crRNA 4 guide RNAs was kept equivalent (50 nM each).

As shown in FIG. 44B, combining crRNA 2 and 4 markedly increased the slope of the detection reaction and thus increased the sensitivity of the reaction when measured with a fixed activator RNA concentration (480 fM). The slope increased from 213 AU/min (SE±1.6) (crRNA 2) and 159 AU/min (SE±1.7) (crRNA 4) individually, to 383 AU/min (SE±3.0) when the two crRNAs were used in combination. This increased sensitivity was obtained without an increase in the slope of the RNP control reactions (FIG. 44B). Hence, use of two crRNAs can double the average slope (or rate) of detecting SARS-CoV-2 RNA, thereby reducing the time needed for Covid-19 tests.

To determine how combinations affected the limit of detection, the combined guide reaction was evaluated with a series of diluted N gene RNAs. As shown in FIG. 44C, use of the combination of crRNA 2 and crRNA 4 shifted the limit of detection to below 1000-fold of in vitro transcribed target N gene RNA, when compared to the control signal for RNPs containing crRNA 2 and crRNA 4 without the target RNA.

The same assay, with both the crRNA 2 and crRNA 4 guide RNAs, was performed with full-length SARS-CoV-2 RNA isolated from the supernatant of SARS-CoV-2-infected Vero CCL81 cells. As shown in FIG. 44D, the detection limit of the guide combination was 270 full-length viral copies/μL. The detection limit difference between the targets (in vitro transcribed N gene vs. full length SARS-CoV-2 RNA) may be due to different quantification techniques used for the target RNA or the considerable secondary structure predicted for the viral RNA (Manfredonia et al., 2020; Sanders et al., 2020) that may lower guide affinity (Abudayyeh et al., 2016).

CRISPR-based diagnostics can be highly specific. To confirm the specificity of the guide RNAs for SARS-CoV-2, they were evaluated in assays containing other respiratory viruses that might be present in human samples. The alpha-coronavirus HCoV-NL63, and betacoronaviruses HCoV-OC43 and Middle East respiratory syndrome coronavirus (MERS-CoV) are among seven coronaviruses known to infect human hosts and cause respiratory diseases (Fung and Liu, 2019). To ensure that the crRNA guides did not cross-react with these coronaviruses, RNA was extracted from supernatant of Huh 7.5.1-ACE2 or Vero E6 cells infected with HCoV-NL63 or HCoV-OC43, respectively. In addition, in vitro transcribed N gene RNA was produced from MERS-CoV.

As shown in FIG. 45A, no signal was detected with guides crRNA 2 and 4 above RNP background for any of the HCoV-NL63, HCoV-OC43, or MERS-CoV viral RNA. Similarly, as shown in FIG. 45B, no signal was detected with H1N1 Influenza A or Influenza B viral RNA, or with RNA extracted from primary human airway organoids.

Additional guides were tested for detection of the SARS-CoV-2 viral E gene to further increase sensitivity and specificity based on previously published PCR primer or Cas12 guide sets (Corman et al., 2020) (Broughton et al., 2020). The positions detected by crRNAs 19-22 on the SARS-CoV-2 viral E gene are shown in FIG. 45C-1. When tested against a single concentration of full-length SARS-CoV-2 RNA, crRNA 21 (SEQ ID NO:23) performed best, both individually and in combination with guide crRNA 2 and crRNA 4 (FIG. 45C-2). When tested on RNA from five nasal swab samples that were confirmed to be SARS-CoV-2-negative, the triple combination of crRNAs (RNP 2+4+21) also did not exhibit signal above the RNP control reaction (FIG. 45C-3).

Example 14: Cas13a Directly Detects SARS-CoV-2 RNA in Patient Samples

The Example illustrates results of testing the detection assay with patient samples.

To determine if adding crRNA 21 would improve the limit of detection of the Cas13a assay, a combination reaction was tested that included crRNAs 2+4+21 with precisely tittered SARS-CoV-2 genomic RNA obtained from the Biodefense and Emerging Infections Research Resources Repository (BEI Resources).

In serial dilution experiments performed over two hours using 20-replicate reactions, the triple combination detected as few as 31 copies/μL (FIG. 45D), based on viral copy number independently determined by BEI with digital droplet (dd) PCR. By analyzing the uncertainty in the slopes of individual reactions, 100% of twenty individual tests for each dilution were correctly identified as positive at this sensitivity when 95% confidence intervals were applied (FIG. 45D).

Five RNA samples were purified from nasal swabs taken from SARS-CoV-2-positive individuals. A SARS-CoV-2-negative swab sample was processed in the same manner as the positive samples. RT-qPCR measurements were performed, and the Ct values were in the range of 14.37 to 22.13 for the patient samples, correlating with SARS-CoV-2 copy numbers ranging from $3.2 \times 10^5$ to $1.65 \times 10^3$ copies/μL.

As shown in FIG. 45E, the direct detection assay correctly identified the five positive samples, which were all significantly above the signal elicited by the negative swab or the RNP reaction without target.

Example 15: Harnessing the Mobile Phone Camera as Portable Assay Reader

To allow measurements of the assay outside the laboratory, the inventors built on their expertise with the cell scope technology (see U.S. Pat. Nos. 10,578,852 and 10,542,885, which are specifically incorporated herein in their entireties), and designed a mobile phone-based fluorescent microscope for detection and quantification of the fluorescent signal emitted by the Cas13 direct detection assay (FIG. 46A). The device was based on the phone camera of a Google Pixel 4 XL phone, an f=20 mm eyepiece and an interference filter for image collection. The device also included a 488 nm diode laser, a glass collimation lens, and two ND4 filters used as mirrors for illumination. All optical and illumination components were enclosed in a custom-made black acrylic box for optical insulation. To analyze the assay reaction on the device, custom-built imaging sample chambers were made by casting polydimethylsiloxane (PDMS) onto acrylic molds. The imaging chambers contain three separate channels that can be filled independently with a reaction volume of 40 μL. Automated time-lapse imaging is controlled by a custom Android application and a Bluetooth receiver, which controls the triggering of the laser and image acquisition. Images are subsequently retrieved from the phone and analyzed offline using a custom Matlab code.

Contrary to expectations that a mobile phone-based detection system would be less sensitive than a commercial laboratory plate reader, the inventors found that the device was approximately an order of magnitude more sensitive due to reduced measurement noise and the ability to collect more time points, which decreased uncertainty in slope.

Performance of the device in detecting SARS-CoV-2 RNA with the triple-guide Cas13 assay was assessed in dilution assays of the viral RNA isolated from supernatants of virally infected Vero E6 cells (FIG. 46B-46D).

The triple-guide crRNAs included the crRNA 2 (SEQ ID NO:2), crRNA 4 (SEQ ID NO:4) and crRNA 21 (SEQ ID NO:23) guide RNAs. Dilutions of 1:10, 1:25, 1:50 and 1:100 of the original virus stock were tested, which corresponded to differing (increasing) copies of the SARS-CoV-2 N-gene, where the numbers of SARS-CoV RNA copies were determined by RT-qPCR. Several replicates of each dilution were tested on the device, each accompanied by the control reaction consisting of the triple-guide multiplexed RNP without viral RNA.

As with the plate reader, fluorescence generated in each reaction chamber was collected over time, with measurements every 30 seconds, showing a steady increase in fluorescence for full-length virus concentrations of 500-200 copies/µL, compared to RNP controls (FIG. 46B). Each replicate was imaged for 60 minutes immediately after loading onto the sample chamber, the slope was calculated, and the slopes were compared to the slopes of the control channel. The slopes, as well as each slope's 95% confidence interval were determined using the linear fit of the signal by simple linear regression (FIG. 46C). The sample was considered positive when the slope of the sample did not overlap with the slope of the control reaction within their 95% confidence intervals. To determine the limit of detection replicates each of dilutions of virus corresponding to 500, 200, 100, and 50 copies/□L were measured, as determined by RT-qPCR. Slopes were calculated based on data for the first 30, 20, and 10 min of the assay, and each slope was then compared to the RNP control slope calculated over the same time. For each dilution and assay time, the ability of the assay to detect the target RNA relative to the RNP control was quantified as % accurate, with five positive tests out of five replicates for 1:10 dilution for all assay times corresponding to 100% accuracy (FIG. 46D). The results over all dilutions indicate that the limit of detection was approximately 250 copies/µL in under 30 minutes, with accuracy dropping to 50% at 50 copies/µL.

The same patient samples were then analyzed to compare detection on the plate reader versus the mobile phone device. Each reaction was imaged for 60 minutes, along with the RNP control. The slope for a patient with Ct=17.65 (Positive Swab #3) was significantly greater than the slope for a patient with Ct=20.37 (Positive Swab #4) (FIG. 46E-46F). FIG. 46E graphically illustrates results from a Cas13 assay run on the mobile device with two different nasopharyngeal samples from human patients, each confirmed as positive for SARS-CoV-2 using RT-qPCR, using the guide combination of crRNA 2, crRNA 4 and crRNA 21. The RNP alone control had no nasopharyngeal sample. FIG. 46F graphically illustrates the final signal slope values determined from the assays described in FIG. 46E after the assay mixtures were incubated for 60 minutes.

To assess the detection accuracy, a linear fit was performed using data from the first 5, 10, 15 and 20 minutes from the beginning of the run, and the slope of each sample was compared to the RNP control. As shown in FIG. 46G, all five samples were validated and successfully identified as positive within the first 5 minutes of the assay when using the device. Hence, the mobile device detection system and the reaction assay described herein provided very fast turnaround time for obtaining results of patient samples with clinically relevant viral loads. High viral loads can be detected very rapidly because their high signals can be quickly determined to be above the control, while low viral loads can be detected at longer times once their signal can be distinguished above the control. The assay described herein has a time-dependent sensitivity that can be tuned to address both screening applications and more sensitive diagnostic applications.

Contrary to some expectations that a mobile phone-based detection system would be less sensitive than a commercial laboratory plate reader, the inventors found that our device was approximately an order of magnitude more sensitive due to reduced measurement noise and the ability to collect more time points, which decreased uncertainty in slope (FIG. 47A-47B).

Example 16: SARS-CoV-2 Eight Guide Combination Improves Detection of Viral RNA and Specifically Detects SARS-CoV-2 RNA This Example illustrates that use of a combination of the 8G crRNAs (SEQ ID Nos: 27-34) improves detection of SARS-CoV-2 RNA.

To further evaluate combinations of guide RNAs, assay mixtures containing three crRNAs were compared with assay mixtures containing eight crRNAs. The three crRNA guide combination included crRNAs 2+4+21 (SEQ ID NOs: 27, 28, 23 or 35), sequences shown in Table 3 below.

TABLE 3

| Three guide (3G) crRNA Combination | | | | |
|---|---|---|---|---|
| SEQ ID NO: | Guide Name | Viral Gene Target | Alternate Name | Guide Sequence (stem + TARGET) |
| 27 | guide2 | N | cr2 | uagaccaccccaaaaaug aaggggacuaaaacCGCA UUACGUUUGGUGGACC |
| 28 | guide4 | N | cr4 | uagaccaccccaaaaaug aaggggacuaaaacUUAC AAACAUUGGCCGCAAA |
| 35 | guide21 | E | cr21 | uagaccaccccaaaaaug aaggggacuaaaacAGCG CAGUAAGGAUGGCUAG |

The eight crRNA combination was the 8G crRNA combination (SEQ ID Nos:27-34), sequences shown below in Table 4.

TABLE 4

| Eight Guide (8G) crRNA Combination | | | | |
|---|---|---|---|---|
| SEQ ID NO: | Guide Name | Viral Gene Target | Alternate Name | Guide Sequence (stem + TARGET) |
| 27 | guide2 | N | cr2 | Uagaccac cccaaaaa ugaagggg acuaaaac CGCAUUAC GUUUGGUG GACC |
| 28 | guide4 | N | cr4 | Uagaccac cccaaaaa ugaagggg acuaaaac UUACAAAC AUUGGCCG CAAA |
| 29 | D3 | ORF1ab (NSP5) | NCR_542 | Uagaccac cccaaaaa ugaagggg acuaaaac AAACUACG UCAUCAAG CCAA |

TABLE 4-continued

| | | | | Guide |
| | | Viral | | Sequence |
| SEQ ID | Guide | Gene | Alternate | (stem + |
| NO: | Name | Target | Name | TARGET) |
| --- | --- | --- | --- | --- |
| 30 | D7 | ORF1ab (NSP5) | NCR_546 | Uagaccac cccaaaaa ugaagggg acuaaaac CACAGUCA UAAUCUAU GUUA |
| 31 | F1 | ORF1ab (NSP16) | NCR_564 | Uagaccac cccaaaaa ugaagggg acuaaaac UCACACUU UUCUAAUA GCAU |
| 32 | F6 | S | NCR_569 | Uagaccac cccaaaaa ugaagggg acuaaaac UGUAAGAU UAACACAC UGAC |
| 33 | H1 | N | NCR_588 | Uagaccac cccaaaaa ugaagggg acuaaaac UUAAUUGU GUACAAAA ACUG |
| 34 | H9 | ORF8 | NCR_596 | Uagaccac cccaaaaa ugaagggg acuaaaac CAGUUGUG AUGAUUCC UAAG |

The 3G and 8G crRNA combinations were evaluated using different target RNAs to test the specificities of the crRNA combinations. Thus, viral RNA from Influenza A, Influenza B, human coronavirus NL63, human coronavirus OC43, HIV, or SARS-CoV-2 viral RNA was mixed with aliquots of either the 3G crRNA combination or the 8G crRNA combination. The assays performed using the methods described herein and the fluorescent signals from each assay mixture were detected.

As shown in FIG. 48, use of the 8G combination of crRNAs (SEQ ID NOs: 27-34) improved SARS-CoV-2 viral RNA detection compared to 3G crRNA combination (SEQ ID NOs: 27, 28, 23 or 35). Moreover, the 8G combination of crRNAs was highly specific for SARS-CoV-2. Signals from the Influenza A. Influenza B, human coronaviruses NL63 & OC43, or HIV viral RNA assays were not detectably different from assay mixtures that contained no viral target RNA (e.g., the RNP alone assays) (see FIG. 48).

The limits of detecting SARS-CoV-2 by the 8G combination of crRNA guides was then evaluated by the Limit of Detection method pursuant to FDA guidelines. Assay mixtures were prepared using 100, 50, or 10 copies per ul of SARS-CoV-2 viral RNA with incubation for 30 min, 60 min, or 120 min. Twenty (20) replicates were individually compared pursuant to FDA guidelines (see FIG. 49).

FIG. 49A-49C illustrate the limits of detection for the 8G combination of crRNAs (SEQ ID NOs:27-34). As shown in FIG. 49, as few as 10 copies per microliter of SARS-CoV-2 viral RNA were detectable when using the 8G combination of crRNA guides, especially when the assay is incubated for longer than 30 minutes.

To further evaluate the methods described herein, assay mixtures containing the 8G combination of crRNA guides (designed to detect wild type SARS-CoV-2 strains) were tested for their ability to detect mutant and variant types of SARS-CoV-2. As shown in FIG. 50, the 8G combination of crRNA guides does detect various SARS-CoV-2 strains, including Wuhan, UK, South Africa, and California variants.

Example 17: Detection of Different SARS-CoV-2 Strains, Mutants and Variants

This Example illustrates that various SARS-CoV-2 strains, mutants and variants can be detected and distinguished using the methods and compositions described herein.

Table 5 provided below shows crRNA guide sequences (SEQ ID NOs: 58-147) for detecting various SARS-CoV-2 strains, mutants and variants. Particularly useful crRNAs identified by **.

Different crRNA guide RNAs were designed to detect wild type SARS-CoV-2 strains (WA1 crRNA) or to detect variant and mutant SARS-CoV-2 strains such as the UK, California (CA), South African (SA), and Brazilian strains. The different crRNA guide RNAs were tested using the methods described herein to ascertain whether they were strain specific and/or if they could distinguish one SARS-CoV-2 type from another.

The WA1 guides (for example, designed to detect wild type (WT), US strains) and variant guides (for example, designed to detect California (CA), UK, etc. strains) were tested against WA1 or variant target RNA, including genomic RNA, in vitro transcribed RNA, synthetic RNA, etc. from the different SARS-CoV-2 RNA strains. The algorithm illustrated in FIG. 51A was determined by measuring the signals from wild type SARS-CoV-2 reactions (using wild type crRNAs) and by measuring the signals from variant SARS-CoV-2 strains (using variant crRNAs described in Table 5) over 2 hours and the signal slopes over time were calculated. Slope ratios were calculated by dividing the slope of a guide RNA+target (i.e. RNP+target RNA) reaction by the slope of guide RNA+no target (i.e. RNP only) reaction. To prepare the graph key shown in FIG. 51B, the slope ratio of a WA1 (WT) strain was divided by slope ratio of Variant strain to determine comparative ratio between WT and variant detection. The Y-axis of the graph key shown in FIG. 51B is a log 2 scale. When the comparative ratio is high (greater than 1), the guide RNAs employed in the assay mixture detect wild type (WA1) strains more efficiently. But when the comparative ratio is low (less than 1), the guide RNAs employed in the assay mixture detect variant strains more efficiently.

TABLE 5 crRNAs for SARS-CoV-2 wild type, mutants and variants

| Guide Name | Type | SARS-CoV-2 strain | Variant | Spacer Sequence | Full crRNA (with stem) |
|---|---|---|---|---|---|
| F4 ** | WT | WA1/2020 | S13I | AACACACUG ACUAGAGACUA (SEQ ID NO: 148) | GACCACCCCAAAAAUGAAGGGGACUA AAACAACACACUGACUAGAGACUA (SEQ ID NO: 58) |
| JS_cr001_WT_3 | WT | WA1/2020 | 69/70 deletion | ccagagacau guauagcaug (SEQ ID NO: 149) | GACCACCCCAAAAAUGAAGGGGACUA AAAccagagacauguauagcaug (SEQ ID NO: 59) |
| JS_cr002_WT_4 | WT | WA1/2020 | 144 deletion | uugugguaau aaacacccaa (SEQ ID NO: 150) | GACCACCCCAAAAAUGAAGGGGACUA AAACuugugguaauaaacacccaa (SEQ ID NO: 60) |
| JS_cr003_WT_5 | WT | WA1/2020 | N501Y | caacaccauU aguggguugg (SEQ ID NO: 151) | GACCACCCCAAAAAUGAAGGGGACUA AAACcaacaccauUaguggguugg (SEQ ID NO: 61) |
| JS_cr004_WT_6 ** | WT | WA1/2020 | D614G | aguuaacaC ccugauaaaga (SEQ ID NO: 152) | GACCACCCCAAAAAUGAAGGGGACUA AAACaguuaacaCccugauaaaga (SEQ ID NO: 62) |
| JS_cr005_WT_7 | WT | WA1/2020 | N501Y | ccuuuagug gguuggaaacc (SEQ ID NO: 153) | GACCACCCCAAAAAUGAAGGGGACUA AAACccuuuaguggguuggaaacc (SEQ ID NO: 63) |
| JS_cr006_WT_8 ** | WT | WA1/2020 | D614G | aagauccuga uaaagaacag (SEQ ID NO: 154) | GACCACCCCAAAAAUGAAGGGGACUA AAACaagauccugauaaagaacag (SEQ ID NO: 64) |
| JS_cr007_UK_3 | B117 | UK/B.1.1.7 | 69/70 deletion | GUCCCAGAGA UAGCAUGGAA (SEQ ID NO: 155) | GACCACCCCAAAAAUGAAGGGGACUA AAACGUCCCAGAGAUAGCAUGGAA (SEQ ID NO: 65) |
| JS_cr008_UK_4 | B117 | UK/B.1.1.7 | 144 deletion | UUUGUGGUAA ACACCCAAAA (SEQ ID NO: 156) | GACCACCCCAAAAAUGAAGGGGACUA AAACUUUGUGGUAAACACCCAAAA (SEQ ID NO: 66) |
| JS_cr009_UK_5 | B117 | UK/B.1.1.7 | N501Y | CAACACCAUA AGUGGGUUGG (SEQ ID NO: 157) | GACCACCCCAAAAAUGAAGGGGACUA AAACCAACACCAUAAGUGGGUUGG (SEQ ID NO: 67) |
| JS_cr0010_UK_6 | B117 | UK/B.1.1.7 | D614G | AGUUAACACC CUGAUAAAGA (SEQ ID NO: 158) | GACCACCCCAAAAAUGAAGGGGACUA AAACAGUUAACACCCUGAUAAAGA (SEQ ID NO: 68) |
| JS_cr0011_UK_7 | B117 | UK/B.1.1.7 | N501Y | CCUUAAGUGG GUUGGAAACC (SEQ ID NO: 159) | GACCACCCCAAAAAUGAAGGGGACUA AAACCCUUAAGUGGGUUGGAAACC (SEQ ID NO: 69) |
| JS_cr0012_UK_8 | B117 | UK/B.1.1.7 | D614G | AAGACCCUGA UAAAGAACAG (SEQ ID NO: 160) | GACCACCCCAAAAAUGAAGGGGACUA AAACAAGACCCUGAUAAAGAACAG (SEQ ID NO: 70) |
| JS_cr013_ L452R_A | CA clade 20C | CA/B.1.429 | L452R mutant | AUUCCGGUAA UUAUAAUUAC (SEQ ID NO: 161) | GACCACCCCAAAAAUGAAGGGGACUA AAACauUcCgguaauuauaauuac (SEQ ID NO: 71) |
| JS_cr014_ L452R_B | CA clade 20C | CA/B.1.429 | L452R mutant | AUCUAUACCG GUAAUUAUAA (SEQ ID NO: 162) | GACCACCCCAAAAAUGAAGGGGACUA AAACAUCUAUACCGGUAAUUAUAA (SEQ ID NO: 72) |
| JS_cr015_ L452_A | CA clade 20C | CA/B.1.429 | L452 wt | AUUCAGGUA AUUAUAAUUAC (SEQ ID NO: 163) | GACCACCCCAAAAAUGAAGGGGACUA AAACauUcAgguaauuauaauuac (SEQ ID NO: 73) |
| JS_cr016_ L452_B | CA clade 20C | CA/B.1.429 | L452 wt | AUCUAUACAG GUAAUUAUAA (SEQ ID NO: 164) | GACCACCCCAAAAAUGAAGGGGACUA AAACAUCUAUACAGGUAAUUAUAA (SEQ ID NO: 74) |
| JS_T017_ L452R_Mut | CA clade 20C | CA/B.1.429 | L452R mutant | | aaggUUggUggUaaUUaUaaUUaccUgUaU agaUUgUUUaggaagUcUaa (SEQ ID NO: 75) |
| JS_T018_ L452R_WT | WT | WA1/2020 | L452 wt | | AAGGUUGGUGGUAAUUAUAAUUACC UGUAUAGAUUGUUUAGGAAGUCUAA (SEQ ID NO: 76) |

TABLE 5-continued

| crRNAs for SARS-CoV-2 wild type, mutants and variants | | | | | |
|---|---|---|---|---|---|
| Guide Name | Type | SARS-CoV-2 strain | Variant | Spacer Sequence | Full crRNA (with stem) |
| JS_T019_ D614G_mut | B117 | UK/B.1.1.7 | D641G | | AACCAGGuuGCuGuuCuuuAuCAGGG uGuuAACuGCACAGAAGuCCCuGu (SEQ ID NO: 77) |
| JS_T020_ D614_wt | WT | WA1/2020 | D641G | | aaccagguugcuguucuuuaucaggauguu aacugcacagaagucccugu (SEQ ID NO: 78) |
| JS_T021_ N501Y_mut | B117 | UK/B.1.1.7 | N501Y | | ACAAuCAuAuGGuuuCCAACCCAC uuAuGGuGuuGGuuACCACCAuACA (SEQ ID NO: 79) |
| JS_T022_ N501_wt | WT | WA1/2020 | N501Y | | acaaucauaugguuuccaacccacuaaugg uguugguuaccaaccauaca (SEQ ID NO: 80) |
| JS_T023_ 69-70_mut | B117 | UK/B.1.1.7 | 69/70 deletion | | uCCAAuGuuACuuGGuuCCAuGCuA uCuCuGGGACCAAuGGuACuAAGAG (SEQ ID NO: 81) |
| JS_T024_ 69-70_wt | WT | WA1/2020 | 69/70 deletion | | aauguuacuugguuccaugcuauacugu cucugggaccaaugguacuaa (SEQ ID NO: 82) |
| JS_T025_ I4205V_mut | CA clade 20C | UK/B.1.1.7 | ORF1AB- I4205V_mut | | CCCuAAGAGuGAuGGAACuGGuAC uGuCuAuACAGAACuGGAACCACCuu (SEQ ID NO: 83) |
| JS_T026_ I4205_wt | WT | WA1/2020 | ORF1AB- I4205_wt | | cccuaagagugauggaacugguacuaucua uacagaacuggaaccaccuu (SEQ ID NO: 84) |
| JS_T027_ D1183Y_mut | CA clade 20C | UK/B.1.1.7 | ORF_1AB: D1183Y_mut | | uuAuACCCAACACuCAAuAuCuC AuAuGAGuuuuCuAGCAAuGuuGCAAA (SEQ ID NO: 85) |
| JS_T028_ D1183_wt | WT | WA1/2020 | ORF_1AB: D1183_wt | | uuauacccaacacucaauaucucagauga guuuucuagcaauguugcaaa (SEQ ID NO: 86) |
| JS_T029_ S13I_mut | CA clade 20C | UK/B.1.1.7 | S13I | | AuuACCACAAAAACAACAAAA GuuGuAuGGAAAGuGAGuuCAGAGuuuAu (SEQ ID NO: 87) |
| JS_T030_ S13_wt | WT | WA1/2020 | S13I | | auuaccacaaaaacaacaaaaguugg auggaaagugaguucagaguuuau (SEQ ID NO: 88) |
| JS_T031_ W152C_mut | CA clade 20C | UK/B.1.1.7 | W152C | | CuuGuuuuAuuGCCACuAGuCu CuAuuCAGuGuGuuAAuCuuACAACCAG (SEQ ID NO: 89) |
| JS_T032_ W152_wt | WT | WA1/2020 | W152C | | cuuguuuuauugccacuagucucua gucaguguguuaaucuuacaaccag (SEQ ID NO: 91) |
| JS_cr033_ I4205V_mutA | CA clade 20C | UK/B.1.1.7 | ORF1AB- I4205V_mut | UAcACAGUAC CAGUUCCAUC (SEQ ID NO: 165) | GACCACCCCAAAAAUGAAGGG GACUAAAACUAcACAGUACCAGUUCCAUC (SEQ ID NO: 92) |
| JS_cr034_ I4205V_wtA | WT | WA1/2020 | ORF1AB- I4205_wt | uacauaguacc aguuccauc (SEQ ID NO: 166) | GACCACCCCAAAAAUGAAGGG GACUAAAACuacauaguaccaguuccauc (SEQ ID NO: 93) |
| JS_cr035_ D1183Y_mutA ** | CA clade 20C | UK/B.1.1.7 | ORF_1AB: D1183Y_mut | UCuUAUGAGA UAUUGAGUGU (SEQ ID NO: 167) | GACCACCCCAAAAAUGAAGGG GACUAAAACUCuUAUGAGAUAUUGAGUGU (SEQ ID NO: 94) |
| JS_cr036_ D1183Y_wtA | WT | WA1/2020 | ORF_1AB: D1183_wt | ucuucugagau auugagugu (SEQ ID NO: 168) | GACCACCCCAAAAAUGAAGGG GACUAAAACucuucugagauauugagugu (SEQ ID NO: 95) |

TABLE 5-continued

| | | | | | |
|---|---|---|---|---|---|
| | | | | Spacer | |
| Guide Name | Type | SARS-CoV-2 strain | Variant | Sequence | Full crRNA (with stem) |
| JS_cr037_ S13I_mutA | CA clade 20C | UK/B.1.1.7 | S13I_mut | CCuUACAACU UUUGUUGUUU (SEQ ID NO: 169) | GACCACCCCAAAAAUGAAGGG GACUAAAACCCuUACAACUUUUGUUGUUU (SEQ ID NO: 96) |
| JS_cr038_ S13_wtA | WT | WA1/2020 | S13_wt | ccUuccaacuu uuguuguuu (SEQ ID NO: 170) | GACCACCCCAAAAAUGAAGGGG ACUAAAACccUuccaacuuuuuguuguuu (SEQ ID NO: 97) |
| JS_cr039_ W152C_mutA | CA clade 20C | UK/B.1.1.7 | W152C_mut | CUCAAUAGAG ACUAGUGGCA (SEQ ID NO: 171) | GACCACCCCAAAAAUGAAGGGG ACUAAAACCUCAAUAGAGACUAGUGGCA (SEQ ID NO: 98) |
| JS_cr040_ W152_wtA | WT | WA1/2020 | W152_wt | cuCacuagag acuaguggca (SEQ ID NO: 172) | GACCACCCCAAAAAUGAAGGGG ACUAAAACcuCacuagagacuaguggca (SEQ ID NO: 99) |
| JS_cr041_ I4205V_mutB | CA clade 20C | UK/B.1.1.7 | ORF1AB-I4205V_mut | UGUAUAGACA GUACCAGUUC (SEQ ID NO: 173) | GACCACCCCAAAAAUGAAGGGGAC UAAAACUGUAUAGACAGUACCAGUUC (SEQ ID NO: 100) |
| JS_cr042_ I4205V_wtB | WT | WA1/2020 | ORF1AB-I4205_wt | uguauagaua guaccaguuc (SEQ ID NO: 174) | GACCACCCCAAAAAUGAAGGGGAC UAAAACuguauagauaguaccaguuc (SEQ ID NO: 101) |
| JS_cr043_ D1183Y_mutB ** | CA clade 20C | UK/B.1.1.7 | ORF_1AB: D1183Y_mut | AAACUCAUAU GAGAUAUUGA (SEQ ID NO: 175) | GACCACCCCAAAAAUGAAGGGGAC UAAAACAAACUCAUAUGAGAUAUUGA (SEQ ID NO: 102) |
| JS_cr044_ D1183Y_wtB | WT | WA1/2020 | ORF_1AB: D1183_wt | aaacucauc ugagauauuga (SEQ ID NO: 176) | GACCACCCCAAAAAUGAAGGGGACU AAAACaaacucaucugagauauuga (SEQ ID NO: 103) |
| JS_cr045_ S13I_mutB ** | CA clade 20C | UK/B.1.1.7 | S13I_mut | CUUUCCAUAC AACUUUUGUU (SEQ ID NO: 177) | GACCACCCCAAAAAUGAAGGGA CUAAAACCUUUCCAUACAACUUUUGUU (SEQ ID NO: 104) |
| JS_cr046_ S13_wtB | WT | WA1/2020 | S13_wt | cuuuccaucc aacuuuuguu (SEQ ID NO: 178) | GACCACCCCAAAAAUGAAGGGA CUAAAACcuuuccauccaacuuuuguu (SEQ ID NO: 105) |
| JS_cr047_ W152C_mutB ** | CA clade 20C | UK/B.1.1.7 | W152C_mut | CACACUGAAU AGAGACUAGU (SEQ ID NO: 179) | GACCACCCCAAAAAUGAAGGGAC UAAAACCACACUGAAUAGAGACUAGU (SEQ ID NO: 106) |
| JS_cr048_ W152_wtB | WT | | W152_wt | cacacugacua gagacuagu (SEQ ID NO: 180) | GACCACCCCAAAAAUGAAGGGAC UAAAACcacacugacuagagacuagu (SEQ ID NO: 107) |
| SS_cr1_P1_ K417T_wt ** | WT | WA1/2020 | K417_wt | aucagcaauc uuuccaguuu (SEQ ID NO: 181) | GACCACCCCAAAAAUGAAGGGA CUAAAACaucagcaaucuuuccaguuu (SEQ ID NO: 108) |
| SS_cr2_P1_ K417T_mt | P1 | Brazil/P.1 | K417T_mt | AuCAGCAAu CGuuCCAGuuu (SEQ ID NO: 182) | GACACCCCAAAAAUGAAGGGA CUAAAACAuCAGCAAuCGuuCCAGuuu (SEQ ID NO: 109) |
| SS_cr3_P1_ K417T_wt ** | WT | WA1/2020 | K417_wt | aaucuuuccag uuugcccug (SEQ ID NO: 183) | GACCACCCCAAAAAUGAAGGGA CUAAAACaaucuuuccaguuugcccug (SEQ ID NO: 110) |
| SS_cr4_P1_ K417T_mt | P1 | Brazil/P.1 | K417T_mt | AACCGuuCC AGuuuGCCCuG (SEQ ID NO: 184) | GACCACCCCAAAAAUGAAGGGA CUAAAACAACCGuuCCAGuuuGCCCuG (SEQ ID NO: 111) |
| SS_cr5_P1_ E484K_wt ** | WT | WA1/2020 | E484_wt | uaaaaccuuca acaccauua (SEQ ID NO: 185) | GACCACCCCAAAAAUGAAGGGAC UAAAACuaaaaccuucaacaccauua (SEQ ID NO: 112) |
| SS_cr6_P1_ E484K_mt ** | P1 | Brazil/P.1 | E484K_mt | uAAAACCu uuAACACCAuuA (SEQ ID NO: 186) | GACCACCCCAAAAAUGAAGGGAC UAAAACuAAAACCuuuAACACCAuuA (SEQ ID NO: 113) |
| SS_cr7_P1_ E484K_wt ** | WT | WA1/2020 | E484_wt | ccuucaacacc auuacaagg (SEQ ID NO: 187) | GACCACCCCAAAAAUGAAGGGAC UAAAACccuucaacaccauuacaagg (SEQ ID NO: 114) |

TABLE 5-continued

| crRNAs for SARS-CoV-2 wild type, mutants and variants | | | | | |
| --- | --- | --- | --- | --- | --- |
| Guide Name | Type | SARS-CoV-2 strain | Variant | Spacer Sequence | Full crRNA (with stem) |
| SS_cr8_P1_ E484K_mt ** | P1 | Brazil/P.1 | E484K_mt | CCAuuAACA CCAuuACAAGG (SEQ ID NO: 188) | GACCACCCCAAAAAUGAAGGGGAC UAAAACCCAuuAACACCAuuACAAGG (SEQ ID NO: 115) |
| SS_cr9_P1_ N501Y_wt ** | WT | WA1/2020 | N501_wt | accaacacc auuaguggguu (SEQ ID NO: 189) | GACCACCCCAAAAAUGAAGGGGAC UAAAACaccaacaccauuaguggguu (SEQ ID NO: 116) |
| SS_cr10_P1_ N501Y_mt ** | P1 | Brazil/P.1 | N501Y_mt | ACCAACACC AuAAGuGGGuu (SEQ ID NO: 190) | GACCACCCCAAAAAUGAAGGGGAC UAAAACACCAACACCAuAAGuGGGuu (SEQ ID NO: 117) |
| SS_cr11_P1_ N501Y_wt | WT | WA1/2020 | N501_wt | ccauuagug gguuggaaacc (SEQ ID NO: 191) | GACCACCCCAAAAAUGAAGGGGAC UAAAACccauuagugggguuggaaacc (SEQ ID NO: 118) |
| SS_cr12_P1_ N501Y_mt | P1 | Brazil/P.1 | N501Y_mt | CCGuAAGuG GGuGGAAACC (SEQ ID NO: 192) | GACCACCCCAAAAAUGAAGGGGAC UAAAACCGuAAGuGGGuuGGAAACC (SEQ ID NO: 119) |
| SS_cr13_P1_ D614G_wt | WT | WA1/2020 | D614_wt | aguuaacau ccugauaaaga (SEQ ID NO: 193) | GACCACCCCAAAAAUGAAGGGGAC UAAAACaguuaacauccugauaaaga (SEQ ID NO: 120) |
| SS_cr14_P1_ D614G_mt | P1 | Brazil/P.1 | D614G_mt | AGuuAACAC CCuGAuAAAGA (SEQ ID NO: 194) | GACCACCCCAAAAAUGAAGGGGAC UAAAACAGuuAACACCCuGAuAAAGA (SEQ ID NO: 121) |
| SS_cr15_P1_ D614G_wt | WT | WA1/2020 | D614_wt | aacauccugau aaagaacag (SEQ ID NO: 195) | GACCACCCCAAAAAUGAAGGGGAC UAAAACaacauccugauaaagaacag (SEQ ID NO: 122) |
| SS_cr16_P1_ D614G_wt | P1 | Brazil/P.1 | D614G_mt | AAGACCCuG AuAAAGAACAG (SEQ ID NO: 196) | GACCACCCCAAAAAUGAAGGGGAC UAAAACAAGACCCuGAuAAAGAACAG (SEQ ID NO: 123) |
| JS_cr049_ D614G_p6 | B117 | UK/B.1.1.7 | D614G_mt | uaacaCccu gauaaagaaca (SEQ ID NO: 197) | GACCACCCCAAAAAUGAAGGGGACUA AAACuaacaCccugauaaagaaca (SEQ ID NO: 124) |
| JS_cr050_ D614G_p6s7 | B117 | UK/B.1.1.7 | D614G_mt | uaacaCGcug auaaagaaca (SEQ ID NO: 198) | GACCACCCCAAAAAUGAAGGGGACUA AAACuaacaCGcugauaaagaaca (SEQ ID NO: 125) |
| JS_cr051_ D614G_p16 | B117 | UK/B.1.1.7 | D614G_mt | ucugugcagu uaacaCccug (SEQ ID NO: 199) | GACCACCCCAAAAAUGAAGGGGACUA AAACucugugcaguuaacaCccug (SEQ ID NO: 126) |
| JS_cr052_ D614G_p14 | B117 | UK/B.1.1.7 | D614G_mt | ugugcaguua acaCccugau (SEQ ID NO: 200) | GACCACCCCAAAAAUGAAGGGGACUA AAACugugcaguuaacaCccugau (SEQ ID NO: 127) |
| JS_cr053_ D614G_p17 | B117 | UK/B.1.1.7 | D614G_mt | UUCUGUGCA GUUAACAcCCU (SEQ ID NO: 201) | GACCACCCCAAAAAUGAAGGGGACUA AAACUUCUGUGCAGUUAACAcCCU (SEQ ID NO: 128) |
| JScr054_ D614G_s16p17 | B117 | UK/B.1.1.7 | D614G_mt | UUCUGUGCA GUUAACucCCU (SEQ ID NO: 202) | GACCACCCCAAAAAUGAAGGGGACUA AAACUUCUGUGCAGUUAACucCCU (SEQ ID NO: 129) |
| JScr055_ D614G_s15p17 | B117 | UK/B.1.1.7 | D614G_mt | UUCUGUGCA GUUAAgAcCCU (SEQ ID NO: 203) | GACCACCCCAAAAAUGAAGGGGACUA AAACUUCUGUGCAGUUAAgAcCCU (SEQ ID NO: 130) |
| JS_cr056_ S13I_s10p11 ** | CA clade 20C | CA/B.1.429 | S13I_wt | aacacacugU Cuagagacua (SEQ ID NO: 204) | GACCACCCCAAAAAUGAAGGGGACUA AAACaacacacugUCuagagacua (SEQ ID NO: 131) |
| JS_cr057_ S13I_s9p11 ** | CA clade 20C | CA/B.1.429 | S13I_wt | aacacacuCaC uagagacua (SEQ ID NO: 205) | GACCACCCCAAAAAUGAAGGGGACUA AAACaacacacuCaCuagagacua (SEQ ID NO: 132) |

TABLE 5-continued crRNAs for SARS-CoV-2 wild type, mutants and variants

| Guide Name | Type | SARS-CoV-2 strain | Variant | Spacer Sequence | Full crRNA (with stem) |
|---|---|---|---|---|---|
| JS_cr058_ S13I_p11s14 | CA clade 20C | CA/B.1.429 | S13I_wt | aacacacuga CuaCagacua (SEQ ID NO: 206) | GACCACCCCAAAAAUGAAGGGGACU AAAACaacacacugaCuaCagacua (SEQ ID NO: 133) |
| SS_cr13_242-244Del_wt | WA1 | WA1/2020 | L242, A243, L244 Deletion | cuauguaaag caaguaaagu (SEQ ID NO: 207) | GACCACCCCAAAAAUGAAGGGG ACUAAAACcuauguaaagcaaguaaagu (SEQ ID NO: 134) |
| SS_cr14_ B1153_242-222Del_mt | South Africa (B1153) | SA/B.1.351 | L242, A243, L244 Deletion | AAAuAACuu CuAuGuAAAGu (SEQ ID NO: 208) | GACCACCCCAAAAAUGAAGGGGACU AAAACAAAuAACuuCuAuGuAAAGu (SEQ ID NO: 135) |
| SS_cr15_ B1153_K417N_mt | South Africa (B1153) | SA/B.1.351 | K417N | AuCAGCAA uAuuuCCAGuuu (SEQ ID NO: 209) | GACCACCCCAAAAAUGAAGGGGA CUAAAACAuCAGCAAuAuuuCCAGuuu (SEQ ID NO: 136) |
| SS_cr16_ B1153_K417N_mt | South Africa (B1153) | SA/B.1.351 | K417N | CAuuAuuuC CAGuuuGCCCu (SEQ ID NO: 210) | GACCACCCCAAAAAUGAAGGGGA CUAAAACCAuuAuuuCCAGuuuGCCCu (SEQ ID NO: 137) |
| SS_cr17_ A701V_wt | WA1 | WA1/2020 | A701V | ugaauuuuc ugcaccaagug (SEQ ID NO: 211) | GACCACCCCAAAAAUGAAGGGGA CUAAAACugaauuuucugcaccaagug (SEQ ID NO: 138) |
| SS_cr18_ B1153_A701V_mt | South Africa (B1153) | SA/B.1.351 | A701V | uGAAuuuuGu ACACCAAGuG (SEQ ID NO: 212) | GACCACCCCAAAAAUGAAGGGGA CUAAACuGAAuuuuGuACACCAAGuG (SEQ ID NO: 139) |
| SS_cr19_ A701V_wt | WA1 | WA1/2020 | A701V | uucugcacca agugacauag (SEQ ID NO: 213) | GACCACCCCAAAAAUGAAGGGGA CUAAAACuucugcaccaagugacauag (SEQ ID NO: 140) |
| SS_cr20_ B1153_A701V_m | South Africa (B1153) | SA/B.1.351 | A701V | uuGuACACCA AGuGACAuAG (SEQ ID NO: 217) | GACCACCCCAAAAAUGAAGGGGA CUAAAACuuGuACACCAAGuGACAuAG (SEQ ID NO: 141) |
| SS_cr21_ D80A_wt | WA1 | WA1/2020 | D80A | acaggguua ucaaaccucuu (SEQ ID NO: 215) | GACCACCCCAAAAAUGAAGGGGA CUAAAACacaggguuaucaaaccucuu (SEQ ID NO: 142) |
| SS_cr22_ B1153_D80A_mt | South Africa (B1153) | SA/B.1.351 | D80A | ACAGGGuu AGCuAACCuCuu (SEQ ID NO: 216) | GACCACCCCAAAAAUGAAGGGGA CUAAAACACAGGGuuAGCuAACCuCuu (SEQ ID NO: 143) |
| SS_cr23_ B1153_D80A_mt | South Africa (B1153) | SA/B.1.351 | D80A | ACAGGGuu AGCAAACCuCuu (SEQ ID NO: 217) | GACCACCCCAAAAAUGAAGGGGA CUAAAACACAGGGuuAGCAAACCuCuu (SEQ ID NO: 144) |
| SS_cr24_ D215G_wt | WA1 | WA1/2020 | D251G | gagggagau cacgcacuaaa (SEQ ID NO: 218) | GACCACCCCAAAAAUGAAGGGGA CUAAAACgagggagaucacgcacuaaa (SEQ ID NO: 145) |
| SS_cr25_ B1153_D215G_mt | South Africa (B1153) | SA/B.1.351 | D251G | GAGGGAGACC ACGCACuAAA (SEQ ID NO: 219) | GACCACCCCAAAAAUGAAGGGGA CUAAAACGAGGGAGACCACGCACuAAA (SEQ ID NO: 146) |
| SS_cr26_ B1153_D215G_mt | South Africa (B1153) | SA/B.1.351 | D251G | GAGGGAGACC uCGCACuAAA (SEQ ID NO: 220) | GACCACCCCAAAAAUGAAGGGGA CUAAAACGAGGGAGACCuCGCACuAAA (SEQ ID NO: 147) |

To further evaluate the crRNAs, assay mixtures were prepared containing some of the crRNAs described in Table 5 that can detect either wild type SARS-CoV-2 strains or mutant/variant SARS-CoV-2 strains.

As shown in FIG. 52A-52B, the WA1 crRNAs designed to detect wild type SARS-CoV-2 strains and the crRNAs designed to detect Brazil P.1 (BZ (P.1)) variant SARS-CoV-2 strains were able to distinguish wild type and variant K417T, E484K, and N501Y mutations in Brazilian SARS-CoV-2 strains (FIG. 52A) when tested using synthetic RNA as target. The crRNAs also efficiently detected the E484K mutation when tested against full length viral RNA (FIG.

52B). Hence, use of WA1 crRNAs can identify that a SARS-CoV-2 is present and use of the guide RNAs that target specific mutations can identify which variant SARS-CoV-2 strain is responsible for the infection and even which type(s) of SARS-CoV-2 mutations are present.

FIG. 53A-53B show that guide crRNAs specifically designed to detect mutant SARS-CoV-2 strains could distinguish mutant California (CA B.1.429) strains from their wild type parental strains. The crRNAs were designed by the Sherlock method (FIG. 53A) or Central Seed (CS, FIG. 53B) method. The data shown identifies JS_cr034 crRNA is a WA1 specific guide RNA while the JS_cr037, JS_cr043, JS_cr045, JS_cr047 guides are CA specific guide RNAs. The SARS-CoV-2 wild type and mutation positions detected by the crRNAs are shown below the graphs. An especially promising guide for detecting a ORF1AB:I4205_wt mutation in a wild strain was identified as being the JS_cr034_I4205V_wtA crRNA guide. Especially promising guides for detecting the Spike S131_mut mutation found in CA clade 20C were identified as being the JS_cr037_S13I_mutA crRNA and the JS_cr045_S131_mutB crRNA. A promising guide for detecting ORF1AB:D1183Y_mut mutation found in CA clade 20C was identified as being the JS_cr043_D1183Y_mutB crRNA. A promising guide for detecting Spike:W152C_mut mutation found in CA clade 20C was identified as being the JS_cr047_W152C_mutB crRNA.

FIG. 54A-54B illustrates detection of 20C CA/B.1.429 mutant and wild type SARS-CoV-2 of the California (CA) clade using various crRNAs designed to detect such SARS-CoV-2 strains. The graph key shown in FIG. 54A shows a comparative ratio between wild type and variant California (CA) SARS-CoV-2 strains on the Y-axis using a log 2 scale. When the comparative ratio is high (greater than 1), the guide RNAs employed in the assay mixture detects wild type (e.g., WA1) strains more efficiently. But when the comparative ratio is low (less than 1), the guide RNAs employed in the assay mixture detect variant strains (e.g., CA variant strains) more efficiently. This experiment demonstrates that JScr56, JScr57, JScr58, JScr46 guides are specific for WA1 (wt) and JScr37, JScr45 are guides specific for the CA strain (FIG. 54B)

FIG. 55 illustrates a specific mutation (D614G) in wild type SARS-CoV-2 (WA1 with the D614 amino acid in the Spike protein) and variant SARS-CoV-2 (UK and several others with the G614 amino acid in the Spike protein) using some of the crRNAs described in Table 5. As illustrated, various crRNAs can detect strains with the spike D614G amino acid mutation caused by an A-to-G nucleotide mutation at position 23,403 in the Wuhan reference strain. The original isolate had D614 and over time G614 has taken over the population and is basically now the wild type sequence.

To obtain the data in FIG. 55, several crRNA were tested against SARS-CoV-2 with mutations of interest in newly circulating strains. FIG. 55 demonstrates which guide RNAs are good at differentiating between D614 vs. G614 mutations (using JScr4 vs. JScr12, respectively).

REFERENCES

Abudayyeh O O, Gootenberg J S, Essletzbichler P, Han S, Joung J, Belanto J J, Verdine V, Cox D B T, Kellner M J, Regev A, Lander E S, Voytas D F, Ting A Y, Zhang F. RNA targeting with CRISPR-Cas13. Nature. Nature Publishing Group; 2017 Oct. 12; 550(7675):280-4.

Abudayyeh, O. O., Gootenberg, J. S., Konermann, S., Joung, J., Slaymaker, I. M., Cox, D. B., Shmakov, S., Makarova, K. S., Semenova, E., Minakhin, L., et al. (2016). C2c2 is a single-component programmable RNA-guided RNA-targeting CRISPR effector. Science. 353(6299): 353, aaf5573.

Alexandersen, S., Chamings, A., and Bhatta, T. R. (2020). SARS-CoV-2 genomic and subgenomic RNAs in diagnostic samples are not an indicator of active replication. medRxiv.

Arizti-Sanz, J., Freije, C. A., Stanton, A. C., Boehm, C. K., Petros, B. A., Siddiqui, S., Shaw, B. M., Adams, G., Kosoko-Thoroddsen, T. F., Kemball, M. E., et al. (2020). Integrated sample inactivation, amplification, and Cas13-based detection of SARS-CoV-2. bioRxiv.

Babin, S. M., Hsieh, Y. H., Rothman, R. E., and Gaydos, C. A. (2011). A meta-analysis of point-of-care laboratory tests in the diagnosis of novel 2009 swine-lineage pandemic influenza A (H1N1). Diagn Microbiol Infect Dis. 69(4), 410418.

Bai, Y., Yao, L., Wei, T., Tian, F., Jin, D. Y., Chen, L., and Wang, M. (2020). Presumed Asymptomatic Carrier Transmission of COVID-19. JAMA. Published online 2020 Feb. 23 DOI: 10.1001/jama.2020.2565.

Berg B, Cortazar B, Tseng D. Ozkan H, Feng S, Wei Q. Chan R Y-L, Burbano J, Farooqui Q. Lewinski M, Di Carlo D. Gamer O B, Ozcan A. Cellphone-Based Hand-Held Microplate Reader for Point-of-Care Testing of Enzyme-Linked Immunosorbent Assays. ACS Nano. 2015 Aug. 25; 9(8):7857-66.

Breslauer D N. Maamari R N, Switz N A, Lam W A, Fletcher D A. Mobile phone based clinical microscopy for global health applications. PLoS ONE. 2009 Jul. 22:4(7): e6320.

Brian D A, Baric R S. Coronavirus genome structure and replication. Curr. Top. Microbiol. Immunol. Fourth Edition. Berlin/Heidelberg: Springer-Verlag; 2005; 287 (Suppl):1-30.

Broughton, J. P., Deng, X., Yu. G., Fasching, C. L., Servellita, V., Singh, J., Miao, X., Streithorst, J. A., Granados, A., Sotomayor-Gonzalez, A., et al. (2020). CRISPR-Cas12-based detection of SARS-CoV-2. Nature Biotechnology. 38(7), 870-874. DOI: doi:10.1038/s41587-020-0513-4.

Broughton, J P, Deng, X, Yu G, Fasching, C. L., medRxiv J S, 2020. Rapid Detection of 2019 Novel Coronavirus SARS-CoV-2 Using a CRISPR-based DETECTR Lateral Flow Assay. medrxiv.org.

Chan, J. F., Yuan, S., Kok, K. H., To, K. K., Chu, H., Yang, J., Xing, F., Liu, J., Yip, C. C., Poon, R. W., et al. (2020). A familial cluster of pneumonia associated with the 2019 novel coronavirus indicating person-to-person transmission: a study of a family cluster. Lancet. 395(10223), 514-523. Published online 2020 Jan. 28 DOI: 10.1016/S0140-6736(20)30154-9.

Chartrand, C., Leeflang, M. M., Minion, J., Brewer, T., and Pai, M. (2012). Accuracy of rapid influenza diagnostic tests: a meta-analysis. Ann Intern Med. 156(7), 500-511. Published online 2012 Mar. 1 DOI: 10.7326/00034819-156-7-201204030-00403.

Chen, J. S., Ma, E., Harrington, L. B., Da Costa, M., Tian, X., Palefsky, J. M., and Doudna, J. A. (2018). CRISPR-Cas12a target binding unleashes indiscriminate single-stranded DNase activity. Science. 360(6387), 436-439. Published online 2018 Feb. 17 DOI: 10.1126/science.aar6245.

Chen S-C, Olsthoom R C L. Group-specific structural features of the 5'-proximal sequences of coronavirus genomic RNAs. Virology. 2010 May 25; 401(1):29-41.

Cherry, J. D., and Krogstad, P. (2004). SARS: the first pandemic of the 21st century. Pediatr Res. 56(1), 1-5. Published online 2004 May 21 DOI: 10.1203/01.PDR.0000129184.87042.FC.

Chaisson L H, Reber C, Phan H. Switz N, Nilsson L M, Myers F, Nhung N V, Luu L, Pham T, Vu C, Nguyen H, Nguyen A, Dinh T, Nahid P, Fletcher D A, Cattamanchi A. Evaluation of mobile digital light-emitting diode fluorescence microscopy in Hanoi, Viet Nam. Int. J. Tuberc. Lung Dis. 2015 September; 19(9):1068-72.

Chu, H., Lofgren. E. T., Halloran, M. E., Kuan, P. F., Hudgens, M., and Cole. S. R. (2012). Performance of rapid influenza H1N1 diagnostic tests: a meta-analysis. Influenza Other Respir Viruses. 6(2), 80-86. Published online 2011 Sep. 3 DOI: 10.1111/j.1750-2659.2011.00284.x.

Corman, V. M., Landt, O., Kaiser, M., Molenkamp, R., Meijer, A., Chu, D. K., Bleicker, T., Brunink, S., Schneider, J., Schmidt, M. L., et al. (2020). Detection of 2019 novel coronavirus (2019-nCoV) by real-time RT-PCR. Euro Surveill. 25(3). Published online 2020 Jan. 30 DOI: 10.2807/1560-7917.ES.2020.25.3.2000045.

D'Ambrosio, M. V., Bakalar, M., Bennuru, S., Reber, C., Skandarajah, A., Nilsson, L., Switz, N., Kamgno, J., Pion, S., Boussinesq, M., et al. (2015). Point-of-care quantification of blood-borne filarial parasites with a mobile phone microscope. Sci Transl Med. 7(286), 286re284. Published online 2015 May 8 DOI: 10.1126/scitranslmed.aaa3480.

Dong, E., Du, H., and Gardner, L. (2020). An interactive web-based dashboard to track COVID-19 in real time. Lancet Infect Dis. 20(5), 533-534.

East-Seletskv, A., O'Connell, M. R., Burstein, D., Knott, G. J., and Doudna. J. A. (2017). RNA Targeting by Functionally Orthogonal Type VI-A CRISPR-Cas Enzymes. Mol Cell. 66(3), 373-383 e373.

East-Seletsky, A., O'Connell, M. R., Knight, S. C., Burstein. D., Cate, J. H., Tjian, R., and Doudna, J. A. (2016). Two distinct RNase activities of CRISPR-C2c2 enable guide-RNA processing and RNA detection. Nature. 538(7624). 270-273.

Fung, T. S., and Liu, D.X. (2019). Human Coronavirus: Host-Pathogen Interaction. doi.org/10. 1146/annurev-micro-0205 J8-115759. DOI: 1 0. 1 146/annurev-micro-020518-11 5759.

Gootenberg, J. S., Abudayyeh, O. O., Kellner, M. J., Joung, J., Collins, J. J., and Zhang, F. (2018). Multiplexed and portable nucleic acid detection platform with Cas13, Cas12a, and Csm6. Science. 360(6387), 439-444.

Gootenberg, J. S., Abudayyeh, O. O., Lee. J. W., Essletzbichler, P., Dy, A. J., Joung, J., Verdine, V., Donghia, N., Daringer, N. M., Freije, C. A., et al. (2017). Nucleic acid detection with CRISPR-Cas13a/C2c2. Science. 356 (6336), 438-442.

Green, D. A., and StGeorge, K. (2018). Rapid Antigen Tests for Influenza: Rationale and Significance of the FDA Reclassification. J Clin Microbiol. 56(10). Published online 2018 Jun. 15 DOI: 10.1128/JCM.00711-18.

Gu W, Crawford E D, O'Donovan B D, Wilson M R, Chow E D, Retallack H, DeRisi J L. Depletion of Abundant Sequences by Hybridization (DASH): using Cas9 to remove unwanted high-abundance species in sequencing libraries and molecular counting applications. Genome Biol. BioMed Central, 2016 Mar. 4; 17(1):41.

Hoffmann M, Kleine-Weber H, Schroeder S, Krüger N. Herder T, Erichsen S, Schiergens T S, Herder G. Wu N-H, Nitsche A, Müller M A, Drosten C. Pöhlmann S. SARS-CoV-2 Cell Entry Depends on ACE2 and TMPRSS2 and Is Blocked by a Clinically Proven Protease Inhibitor. Cell. 2020 Mar. 4.

Hou, T., Zeng, W., Yang, M., Chen, W., Ren, L., Ai, J., Wu, J., Liao, Y., Gou, X., Li, Y., et al. (2020). Development and evaluation of a rapid CRISPR-based diagnostic for COVID-19. PLoS Pathog. 16(8), e1008705. Published online 2020 Aug. 28 DOI: 10.1371/journal.ppat.1008705.

Joung, J., Ladha, A., Saito, M., Segel, M., Bruneau, R., Huang, M. W., Kim, N. G., Yu, X., Li, J., Walker, B. D., et al. (2020). Point-of-care testing for COVID-19 using SHERLOCK diagnostics. medRxiv. Published online 2020 Jun. 9 DOI: 10.1101/2020.05.04.20091231.

Kamgno J, Pion S D, Chesnais C B, Bakalar M H, D'Ambrosio M V, Mackenzie C D, Nana-Djeunga H C, Gounoue-Kamkumo R, Njitchouang G-R, Nwane P, Tchatchueng-Mbouga J B, Wanji S. Stolk W A, Fletcher D A, Klion A D, Nutman T B, Boussinesq M. A Test-and-Not-Treat Strategy for Onchocerciasis in *Loa loa*-Endemic Areas. N Engl J Med. 2017 Nov. 23; 377(21): 2044-52.

Kang H, Feng M, Schroeder M E, Giedroc D P, Leibowitz J L. Putative cis-acting stem-loops in the 5' untranslated region of the severe acute respiratory syndrome coronavirus can substitute for their mouse hepatitis virus counterparts. Journal of Virology. 2006 November; 80(21): 10600-14.

La Scola, B., Le Bideau, M., Andreani, J., Hoang, V. T., Grimaldier, C., Colson, P., Gautret, P., and Raoult, D. (2020). Viral RNA load as determined by cell culture as a management tool for discharge of SARS-CoV-2 patients from infectious disease wards. Eur J Clin Microbiol Infect Dis. 39(6), 1059-1061. Published online 2020 Apr. 29 DOI: 10.1007/s10096-020-03913-9.

Larremore, D. B., Wilder, B., Lester, E., Shehata, S., Burke, J. M., Hay, J. A., Tambe, M., Mina, M. J., and Parker. R. (2020). Test sensitivity is secondary to frequency and turnaround time for COVID-19 surveillance. medRxiv. Published online 2020 Jul. 2 DOI: 10.1101/2020.06.22.20136309.

Lavezzo, E., Franchin, E., Ciavarella, C., Cuomo-Dannenburg, G., Barzon, L., Vecchio, C. D., Rossi, L., Manganelli, R., Loregian, A., Navarin, N., et al. (2020). Suppression of a SARS-CoV-2 outbreak in the Italian municipality of Vo'. Nature. 1-5. DOI: doi:10.1038/s41586-020-2488-1.

LeDuc, J. W., and Barry, M. A. (2004). SARS, the First Pandemic of the 21st Century1. In: Emerg Infect Dis, p. e26.

Lee, S., Kim, T., Lee, E., Lee, C., Kim, H., Rhee. H., Park, S. Y., Son, H. J., Yu, S., Park, J. W., et al. (2020). Clinical Course and Molecular Viral Shedding Among Asymptomatic and Symptomatic Patients With SARS-CoV-2 Infection in a Community Treatment Center in the Republic of Korea. JAMA Intern Med. Published online 2020 Aug. 12 DOI: 10.1001/jamainternmed.2020.3862.

Lin R, Skandarajah A, Gerver R E, Neira H D, Fletcher D A, Herr A E. A lateral electrophoretic flow diagnostic assay. Lab Chip. The Royal Society of Chemistry; 2015 Mar. 21; 15(6):1488-96.

Manfredonia, I., Nithin, C., Ponce-Salvatierra, A., Ghosh, P., Wirecki, T. K., Marinus, T., Ogando, N. S., Snider, E. J., Hemert, M. J. v., Bujnicki, J. M., et al. (2020). Genome-wide mapping of therapeutically-relevant SARS-CoV-2 RNA structures. DOI: 10.1101/2020.06.15.151647.

Myhrvold, C., Freije, C. A., Gootenberg, J S., Abudayych, O. O., Metsky, H. C., Durbin, A. F., Kellner, M. J., Tan, A. L., Paul, L. M., Parham, L. A., et al. (2018). Field-deployable viral diagnostics using CRISPR-Cas13. Science. 360(6387), 444-448. Published online 2018 Apr. 28 DOI: 10.1126/science.aas8836.

Osorio, N. S., and Correia-Neves, M. (2020). Implication of SARS-CoV-2 evolution in the sensitivity of R T-qPCR diagnostic assays. Lancet Infect Dis. Published online 2020 Jun. 1 DOI: 10.1016/S1473-3099(20)30435-7.

Quicke, K., Gallichote, E., Sexton, N., Young, M., Janich, A., Gahm, G., Carlton, E. J., Ehrhart, N., and Ebel, G. D.

(2020). Longitudinal Surveillance for SARS-CoV-2 RNA Among Asymptomatic Staff in Five Colorado Skilled Nursing Facilities: Epidemiologic, Virologic and Sequence Analysis. medRxiv. Published online 2020 Jun. 25 DOI: 10.1101/2020.06.08.20125989.

Richard, M., Kok, A., de Meulder, D., Bestebroer, T. M., Lamers, M. M., Okba, N. M. A., Fentener van Vlissingen, M., Rockx, B., Haagmans, B. L., Koopmans, M. P. G., et al. (2020). SARS-CoV-2 is transmitted via contact and via the air between ferrets. Nat Commun. 11(1), 3496. Published online 2020 Jul. 10 DOI: 10.1038/s41467-020-17367-2.

Sanders, W., Fritch, E. J., Madden, E. A., Graham, R. L., Vincent, H. A., Heise, M. T., Baric. R. S., and Moorman, N. J. (2020). Comparative analysis of coronavirus genomic RNA structure reveals conservation in SARS-like coronaviruses. bioRxiv. Published online 2020 Jun. 27 DOI: 10.1101/2020.06.15.153197.

Sharfstein J M, Becker S J, Mello M M. Diagnostic Testing for the Novel Coronavirus. JAMA. 2020 Mar. 9.

Skandarajah A, Reber C D. Switz N A, Fletcher D A. Quantitative imaging with a mobile phone microscope. PLoS ONE. 2014:9(5):e96906.

Smith Z J, Chu K, Espenson A R, Rahimzadeh M, Gryshuk A, Molinaro M, Dwyre D M, Lane S. Matthews D. Wachsmann-Hogiu S. Cell-phone-based platform for biomedical device development and education applications. PLoS ONE. 2011 Mar. 2; 6(3):c17150.

Smith, A. M., and Perelson, A. S. (2011). Influenza A virus infection kinetics: quantitative data and models. Wiley Interdiscip Rev Syst Biol Med. 3(4), 429-445. Published online 2011 Jan. 5 DOI: 10.1002/wsbm.129.

Vanaerschot, M., Mann, S. A., Webber, J. T., Kamm, J., Bell, S. M., Bell, J., Hong, S. N., Nguyen, M. P., Chan, L. Y., Bhatt, K. D., et al. (2020). Identification of a polymorphism in the N gene of SARS-CoV-2 that adversely impacts detection by a widely-used RT-PCR assay. bioRxiv.

Vogels, C. B. F., Brito, A. F., Wyllie, A. L., Fauver, J. R., Ott, I. M., Kalinich, C. C., Petrone, M. E., Casanovas-Massana, A., Muenker, M. C., Moore, A. J., et al. (2020). Analytical sensitivity and efficiency comparisons of SARS-CoV-2 RT-qPCR primer-probe sets. Nature Microbiology. 1-7. DOI: doi:10.1038/s41564-020-0761-6.

Wang, C., Horby, P. W., Hayden. F. G., and Gao, G. F. (2020). A novel coronavirus outbreak of global health concern. Lancet. 395(10223), 470-473. Published online 2020 Jan. 28 DOI: 10.1016/S0140-6736(20)30185-9.

Wang, W., Xu, Y., Gao, R., Lu, R., Han, K., Wu, G., and Tan, W. (2020). Detection of SARS-CoV-2 in Different Types of Clinical Specimens. JAMA. Published online 2020 Mar. 12 DOI: 10.1001/jama.2020.3786.

Wang D, Hu B, Hu C, Zhu F, Liu X. Zhang J. Wang B, Xiang H. Cheng Z. Xiong Y, Zhao Y, Li Y, Wang X, Peng Z. Clinical Characteristics of 138 Hospitalized Patients With 2019 Novel Coronavirus-Infected Pneumonia in Wuhan, China. JAMA. 2020 Feb. 7.

Walls A C, Park Y-J, Tortorici M A, Wall A. McGuire A T, Veesler D. Structure, Function, and Antigenicity of the SARS-CoV-2 Spike Glycoprotein. Cell. (Mar. 6, 2020).

Wiersinga, W. J., Division of Infectious Diseases, D.o.M., Amsterdam UMC, location AMC, University of Amsterdam, Amsterdam, the Netherlands, Center for Experimental and Molecular Medicine (CEMM), A.U., location AMC, University of Amsterdam, Amsterdam, the Netherlands, Rhodes, A., Department of Intensive Care Medicine, S.G.s.U.H.F.T., London, United Kingdom, Cheng, A. C., Infection Prevention and Healthcare Epidemiology Unit, A. H., Melbourne, Australia, School of Public Health and Preventive Medicine, M. U., Monash University, Melbourne, Australia, Peacock, S. J., National Infection Service, P.H.E., London, United Kingdom, et al. (2020). Pathophysiology, Transmission, Diagnosis, and Treatment of Coronavirus Disease 2019 (COVID-19): A Review. JAMA. 324(8), 782-793. DOI: 10.1001/jama.2020.12839.

Wolfel, R., Corman, V. M., Guggemos, W., Seilmaier, M., Zange, S., Muller, M. A., Niemeyer, D., Jones, T. C., Vollmar, P., Rothe, C., et al. (2020). Virological assessment of hospitalized patients with COVID-2019. Nature. 581(7809). 465-469.

Woelfel R, Corman V M, Guggemos W. Seilmaier M, Zange S. Mueller M A, Niemeyer D, Vollmar P, Rothe C. Hoelscher M, Bleicker T, Bruenink S, Schneider J. Ehmann R. Zwirglmaier K, Drosten C, Wendtner C. Clinical presentation and virological assessment of hospitalized cases of coronavirus disease 2019 in a travel-associated transmission cluster. medRxiv. Cold Spring Harbor Laboratory Press: 2020 Mar. 5: 1-16.

Wood, C. S., Thomas, M. R., Budd, J., Mashamba-Thompson. T. P., Herbst, K., Pillay. D., Peeling, R. W., Johnson, A. M., McKendry, R. A., and Stevens, M. M. (2019). Taking connected mobile-health diagnostics of infectious diseases to the field. Nature. 566(7745), 467-474. Published online 2019 Mar. 1 DOI: 10.1038/s41586-019-0956-2.

Wu Z, McGoogan J M. Characteristics of and Important Lessons From the Coronavirus Disease 2019 (COVID-19) Outbreak in China: Summary of a Report of 72 314 Cases From the Chinese Center for Disease Control and Prevention. JAMA. 2020 Feb. 24.

Yan R, Zhang Y, Li Y, Xia L, Guo Y, Zhou Q. Structural basis for the recognition of the SARS-CoV-2 by full-length human ACE2. Science. 2020 Mar. 4::eabb2762.

Yang D. Leibowitz J L. The structure and functions of coronavirus genomic 3' and 5' ends. Virus Research. 2015 Aug. 3; 206:120-33.

Young B E, Ong S W X, Kalimuddin S. Low J G, Tan S Y, Loh J, Ng O T, Marimuthu K, Ang L W, Mak T M, Lau S K, Anderson D E, Chan K S, Tan T Y, Ng T Y, Cui L, Said Z, Kurupatham L, Chen M I-C, Chan M, Vasoo S, Wang L-F, Tan B H, Lin R T P, Lee V J M, Leo Y S, Lye D C. for the Singapore 2019 Novel Coronavirus Outbreak Research Team. Epidemiologic Features and Clinical Course of Patients Infected With SARS-CoV-2 in Singapore. JAMA. 2020 Mar. 3; 1-7.

Zappa, A., Amendola, A., Romano, L., and Zanetti, A. (2009). Emerging and re-emerging viruses in the era of globalisation. Blood Transfus. 7(3), 167-171. Published online 2009 Aug. 7 DOI: 10.2450/2009.0076-08.

Zetsche, B., Gootenberg, J. S., Abudayyeh, O. O., Slaymaker, I. M., Makarova, K. S., Essletzbichler. P., Volz, S. E., Joung, J., van der Oost, J., Regev. A., et al. (2015). Cpf1 is a single RNA-guided endonuclease of a class 2 CRISPR-Cas system. Cell. 163(3), 759-771. Published online 2015 Oct. 1 DOI: 10.1016/j.cell.2015.09.038.

Zhang F, Abudayyeh 00, Jonathan S G. A protocol for detection of COVID-19 using CRISPR diagnostics.

Zhu, N., Zhang, D., Wang, W., Li, X., Yang, B., Song, J., Zhao, X., Huang, B., Shi, W., Lu, R., et al. (2020). A Novel Coronavirus from Patients with Pneumonia in China. 2019. N Engl J Med. 382(8), 727-733. Published online 2020 Jan. 25 DOI: 10.1056/NEJMoa2001017.

Zou L. Ruan F, Huang M, Liang L, Huang H. Hong Z, Yu J. Kang M, Song Y, Xia J, Guo Q, Song T, He J, Yen H-L, Peiris M, Wu J. SARS-CoV-2 Viral Load in Upper Respiratory Specimens of Infected Patients. N Engl J Med. 2020 Feb. 19.

All publications, patent applications, patents and other references mentioned herein are expressly incorporated by reference in their entirety, to the same extent as if each were incorporated by reference individually. In case of conflict, the present specification, including definitions, will control.

The following statements provide a summary of some aspects of the inventive nucleic acids and methods described herein.

Statements:

1. A method for diagnosing the presence or absence of a SARS-CoV-2 infection comprising:
   (a) incubating a sample suspected of containing RNA with a Cas13 protein, at least one CRISPR guide RNA (crRNA), and a reporter RNA for a period of time sufficient to form at least one RNA cleavage product: and
   (b) detecting any level of RNA cleavage product with a detector.

2. The method of statement 1, wherein the sample suspected of containing RNA is a lysed biological sample.

3. The method of any of the preceding statements, wherein the sample suspected of containing RNA is RNA extracted from a lysed biological sample.

4. The method of any of the preceding statements, wherein Cas13 protein and at least one CRISPR guide RNA (crRNA) are pre-incubated to from a ribonucleoprotein (RNP) complex, and the sample suspected of containing RNA is added to the ribonucleoprotein complex.

5. The method of any of the preceding statements, wherein cleavage of the reporter RNA produces a light signal (e.g., fluorescence or a detectable dye), an electronic signal, an electrochemical signal, an electrostatic signal, a steric signal, a van der Waals interaction signal, a hydration signal, a Resonant frequency shift signal, or a combination thereof.

6. The method of any of the preceding statements, wherein the reporter RNA is attached to a solid surface.

7. The method of any of statements 1-5, wherein the reporter RNA is not attached to a solid surface (e.g., not covalently bond to a solid surface).

8. The method of any of the preceding statements, wherein the reporter RNA reporter comprises at least one fluorophore and at least one fluorescence quencher.

9. The method of any of statement 8, wherein the at least one fluorophore is ALEXA FLUOR™430, STAR 520, BRILLIANT VIOLET™510, BRILLIANT VIOLET™605, BRILLIANT VIOLET™610, or a combination thereof.

10. The method of any of the preceding statements, wherein RNA in the sample suspected of containing RNA and/or the SARS-CoV-2 RNA cleavage product are not amplified.

11. The method of any of statements 1-9, wherein the RNA in the sample suspected of containing RNA and/or the SARS-CoV-2 RNA cleavage product is amplified using an RNA-Dependent RNA polymerase, a Qβ replicase, a SARS-CoV2 polymerase, or a combination thereof.

12. The method of any of the preceding statements, performed in an array comprising wells wherein each well comprises a Cas13 protein and at least one CRISPR guide RNA (crRNA) prior to incubating the sample suspected of containing RNA.

13. The method of any of the preceding statements, performed in a droplet assay.

14. The method of any of the preceding statements, wherein the sample suspected of containing RNA is saliva, sputum, mucus, nasopharyngeal materials, blood, serum, plasma, urine, aspirate, biopsy tissue, or a combination thereof.

15. The method of any of the preceding statements, wherein the detector comprises a light detector, a fluorescence detector, a color filter, an electronic detector, an electrochemical signal detector, an electrostatic signal detector, a steric signal detector, a van der Waals interaction signal detector, a hydration signal detector, a Resonant frequency shift signal detector, or a combination 16. The method of any one of the preceding statements, wherein the detector is a fluorescence detector.

17. The method of any one of the preceding statements, wherein the detector is a short quenched-fluorescent RNA detector, or Total Internal Reflection Fluorescence (TIRF) detector.

18. The method of any one of the preceding statements, wherein the detector is a mobile device.

19. The method of any of the preceding statements, further comprising reporting the presence or absence of SARS-CoV-2 in the sample to a subject who provided the sample suspected of containing RNA, to one or more medical personnel, to one or more government authorities, to a database, or to a combination thereof.

20. The method of any of the preceding statements, further comprising reporting a location of the subject who provided the sample suspected of containing RNA to one or more medical personnel, to one or more government authorities, to a database, or to a combination thereof.

21. The method of any one of the preceding statements, wherein at least one of the crRNA comprises a segment complementary to a SARS-CoV-2 RNA.

22. The method of any one of the preceding statements, wherein at least one of the crRNA comprises a segment that is not complementary to a SARS-CoV-2 RNA.

23. The method of any one of the preceding statements, wherein at least one of the crRNA comprises a segment complementary to a SARS-CoV-2 RNA and a spacer sequence.

24. The method of any one of the preceding statements, wherein the at least one crRNA comprises any one of SEQ ID NO: 1-35.

25. The method of any one of the preceding statements, wherein the at least one crRNA is or has a segment with a sequence corresponding to any of SEQ ID NO: 2, 3, 4, 7, 8, 9, 14, 23, or a combination thereof.

26. The method of any one of the preceding statements, wherein the at least one crRNA is or has a segment with sequence corresponding to any of SEQ ID NO:27-34.

27. The method of any one of the preceding statements, wherein the at least one crRNA has a segment comprising a sequence corresponding to any of crRNA sequences in Table 5 (SEQ ID NOs:58-147).

28. The method of any one of the preceding statements, wherein the sample is incubated with 2, 3, 4, 5, 6, 7, 8, 9, 10 or more crRNAs.

29. The method of any one of the preceding statements, further comprising depleting a portion of the sample prior to detecting step.

30. The method of statement 29, wherein the portion of the sample is a nucleic acid or protein.

31. The method of any one of the preceding statements, further comprising removing RNase from the sample.

32. The method of any one of the preceding statements, wherein the sample suspected of containing RNA with a Cas13 protein comprises an RNase inhibitor (e.g., added after collection).

33. The method of any one of the preceding statements, wherein the Cas13 protein and/or crRNA is lyophilized prior to incubation with the sample.

34. The method of any of the preceding statements, wherein the Cas 13 protein is a Cas13a or Cas13b protein.

35. The method of any of the preceding statements further comprising quantifying SARS-CoV-2 RNA concentration in the sample suspected of containing RNA.

36. The method of any of the preceding statements, wherein the SARS-CoV-2 RNA concentration or amount is determined using a standard curve of RNA reporter signals relative to known SARS-CoV-2 RNA concentrations or amounts.

37. The method of any of the preceding statements, wherein the SARS-CoV-2 RNA concentration or amount is determined using a ratio signal slope detected over a control signal slope.

38. The method of any of the preceding statements, wherein detectable SARS-CoV-2 is at least 2 copies SARS-CoV-2/µl sample, at least 5 copies SARS-CoV-2/µl sample, or at least 10 copies SARS-CoV-2/µl sample, or at least 20 copies SARS-CoV-2/µl sample, or at least 30 copies SARS-CoV-2/µl sample, or at least 40 copies SARS-CoV-2/µl sample, or at least 50 copies SARS-CoV-2/µl sample.

39. The method any of the preceding statements, wherein detectable SARS-CoV-2 is at least 2 copies SARS-CoV-2/ml sample, at least 5 copies SARS-CoV-2/ml sample, or at least 10 copies SARS-CoV-2/ml sample, or at least 20 copies SARS-CoV-2/ml sample, or at least 30 copies SARS-CoV-2/ml sample, or at least 40 copies SARS-CoV-2/ml sample, or at least 50 copies SARS-CoV-2/ml sample.

40. The method of any of the preceding statements, which has attomolar and zeptomolar sensitivity.

41. The method of any of the preceding statements, further comprising treating a patient with a sample that has detectable SARS-CoV-2 RNA.

42. A method comprising treating a subject with detectable SARS-CoV-2 detected by the method of any of statements 1-41.

43. The method of statement 42, comprising:
(a) incubating a reaction mixture comprising an RNA sample from the patient with a Cas13 protein, at least one CRISPR guide RNA (crRNA), and at least one RNA reporter for a period of time sufficient to form at least one RNA cleavage product;
(b) detecting a level of any RNA cleavage product(s) that are in the mixture with a detector; and
(c) treating a subject having detectable SARS-CoV-2 in the sample with a SARS-CoV-2 therapy.

44. The method of statement 43, wherein detectable SARS-CoV-2 is at least 2 copies SARS-CoV-2/µl sample, at least 5 copies SARS-CoV-2/µl sample, or at least 10 copies SARS-CoV-2/µl sample, or at least 20 copies SARS-CoV-2/µl sample, or at least 30 copies SARS-CoV-2/µl sample, or at least 40 copies SARS-CoV-2/µl sample, or at least 50 copies SARS-CoV-2/µl sample.

45. The method of statement 43, wherein detectable SARS-COV-2 is at least 2 copies SARS-COV-2/ml sample, at least 5 copies SARS-COV-2/ml sample, or at least 10 copies SARS-COV-2/ml sample, or at least 20 copies SARS-COV-2/ml sample, or at least 30 copies SARS-COV-2/ml sample, or at least 40 copies SARS-COV-2/ml sample, or at least 50 copies SARS-COV-2/ml sample.

46. The method of any of statements 43-45, wherein treating comprises administering to the subject one or more antiviral agent, antiretroviral therapy (ART), anti-viral antibody therapy, breathing support, steroids to reduce inflammation, steroids to reduce lung swelling, blood plasma transfusions, or a combination thereof.

47. The method of any of statements 43-46, wherein the reaction mixture comprises at least two, or at least three, or at least four, or at least five, or at least six, or at least seven, or at least eight CRISPR guide RNAs (crRNAs).

48. The method of any one of the preceding method statements, wherein the lysis buffer is or comprises PBS+1% Tween-20 with heating at 85° C. or above for 5 minutes.

49. The method of any one of the preceding method statements, wherein the buffer is at a pH of about 7.2 (or a range from a pH of about 6.0 to 8.0).

50. The method of any one of the preceding method statements, wherein two guides targeting the N gene (crRNA_2 and crRNA_4) and one guide targeting the E gene (crRNA_21) complexed together (for use in detection of SARS-CoV-2 virus).

51. The method of any one of the preceding method statements, wherein the guide length is about 30 nucleotide (nt) and 32 nt stem lengths (total 50 or 52 nt).

52. The method of any one of the preceding method statements, wherein background signal is reduced with size-based separation of cleaved and uncleaved probe.

53. The method of any one of the preceding method statements, wherein an increase in reaction signal is achieved with bead-based concentration of the cleaved probe.

54. The method of any one of the preceding method statements, wherein an increase in reaction signal is achieved with a droplet-based concentration of reaction signal in small volumes using polydisperse droplets.

55. The method of any one of the preceding method statements, wherein the detection of SARS-VoV-2 is guide-specific.

56. The method of any one of the preceding method statements, wherein assay is performed with a single guide.

57. The method of any one of the preceding method statements, wherein the assay is performed with multiple guides/a combination of guides.

58. A kit comprising a package containing at least one Cas13 protein, at least one SARS-CoV-2-specific CRISPR guide RNA (crRNA), at least one reporter RNA, and instructions for detecting and/or quantifying SARS-CoV-2 RNA in a sample (e.g., pursuant to the method of any of statements 1-35), where each of the CRISPR guide RNA(s) can have a sequence with at least 70% sequence identity to any one of SEQ ID NO: 1-35 (e.g., any of SEQ ID NO:1-15, 23, or 35) or at least 70% sequence identity to any one of the crRNA sequences shown in Table 5 (SEQ ID NOs: 58-147).

59. The kit of statement 58, wherein upon the reporter RNA comprises a fluorophore, a fluorescence quencher, a detectable dye, electrochemical moiety, a charged moiety, a sterically hindered moiety, sterically hindered configuration, or a combination thereof.

60. The kit of any of statements 58-59, wherein upon cleavage the reporter RNA produces a light signal (e.g., fluorescence or a detectable dye), an electronic signal, an electrochemical signal, an electrostatic signal, a steric signal, a van der Waals interaction signal, a hydration signal, a Resonant frequency shift signal, or a combination thereof.

61. The kit of any of statements 58-60, wherein the reporter RNA is at least one, at least two, or at least three short quenched-fluorescent RNA reporter.

62. The kit of any of statements 59-61, wherein the at least one fluorophore is ALEXA FLUOR™430, STAR 520, BRILLIANT VIOLET™510, BRILLIANT VIO-LET™605, BRILLIANT VIOLET™610, or a combination thereof.

63. The kit of any of statements 58-62, further comprising nuclease-free water, RNase, a buffer to regulate the pH of a solution, reaction vessel(s), one or more implements for collection of a sample from a patient.

64. The kit of any of statements 58-63, further comprising a therapeutic agent for treatment of SARS-CoV-2 infection.

65. The kit of any of statements 58-64, further comprising components for collecting the sample.

66. The kit of any of statements 58-65, further comprising components or instructions for reporting SARS-CoV-2 RNA in the sample.

67. The kit of any of statements 58-66, further comprising hardware for detecting fluorescence.

68. The kit of statement 67, wherein the hardware comprises a mobile device, a reaction chamber, an excitation source, an excitation filter, or a combination thereof.

69. The kit of any of statements 58-68, further comprising software for evaluating fluorescence signals, software for reporting SARS-CoV-2 RNA in the sample, or a combination thereof.

70. A composition comprising one or more CRISPR guide RNA(s) comprising a sequence comprising at least 70% sequence identity to any one of SEQ ID NO: 1-35 or a sequence comprising at least 70% sequence identity to any one of the crRNA sequences shown in Table 5 (SEQ ID NOs: 58-147).

71. The composition of statement 70, further comprising at least one Cas13a or Cas13b protein.

72. The composition of statement 70 or 71, further comprising at least one reporter RNA.

73. The composition of any one of statements 70-72, formulated so the one or more CRISPR guide RNA(s) form a complex with at least one Cas13a or Cas13b protein.

74. The composition of any one of statements 70-73, wherein the one or more CRISPR guide RNA(s) are complementary to a segment of a wild type SARS-CoV-2 RNA, a variant SARS-CoV-2 RNA, or a mutant SARS-CoV-2 RNA.

75. A system for detecting and/or quantifying SARS-CoV-2 RNA in a sample, the system comprising:
a signal generating system to excite the sample using a light signal of a first frequency;

a camera system to detect fluorescence in the sample; and processing circuitry to detect SARS-CoV-2 RNA in the sample based on the fluorescence.

76. The system of statement 75, wherein the camera system is included within a mobile device (in one embodiment the mobile device is a phone; in one embodiment, the phone has a camera in another embodiment, a microscope is used with the camera).

77. The system of any of statements 75 or 76, further comprising a communication interface and wherein the processing circuitry is configured to provide an indication, over the communication interface, of whether SARS-CoV-2 RNA was detected in the sample.

78. The system of any of statements 75-77, wherein the camera system includes a complementary metal-oxide semiconductor (CMOS) sensor.

79. The system of statement 78, wherein the sensor includes at least one-color filter.

80. The system of statement 78, wherein the color filter is positioned over alternating pixels in a pattern.

81. A system for detecting for detecting and/or quantifying SARS-CoV-2 RNA in a sample, the system comprising:
a cantilever sensor assembly including a reference cantilever and a sensor cantilever;

circuitry coupled to the cantilever sensor assembly and configured to detect a shift of resonant frequency of the sensor cantilever, the shift generated by binding of a molecule to the sensor cantilever.

82. The system of statement 81, wherein binding of the molecule changes stiffness of the sensor cantilever.

83. The system of statement 82, wherein the sensor cantilever comprises diamond.

84. The system of any of statements 81-83, further comprising a communication interface and wherein the processing circuitry is configured to provide an indication, over the communication interface, of whether SARS-CoV-2 RNA was detected in the sample.

85. The system of any of statements 81-84, wherein the circuitry comprises interferometry equipment.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

In addition, where the features or aspects of the invention are described in terms of Markush groups, those skilled in the art will recognize that the invention is also thereby described in terms of any individual member or subgroup members of the Markush group.

What is claimed is:

1. A method for diagnosing detecting the presence or absence of a SARS-CoV-2 infection comprising:

(a) incubating a sample suspected of containing SARS-COV-2 RNA with one or more Cas13 proteins comprising a sequence comprising at least 95% sequence identity to SEQ ID NO: 43 and a lysine at position 436, at least one CRISPR guide RNA (crRNA), and at least one reporter RNA for a period of time sufficient to form at least one RNA cleavage product; and (b) detecting reporter RNA cleavage product(s) with a detector.

2. The method of claim 1, wherein the at least one CRISPR guide RNA (crRNA) binds to a wild type SARS-COV-2 RNA.

3. The method of claim 1, wherein the at least one CRISPR guide RNA (crRNA) binds to a variant or mutant SARS-COV-2 RNA.

4. The method of claim 1, wherein the at least one CRISPR guide RNA (crRNA) has a sequence segment with at least 95% sequence identity to any of SEQ ID NO:1-35, 58-146, or 147.

5. The method of claim 1, wherein at least one of the CRISPR guide RNAs (crRNAs) has one of the following sequences: SEQ ID NO: 1-35, 58-146, or 147.

6. The method of claim 1, wherein the at least one CRISPR guide RNA (crRNA) is at least two, or at least three, or at least eight CRISPR guide RNAs (crRNAs).

7. The method of claim 1, wherein the Cas13 protein is complexed with the at least one CRISPR guide RNA (crRNA) prior to incubating the sample suspected of containing SARS-CoV-2 RNA with the Cas13 protein, the at least one CRISPR guide RNA (crRNA), and the at least one reporter RNA.

8. The method of claim 1, wherein the sample suspected of containing RNA is saliva, sputum, mucus, nasopharyngeal materials, blood, serum, plasma, urine, aspirate, biopsy tissue, or a combination thereof.

9. The method of claim 1, wherein the sample suspected of containing RNA is a lysed biological sample.

10. The method of claim 1, wherein cleavage of the at least one reporter RNA produces a light signal, an electronic signal, an electrochemical signal, an electrostatic signal, a steric signal, a van der Waals interaction signal, a hydration signal, a Resonant frequency shift signal, or a combination thereof.

11. The method of claim 1, wherein the at least one reporter RNA reporter comprises at least one fluorophore and at least one fluorescence quencher.

12. The method of claim 1, wherein the detector comprises a light detector, a fluorescence detector, a color filter, an electronic detector, an electrochemical signal detector, an electrostatic signal detector, a steric signal detector, a van der Waals interaction signal detector, a hydration signal detector, a Resonant frequency shift signal detector, or a combination thereof.

13. The method of claim 1, wherein SARS-COV-2 RNA is detected when a signal from the at least one reporter RNA cleavage product(s) is distinguishable from a signal from a control assay.

14. The method of claim 13, wherein the control assay contains no SARS-COV-2 viral RNA.

15. A method comprising treating a subject having SARS-COV-2 RNA, wherein the SARS-COV-2 RNA is detected by the method of claim 1.

16. The method of claim 1, wherein treating comprises administering to the subject antiviral therapy, antiretroviral therapy, breathing support, steroids, blood plasma transfusions, anti-SARS-COV-2 antibodies, or a combination thereof.

17. A kit comprising a package containing at least one Cas13 protein comprising a sequence having at least 95% sequence identity to SEQ ID NO: 43 and a lysine at position 436, at least one SARS-COV-2-specific CRISPR guide RNA (crRNA), at least one reporter RNA, and instructions for detecting and/or quantifying SARS-COV-2 RNA in a sample.

18. The kit of claim 17 wherein the at least one CRISPR guide RNA (crRNA) has a sequence with at least 95% sequence identity to any of SEQ ID NO:1-35, 58-146, or 147.

19. The kit of claim 17, wherein at least one of the at least one CRISPR guide RNAs (crRNAs) has the sequence of SEQ ID NO: 1-35, 58-146, or 147.

20. The kit of claim 17, wherein the at least one CRISPR guide RNA (crRNA) is at least two, or at least three, or at least eight CRISPR guide RNAs (crRNAs).

21. The kit of claim 17, wherein the at least one Cas13 protein is complexed with the at least one CRISPR guide RNA (crRNA).

22. The kit of claim 17, wherein the at least one reporter RNA comprises at least one fluorophore and at least one fluorescence quencher.

23. The kit of claim 17, further comprising a sample chamber, assay mixture reaction chamber, or a combination thereof.

24. The kit of claim 17, further comprising a detector.

25. A system for detecting and/or quantifying SARS-COV-2RNA in a sample, the system comprising:
a signal generating system to excite the sample using a signal of a first frequency;
a camera system to detect fluorescence in the sample;
a sample cartridge arranged to receive the signal, the sample cartridge comprising at least one Cas13 protein and at least one reporter RNA, the least one Cas13 protein having comprising a sequence having at least 95% sequence identity to SEQ ID NO: 43 and a lysine at position 436; and
processing circuitry to detect SARS-COV-2 RNA in the sample based on the fluorescence.

26. The system of claim 25, further comprising at least one CRISPR guide RNA (crRNA) comprising a sequence having at least 95% sequence identity to any of SEQ ID NO:1-35, 58-146, or 147.

27. The system of claim 25, further comprising at least one CRISPR guide RNA (crRNA) comprising one of the following sequences: SEQ ID NO:1-35,58-146, or 147.

28. A fluorescence imaging system comprising:
a system housing;
an excitation source that generates excitation illumination along an illumination vector within the system housing;
a sample cartridge having one or more cartridge chambers having elongate profiles, the one or more cartridge chambers that retain one or more samples therein, wherein the sample cartridge contains at least one CRISPR guide RNA (crRNA) that comprises a sequence having at least 95% sequence identity to any of SEQ ID NO:1-35, 58-89 91-146, or 147;
a cartridge socket that receives the sample cartridge;
an optical sensor; and
wherein reception of the sample cartridge by the cartridge socket orients the one or more cartridge chambers to an excitation orientation and an observation orientation;

in the excitation orientation the elongate profiles of the cartridge chambers are aligned with the illumination vector of the excitation illumination; and the excitation illumination extends along the elongate profiles according to the alignment; and
in the observation orientation the cartridge chambers and fluorescence from the cartridge chambers are directed toward the optical sensor, wherein;
the sample cartridge further contains at least one Cas13 protein and at least one reporter RNA;
the at least one Cas13 protein comprising a sequence having at least 95% sequence identity to SEQ ID NO: 43 and a lysine at position 436.

29. The fluorescence imaging system of claim 28, wherein the at least one of CRISPR guide RNA (crRNAs) comprises one of the following sequences: SEQ ID NO: 1-35, 58-89, 91-146, or 147.

30. The fluorescence imaging system of claim 28, wherein the cartridge socket has a complementary socket profile to a cartridge profile of the sample cartridge, and coupling of the cartridge profile with the complementary socket profile orients the one or more cartridge chambers to the excitation orientation and the observation orientation.

31. The fluorescence imaging system of claim 28, wherein in the excitation orientation the one or more cartridge chambers is aligned with a component vector of the excitation illumination.

32. The fluorescence imaging system of claim 28, wherein the sample cartridge includes chamber walls surrounding the cartridge chambers; and
in the excitation orientation the cartridge chambers aligned with the excitation illumination includes the excitation illumination aligned with the chamber walls.

33. The fluorescence imaging system of claim 28, wherein in the excitation orientation the cartridge chambers aligned with the excitation illumination includes the cartridge chambers parallel to the excitation illumination.

34. The fluorescence imaging system of claim 28, wherein in the observation orientation scattered illumination from the sample cartridge is misaligned with the optical sensor.

35. The fluorescence imaging system of claim 28, comprising a mobile device, wherein the mobile device comprises the optical sensor.

36. The fluorescence imaging system of claim 28, comprising an emission filter interposed between the sample cartridge and the optical sensor, wherein the emission filter transmits light having a wavelength between 500 to 570 nanometers.

37. The fluorescence imaging system of claim 28 comprising:
objective optics proximate to the sample cartridge and remote relative to the optical sensor, the objective optics having one or more component objective lenses; and
imaging optics proximate to the optical sensor and remote relative to the sample cartridge, the imaging optics having one or more component imaging lenses.

38. The fluorescence imaging system of claim 37, wherein in the excitation orientation the objective optics telecentrically illuminates the cartridge chambers with the excitation illumination.

39. The fluorescence imaging system of claim 37, wherein in the observation orientation, the objective optics and the imaging optics telecentrically direct the fluorescence toward the optical sensor.

40. The fluorescence imaging system of claim 37, comprising an emission filter interposed between the imaging optics and the optical sensor; and in the observation orientation, the imaging optics telecentrically direct the fluorescence toward the emission filter.

41. The fluorescence imaging system of claim 37, comprising a dichromatic mirror interposed between the objective optics and the imaging optics, and the dichromatic mirror directs the excitation illumination toward the cartridge chambers and transmits the fluorescence from the cartridge chambers toward the optical sensor.

42. The fluorescence imaging system of claim 37, wherein the objective optics and imaging optics provide a numerical aperture (NA) of 0.04 to 0.09, a field of view (FOV) of 10 mm to 20 mm diameter, and an optical track length of 70 mm to 80 mm.

43. The fluorescence imaging system of claim 42, wherein the objective optics and imaging optics provide a numerical aperture (NA) of 0.09, a field of view (FOV) of 12 mm diameter, and an optical track length of 75 mm.

44. The fluorescence imaging system of claim 43, wherein each of the one or more cartridge chambers are within the FOV.

45. The fluorescence imaging system of claim 28 comprising imaging optics interposed between the optical sensor and the sample cartridge, the imaging optics having one or more component imaging lenses.

46. The fluorescence imaging system of claim 45, wherein the imaging optics provide a numerical aperture (NA) of 0.06, a field of view (FOV) of 15×15 mm, and an excitation illumination power of 20 mW.

47. The fluorescence imaging system of claim 45 comprising a mobile device having mobile device optics and the optical sensor, wherein the imaging optics include the mobile device optics.

48. The fluorescence imaging system of claim 28, wherein the excitation source includes one or more of an LED generator or laser generator.

49. The fluorescence imaging system of claim 28, wherein in the excitation orientation, alignment between the elongate profiles of the cartridge chambers and the illumination vector of the excitation illumination decreases shadows cast into the cartridge chambers.

50. The fluorescence imaging system of claim 28, wherein in the excitation orientation, alignment between the elongate profiles of the cartridge chambers and the illumination vector of the excitation illumination fills chamber volumes of the cartridge chambers.

51. The fluorescence imaging system of claim 28, wherein the sample cartridge further comprises at least one or more Cas13 proteins having the sequence of any of SEQ ID NO: 36-48.

52. A composition comprising one or more CRISPR guide RNA(s) comprising a sequence having at least 95% sequence identity to any one of SEQ ID NO:1-35, 58-146, or 147 and at least one Cas13 protein comprising a sequence having at least 95% sequence identity to SEQ ID NO: 43 and a lysine at position 436.

53. The composition of claim 52, comprising one or more CRISPR guide RNA(s) comprising any one of SEQ ID NO:1-35, 58-146, or 147.

54. A modified Cas13 protein with increased in vivo endonuclease activity compared to an unmodified Cas13 protein, wherein the modified Cas13 protein has at least 95% sequence identity to SEQ ID NO: 43 and has a lysine (K) at position 436 of a wildtype Cas13 protein.

55. The modified Cas13 protein of claim 54, wherein the wild type Cas13 protein has a glutamic acid (E) at position 436.

56. The modified Cas13 protein of claim 54, which increases sensitivity of detecting at least one reporter RNA by about 10-fold to 100-fold in a method comprising:

(a) incubating a sample suspected of containing SARS-COV-2 RNA with the modified Cas13 protein, at least one CRISPR guide RNA (crRNA), and the at least one reporter RNA for a period of time sufficient to form at least one RNA cleavage product; and (b) detecting reporter RNA cleavage product(s) with a detector.

57. The modified Cas13 protein of claim 54, wherein the modified Cas13 protein has the sequence of SEQ ID NO:43.

\* \* \* \* \*

SEQUENCE LISTING

<160> NUMBER OF SEQ ID NOS: 220

<210> SEQ ID NO 1
<211> LENGTH: 50
<212> TYPE: RNA
<213> ORGANISM: Artificial Sequence
<220> FEATURE:
<223> OTHER INFORMATION: A synthetic sequence

<400> SEQUENCE: 1
gaccacccca aaaaugaagg ggacuaaaac uuucgcugau uuuggggucc                50

<210> SEQ ID NO 2
<211> LENGTH: 50
<212> TYPE: RNA
<213> ORGANISM: Artificial Sequence
<220> FEATURE:
<223> OTHER INFORMATION: A synthetic sequence

<400> SEQUENCE: 2
gaccacccca aaaaugaagg ggacuaaaac gguccaccaa acguaaugcg                50

<210> SEQ ID NO 3
<211> LENGTH: 50
<212> TYPE: RNA
<213> ORGANISM: Artificial Sequence
<220> FEATURE:
<223> OTHER INFORMATION: A synthetic sequence

<400> SEQUENCE: 3
gaccacccca aaaaugaagg ggacuaaaac ucugguuacu gccaguugaa                50

<210> SEQ ID NO 4
<211> LENGTH: 50
<212> TYPE: RNA
<213> ORGANISM: Artificial Sequence
<220> FEATURE:
<223> OTHER INFORMATION: A synthetic sequence

<400> SEQUENCE: 4
gaccacccca aaaaugaagg ggacuaaaac uuugcggcca auguuuguaa                50

<210> SEQ ID NO 5
<211> LENGTH: 50
<212> TYPE: RNA
<213> ORGANISM: Artificial Sequence
<220> FEATURE:
<223> OTHER INFORMATION: A synthetic sequence

<400> SEQUENCE: 5
gaccacccca aaaaugaagg ggacuaaaac gaagcgcugg gggcaaauug                50

<210> SEQ ID NO 6
<211> LENGTH: 50
<212> TYPE: RNA
<213> ORGANISM: Artificial Sequence
<220> FEATURE:
<223> OTHER INFORMATION: A synthetic sequence

<400> SEQUENCE: 6
gaccacccca aaaaugaagg ggacuaaaac augcgcgaca uuccgaagaa                50

<210> SEQ ID NO 7
<211> LENGTH: 50
<212> TYPE: RNA
<213> ORGANISM: Artificial Sequence -continued
<220> FEATURE:
<223> OTHER INFORMATION: A synthetic sequence

<400> SEQUENCE: 7 gaccaccccca aaaaugaagg ggacuaaaac uuggguguauu caaggcuccc                50

<210> SEQ ID NO 8
<211> LENGTH: 50
<212> TYPE: RNA
<213> ORGANISM: Artificial Sequence
<220> FEATURE:
<223> OTHER INFORMATION: A synthetic sequence

<400> SEQUENCE: 8 gaccaccccca aaaaugaagg ggacuaaaac ggauugcggg ugccaaugug                50

<210> SEQ ID NO 9
<211> LENGTH: 50
<212> TYPE: RNA
<213> ORGANISM: Artificial Sequence
<220> FEATURE:
<223> OTHER INFORMATION: A synthetic sequence

<400> SEQUENCE: 9 gaccaccccca aaaaugaagg ggacuaaaac uguagcacga uugcagcauu                50

<210> SEQ ID NO 10
<211> LENGTH: 50
<212> TYPE: RNA
<213> ORGANISM: Artificial Sequence
<220> FEATURE:
<223> OTHER INFORMATION: A synthetic sequence

<400> SEQUENCE: 10 gaccaccccca aaaaugaagg ggacuaaaac uaaguguaaa acccacaggg                50

<210> SEQ ID NO 11
<211> LENGTH: 50
<212> TYPE: RNA
<213> ORGANISM: Artificial Sequence
<220> FEATURE:
<223> OTHER INFORMATION: A synthetic sequence

<400> SEQUENCE: 11 gaccaccccca aaaaugaagg ggacuaaaac uaaccuuucc acauaccgca                50

<210> SEQ ID NO 12
<211> LENGTH: 50
<212> TYPE: RNA
<213> ORGANISM: Artificial Sequence
<220> FEATURE:
<223> OTHER INFORMATION: A synthetic sequence

<400> SEQUENCE: 12 gaccaccccca aaaaugaagg ggacuaaaac ucagcugaug cacaaucguu                50

<210> SEQ ID NO 13
<211> LENGTH: 50
<212> TYPE: RNA
<213> ORGANISM: Artificial Sequence
<220> FEATURE:
<223> OTHER INFORMATION: A synthetic sequence

<400> SEQUENCE: 13 gaccaccccca aaaaugaagg ggacuaaaac ucuagcagga gaaguucccc                50

-continued

```
<210> SEQ ID NO 14
<211> LENGTH: 50
<212> TYPE: RNA
<213> ORGANISM: Artificial Sequence
<220> FEATURE:
<223> OTHER INFORMATION: A synthetic sequence

<400> SEQUENCE: 14 gaccaccccca aaaugaagg ggacuaaaac ucugucaagc agcagcaaag          50

<210> SEQ ID NO 15
<211> LENGTH: 50
<212> TYPE: RNA
<213> ORGANISM: Artificial Sequence
<220> FEATURE:
<223> OTHER INFORMATION: A synthetic sequence

<400> SEQUENCE: 15 gaccaccccca aaaugaagg ggacuaaaac cuuugcugcu gcuugacaga          50

<210> SEQ ID NO 16
<211> LENGTH: 50
<212> TYPE: RNA
<213> ORGANISM: Artificial Sequence
<220> FEATURE:
<223> OTHER INFORMATION: A synthetic sequence

<400> SEQUENCE: 16 gaccaccccca aaaugaagg ggacuaaaac aacgauugug caucagcuga          50

<210> SEQ ID NO 17
<211> LENGTH: 50
<212> TYPE: RNA
<213> ORGANISM: Artificial Sequence
<220> FEATURE:
<223> OTHER INFORMATION: A synthetic sequence

<400> SEQUENCE: 17 gaccaccccca aaaugaagg ggacuaaaac gacauuuugc ucucaagcug          50

<210> SEQ ID NO 18
<211> LENGTH: 50
<212> TYPE: RNA
<213> ORGANISM: Artificial Sequence
<220> FEATURE:
<223> OTHER INFORMATION: A synthetic sequence

<400> SEQUENCE: 18 gaccaccccca aaaugaagg ggacuaaaac guuccugguc cccaaaauuu          50

<210> SEQ ID NO 19
<211> LENGTH: 50
<212> TYPE: RNA
<213> ORGANISM: Artificial Sequence
<220> FEATURE:
<223> OTHER INFORMATION: A synthetic sequence

<400> SEQUENCE: 19 gaccaccccca aaaugaagg ggacuaaaac uggcaccugu guaggucaac          50

<210> SEQ ID NO 20
<211> LENGTH: 50
<212> TYPE: RNA
<213> ORGANISM: Artificial Sequence
<220> FEATURE:
<223> OTHER INFORMATION: A synthetic sequence
```

-continued

<400> SEQUENCE: 20
gaccacccca aaaaugaagg ggacuaaaac uccaugccaa ugcgcgacau                50

<210> SEQ ID NO 21
<211> LENGTH: 50
<212> TYPE: RNA
<213> ORGANISM: Artificial Sequence
<220> FEATURE:
<223> OTHER INFORMATION: A synthetic sequence

<400> SEQUENCE: 21
gaccacccca aaaugaagg ggacuaaaac cuauuaacua uuaacguacc                50

<210> SEQ ID NO 22
<211> LENGTH: 50
<212> TYPE: RNA
<213> ORGANISM: Artificial Sequence
<220> FEATURE:
<223> OTHER INFORMATION: A synthetic sequence

<400> SEQUENCE: 22
gaccacccca aaaugaagg ggacuaaaac uauugcagca guacgcacac                50

<210> SEQ ID NO 23
<211> LENGTH: 50
<212> TYPE: RNA
<213> ORGANISM: Artificial Sequence
<220> FEATURE:
<223> OTHER INFORMATION: A synthetic sequence

<400> SEQUENCE: 23
gaccacccca aaaugaagg ggacuaaaac agcgcaguaa ggauggcuag                50

<210> SEQ ID NO 24
<211> LENGTH: 50
<212> TYPE: RNA
<213> ORGANISM: Artificial Sequence
<220> FEATURE:
<223> OTHER INFORMATION: A synthetic sequence

<400> SEQUENCE: 24
gaccacccca aaaugaagg ggacuaaaac guaacuagca agaauaccac                50

<210> SEQ ID NO 25
<211> LENGTH: 52
<212> TYPE: RNA
<213> ORGANISM: Artificial Sequence
<220> FEATURE:
<223> OTHER INFORMATION: A synthetic sequence

<400> SEQUENCE: 25
uagaccaccc caaaaaugaa ggggacuaaa acgguccacc aaacguaaug cg             52

<210> SEQ ID NO 26
<211> LENGTH: 52
<212> TYPE: RNA
<213> ORGANISM: Artificial Sequence
<220> FEATURE:
<223> OTHER INFORMATION: A synthetic sequence

<400> SEQUENCE: 26
uagaccaccc caaaaaugaa ggggacuaaa acgguccacc aaacguaaug cg             52

<210> SEQ ID NO 27

```
<211> LENGTH: 52
<212> TYPE: RNA
<213> ORGANISM: Artificial Sequence
<220> FEATURE:
<223> OTHER INFORMATION: A synthetic sequence

<400> SEQUENCE: 27
uagaccaccc caaaaaugaa ggggacuaaa accgcauuac guuuggugga cc                52

<210> SEQ ID NO 28
<211> LENGTH: 52
<212> TYPE: RNA
<213> ORGANISM: Artificial Sequence
<220> FEATURE:
<223> OTHER INFORMATION: A synthetic sequence

<400> SEQUENCE: 28
uagaccaccc caaaaaugaa ggggacuaaa acuuacaaac auuggccgca aa                52

<210> SEQ ID NO 29
<211> LENGTH: 52
<212> TYPE: RNA
<213> ORGANISM: Artificial Sequence
<220> FEATURE:
<223> OTHER INFORMATION: A synthetic sequence

<400> SEQUENCE: 29
uagaccaccc caaaaaugaa ggggacuaaa acaaacuacg ucaucaagcc aa                52

<210> SEQ ID NO 30
<211> LENGTH: 52
<212> TYPE: RNA
<213> ORGANISM: Artificial Sequence
<220> FEATURE:
<223> OTHER INFORMATION: A synthetic sequence

<400> SEQUENCE: 30
uagaccaccc caaaaaugaa ggggacuaaa accacaguca uaaucuaugu ua                52

<210> SEQ ID NO 31
<211> LENGTH: 52
<212> TYPE: RNA
<213> ORGANISM: Artificial Sequence
<220> FEATURE:
<223> OTHER INFORMATION: A synthetic sequence

<400> SEQUENCE: 31
uagaccaccc caaaaaugaa ggggacuaaa acucacacuu uucuaauagc au                52

<210> SEQ ID NO 32
<211> LENGTH: 52
<212> TYPE: RNA
<213> ORGANISM: Artificial Sequence
<220> FEATURE:
<223> OTHER INFORMATION: A synthetic sequence

<400> SEQUENCE: 32
uagaccaccc caaaaaugaa ggggacuaaa acuguaagau uaacacacug ac                52

<210> SEQ ID NO 33
<211> LENGTH: 52
<212> TYPE: RNA
<213> ORGANISM: Artificial Sequence
<220> FEATURE:
<223> OTHER INFORMATION: A synthetic sequence

<400> SEQUENCE: 33
``` uagaccacccc caaaaaugaa ggggacuaaa acuuaauugu guacaaaaac ug                52

<210> SEQ ID NO 34
<211> LENGTH: 52
<212> TYPE: RNA
<213> ORGANISM: Artificial Sequence
<220> FEATURE:
<223> OTHER INFORMATION: A synthetic sequence

<400> SEQUENCE: 34 uagaccacccc caaaaaugaa ggggacuaaa accaguugug augauuccua ag                52

<210> SEQ ID NO 35
<211> LENGTH: 52
<212> TYPE: RNA
<213> ORGANISM: Artificial Sequence
<220> FEATURE:
<223> OTHER INFORMATION: A synthetic sequence

<400> SEQUENCE: 35 uagaccacccc caaaaaugaa ggggacuaaa acagcgcagu aaggauggcu ag                52

<210> SEQ ID NO 36
<211> LENGTH: 1177
<212> TYPE: PRT
<213> ORGANISM: Leptotrichia wadei

<400> SEQUENCE: 36

Met Lys Ile Thr Lys Ile Asp Gly Val Ser His Tyr Lys Lys Gln Asp
1               5                   10                  15

Lys Gly Ile Leu Lys Lys Lys Trp Lys Asp Leu Asp Glu Arg Lys Gln
            20                  25                  30

Arg Glu Lys Ile Glu Ala Arg Tyr Asn Lys Gln Ile Glu Ser Lys Ile
        35                  40                  45

Tyr Lys Glu Phe Phe Arg Leu Lys Asn Lys Lys Arg Ile Glu Lys Glu
    50                  55                  60

Glu Asp Gln Asn Ile Lys Ser Leu Tyr Phe Phe Ile Lys Glu Leu Tyr
65                  70                  75                  80

Leu Asn Glu Lys Asn Glu Glu Trp Glu Leu Lys Asn Ile Asn Leu Glu
                85                  90                  95

Ile Leu Asp Asp Lys Glu Arg Val Ile Lys Gly Tyr Lys Phe Lys Glu
            100                 105                 110

Asp Val Tyr Phe Phe Lys Glu Gly Tyr Lys Glu Tyr Tyr Leu Arg Ile
            115                 120                 125

Leu Phe Asn Asn Leu Ile Glu Lys Val Gln Asn Glu Asn Arg Glu Lys
        130                 135                 140

Val Arg Lys Asn Lys Glu Phe Leu Asp Leu Lys Glu Ile Phe Lys Lys
145                 150                 155                 160

Tyr Lys Asn Arg Lys Ile Asp Leu Leu Leu Lys Ser Ile Asn Asn Asn
                165                 170                 175

Lys Ile Asn Leu Glu Tyr Lys Lys Glu Asn Val Asn Glu Glu Ile Tyr
            180                 185                 190

Gly Ile Asn Pro Thr Asn Asp Arg Glu Met Thr Phe Tyr Glu Leu Leu
            195                 200                 205

Lys Glu Ile Ile Glu Lys Lys Asp Glu Gln Lys Ser Ile Leu Glu Glu
    210                 215                 220

Lys Leu Asp Asn Phe Asp Ile Thr Asn Phe Leu Glu Asn Ile Glu Lys
225                 230                 235                 240

-continued

```
Ile Phe Asn Glu Glu Thr Glu Ile Asn Ile Ile Lys Gly Lys Val Leu
              245                 250                 255

Asn Glu Leu Arg Glu Tyr Ile Lys Glu Lys Glu Glu Asn Asn Ser Asp
              260                 265                 270

Asn Lys Leu Lys Gln Ile Tyr Asn Leu Glu Leu Lys Lys Tyr Ile Glu
              275                 280                 285

Asn Asn Phe Ser Tyr Lys Lys Gln Lys Ser Lys Ser Lys Asn Gly Lys
    290                 295                 300

Asn Asp Tyr Leu Tyr Leu Asn Phe Leu Lys Lys Ile Met Phe Ile Glu
305                 310                 315                 320

Glu Val Asp Glu Lys Lys Glu Ile Asn Lys Glu Lys Phe Lys Asn Lys
              325                 330                 335

Ile Asn Ser Asn Phe Lys Asn Leu Phe Val Gln His Ile Leu Asp Tyr
              340                 345                 350

Gly Lys Leu Leu Tyr Tyr Lys Glu Asn Asp Glu Tyr Ile Lys Asn Thr
              355                 360                 365

Gly Gln Leu Glu Thr Lys Asp Leu Glu Tyr Ile Lys Thr Lys Glu Thr
    370                 375                 380

Leu Ile Arg Lys Met Ala Val Leu Val Ser Phe Ala Ala Asn Ser Tyr
385                 390                 395                 400

Tyr Asn Leu Phe Gly Arg Val Ser Gly Asp Ile Leu Gly Thr Glu Val
              405                 410                 415

Val Lys Ser Ser Lys Thr Asn Val Ile Lys Val Gly Ser His Ile Phe
              420                 425                 430

Lys Glu Lys Met Leu Asn Tyr Phe Phe Asp Phe Glu Ile Phe Asp Ala
              435                 440                 445

Asn Lys Ile Val Glu Ile Leu Glu Ser Ile Ser Tyr Ser Ile Tyr Asn
    450                 455                 460

Val Arg Asn Gly Val Gly His Phe Asn Lys Leu Ile Leu Gly Lys Tyr
465                 470                 475                 480

Lys Lys Lys Asp Ile Asn Thr Asn Lys Arg Ile Glu Glu Asp Leu Asn
              485                 490                 495

Asn Asn Glu Glu Ile Lys Gly Tyr Phe Ile Lys Lys Arg Gly Glu Ile
              500                 505                 510

Glu Arg Lys Val Lys Glu Lys Phe Leu Ser Asn Asn Leu Gln Tyr Tyr
              515                 520                 525

Tyr Ser Lys Glu Lys Ile Glu Asn Tyr Phe Glu Val Tyr Glu Phe Glu
    530                 535                 540

Ile Leu Lys Arg Lys Ile Pro Phe Ala Pro Asn Phe Lys Arg Ile Ile
545                 550                 555                 560

Lys Lys Gly Glu Asp Leu Phe Asn Asn Lys Asn Asn Lys Lys Tyr Glu
              565                 570                 575

Tyr Phe Lys Asn Phe Asp Lys Asn Ser Ala Glu Glu Lys Lys Glu Phe
              580                 585                 590

Leu Lys Thr Arg Asn Phe Leu Leu Lys Glu Leu Tyr Tyr Asn Asn Phe
              595                 600                 605

Tyr Lys Glu Phe Leu Ser Lys Lys Glu Glu Phe Glu Lys Ile Val Leu
    610                 615                 620

Glu Val Lys Glu Glu Lys Lys Ser Arg Gly Asn Ile Asn Asn Lys Lys
625                 630                 635                 640

Ser Gly Val Ser Phe Gln Ser Ile Asp Asp Tyr Asp Thr Lys Ile Asn
              645                 650                 655
```

```
Ile Ser Asp Tyr Ile Ala Ser Ile His Lys Lys Glu Met Glu Arg Val
            660                 665                 670

Glu Lys Tyr Asn Glu Glu Lys Gln Lys Asp Thr Ala Lys Tyr Ile Arg
            675                 680                 685

Asp Phe Val Glu Glu Ile Phe Leu Thr Gly Phe Ile Asn Tyr Leu Glu
            690                 695                 700

Lys Asp Lys Arg Leu His Phe Leu Lys Glu Glu Phe Ser Ile Leu Cys
705                 710                 715                 720

Asn Asn Asn Asn Asn Val Val Asp Phe Asn Ile Asn Ile Asn Glu Glu
                725                 730                 735

Lys Ile Lys Glu Phe Leu Lys Glu Asn Asp Ser Lys Thr Leu Asn Leu
            740                 745                 750

Tyr Leu Phe Phe Asn Met Ile Asp Ser Lys Arg Ile Ser Glu Phe Arg
            755                 760                 765

Asn Glu Leu Val Lys Tyr Lys Gln Phe Thr Lys Lys Arg Leu Asp Glu
            770                 775                 780

Glu Lys Glu Phe Leu Gly Ile Lys Ile Glu Leu Tyr Glu Thr Leu Ile
785                 790                 795                 800

Glu Phe Val Ile Leu Thr Arg Glu Lys Leu Asp Thr Lys Lys Ser Glu
                805                 810                 815

Glu Ile Asp Ala Trp Leu Val Asp Lys Leu Tyr Val Lys Asp Ser Asn
                820                 825                 830

Glu Tyr Lys Glu Tyr Glu Glu Ile Leu Lys Leu Phe Val Asp Glu Lys
            835                 840                 845

Ile Leu Ser Ser Lys Glu Ala Pro Tyr Tyr Ala Thr Asp Asn Lys Thr
            850                 855                 860

Pro Ile Leu Leu Ser Asn Phe Glu Lys Thr Arg Lys Tyr Gly Thr Gln
865                 870                 875                 880

Ser Phe Leu Ser Glu Ile Gln Ser Asn Tyr Lys Tyr Ser Lys Val Glu
                885                 890                 895

Lys Glu Asn Ile Glu Asp Tyr Asn Lys Lys Glu Glu Ile Glu Gln Lys
            900                 905                 910

Lys Lys Ser Asn Ile Glu Lys Leu Gln Asp Leu Lys Val Glu Leu His
            915                 920                 925

Lys Lys Trp Glu Gln Asn Lys Ile Thr Glu Lys Glu Ile Glu Lys Tyr
            930                 935                 940

Asn Asn Thr Thr Arg Lys Ile Asn Glu Tyr Asn Tyr Leu Lys Asn Lys
945                 950                 955                 960

Glu Glu Leu Gln Asn Val Tyr Leu Leu His Glu Met Leu Ser Asp Leu
            965                 970                 975

Leu Ala Arg Asn Val Ala Phe Phe Asn Lys Trp Glu Arg Asp Phe Lys
            980                 985                 990

Phe Ile Val Ile Ala Ile Lys Gln Phe Leu Arg Glu Asn Asp Lys Glu
            995                 1000                1005

Lys Val Asn Glu Phe Leu Asn Pro Pro Asp Asn Ser Lys Gly Lys Lys
            1010                1015                1020

Val Tyr Phe Ser Val Ser Lys Tyr Lys Asn Thr Val Glu Asn Ile Asp
1025                1030                1035                1040

Gly Ile His Lys Asn Phe Met Asn Leu Ile Phe Leu Asn Asn Lys Phe
                1045                1050                1055

Met Asn Arg Lys Ile Asp Lys Met Asn Cys Ala Ile Trp Val Tyr Phe
                1060                1065                1070

Arg Asn Tyr Ile Ala His Phe Leu His Leu His Thr Lys Asn Glu Lys
```

-continued

```
             1075              1080              1085

Ile Ser Leu Ile Ser Gln Met Asn Leu Leu Ile Lys Leu Phe Ser Tyr
        1090              1095              1100

Asp Lys Lys Val Gln Asn His Ile Leu Lys Ser Thr Lys Thr Leu Leu
1105              1110              1115              1120

Glu Lys Tyr Asn Ile Gln Ile Asn Phe Glu Ile Ser Asn Asp Lys Asn
                  1125              1130              1135

Glu Val Phe Lys Tyr Lys Ile Lys Asn Arg Leu Tyr Ser Lys Lys Gly
              1140              1145              1150

Lys Met Leu Gly Lys Asn Asn Lys Leu Glu Asn Glu Phe Leu Glu Asn
              1155              1160              1165

Val Lys Ala Met Leu Glu Tyr Ser Glu
        1170              1175

<210> SEQ ID NO 37
<211> LENGTH: 1285
<212> TYPE: PRT
<213> ORGANISM: Herbinix hemicellulosilytica

<400> SEQUENCE: 37

Met Lys Leu Thr Arg Arg Arg Ile Ser Gly Asn Ser Val Asp Gln Lys
1                 5                 10                15

Ile Thr Ala Ala Phe Tyr Arg Asp Met Ser Gln Gly Leu Leu Tyr Tyr
              20                25                30

Asp Ser Glu Asp Asn Asp Cys Thr Asp Lys Val Ile Glu Ser Met Asp
        35                40                45

Phe Glu Arg Ser Trp Arg Gly Arg Ile Leu Lys Asn Gly Glu Asp Asp
        50                55                60

Lys Asn Pro Phe Tyr Met Phe Val Lys Gly Leu Val Gly Ser Asn Asp
65                70                75                80

Lys Ile Val Cys Glu Pro Ile Asp Val Asp Ser Asp Pro Asp Asn Leu
              85                90                95

Asp Ile Leu Ile Asn Lys Asn Leu Thr Gly Phe Gly Arg Asn Leu Lys
              100               105               110

Ala Pro Asp Ser Asn Asp Thr Leu Glu Asn Leu Ile Arg Lys Ile Gln
              115               120               125

Ala Gly Ile Pro Glu Glu Glu Val Leu Pro Glu Leu Lys Lys Ile Lys
        130               135               140

Glu Met Ile Gln Lys Asp Ile Val Asn Arg Lys Glu Gln Leu Leu Lys
145               150               155               160

Ser Ile Lys Asn Asn Arg Ile Pro Phe Ser Leu Glu Gly Ser Lys Leu
                  165               170               175

Val Pro Ser Thr Lys Lys Met Lys Trp Leu Phe Lys Leu Ile Asp Val
              180               185               190

Pro Asn Lys Thr Phe Asn Glu Lys Met Leu Glu Lys Tyr Trp Glu Ile
              195               200               205

Tyr Asp Tyr Asp Lys Leu Lys Ala Asn Ile Thr Asn Arg Leu Asp Lys
        210               215               220

Thr Asp Lys Lys Ala Arg Ser Ile Ser Arg Ala Val Ser Glu Glu Leu
225               230               235               240

Arg Glu Tyr His Lys Asn Leu Arg Thr Asn Tyr Asn Arg Phe Val Ser
                  245               250               255

Gly Asp Arg Pro Ala Ala Gly Leu Asp Asn Gly Gly Ser Ala Lys Tyr
              260               265               270
```

```
Asn Pro Asp Lys Glu Glu Phe Leu Leu Phe Leu Lys Glu Val Glu Gln
        275                 280                 285

Tyr Phe Lys Lys Tyr Phe Pro Val Lys Ser Lys His Ser Asn Lys Ser
        290                 295                 300

Lys Asp Lys Ser Leu Val Asp Lys Tyr Lys Asn Tyr Cys Ser Tyr Lys
305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
                340                 345                 350

Thr Trp Gln Glu Asp Phe Leu Asn Ser Tyr Gly Leu Ser Tyr Ile Gln
        355                 360                 365

Val Glu Glu Ala Phe Lys Lys Ser Val Met Thr Ser Leu Ser Trp Gly
        370                 375                 380

Ile Asn Arg Leu Thr Ser Phe Phe Ile Asp Asp Ser Asn Thr Val Lys
385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
                420                 425                 430

Glu Lys Leu Ala Phe Phe Tyr Pro Val Tyr Val Lys Asp Lys Lys Asp
                435                 440                 445

Arg Pro Asp Asp Asp Ile Glu Asn Leu Ile Val Leu Val Lys Asn Ala
        450                 455                 460

Ile Glu Ser Val Ser Tyr Leu Arg Asn Arg Thr Phe His Phe Lys Glu
465                 470                 475                 480

Ser Ser Leu Leu Glu Leu Leu Lys Glu Leu Asp Asp Lys Asn Ser Gly
                485                 490                 495

Gln Asn Lys Ile Asp Tyr Ser Val Ala Ala Glu Phe Ile Lys Arg Asp
                500                 505                 510

Ile Glu Asn Leu Tyr Asp Val Phe Arg Glu Gln Ile Arg Ser Leu Gly
                515                 520                 525

Ile Ala Glu Tyr Tyr Lys Ala Asp Met Ile Ser Asp Cys Phe Lys Thr
        530                 535                 540

Cys Gly Leu Glu Phe Ala Leu Tyr Ser Pro Lys Asn Ser Leu Met Pro
545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
                580                 585                 590

Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
        610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
                660                 665                 670

Glu Asn Asp Asp Ile Thr Val Asn Thr Tyr Arg Tyr Glu Ser Ile Pro
        675                 680                 685

Asp Tyr Gln Gly Glu Ser Leu Asp Asp Tyr Leu Lys Val Leu Gln Arg
```

-continued

```
      690               695               700

Lys Gln Met Ala Arg Ala Lys Glu Val Asn Glu Lys Glu Glu Gly Asn
705                     710               715               720

Asn Asn Tyr Ile Gln Phe Ile Arg Asp Val Val Val Trp Ala Phe Gly
                    725               730               735

Ala Tyr Leu Glu Asn Lys Leu Lys Asn Tyr Lys Asn Glu Leu Gln Pro
            740               745               750

Pro Leu Ser Lys Glu Asn Ile Gly Leu Asn Asp Thr Leu Lys Glu Leu
            755               760               765

Phe Pro Glu Glu Lys Val Lys Ser Pro Phe Asn Ile Lys Cys Arg Phe
    770               775               780

Ser Ile Ser Thr Phe Ile Asp Asn Lys Gly Lys Ser Thr Asp Asn Thr
785               790               795               800

Ser Ala Glu Ala Val Lys Thr Asp Gly Lys Glu Asp Glu Lys Asp Lys
                805               810               815

Lys Asn Ile Lys Arg Lys Asp Leu Leu Cys Phe Tyr Leu Phe Leu Arg
                820               825               830

Leu Leu Asp Glu Asn Glu Ile Cys Lys Leu Gln His Gln Phe Ile Lys
                835               840               845

Tyr Arg Cys Ser Leu Lys Glu Arg Arg Phe Pro Gly Asn Arg Thr Lys
    850               855               860

Leu Glu Lys Glu Thr Glu Leu Leu Ala Glu Leu Glu Glu Leu Met Glu
865               870               875               880

Leu Val Arg Phe Thr Met Pro Ser Ile Pro Glu Ile Ser Ala Lys Ala
                885               890               895

Glu Ser Gly Tyr Asp Thr Met Ile Lys Lys Tyr Phe Lys Asp Phe Ile
                900               905               910

Glu Lys Lys Val Phe Lys Asn Pro Lys Thr Ser Asn Leu Tyr Tyr His
                915               920               925

Ser Asp Ser Lys Thr Pro Val Thr Arg Lys Tyr Met Ala Leu Leu Met
    930               935               940

Arg Ser Ala Pro Leu His Leu Tyr Lys Asp Ile Phe Lys Gly Tyr Tyr
945               950               955               960

Leu Ile Thr Lys Lys Glu Cys Leu Glu Tyr Ile Lys Leu Ser Asn Ile
                965               970               975

Ile Lys Asp Tyr Gln Asn Ser Leu Asn Glu Leu His Glu Gln Leu Glu
                980               985               990

Arg Ile Lys Leu Lys Ser Glu Lys Gln Asn Gly Lys Asp Ser Leu Tyr
            995               1000              1005

Leu Asp Lys Lys Asp Phe Tyr Lys Val Lys Glu Tyr Val Glu Asn Leu
    1010              1015              1020

Glu Gln Val Ala Arg Tyr Lys His Leu Gln His Lys Ile Asn Phe Glu
1025              1030              1035              1040

Ser Leu Tyr Arg Ile Phe Arg Ile His Val Asp Ile Ala Ala Arg Met
            1045              1050              1055

Val Gly Tyr Thr Gln Asp Trp Glu Arg Asp Met His Phe Leu Phe Lys
            1060              1065              1070

Ala Leu Val Tyr Asn Gly Val Leu Glu Glu Arg Arg Phe Glu Ala Ile
            1075              1080              1085

Phe Asn Asn Asn Asp Asp Asn Asn Asp Gly Arg Ile Val Lys Lys Ile
    1090              1095              1100

Gln Asn Asn Leu Asn Asn Lys Asn Arg Glu Leu Val Ser Met Leu Cys
1105              1110              1115              1120
```

```
Trp Asn Lys Lys Leu Asn Lys Asn Glu Phe Gly Ala Ile Ile Trp Lys
            1125                1130                1135

Arg Asn Pro Ile Ala His Leu Asn His Phe Thr Gln Thr Glu Gln Asn
            1140                1145                1150

Ser Lys Ser Ser Leu Glu Ser Leu Ile Asn Ser Leu Arg Ile Leu Leu
        1155                1160                1165

Ala Tyr Asp Arg Lys Arg Gln Asn Ala Val Thr Lys Thr Ile Asn Asp
        1170                1175                1180

Leu Leu Leu Asn Asp Tyr His Ile Arg Ile Lys Trp Glu Gly Arg Val
1185                1190                1195                1200

Asp Glu Gly Gln Ile Tyr Phe Asn Ile Lys Glu Lys Glu Asp Ile Glu
                1205                1210                1215

Asn Glu Pro Ile Ile His Leu Lys His Leu His Lys Lys Asp Cys Tyr
            1220                1225                1230

Ile Tyr Lys Asn Ser Tyr Met Phe Asp Lys Gln Lys Glu Trp Ile Cys
        1235                1240                1245

Asn Gly Ile Lys Glu Glu Val Tyr Asp Lys Ser Ile Leu Lys Cys Ile
        1250                1255                1260

Gly Asn Leu Phe Lys Phe Asp Tyr Glu Asp Lys Asn Lys Ser Ser Ala
1265                1270                1275                1280

Asn Pro Lys His Thr
                1285
```

```
<210> SEQ ID NO 38
<211> LENGTH: 1159
<212> TYPE: PRT
<213> ORGANISM: Leptotrichia buccalis

<400> SEQUENCE: 38

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
        50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
            85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Lys Leu Asn Lys Ile Asn Ser Leu
        130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
            165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
```

```
                195                    200                    205

Val Leu Glu Ile Glu Asn Leu Thr Lys Leu Glu Lys Tyr Lys Ile Arg
    210                    215                    220

Glu Phe Tyr His Glu Ile Ile Gly Arg Lys Asn Asp Lys Glu Asn Phe
225                    230                    235                    240

Ala Lys Ile Ile Tyr Glu Glu Ile Gln Asn Val Asn Asn Met Lys Glu
                245                    250                    255

Leu Ile Glu Lys Val Pro Asp Met Ser Glu Leu Lys Lys Ser Gln Val
                260                    265                    270

Phe Tyr Lys Tyr Tyr Leu Asp Lys Glu Glu Leu Asn Asp Lys Asn Ile
                275                    280                    285

Lys Tyr Ala Phe Cys His Phe Val Glu Ile Glu Met Ser Gln Leu Leu
    290                    295                    300

Lys Asn Tyr Val Tyr Lys Arg Leu Ser Asn Ile Ser Asn Asp Lys Ile
305                    310                    315                    320

Lys Arg Ile Phe Glu Tyr Gln Asn Leu Lys Lys Leu Ile Glu Asn Lys
                325                    330                    335

Leu Leu Asn Lys Leu Asp Thr Tyr Val Arg Asn Cys Gly Lys Tyr Asn
                340                    345                    350

Tyr Tyr Leu Gln Asp Gly Glu Ile Ala Thr Ser Asp Phe Ile Ala Arg
                355                    360                    365

Asn Arg Gln Asn Glu Ala Phe Leu Arg Asn Ile Ile Gly Val Ser Ser
    370                    375                    380

Val Ala Tyr Phe Ser Leu Arg Asn Ile Leu Glu Thr Glu Asn Glu Asn
385                    390                    395                    400

Asp Ile Thr Gly Arg Met Arg Gly Lys Thr Val Lys Asn Asn Lys Gly
                405                    410                    415

Glu Glu Lys Tyr Val Ser Gly Glu Val Asp Lys Ile Tyr Asn Glu Asn
                420                    425                    430

Lys Lys Asn Glu Val Lys Glu Asn Leu Lys Met Phe Tyr Ser Tyr Asp
                435                    440                    445

Phe Asn Met Asp Asn Lys Asn Glu Ile Glu Asp Phe Phe Ala Asn Ile
    450                    455                    460

Asp Glu Ala Ile Ser Ser Ile Arg His Gly Ile Val His Phe Asn Leu
465                    470                    475                    480

Glu Leu Glu Gly Lys Asp Ile Phe Ala Phe Lys Asn Ile Ala Pro Ser
                485                    490                    495

Glu Ile Ser Lys Lys Met Phe Gln Asn Glu Ile Asn Glu Lys Lys Leu
                500                    505                    510

Lys Leu Lys Ile Phe Arg Gln Leu Asn Ser Ala Asn Val Phe Arg Tyr
                515                    520                    525

Leu Glu Lys Tyr Lys Ile Leu Asn Tyr Leu Lys Arg Thr Arg Phe Glu
    530                    535                    540

Phe Val Asn Lys Asn Ile Pro Phe Val Pro Ser Phe Thr Lys Leu Tyr
545                    550                    555                    560

Ser Arg Ile Asp Asp Leu Lys Asn Ser Leu Gly Ile Tyr Trp Lys Thr
                565                    570                    575

Pro Lys Thr Asn Asp Asp Asn Lys Thr Lys Glu Ile Ile Asp Ala Gln
                580                    585                    590

Ile Tyr Leu Leu Lys Asn Ile Tyr Tyr Gly Glu Phe Leu Asn Tyr Phe
                595                    600                    605

Met Ser Asn Asn Gly Asn Phe Phe Glu Ile Ser Lys Glu Ile Ile Glu
                610                    615                    620
```

-continued

```
Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
                660                 665                 670

Glu Lys Asp Thr Tyr Ile Asp Phe Ile Gln Lys Ile Phe Leu Lys Gly
                675                 680                 685

Phe Met Thr Tyr Leu Ala Asn Asn Gly Arg Leu Ser Leu Ile Tyr Ile
                690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Asn Ile Lys Ile
                725                 730                 735

Pro Tyr Glu Ile Asn Glu Phe Leu Arg Glu Ile Lys Leu Gly Asn Ile
                740                 745                 750

Leu Lys Tyr Thr Glu Arg Leu Asn Met Phe Tyr Leu Ile Leu Lys Leu
                755                 760                 765

Leu Asn His Lys Glu Leu Thr Asn Leu Lys Gly Ser Leu Glu Lys Tyr
                770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
                805                 810                 815

Glu Ala Asp Glu Ile Gly Lys Phe Leu Asp Phe Asn Gly Asn Lys Val
                820                 825                 830

Lys Asp Asn Lys Glu Leu Lys Lys Phe Asp Thr Asn Lys Ile Tyr Phe
                835                 840                 845

Asp Gly Glu Asn Ile Ile Lys His Arg Ala Phe Tyr Asn Ile Lys Lys
                850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
                900                 905                 910

Arg Pro Arg Lys Asp Glu Lys Phe Thr Asp Glu Asp Tyr Glu Ser Tyr
                915                 920                 925

Lys Gln Ala Ile Glu Asn Ile Glu Glu Tyr Thr His Leu Lys Asn Lys
                930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Glu Ile
                980                 985                 990

Phe Asn Phe Glu Asn Lys Lys Asn Val Lys Tyr Lys Gly Gly Gln Ile
                995                 1000                1005

Val Glu Lys Tyr Ile Lys Phe Tyr Lys Glu Leu His Gln Asn Asp Glu
                1010                1015                1020

Val Lys Ile Asn Lys Tyr Ser Ser Ala Asn Ile Lys Val Leu Lys Gln
1025                1030                1035                1040
```

-continued

```
Glu Lys Lys Asp Leu Tyr Ile Arg Asn Tyr Ile Ala His Phe Asn Tyr
              1045                1050                1055

Ile Pro His Ala Glu Ile Ser Leu Leu Glu Val Leu Glu Asn Leu Arg
              1060                1065                1070

Lys Leu Leu Ser Tyr Asp Arg Lys Leu Lys Asn Ala Val Met Lys Ser
              1075                1080                1085

Val Val Asp Ile Leu Lys Glu Tyr Gly Phe Val Ala Thr Phe Lys Ile
              1090                1095                1100

Gly Ala Asp Lys Lys Ile Gly Ile Gln Thr Leu Glu Ser Glu Lys Ile
         1105                1110                1115                1120

Val His Leu Lys Asn Leu Lys Lys Lys Leu Met Thr Asp Arg Asn
              1125                1130                1135

Ser Glu Glu Leu Cys Lys Leu Val Lys Ile Met Phe Glu Tyr Lys Met
              1140                1145                1150

Glu Glu Lys Lys Ser Glu Asn
         1155

<210> SEQ ID NO 39
<211> LENGTH: 1120
<212> TYPE: PRT
<213> ORGANISM: Leptotrichia seeligeri

<400> SEQUENCE: 39

Met Trp Ile Ser Ile Lys Thr Leu Ile His His Leu Gly Val Leu Phe
1                5                  10                  15

Phe Cys Asp Tyr Met Tyr Asn Arg Arg Glu Lys Lys Ile Ile Glu Val
              20                  25                  30

Lys Thr Met Arg Ile Thr Lys Val Glu Val Asp Arg Lys Lys Val Leu
              35                  40                  45

Ile Ser Arg Asp Lys Asn Gly Gly Lys Leu Val Tyr Glu Asn Glu Met
         50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
              85                  90                  95

Lys Lys Leu Val His Gly Leu Leu Gln Glu Asn Ser Gln Glu Lys Ile
              100                 105                 110

Lys Val Ser Asp Val Thr Lys Leu Asn Ile Ser Asn Phe Leu Asn His
              115                 120                 125

Arg Phe Lys Lys Ser Leu Tyr Tyr Phe Pro Glu Asn Ser Pro Asp Lys
         130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
              165                 170                 175

Lys Asp Met Glu Leu Tyr Ile Asn Trp Ala Glu Asn Tyr Ile Ser Ser
              180                 185                 190

Lys Thr Lys Leu Ile Lys Lys Ser Ile Arg Asn Asn Arg Ile Gln Ser
         195                 200                 205

Thr Glu Ser Arg Ser Gly Gln Leu Met Asp Arg Tyr Met Lys Asp Ile
         210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
              245                 250                 255
```

-continued

```
Lys Lys Asn Asp Lys Glu Ile Asn Tyr Lys Leu Lys Ser Thr Leu Gln
        260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
        290                 295                 300

Ile Lys Lys Thr Asn Arg Lys Val Gly Asp Ile Arg Asn Leu Glu Ile
305                 310                 315                 320

Gly Glu Ile Gln Lys Ile Val Asn His Arg Leu Lys Asn Lys Ile Val
                325                 330                 335

Gln Arg Ile Leu Gln Glu Gly Lys Leu Ala Ser Tyr Glu Ile Glu Ser
            340                 345                 350

Thr Val Asn Ser Asn Ser Leu Gln Lys Ile Lys Ile Glu Glu Ala Phe
            355                 360                 365

Ala Leu Lys Phe Ile Asn Ala Cys Leu Phe Ala Ser Asn Asn Leu Arg
        370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
            420                 425                 430

Ala Ser Trp Gly Leu Arg Gly Ala Ile Ala Pro Ile Arg Asn Glu Ile
            435                 440                 445

Ile His Leu Lys Lys His Ser Trp Lys Lys Phe Phe Asn Asn Pro Thr
        450                 455                 460

Phe Lys Val Lys Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495

Ser Glu Leu Asp Ser Val Pro Glu Leu Ile Ile Asn Lys Met Glu Ser
            500                 505                 510

Ser Lys Ile Leu Asp Tyr Tyr Ser Ser Asp Gln Leu Asn Gln Val Phe
            515                 520                 525

Thr Ile Pro Asn Phe Glu Leu Ser Leu Leu Thr Ser Ala Val Pro Phe
        530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
            580                 585                 590

Lys Met Val Tyr Tyr Gln Val Phe Leu Pro Gln Phe Thr Thr Asn Asn
            595                 600                 605

Asp Leu Phe Lys Ser Ser Val Asp Phe Ile Leu Thr Leu Asn Lys Glu
        610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
        660                 665                 670
```

```
Lys Phe Ile Asn Gln Val Phe Ile Lys Gly Phe Asn Ser Phe Ile Glu
        675                 680                 685

Lys Asn Arg Leu Thr Tyr Ile Cys His Pro Thr Lys Asn Thr Val Pro
        690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735

Ser Glu Leu Arg Asn Glu Met Ile Lys Phe Ser Cys Ser Leu Gln Ser
                740                 745                 750

Thr Glu Glu Ile Ser Thr Phe Thr Lys Ala Arg Glu Val Ile Gly Leu
                755                 760                 765

Ala Leu Leu Asn Gly Glu Lys Gly Cys Asn Asp Trp Lys Glu Leu Phe
        770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
                820                 825                 830

Ile Leu Glu Lys Leu Phe Ser Ser Asp Asp Tyr Lys Val Ser Ala
                835                 840                 845

Lys Asp Ile Ala Lys Leu His Glu Tyr Asp Val Thr Glu Lys Ile Ala
        850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
                900                 905                 910

His Leu His Gln Leu Thr Ile Asp Leu Leu Ser Arg Leu Ala Gly Tyr
                915                 920                 925

Met Ser Ile Ala Asp Arg Asp Phe Gln Phe Ser Ser Asn Tyr Ile Leu
        930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
                965                 970                 975

Lys Asn Ala Ser Ile Lys Val Ser Ser Lys Asn Asp Pro Gln Leu Lys
                980                 985                 990

Val Asp Leu Lys Gln Leu Arg Leu Thr Leu Glu Tyr Leu Glu Leu Phe
        995                 1000                1005

Asp Asn Arg Leu Lys Glu Lys Arg Asn Asn Ile Ser His Phe Asn Tyr
        1010                1015                1020

Leu Asn Gly Gln Leu Gly Asn Ser Ile Leu Glu Leu Phe Asp Asp Ala
1025                1030                1035                1040

Arg Asp Val Leu Ser Tyr Asp Arg Lys Leu Lys Asn Ala Val Ser Lys
                1045                1050                1055

Ser Leu Lys Glu Ile Leu Ser Ser His Gly Met Glu Val Thr Phe Lys
                1060                1065                1070

Pro Leu Tyr Gln Thr Asn His His Leu Lys Ile Asp Lys Leu Gln Pro
                1075                1080                1085

Lys Lys Ile His His Leu Gly Glu Lys Ser Thr Val Ser Ser Asn Gln
```

-continued

```
            1090                1095                1100
Val Ser Asn Glu Tyr Cys Gln Leu Val Arg Thr Leu Leu Thr Met Lys
1105                1110                1115                1120

<210> SEQ ID NO 40
<211> LENGTH: 1437
<212> TYPE: PRT
<213> ORGANISM: Lachnospiraceae bacterium

<400> SEQUENCE: 40

Met Lys Ile Ser Lys Val Arg Glu Glu Asn Arg Gly Ala Lys Leu Thr
1               5                   10                  15

Val Asn Ala Lys Thr Ala Val Val Ser Glu Asn Arg Ser Gln Glu Gly
            20                  25                  30

Ile Leu Tyr Asn Asp Pro Ser Arg Tyr Gly Lys Ser Arg Lys Asn Asp
        35                  40                  45

Glu Asp Arg Asp Arg Tyr Ile Glu Ser Arg Leu Lys Ser Ser Gly Lys
    50                  55                  60

Leu Tyr Arg Ile Phe Asn Glu Asp Lys Asn Lys Arg Glu Thr Asp Glu
65                  70                  75                  80

Leu Gln Trp Phe Leu Ser Glu Ile Val Lys Lys Ile Asn Arg Arg Asn
                85                  90                  95

Gly Leu Val Leu Ser Asp Met Leu Ser Val Asp Asp Arg Ala Phe Glu
            100                 105                 110

Lys Ala Phe Glu Lys Tyr Ala Glu Leu Ser Tyr Thr Asn Arg Arg Asn
            115                 120                 125

Lys Val Ser Gly Ser Pro Ala Phe Glu Thr Cys Gly Val Asp Ala Ala
            130                 135                 140

Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
            180                 185                 190

Lys Arg Gly Leu Lys Lys Leu Leu Met Asn Ala Phe Asp Leu Pro Tyr
            195                 200                 205

Ser Asp Pro Asp Ile Asp Val Gln Arg Asp Phe Ile Asp Tyr Val Leu
    210                 215                 220

Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
                245                 250                 255

Ile Thr Val Ser Lys Gly Gly Thr Glu Ser Gly Asn Lys Arg Ser Ala
            260                 265                 270

Glu Lys Glu Ala Phe Lys Lys Phe Leu Ser Asp Tyr Ala Ser Leu Asp
            275                 280                 285

Glu Arg Val Arg Asp Asp Met Leu Arg Arg Met Arg Arg Leu Val Val
    290                 295                 300

Leu Tyr Phe Tyr Gly Ser Asp Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
            340                 345                 350
```

```
Asp Lys Asp Ala Glu Arg Ile Arg Lys Asn Thr Val Lys Glu Leu Tyr
    355             360             365

Arg Asn Gln Asn Ile Gly Cys Tyr Arg Gln Ala Val Lys Ala Val Glu
    370             375             380

Glu Asp Asn Asn Gly Arg Tyr Phe Asp Asp Lys Met Leu Asn Met Phe
385             390             395             400

Phe Ile His Arg Ile Glu Tyr Gly Val Glu Lys Ile Tyr Ala Asn Leu
                405             410             415

Lys Gln Val Thr Glu Phe Lys Ala Arg Thr Gly Tyr Leu Ser Glu Lys
            420             425             430

Ile Trp Lys Asp Leu Ile Asn Tyr Ile Ser Ile Lys Tyr Ile Ala Met
            435             440             445

Gly Lys Ala Val Tyr Asn Tyr Ala Met Asp Glu Leu Asn Ala Ser Asp
    450             455             460

Lys Lys Glu Ile Glu Leu Gly Lys Ile Ser Glu Glu Tyr Leu Ser Gly
465             470             475             480

Ile Ser Ser Phe Asp Tyr Glu Leu Ile Lys Ala Glu Glu Met Leu Gln
                485             490             495

Arg Glu Thr Ala Val Tyr Val Ala Phe Ala Ala Arg His Leu Ser Ser
            500             505             510

Gln Thr Val Glu Leu Asp Ser Glu Asn Ser Asp Phe Leu Leu Leu Lys
            515             520             525

Pro Lys Gly Thr Met Asp Lys Asn Asp Lys Asn Lys Leu Ala Ser Asn
    530             535             540

Asn Ile Leu Asn Phe Leu Lys Asp Lys Glu Thr Leu Arg Asp Thr Ile
545             550             555             560

Leu Gln Tyr Phe Gly Gly His Ser Leu Trp Thr Asp Phe Pro Phe Asp
                565             570             575

Lys Tyr Leu Ala Gly Gly Lys Asp Asp Val Asp Phe Leu Thr Asp Leu
            580             585             590

Lys Asp Val Ile Tyr Ser Met Arg Asn Asp Ser Phe His Tyr Ala Thr
            595             600             605

Glu Asn His Asn Asn Gly Lys Trp Asn Lys Glu Leu Ile Ser Ala Met
    610             615             620

Phe Glu His Glu Thr Glu Arg Met Thr Val Val Met Lys Asp Lys Phe
625             630             635             640

Tyr Ser Asn Asn Leu Pro Met Phe Tyr Lys Asn Asp Asp Leu Lys Lys
                645             650             655

Leu Leu Ile Asp Leu Tyr Lys Asp Asn Val Glu Arg Ala Ser Gln Val
            660             665             670

Pro Ser Phe Asn Lys Val Phe Val Arg Lys Asn Phe Pro Ala Leu Val
            675             680             685

Arg Asp Lys Asp Asn Leu Gly Ile Glu Leu Asp Leu Lys Ala Asp Ala
    690             695             700

Asp Lys Gly Glu Asn Glu Leu Lys Phe Tyr Asn Ala Leu Tyr Tyr Met
705             710             715             720

Phe Lys Glu Ile Tyr Tyr Asn Ala Phe Leu Asn Asp Lys Asn Val Arg
                725             730             735

Glu Arg Phe Ile Thr Lys Ala Thr Lys Val Ala Asp Asn Tyr Asp Arg
            740             745             750

Asn Lys Glu Arg Asn Leu Lys Asp Arg Ile Lys Ser Ala Gly Ser Asp
    755             760             765

Glu Lys Lys Lys Leu Arg Glu Gln Leu Gln Asn Tyr Ile Ala Glu Asn
```

```
          770              775              780

Asp Phe Gly Gln Arg Ile Lys Asn Ile Val Gln Val Asn Pro Asp Tyr
785              790              795              800

Thr Leu Ala Gln Ile Cys Gln Leu Ile Met Thr Glu Tyr Asn Gln Gln
              805              810              815

Asn Asn Gly Cys Met Gln Lys Lys Ser Ala Ala Arg Lys Asp Ile Asn
              820              825              830

Lys Asp Ser Tyr Gln His Tyr Lys Met Leu Leu Leu Val Asn Leu Arg
              835              840              845

Lys Ala Phe Leu Glu Phe Ile Lys Glu Asn Tyr Ala Phe Val Leu Lys
              850              855              860

Pro Tyr Lys His Asp Leu Cys Asp Lys Ala Asp Phe Val Pro Asp Phe
865              870              875              880

Ala Lys Tyr Val Lys Pro Tyr Ala Gly Leu Ile Ser Arg Val Ala Gly
              885              890              895

Ser Ser Glu Leu Gln Lys Trp Tyr Ile Val Ser Arg Phe Leu Ser Pro
              900              905              910

Ala Gln Ala Asn His Met Leu Gly Phe Leu His Ser Tyr Lys Gln Tyr
              915              920              925

Val Trp Asp Ile Tyr Arg Arg Ala Ser Glu Thr Gly Thr Glu Ile Asn
930              935              940

His Ser Ile Ala Glu Asp Lys Ile Ala Gly Val Asp Ile Thr Asp Val
945              950              955              960

Asp Ala Val Ile Asp Leu Ser Val Lys Leu Cys Gly Thr Ile Ser Ser
              965              970              975

Glu Ile Ser Asp Tyr Phe Lys Asp Asp Glu Val Tyr Ala Glu Tyr Ile
              980              985              990

Ser Ser Tyr Leu Asp Phe Glu Tyr Asp Gly Gly Asn Tyr Lys Asp Ser
              995              1000             1005

Leu Asn Arg Phe Cys Asn Ser Asp Ala Val Asn Asp Gln Lys Val Ala
     1010             1015             1020

Leu Tyr Tyr Asp Gly Glu His Pro Lys Leu Asn Arg Asn Ile Ile Leu
1025             1030             1035             1040

Ser Lys Leu Tyr Gly Glu Arg Arg Phe Leu Glu Lys Ile Thr Asp Arg
              1045             1050             1055

Val Ser Arg Ser Asp Ile Val Glu Tyr Tyr Lys Leu Lys Lys Glu Thr
              1060             1065             1070

Ser Gln Tyr Gln Thr Lys Gly Ile Phe Asp Ser Glu Asp Glu Gln Lys
              1075             1080             1085

Asn Ile Lys Lys Phe Gln Glu Met Lys Asn Ile Val Glu Phe Arg Asp
     1090             1095             1100

Leu Met Asp Tyr Ser Glu Ile Ala Asp Glu Leu Gln Gly Gln Leu Ile
1105             1110             1115             1120

Asn Trp Ile Tyr Leu Arg Glu Arg Asp Leu Met Asn Phe Gln Leu Gly
              1125             1130             1135

Tyr His Tyr Ala Cys Leu Asn Asn Asp Ser Asn Lys Gln Ala Thr Tyr
              1140             1145             1150

Val Thr Leu Asp Tyr Gln Gly Lys Lys Asn Arg Lys Ile Asn Gly Ala
              1155             1160             1165

Ile Leu Tyr Gln Ile Cys Ala Met Tyr Ile Asn Gly Leu Pro Leu Tyr
     1170             1175             1180

Tyr Val Asp Lys Asp Ser Ser Glu Trp Thr Val Ser Asp Gly Lys Glu
1185             1190             1195             1200
```

```
Ser Thr Gly Ala Lys Ile Gly Glu Phe Tyr Arg Tyr Ala Lys Ser Phe
            1205                1210                1215

Glu Asn Thr Ser Asp Cys Tyr Ala Ser Gly Leu Glu Ile Phe Glu Asn
            1220                1225                1230

Ile Ser Glu His Asp Asn Ile Thr Glu Leu Arg Asn Tyr Ile Glu His
        1235                1240                1245

Phe Arg Tyr Tyr Ser Ser Phe Asp Arg Ser Phe Leu Gly Ile Tyr Ser
    1250                1255                1260

Glu Val Phe Asp Arg Phe Phe Thr Tyr Asp Leu Lys Tyr Arg Lys Asn
1265                1270                1275                1280

Val Pro Thr Ile Leu Tyr Asn Ile Leu Leu Gln His Phe Val Asn Val
            1285                1290                1295

Arg Phe Glu Phe Val Ser Gly Lys Lys Met Ile Gly Ile Asp Lys Lys
            1300                1305                1310

Asp Arg Lys Ile Ala Lys Glu Lys Glu Cys Ala Arg Ile Thr Ile Arg
        1315                1320                1325

Glu Lys Asn Gly Val Tyr Ser Glu Gln Phe Thr Tyr Lys Leu Lys Asn
    1330                1335                1340

Gly Thr Val Tyr Val Asp Ala Arg Asp Lys Arg Tyr Leu Gln Ser Ile
1345                1350                1355                1360

Ile Arg Leu Leu Phe Tyr Pro Glu Lys Val Asn Met Asp Glu Met Ile
            1365                1370                1375

Glu Val Lys Glu Lys Lys Lys Pro Ser Asp Asn Asn Thr Gly Lys Gly
            1380                1385                1390

Tyr Ser Lys Arg Asp Arg Gln Gln Asp Arg Lys Glu Tyr Asp Lys Tyr
        1395                1400                1405

Lys Glu Lys Lys Lys Lys Glu Gly Asn Phe Leu Ser Gly Met Gly Gly
    1410                1415                1420

Asn Ile Asn Trp Asp Glu Ile Asn Ala Gln Leu Lys Asn
1425                1430                1435

<210> SEQ ID NO 41
<211> LENGTH: 1389
<212> TYPE: PRT
<213> ORGANISM: Leptotrichia shahii

<400> SEQUENCE: 41

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Asn Lys Glu Lys
        35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
            85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
        115                 120                 125

Ile Asp Glu Ala Ile Arg Gln Gly Ile Thr Lys Asp Asp Lys Lys Ile
```

-continued

```
          130                 135                 140

Glu Ile Lys Arg Gln Glu Asn Glu Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
                180                 185                 190

Phe Lys Asn Ile Asn Met Ser Leu Tyr Lys Ile Ile Glu Lys Ile Ile
                195                 200                 205

Glu Asn Glu Thr Glu Lys Val Phe Glu Asn Arg Tyr Tyr Glu Glu His
     210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
                260                 265                 270

Lys Asn Lys Lys Met Leu Val Glu Lys Ile Leu Asn Ile Asn Val Asp
                275                 280                 285

Leu Thr Val Glu Asp Ile Ala Asp Phe Val Ile Lys Glu Leu Glu Phe
     290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
                340                 345                 350

Lys Ile Val Lys Phe Phe Val Glu Asn Ile Lys Asn Asn Ser Ile Lys
                355                 360                 365

Glu Lys Ile Glu Lys Ile Leu Ala Glu Phe Lys Ile Asp Glu Leu Ile
     370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

Phe Ser Lys Lys Ser Asp Glu Glu Lys Glu Leu Tyr Lys Ile Ile Tyr
                420                 425                 430

Arg Tyr Leu Lys Gly Arg Ile Glu Lys Ile Leu Val Asn Glu Gln Lys
                435                 440                 445

Val Arg Leu Lys Lys Met Glu Lys Ile Glu Ile Glu Lys Ile Leu Asn
     450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                485                 490                 495

Met Thr Thr Val Asn Thr Asp Asp Phe Ser Arg Leu His Ala Lys Glu
                500                 505                 510

Glu Leu Asp Leu Glu Leu Ile Thr Phe Phe Ala Ser Thr Asn Met Glu
                515                 520                 525

Leu Asn Lys Ile Phe Ser Arg Glu Asn Ile Asn Asn Asp Glu Asn Ile
     530                 535                 540

Asp Phe Phe Gly Gly Asp Arg Glu Lys Asn Tyr Val Leu Asp Lys Lys
545                 550                 555                 560
```

```
Ile Leu Asn Ser Lys Ile Lys Ile Ile Arg Asp Leu Asp Phe Ile Asp
                565             570             575

Asn Lys Asn Asn Ile Thr Asn Asn Phe Ile Arg Lys Phe Thr Lys Ile
            580             585             590

Gly Thr Asn Glu Arg Asn Arg Ile Leu His Ala Ile Ser Lys Glu Arg
        595             600             605

Asp Leu Gln Gly Thr Gln Asp Asp Tyr Asn Lys Val Ile Asn Ile Ile
    610             615             620

Gln Asn Leu Lys Ile Ser Asp Glu Glu Val Ser Lys Ala Leu Asn Leu
625             630             635             640

Asp Val Val Phe Lys Asp Lys Lys Asn Ile Ile Thr Lys Ile Asn Asp
            645             650             655

Ile Lys Ile Ser Glu Glu Asn Asn Asn Asp Ile Lys Tyr Leu Pro Ser
        660             665             670

Phe Ser Lys Val Leu Pro Glu Ile Leu Asn Leu Tyr Arg Asn Asn Pro
    675             680             685

Lys Asn Glu Pro Phe Asp Thr Ile Glu Thr Glu Lys Ile Val Leu Asn
    690             695             700

Ala Leu Ile Tyr Val Asn Lys Glu Leu Tyr Lys Lys Leu Ile Leu Glu
705             710             715             720

Asp Asp Leu Glu Glu Asn Glu Ser Lys Asn Ile Phe Leu Gln Glu Leu
            725             730             735

Lys Lys Thr Leu Gly Asn Ile Asp Glu Ile Asp Glu Asn Ile Ile Glu
            740             745             750

Asn Tyr Tyr Lys Asn Ala Gln Ile Ser Ala Ser Lys Gly Asn Asn Lys
            755             760             765

Ala Ile Lys Lys Tyr Gln Lys Lys Val Ile Glu Cys Tyr Ile Gly Tyr
    770             775             780

Leu Arg Lys Asn Tyr Glu Glu Leu Phe Asp Phe Ser Asp Phe Lys Met
785             790             795             800

Asn Ile Gln Glu Ile Lys Lys Gln Ile Lys Asp Ile Asn Asp Asn Lys
            805             810             815

Thr Tyr Glu Arg Ile Thr Val Lys Thr Ser Asp Lys Thr Ile Val Ile
        820             825             830

Asn Asp Asp Phe Glu Tyr Ile Ile Ser Ile Phe Ala Leu Leu Asn Ser
        835             840             845

Asn Ala Val Ile Asn Lys Ile Arg Asn Arg Phe Phe Ala Thr Ser Val
    850             855             860

Trp Leu Asn Thr Ser Glu Tyr Gln Asn Ile Ile Asp Ile Leu Asp Glu
865             870             875             880

Ile Met Gln Leu Asn Thr Leu Arg Asn Glu Cys Ile Thr Glu Asn Trp
            885             890             895

Asn Leu Asn Leu Glu Glu Phe Ile Gln Lys Met Lys Glu Ile Glu Lys
            900             905             910

Asp Phe Asp Asp Phe Lys Ile Gln Thr Lys Lys Glu Ile Phe Asn Asn
        915             920             925

Tyr Tyr Glu Asp Ile Lys Asn Asn Ile Leu Thr Glu Phe Lys Asp Asp
    930             935             940

Ile Asn Gly Cys Asp Val Leu Glu Lys Lys Leu Glu Lys Ile Val Ile
945             950             955             960

Phe Asp Asp Glu Thr Lys Phe Glu Ile Asp Lys Lys Ser Asn Ile Leu
            965             970             975
```

-continued

```
Gln Asp Glu Gln Arg Lys Leu Ser Asn Ile Asn Lys Lys Asp Leu Lys
            980                 985                 990

Lys Lys Val Asp Gln Tyr Ile Lys Asp Lys Asp Gln Glu Ile Lys Ser
            995                 1000                1005

Lys Ile Leu Cys Arg Ile Ile Phe Asn Ser Asp Phe Leu Lys Lys Tyr
            1010                1015                1020

Lys Lys Glu Ile Asp Asn Leu Ile Glu Asp Met Glu Ser Glu Asn Glu
    1025                1030                1035                1040

Asn Lys Phe Gln Glu Ile Tyr Tyr Pro Lys Glu Arg Lys Asn Glu Leu
                1045                1050                1055

Tyr Ile Tyr Lys Lys Asn Leu Phe Leu Asn Ile Gly Asn Pro Asn Phe
            1060                1065                1070

Asp Lys Ile Tyr Gly Leu Ile Ser Asn Asp Ile Lys Met Ala Asp Ala
            1075                1080                1085

Lys Phe Leu Phe Asn Ile Asp Gly Lys Asn Ile Arg Lys Asn Lys Ile
    1090                1095                1100

Ser Glu Ile Asp Ala Ile Leu Lys Asn Leu Asn Asp Lys Leu Asn Gly
1105                1110                1115                1120

Tyr Ser Lys Glu Tyr Lys Glu Lys Tyr Ile Lys Lys Leu Lys Glu Asn
            1125                1130                1135

Asp Asp Phe Phe Ala Lys Asn Ile Gln Asn Lys Asn Tyr Lys Ser Phe
            1140                1145                1150

Glu Lys Asp Tyr Asn Arg Val Ser Glu Tyr Lys Lys Ile Arg Asp Leu
            1155                1160                1165

Val Glu Phe Asn Tyr Leu Asn Lys Ile Glu Ser Tyr Leu Ile Asp Ile
    1170                1175                1180

Asn Trp Lys Leu Ala Ile Gln Met Ala Arg Phe Glu Arg Asp Met His
1185                1190                1195                1200

Tyr Ile Val Asn Gly Leu Arg Glu Leu Gly Ile Ile Lys Leu Ser Gly
            1205                1210                1215

Tyr Asn Thr Gly Ile Ser Arg Ala Tyr Pro Lys Arg Asn Gly Ser Asp
            1220                1225                1230

Gly Phe Tyr Thr Thr Thr Ala Tyr Tyr Lys Phe Phe Asp Glu Glu Ser
            1235                1240                1245

Tyr Lys Lys Phe Glu Lys Ile Cys Tyr Gly Phe Gly Ile Asp Leu Ser
    1250                1255                1260

Glu Asn Ser Glu Ile Asn Lys Pro Glu Asn Glu Ser Ile Arg Asn Tyr
1265                1270                1275                1280

Ile Ser His Phe Tyr Ile Val Arg Asn Pro Phe Ala Asp Tyr Ser Ile
            1285                1290                1295

Ala Glu Gln Ile Asp Arg Val Ser Asn Leu Leu Ser Tyr Ser Thr Arg
            1300                1305                1310

Tyr Asn Asn Ser Thr Tyr Ala Ser Val Phe Glu Val Phe Lys Lys Asp
            1315                1320                1325

Val Asn Leu Asp Tyr Asp Glu Leu Lys Lys Lys Phe Lys Leu Ile Gly
    1330                1335                1340

Asn Asn Asp Ile Leu Glu Arg Leu Met Lys Pro Lys Lys Val Ser Val
1345                1350                1355                1360

Leu Glu Leu Glu Ser Tyr Asn Ser Asp Tyr Ile Lys Asn Leu Ile Ile
            1365                1370                1375

Glu Leu Leu Thr Lys Ile Glu Asn Thr Asn Asp Thr Leu
            1380                1385
```

<210> SEQ ID NO 42
<211> LENGTH: 1159
<212> TYPE: PRT
<213> ORGANISM: Leptotrichia buccalis

<400> SEQUENCE: 42

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
        195                 200                 205

Val Leu Glu Ile Glu Asn Leu Thr Lys Leu Glu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
    290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
        355                 360                 365

Asn Arg Gln Asn Glu Ala Phe Leu Arg Asn Ile Ile Gly Val Ser Ser
    370                 375                 380

-continued

```
Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
                405                 410                 415

Glu Glu Lys Tyr Val Ser Gly Glu Val Asp Lys Ile Tyr Asn Glu Asn
                420                 425                 430

Lys Lys Asn Glu Val Lys Glu Asn Leu Lys Met Phe Tyr Ser Tyr Asp
                435                 440                 445

Phe Asn Met Asp Asn Lys Asn Glu Ile Glu Asp Phe Phe Ala Asn Ile
        450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
                500                 505                 510

Lys Leu Lys Ile Phe Arg Gln Leu Asn Ser Ala Asn Val Phe Arg Tyr
                515                 520                 525

Leu Glu Lys Tyr Lys Ile Leu Asn Tyr Leu Lys Arg Thr Arg Phe Glu
        530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
                580                 585                 590

Ile Tyr Leu Leu Lys Asn Ile Tyr Tyr Gly Glu Phe Leu Asn Tyr Phe
        595                 600                 605

Met Ser Asn Asn Gly Asn Phe Phe Glu Ile Ser Lys Glu Ile Ile Glu
        610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
                660                 665                 670

Glu Lys Asp Thr Tyr Ile Asp Phe Ile Gln Lys Ile Phe Leu Lys Gly
                675                 680                 685

Phe Met Thr Tyr Leu Ala Asn Asn Gly Arg Leu Ser Leu Ile Tyr Ile
        690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Asn Ile Lys Ile
                725                 730                 735

Pro Tyr Glu Ile Asn Glu Phe Leu Arg Glu Ile Lys Leu Gly Asn Ile
                740                 745                 750

Leu Lys Tyr Thr Glu Arg Leu Asn Met Phe Tyr Leu Ile Leu Lys Leu
                755                 760                 765

Leu Asn His Lys Glu Leu Thr Asn Leu Lys Gly Ser Leu Glu Lys Tyr
        770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
```

-continued

```
                    805              810              815

Glu Ala Asp Glu Ile Gly Lys Phe Leu Asp Phe Asn Gly Asn Lys Val
            820              825              830

Lys Asp Asn Lys Glu Leu Lys Lys Phe Asp Thr Asn Lys Ile Tyr Phe
            835              840              845

Asp Gly Glu Asn Ile Ile Lys His Arg Ala Phe Tyr Asn Ile Lys Lys
        850              855              860

Tyr Gly Met Leu Asn Leu Leu Glu Lys Ile Ala Asp Lys Ala Gly Tyr
865              870              875              880

Lys Ile Ser Ile Glu Glu Leu Lys Lys Tyr Ser Asn Lys Lys Asn Glu
            885              890              895

Ile Glu Lys Asn His Lys Met Gln Glu Asn Leu His Arg Lys Tyr Ala
            900              905              910

Arg Pro Arg Lys Asp Glu Lys Phe Thr Asp Glu Asp Tyr Glu Ser Tyr
            915              920              925

Lys Gln Ala Ile Glu Asn Ile Glu Glu Tyr Thr His Leu Lys Asn Lys
        930              935              940

Val Glu Phe Asn Glu Leu Asn Leu Leu Gln Gly Leu Leu Leu Arg Ile
945              950              955              960

Leu His Arg Leu Val Gly Tyr Thr Ser Ile Trp Glu Arg Asp Leu Arg
            965              970              975

Phe Arg Leu Lys Gly Glu Phe Pro Glu Asn Gln Tyr Ile Glu Glu Ile
            980              985              990

Phe Asn Phe Glu Asn Lys Lys Asn Val Lys Tyr Lys Gly Gly Gln Ile
            995              1000             1005

Val Glu Lys Tyr Ile Lys Phe Tyr Lys Glu Leu His Gln Asn Asp Glu
        1010             1015             1020

Val Lys Ile Asn Lys Tyr Ser Ser Ala Asn Ile Lys Val Leu Lys Gln
1025             1030             1035             1040

Glu Lys Lys Asp Leu Tyr Ile Arg Asn Tyr Ile Ala His Phe Asn Tyr
            1045             1050             1055

Ile Pro His Ala Glu Ile Ser Leu Leu Glu Val Leu Glu Asn Leu Arg
            1060             1065             1070

Lys Leu Leu Ser Tyr Asp Arg Lys Leu Lys Asn Ala Val Met Lys Ser
            1075             1080             1085

Val Val Asp Ile Leu Lys Glu Tyr Gly Phe Val Ala Thr Phe Lys Ile
            1090             1095             1100

Gly Ala Asp Lys Lys Ile Gly Ile Gln Thr Leu Glu Ser Glu Lys Ile
1105             1110             1115             1120

Val His Leu Lys Asn Leu Lys Lys Lys Leu Met Thr Asp Arg Asn
            1125             1130             1135

Ser Glu Glu Leu Cys Lys Leu Val Lys Ile Met Phe Glu Tyr Lys Met
            1140             1145             1150

Glu Glu Lys Lys Ser Glu Asn
        1155
```

<210> SEQ ID NO 43
<211> LENGTH: 1159
<212> TYPE: PRT
<213> ORGANISM: Leptotrichia buccalis

<400> SEQUENCE: 43

```
Met Lys Val Thr Lys Val Gly Gly Ile Ser His Lys Lys Tyr Thr Ser
1               5               10              15
```

```
Glu Gly Arg Leu Val Lys Ser Glu Ser Glu Glu Asn Arg Thr Asp Glu
         20                  25                  30

Arg Leu Ser Ala Leu Leu Asn Met Arg Leu Asp Met Tyr Ile Lys Asn
         35                  40                  45

Pro Ser Ser Thr Glu Thr Lys Glu Asn Gln Lys Arg Ile Gly Lys Leu
         50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                 85                  90                  95

Thr Asp Ile Leu Glu Ser Asp Val Arg Asp Lys Lys Asn Phe Ala Val
             100                 105                 110

Leu Lys Lys Ile Tyr Leu Asn Glu Asn Val Asn Ser Glu Glu Leu Glu
             115                 120                 125

Val Phe Arg Asn Asp Ile Lys Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
             165                 170                 175

Asp Tyr Tyr Arg Glu Ser Ala Lys Arg Asp Ala Tyr Val Ser Asn Val
             180                 185                 190

Lys Glu Ala Phe Asp Lys Leu Tyr Lys Glu Glu Asp Ile Ala Lys Leu
         195                 200                 205

Val Leu Glu Ile Glu Asn Leu Thr Lys Leu Glu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
             245                 250                 255

Leu Ile Glu Lys Val Pro Asp Met Ser Glu Leu Lys Lys Ser Gln Val
         260                 265                 270

Phe Tyr Lys Tyr Tyr Leu Asp Lys Glu Glu Leu Asn Asp Lys Asn Ile
         275                 280                 285

Lys Tyr Ala Phe Cys His Phe Val Glu Ile Glu Met Ser Gln Leu Leu
    290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
             325                 330                 335

Leu Leu Asn Lys Leu Asp Thr Tyr Val Arg Asn Cys Gly Lys Tyr Asn
         340                 345                 350

Tyr Tyr Leu Gln Asp Gly Glu Ile Ala Thr Ser Asp Phe Ile Ala Arg
         355                 360                 365

Asn Arg Gln Asn Glu Ala Phe Leu Arg Asn Ile Ile Gly Val Ser Ser
    370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
             405                 410                 415

Glu Glu Lys Tyr Val Ser Gly Glu Val Asp Lys Ile Tyr Asn Glu Asn
         420                 425                 430

Lys Lys Asn Lys Val Lys Glu Asn Leu Lys Met Phe Tyr Ser Tyr Asp
```

```
                    435                 440                 445

Phe Asn Met Asp Asn Lys Asn Glu Ile Glu Asp Phe Phe Ala Asn Ile
    450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
                500                 505                 510

Lys Leu Lys Ile Phe Arg Gln Leu Asn Ser Ala Asn Val Phe Arg Tyr
                515                 520                 525

Leu Glu Lys Tyr Lys Ile Leu Asn Tyr Leu Lys Arg Thr Arg Phe Glu
    530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
                580                 585                 590

Ile Tyr Leu Leu Lys Asn Ile Tyr Tyr Gly Glu Phe Leu Asn Tyr Phe
                595                 600                 605

Met Ser Asn Asn Gly Asn Phe Phe Glu Ile Ser Lys Glu Ile Ile Glu
    610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
                660                 665                 670

Glu Lys Asp Thr Tyr Ile Asp Phe Ile Gln Lys Ile Phe Leu Lys Gly
                675                 680                 685

Phe Met Thr Tyr Leu Ala Asn Asn Gly Arg Leu Ser Leu Ile Tyr Ile
    690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Asn Ile Lys Ile
                725                 730                 735

Pro Tyr Glu Ile Asn Glu Phe Leu Arg Glu Ile Lys Leu Gly Asn Ile
                740                 745                 750

Leu Lys Tyr Thr Glu Arg Leu Asn Met Phe Tyr Leu Ile Leu Lys Leu
                755                 760                 765

Leu Asn His Lys Glu Leu Thr Asn Leu Lys Gly Ser Leu Glu Lys Tyr
    770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
                805                 810                 815

Glu Ala Asp Glu Ile Gly Lys Phe Leu Asp Phe Asn Gly Asn Lys Val
                820                 825                 830

Lys Asp Asn Lys Glu Leu Lys Lys Phe Asp Thr Asn Lys Ile Tyr Phe
                835                 840                 845

Asp Gly Glu Asn Ile Ile Lys His Arg Ala Phe Tyr Asn Ile Lys Lys
    850                 855                 860
```

```
Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
            900                 905                 910

Arg Pro Arg Lys Asp Glu Lys Phe Thr Asp Glu Asp Tyr Glu Ser Tyr
            915                 920                 925

Lys Gln Ala Ile Glu Asn Ile Glu Glu Tyr Thr His Leu Lys Asn Lys
        930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Glu Ile
            980                 985                 990

Phe Asn Phe Glu Asn Lys Lys Asn Val Lys Tyr Lys Gly Gly Gln Ile
            995                 1000                1005

Val Glu Lys Tyr Ile Lys Phe Tyr Lys Glu Leu His Gln Asn Asp Glu
        1010                1015                1020

Val Lys Ile Asn Lys Tyr Ser Ser Ala Asn Ile Lys Val Leu Lys Gln
1025                1030                1035                1040

Glu Lys Lys Asp Leu Tyr Ile Arg Asn Tyr Ile Ala His Phe Asn Tyr
                1045                1050                1055

Ile Pro His Ala Glu Ile Ser Leu Leu Glu Val Leu Glu Asn Leu Arg
                1060                1065                1070

Lys Leu Leu Ser Tyr Asp Arg Lys Leu Lys Asn Ala Val Met Lys Ser
                1075                1080                1085

Val Val Asp Ile Leu Lys Glu Tyr Gly Phe Val Ala Thr Phe Lys Ile
            1090                1095                1100

Gly Ala Asp Lys Lys Ile Gly Ile Gln Thr Leu Glu Ser Glu Lys Ile
1105                1110                1115                1120

Val His Leu Lys Asn Leu Lys Lys Lys Leu Met Thr Asp Arg Asn
                1125                1130                1135

Ser Glu Glu Leu Cys Lys Leu Val Lys Ile Met Phe Glu Tyr Lys Met
                1140                1145                1150

Glu Glu Lys Lys Ser Glu Asn
            1155
```

```
<210> SEQ ID NO 44
<211> LENGTH: 1127
<212> TYPE: PRT
<213> ORGANISM: Prevotella buccae

<400> SEQUENCE: 44
```

```
Met Gln Lys Gln Asp Lys Leu Phe Val Asp Arg Lys Lys Asn Ala Ile
1                   5                   10                  15

Phe Ala Phe Pro Lys Tyr Ile Thr Ile Met Glu Asn Lys Glu Lys Pro
                20                  25                  30

Glu Pro Ile Tyr Tyr Glu Leu Thr Asp Lys His Phe Trp Ala Ala Phe
            35                  40                  45

Leu Asn Leu Ala Arg His Asn Val Tyr Thr Thr Ile Asn His Ile Asn
    50                  55                  60

Arg Arg Leu Glu Ile Ala Glu Leu Lys Asp Asp Gly Tyr Met Met Gly
```

```
65                    70                    75                    80

Ile Lys Gly Ser Trp Asn Glu Gln Ala Lys Lys Leu Asp Lys Lys Val
                85                    90                    95

Arg Leu Arg Asp Leu Ile Met Lys His Phe Pro Phe Leu Glu Ala Ala
                100                   105                   110

Ala Tyr Glu Met Thr Asn Ser Lys Ser Pro Asn Asn Lys Glu Gln Arg
                115                   120                   125

Glu Lys Glu Gln Ser Glu Ala Leu Ser Leu Asn Asn Leu Lys Asn Val
     130                   135                   140

Leu Phe Ile Phe Leu Glu Lys Leu Gln Val Leu Arg Asn Tyr Tyr Ser
145                   150                   155                   160

His Tyr Lys Tyr Ser Glu Glu Ser Pro Lys Pro Ile Phe Glu Thr Ser
                165                   170                   175

Leu Leu Lys Asn Met Tyr Lys Val Phe Asp Ala Asn Val Arg Leu Val
                180                   185                   190

Lys Arg Asp Tyr Met His His Glu Asn Ile Asp Met Gln Arg Asp Phe
                195                   200                   205

Thr His Leu Asn Arg Lys Lys Gln Val Gly Arg Thr Lys Asn Ile Ile
     210                   215                   220

Asp Ser Pro Asn Phe His Tyr His Phe Ala Asp Lys Glu Gly Asn Met
225                   230                   235                   240

Thr Ile Ala Gly Leu Leu Phe Phe Val Ser Leu Phe Leu Asp Lys Lys
                245                   250                   255

Asp Ala Ile Trp Met Gln Lys Lys Leu Lys Gly Phe Lys Asp Gly Arg
                260                   265                   270

Asn Leu Arg Glu Gln Met Thr Asn Glu Val Phe Cys Arg Ser Arg Ile
                275                   280                   285

Ser Leu Pro Lys Leu Lys Leu Glu Asn Val Gln Thr Lys Asp Trp Met
     290                   295                   300

Gln Leu Asp Met Leu Asn Glu Leu Val Arg Cys Pro Lys Ser Leu Tyr
305                   310                   315                   320

Glu Arg Leu Arg Glu Lys Asp Arg Glu Ser Phe Lys Val Pro Phe Asp
                325                   330                   335

Ile Phe Ser Asp Asp Tyr Asn Ala Glu Glu Pro Phe Lys Asn Thr
                340                   345                   350

Leu Val Arg His Gln Asp Arg Phe Pro Tyr Phe Val Leu Arg Tyr Phe
                355                   360                   365

Asp Leu Asn Glu Ile Phe Glu Gln Leu Arg Phe Gln Ile Asp Leu Gly
     370                   375                   380

Thr Tyr His Phe Ser Ile Tyr Asn Lys Arg Ile Gly Asp Glu Asp Glu
385                   390                   395                   400

Val Arg His Leu Thr His His Leu Tyr Gly Phe Ala Arg Ile Gln Asp
                405                   410                   415

Phe Ala Pro Gln Asn Gln Pro Glu Glu Trp Arg Lys Leu Val Lys Asp
                420                   425                   430

Leu Asp His Phe Glu Thr Ser Gln Glu Pro Tyr Ile Ser Lys Thr Ala
                435                   440                   445

Pro His Tyr His Leu Glu Asn Glu Lys Ile Gly Ile Lys Phe Cys Ser
     450                   455                   460

Ala His Asn Asn Leu Phe Pro Ser Leu Gln Thr Asp Lys Thr Cys Asn
465                   470                   475                   480

Gly Arg Ser Lys Phe Asn Leu Gly Thr Gln Phe Thr Ala Glu Ala Phe
                485                   490                   495
```

-continued

```
Leu Ser Val His Glu Leu Leu Pro Met Met Phe Tyr Tyr Leu Leu Leu
            500                 505                 510

Thr Lys Asp Tyr Ser Arg Lys Glu Ser Ala Asp Lys Val Glu Gly Ile
            515                 520                 525

Ile Arg Lys Glu Ile Ser Asn Ile Tyr Ala Ile Tyr Asp Ala Phe Ala
            530                 535                 540

Asn Asn Glu Ile Asn Ser Ile Ala Asp Leu Thr Arg Arg Leu Gln Asn
545                 550                 555                 560

Thr Asn Ile Leu Gln Gly His Leu Pro Lys Gln Met Ile Ser Ile Leu
            565                 570                 575

Lys Gly Arg Gln Lys Asp Met Gly Lys Glu Ala Glu Arg Lys Ile Gly
            580                 585                 590

Glu Met Ile Asp Asp Thr Gln Arg Arg Leu Asp Leu Leu Cys Lys Gln
            595                 600                 605

Thr Asn Gln Lys Ile Arg Ile Gly Lys Arg Asn Ala Gly Leu Leu Lys
            610                 615                 620

Ser Gly Lys Ile Ala Asp Trp Leu Val Asn Asp Met Met Arg Phe Gln
625                 630                 635                 640

Pro Val Gln Lys Asp Gln Asn Asn Ile Pro Ile Asn Asn Ser Lys Ala
            645                 650                 655

Asn Ser Thr Glu Tyr Arg Met Leu Gln Arg Ala Leu Ala Leu Phe Gly
            660                 665                 670

Ser Glu Asn Phe Arg Leu Lys Ala Tyr Phe Asn Gln Met Asn Leu Val
            675                 680                 685

Gly Asn Asp Asn Pro His Pro Phe Leu Ala Glu Thr Gln Trp Glu His
            690                 695                 700

Gln Thr Asn Ile Leu Ser Phe Tyr Arg Asn Tyr Leu Glu Ala Arg Lys
705                 710                 715                 720

Lys Tyr Leu Lys Gly Leu Lys Pro Gln Asn Trp Lys Gln Tyr Gln His
            725                 730                 735

Phe Leu Ile Leu Lys Val Gln Lys Thr Asn Arg Asn Thr Leu Val Thr
            740                 745                 750

Gly Trp Lys Asn Ser Phe Asn Leu Pro Arg Gly Ile Phe Thr Gln Pro
            755                 760                 765

Ile Arg Glu Trp Phe Glu Lys His Asn Asn Ser Lys Arg Ile Tyr Asp
            770                 775                 780

Gln Ile Leu Ser Phe Asp Arg Val Gly Phe Val Ala Lys Ala Ile Pro
785                 790                 795                 800

Leu Tyr Phe Ala Glu Glu Tyr Lys Asp Asn Val Gln Pro Phe Tyr Asp
            805                 810                 815

Tyr Pro Phe Asn Ile Gly Asn Arg Leu Lys Pro Lys Lys Arg Gln Phe
            820                 825                 830

Leu Asp Lys Lys Glu Arg Val Glu Leu Trp Gln Lys Asn Lys Glu Leu
            835                 840                 845

Phe Lys Asn Tyr Pro Ser Glu Lys Lys Lys Thr Asp Leu Ala Tyr Leu
            850                 855                 860

Asp Phe Leu Ser Trp Lys Lys Phe Glu Arg Glu Leu Arg Leu Ile Lys
865                 870                 875                 880

Asn Gln Asp Ile Val Thr Trp Leu Met Phe Lys Glu Leu Phe Asn Met
            885                 890                 895

Ala Thr Val Glu Gly Leu Lys Ile Gly Glu Ile His Leu Arg Asp Ile
            900                 905                 910
```

-continued

```
Asp Thr Asn Thr Ala Asn Glu Glu Ser Asn Asn Ile Leu Asn Arg Ile
    915                 920                 925

Met Pro Met Lys Leu Pro Val Lys Thr Tyr Glu Thr Asp Asn Lys Gly
    930                 935                 940

Asn Ile Leu Lys Glu Arg Pro Leu Ala Thr Phe Tyr Ile Glu Glu Thr
945                 950                 955                 960

Glu Thr Lys Val Leu Lys Gln Gly Asn Phe Lys Ala Leu Val Lys Asp
                965                 970                 975

Arg Arg Leu Asn Gly Leu Phe Ser Phe Ala Glu Thr Thr Asp Leu Asn
            980                 985                 990

Leu Glu Glu His Pro Ile Ser Lys Leu Ser Val Asp Leu Glu Leu Ile
            995                 1000                1005

Lys Tyr Gln Thr Thr Arg Ile Ser Ile Phe Glu Met Thr Leu Gly Leu
    1010                1015                1020

Glu Lys Lys Leu Ile Asp Lys Tyr Ser Thr Leu Pro Thr Asp Ser Phe
1025                1030                1035                1040

Arg Asn Met Leu Glu Arg Trp Leu Gln Cys Lys Ala Asn Arg Pro Glu
                1045                1050                1055

Leu Lys Asn Tyr Val Asn Ser Leu Ile Ala Val Arg Asn Ala Phe Ser
            1060                1065                1070

His Asn Gln Tyr Pro Met Tyr Asp Ala Thr Leu Phe Ala Glu Val Lys
            1075                1080                1085

Lys Phe Thr Leu Phe Pro Ser Val Asp Thr Lys Lys Ile Glu Leu Asn
    1090                1095                1100

Ile Ala Pro Gln Leu Leu Glu Ile Val Gly Lys Ala Ile Lys Glu Ile
1105                1110                1115                1120

Glu Lys Ser Glu Asn Lys Asn
                1125
```

```
<210> SEQ ID NO 45
<211> LENGTH: 1127
<212> TYPE: PRT
<213> ORGANISM: Prevotella buccae

<400> SEQUENCE: 45

Met Gln Lys Gln Asp Lys Leu Phe Val Asp Arg Lys Lys Asn Ala Ile
1                 5                   10                  15

Phe Ala Phe Pro Lys Tyr Ile Thr Ile Met Glu Asn Gln Glu Lys Pro
            20                  25                  30

Glu Pro Ile Tyr Tyr Glu Leu Thr Asp Lys His Phe Trp Ala Ala Phe
        35                  40                  45

Leu Asn Leu Ala Arg His Asn Val Tyr Thr Thr Ile Asn His Ile Asn
    50                  55                  60

Arg Arg Leu Glu Ile Ala Glu Leu Lys Asp Asp Gly Tyr Met Met Asp
65                  70                  75                  80

Ile Lys Gly Ser Trp Asn Glu Gln Ala Lys Lys Leu Asp Lys Lys Val
            85                  90                  95

Arg Leu Arg Asp Leu Ile Met Lys His Phe Pro Phe Leu Glu Ala Ala
            100                 105                 110

Ala Tyr Glu Ile Thr Asn Ser Lys Ser Pro Asn Asn Lys Glu Gln Arg
        115                 120                 125

Glu Lys Glu Gln Ser Glu Ala Leu Ser Leu Asn Asn Leu Lys Asn Val
    130                 135                 140

Leu Phe Ile Phe Leu Glu Lys Leu Gln Val Leu Arg Asn Tyr Tyr Ser
145                 150                 155                 160
```

-continued

```
His Tyr Lys Tyr Ser Glu Glu Ser Pro Lys Pro Ile Phe Glu Thr Ser
                165             170             175

Leu Leu Lys Asn Met Tyr Lys Val Phe Asp Ala Asn Val Arg Leu Val
            180             185             190

Lys Arg Asp Tyr Met His His Glu Asn Ile Asp Met Gln Arg Asp Phe
        195             200             205

Thr His Leu Asn Arg Lys Lys Gln Val Gly Arg Thr Lys Asn Ile Ile
    210             215             220

Asp Ser Pro Asn Phe His Tyr His Phe Ala Asp Lys Glu Gly Asn Met
225             230             235             240

Thr Ile Ala Gly Leu Leu Phe Phe Val Ser Leu Phe Leu Asp Lys Lys
            245             250             255

Asp Ala Ile Trp Met Gln Lys Lys Leu Lys Gly Phe Lys Asp Gly Arg
            260             265             270

Asn Leu Arg Glu Gln Met Thr Asn Glu Val Phe Cys Arg Ser Arg Ile
        275             280             285

Ser Leu Pro Lys Leu Lys Leu Glu Asn Val Gln Thr Lys Asp Trp Met
    290             295             300

Gln Leu Asp Met Leu Asn Glu Leu Val Arg Cys Pro Lys Ser Leu Tyr
305             310             315             320

Glu Arg Leu Arg Glu Lys Asp Arg Glu Ser Phe Lys Val Pro Phe Asp
            325             330             335

Ile Phe Ser Asp Asp Tyr Asp Ala Glu Glu Glu Pro Phe Lys Asn Thr
            340             345             350

Leu Val Arg His Gln Asp Arg Phe Pro Tyr Phe Val Leu Arg Tyr Phe
            355             360             365

Asp Leu Asn Glu Ile Phe Glu Gln Leu Arg Phe Gln Ile Asp Leu Gly
    370             375             380

Thr Tyr His Phe Ser Ile Tyr Asn Lys Arg Ile Gly Asp Glu Asp Glu
385             390             395             400

Val Arg His Leu Thr His His Leu Tyr Gly Phe Ala Arg Ile Gln Asp
            405             410             415

Phe Ala Gln Gln Asn Gln Pro Glu Val Trp Arg Lys Leu Val Lys Asp
        420             425             430

Leu Asp Tyr Phe Glu Ala Ser Gln Glu Pro Tyr Ile Pro Lys Thr Ala
        435             440             445

Pro His Tyr His Leu Glu Asn Glu Lys Ile Gly Ile Lys Phe Cys Ser
    450             455             460

Thr His Asn Asn Leu Phe Pro Ser Leu Lys Thr Glu Lys Thr Cys Asn
465             470             475             480

Gly Arg Ser Lys Phe Asn Leu Gly Thr Gln Phe Thr Ala Glu Ala Phe
            485             490             495

Leu Ser Val His Glu Leu Leu Pro Met Met Phe Tyr Tyr Leu Leu Leu
            500             505             510

Thr Lys Asp Tyr Ser Arg Lys Glu Ser Ala Asp Lys Val Glu Gly Ile
        515             520             525

Ile Arg Lys Glu Ile Ser Asn Ile Tyr Ala Ile Tyr Asp Ala Phe Ala
        530             535             540

Asn Gly Glu Ile Asn Ser Ile Ala Asp Leu Thr Cys Arg Leu Gln Lys
545             550             555             560

Thr Asn Ile Leu Gln Gly His Leu Pro Lys Gln Met Ile Ser Ile Leu
            565             570             575
```

-continued

```
Glu Gly Arg Gln Lys Asp Met Glu Lys Glu Ala Glu Arg Lys Ile Gly
            580             585             590

Glu Met Ile Asp Asp Thr Gln Arg Arg Leu Asp Leu Leu Cys Lys Gln
            595             600             605

Thr Asn Gln Lys Ile Arg Ile Gly Lys Arg Asn Ala Gly Leu Leu Lys
        610             615             620

Ser Gly Lys Ile Ala Asp Trp Leu Val Asn Asp Met Met Arg Phe Gln
    625             630             635             640

Pro Val Gln Lys Asp Gln Asn Asn Ile Pro Ile Asn Asn Ser Lys Ala
            645             650             655

Asn Ser Thr Glu Tyr Arg Met Leu Gln Arg Ala Leu Ala Leu Phe Gly
            660             665             670

Ser Glu Asn Phe Arg Leu Lys Ala Tyr Phe Asn Gln Met Asn Leu Val
            675             680             685

Gly Asn Asp Asn Pro His Pro Phe Leu Ala Glu Thr Gln Trp Glu His
        690             695             700

Gln Thr Asn Ile Leu Ser Phe Tyr Arg Asn Tyr Leu Glu Ala Arg Lys
    705             710             715             720

Lys Tyr Leu Lys Gly Leu Lys Pro Gln Asn Trp Lys Gln Tyr Gln His
            725             730             735

Phe Leu Ile Leu Lys Val Gln Lys Thr Asn Arg Asn Thr Leu Val Thr
            740             745             750

Gly Trp Lys Asn Ser Phe Asn Leu Pro Arg Gly Ile Phe Thr Gln Pro
            755             760             765

Ile Arg Glu Trp Phe Glu Lys His Asn Asn Ser Lys Arg Ile Tyr Asp
    770             775             780

Gln Ile Leu Ser Phe Asp Arg Val Gly Phe Val Ala Lys Ala Ile Pro
785             790             795             800

Leu Tyr Phe Ala Glu Glu Tyr Lys Asp Asn Val Gln Pro Phe Tyr Asp
            805             810             815

Tyr Pro Phe Asn Ile Gly Asn Lys Leu Lys Pro Gln Lys Gly Gln Phe
            820             825             830

Leu Asp Lys Lys Glu Arg Val Glu Leu Trp Gln Lys Asn Lys Glu Leu
            835             840             845

Phe Lys Asn Tyr Pro Ser Glu Lys Lys Thr Asp Leu Ala Tyr Leu
    850             855             860

Asp Phe Leu Ser Trp Lys Lys Phe Glu Arg Glu Leu Arg Leu Ile Lys
865             870             875             880

Asn Gln Asp Ile Val Thr Trp Leu Met Phe Lys Glu Leu Phe Asn Met
            885             890             895

Ala Thr Val Glu Gly Leu Lys Ile Gly Glu Ile His Leu Arg Asp Ile
            900             905             910

Asp Thr Asn Thr Ala Asn Glu Glu Ser Asn Asn Ile Leu Asn Arg Ile
    915             920             925

Met Pro Met Lys Leu Pro Val Lys Thr Tyr Glu Thr Asp Asn Lys Gly
    930             935             940

Asn Ile Leu Lys Glu Arg Pro Leu Ala Thr Phe Tyr Ile Glu Glu Thr
945             950             955             960

Glu Thr Lys Val Leu Lys Gln Gly Asn Phe Lys Val Leu Ala Lys Asp
            965             970             975

Arg Arg Leu Asn Gly Leu Leu Ser Phe Ala Glu Thr Thr Asp Ile Asp
            980             985             990

Leu Glu Lys Asn Pro Ile Thr Lys Leu Ser Val Asp His Glu Leu Ile
```

-continued

```
           995                    1000                   1005

Lys Tyr Gln Thr Thr Arg Ile Ser Ile Phe Glu Met Thr Leu Gly Leu
        1010                    1015                   1020

Glu Lys Lys Leu Ile Asn Lys Tyr Pro Thr Leu Pro Thr Asp Ser Phe
1025                    1030                   1035                   1040

Arg Asn Met Leu Glu Arg Trp Leu Gln Cys Lys Ala Asn Arg Pro Glu
                    1045                   1050                   1055

Leu Lys Asn Tyr Val Asn Ser Leu Ile Ala Val Arg Asn Ala Phe Ser
                1060                   1065                   1070

His Asn Gln Tyr Pro Met Tyr Asp Ala Thr Leu Phe Ala Glu Val Lys
                1075                   1080                   1085

Lys Phe Thr Leu Phe Pro Ser Val Asp Thr Lys Lys Ile Glu Leu Asn
        1090                    1095                   1100

Ile Ala Pro Gln Leu Leu Glu Ile Val Gly Lys Ala Ile Lys Glu Ile
1105                    1110                   1115                   1120

Glu Lys Ser Glu Asn Lys Asn
                1125
```

```
<210> SEQ ID NO 46
<211> LENGTH: 1232
<212> TYPE: PRT
<213> ORGANISM: Bergeyella zoohelcum
<220> FEATURE:
<221> NAME/KEY: VARIANT
<222> LOCATION: (1)...(1232)
<223> OTHER INFORMATION: Xaa = Any Amino Acid

<400> SEQUENCE: 46

Xaa Glu Asn Lys Thr Ser Leu Gly Asn Asn Ile Tyr Tyr Asn Pro Phe
1               5                   10                  15

Lys Pro Gln Asp Lys Ser Tyr Phe Ala Gly Tyr Phe Asn Ala Ala Xaa
            20                  25                  30

Glu Asn Thr Asp Ser Val Phe Arg Glu Leu Gly Lys Arg Leu Lys Gly
        35                  40                  45

Lys Glu Tyr Thr Ser Glu Asn Phe Phe Asp Ala Ile Phe Lys Glu Asn
    50                  55                  60

Ile Ser Leu Val Glu Tyr Glu Arg Tyr Val Lys Leu Leu Ser Asp Tyr
65                  70                  75                  80

Phe Pro Xaa Ala Arg Leu Leu Asp Lys Lys Glu Val Pro Ile Lys Glu
                85                  90                  95

Arg Lys Glu Asn Phe Lys Lys Asn Phe Lys Gly Ile Ile Lys Ala Val
            100                 105                 110

Arg Asp Leu Arg Asn Phe Tyr Thr His Lys Glu His Gly Glu Val Glu
        115                 120                 125

Ile Thr Asp Glu Ile Phe Gly Val Leu Asp Glu Xaa Leu Lys Ser Thr
        130                 135                 140

Val Leu Thr Val Lys Lys Lys Lys Val Lys Thr Asp Lys Thr Lys Glu
145                 150                 155                 160

Ile Leu Lys Lys Ser Ile Glu Lys Gln Leu Asp Ile Leu Cys Gln Lys
            165                 170                 175

Lys Leu Glu Tyr Leu Arg Asp Thr Ala Arg Lys Ile Glu Glu Lys Arg
            180                 185                 190

Arg Asn Gln Arg Glu Arg Gly Glu Lys Glu Leu Val Ala Pro Phe Lys
        195                 200                 205

Tyr Ser Asp Lys Arg Asp Asp Leu Ile Ala Ala Ile Tyr Asn Asp Ala
    210                 215                 220
```

```
Phe Asp Val Tyr Ile Asp Lys Lys Asp Ser Leu Lys Glu Ser Ser
225             230             235             240

Lys Ala Lys Tyr Asn Thr Lys Ser Asp Pro Gln Gln Glu Glu Gly Asp
                245             250             255

Leu Lys Ile Pro Ile Ser Lys Asn Gly Val Val Phe Leu Leu Ser Leu
                260             265             270

Phe Leu Thr Lys Gln Glu Ile His Ala Phe Lys Ser Lys Ile Ala Gly
            275             280             285

Phe Lys Ala Thr Val Ile Asp Glu Ala Thr Val Ser Glu Ala Thr Val
            290             295             300

Ser His Gly Lys Asn Ser Ile Cys Phe Xaa Ala Thr His Glu Ile Phe
305             310             315             320

Ser His Leu Ala Tyr Lys Lys Leu Lys Arg Lys Val Arg Thr Ala Glu
                325             330             335

Ile Asn Tyr Gly Glu Ala Glu Asn Ala Glu Gln Leu Ser Val Tyr Ala
                340             345             350

Lys Glu Thr Leu Xaa Xaa Gln Xaa Leu Asp Glu Leu Ser Lys Val Pro
            355             360             365

Asp Val Val Tyr Gln Asn Leu Ser Glu Asp Val Gln Lys Thr Phe Ile
            370             375             380

Glu Asp Trp Asn Glu Tyr Leu Lys Glu Asn Asn Gly Asp Val Gly Thr
385             390             395             400

Xaa Glu Glu Glu Gln Val Ile His Pro Val Ile Arg Lys Arg Tyr Glu
                405             410             415

Asp Lys Phe Asn Tyr Phe Ala Ile Arg Phe Leu Asp Glu Phe Ala Gln
                420             425             430

Phe Pro Thr Leu Arg Phe Gln Val His Leu Gly Asn Tyr Leu His Asp
            435             440             445

Ser Arg Pro Lys Glu Asn Leu Ile Ser Asp Arg Arg Ile Lys Glu Lys
            450             455             460

Ile Thr Val Phe Gly Arg Leu Ser Glu Leu Glu His Lys Lys Ala Leu
465             470             475             480

Phe Ile Lys Asn Thr Glu Thr Asn Glu Asp Arg Glu His Tyr Trp Glu
                485             490             495

Ile Phe Pro Asn Pro Asn Tyr Asp Phe Pro Lys Glu Asn Ile Ser Val
                500             505             510

Asn Asp Lys Asp Phe Pro Ile Ala Gly Ser Ile Leu Asp Arg Glu Lys
            515             520             525

Gln Pro Val Ala Gly Lys Ile Gly Ile Lys Val Lys Leu Leu Asn Gln
            530             535             540

Gln Tyr Val Ser Glu Val Asp Lys Ala Val Lys Ala His Gln Leu Lys
545             550             555             560

Gln Arg Lys Ala Ser Lys Pro Ser Ile Gln Asn Ile Ile Glu Glu Ile
                565             570             575

Val Pro Ile Asn Glu Ser Asn Pro Lys Glu Ala Ile Val Phe Gly Gly
                580             585             590

Gln Pro Thr Ala Tyr Leu Ser Xaa Asn Asp Ile His Ser Ile Leu Tyr
            595             600             605

Glu Phe Phe Asp Lys Trp Glu Lys Lys Glu Lys Leu Glu Lys Lys
            610             615             620

Gly Glu Lys Glu Leu Arg Lys Glu Ile Gly Lys Glu Leu Glu Lys Lys
625             630             635             640
```

-continued

```
Ile Val Gly Lys Ile Gln Ala Gln Ile Gln Gln Ile Ile Asp Lys Asp
                645                 650                 655

Thr Asn Ala Lys Ile Leu Lys Pro Tyr Gln Asp Gly Asn Ser Thr Ala
                660                 665                 670

Ile Asp Lys Glu Lys Leu Ile Lys Asp Leu Lys Gln Glu Gln Asn Ile
                675                 680                 685

Leu Gln Lys Leu Lys Asp Glu Gln Thr Val Arg Glu Lys Glu Tyr Asn
                690                 695                 700

Asp Phe Ile Ala Tyr Gln Asp Lys Asn Arg Glu Ile Asn Lys Val Arg
705                 710                 715                 720

Asp Arg Asn His Lys Gln Tyr Leu Lys Asp Asn Leu Lys Arg Lys Tyr
                725                 730                 735

Pro Glu Ala Pro Ala Arg Lys Glu Val Leu Tyr Tyr Arg Glu Lys Gly
                740                 745                 750

Lys Val Ala Val Trp Leu Ala Asn Asp Ile Lys Arg Phe Xaa Pro Thr
                755                 760                 765

Asp Phe Lys Asn Glu Trp Lys Gly Glu Gln His Ser Leu Leu Gln Lys
                770                 775                 780

Ser Leu Ala Tyr Tyr Glu Gln Cys Lys Glu Glu Leu Lys Asn Leu Leu
785                 790                 795                 800

Pro Glu Lys Val Phe Gln His Leu Pro Phe Lys Leu Gly Gly Tyr Phe
                805                 810                 815

Gln Gln Lys Tyr Leu Tyr Gln Phe Tyr Thr Cys Tyr Leu Asp Lys Arg
                820                 825                 830

Leu Glu Tyr Ile Ser Gly Leu Val Gln Gln Ala Glu Asn Phe Lys Ser
                835                 840                 845

Glu Asn Lys Val Phe Lys Lys Val Glu Asn Glu Cys Phe Lys Phe Leu
                850                 855                 860

Lys Lys Gln Asn Tyr Thr His Lys Glu Leu Asp Ala Arg Val Gln Ser
865                 870                 875                 880

Ile Leu Gly Tyr Pro Ile Phe Leu Glu Arg Gly Phe Xaa Asp Glu Lys
                885                 890                 895

Pro Thr Ile Ile Lys Gly Lys Thr Phe Lys Gly Asn Glu Ala Leu Phe
                900                 905                 910

Ala Asp Trp Phe Arg Tyr Tyr Lys Glu Tyr Gln Asn Phe Gln Thr Phe
                915                 920                 925

Tyr Asp Thr Glu Asn Tyr Pro Leu Val Glu Leu Glu Lys Lys Gln Ala
                930                 935                 940

Asp Arg Lys Arg Lys Thr Lys Ile Tyr Gln Gln Lys Lys Asn Asp Val
945                 950                 955                 960

Phe Thr Leu Leu Xaa Ala Lys His Ile Phe Lys Ser Val Phe Lys Gln
                965                 970                 975

Asp Ser Ile Asp Gln Phe Ser Leu Glu Asp Leu Tyr Gln Ser Arg Glu
                980                 985                 990

Glu Arg Leu Gly Asn Gln Glu Arg Ala Arg Gln Thr Gly Glu Arg Asn
                995                 1000                1005

Thr Asn Tyr Ile Trp Asn Lys Thr Val Asp Leu Lys Leu Cys Asp Gly
                1010                1015                1020

Lys Ile Thr Val Glu Asn Val Lys Leu Lys Asn Val Gly Asp Phe Ile
1025                1030                1035                1040

Lys Tyr Glu Tyr Asp Gln Arg Val Gln Ala Phe Leu Lys Tyr Glu Glu
                1045                1050                1055

Asn Ile Glu Trp Gln Ala Phe Leu Ile Lys Glu Ser Lys Glu Glu Glu
```

-continued

```
              1060                1065               1070

Asn Tyr Pro Tyr Val Val Glu Arg Glu Ile Glu Gln Tyr Glu Lys Val
           1075                1080               1085

Arg Arg Glu Glu Leu Leu Lys Glu Val His Leu Ile Glu Glu Tyr Ile
   1090                1095               1100

Leu Glu Lys Val Lys Asp Lys Glu Ile Leu Lys Lys Gly Asp Asn Gln
1105                1110               1115               1120

Asn Phe Lys Tyr Tyr Ile Leu Asn Gly Leu Leu Lys Gln Leu Lys Asn
           1125                1130               1135

Glu Asp Val Glu Ser Tyr Lys Val Phe Asn Leu Asn Thr Glu Pro Glu
           1140                1145               1150

Asp Val Asn Ile Asn Gln Leu Lys Gln Glu Ala Thr Asp Leu Glu Gln
           1155                1160               1165

Lys Ala Phe Val Leu Thr Tyr Ile Ala Asn Lys Phe Ala His Asn Gln
   1170                1175               1180

Leu Pro Lys Lys Glu Phe Trp Asp Tyr Cys Gln Glu Lys Tyr Gly Lys
1185                1190               1195               1200

Ile Glu Lys Glu Lys Thr Tyr Ala Glu Tyr Phe Ala Glu Val Phe Lys
           1205                1210               1215

Lys Glu Lys Glu Ala Leu Ile Lys Leu Glu His His His His His
           1220                1225               1230
```

<210> SEQ ID NO 47
<211> LENGTH: 1127
<212> TYPE: PRT
<213> ORGANISM: Prevotella sp. MSX73

<400> SEQUENCE: 47

```
Met Gln Lys Gln Asp Lys Leu Phe Val Asp Arg Lys Lys Asn Ala Ile
1               5                  10                  15

Phe Ala Phe Pro Lys Tyr Ile Thr Ile Met Glu Asn Gln Glu Lys Pro
           20                  25                  30

Glu Pro Ile Tyr Tyr Glu Leu Thr Asp Lys His Phe Trp Ala Ala Phe
       35                  40                  45

Leu Asn Leu Ala Arg His Asn Val Tyr Thr Thr Ile Asn His Ile Asn
   50                  55                  60

Arg Arg Leu Glu Ile Ala Glu Leu Lys Asp Asp Gly Tyr Met Met Gly
65                  70                  75                  80

Ile Lys Gly Ser Trp Asn Glu Gln Ala Lys Lys Leu Asp Lys Lys Val
               85                  90                  95

Arg Leu Arg Asp Leu Ile Met Lys His Phe Pro Phe Leu Glu Ala Ala
           100                 105                 110

Ala Tyr Glu Ile Thr Asn Ser Lys Ser Pro Asn Asn Lys Glu Gln Arg
       115                 120                 125

Glu Lys Glu Gln Ser Glu Ala Leu Ser Leu Asn Asn Leu Lys Asn Val
   130                 135                 140

Leu Phe Ile Phe Leu Glu Lys Leu Gln Val Leu Arg Asn Tyr Tyr Ser
145                 150                 155                 160

His Tyr Lys Tyr Ser Glu Glu Ser Pro Lys Pro Ile Phe Glu Thr Ser
               165                 170                 175

Leu Leu Lys Asn Met Tyr Lys Val Phe Asp Ala Asn Val Arg Leu Val
           180                 185                 190

Lys Arg Asp Tyr Met His His Glu Asn Ile Asp Met Gln Arg Asp Phe
           195                 200                 205
```

```
Thr His Leu Asn Arg Lys Lys Gln Val Gly Arg Thr Lys Asn Ile Ile
    210             215             220

Asp Ser Pro Asn Phe His Tyr His Phe Ala Asp Lys Glu Gly Asn Met
225             230             235             240

Thr Ile Ala Gly Leu Leu Phe Phe Val Ser Leu Phe Leu Asp Lys Lys
            245             250             255

Asp Ala Ile Trp Met Gln Lys Lys Leu Lys Gly Phe Lys Asp Gly Arg
            260             265             270

Asn Leu Arg Glu Gln Met Thr Asn Glu Val Phe Cys Arg Ser Arg Ile
            275             280             285

Ser Leu Pro Lys Leu Lys Leu Glu Asn Val Gln Thr Lys Asp Trp Met
    290             295             300

Gln Leu Asp Met Leu Asn Glu Leu Val Arg Cys Pro Lys Ser Leu Tyr
305             310             315             320

Glu Arg Leu Arg Glu Lys Asp Arg Glu Ser Phe Lys Val Pro Phe Asp
            325             330             335

Ile Phe Ser Asp Asp Tyr Asp Ala Glu Glu Glu Pro Phe Lys Asn Thr
            340             345             350

Leu Val Arg His Gln Asp Arg Phe Pro Tyr Phe Val Leu Arg Tyr Phe
    355             360             365

Asp Leu Asn Glu Ile Phe Glu Gln Leu Arg Phe Gln Ile Asp Leu Gly
    370             375             380

Thr Tyr His Phe Ser Ile Tyr Asn Lys Arg Ile Gly Asp Glu Asp Glu
385             390             395             400

Val Arg His Leu Thr His His Leu Tyr Gly Phe Ala Arg Ile Gln Asp
            405             410             415

Phe Ala Pro Gln Asn Gln Pro Glu Glu Trp Arg Lys Leu Val Lys Asp
            420             425             430

Leu Asp His Phe Glu Thr Ser Gln Glu Pro Tyr Ile Ser Lys Thr Ala
            435             440             445

Pro His Tyr His Leu Glu Asn Glu Lys Ile Gly Ile Lys Phe Cys Ser
    450             455             460

Thr His Asn Asn Leu Phe Pro Ser Leu Lys Arg Glu Lys Thr Cys Asn
465             470             475             480

Gly Arg Ser Lys Phe Asn Leu Gly Thr Gln Phe Thr Ala Glu Ala Phe
            485             490             495

Leu Ser Val His Glu Leu Leu Pro Met Met Phe Tyr Tyr Leu Leu Leu
            500             505             510

Thr Lys Asp Tyr Ser Arg Lys Glu Ser Ala Asp Lys Val Glu Gly Ile
            515             520             525

Ile Arg Lys Glu Ile Ser Asn Ile Tyr Ala Ile Tyr Asp Ala Phe Ala
    530             535             540

Asn Asn Glu Ile Asn Ser Ile Ala Asp Leu Thr Cys Arg Leu Gln Lys
545             550             555             560

Thr Asn Ile Leu Gln Gly His Leu Pro Lys Gln Met Ile Ser Ile Leu
            565             570             575

Glu Gly Arg Gln Lys Asp Met Glu Lys Glu Ala Glu Arg Lys Ile Gly
            580             585             590

Glu Met Ile Asp Asp Thr Gln Arg Arg Leu Asp Leu Leu Cys Lys Gln
            595             600             605

Thr Asn Gln Lys Ile Arg Ile Gly Lys Arg Asn Ala Gly Leu Leu Lys
    610             615             620

Ser Gly Lys Ile Ala Asp Trp Leu Val Ser Asp Met Met Arg Phe Gln
```

-continued

```
625                 630                 635                 640

Pro Val Gln Lys Asp Thr Asn Asn Ala Pro Ile Asn Asn Ser Lys Ala
                645                 650                 655

Asn Ser Thr Glu Tyr Arg Met Leu Gln His Ala Leu Ala Leu Phe Gly
                660                 665                 670

Ser Glu Ser Ser Arg Leu Lys Ala Tyr Phe Arg Gln Met Asn Leu Val
                675                 680                 685

Gly Asn Ala Asn Pro His Pro Phe Leu Ala Glu Thr Gln Trp Glu His
                690                 695                 700

Gln Thr Asn Ile Leu Ser Phe Tyr Arg Asn Tyr Leu Glu Ala Arg Lys
705                 710                 715                 720

Lys Tyr Leu Lys Gly Leu Lys Pro Gln Asn Trp Lys Gln Tyr Gln His
                725                 730                 735

Phe Leu Ile Leu Lys Val Gln Lys Thr Asn Arg Asn Thr Leu Val Thr
                740                 745                 750

Gly Trp Lys Asn Ser Phe Asn Leu Pro Arg Gly Ile Phe Thr Gln Pro
                755                 760                 765

Ile Arg Glu Trp Phe Glu Lys His Asn Asn Ser Lys Arg Ile Tyr Asp
                770                 775                 780

Gln Ile Leu Ser Phe Asp Arg Val Gly Phe Val Ala Lys Ala Ile Pro
785                 790                 795                 800

Leu Tyr Phe Ala Glu Glu Tyr Lys Asp Asn Val Gln Pro Phe Tyr Asp
                805                 810                 815

Tyr Pro Phe Asn Ile Gly Asn Lys Leu Lys Pro Gln Lys Gly Gln Phe
                820                 825                 830

Leu Asp Lys Lys Glu Arg Val Glu Leu Trp Gln Lys Asn Lys Glu Leu
                835                 840                 845

Phe Lys Asn Tyr Pro Ser Glu Lys Asn Lys Thr Asp Leu Ala Tyr Leu
                850                 855                 860

Asp Phe Leu Ser Trp Lys Lys Phe Glu Arg Glu Leu Arg Leu Ile Lys
865                 870                 875                 880

Asn Gln Asp Ile Val Thr Trp Leu Met Phe Lys Glu Leu Phe Lys Thr
                885                 890                 895

Thr Thr Val Glu Gly Leu Lys Ile Gly Glu Ile His Leu Arg Asp Ile
                900                 905                 910

Asp Thr Asn Thr Ala Asn Glu Glu Ser Asn Asn Ile Leu Asn Arg Ile
                915                 920                 925

Met Pro Met Lys Leu Pro Val Lys Thr Tyr Glu Thr Asp Asn Lys Gly
                930                 935                 940

Asn Ile Leu Lys Glu Arg Pro Leu Ala Thr Phe Tyr Ile Glu Glu Thr
945                 950                 955                 960

Glu Thr Lys Val Leu Lys Gln Gly Asn Phe Lys Val Leu Ala Lys Asp
                965                 970                 975

Arg Arg Leu Asn Gly Leu Leu Ser Phe Ala Glu Thr Thr Asp Ile Asp
                980                 985                 990

Leu Glu Lys Asn Pro Ile Thr Lys Leu Ser Val Asp Tyr Glu Leu Ile
                995                 1000                1005

Lys Tyr Gln Thr Thr Arg Ile Ser Ile Phe Glu Met Thr Leu Gly Leu
                1010                1015                1020

Glu Lys Lys Leu Ile Asp Lys Tyr Ser Thr Leu Pro Thr Asp Ser Phe
1025                1030                1035                1040

Arg Asn Met Leu Glu Arg Trp Leu Gln Cys Lys Ala Asn Arg Pro Glu
                1045                1050                1055
```

```
Leu Lys Asn Tyr Val Asn Ser Leu Ile Ala Val Arg Asn Ala Phe Ser
        1060                1065                1070

His Asn Gln Tyr Pro Met Tyr Asp Ala Thr Leu Phe Ala Glu Val Lys
        1075                1080                1085

Lys Phe Thr Leu Phe Pro Ser Val Asp Thr Lys Lys Ile Glu Leu Asn
        1090                1095                1100

Ile Ala Pro Gln Leu Leu Glu Ile Val Gly Lys Ala Ile Lys Glu Ile
1105                1110                1115                1120

Glu Lys Ser Glu Asn Lys Asn
        1125

<210> SEQ ID NO 48
<211> LENGTH: 1154
<212> TYPE: PRT
<213> ORGANISM: Paludibacter propionicigenes

<400> SEQUENCE: 48

Met Arg Val Ser Lys Val Lys Val Lys Asp Gly Gly Lys Asp Lys Met
1                   5                   10                  15

Val Leu Val His Arg Lys Thr Thr Gly Ala Gln Leu Val Tyr Ser Gly
            20                  25                  30

Gln Pro Val Ser Asn Glu Thr Ser Asn Ile Leu Pro Glu Lys Lys Arg
        35                  40                  45

Gln Ser Phe Asp Leu Ser Thr Leu Asn Lys Thr Ile Ile Lys Phe Asp
        50                  55                  60

Thr Ala Lys Lys Gln Lys Leu Asn Val Asp Gln Tyr Lys Ile Val Glu
65                  70                  75                  80

Lys Ile Phe Lys Tyr Pro Lys Gln Glu Leu Pro Lys Gln Ile Lys Ala
            85                  90                  95

Glu Glu Ile Leu Pro Phe Leu Asn His Lys Phe Gln Glu Pro Val Lys
            100                 105                 110

Tyr Trp Lys Asn Gly Lys Glu Glu Ser Phe Asn Leu Thr Leu Leu Ile
            115                 120                 125

Val Glu Ala Val Gln Ala Gln Asp Lys Arg Lys Leu Gln Pro Tyr Tyr
        130                 135                 140

Asp Trp Lys Thr Trp Tyr Ile Gln Thr Lys Ser Asp Leu Leu Lys Lys
145                 150                 155                 160

Ser Ile Glu Asn Asn Arg Ile Asp Leu Thr Glu Asn Leu Ser Lys Arg
                165                 170                 175

Lys Lys Ala Leu Leu Ala Trp Glu Thr Glu Phe Thr Ala Ser Gly Ser
            180                 185                 190

Ile Asp Leu Thr His Tyr His Lys Val Tyr Met Thr Asp Val Leu Cys
            195                 200                 205

Lys Met Leu Gln Asp Val Lys Pro Leu Thr Asp Asp Lys Gly Lys Ile
        210                 215                 220

Asn Thr Asn Ala Tyr His Arg Gly Leu Lys Lys Ala Leu Gln Asn His
225                 230                 235                 240

Gln Pro Ala Ile Phe Gly Thr Arg Glu Val Pro Asn Glu Ala Asn Arg
                245                 250                 255

Ala Asp Asn Gln Leu Ser Ile Tyr His Leu Glu Val Val Lys Tyr Leu
            260                 265                 270

Glu His Tyr Phe Pro Ile Lys Thr Ser Lys Arg Arg Asn Thr Ala Asp
            275                 280                 285

Asp Ile Ala His Tyr Leu Lys Ala Gln Thr Leu Lys Thr Thr Ile Glu
```

-continued

```
        290             295             300

Lys Gln Leu Val Asn Ala Ile Arg Ala Asn Ile Ile Gln Gln Gly Lys
305             310             315             320

Thr Asn His His Glu Leu Lys Ala Asp Thr Thr Ser Asn Asp Leu Ile
                325             330             335

Arg Ile Lys Thr Asn Glu Ala Phe Val Leu Asn Leu Thr Gly Thr Cys
            340             345             350

Ala Phe Ala Ala Asn Asn Ile Arg Asn Met Val Asp Asn Glu Gln Thr
            355             360             365

Asn Asp Ile Leu Gly Lys Gly Asp Phe Ile Lys Ser Leu Leu Lys Asp
        370             375             380

Asn Thr Asn Ser Gln Leu Tyr Ser Phe Phe Phe Gly Glu Gly Leu Ser
385             390             395             400

Thr Asn Lys Ala Glu Lys Glu Thr Gln Leu Trp Gly Ile Arg Gly Ala
                405             410             415

Val Gln Gln Ile Arg Asn Asn Val Asn His Tyr Lys Lys Asp Ala Leu
            420             425             430

Lys Thr Val Phe Asn Ile Ser Asn Phe Glu Asn Pro Thr Ile Thr Asp
            435             440             445

Pro Lys Gln Gln Thr Asn Tyr Ala Asp Thr Ile Tyr Lys Ala Arg Phe
        450             455             460

Ile Asn Glu Leu Glu Lys Ile Pro Glu Ala Phe Ala Gln Gln Leu Lys
465             470             475             480

Thr Gly Gly Ala Val Ser Tyr Tyr Thr Ile Glu Asn Leu Lys Ser Leu
                485             490             495

Leu Thr Thr Phe Gln Phe Ser Leu Cys Arg Ser Thr Ile Pro Phe Ala
            500             505             510

Pro Gly Phe Lys Lys Val Phe Asn Gly Gly Ile Asn Tyr Gln Asn Ala
            515             520             525

Lys Gln Asp Glu Ser Phe Tyr Glu Leu Met Leu Glu Gln Tyr Leu Arg
        530             535             540

Lys Glu Asn Phe Ala Glu Glu Ser Tyr Asn Ala Arg Tyr Phe Met Leu
545             550             555             560

Lys Leu Ile Tyr Asn Asn Leu Phe Leu Pro Gly Phe Thr Thr Asp Arg
                565             570             575

Lys Ala Phe Ala Asp Ser Val Gly Phe Val Gln Met Gln Asn Lys Lys
            580             585             590

Gln Ala Glu Lys Val Asn Pro Arg Lys Lys Glu Ala Tyr Ala Phe Glu
        595             600             605

Ala Val Arg Pro Met Thr Ala Ala Asp Ser Ile Ala Asp Tyr Met Ala
        610             615             620

Tyr Val Gln Ser Glu Leu Met Gln Glu Gln Asn Lys Lys Glu Glu Lys
625             630             635             640

Val Ala Glu Glu Thr Arg Ile Asn Phe Glu Lys Phe Val Leu Gln Val
                645             650             655

Phe Ile Lys Gly Phe Asp Ser Phe Leu Arg Ala Lys Glu Phe Asp Phe
                660             665             670

Val Gln Met Pro Gln Pro Gln Leu Thr Ala Thr Ala Ser Asn Gln Gln
            675             680             685

Lys Ala Asp Lys Leu Asn Gln Leu Glu Ala Ser Ile Thr Ala Asp Cys
        690             695             700

Lys Leu Thr Pro Gln Tyr Ala Lys Ala Asp Asp Ala Thr His Ile Ala
705             710             715             720
```

-continued

```
Phe Tyr Val Phe Cys Lys Leu Leu Asp Ala Ala His Leu Ser Asn Leu
            725                 730                 735

Arg Asn Glu Leu Ile Lys Phe Arg Glu Ser Val Asn Glu Phe Lys Phe
            740                 745                 750

His His Leu Leu Glu Ile Ile Glu Ile Cys Leu Leu Ser Ala Asp Val
            755                 760                 765

Val Pro Thr Asp Tyr Arg Asp Leu Tyr Ser Ser Glu Ala Asp Cys Leu
    770                 775                 780

Ala Arg Leu Arg Pro Phe Ile Glu Gln Gly Ala Asp Ile Thr Asn Trp
785                 790                 795                 800

Ser Asp Leu Phe Val Gln Ser Asp Lys His Ser Pro Val Ile His Ala
            805                 810                 815

Asn Ile Glu Leu Ser Val Lys Tyr Gly Thr Thr Lys Leu Leu Glu Gln
            820                 825                 830

Ile Ile Asn Lys Asp Thr Gln Phe Lys Thr Thr Glu Ala Asn Phe Thr
            835                 840                 845

Ala Trp Asn Thr Ala Gln Lys Ser Ile Glu Gln Leu Ile Lys Gln Arg
    850                 855                 860

Glu Asp His His Glu Gln Trp Val Lys Ala Lys Asn Ala Asp Asp Lys
865                 870                 875                 880

Glu Lys Gln Glu Arg Lys Arg Glu Lys Ser Asn Phe Ala Gln Lys Phe
            885                 890                 895

Ile Glu Lys His Gly Asp Asp Tyr Leu Asp Ile Cys Asp Tyr Ile Asn
            900                 905                 910

Thr Tyr Asn Trp Leu Asp Asn Lys Met His Phe Val His Leu Asn Arg
            915                 920                 925

Leu His Gly Leu Thr Ile Glu Leu Leu Gly Arg Met Ala Gly Phe Val
    930                 935                 940

Ala Leu Phe Asp Arg Asp Phe Gln Phe Phe Asp Glu Gln Gln Ile Ala
945                 950                 955                 960

Asp Glu Phe Lys Leu His Gly Phe Val Asn Leu His Ser Ile Asp Lys
            965                 970                 975

Lys Leu Asn Glu Val Pro Thr Lys Lys Ile Lys Glu Ile Tyr Asp Ile
            980                 985                 990

Arg Asn Lys Ile Ile Gln Ile Asn Gly Asn Lys Ile Asn Glu Ser Val
            995                 1000                1005

Arg Ala Asn Leu Ile Gln Phe Ile Ser Ser Lys Arg Asn Tyr Tyr Asn
    1010                1015                1020

Asn Ala Phe Leu His Val Ser Asn Asp Glu Ile Lys Glu Lys Gln Met
1025                1030                1035                1040

Tyr Asp Ile Arg Asn His Ile Ala His Phe Asn Tyr Leu Thr Lys Asp
            1045                1050                1055

Ala Ala Asp Phe Ser Leu Ile Asp Leu Ile Asn Glu Leu Arg Glu Leu
            1060                1065                1070

Leu His Tyr Asp Arg Lys Leu Lys Asn Ala Val Ser Lys Ala Phe Ile
            1075                1080                1085

Asp Leu Phe Asp Lys His Gly Met Ile Leu Lys Leu Lys Leu Asn Ala
    1090                1095                1100

Asp His Lys Leu Lys Val Glu Ser Leu Glu Pro Lys Lys Ile Tyr His
1105                1110                1115                1120

Leu Gly Ser Ser Ala Lys Asp Lys Pro Glu Tyr Gln Tyr Cys Thr Asn
            1125                1130                1135
```

-continued

```
       Gln Val Met Met Ala Tyr Cys Asn Met Cys Arg Ser Leu Leu Glu Met
                 1140                1145                1150

Lys Lys

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55
<211> LENGTH: 29903
<212> TYPE: DNA
<213> ORGANISM: SARS-CoV 2

<400> SEQUENCE: 55
attaaaggtt tataccttcc caggtaacaa accaaccaac tttcgatctc ttgtagatct      60
gttctctaaa cgaactttaa aatctgtgtg gctgtcactc ggctgcatgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaagatgga gagccttgtc cctggtttca acgagaaaac     300
acacgtccaa ctcagtttgc ctgttttaca ggttcgcgac gtgctcgtac gtggctttgg     360
agactccgtg gaggaggtct tatcagaggc acgtcaacat cttaaagatg gcacttgtgg     420
cttagtagaa gttgaaaaag gcgttttgcc tcaacttgaa cagccctatg tgttcatcaa     480
acgttcggat gctcgaactg cacctcatgg tcatgttatg gttgagctgg tagcagaact     540
cgaaggcatt cagtacggtc gtagtggtga cacttggt gtccttgtcc tcatgtgggg      600
cgaaatacca gtggcttacc gcaaggttct tcttcgtaag aacggtaata aaggagctgg     660
tggccatagt tacggcgccg atctaaagtc atttgactta ggcgacgagc ttggcactga     720
```

-continued

```
tccttatgaa gattttcaag aaaactggaa cactaaacat agcagtggtg ttacccgtga   780
actcatgcgt gagcttaacg gaggggcata cactcgctat gtcgataaca acttctgtgg   840
ccctgatggc taccctcttg agtgcattaa agaccttcta gcacgtgctg gtaaagcttc   900
atgcactttg tccgaacaac tggactttat tgacactaag aggggtgtat actgctgccg   960
tgaacatgag catgaaattg cttggtacac ggaacgttct gaaaagagct atgaattgca   1020
gacacctttt gaaattaaat tggcaaagaa atttgacacc ttcaatgggg aatgtccaaa   1080
ttttgtattt cccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata tgaatctgg   1440 cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat cttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacgtg tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
```

```
agatgattac caaggtaaac ctttggaatt tggtgccact tctgctgctc ttcaacctga    3180
agaagagcaa gaagaagatt ggttagatga tgatagtcaa caaactgttg gtcaacaaga    3240
cggcagtgag gacaatcaga caactactat tcaaacaatt gttgaggttc aacctcaatt    3300
agagatggaa cttacaccag ttgttcagac tattgaagtg aatagtttta gtggttattt    3360
aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta aataaggcta ctaacaatgc catgcaagtt gaatctgatg attacatagc    3540
tactaatgga ccacttaaag tgggtggtag ttgtgtttta agcggacaca atcttgctaa    3600
acactgtctt catgttgtcg gcccaaatgt taacaaaggt gaagacattc aacttcttaa    3660
gagtgcttat gaaaatttta atcagcacga agttctactt gcaccattat tatcagctgg    3720 tattttttggt gctgaccta tacattcttt aagagtttgt gtagatactg ttcgcacaaa    3780
tgtctactta gctgtctttg ataaaaatct ctatgacaaa cttgtttcaa gcttttttgga    3840 aatgaagagt gaaaagcaag ttgaacaaaa gatcgctgag attcctaaag aggaagttaa    3900
gccatttata actgaaagta aaccttcagt tgaacagaga aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct taaagaaaga tgctccatat atagtgggtg atgttgttca    4140 agaggggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320
cttttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500 agaggggtgtg gttgattatg tgctagatt ttacttttac accagtaaaa caactgtagc    4560
gtcacttatc aacacactta acgatctaaa tgaaactctt gttacaatgc cacttggcta    4620
tgtaacacat ggcttaaatt tggaagaagc tgctcggtat atgagatctc tcaaagtgcc    4680
agctacagtt tctgtttctt cacctgatgc tgttacagcg tataatggtt atcttacttc    4740
ttcttctaaa acacctgaag aacattttat tgaaaccatc tcacttgctg gttcctataa    4800
agattggtcc tattctggac aatctacaca actaggtata gaatttctta agagaggtga    4860
taaaagtgta tattacacta gtaatcctac cacattccac ctagatggtg aagttatcac    4920
ctttgacaat cttaagacac ttctttcttt gagagaagtg aggactatta aggtgtttac    4980
aacagtagac aacattaacc tccacacgca agttgtggac atgtcaatga catatggaca    5040
acagtttggt ccaacttatt tggatggagc tgatgttact aaaataaaac ctcataattc    5100
acatgaaggt aaaacatttt atgttttacc taatgatgac actctacgtg ttgaggcttt    5160
tgagtactac cacacaactg atcctagttt tctgggtagg tacatgtcag cattaaatca    5220
cactaaaaag tggaaatacc cacaagttaa tggtttaact ctattaaat gggcagataa    5280 caactgttat cttgccactg cattgttaac actccaacaa atagagttga gtttaatcc    5340 acctgctcta caagatgctt attacagagc aaagggctggt gaagctgcta cttttgttgc    5400
acttatctta gcctactgta ataagacagt aggtgagtta ggtgatgtta gagaaacaat    5460
```

```
gagttacttg tttcaacatg ccaatttaga ttcttgcaaa agagtcttga acgtggtgtg    5520
taaaacttgt ggacaacagc agacaaccct taagggtgta gaagctgtta tgtacatggg    5580
cacactttct tatgaacaat ttaagaaagg tgttcagata ccttgtacgt gtggtaaaca    5640
agctacaaaa tatctagtac aacaggagtc accttttgtt atgatgtcag caccacctgc    5700
tcagtatgaa cttaagcatg gtacatttac ttgtgctagt gagtacactg gtaattacca    5760
gtgtggtcac tataaacata taacttctaa agaaactttg tattgcatag acggtgcttt    5820
acttacaaag tcctcagaat acaaaggtcc tattacggat gttttctaca aagaaaacag    5880
ttacacaaca accataaaac cagttactta taaattggat ggtgttgttt gtacagaaat    5940
tgaccctaag ttggacaatt attataagaa agacaattct tatttcacag agcaaccaat    6000
tgatcttgta ccaaaccaac catatccaaa cgcaagcttc gataatttta agtttgtatg    6060 tgataaatatc aaatttgctg atgatttaaa ccagttaact ggttataaga aacctgcttc    6120
aagagagctt aaagttacat tttttccctga cttaaatggt gatgtggtgg ctattgatta    6180
taaacactac acaccctctt ttaagaaagg agctaaattg ttacataaac ctattgtttg    6240
gcatgttaac aatgcaacta ataaagccac gtataaacca aatacctggt gtatacgttg    6300
tctttggagc acaaaaccag ttgaaacatc aaattcgttt gatgtactga agtcagagga    6360
cgcgcaggga atggataatc ttgcctgcga agatctaaaa ccagtctctg aagaagtagt    6420
ggaaaatcct accatacaga aagacgttct tgagtgtaat gtgaaaacta ccgaagttgt    6480
aggagacatt atacttaaac cagcaaataa tagtttaaaa attacagaag aggttggcca    6540
cacagatcta atggctgctt atgtagacaa ttctagtctt actattaaga aacctaatga    6600
attatctaga gtattaggtt tgaaaaccct tgctactcat ggtttagctg ctgttaatag    6660
tgtcccttgg gatactatag ctaattatgc taagcctttt cttaacaaag ttgttagtac    6720
aactactaac atagttacac ggtgtttaaa ccgtgtttgt actaattata tgccttattt    6780
ctttacttta ttgctacaat tgtgtacttt tactagaagt acaaattcta gaattaaagc    6840
atctatgccg actactatag caaagaatac tgttaagagt gtcggtaaat tttgtctaga    6900
ggcttcattt aattatttga agtcacctaa tttttctaaa ctgataaaata ttataaatttg    6960 gttttttacta ttaagtgttt gcctaggttc tttaatctac tcaaccgctg ctttaggtgt    7020
tttaatgtct aatttaggca tgccttctta ctgtactggt tacagagaag gctatttgaa    7080
ctctactaat gtcactattg caacctactg tactggttct ataccttgta gtgtttgtct    7140 tagtggtttta gattctttag acacctatcc ttctttagaa actatacaaa ttaccatttc    7200 atctttttaaa tgggatttaa ctgctttttgg cttagttgca gagtggtttt tggcatatat    7260 tcttttttcact aggttttttct atgtacttgg attggctgca atcatgcaat tgtttttcag    7320
ctattttgca gtacatttta ttagtaattc ttggcttatg tggttaataa ttaatcttgt    7380
acaaatggcc ccgatttcag ctatggttag aatgtacatc ttctttgcat cattttatta    7440
tgtatggaaa agttatgtgc atgttgtaga cggttgtaat tcatcaactt gtatgatgtg    7500
ttacaaacgt aatagagcaa caagagtcga atgtacaact attgttaatg gtgttagaag    7560
gtccttttat gtctatgcta atggaggtaa aggcttttgc aaactacaca attggaattg    7620
tgttaattgt gatacattct gtgctggtag tacatttatt agtgatgaag ttgcgagaga    7680
cttgtcacta cagtttaaaa gaccaataaa tcctactgac cagtcttctt acatcgttga    7740
tagtgttaca gtgaagaatg gttccatcca tctttacttt gataaagctg gtcaaaagac    7800
ttatgaaaga cattctctct ctcattttgt taacttagac aacctgagag ctaataacac    7860
```

-continued

```
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggtttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600 gacatttttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780 tagtacttttt gaagaagctg cgctgtgcac cttttttgtta ataaagaaa tgtatctaaa   9840 gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc   10020
accacaaacc tctatcacct cagctgtttt gcagagtggt tttagaaaaa tggcattccc   10080
atctggtaaa gttgaggggtt gtatggtaca agtaacttgt ggtacaacta cacttaacgg   10140
tctttggctt gatgacgtag tttactgtcc aagacatgtg atctgcacct ctgaagacat   10200
```

```
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgcctttt  11100 acctttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520 gttttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctctttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca gctttgtga  12060 agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
```

-continued

```
tgaaattagt atggacaatt cacctaattt agcatggcct cttattgtaa cagctttaag   12660
ggccaattct gctgtcaaat tacagaataa tgagcttagt cctgttgcac tacgacagat   12720
gtcttgtgct gccggtacta cacaaactgc ttgcactgat gacaatgcgt tagcttacta   12780
caacacaaca aagggaggta ggtttgtact tgcactgtta tccgatttac aggatttgaa   12840
atgggctaga ttccctaaga gtgatggaac tggtactatc tatacagaac tggaaccacc   12900
ttgtaggttt gttacagaca cacctaaagg tcctaaagtg aagtatttat actttattaa   12960
aggattaaac aacctaaata gaggtatggt acttggtagt ttagctgcca cagtacgtct   13020
acaagctggt aatgcaacag aagtgcctgc caattcaact gtattatctt tctgtgcttt   13080
tgctgtagat gctgctaaag cttacaaaga ttatctagct agtgggggac aaccaatcac   13140
taattgtgtt aagatgttgt gtacacacac tggtactggt caggcaataa cagttacacc   13200
ggaagccaat atggatcaag aatcctttgg tggtgcatcg tgttgtctgt actgccgttg   13260
ccacatagat catccaaatc ctaaaggatt ttgtgactta aaaggtaagt atgtacaaat   13320
acctacaact tgtgctaatg accctgtggg ttttacactt aaaaacacag tctgtaccgt   13380
ctgcggtatg tggaaaggtt atggctgtag ttgtgatcaa ctccgcgaac ccatgcttca   13440
gtcagctgat gcacaatcgt ttttaaacgg gtttgcggtg taagtgcagc ccgtcttaca   13500
ccgtgcggca caggcactag tactgatgtc gtatacaggg cttttgacat ctacaatgat   13560
aaagtagctg gttttgctaa attcctaaaa actaattgtt gtcgcttcca agaaaaggac   13620
gaagatgaca atttaattga ttcttacttt gtagttaaga gacacacttt ctctaactac   13680
caacatgaag aaacaattta taatttactt aaggattgtc cagctgttgc taaacatgac   13740
ttctttaagt ttagaataga cggtgacatg gtaccacata tatcacgtca acgtcttact   13800
aaatacacaa tggcagacct cgtctatgct ttaaggcatt ttgatgaagg taattgtgac   13860
acattaaaag aaatacttgt cacatacaat tgttgtgatg atgattattt caataaaaag   13920
gactggtatg attttgtaga aaacccagat atattacgcg tatacgccaa cttaggtgaa   13980
cgtgtacgcc aagctttgtt aaaaacagta caattctgtg atgccatgcg aaatgctggt   14040
attgttggtg tactgacatt agataatcaa gatctcaatg gtaactggta tgatttcggt   14100
gatttcatac aaaccacgcc aggtagtgga gttcctgttg tagattctta ttattcattg   14160
ttaatgccta tattaacctt gaccaggggct ttaactgcag agtcacatgt tgacactgac   14220
ttaacaaagc cttacattaa gtgggatttg ttaaaatatg acttcacgga agagaggtta   14280
aaactctttg accgttattt taaatattgg gatcagacat accacccaaa ttgtgttaac   14340
tgtttggatg acagatgcat tctgcattgt gcaaacttta atgtttttat ctctacagtg   14400
ttcccaccta caagttttgg accactagtg agaaaaatat ttgttgatgg tgttccattt   14460
gtagtttcaa ctggatacca cttcagagag ctaggtgttg tacataatca ggatgtaaac   14520
ttacatagct ctagacttag ttttaaggaa ttacttgtgt atgctgctga ccctgctatg   14580
cacgctgctt ctggtaatct attactagat aaacgcacta cgtgcttttc agtagctgca   14640
cttactaaca atgttgcttt tcaaactgtc aaacccggta tttttaacaa agacttctat   14700
gactttgctg tgtctaaggg tttctttaag gaaggaagtt ctgttgaatt aaaacacttc   14760
ttctttgctc aggatggtaa tgctgctatc agcgattatg actactatcg ttataatcta   14820
ccaacaatgt gtgatatcag acaactacta tttgtagttg aagttgttga taagtacttt   14880
gattgttacg atggtggctg tattaatgct aaccaagtca tcgtcaacaa cctagacaaa   14940
```

-continued

```
tcagctggtt ttccatttaa taaatggggt aaggctagac tttattatga ttcaatgagt   15000
tatgaggatc aagatgcact tttcgcatat acaaaacgta atgtcatccc tactataact   15060
caaatgaatc ttaagtatgc cattagtgca aagaatagag ctcgcaccgt agctggtgtc   15120
tctatctgta gtactatgac caatagacag tttcatcaaa aattattgaa atcaatagcc   15180
gccactagag gagctactgt agtaattgga acaagcaaat tctatggtgg ttggcacaac   15240
atgttaaaaa ctgtttatag tgatgtagaa aaccctcacc ttatgggttg ggattatcct   15300
aaatgtgata gagccatgcc taacatgctt agaattatgg cctcacttgt tcttgctcgc   15360
aaacatacaa cgtgttgtag cttgtcacac cgtttctata gattagctaa tgagtgtgct   15420
caagtattga gtgaaatggt catgtgtggc ggttcactat atgttaaacc aggtggaacc   15480
tcatcaggag atgccacaac tgcttatgct aatagtgttt ttaacatttg tcaagctgtc   15540
acggccaatg ttaatgcact tttatctact gatggtaaca aaattgccga taagtatgtc   15600
cgcaatttac aacacagact ttatgagtgt ctctatagaa atagagatgt tgacacagac   15660
tttgtgaatg agttttacgc atatttgcgt aaacatttct caatgatgat actctctgac   15720
gatgctgttg tgtgtttcaa tagcacttat gcatctcaag gtctagtggc tagcataaag   15780
aactttaagt cagttcttta ttatcaaaac aatgttttta tgtctgaagc aaaatgttgg   15840
actgagactg accttactaa aggacctcat gaattttgct ctcaacatac aatgctagtt   15900
aaacagggtg atgattatgt gtaccttcct tacccagatc catcaagaat cctaggggcc   15960
ggctgttttg tagatgatat cgtaaaaaca gatggtacac ttatgattga acggttcgtg   16020
tctttagcta tagatgctta cccacttact aaacatccta atcaggagta tgctgatgtc   16080
tttcatttgt acttacaata cataagaaag ctacatgatg agttaacagg acacatgtta   16140
gacatgtatt ctgttatgct tactaatgat aacacttcaa ggtattggga acctgagttt   16200
tatgaggcta tgtacacacc gcatacagtc ttacaggctg ttggggcttg tgttctttgc   16260
aattcacaga cttcattaag atgtggtgct tgcatacgta gaccattctt atgttgtaaa   16320
tgctgttacg accatgtcat atcaacatca cataaattag tcttgtctgt taatccgtat   16380
gtttgcaatg ctccaggttg tgatgtcaca gatgtgactc aactttactt aggaggtatg   16440
agctattatt gtaaatcaca taaaccaccc attagttttc cattgtgtgc taatggacaa   16500 gttttttggtt tatataaaaa tacatgtgtt ggtagcgata atgttactga ctttaatgca   16560
attgcaacat gtgactggac aaatgctggt gattacattt tagctaacac ctgtactgaa   16620
agactcaagc tttttgcagc agaaacgctc aaagctactg aggagacatt taaactgtct   16680
tatggtattg ctactgtacg tgaagtgctg tctgacagag aattacatct ttcatgggaa   16740
gttggtaaac ctagaccacc acttaaccga aattatgtct ttactggtta tcgtgtaact   16800
aaaaacagta aagtacaaat aggagagtac acctttgaaa aaggtgacta tggtgatgct   16860
gttgtttacc gaggtacaac aacttacaaa ttaaatgttg gtgattattt tgtgctgaca   16920
tcacatacag taatgccatt aagtgcacct acactagtgc cacaagagca ctatgttaga   16980
attactggct tatacccaac actcaatatc tcagatgagt tttctagcaa tgttgcaaat   17040
tatcaaaagg ttggtatgca aaagtattct acactccagg accacctggg tactggtaag   17100
agtcattttg ctattggcct agctctctac taccttctg ctcgcatagt gtatacagct   17160
tgctctcatg ccgctgttga tgcactatgt gagaaggcat taaatatttt gcctatagat   17220
aaatgtagta gaattatacc tgcacgtgct cgtgtagagt gttttgataa attcaaagtg   17280
aattcaacat tagaacagta tgtctttttgt actgtaaatg cattgcctga gacgacagca   17340
```

-continued

```
gatatagttg tctttgatga aatttcaatg gccacaaatt atgatttgag tgttgtcaat    17400
gccagattac gtgctaagca ctatgtgtac attggcgacc ctgctcaatt acctgcacca    17460
cgcacattgc taactaaggg cacactagaa ccagaatatt tcaattcagt gtgtagactt    17520
atgaaaacta taggtccaga catgttcctc ggaacttgtc ggcgttgtcc tgctgaaatt    17580
gttgacactg tgagtgcttt ggtttatgat aataagctta aagcacataa agacaaatca    17640
gctcaatgct ttaaaatgtt ttataagggt gttatcacgc atgatgtttc atctgcaatt    17700
aacaggccac aaataggcgt ggtaagagaa ttccttacac gtaaccctgc ttggagaaaa    17760
gctgtcttta tttcacctta taattcacag aatgctgtag cctcaaagat tttgggacta    17820
ccaactcaaa ctgttgattc atcacagggc tcagaatatg actatgtcat attcactcaa    17880
accactgaaa cagctcactc ttgtaatgta aacagattta atgttgctat taccagagca    17940
aaagtaggca tactttgcat aatgtctgat agagaccttt atgacaagtt gcaatttaca    18000
agtcttgaaa ttccacgtag gaatgtggca actttacaag ctgaaaatgt aacaggactc    18060
tttaaagatt gtagtaaggt aatcactggg ttacatccta cacaggcacc tacacacctc    18120
agtgttgaca ctaaaattcaa aactgaaggt ttatgtgttg acatacctgg catacctaag    18180
gacatgacct atagaagact catctctatg atgggtttta aaatgaatta tcaagttaat    18240
ggttacccta acatgtttat cacccgcgaa gaagctataa gacatgtacg tgcatggatt    18300
ggcttcgatg tcgaggggtg tcatgctact agagaagctg ttggtaccaa tttacccttta    18360 cagctaggtt tttctacagg tgttaaccta gttgctgtac ctacaggtta tgttgataca    18420
cctaataata cagattttc cagagttagt gctaaaccac cgcctggaga tcaatttaaa    18480
cacctcatac cacttatgta caaaggactt ccttggaatg tagtgcgtat aaagattgta    18540
caaatgttaa gtgacacact taaaaatctc tctgacagag tcgtatttgt cttatgggca    18600
catggctttg agttgacatc tatgaagtat tttgtgaaaa taggacctga gcgcacctgt    18660
tgtctatgtg atagacgtgc cacatgcttt tccactgctt cagacactta tgcctgttgg    18720
catcattcta ttggatttga ttacgtctat aatccgttta tgattgatgt tcaacaatgg    18780
ggttttacag gtaacctaca aagcaaccat gatctgtatt gtcaagtcca tggtaatgca    18840
catgtagcta gttgtgatgc aatcatgact aggtgtctag ctgtccacga gtgctttgtt    18900
aagcgtgttg actggactat tgaatatcct ataattggtg atgaactgaa gattaatgcg    18960
gcttgtagaa aggttcaaca catggttgtt aaagctgcat tattagcaga caaattccca    19020
gttcttcacg acattggtaa ccctaaagct attaagtgtg tacctcaagc tgatgtagaa    19080
tggaagttct atgatgcaca gccttgtagt gacaaagctt ataaaataga agaattattc    19140
tattcttatg ccacacattc tgacaaattc acagatggtg tatgcctatt ttggaattgc    19200
aatgtcgata gatatcctgc taattccatt gtttgtagat ttgacactag agtgctatct    19260
aaccttaact tgcctggttg tgatggtggc agtttgtatg taaataaaca tgcattccac    19320
acaccagctt ttgataaaag tgcttttgtt aatttaaaac aattaccatt tttctattac    19380
tctgacagtc catgtgagtc tcatggaaaa caagtagtgt cagatataga ttatgtacca    19440
ctaaagtctg ctacgtgtat aacacgttgc aatttaggt gtgctgtctg tagacatcat    19500
gctaatgagt acagattgta tctcgatgct tataacatga tgatctcagc tggctttagc    19560
ttgtgggttt acaaacaatt tgatacttat aacctctgga acacttttac aagacttcag    19620
agtttagaaa atgtggcttt taatgttgta aataagggac actttgatgg acaacagggt    19680
```

```
gaagtaccag tttctatcat taataacact gtttacacaa aagttgatgg tgttgatgta    19740
gaattgtttg aaaataaaac aacattacct gttaatgtag catttgagct ttgggctaag    19800
cgcaacatta aaccagtacc agaggtgaaa atactcaata atttgggtgt ggacattgct    19860
gctaatactg tgatctggga ctacaaaaga gatgctccag cacatatatc tactattggt    19920
gtttgttcta tgactgacat agccaagaaa ccaactgaaa cgatttgtgc accactcact    19980
gtcttttttg atggtagagt tgatggtcaa gtagacttat ttagaaatgc ccgtaatggt    20040
gttcttatta cagaaggtag tgttaaaggt ttacaaccat ctgtaggtcc caaacaagct    20100
agtcttaatg gagtcacatt aattggagaa gccgtaaaaa cacagttcaa ttattataag    20160
aaagttgatg gtgttgtcca acaattacct gaaacttact ttactcagag tagaaattta    20220
caagaattta aacccaggag tcaaatggaa attgatttct tagaattagc tatggatgaa    20280
ttcattgaac ggtataaatt agaaggctat gccttcgaac atatcgttta tggagatttt    20340
agtcatagtc agttaggtgg tttacatcta ctgattggac tagctaaacg ttttaaggaa    20400
tcaccttttg aattagaaga ttttattcct atggacagta cagttaaaaa ctatttcata    20460
acagatgcgc aaacaggttc atctaagtgt gtgtgttctg ttattgattt attacttgat    20520
gattttgttg aaataataaa atcccaagat ttatctgtag tttctaaggt tgtcaaagtg    20580
actattgact atacagaaat ttcatttatg ctttggtgta agatggcca tgtagaaaca    20640 ttttacccaa aattacaatc tagtcaagcg tggcaaccgg gtgttgctat gcctaatctt    20700
tacaaaatgc aaagaatgct attagaaaag tgtgaccttc aaaattatgg tgatagtgca    20760
acattaccta aaggcataat gatgaatgtc gcaaaatata ctcaactgtg tcaatattta    20820
aacacattaa cattagctgt accctataat atgagagtta tacattttgg tgctggttct    20880
gataaaggag ttgcaccagg tacagctgtt ttaagacagt ggttgcctac gggtacgctg    20940
cttgtcgatt cagatcttaa tgactttgtc tctgatgcag attcaacttt gattggtgat    21000
tgtgcaactg tacatacagc taataaatgg gatctcatta ttagtgatat gtacgaccct    21060
aagactaaaa atgttacaaa agaaaatgac tctaagagg gttttttcac ttacatttgt    21120
gggtttatac aacaaagct agctcttgga ggttccgtgg ctataaagat aacagaacat    21180
tcttggaatg ctgatctta taagctcatg ggacacttcg catggtggac agcctttgtt    21240
actaatgtga atgcgtcatc atctgaagca ttttttaattg gatgtaatta tcttggcaaa    21300
ccacgcgaac aaatagatgg ttatgtcatg catgcaaatt acatattttg gaggaataca    21360
aatccaattc agttgtcttc ctattcttta tttgacatga gtaaatttcc ccttaaatta    21420
aggggtactg ctgttatgtc tttaaaagaa ggtcaaatca atgatatgat tttatctctt    21480
cttagtaaag gtagacttat aattagagaa aacaacagag ttgttatttc tagtgatgtt    21540
cttgttaaca actaaacgaa caatgtttgt ttttcttgtt ttattgccac tagtctctag    21600
tcagtgtgtt aatcttacaa ccagaactca attacccct gcatacacta attctttcac    21660
acgtggtgtt tattaccctg acaaagtttt cagatcctca gttttacatt caactcagga    21720
cttgttctta cctttctttt ccaatgttac ttggttccat gctatacatg tctctgggac    21780
caatggtact aagaggtttg ataaccctgt cctaccattt aatgatggtg tttattttgc    21840
ttccactgag aagtctaaca taataagagg ctggattttt ggtactactt tagattcgaa    21900
gacccagtcc ctacttattg ttaataacgc tactaatgtt gttattaaag tctgtgaatt    21960
tcaattttgt aatgatccat tttttgggtgt ttattaccac aaaaacaaca aaagttggat    22020
ggaaagtgag ttcagagttt attctagtgc gaataattgc acttttgaat atgtctctca    22080
```

-continued

```
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc taatattac  22560 aaacttgtgc ccttttggtg aagttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt aatagggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaattttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg tttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
```

-continued

```
ccaaaatgca caagctttaa acacgcttgt taaacaactt agctccaatt ttggtgcaat   24480
ttcaagtgtt ttaaatgata tccttttcacg tcttgacaaa gttgaggctg aagtgcaaat   24540
tgataggttg atcacaggca gacttcaaag tttgcagaca tatgtgactc aacaattaat   24600
tagagctgca gaaatcagag cttctgctaa tcttgctgct actaaaatgt cagagtgtgt   24660
acttggacaa tcaaaaagag ttgatttttg tggaaagggc tatcatctta tgtccttccc   24720
tcagtcagca cctcatggtg tagtcttctt gcatgtgact tatgtccctg cacaagaaaa   24780
gaacttcaca actgctcctg ccatttgtca tgatggaaaa gcacactttc ctcgtgaagg   24840
tgtctttgtt tcaaatggca cacactggtt tgtaacacaa aggaattttt atgaaccaca   24900
aatcattact acagacaaca catttgtgtc tggtaactgt gatgttgtaa taggaattgt   24960
caacaacaca gtttatgatc ctttgcaacc tgaattagac tcattcaagg aggagttaga   25020
taaatatttt aagaatcata catcaccaga tgttgattta ggtgacatct ctggcattaa   25080
tgcttcagtt gtaaacattc aaaaagaaat tgaccgcctc aatgaggttg ccaagaattt   25140
aaatgaatct ctcatcgatc tccaagaact tggaaagtat gagcagtata taaaatggcc   25200
atggtacatt tggctaggtt ttatagctgg cttgattgcc atagtaatgg tgacaattat   25260
gctttgctgt atgaccagtt gctgtagttg tctcaagggc tgttgttctt gtggatcctg   25320
ctgcaaattt gatgaagacg actctgagcc agtgctcaaa ggagtcaaat tacattacac   25380
ataaacgaac ttatggattt gtttatgaga atcttcacaa ttggaactgt aactttgaag   25440
caaggtgaaa tcaaggatgc tactccttca gattttgttc gcgctactgc aacgataccg   25500
atacaagcct cactcccttt cggatggctt attgttggcg ttgcacttct tgctgttttt   25560
cagagcgctt ccaaaatcat aaccctcaaa aagagatggc aactagcact ctccaagggt   25620
gttcactttg tttgcaactt gctgttgttg tttgtaacag tttactcaca ccttttgctc   25680
gttgctgctg gccttgaagc cccttttctc tatctttatg ctttagtcta cttcttgcag   25740
agtataaact ttgtaagaat aataatgagg ctttggcttt gctggaaatg ccgttccaaa   25800
aacccattac tttatgatgc caactatttt ctttgctggc atactaattg ttacgactat   25860
tgtatacctt acaatagtgt aacttcttca attgtcatta cttcaggtga tggcacaaca   25920
agtcctattt ctgaacatga ctaccagatt ggtggttata ctgaaaaatg ggaatctgga   25980
gtaaaagact gtgttgtatt acacagttac ttcacttcag actattacca gctgactca   26040 actcaattga gtacagacac tggtgttgaa catgttacct tcttcatcta caataaaatt   26100
gttgatgagc ctgaagaaca tgtccaaatt cacacaatcg acggttcatc cggagttgtt   26160
aatccagtaa tggaaccaat ttatgatgaa ccgacgacga ctactagcgt gcctttgtaa   26220
gcacaagctg atgagtacga acttatgtac tcattcgttt cggaagagac aggtacgtta   26280
atagttaata gcgtacttct ttttcttgct ttcgtggtat tcttgctagt tacactagcc   26340
atccttactg cgcttcgatt gtgtgcgtac tgctgcaata ttgttaacgt gagtcttgta   26400
aaaccttctt tttacgttta ctctcgtgtt aaaaatctga attcttctag agttcctgat   26460
cttctggtct aaacgaacta aatattatat tagtttttct gtttggaact ttaattttag   26520
ccatggcaga ttccaacggt actattaccg ttgaagagct aaaaagctc cttgaacaat   26580 ggaacctagt aataggtttc ctattcctta catggatttg tcttctacaa tttgcctatg   26640
ccaacaggaa taggtttttg tatataatta agttaatttt cctctggctg ttatggccag   26700
taactttagc ttgttttgtg cttgctgctg tttacagaat aaattggatc accggtggaa   26760
ttgctatcgc aatggcttgt cttgtaggct tgatgtggct cagctacttc attgcttctt   26820
```

-continued

```
tcagactgtt tgcgcgtacg cgttccatgt ggtcattcaa tccagaaact aacattcttc   26880
tcaacgtgcc actccatggc actattctga ccagaccgct tctagaaagt gaactcgtaa   26940
tcggagctgt gatccttcgt ggacatcttc gtattgctgg acaccatcta ggacgctgtg   27000
acatcaagga cctgcctaaa gaaatcactg ttgctacatc acgaacgctt tcttattaca   27060
aattgggagc ttcgcagcgt gtagcaggtg actcaggttt tgctgcatac agtcgctaca   27120
ggattggcaa ctataaatta aacacagacc attccagtag cagtgacaat attgctttgc   27180
ttgtacagta agtgacaaca gatgtttcat ctcgttgact ttcaggttac tatagcagag   27240
atattactaa ttattatgag gacttttaaa gtttccattt ggaatcttga ttacatcata   27300
aacctcataa ttaaaaattt atctaagtca ctaactgaga ataaatattc tcaattagat   27360
gaagagcaac caatggagat tgattaaacg aacatgaaaa ttattctttt cttggcactg   27420
ataacactcg ctacttgtga gctttatcac taccaagagt gtgttagagg tacaacagta   27480
cttttaaaag aaccttgctc ttctggaaca tacgagggca attcaccatt tcatcctcta   27540
gctgataaca aatttgcact gacttgcttt agcactcaat ttgcttttgc ttgtcctgac   27600
ggcgtaaaac acgtctatca gttacgtgcc agatcagttt cacctaaact gttcatcaga   27660
caagaggaag ttcaagaact ttactctcca atttttctta ttgttgcggc aatagtgttt   27720
ataacacttt gcttcacact caaaagaaag acagaatgat tgaactttca ttaattgact   27780
tctatttgtg cttttttagcc tttctgctat tccttgtttt aattatgctt attatctttt   27840
ggttctcact tgaactgcaa gatcataatg aaacttgtca cgcctaaacg aacatgaaat   27900
ttcttgtttt cttaggaatc atcacaactg tagctgcatt tcaccaagaa tgtagtttac   27960
agtcatgtac tcaacatcaa ccatatgtag ttgatgaccc gtgtcctatt cacttctatt   28020
ctaaatggta tattagagta ggagctagaa aatcagcacc tttaattgaa ttgtgcgtgg   28080
atgaggctgg ttctaaatca cccattcagt acatcgatat cggtaattat acagtttcct   28140 gtttacctttt tacaattaat tgccaggaac ctaaattggg tagtcttgta gtgcgttgtt   28200
cgttctatga agactttttta gagtatcatg acgttcgtgt tgttttagat ttcatctaaa   28260
cgaacaaact aaaatgtctg ataatggacc ccaaaatcag cgaaatgcac cccgcattac   28320
gtttggtgga ccctcagatt caactggcag taaccagaat ggagaacgca gtggggcgcg   28380
atcaaaacaa cgtcggcccc aaggtttacc caataatact gcgtcttggt tcaccgctct   28440
cactcaacat ggcaaggaag accttaaatt ccctcgagga caaggcgttc caattaacac   28500
caatagcagt ccagatgacc aaattggcta ctaccgaaga gctaccagac gaattcgtgg   28560
tggtgacggt aaaatgaaag atctcagtcc aagatggtat ttctactacc taggaactgg   28620
gccagaagct ggacttccct atggtgctaa caaagacggc atcatatggg ttgcaactga   28680
gggagccttg aatacaccaa aagatcacat ggcacccgc aatcctgcta caatgctgc    28740 aatcgtgcta caacttcctc aaggaacaac attgccaaaa ggcttctacg cagaagggag   28800
cagaggcggc agtcaagcct cttctcgttc ctcatcacgt agtcgcaaca gttcaagaaa   28860
ttcaactcca ggcagcagta ggggaacttc tcctgctaga atggctggca atggcggtga   28920
tgctgctctt gctttgctgc tgcttgacag attgaaccag cttgagagca aaatgtctgg   28980
taaaggccaa caacaacaag gccaaactgt cactaagaaa tctgctgctg aggcttctaa   29040
gaagcctcgg caaaaacgta ctgccactaa agcatacaat gtaacacaag ctttcggcag   29100
acgtggtcca gaacaaaccc aaggaaattt tggggaccag gaactaatca gacaaggaac   29160
```

-continued

```
tgattacaaa cattggccgc aaattgcaca atttgccccc agcgcttcag cgttcttcgg    29220
aatgtcgcgc attggcatgg aagtcacacc ttcgggaacg tggttgacct acacaggtgc    29280
catcaaattg gatgacaaag atccaaattt caaagatcaa gtcattttgc tgaataagca    29340
tattgacgca tacaaaacat tcccaccaac agagcctaaa aaggacaaaa agaagaaggc    29400
tgatgaaact caagccttac cgcagagaca gaagaaacag caaactgtga ctcttcttcc    29460
tgctgcagat ttggatgatt tctccaaaca attgcaacaa tccatgagca gtgctgactc    29520
aactcaggcc taaactcatg cagaccacac aaggcagatg ggctatataa acgttttcgc    29580
ttttccgttt acgatatata gtctactctt gtgcagaatg aattctcgta actacatagc    29640
acaagtagat gtagttaact ttaatctcac atagcaatct ttaatcagtg tgtaacatta    29700
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aaaaaaaaaa aaaaaaaaaa aaa                                           29903
```

```
<210> SEQ ID NO 56
<211> LENGTH: 932
<212> TYPE: PRT
<213> ORGANISM: SARS-CoV 2

<400> SEQUENCE: 56

Ser Ala Asp Ala Gln Ser Phe Leu Asn Arg Val Cys Gly Val Ser Ala
1               5                   10                  15

Ala Arg Leu Thr Pro Cys Gly Thr Gly Thr Ser Thr Asp Val Val Tyr
            20                  25                  30

Arg Ala Phe Asp Ile Tyr Asn Asp Lys Val Ala Gly Phe Ala Lys Phe
        35                  40                  45

Leu Lys Thr Asn Cys Cys Arg Phe Gln Glu Lys Asp Glu Asp Asp Asn
    50                  55                  60

Leu Ile Asp Ser Tyr Phe Val Val Lys Arg His Thr Phe Ser Asn Tyr
65                  70                  75                  80

Gln His Glu Glu Thr Ile Tyr Asn Leu Leu Lys Asp Cys Pro Ala Val
                85                  90                  95

Ala Lys His Asp Phe Phe Lys Phe Arg Ile Asp Gly Asp Met Val Pro
            100                 105                 110

His Ile Ser Arg Gln Arg Leu Thr Lys Tyr Thr Met Ala Asp Leu Val
            115                 120                 125

Tyr Ala Leu Arg His Phe Asp Glu Gly Asn Cys Asp Thr Leu Lys Glu
        130                 135                 140

Ile Leu Val Thr Tyr Asn Cys Cys Asp Asp Asp Tyr Phe Asn Lys Lys
145                 150                 155                 160

Asp Trp Tyr Asp Phe Val Glu Asn Pro Asp Ile Leu Arg Val Tyr Ala
                165                 170                 175

Asn Leu Gly Glu Arg Val Arg Gln Ala Leu Leu Lys Thr Val Gln Phe
            180                 185                 190

Cys Asp Ala Met Arg Asn Ala Gly Ile Val Gly Val Leu Thr Leu Asp
            195                 200                 205

Asn Gln Asp Leu Asn Gly Asn Trp Tyr Asp Phe Gly Asp Phe Ile Gln
        210                 215                 220

Thr Thr Pro Gly Ser Gly Val Pro Val Val Asp Ser Tyr Tyr Ser Leu
225                 230                 235                 240
```

```
Leu Met Pro Ile Leu Thr Leu Thr Arg Ala Leu Thr Ala Glu Ser His
                245                 250                 255

Val Asp Thr Asp Leu Thr Lys Pro Tyr Ile Lys Trp Asp Leu Leu Lys
            260                 265                 270

Tyr Asp Phe Thr Glu Glu Arg Leu Lys Leu Phe Asp Arg Tyr Phe Lys
        275                 280                 285

Tyr Trp Asp Gln Thr Tyr His Pro Asn Cys Val Asn Cys Leu Asp Asp
    290                 295                 300

Arg Cys Ile Leu His Cys Ala Asn Phe Asn Val Leu Phe Ser Thr Val
305                 310                 315                 320

Phe Pro Pro Thr Ser Phe Gly Pro Leu Val Arg Lys Ile Phe Val Asp
                325                 330                 335

Gly Val Pro Phe Val Val Ser Thr Gly Tyr His Phe Arg Glu Leu Gly
            340                 345                 350

Val Val His Asn Gln Asp Val Asn Leu His Ser Ser Arg Leu Ser Phe
        355                 360                 365

Lys Glu Leu Leu Val Tyr Ala Ala Asp Pro Ala Met His Ala Ala Ser
    370                 375                 380

Gly Asn Leu Leu Leu Asp Lys Arg Thr Thr Cys Phe Ser Val Ala Ala
385                 390                 395                 400

Leu Thr Asn Asn Val Ala Phe Gln Thr Val Lys Pro Gly Asn Phe Asn
                405                 410                 415

Lys Asp Phe Tyr Asp Phe Ala Val Ser Lys Gly Phe Phe Lys Glu Gly
            420                 425                 430

Ser Ser Val Glu Leu Lys His Phe Phe Phe Ala Gln Asp Gly Asn Ala
        435                 440                 445

Ala Ile Ser Asp Tyr Asp Tyr Tyr Arg Tyr Asn Leu Pro Thr Met Cys
    450                 455                 460

Asp Ile Arg Gln Leu Leu Phe Val Val Glu Val Val Asp Lys Tyr Phe
465                 470                 475                 480

Asp Cys Tyr Asp Gly Gly Cys Ile Asn Ala Asn Gln Val Ile Val Asn
                485                 490                 495

Asn Leu Asp Lys Ser Ala Gly Phe Pro Phe Asn Lys Trp Gly Lys Ala
            500                 505                 510

Arg Leu Tyr Tyr Asp Ser Met Ser Tyr Glu Asp Gln Asp Ala Leu Phe
        515                 520                 525

Ala Tyr Thr Lys Arg Asn Val Ile Pro Thr Ile Thr Gln Met Asn Leu
    530                 535                 540

Lys Tyr Ala Ile Ser Ala Lys Asn Arg Ala Arg Thr Val Ala Gly Val
545                 550                 555                 560

Ser Ile Cys Ser Thr Met Thr Asn Arg Gln Phe His Gln Lys Leu Leu
                565                 570                 575

Lys Ser Ile Ala Ala Thr Arg Gly Ala Thr Val Val Ile Gly Thr Ser
            580                 585                 590

Lys Phe Tyr Gly Gly Trp His Asn Met Leu Lys Thr Val Tyr Ser Asp
        595                 600                 605

Val Glu Asn Pro His Leu Met Gly Trp Asp Tyr Pro Lys Cys Asp Arg
    610                 615                 620

Ala Met Pro Asn Met Leu Arg Ile Met Ala Ser Leu Val Leu Ala Arg
625                 630                 635                 640

Lys His Thr Thr Cys Cys Ser Leu Ser His Arg Phe Tyr Arg Leu Ala
                645                 650                 655

Asn Glu Cys Ala Gln Val Leu Ser Glu Met Val Met Cys Gly Gly Ser
```

```
                660             665             670

Leu Tyr Val Lys Pro Gly Gly Thr Ser Ser Gly Asp Ala Thr Thr Ala
            675             680             685

Tyr Ala Asn Ser Val Phe Asn Ile Cys Gln Ala Val Thr Ala Asn Val
        690             695             700

Asn Ala Leu Leu Ser Thr Asp Gly Asn Lys Ile Ala Asp Lys Tyr Val
705             710             715             720

Arg Asn Leu Gln His Arg Leu Tyr Glu Cys Leu Tyr Arg Asn Arg Asp
            725             730             735

Val Asp Thr Asp Phe Val Asn Glu Phe Tyr Ala Tyr Leu Arg Lys His
            740             745             750

Phe Ser Met Met Ile Leu Ser Asp Asp Ala Val Val Cys Phe Asn Ser
        755             760             765

Thr Tyr Ala Ser Gln Gly Leu Val Ala Ser Ile Lys Asn Phe Lys Ser
770             775             780

Val Leu Tyr Tyr Gln Asn Asn Val Phe Met Ser Glu Ala Lys Cys Trp
785             790             795             800

Thr Glu Thr Asp Leu Thr Lys Gly Pro His Glu Phe Cys Ser Gln His
            805             810             815

Thr Met Leu Val Lys Gln Gly Asp Asp Tyr Val Tyr Leu Pro Tyr Pro
            820             825             830

Asp Pro Ser Arg Ile Leu Gly Ala Gly Cys Phe Val Asp Asp Ile Val
            835             840             845

Lys Thr Asp Gly Thr Leu Met Ile Glu Arg Phe Val Ser Leu Ala Ile
        850             855             860

Asp Ala Tyr Pro Leu Thr Lys His Pro Asn Gln Glu Tyr Ala Asp Val
865             870             875             880

Phe His Leu Tyr Leu Gln Tyr Ile Arg Lys Leu His Asp Glu Leu Thr
            885             890             895

Gly His Met Leu Asp Met Tyr Ser Val Met Leu Thr Asn Asp Asn Thr
            900             905             910

Ser Arg Tyr Trp Glu Pro Glu Phe Tyr Glu Ala Met Tyr Thr Pro His
        915             920             925

Thr Val Leu Gln
    930
```

<210> SEQ ID NO 57

<400> SEQUENCE: 57

000

<210> SEQ ID NO 58
<211> LENGTH: 50
<212> TYPE: RNA
<213> ORGANISM: Artificial Sequence
<220> FEATURE:
<223> OTHER INFORMATION: A synthetic sequence

<400> SEQUENCE: 58
gaccacccca aaaugaagg ggacuaaaac aacacacuga cuagagacua          50

<210> SEQ ID NO 59
<211> LENGTH: 50
<212> TYPE: RNA
<213> ORGANISM: Artificial Sequence
<220> FEATURE:
<223> OTHER INFORMATION: A synthetic sequence

<400> SEQUENCE: 59 gaccaccccca aaaaugaagg ggacuaaaac ccagagacau guauagcaug                50

<210> SEQ ID NO 60
<211> LENGTH: 50
<212> TYPE: RNA
<213> ORGANISM: Artificial Sequence
<220> FEATURE:
<223> OTHER INFORMATION: A synthetic sequence

<400> SEQUENCE: 60 gaccaccccca aaaaugaagg ggacuaaaac uugugguaau aaacacccaa                50

<210> SEQ ID NO 61
<211> LENGTH: 50
<212> TYPE: RNA
<213> ORGANISM: Artificial Sequence
<220> FEATURE:
<223> OTHER INFORMATION: A synthetic sequence

<400> SEQUENCE: 61 gaccaccccca aaaaugaagg ggacuaaaac caacaccauu aguggguugg                50

<210> SEQ ID NO 62
<211> LENGTH: 50
<212> TYPE: DNA
<213> ORGANISM: Artificial Sequence
<220> FEATURE:
<223> OTHER INFORMATION: A synthetic sequence

<400> SEQUENCE: 62 gaccaccccca aaaaugaagg ggacuaaaac aguuaacacc cugauaaaga                50

<210> SEQ ID NO 63
<211> LENGTH: 50
<212> TYPE: RNA
<213> ORGANISM: Artificial Sequence
<220> FEATURE:
<223> OTHER INFORMATION: A synthetic sequence

<400> SEQUENCE: 63 gaccaccccca aaaaugaagg ggacuaaaac ccuuuagugg guuggaaacc                50

<210> SEQ ID NO 64
<211> LENGTH: 50
<212> TYPE: RNA
<213> ORGANISM: Artificial Sequence
<220> FEATURE:
<223> OTHER INFORMATION: A synthetic sequence

<400> SEQUENCE: 64 gaccaccccca aaaaugaagg ggacuaaaac aagauccuga uaaagaacag                50

<210> SEQ ID NO 65
<211> LENGTH: 50
<212> TYPE: RNA
<213> ORGANISM: Artificial Sequence
<220> FEATURE:
<223> OTHER INFORMATION: A synthetic sequence

<400> SEQUENCE: 65 gaccaccccca aaaaugaagg ggacuaaaac gucccagaga uagcauggaa                50

<210> SEQ ID NO 66

-continued

```
<211> LENGTH: 50
<212> TYPE: RNA
<213> ORGANISM: Artificial Sequence
<220> FEATURE:
<223> OTHER INFORMATION: A synthetic sequence

<400> SEQUENCE: 66 gaccaccccca aaaaugaagg ggacuaaaac uuuguggulaa acacccaaaa              50

<210> SEQ ID NO 67
<211> LENGTH: 50
<212> TYPE: RNA
<213> ORGANISM: Artificial Sequence
<220> FEATURE:
<223> OTHER INFORMATION: A synthetic sequence

<400> SEQUENCE: 67 gaccaccccca aaaaugaagg ggacuaaaac caacaccaua aguggguugg              50

<210> SEQ ID NO 68
<211> LENGTH: 50
<212> TYPE: RNA
<213> ORGANISM: Artificial Sequence
<220> FEATURE:
<223> OTHER INFORMATION: A synthetic sequence

<400> SEQUENCE: 68 gaccaccccca aaaaugaagg ggacuaaaac aguuaacacc cugauaaaga              50

<210> SEQ ID NO 69
<211> LENGTH: 50
<212> TYPE: RNA
<213> ORGANISM: Artificial Sequence
<220> FEATURE:
<223> OTHER INFORMATION: A synthetic sequence

<400> SEQUENCE: 69 gaccaccccca aaaaugaagg ggacuaaaac ccuuaagugg guuggaaacc              50

<210> SEQ ID NO 70
<211> LENGTH: 50
<212> TYPE: RNA
<213> ORGANISM: Artificial Sequence
<220> FEATURE:
<223> OTHER INFORMATION: A synthetic sequence

<400> SEQUENCE: 70 gaccaccccca aaaaugaagg ggacuaaaac aagacccuga uaaagaacag              50

<210> SEQ ID NO 71
<211> LENGTH: 50
<212> TYPE: RNA
<213> ORGANISM: Artificial Sequence
<220> FEATURE:
<223> OTHER INFORMATION: A synthetic sequence

<400> SEQUENCE: 71 gaccaccccca aaaaugaagg ggacuaaaac auuccgguaa uuauaauuac              50

<210> SEQ ID NO 72
<211> LENGTH: 50
<212> TYPE: RNA
<213> ORGANISM: Artificial Sequence
<220> FEATURE:
<223> OTHER INFORMATION: A synthetic sequence

<400> SEQUENCE: 72
``` gaccaccccca aaaaugaagg ggacuaaaac aucuauaccg guaauuauaa                    50

<210> SEQ ID NO 73
<211> LENGTH: 50
<212> TYPE: RNA
<213> ORGANISM: Artificial Sequence
<220> FEATURE:
<223> OTHER INFORMATION: A synthetic sequence

<400> SEQUENCE: 73 gaccaccccca aaaugaagg ggacuaaaac auucagguaa uuauaauuac                    50

<210> SEQ ID NO 74
<211> LENGTH: 50
<212> TYPE: RNA
<213> ORGANISM: Artificial Sequence
<220> FEATURE:
<223> OTHER INFORMATION: A synthetic sequence

<400> SEQUENCE: 74 gaccaccccca aaaugaagg ggacuaaaac aucuauacag guaauuauaa                    50

<210> SEQ ID NO 75
<211> LENGTH: 50
<212> TYPE: RNA
<213> ORGANISM: Artificial Sequence
<220> FEATURE:
<223> OTHER INFORMATION: A synthetic sequence

<400> SEQUENCE: 75
aagguuggug guaauuauaa uuaccuguau agauuguuua ggaagucuaa                    50

<210> SEQ ID NO 76
<211> LENGTH: 50
<212> TYPE: RNA
<213> ORGANISM: Artificial Sequence
<220> FEATURE:
<223> OTHER INFORMATION: A synthetic sequence

<400> SEQUENCE: 76
aagguuggug guaauuauaa uuaccuguau agauuguuua ggaagucuaa                    50

<210> SEQ ID NO 77
<211> LENGTH: 50
<212> TYPE: RNA
<213> ORGANISM: Artificial Sequence
<220> FEATURE:
<223> OTHER INFORMATION: A synthetic sequence

<400> SEQUENCE: 77
aaccagguug cuguucuuua ucaggguguu aacugcacag aagucccugu                    50

<210> SEQ ID NO 78
<211> LENGTH: 50
<212> TYPE: RNA
<213> ORGANISM: Artificial Sequence
<220> FEATURE:
<223> OTHER INFORMATION: A synthetic sequence

<400> SEQUENCE: 78
aaccagguug cuguucuuua ucaggauguu aacugcacag aagucccugu                    50

<210> SEQ ID NO 79
<211> LENGTH: 50
<212> TYPE: RNA

-continued

```
<213> ORGANISM: Artificial Sequence
<220> FEATURE:
<223> OTHER INFORMATION: A synthetic sequence

<400> SEQUENCE: 79
acaaucauau gguuuccaac ccacuuaugg uguugguuac caaccauaca              50

<210> SEQ ID NO 80
<211> LENGTH: 50
<212> TYPE: RNA
<213> ORGANISM: Artificial Sequence
<220> FEATURE:
<223> OTHER INFORMATION: A synthetic sequence

<400> SEQUENCE: 80
acaaucauau gguuuccaac ccacuaaugg uguugguuac caaccauaca              50

<210> SEQ ID NO 81
<211> LENGTH: 50
<212> TYPE: RNA
<213> ORGANISM: Artificial Sequence
<220> FEATURE:
<223> OTHER INFORMATION: A synthetic sequence

<400> SEQUENCE: 81
uccaauguua cuugguucca ugcuaucucu gggaccaaug guacuaagag              50

<210> SEQ ID NO 82
<211> LENGTH: 50
<212> TYPE: RNA
<213> ORGANISM: Artificial Sequence
<220> FEATURE:
<223> OTHER INFORMATION: A synthetic sequence

<400> SEQUENCE: 82
aauguuacuu gguuccaugc uauacauguc ucugggacca augguacuaa              50

<210> SEQ ID NO 83
<211> LENGTH: 50
<212> TYPE: RNA
<213> ORGANISM: Artificial Sequence
<220> FEATURE:
<223> OTHER INFORMATION: A synthetic sequence

<400> SEQUENCE: 83
cccuaagagu gauggaacug guacugucua uacagaacug gaaccaccuu              50

<210> SEQ ID NO 84
<211> LENGTH: 50
<212> TYPE: RNA
<213> ORGANISM: Artificial Sequence
<220> FEATURE:
<223> OTHER INFORMATION: A synthetic sequence

<400> SEQUENCE: 84
cccuaagagu gauggaacug guacuaucua uacagaacug gaaccaccuu              50

<210> SEQ ID NO 85
<211> LENGTH: 50
<212> TYPE: RNA
<213> ORGANISM: Artificial Sequence
<220> FEATURE:
<223> OTHER INFORMATION: A synthetic sequence

<400> SEQUENCE: 85
uuauacccaa cacucaauau cucauaugag uuuucuagca auguugcaaa              50
```

<210> SEQ ID NO 86
<211> LENGTH: 50
<212> TYPE: RNA
<213> ORGANISM: Artificial Sequence
<220> FEATURE:
<223> OTHER INFORMATION: A synthetic sequence

<400> SEQUENCE: 86
uuauacccaa cacucaauau cucagaugag uuuucuagca auguugcaaa                50

<210> SEQ ID NO 87
<211> LENGTH: 50
<212> TYPE: RNA
<213> ORGANISM: Artificial Sequence
<220> FEATURE:
<223> OTHER INFORMATION: A synthetic sequence

<400> SEQUENCE: 87
auuaccacaa aaacaacaaa aguuguaugg aaagugaguu cagaguuuau                50

<210> SEQ ID NO 88
<211> LENGTH: 50
<212> TYPE: RNA
<213> ORGANISM: Artificial Sequence
<220> FEATURE:
<223> OTHER INFORMATION: A synthetic sequence

<400> SEQUENCE: 88
auuaccacaa aaacaacaaa aguuggaugg aaagugaguu cagaguuuau                50

<210> SEQ ID NO 89
<211> LENGTH: 50
<212> TYPE: RNA
<213> ORGANISM: Artificial Sequence
<220> FEATURE:
<223> OTHER INFORMATION: A synthetic sequence

<400> SEQUENCE: 89
cuuguuuuau ugccacuagu cucuauucag uguguuaauc uuacaaccag                50

<210> SEQ ID NO 90

<400> SEQUENCE: 90

000

<210> SEQ ID NO 91
<211> LENGTH: 50
<212> TYPE: RNA
<213> ORGANISM: Artificial Sequence
<220> FEATURE:
<223> OTHER INFORMATION: A synthetic sequence

<400> SEQUENCE: 91
cuuguuuuau ugccacuagu cucuagucag uguguuaauc uuacaaccag                50

<210> SEQ ID NO 92
<211> LENGTH: 50
<212> TYPE: RNA
<213> ORGANISM: Artificial Sequence
<220> FEATURE:
<223> OTHER INFORMATION: A synthetic sequence

<400> SEQUENCE: 92
gaccacccca aaaaugaagg ggacuaaaac uacacaguac caguuccauc                50

```
<210> SEQ ID NO 93
<211> LENGTH: 50
<212> TYPE: RNA
<213> ORGANISM: Artificial Sequence
<220> FEATURE:
<223> OTHER INFORMATION: A synthetic sequence

<400> SEQUENCE: 93 gaccaccccca aaaugaagg ggacuaaaac uacauaguac caguuccauc          50

<210> SEQ ID NO 94
<211> LENGTH: 50
<212> TYPE: RNA
<213> ORGANISM: Artificial Sequence
<220> FEATURE:
<223> OTHER INFORMATION: A synthetic sequence

<400> SEQUENCE: 94 gaccaccccca aaaugaagg ggacuaaaac ucuuaugaga uauugagugu          50

<210> SEQ ID NO 95
<211> LENGTH: 50
<212> TYPE: RNA
<213> ORGANISM: Artificial Sequence
<220> FEATURE:
<223> OTHER INFORMATION: A synthetic sequence

<400> SEQUENCE: 95 gaccaccccca aaaugaagg ggacuaaaac ucuucugaga uauugagugu          50

<210> SEQ ID NO 96
<211> LENGTH: 50
<212> TYPE: RNA
<213> ORGANISM: Artificial Sequence
<220> FEATURE:
<223> OTHER INFORMATION: A synthetic sequence

<400> SEQUENCE: 96 gaccaccccca aaaugaagg ggacuaaaac ccuuacaacu uuuguuguuu          50

<210> SEQ ID NO 97
<211> LENGTH: 50
<212> TYPE: RNA
<213> ORGANISM: Artificial Sequence
<220> FEATURE:
<223> OTHER INFORMATION: A synthetic sequence

<400> SEQUENCE: 97 gaccaccccca aaaugaagg ggacuaaaac ccuuccaacu uuuguuguuu          50

<210> SEQ ID NO 98
<211> LENGTH: 50
<212> TYPE: RNA
<213> ORGANISM: Artificial Sequence
<220> FEATURE:
<223> OTHER INFORMATION: A synthetic sequence

<400> SEQUENCE: 98 gaccaccccca aaaugaagg ggacuaaaac cucaauagag acuaguggca          50

<210> SEQ ID NO 99
<211> LENGTH: 50
<212> TYPE: RNA
<213> ORGANISM: Artificial Sequence
<220> FEATURE:
```

-continued

```
<223> OTHER INFORMATION: A synthetic sequence

<400> SEQUENCE: 99
gaccacccca aaaaugaagg ggacuaaaac cucacuagag acuaguggca                50

<210> SEQ ID NO 100
<211> LENGTH: 50
<212> TYPE: RNA
<213> ORGANISM: Artificial Sequence
<220> FEATURE:
<223> OTHER INFORMATION: A synthetic sequence

<400> SEQUENCE: 100
gaccacccca aaaaugaagg ggacuaaaac uguauagaca guaccaguuc                50

<210> SEQ ID NO 101
<211> LENGTH: 50
<212> TYPE: RNA
<213> ORGANISM: Artificial Sequence
<220> FEATURE:
<223> OTHER INFORMATION: A synthetic sequence

<400> SEQUENCE: 101
gaccacccca aaaaugaagg ggacuaaaac uguauagaua guaccaguuc                50

<210> SEQ ID NO 102
<211> LENGTH: 50
<212> TYPE: RNA
<213> ORGANISM: Artificial Sequence
<220> FEATURE:
<223> OTHER INFORMATION: A synthetic sequence

<400> SEQUENCE: 102
gaccacccca aaaaugaagg ggacuaaaac aaacucauau gagauauuga                50

<210> SEQ ID NO 103
<211> LENGTH: 50
<212> TYPE: RNA
<213> ORGANISM: Artificial Sequence
<220> FEATURE:
<223> OTHER INFORMATION: A synthetic sequence

<400> SEQUENCE: 103
gaccacccca aaaaugaagg ggacuaaaac aaacucaucu gagauauuga                50

<210> SEQ ID NO 104
<211> LENGTH: 50
<212> TYPE: RNA
<213> ORGANISM: Artificial Sequence
<220> FEATURE:
<223> OTHER INFORMATION: A synthetic sequence

<400> SEQUENCE: 104
gaccacccca aaaaugaagg ggacuaaaac cuuuccauac aacuuuuguu                50

<210> SEQ ID NO 105
<211> LENGTH: 50
<212> TYPE: RNA
<213> ORGANISM: Artificial Sequence
<220> FEATURE:
<223> OTHER INFORMATION: A synthetic sequence

<400> SEQUENCE: 105
gaccacccca aaaaugaagg ggacuaaaac cuuuccaucc aacuuuuguu                50
```

<210> SEQ ID NO 106
<211> LENGTH: 50
<212> TYPE: RNA
<213> ORGANISM: Artificial Sequence
<220> FEATURE:
<223> OTHER INFORMATION: A synthetic sequence

<400> SEQUENCE: 106
gaccacccca aaaaugaagg ggacuaaaac cacacugaau agagacuagu                50

<210> SEQ ID NO 107
<211> LENGTH: 50
<212> TYPE: RNA
<213> ORGANISM: Artificial Sequence
<220> FEATURE:
<223> OTHER INFORMATION: A synthetic sequence

<400> SEQUENCE: 107
gaccacccca aaaaugaagg ggacuaaaac cacacugacu agagacuagu                50

<210> SEQ ID NO 108
<211> LENGTH: 50
<212> TYPE: RNA
<213> ORGANISM: Artificial Sequence
<220> FEATURE:
<223> OTHER INFORMATION: A synthetic sequence

<400> SEQUENCE: 108
gaccacccca aaaaugaagg ggacuaaaac aucagcaauc uuuccaguuu                50

<210> SEQ ID NO 109
<211> LENGTH: 50
<212> TYPE: RNA
<213> ORGANISM: Artificial Sequence
<220> FEATURE:
<223> OTHER INFORMATION: A synthetic sequence

<400> SEQUENCE: 109
gaccacccca aaaaugaagg ggacuaaaac aucagcaauc guuccaguuu                50

<210> SEQ ID NO 110
<211> LENGTH: 50
<212> TYPE: RNA
<213> ORGANISM: Artificial Sequence
<220> FEATURE:
<223> OTHER INFORMATION: A synthetic sequence

<400> SEQUENCE: 110
gaccacccca aaaaugaagg ggacuaaaac aaucuuucca guuugcccug                50

<210> SEQ ID NO 111
<211> LENGTH: 50
<212> TYPE: RNA
<213> ORGANISM: Artificial Sequence
<220> FEATURE:
<223> OTHER INFORMATION: A synthetic sequence

<400> SEQUENCE: 111
gaccacccca aaaaugaagg ggacuaaaac aaccguucca guuugcccug                50

<210> SEQ ID NO 112
<211> LENGTH: 50
<212> TYPE: RNA
<213> ORGANISM: Artificial Sequence
<220> FEATURE:
<223> OTHER INFORMATION: A synthetic sequence -continued

<400> SEQUENCE: 112
gaccacccca aaaaugaagg ggacuaaaac uaaaaccuuc aacaccauua                    50

<210> SEQ ID NO 113
<211> LENGTH: 50
<212> TYPE: RNA
<213> ORGANISM: Artificial Sequence
<220> FEATURE:
<223> OTHER INFORMATION: A synthetic sequence

<400> SEQUENCE: 113
gaccacccca aaaugaagg ggacuaaaac uaaaaccuuu aacaccauua                     50

<210> SEQ ID NO 114
<211> LENGTH: 50
<212> TYPE: RNA
<213> ORGANISM: Artificial Sequence
<220> FEATURE:
<223> OTHER INFORMATION: A synthetic sequence

<400> SEQUENCE: 114
gaccacccca aaaugaagg ggacuaaaac ccuucaacac cauuacaagg                     50

<210> SEQ ID NO 115
<211> LENGTH: 50
<212> TYPE: RNA
<213> ORGANISM: Artificial Sequence
<220> FEATURE:
<223> OTHER INFORMATION: A synthetic sequence

<400> SEQUENCE: 115
gaccacccca aaaugaagg ggacuaaaac ccauuaacac cauuacaagg                     50

<210> SEQ ID NO 116
<211> LENGTH: 50
<212> TYPE: RNA
<213> ORGANISM: Artificial Sequence
<220> FEATURE:
<223> OTHER INFORMATION: A synthetic sequence

<400> SEQUENCE: 116
gaccacccca aaaugaagg ggacuaaaac accaacacca uuaguggguu                     50

<210> SEQ ID NO 117
<211> LENGTH: 50
<212> TYPE: RNA
<213> ORGANISM: Artificial Sequence
<220> FEATURE:
<223> OTHER INFORMATION: A synthetic sequence

<400> SEQUENCE: 117
gaccacccca aaaugaagg ggacuaaaac accaacacca uaaguggguu                     50

<210> SEQ ID NO 118
<211> LENGTH: 50
<212> TYPE: RNA
<213> ORGANISM: Artificial Sequence
<220> FEATURE:
<223> OTHER INFORMATION: A synthetic sequence

<400> SEQUENCE: 118
gaccacccca aaaugaagg ggacuaaaac ccauuagugg guuggaaacc                     50

<210> SEQ ID NO 119
<211> LENGTH: 50

-continued

<212> TYPE: RNA
<213> ORGANISM: Artificial Sequence
<220> FEATURE:
<223> OTHER INFORMATION: A synthetic sequence

<400> SEQUENCE: 119
gaccacccca aaaaugaagg ggacuaaaac ccguaagugg guuggaaacc                50

<210> SEQ ID NO 120
<211> LENGTH: 50
<212> TYPE: RNA
<213> ORGANISM: Artificial Sequence
<220> FEATURE:
<223> OTHER INFORMATION: A synthetic sequence

<400> SEQUENCE: 120
gaccacccca aaaaugaagg ggacuaaaac aguuaacauc cugauaaaga                50

<210> SEQ ID NO 121
<211> LENGTH: 50
<212> TYPE: RNA
<213> ORGANISM: Artificial Sequence
<220> FEATURE:
<223> OTHER INFORMATION: A synthetic sequence

<400> SEQUENCE: 121
gaccacccca aaaaugaagg ggacuaaaac aguuaacacc cugauaaaga                50

<210> SEQ ID NO 122
<211> LENGTH: 50
<212> TYPE: RNA
<213> ORGANISM: Artificial Sequence
<220> FEATURE:
<223> OTHER INFORMATION: A synthetic sequence

<400> SEQUENCE: 122
gaccacccca aaaaugaagg ggacuaaaac aacauccuga uaaagaacag                50

<210> SEQ ID NO 123
<211> LENGTH: 50
<212> TYPE: RNA
<213> ORGANISM: Artificial Sequence
<220> FEATURE:
<223> OTHER INFORMATION: A synthetic sequence

<400> SEQUENCE: 123
gaccacccca aaaaugaagg ggacuaaaac aagacccuga uaaagaacag                50

<210> SEQ ID NO 124
<211> LENGTH: 50
<212> TYPE: RNA
<213> ORGANISM: Artificial Sequence
<220> FEATURE:
<223> OTHER INFORMATION: A synthetic sequence

<400> SEQUENCE: 124
gaccacccca aaaaugaagg ggacuaaaac uaacacccug auaaagaaca                50

<210> SEQ ID NO 125
<211> LENGTH: 50
<212> TYPE: RNA
<213> ORGANISM: Artificial Sequence
<220> FEATURE:
<223> OTHER INFORMATION: A synthetic sequence

<400> SEQUENCE: 125

-continued

```
gaccaccccca aaaaugaagg ggacuaaaac uaacacgcug auaaagaaca                    50
```

<210> SEQ ID NO 126
<211> LENGTH: 50
<212> TYPE: RNA
<213> ORGANISM: Artificial Sequence
<220> FEATURE:
<223> OTHER INFORMATION: A synthetic sequence

<400> SEQUENCE: 126

```
gaccaccccca aaaaugaagg ggacuaaaac ucugugcagu uaacacccug                    50
```

<210> SEQ ID NO 127
<211> LENGTH: 50
<212> TYPE: RNA
<213> ORGANISM: Artificial Sequence
<220> FEATURE:
<223> OTHER INFORMATION: A synthetic sequence

<400> SEQUENCE: 127

```
gaccaccccca aaaaugaagg ggacuaaaac ugugcaguua acacccugau                    50
```

<210> SEQ ID NO 128
<211> LENGTH: 50
<212> TYPE: RNA
<213> ORGANISM: Artificial Sequence
<220> FEATURE:
<223> OTHER INFORMATION: A synthetic sequence

<400> SEQUENCE: 128

```
gaccaccccca aaaaugaagg ggacuaaaac uucugugcag uuaacacccu                    50
```

<210> SEQ ID NO 129
<211> LENGTH: 50
<212> TYPE: RNA
<213> ORGANISM: Artificial Sequence
<220> FEATURE:
<223> OTHER INFORMATION: A synthetic sequence

<400> SEQUENCE: 129

```
gaccaccccca aaaaugaagg ggacuaaaac uucugugcag uuaacucccu                    50
```

<210> SEQ ID NO 130
<211> LENGTH: 50
<212> TYPE: RNA
<213> ORGANISM: Artificial Sequence
<220> FEATURE:
<223> OTHER INFORMATION: A synthetic sequence

<400> SEQUENCE: 130

```
gaccaccccca aaaaugaagg ggacuaaaac uucugugcag uuaagacccu                    50
```

<210> SEQ ID NO 131
<211> LENGTH: 50
<212> TYPE: RNA
<213> ORGANISM: Artificial Sequence
<220> FEATURE:
<223> OTHER INFORMATION: A synthetic sequence

<400> SEQUENCE: 131

```
gaccaccccca aaaaugaagg ggacuaaaac aacacacugu cuagagacua                    50
```

<210> SEQ ID NO 132
<211> LENGTH: 50
<212> TYPE: RNA
<213> ORGANISM: Artificial Sequence -continued
<220> FEATURE:
<223> OTHER INFORMATION: A synthetic sequence

<400> SEQUENCE: 132 gaccaccccca aaaaugaagg ggacuaaaac aacacacuca cuagagacua                50

<210> SEQ ID NO 133
<211> LENGTH: 50
<212> TYPE: RNA
<213> ORGANISM: Artificial Sequence
<220> FEATURE:
<223> OTHER INFORMATION: A synthetic sequence

<400> SEQUENCE: 133 gaccaccccca aaaaugaagg ggacuaaaac aacacacuga cuacagacua                50

<210> SEQ ID NO 134
<211> LENGTH: 50
<212> TYPE: RNA
<213> ORGANISM: Artificial Sequence
<220> FEATURE:
<223> OTHER INFORMATION: A synthetic sequence

<400> SEQUENCE: 134 gaccaccccca aaaaugaagg ggacuaaaac cuauguaaag caaguaaagu                50

<210> SEQ ID NO 135
<211> LENGTH: 49
<212> TYPE: RNA
<213> ORGANISM: Artificial Sequence
<220> FEATURE:
<223> OTHER INFORMATION: A synthetic sequence

<400> SEQUENCE: 135 gaccaccccca aaaaugaagg ggacuaaaac aaauaacuuc uauguaaag                 49

<210> SEQ ID NO 136
<211> LENGTH: 50
<212> TYPE: RNA
<213> ORGANISM: Artificial Sequence
<220> FEATURE:
<223> OTHER INFORMATION: A synthetic sequence

<400> SEQUENCE: 136 gaccaccccca aaaaugaagg ggacuaaaac aucagcaaua uuuccaguuu                50

<210> SEQ ID NO 137
<211> LENGTH: 50
<212> TYPE: RNA
<213> ORGANISM: Artificial Sequence
<220> FEATURE:
<223> OTHER INFORMATION: A synthetic sequence

<400> SEQUENCE: 137 gaccaccccca aaaaugaagg ggacuaaaac cauuauuucc aguuugcccu                50

<210> SEQ ID NO 138
<211> LENGTH: 50
<212> TYPE: RNA
<213> ORGANISM: Artificial Sequence
<220> FEATURE:
<223> OTHER INFORMATION: A synthetic sequence

<400> SEQUENCE: 138 gaccaccccca aaaaugaagg ggacuaaaac ugaauuuucu gcaccaagug                50

<210> SEQ ID NO 139
<211> LENGTH: 50
<212> TYPE: RNA
<213> ORGANISM: Artificial Sequence
<220> FEATURE:
<223> OTHER INFORMATION: A synthetic sequence

<400> SEQUENCE: 139
gaccacccca aaaugaagg ggacuaaaac ugaauuuugu acaccaagug                    50

<210> SEQ ID NO 140
<211> LENGTH: 50
<212> TYPE: RNA
<213> ORGANISM: Artificial Sequence
<220> FEATURE:
<223> OTHER INFORMATION: A synthetic sequence

<400> SEQUENCE: 140
gaccacccca aaaugaagg ggacuaaaac uucugcacca agugacauag                    50

<210> SEQ ID NO 141
<211> LENGTH: 50
<212> TYPE: RNA
<213> ORGANISM: Artificial Sequence
<220> FEATURE:
<223> OTHER INFORMATION: A synthetic sequence

<400> SEQUENCE: 141
gaccacccca aaaugaagg ggacuaaaac uuguacacca agugacauag                    50

<210> SEQ ID NO 142
<211> LENGTH: 50
<212> TYPE: RNA
<213> ORGANISM: Artificial Sequence
<220> FEATURE:
<223> OTHER INFORMATION: A synthetic sequence

<400> SEQUENCE: 142
gaccacccca aaaugaagg ggacuaaaac acaggguuau caaaccucuu                    50

<210> SEQ ID NO 143
<211> LENGTH: 50
<212> TYPE: RNA
<213> ORGANISM: Artificial Sequence
<220> FEATURE:
<223> OTHER INFORMATION: A synthetic sequence

<400> SEQUENCE: 143
gaccacccca aaaugaagg ggacuaaaac acaggguuag cuaaccucuu                    50

<210> SEQ ID NO 144
<211> LENGTH: 50
<212> TYPE: RNA
<213> ORGANISM: Artificial Sequence
<220> FEATURE:
<223> OTHER INFORMATION: A synthetic sequence

<400> SEQUENCE: 144
gaccacccca aaaugaagg ggacuaaaac acaggguuag caaaccucuu                    50

<210> SEQ ID NO 145
<211> LENGTH: 50
<212> TYPE: RNA
<213> ORGANISM: Artificial Sequence
<220> FEATURE:
<223> OTHER INFORMATION: A synthetic sequence

<400> SEQUENCE: 145 gaccaccccca aaaaugaagg ggacuaaaac gagggagauc acgcacuaaa                50

<210> SEQ ID NO 146
<211> LENGTH: 50
<212> TYPE: RNA
<213> ORGANISM: Artificial Sequence
<220> FEATURE:
<223> OTHER INFORMATION: A synthetic sequence

<400> SEQUENCE: 146 gaccaccccca aaaugaagg ggacuaaaac gagggagacc acgcacuaaa                 50

<210> SEQ ID NO 147
<211> LENGTH: 50
<212> TYPE: RNA
<213> ORGANISM: Artificial Sequence
<220> FEATURE:
<223> OTHER INFORMATION: A synthetic sequence

<400> SEQUENCE: 147 gaccaccccca aaaugaagg ggacuaaaac gagggagacc ucgcacuaaa                 50

<210> SEQ ID NO 148
<211> LENGTH: 20
<212> TYPE: RNA
<213> ORGANISM: Artificial Sequence
<220> FEATURE:
<223> OTHER INFORMATION: A synthetic sequence

<400> SEQUENCE: 148
aacacacuga cuagagacua                                                  20

<210> SEQ ID NO 149
<211> LENGTH: 20
<212> TYPE: RNA
<213> ORGANISM: Artificial Sequence
<220> FEATURE:
<223> OTHER INFORMATION: A synthetic sequence

<400> SEQUENCE: 149
ccagagacau guauagcaug                                                  20

<210> SEQ ID NO 150
<211> LENGTH: 20
<212> TYPE: RNA
<213> ORGANISM: Artificial Sequence
<220> FEATURE:
<223> OTHER INFORMATION: A synthetic sequence

<400> SEQUENCE: 150 uuguggguaau aaacacccaa                                                 20

<210> SEQ ID NO 151
<211> LENGTH: 20
<212> TYPE: RNA
<213> ORGANISM: Artificial Sequence
<220> FEATURE:
<223> OTHER INFORMATION: A synthetic sequence

<400> SEQUENCE: 151
caacaccauu aguggguugg                                                  20

<210> SEQ ID NO 152

```
<211> LENGTH: 20
<212> TYPE: RNA
<213> ORGANISM: Artificial Sequence
<220> FEATURE:
<223> OTHER INFORMATION: A synthetic sequence

<400> SEQUENCE: 152
aguuaacacc cugauaaaga                                             20

<210> SEQ ID NO 153
<211> LENGTH: 20
<212> TYPE: RNA
<213> ORGANISM: Artificial Sequence
<220> FEATURE:
<223> OTHER INFORMATION: A synthetic sequence

<400> SEQUENCE: 153
ccuuuagugg guuggaaacc                                             20

<210> SEQ ID NO 154
<211> LENGTH: 20
<212> TYPE: RNA
<213> ORGANISM: Artificial Sequence
<220> FEATURE:
<223> OTHER INFORMATION: A synthetic sequence

<400> SEQUENCE: 154
aagauccuga uaaagaacag                                             20

<210> SEQ ID NO 155
<211> LENGTH: 20
<212> TYPE: RNA
<213> ORGANISM: Artificial Sequence
<220> FEATURE:
<223> OTHER INFORMATION: A synthetic sequence

<400> SEQUENCE: 155
gucccagaga uagcauggaa                                             20

<210> SEQ ID NO 156
<211> LENGTH: 20
<212> TYPE: RNA
<213> ORGANISM: Artificial Sequence
<220> FEATURE:
<223> OTHER INFORMATION: A synthetic sequence

<400> SEQUENCE: 156
uuugugguaa acacccaaaa                                             20

<210> SEQ ID NO 157
<211> LENGTH: 20
<212> TYPE: RNA
<213> ORGANISM: Artificial Sequence
<220> FEATURE:
<223> OTHER INFORMATION: A synthetic sequence

<400> SEQUENCE: 157
caacaccaua aguggguugg                                             20

<210> SEQ ID NO 158
<211> LENGTH: 20
<212> TYPE: RNA
<213> ORGANISM: Artificial Sequence
<220> FEATURE:
<223> OTHER INFORMATION: A synthetic sequence

<400> SEQUENCE: 158
```

-continued aguuaacacc cugauaaaga                                              20

<210> SEQ ID NO 159
<211> LENGTH: 20
<212> TYPE: RNA
<213> ORGANISM: Artificial Sequence
<220> FEATURE:
<223> OTHER INFORMATION: A synthetic sequence

<400> SEQUENCE: 159
ccuuaagugg guuggaaacc                                              20

<210> SEQ ID NO 160
<211> LENGTH: 20
<212> TYPE: RNA
<213> ORGANISM: Artificial Sequence
<220> FEATURE:
<223> OTHER INFORMATION: A synthetic sequence

<400> SEQUENCE: 160
aagacccuga uaaagaacag                                              20

<210> SEQ ID NO 161
<211> LENGTH: 20
<212> TYPE: RNA
<213> ORGANISM: Artificial Sequence
<220> FEATURE:
<223> OTHER INFORMATION: A synthetic sequence

<400> SEQUENCE: 161
auuccgguaa uuauaauuac                                              20

<210> SEQ ID NO 162
<211> LENGTH: 20
<212> TYPE: RNA
<213> ORGANISM: Artificial Sequence
<220> FEATURE:
<223> OTHER INFORMATION: A synthetic sequence

<400> SEQUENCE: 162
aucuauaccg guaauuauaa                                              20

<210> SEQ ID NO 163
<211> LENGTH: 20
<212> TYPE: RNA
<213> ORGANISM: Artificial Sequence
<220> FEATURE:
<223> OTHER INFORMATION: A synthetic sequence

<400> SEQUENCE: 163
auucagguaa uuauaauuac                                              20

<210> SEQ ID NO 164
<211> LENGTH: 20
<212> TYPE: RNA
<213> ORGANISM: Artificial Sequence
<220> FEATURE:
<223> OTHER INFORMATION: A synthetic sequence

<400> SEQUENCE: 164
aucuauacag guaauuauaa                                              20

<210> SEQ ID NO 165
<211> LENGTH: 20
<212> TYPE: RNA

-continued

<213> ORGANISM: Artificial Sequence
<220> FEATURE:
<223> OTHER INFORMATION: A synthetic sequence

<400> SEQUENCE: 165
uacacaguac caguuccauc                                                                  20

<210> SEQ ID NO 166
<211> LENGTH: 20
<212> TYPE: RNA
<213> ORGANISM: Artificial Sequence
<220> FEATURE:
<223> OTHER INFORMATION: A synthetic sequence

<400> SEQUENCE: 166
uacauaguac caguuccauc                                                                  20

<210> SEQ ID NO 167
<211> LENGTH: 20
<212> TYPE: RNA
<213> ORGANISM: Artificial Sequence
<220> FEATURE:
<223> OTHER INFORMATION: A synthetic sequence

<400> SEQUENCE: 167
ucuuaugaga uauugagugu                                                                  20

<210> SEQ ID NO 168
<211> LENGTH: 20
<212> TYPE: RNA
<213> ORGANISM: Artificial Sequence
<220> FEATURE:
<223> OTHER INFORMATION: A synthetic sequence

<400> SEQUENCE: 168
ucuucugaga uauugagugu                                                                  20

<210> SEQ ID NO 169
<211> LENGTH: 20
<212> TYPE: RNA
<213> ORGANISM: Artificial Sequence
<220> FEATURE:
<223> OTHER INFORMATION: A synthetic sequence

<400> SEQUENCE: 169
ccuuacaacu uuuguuguuu                                                                  20

<210> SEQ ID NO 170
<211> LENGTH: 20
<212> TYPE: RNA
<213> ORGANISM: Artificial Sequence
<220> FEATURE:
<223> OTHER INFORMATION: A synthetic sequence

<400> SEQUENCE: 170
ccuuccaacu uuuguuguuu                                                                  20

<210> SEQ ID NO 171
<211> LENGTH: 20
<212> TYPE: RNA
<213> ORGANISM: Artificial Sequence
<220> FEATURE:
<223> OTHER INFORMATION: A synthetic sequence

<400> SEQUENCE: 171
cucaauagag acuaguggca                                                                  20

-continued

```
<210> SEQ ID NO 172
<211> LENGTH: 20
<212> TYPE: RNA
<213> ORGANISM: Artificial Sequence
<220> FEATURE:
<223> OTHER INFORMATION: A synthetic sequence

<400> SEQUENCE: 172
cucacuagag acuaguggca                                              20

<210> SEQ ID NO 173
<211> LENGTH: 20
<212> TYPE: RNA
<213> ORGANISM: Artificial Sequence
<220> FEATURE:
<223> OTHER INFORMATION: A synthetic sequence

<400> SEQUENCE: 173
uguauagaca guaccaguuc                                              20

<210> SEQ ID NO 174
<211> LENGTH: 20
<212> TYPE: RNA
<213> ORGANISM: Artificial Sequence
<220> FEATURE:
<223> OTHER INFORMATION: A synthetic sequence

<400> SEQUENCE: 174
uguauagaua guaccaguuc                                              20

<210> SEQ ID NO 175
<211> LENGTH: 20
<212> TYPE: RNA
<213> ORGANISM: Artificial Sequence
<220> FEATURE:
<223> OTHER INFORMATION: A synthetic sequence

<400> SEQUENCE: 175
aaacucauau gagauauuga                                              20

<210> SEQ ID NO 176
<211> LENGTH: 20
<212> TYPE: RNA
<213> ORGANISM: Artificial Sequence
<220> FEATURE:
<223> OTHER INFORMATION: A synthetic sequence

<400> SEQUENCE: 176
aaacucaucu gagauauuga                                              20

<210> SEQ ID NO 177
<211> LENGTH: 20
<212> TYPE: RNA
<213> ORGANISM: Artificial Sequence
<220> FEATURE:
<223> OTHER INFORMATION: A synthetic sequence

<400> SEQUENCE: 177
cuuuccauac aacuuuuguu                                              20

<210> SEQ ID NO 178
<211> LENGTH: 20
<212> TYPE: RNA
<213> ORGANISM: Artificial Sequence
<220> FEATURE:
```

-continued

<223> OTHER INFORMATION: A synthetic sequence

<400> SEQUENCE: 178
cuuuccaucc aacuuuuguu                                              20

<210> SEQ ID NO 179
<211> LENGTH: 20
<212> TYPE: RNA
<213> ORGANISM: Artificial Sequence
<220> FEATURE:
<223> OTHER INFORMATION: A synthetic sequence

<400> SEQUENCE: 179
cacacugaau agagacuagu                                             20

<210> SEQ ID NO 180
<211> LENGTH: 20
<212> TYPE: RNA
<213> ORGANISM: Artificial Sequence
<220> FEATURE:
<223> OTHER INFORMATION: A synthetic sequence

<400> SEQUENCE: 180
cacacugacu agagacuagu                                             20

<210> SEQ ID NO 181
<211> LENGTH: 20
<212> TYPE: RNA
<213> ORGANISM: Artificial Sequence
<220> FEATURE:
<223> OTHER INFORMATION: A synthetic sequence

<400> SEQUENCE: 181
aucagcaauc uuuccaguuu                                             20

<210> SEQ ID NO 182
<211> LENGTH: 20
<212> TYPE: RNA
<213> ORGANISM: Artificial Sequence
<220> FEATURE:
<223> OTHER INFORMATION: A synthetic sequence

<400> SEQUENCE: 182
aucagcaauc guuccaguuu                                             20

<210> SEQ ID NO 183
<211> LENGTH: 20
<212> TYPE: RNA
<213> ORGANISM: Artificial Sequence
<220> FEATURE:
<223> OTHER INFORMATION: A synthetic sequence

<400> SEQUENCE: 183
aaucuuucca guuugcccug                                             20

<210> SEQ ID NO 184
<211> LENGTH: 20
<212> TYPE: RNA
<213> ORGANISM: Artificial Sequence
<220> FEATURE:
<223> OTHER INFORMATION: A synthetic sequence

<400> SEQUENCE: 184
aaccguucca guuugcccug                                             20

-continued

```
<210> SEQ ID NO 185
<211> LENGTH: 20
<212> TYPE: RNA
<213> ORGANISM: Artificial Sequence
<220> FEATURE:
<223> OTHER INFORMATION: A synthetic sequence

<400> SEQUENCE: 185
uaaaaccuuc aacaccauua                                                    20

<210> SEQ ID NO 186
<211> LENGTH: 20
<212> TYPE: RNA
<213> ORGANISM: Artificial Sequence
<220> FEATURE:
<223> OTHER INFORMATION: A synthetic sequence

<400> SEQUENCE: 186
uaaaaccuuu aacaccauua                                                    20

<210> SEQ ID NO 187
<211> LENGTH: 20
<212> TYPE: RNA
<213> ORGANISM: Artificial Sequence
<220> FEATURE:
<223> OTHER INFORMATION: A synthetic sequence

<400> SEQUENCE: 187
ccuucaacac cauuacaagg                                                    20

<210> SEQ ID NO 188
<211> LENGTH: 20
<212> TYPE: RNA
<213> ORGANISM: Artificial Sequence
<220> FEATURE:
<223> OTHER INFORMATION: A synthetic sequence

<400> SEQUENCE: 188
ccauuaacac cauuacaagg                                                    20

<210> SEQ ID NO 189
<211> LENGTH: 20
<212> TYPE: RNA
<213> ORGANISM: Artificial Sequence
<220> FEATURE:
<223> OTHER INFORMATION: A synthetic sequence

<400> SEQUENCE: 189
accaacacca uuaguggguu                                                    20

<210> SEQ ID NO 190
<211> LENGTH: 20
<212> TYPE: RNA
<213> ORGANISM: Artificial Sequence
<220> FEATURE:
<223> OTHER INFORMATION: A synthetic sequence

<400> SEQUENCE: 190
accaacacca uaaguggguu                                                    20

<210> SEQ ID NO 191
<211> LENGTH: 20
<212> TYPE: RNA
<213> ORGANISM: Artificial Sequence
<220> FEATURE:
<223> OTHER INFORMATION: A synthetic sequence
```

<400> SEQUENCE: 191
ccauuagugg guuggaaacc                                                20

<210> SEQ ID NO 192
<211> LENGTH: 20
<212> TYPE: RNA
<213> ORGANISM: Artificial Sequence
<220> FEATURE:
<223> OTHER INFORMATION: A synthetic sequence

<400> SEQUENCE: 192
ccguaagugg guuggaaacc                                                20

<210> SEQ ID NO 193
<211> LENGTH: 20
<212> TYPE: RNA
<213> ORGANISM: Artificial Sequence
<220> FEATURE:
<223> OTHER INFORMATION: A synthetic sequence

<400> SEQUENCE: 193
aguuaacauc cugauaaaga                                                20

<210> SEQ ID NO 194
<211> LENGTH: 20
<212> TYPE: RNA
<213> ORGANISM: Artificial Sequence
<220> FEATURE:
<223> OTHER INFORMATION: A synthetic sequence

<400> SEQUENCE: 194
aguuaacacc cugauaaaga                                                20

<210> SEQ ID NO 195
<211> LENGTH: 20
<212> TYPE: RNA
<213> ORGANISM: Artificial Sequence
<220> FEATURE:
<223> OTHER INFORMATION: A synthetic sequence

<400> SEQUENCE: 195
aacauccuga uaaagaacag                                                20

<210> SEQ ID NO 196
<211> LENGTH: 20
<212> TYPE: RNA
<213> ORGANISM: Artificial Sequence
<220> FEATURE:
<223> OTHER INFORMATION: A synthetic sequence

<400> SEQUENCE: 196
aagacccuga uaaagaacag                                                20

<210> SEQ ID NO 197
<211> LENGTH: 20
<212> TYPE: RNA
<213> ORGANISM: Artificial Sequence
<220> FEATURE:
<223> OTHER INFORMATION: A synthetic sequence

<400> SEQUENCE: 197
uaacacccug auaaagaaca                                                20

<210> SEQ ID NO 198
<211> LENGTH: 20

```
<212> TYPE: RNA
<213> ORGANISM: Artificial Sequence
<220> FEATURE:
<223> OTHER INFORMATION: A synthetic sequence

<400> SEQUENCE: 198
uaacacgcug auaaagaaca                                               20

<210> SEQ ID NO 199
<211> LENGTH: 20
<212> TYPE: RNA
<213> ORGANISM: Artificial Sequence
<220> FEATURE:
<223> OTHER INFORMATION: A synthetic sequence

<400> SEQUENCE: 199
ucugugcagu uaacacccug                                               20

<210> SEQ ID NO 200
<211> LENGTH: 20
<212> TYPE: RNA
<213> ORGANISM: Artificial Sequence
<220> FEATURE:
<223> OTHER INFORMATION: A synthetic sequence

<400> SEQUENCE: 200
ugugcaguua acacccugau                                               20

<210> SEQ ID NO 201
<211> LENGTH: 20
<212> TYPE: RNA
<213> ORGANISM: Artificial Sequence
<220> FEATURE:
<223> OTHER INFORMATION: A synthetic sequence

<400> SEQUENCE: 201
uucugugcag uuaacacccu                                               20

<210> SEQ ID NO 202
<211> LENGTH: 20
<212> TYPE: RNA
<213> ORGANISM: Artificial Sequence
<220> FEATURE:
<223> OTHER INFORMATION: A synthetic sequence

<400> SEQUENCE: 202
uucugugcag uuaacucccu                                               20

<210> SEQ ID NO 203
<211> LENGTH: 20
<212> TYPE: RNA
<213> ORGANISM: Artificial Sequence
<220> FEATURE:
<223> OTHER INFORMATION: A synthetic sequence

<400> SEQUENCE: 203
uucugugcag uuaagacccu                                               20

<210> SEQ ID NO 204
<211> LENGTH: 20
<212> TYPE: RNA
<213> ORGANISM: Artificial Sequence
<220> FEATURE:
<223> OTHER INFORMATION: A synthetic sequence

<400> SEQUENCE: 204
```
aacacacugu cuagagacua                                                 20

<210> SEQ ID NO 205
<211> LENGTH: 20
<212> TYPE: RNA
<213> ORGANISM: Artificial Sequence
<220> FEATURE:
<223> OTHER INFORMATION: A synthetic sequence

<400> SEQUENCE: 205
aacacacuca cuagagacua                                                 20

<210> SEQ ID NO 206
<211> LENGTH: 20
<212> TYPE: RNA
<213> ORGANISM: Artificial Sequence
<220> FEATURE:
<223> OTHER INFORMATION: A synthetic sequence

<400> SEQUENCE: 206
aacacacuga cuacagacua                                                 20

<210> SEQ ID NO 207
<211> LENGTH: 20
<212> TYPE: RNA
<213> ORGANISM: Artificial Sequence
<220> FEATURE:
<223> OTHER INFORMATION: A synthetic sequence

<400> SEQUENCE: 207
cuauguaaag caaguaaagu                                                 20

<210> SEQ ID NO 208
<211> LENGTH: 20
<212> TYPE: RNA
<213> ORGANISM: Artificial Sequence
<220> FEATURE:
<223> OTHER INFORMATION: A synthetic sequence

<400> SEQUENCE: 208
aaauaacuuc uauguaaagu                                                 20

<210> SEQ ID NO 209
<211> LENGTH: 20
<212> TYPE: RNA
<213> ORGANISM: Artificial Sequence
<220> FEATURE:
<223> OTHER INFORMATION: A synthetic sequence

<400> SEQUENCE: 209
aucagcaaua uuuccaguuu                                                 20

<210> SEQ ID NO 210
<211> LENGTH: 20
<212> TYPE: RNA
<213> ORGANISM: Artificial Sequence
<220> FEATURE:
<223> OTHER INFORMATION: A synthetic sequence

<400> SEQUENCE: 210
cauuauuucc aguuugcccu                                                 20

<210> SEQ ID NO 211
<211> LENGTH: 20
<212> TYPE: RNA
<213> ORGANISM: Artificial Sequence
<220> FEATURE:
<223> OTHER INFORMATION: A synthetic sequence

<400> SEQUENCE: 211
ugaauuuucu gcaccaagug                                                      20

<210> SEQ ID NO 212
<211> LENGTH: 20
<212> TYPE: RNA
<213> ORGANISM: Artificial Sequence
<220> FEATURE:
<223> OTHER INFORMATION: A synthetic sequence

<400> SEQUENCE: 212
ugaauuuugu acaccaagug                                                      20

<210> SEQ ID NO 213
<211> LENGTH: 20
<212> TYPE: RNA
<213> ORGANISM: Artificial Sequence
<220> FEATURE:
<223> OTHER INFORMATION: A synthetic sequence

<400> SEQUENCE: 213
uucugcacca agugacauag                                                      20

<210> SEQ ID NO 214
<211> LENGTH: 10
<212> TYPE: RNA
<213> ORGANISM: Artificial Sequence
<220> FEATURE:
<223> OTHER INFORMATION: A synthetic sequence

<400> SEQUENCE: 214
agugacauag                                                                 10

<210> SEQ ID NO 215
<211> LENGTH: 20
<212> TYPE: RNA
<213> ORGANISM: Artificial Sequence
<220> FEATURE:
<223> OTHER INFORMATION: A synthetic sequence

<400> SEQUENCE: 215
acaggguuau caaaccucuu                                                      20

<210> SEQ ID NO 216
<211> LENGTH: 20
<212> TYPE: RNA
<213> ORGANISM: Artificial Sequence
<220> FEATURE:
<223> OTHER INFORMATION: A synthetic sequence

<400> SEQUENCE: 216
acaggguuag cuaaccucuu                                                      20

<210> SEQ ID NO 217
<211> LENGTH: 20
<212> TYPE: RNA
<213> ORGANISM: Artificial Sequence
<220> FEATURE:
<223> OTHER INFORMATION: A synthetic sequence

<400> SEQUENCE: 217
acaggguuag caaaccucuu                                                      20

-continued

```
<210> SEQ ID NO 218
<211> LENGTH: 20
<212> TYPE: RNA
<213> ORGANISM: Artificial Sequence
<220> FEATURE:
<223> OTHER INFORMATION: A synthetic sequence

<400> SEQUENCE: 218
gagggagauc acgcacuaaa                                                    20

<210> SEQ ID NO 219
<211> LENGTH: 20
<212> TYPE: RNA
<213> ORGANISM: Artificial Sequence
<220> FEATURE:
<223> OTHER INFORMATION: A synthetic sequence

<400> SEQUENCE: 219
gagggagacc acgcacuaaa                                                    20

<210> SEQ ID NO 220
<211> LENGTH: 20
<212> TYPE: RNA
<213> ORGANISM: Artificial Sequence
<220> FEATURE:
<223> OTHER INFORMATION: A synthetic sequence

<400> SEQUENCE: 220
gagggagacc ucgcacuaaa                                                    20
```